United States Patent
Ameriks et al.

(10) Patent No.: US 11,312,712 B2
(45) Date of Patent: Apr. 26, 2022

(54) AZABENZIMIDAZOLES AND THEIR USE AS AMPA RECEPTOR MODULATORS

(71) Applicant: Janssen Pharmaceutica NV, Beerse (BE)

(72) Inventors: Michael K. Ameriks, San Diego, CA (US); Cynthia G. B. Berry, San Diego, CA (US); Gang Chen, San Diego, CA (US); Suchitra Ravula, San Diego, CA (US); Bradley M. Savall, San Diego, CA (US); Devin M. Swanson, Carlsbad, CA (US); Dongpei Wu, San Diego, CA (US); Wei Zhang, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/569,299

(22) PCT Filed: Apr. 28, 2016

(86) PCT No.: PCT/US2016/029801
§ 371 (c)(1),
(2) Date: Oct. 25, 2017

(87) PCT Pub. No.: WO2016/176460
PCT Pub. Date: Nov. 3, 2016

(65) Prior Publication Data
US 2018/0118740 A1 May 3, 2018

Related U.S. Application Data

(60) Provisional application No. 62/154,313, filed on Apr. 29, 2015.

(51) Int. Cl.
*C07D 471/04* (2006.01)
*C07D 471/14* (2006.01)
*A61P 25/00* (2006.01)

(52) U.S. Cl.
CPC ............ *C07D 471/04* (2013.01); *A61P 25/00* (2018.01); *C07D 471/14* (2013.01); *C07C 2601/02* (2017.05); *C07C 2601/04* (2017.05); *C07C 2601/08* (2017.05); *C07C 2601/14* (2017.05); *C07C 2601/16* (2017.05)

(58) Field of Classification Search
CPC .......................... A61K 31/437; C07D 471/04
See application file for complete search history.

(56) References Cited

U.S. PATENT DOCUMENTS

| | | | |
|---|---|---|---|
| 4,370,340 A | 1/1983 | Ueda et al. | |
| 5,565,483 A | 10/1996 | Hewawasam et al. | |
| 5,688,809 A | 11/1997 | Macor | |
| 5,886,008 A * | 3/1999 | Macor | C07D 401/14 |
| | | | 514/217.06 |
| 6,124,285 A | 9/2000 | Watjen et al. | |
| 6,548,576 B1 | 4/2003 | Winter | |
| 7,842,698 B2 * | 11/2010 | Rueckle | C07D 471/04 |
| | | | 514/264.11 |
| 8,283,364 B2 | 10/2012 | Budzik et al. | |
| 8,362,018 B2 | 1/2013 | MacLeod et al. | |
| 8,575,154 B2 | 11/2013 | Kori et al. | |
| 2010/0137276 A1 | 6/2010 | Bradley et al. | |

FOREIGN PATENT DOCUMENTS

| | | |
|---|---|---|
| CA | 2357042 | 6/2000 |
| CN | 1094727 | 9/1994 |
| CN | 1142823 | 2/1997 |
| CN | 1144800 | 3/1997 |
| CN | 1051313 | 4/2000 |
| CN | 101052640 | 10/2007 |
| CN | 101939315 | 1/2011 |
| CN | 102056904 | 5/2011 |
| CN | 101321736 | 4/2012 |
| EP | 869958 | 10/1998 |
| IN | 777/DELNP/2007 | 3/2007 |
| JP | 2000-501432 | 2/2000 |
| JP | 2002-507613 | 3/2002 |
| JP | 2010-508328 | 3/2010 |
| JP | 2010-536825 | 12/2010 |
| JP | 2013-535408 | 9/2013 |
| WO | WO 1995/21836 | 8/1995 |

(Continued)

OTHER PUBLICATIONS

Bagshawe, Drug Dev Res. 1995, 34, 220-230.
Bertolini, et al., J Med Chem. 1997, 40, 2011-2016.
Bodor, Adv Drug Res. 1984, 13, 224-331.
Brewer, G. J. (1997). "Isolation and culture of adult rat hippocampal neurons." Journal of Neuroscience Methods 71(2): 143-155.
Chen et al., Bipolar Disord., 13:1-15, 2011.
Cho et al. (2007). "Two families of TARP isoforms that have distinct effects on the kinetic properties of AMPA receptors and synaptic currents." Neuron 55(6): 890-904.
Du et al., J Neurosci 24: 6578-6589, 2004.
Du et al., J Neurosci 28: 68-79, 2008.
Engin and Treit, Behav Pharmacol 18:365-374, 2007.
Fleisher et al., Adv Drug Delivery Rev., 1996, 19, 115-130.

(Continued)

*Primary Examiner* — Susanna Moore

(57) ABSTRACT

Provided herein are compounds of Formula (I), and pharmaceutically acceptable salts, N-oxides, or solvates thereof,

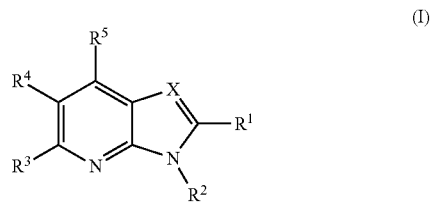

(I)

Also provided herein are pharmaceutical compositions comprising compounds of Formula (I) and methods of using compounds of Formula (I).

11 Claims, No Drawings

(56) References Cited

FOREIGN PATENT DOCUMENTS

| | | |
|---|---|---|
| WO | WO 2000/01376 | 1/2000 |
| WO | WO 2002/10170 | 2/2002 |
| WO | WO 2002/14294 | 2/2002 |
| WO | WO 2006/023109 | 3/2006 |
| WO | WO 2007/135529 | 11/2007 |
| WO | WO 2008/053031 | 5/2008 |
| WO | WO 2008/113795 | 9/2008 |
| WO | WO 2008/148832 | 12/2008 |
| WO | WO 2009/067607 | 5/2009 |
| WO | WO 2010/005528 | 1/2010 |
| WO | WO 2010/066658 | 6/2010 |
| WO | WO 2010/069684 | 6/2010 |
| WO | WO 2011/056985 | 5/2011 |
| WO | WO 2011/156245 | 12/2011 |
| WO | WO 2012/021382 | 2/2012 |
| WO | WO 2013/064984 | 5/2013 |
| WO | WO 2013-130501 | 4/2014 |
| WO | WO 2014/085153 | 6/2014 |
| WO | WO 2014/128585 | 8/2014 |

OTHER PUBLICATIONS

G.D. Considine, ed., Van Nostrand's Encyclopedia of Chemistry, p. 261, 5$^{th}$ ed. (2005).
Gill and Bredt., Neuropsychopharmacology 36(1): 362-363 (2011).
Harrison, Brain 125:1428-1449, 2002.
Heckers and Konradi, Curr Top Behav Neurosci. 4:529-553, 2010.
Lazzaro et al. (2002). "Functional characterization of CP-465,022, a selective, noncompetitive AMPA receptor antagonist." Neuropharmacology 42(2): 143-153.
Macor et al., "The discovery of a novel and potent benzodiazepine receptor pharmacophore", Bioorganic & Medicinal Chemistry Letters, Pergamon, Amsterdam, NL, vol. 5, No. 20, Oct. 19, 1995 (Oct. 19, 1995), pp. 2397-2402.
McNaughton et al., Behav Pharmacol 18: 329-346, 2007.
Nolen and Bloemkolk, Neuropsychobiology, 42 Suppl 1:11-7, 2000.
Robinson et al., J. Med Chem., 1996, 39(1), 10-18.
Paulekuhn, et al., "Trends in Active Pharmaceutical Ingredient Salt Selection based on Analysis of the Orange Book Database", J. Med. Chem., 2007, 50:6665-72.
S.M. Berge, et al., "Pharmaceutical Salts", J Pharm Sci., 1977, 66:1-19.
Schobel et al., Arch Gen Psych, 66:938-946, 2009.
Shan, et al., J Pharm Sci. 1997, 86 (7), 765-767.
Shi et al (2009) "The stoichiometry of AMPA receptors and TARPs varies by neuronal cell type." Neuron 62(5): 633-640.
Small et al, Nat. Rev. Neurosci. 12:585-601, 2011.
Strange et al. (2006). "Functional characterisation of homomeric ionotropic glutamate receptors GluR1-GluR6 in a fluorescence-based high throughput screening assay." Comb Chem High Throughput Screen 9(2): 147-158.
Tomita et al. (2003). "Functional studies and distribution define a family of transmembrane AMPA receptor regulatory proteins." J Cell Biol 161(4): 805-816.2003.
Tregellas et al., Am J Psychiatry 171: 549-556, 2014.
Yeung et al., Hippocampus 23:278-286, 2013.
Yeung et al., Neuropharmacology 62: 155-160, 2012.
International Search Report for PCT/US2016/029780 dated Jun. 14, 2016.
International Search Report for PCT/US2016/029791 dated Jun. 9, 2016.
International Search Report for PCT/US2016/029805 dated Jun. 8, 2016.
Kambe, Tohru; Correia, Bruno E.; Niphakis, Micah J.; Cravatt, Benjamin F., Journal of the American Chemical Society (2014), 136(30), 10777-10782.
Pirotte et al., "AMPA receptor positive allosteric modulators: a patent review", Expert Opinion Therapeutic Patents, vol. 23, No. 5, 2013, pp. 615-628.
Rogawski et al., Epilepsy Currents, 2011, vol. 11(2), pp. 56-63.
Tikhonova et al.,"Virtual screening of organic molecule databases . Design of focused libraries of potential I igands of NMDA and AMPA receptors", Russian Chemical Bulletin , Kluwer Academic Publishers-Plenum Publishers, NE, vol. 53, No. 6, Jun. 1, 2004, pp. 1335-1344.
Rowe, Raymond C, Paul J. Sheskey, and Marian E Quinn. Handbook of Pharmaceutical Excipients. London: Pharmaceutical Press, 6th Edition, 2009, p. 17 (Year: 2009).
Database Registry, 2011, RN 1309289-50-6, Retrieved from STN international [online] retrieved on Feb. 6, 2020.
Hanan et al., "Mild and General One-Pot Reduction and Cyclization of Aromatic and Heteroaromatic 2-Nitroamines to Bicyclic 2H-Imidazoles", Synlett 2010, No. 18, pp. 2759-2764.

* cited by examiner

AZABENZIMIDAZOLES AND THEIR USE AS AMPA RECEPTOR MODULATORS

FIELD OF THE INVENTION

The present invention is related to compounds having AMPA receptor modulating properties, pharmaceutical compositions comprising these compounds, chemical processes for preparing these compounds and their use in the treatment of diseases associated with AMPA receptor activity in animals, in particular humans.

BACKGROUND OF THE INVENTION

Glutamate is the primary excitatory neurotransmitter in mammalian brain. Glutamatergic signaling participates in a wide range of neural functions including learning and memory, long-term potentiation and synaptic plasticity.

Glutamate receptors can be divided into two families. The ionotropic glutamate receptors form ion channels that activate upon binding agonist, opening a pore through the plasma membrane through which cations can flow. The metabotropic glutamate receptors are G-protein-coupled receptors, activating intracellular signal transduction cascades. The ionotropic glutamate receptors can be further subdivided into four sub-families, based upon sequence homology and selectivity to exogenous agonists. These sub-families are the AMPA ($\alpha$-amino-3-hydroxyl-5-methyl-4-isoxazole-propionic acid), NMDA (N-methyl-D-aspartate), kainate, and delta receptors.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. Each GluA subunit can be expressed in multiple splice variants; the two most prominent splice variants are called flop and flip. GluA subunits freely form functional homo- and hetero-tetramers. The majority of RNA encoding GluA2 subunits is edited post-transcriptionally, altering a genetically-encoded glutamine to arginine. This RNA editing causes AMPA receptors to preferentially form with two GluA2 units, and also prevents calcium entry through the activated receptor.

In their native environment, the pore-forming GluA tetramers directly or indirectly associate with numerous auxiliary proteins which modify the trafficking, localization, gating characteristics, and pharmacology of the AMPA receptor (AMPAR). These auxiliary subunits include cytoskeletal and anchoring proteins, other signaling proteins, and several intracellular and transmembrane proteins with unknown function. The wide variety of proteins which can participate in AMPA receptor complexes vastly increases the ability of a neuron to tune the response characteristics of its synapses.

Transmembrane AMPA Receptor Regulatory Proteins (TARPs) are a fairly recently discovered family of proteins that have been found to associate with and modulate the activity of AMPA receptors. (Gill and Bredt., Neuropsychopharmacology 36(1): 362-363 (2011). Several TARPs exhibit regiospecific expression in the brain, leading to physiological differentiation of the AMPA receptor activity. For example, TARP $\gamma$2-dependent AMPA receptors are primarily localized in the cerebellum and cerebral cortex while TARP $\gamma$8-dependent AMPA receptors are localized primarily in the hippocampus.

AMPA receptors mediate the majority of fast neurotransmission across synaptic gaps. Thus, inhibition or negative modulation of AMPA receptors is an attractive strategy for therapeutic intervention in CNS disorders characterized by excessive neuronal activity. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABA $\gamma$-aminobutyric acid) receptor agonism, T-type calcium channel blockers, sodium channel modulators, synaptic vesicle protein SV2A modulation, and inhibition of GABA transaminase. More recently, AMPA receptor antagonists have been investigated for treatment of seizures as well.

AMPA receptor antagonists are known anticonvulsant agents. Typically, AMPA receptor antagonists have very narrow therapeutic dosing windows; the doses needed to obtain anticonvulsant activity are close to or overlap with doses at which undesired effects are observed. (Michael A. Rogawski. "Revisiting AMPA Receptors as an AntiEpileptic Drug Target" Epilepsy Currents 11.2 (2011).) However, certain anticonvulsant agents such as Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-qui-nazolin-3-yl]methanesulfonamide), and perampanel (5'-(2-cyanophenyl)-1'-phenyl-2,3'-bipyridinyl-6'(1'H)-one) are general (non-TARP dependent/non-selective) AMPA receptor antagonists. However, such general antagonism affects most areas of the CNS resulting in undesired effects, Glutamate as an excitatory neurotransmitter has been known to induce neurotoxicity by, for example, abnormal excitation of central nerves. Neurotoxicity is an adverse structural or functional change in the nervous system, and can take the form of subtle or gross biochemical changes, axonal degeneration, dendritic pruning or sprouting, loss or rearrangement of synapses, or cell death. Numerous nervous diseases involve a neurotoxic component, including and not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain and diabetic neuropathy.

Substances showing an antagonistic action to excitatory neurotransmitter receptors are potentially useful for the treatment of the above-mentioned conditions. For example, WO2000001376 suggests that inhibitors of the interaction of glutamate with the AMPA and/or kainate receptor complex could be useful in treating demyelinating disorders such as encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder; for example, CNS lupus erythematodes, polyarteritis nodosa, Sjogren syndrome, sarcoidosis, isolated cerebral vasculitis, etc.

Hippocampus links the limbic system to frontal cortex, thereby linking emotion to cognition (Small et al, Nat. Rev. Neurosci. 12:585-601, 2011). A meta-analysis of post-mortem neuro-pathology studies suggests that hippocampal volume is reduced in volume in patients with mood disorders (Harrison, Brain 125:1428-1449, 2002). Hippocampal neurons are particularly susceptible to stress-related atrophy. Pathological states characterized by excessive activity within hippocampus may be improved by a therapeutic intervention that selectively reduces hippocampal excitability. Modulation of neuronal excitability within hippocampus may provide a therapeutic benefit in mood disorders.

Excess activity in hippocampus has been observed in response to emotionally-charged stimuli in bipolar patients compared to controls (reviewed by Chen et al., Bipolar Disord., 13:1-15, 2011). Chronic treatment with mood stabilizers such as lithium or valproate reduced AMPA receptor surface expression in hippocampus (Du et al., J Neurosci 28: 68-79, 2008). Tricyclic antidepressants can trigger mania in bipolar patients (Nolen and Bloemkolk, Neuropsychobiology, 42 Suppl 1:11-7, 2000); these treatments can increase AMPA receptor surface expression in hippocampus (Du et al., J Neurosci 24: 6578-6589, 2004.)

In Gray's Neuropsychological Theory of Anxiety (2003), septum and hippocampus form a 'behavioral inhibition system' activated during anxiety-provoking conflict situations. A corollary of this theory is that anxiolytic drugs act by suppressing this 'behavioral inhibition system'. Indeed, intrahippocampal micro-infusion of $GABA_A$ agonists is sufficient to replicate their anxiolytic effects (Engin and Treit, Behav Pharmacol 18:365-374, 2007). Traditional anxiolytics with a variety of mechanisms-of-action, including $GABA_A$-receptor antagonists, $5-HT_{1A}$ receptor antagonists, and SSRIs, suppress brainstem-stimulated theta rhythm within hippocampus (McNaughton et al., Behav Pharmacol 18: 329-346, 2007). Direct injection of inhibitors of neuronal excitability into rodent hippocampus was shown to reduce the hippocampal theta rhythm, and to produce an anxiolytic phenotype. Intrahippocampal administration of ZD7288, an HCN channel inhibitor, slowed brainstem-stimulated theta rhythm in anesthetized rat and also increased the amount of time that rats spent in the open arms of an elevated plus maze (Yeung et al., Hippocampus 23:278-286, 2013). Intrahippocampal administration of phenytoin, a voltage-gated sodium channel inhibitor and anti-convulsant, showed similar effects on brainstem-stimulated theta rhythm frequency in anesthetized rat and was anxiolytic in conscious rat (Yeung et al., Neuropharmacology 62: 155-160, 2012).

Hippocampal overactivity has been observed in patients suffering from schizophrenia (Heckers and Konradi, Curr Top Behav Neurosci. 4:529-553, 2010). The degree of hyperactivity was be positively correlated to the severity of the symptoms (Tregellas et al., Am J Psychiatry 171: 549-556, 2014). Hypermetabolism in hippocampus (esp. CA1 region) correlates with disease progression in at-risk individuals, and with disease severity in patients diagnosed with schizophrenia (Schobel et al., Arch Gen Psych, 66:938-946, 2009). This over-activity, combined with the sensitivity of hippocampal neurons to excitotoxic damage, may lead to the observed decrease in hippocampal volume in schizophrenic patients. Neuroprotection in prodromal and early stages may prevent progressive damage (Kaur and Cadenhead, Curr Top Behav Neurosci, 2010).

In view of the clinical importance of AMPA receptors, the identification of compounds that modulate AMPA receptor function represents an attractive avenue into the development of new therapeutic agents. Such compounds are provided herein.

SUMMARY OF THE INVENTION

Provided herein are compounds which are AMPA receptor modulators. In another aspect, provided herein are compounds which modulate certain TARP dependent AMPA receptors. The compounds described herein are suitable for treatment of conditions involving AMPA receptor activity, and for treatment of conditions involving selective modulation of TARP dependent AMPA receptor activity, thereby allowing for treatment of conditions such as, inter alia, abnormal neurotransmission across synaptic gaps, excessive neuronal activity, abnormal excessive or synchronous neuronal activity in the brain, neurotoxicity (e.g., adverse structural or functional changes in the nervous system, subtle or gross biochemical changes, axonal degeneration, dendritic pruning or sprouting, loss or rearrangement of synapses, or cell death), neuronal excitability within hippocampus, neuronal excitotoxicity, hippocampal overactivity, and the like.

The invention is directed to the general and preferred embodiments defined, respectively, by the independent and dependent claims appended hereto, which are incorporated by reference herein. One aspect of this invention concerns compounds of Formula (I):

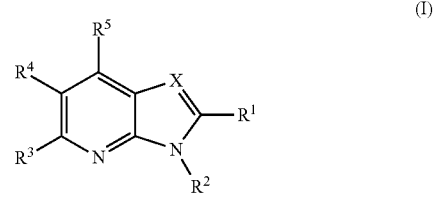

wherein
X is N or $CR^6$;
$R^1$ is a member selected from the group consisting of:
H, —$C_{1-5}$alkyl, —$C_{1-5}$haloalkyl, —$C_{1-5}$alkoxy, —$(CH_2)_2C(=O)OCH_3$, —$(CH_2)_{1-3}OH$, —$(CH_2)_{1-2}O$—$C_{1-5}$alkyl, —$CH(CH_3)OCH_3$, —$C(CH_3)_2OCH_3$, —$CH_2SO_2CH_3$, —$C(=O)H$, —$NH$—$C_{1-5}$alkyl, —$N(C_{1-5}$alkyl$)_2$, —$C(=O)N(H)C_{1-5}$alkyl, —$C(=O)N(C_{1-5}$alkyl$)_2$, —$C_{3-8}$cycloalkyl, —$(CH_2)$—$C_{3-5}$cycloalkyl, —$CH(CH_3)$—$C_{3-8}$cycloalkyl, —$NH$—$C_{3-8}$cycloalkyl, —$C(=O)NH$-cyclopropyl, —$C(=O)$—$NH$-phenyl, —$C(=O)$-azetidinyl, —$C(=O)$-pyrrolidinyl, azetidinyl, phenyl, benzyl, oxetanyl, tetrahydrofuranyl, tetrahydropyranyl, —$CH_2$-pyrazinyl, furanyl, thienyl, and pyridinyl, wherein the —$C_{3-8}$cycloalkyl, phenyl, oxetanyl, azetidinyl, tetrahydrofuranyl, tetrahydropyranyl, pyridinyl, pyrazinyl, furanyl and thienyl rings are each independently optionally substituted with 1-3 substituents selected from the group consisting of:

halo, —C$_{1-5}$alkyl, —C$_{1-5}$haloalkyl, —C$_{1-5}$haloalkoxy, —OH, and —C(=O)OC$_{1-5}$alkyl;

R$^2$ is selected from the group consisting of:

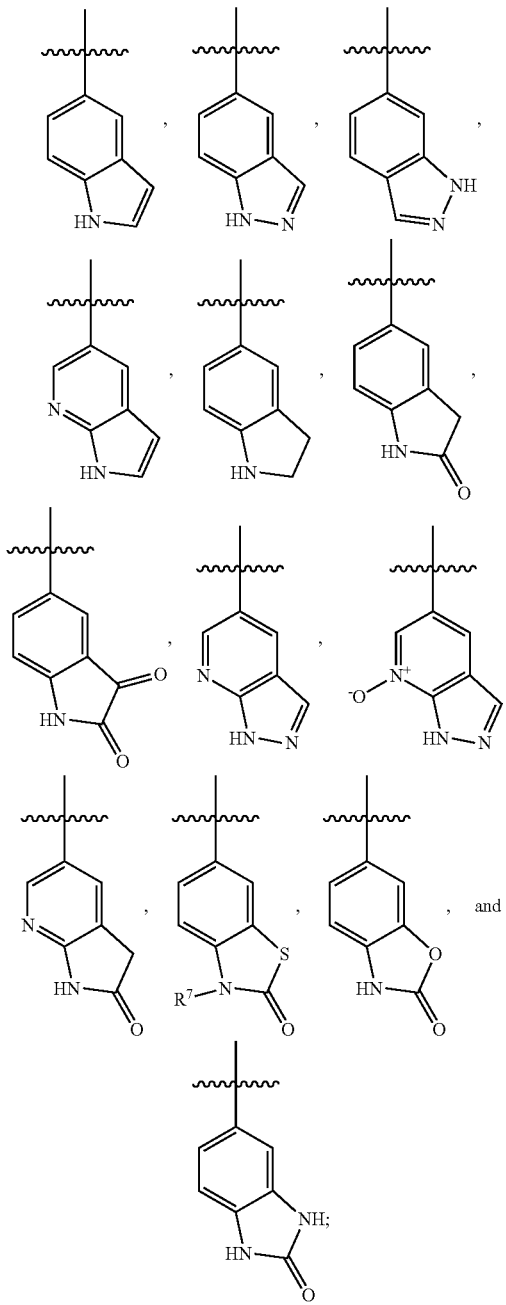

wherein each R$^2$ is independently optionally substituted with a member selected from the group consisting of: $^3$H, halo, —C$_{1-5}$alkyl, —C$_{1-5}$alkenyl, —CN, —OH, CH=CHCH$_2$OH, —(CH$_2$)$_3$COH, C(=O)OC$_{1-5}$alkyl, and phenyl;

R$^3$ is selected from the group consisting of: H, halo, —C$_{1-5}$alkyl, —S—C$_{1-5}$alkyl, —C$_{1-5}$haloalkyl, —C$_{1-5}$alkoxy, —NR$^{3a}$R$^{3b}$, —OH, —(CH$_2$)$_{1-3}$OH, —CH=CHCH$_2$OH, —C$_{3-8}$cycloalkyl, piperidinyl, piperazinyl, morpholinyl, and pyridyl;

each R$^{3a}$ and R$^{3b}$ are independently selected from the group consisting of H and C$_{1-5}$alkyl;

R$^4$ is selected from the group consisting of: H, halo, —CH$_3$, and —CF$_3$;

R$^5$ is selected from the group consisting of: H, —OH, —C$_{1-5}$alkyl, —C$_{1-5}$alkoxy, —C$_{1-5}$haloalkyl, —C$_{1-5}$haloalkoxy, —NR$^{5a}$R$^{5b}$, azetidinyl, and morpholinyl;

each R$^{5a}$ and R$^{5b}$ are independently selected from the group consisting of: —C$_{1-5}$alkyl, and —C$_{1-5}$haloalkyl;

R$^6$ is selected from the group consisting of: H, —OH, —CHF$_2$, and —Br; and

R$^7$ is H or —C$_{1-5}$alkyl;

and pharmaceutically acceptable salts, N-oxides, or solvates of compounds of Formula (I).

Further embodiments are provided by pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as their pharmaceutically acceptable salts.

In a further aspect, the invention relates to pharmaceutical compositions, comprising an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as AMPA receptor modulators. Thus, the invention is directed to a method for modulating AMPA receptor activity, including when such receptor is in a subject, comprising exposing AMPA receptor to an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by AMPA receptor activity, comprising administering to the subject in need of such treatment an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. For example, an $^{18}$F or $^{11}$C labeled compound may be particularly preferred for PET or SPECT studies.

Additional embodiments of this invention include methods of making compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

In another aspect provided herein are compounds of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA). In another aspect provided herein are compounds of Formula (IE), as well as pharmaceutically acceptable salts, N-oxides or solvates of compounds of Formula (IE), pharmaceutically acceptable prodrugs of compounds of Formula (IE), and pharmaceutically active metabolites of Formula (IE). In a further aspect, provided herein are pharmaceutical compositions, comprising an effective amount of a compound of Formula (IA) or Formula (IE), as well as pharmaceutically acceptable salts, N-oxides or solvates of compounds of Formula (IA) or Formula (IE), pharmaceutically acceptable prodrugs of compounds of Formula (IA) or Formula (IE), and pharmaceutically active metabolites of Formula (IA) or Formula (IE). In a further aspect, provided herein are compounds of Formula (IA) or Formula (IE), as well as pharmaceutically acceptable salts, N-oxides or solvates of compounds of Formula (IA) or Formula (IE), pharmaceutically acceptable prodrugs of compounds of Formula (IA) or Formula (IE), and pharmaceutically active metabolites of Formula (IA) or Formula (IE), for the treatment of any condition described herein.

DETAILED DESCRIPTION

In one aspect, provided herein are compounds of Formula (I), and pharmaceutically acceptable salts, N-oxides, or solvates thereof,

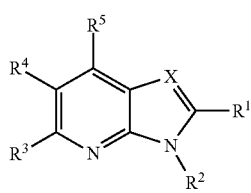

(I)

wherein
X is N or $CR^6$;
$R^1$ is a member selected from the group consisting of: H, —$C_{1-5}$alkyl, —$C_{1-5}$haloalkyl, —$C_{1-5}$alkoxy, —$(CH_2)_2C(=O)OCH_3$, —$(CH_2)_{1-3}OH$, —$(CH_2)_{1-2}$O—$C_{1-5}$alkyl, —$CH(CH_3)OCH_3$, —$C(CH_3)_2$OCH_3$, —$CH_2SO_2CH_3$, —$C(=O)H$, —NH—$C_{1-5}$alkyl, —$N(C_{1-5}alkyl)_2$, —$C(=O)N(H)C_{1-5}$alkyl, —$C(=O)N(C_{1-5}alkyl)_2$, —$C_{3-8}$cycloalkyl, —$(CH_2)$—$C_{3-5}$cycloalkyl, —$CH(CH_3)$—$C_{3-8}$cycloalkyl, —NH—$C_{3-8}$cycloalkyl, —$C(=O)NH$-cyclopropyl, —$C(=O)$—NH-phenyl, —$C(=O)$-azetidinyl, —$C(=O)$-pyrrolidinyl, azetidinyl, phenyl, benzyl, oxetanyl, tetrahydrofuranyl, tetrahydropyranyl, —$CH_2$-pyrazinyl, furanyl, thienyl, or pyridinyl, wherein the —$C_{3-8}$cycloalkyl, phenyl, oxetanyl, azetidinyl, tetrahydrofuranyl, tetrahydropyranyl, pyridinyl, pyrazinyl, furanyl and thienyl rings are each independently optionally substituted with 1-3 substituents selected from the group consisting of: halo, —$C_{1-5}$alkyl, —$C_{1-5}$haloalkyl, —$C_{1-5}$haloalkoxy, —OH, and —$C(=O)OC_{1-5}$alkyl;

$R^2$ is selected from the group consisting of:

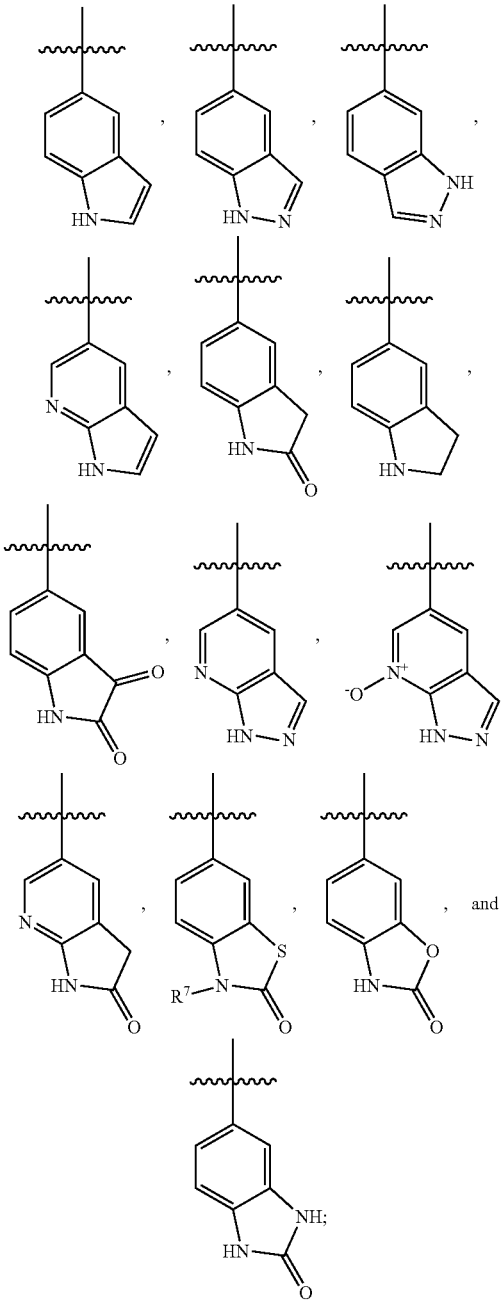

wherein each $R^2$ is independently optionally substituted with a member selected from the group consisting of: $^3$H, halo, —$C_{1-5}$alkyl, —$C_{1-5}$alkenyl, —CN, —OH, CH=CHCH$_2$OH, —$(CH_2)_3$COH, $C(=O)OC_{1-5}$alkyl, and phenyl;

$R^3$ is selected from the group consisting of: H, halo, —$C_{1-5}$alkyl, —S—$C_{1-5}$alkyl, —$C_{1-5}$haloalkyl, —C$_{1-5}$alkoxy, —NR$^{3a}$R$^{3b}$, —OH, —(CH$_2$)$_{1-3}$OH, —CH═CHCH$_2$OH, —C$_{3-8}$cycloalkyl, piperidinyl, piperazinyl, morpholinyl, and pyridyl;

each R$^{3a}$ and R$^{3b}$ are independently selected from the group consisting of H and C$_{1-5}$alkyl;

R$^4$ is selected from the group consisting of: H, halo, —CH$_3$, and —CF$_3$;

R$^5$ is selected from the group consisting of: H, —OH, —C$_{1-5}$alkyl, —C$_{1-5}$alkoxy, —C$_{1-5}$haloalkyl, —C$_{1-5}$haloalkoxy, —NR$^{5a}$R$^{5b}$, azetidinyl, and morpholinyl;

each R$^{5a}$ and R$^{5b}$ are independently selected from the group consisting of: —C$_{1-5}$alkyl, and —C$_{1-5}$haloalkyl; and R$^6$ is selected from the group consisting of: H, —OH, —CHF$_2$, and —Br; and R$^7$ is H or —C$_{1-5}$alkyl.

An additional embodiment of the invention is a compound of Formula (I) wherein X is N.

An additional embodiment of the invention is a compound of Formula (I) wherein X is CR$^6$.

An additional embodiment of the invention is a compound of Formula (I) wherein R$^6$ is H.

An additional embodiment of the invention is a compound of Formula (I) wherein R$^1$ is H, —C$_{1-5}$alkyl, —C$_{1-5}$haloalkyl, —C$_{1-5}$alkoxy, —(CH$_2$)$_2$C(═O)OCH$_3$, —(CH$_2$)$_3$—OH, —C(CH$_3$)$_2$OCH$_3$, —(CH$_2$)$_{1-2}$—O—C$_{1-5}$alkyl, —CH(CH$_3$)OCH$_3$, —CH$_2$SO$_2$CH$_3$, —NH—C$_{1-5}$alkyl, —N(C$_{1-5}$alkyl)$_2$, —C(═O)N(H)C$_{1-5}$alkyl, or —C(═O)N(C$_{1-5}$alkyl)$_2$.

An additional embodiment of the invention is a compound of Formula (I) wherein R$^1$ is H, —C$_{1-5}$alkyl, —C$_{1-5}$haloalkyl, —C$_{1-5}$alkoxy, —(CH$_2$)$_3$—OH, —(CH$_2$)$_{1-2}$—O—C$_{1-5}$alkyl, —C(CH$_3$)$_2$OCH$_3$, or —CH(CH$_3$)OCH$_3$.

An additional embodiment of the invention is a compound of Formula (I) wherein R$^1$ is —C$_{3-5}$cycloalkyl, —(CH$_2$)—C$_{3-8}$cycloalkyl, —CH(CH$_3$)—C$_{3-8}$cycloalkyl, NH—C$_{3-8}$cycloalkyl, —C(═O)NH-cyclopropyl, —C(═O)—NH-phenyl, —C(═O)-azetidinyl, —C(═O)-pyrrolidinyl, azetidinyl, phenyl, benzyl, oxetanyl, tetrahydrofuranyl, tetrahydropyranyl, —CH$_2$-pyrazinyl, furanyl, thienyl, or pyridinyl, wherein the —C$_{3-8}$cycloalkyl, phenyl, oxetanyl, azetidinyl, and pyridinyl rings are each independently optionally substituted with 1-3 substituents independently selected from the group consisting of: halo, —C$_{1-5}$alkyl, —C$_{1-5}$haloalkyl, —C$_{1-5}$haloalkoxy, —OH, and —C(═O)OC$_{1-5}$alkyl.

An additional embodiment of the invention is a compound of Formula (I) wherein R$^1$ is cyclopropyl, cyclobutyl, cyclopentyl, cyclohexyl, 1-fluorocyclopropyl, 3-fluorocyclobutyl, cyclopropanol, 2-furyl, 3-methyloxetan-3-yl, 2-tetrahydrofuran-3-yl, tetrahydropyran-4-yl, 2-thienyl, cyclopentylmethyl, pyrazin-2-ylmethyl, —C(═O)NH-cyclopropyl, —C(═O)—NH-phenyl, —C(═O)-azetidinyl, —C(═O)-pyrrolidinyl, or NH-cyclohexyl.

An additional embodiment of the invention is a compound of Formula (I) wherein R$^1$ is —C$_{3-5}$cycloalkyl, phenyl, —CH$_2$-phenyl, or pyridyl, wherein each phenyl, —CH$_2$-phenyl, or pyridyl is optionally substituted with 1-3 substituents independently selected from the group consisting of: halo, —C$_{1-5}$alkyl, —C$_{1-5}$haloalkyl, —C$_{1-5}$haloalkoxy, and —OH.

An additional embodiment of the invention is a compound of Formula (I) wherein R$^1$ is phenyl, 2-chlorophenyl, 4-fluorophenyl, 4-(difluoromethyl)phenyl, 4-(trifluoromethyl)phenyl, 4-(trifluoromethoxy)phenyl, 4-fluoro-3-methyl-phenyl, p-tolyl, m-tolyl, pyridyl, 2-chloro-4-pyridyl, 2-bromo-4-pyridyl, 2-fluoro-4-pyridyl, 2-[$^{19}$F]fluoro-4-pyridyl, 2-[$^{18}$F]fluoro-4-pyridyl, 5-fluoro-2-pyridyl, 6-fluoro-3-pyridyl, or pyridin-2-ol.

An additional embodiment of the invention is a compound of Formula (I) wherein R$^1$ is —C$_{1-5}$alkyl, —C$_{1-5}$, haloalkyl, or —C$_{3-8}$cycloalkyl, wherein the —C$_{3-8}$cycloalkyl is optionally substituted with halo.

An additional embodiment of the invention is a compound of Formula (I) wherein R$^2$ is

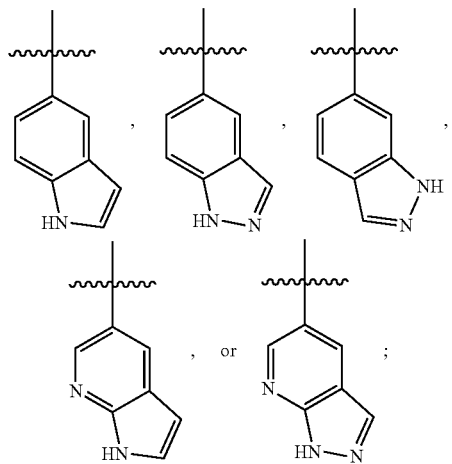

wherein each R$^2$ is independently optionally substituted with a member selected from the group consisting of: halo, —C$_{1-5}$alkyl, —C$_{1-5}$alkenyl, —CN, —OH, CH═CHCH$_2$OH, —(CH$_2$)$_3$COH, C(═O)OC$_{1-5}$alkyl, and phenyl.

An additional embodiment of the invention is a compound of Formula (I) wherein R$^2$ is

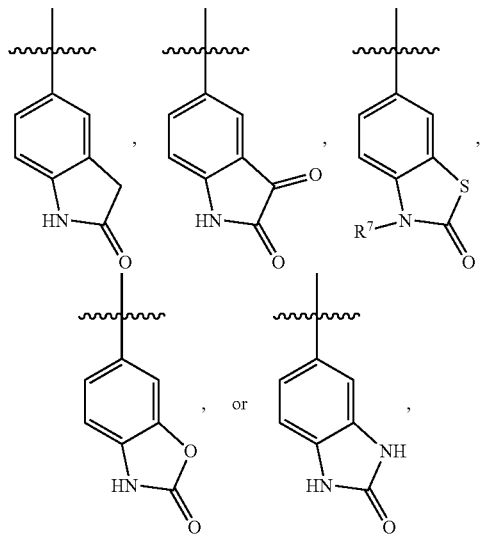

wherein each R$^2$ is independently optionally substituted with a member selected from the group consisting of: halo, —C$_{1-5}$alkyl, —C$_{1-5}$alkenyl, —CN, —OH, CH═CHCH$_2$OH, —(CH$_2$)$_3$COH, C(═O)OC$_{1-5}$alkyl, and phenyl; and R$^7$ is H or —CH$_3$.

An additional embodiment of the invention is a compound of Formula (I) wherein $R^2$ is

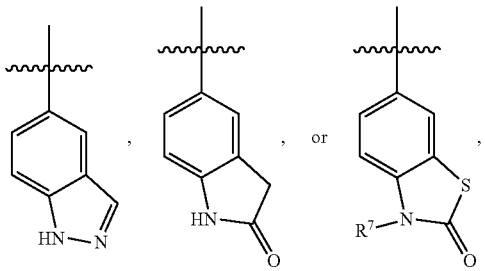

wherein each $R^2$ is independently optionally substituted with a member selected from the group consisting of: halo, —$C_{1-5}$alkyl, —$C_{1-5}$alkenyl, —CN, —OH, CH=CHCH$_2$OH, —(CH$_2$)$_3$COH, C(=O)OC$_{1-5}$alkyl, and phenyl; and $R^7$ is H or —CH$_3$.

An additional embodiment of the invention is a compound of Formula (I) wherein $R^2$ is 1H-indazol-3-ol, 1H-indazol-5-yl, 1H-indazol-6-yl, 3-bomo-1H-indazol-5-yl, 3-fluoro-1H-indazol-5-yl, 1H-indazole-3-carbonitrile, (E)-3-(1H-indazol-7-yl)prop-2-en-1-ol, (1H-indazol-7-yl)propan-1-ol, 4-chloro-1H-indazol-6-yl, 4-methyl-1H-indazol-6-yl, 7-bromo-1H-indazol-5-yl, 7-phenyl-1H-indazol-5-yl, 7-propyl-1H-indazol-5-yl, 5-methyl 1H-indazole-7-carboxylate, tert-butyl 1H-indazole-1-carboxylate, 1H-indol-5-yl, 1H-pyrrolo[2,3-b]pyridin-5-yl, or 1H-pyrazolo[3,4-b]pyridin-5-yl.

An additional embodiment of the invention is a compound of Formula (I) wherein $R^2$ is indolin-2-one, 7-methyl-indolin-2-one, 7-fluoro-indolin-2-one, 7-chloro-indolin-2-one, indoline-2,3-dione, 1,3-dihydropyrrolo[2,3-b]pyridin-2-one, 1,3-dihydrobenzimidazol-2-one, 3H-1,3-benzoxazol-2-one, 4-fluoro-3H-1,3-benzoxazol-2-one, 4-bromo-3H-1,3-benzoxazol-2-one, 3H-1,3-benzothiazol-2-one, 4-methyl-3H-1,3-benzothiazol-2-one, 3-methylbenzo[d]thiazol-2(3H)-one, or 4-chloro-3H-1,3-benzothiazol-2-one.

An additional embodiment of the invention is a compound of Formula (I) wherein $R^2$ is 1H-indazol-3-ol, 1H-indazol-5-yl, 3-bomo-1H-indazol-5-yl, 3-fluoro-1H-indazol-5-yl, 1H-indazole-3-carbonitrile, (E)-3-(1H-indazol-7-yl)prop-2-en-1-ol, (1H-indazol-7-yl)propan-1-ol, 7-bromo-1H-indazol-5-yl, 7-phenyl-1H-indazol-5-yl, 7-propyl-1H-indazol-5-yl, 5-methyl 1H-indazole-7-carboxylate, tert-butyl 1H-indazole-1-carboxylate, indolin-2-one, 7-methyl-indolin-2-one, 7-fluoro-indolin-2-one, 7-chloro-indolin-2-one, 3H-1,3-benzothiazol-2-one, 4-methyl-3H-1,3-benzothiazol-2-one, 3-methylbenzo[d]thiazol-2(3H)-one, or 4-chloro-3H-1,3-benzothiazol-2-one.

An additional embodiment of the invention is a compound of Formula (I) wherein $R^3$ is H, halo, —$C_{1-5}$alkyl, —$C_{1-5}$haloalkyl, —OCH$_3$, —NH$_2$, —N(CH$_3$)$_2$, or —OH.

An additional embodiment of the invention is a compound of Formula (I) wherein $R^4$ is H, fluoro or —CH$_3$.

An additional embodiment of the invention is a compound of Formula (I) wherein $R^5$ is H, —OH, —$C_{1-5}$alkyl, —$C_{1-5}$haloalkyl, or —$C_{1-5}$haloalkoxy.

An additional embodiment of the invention is a compound of Formula (I) wherein $R^5$ is H.

An additional embodiment of the invention is a compound of Formula (I) wherein $R^6$ is H.

An additional embodiment of the invention is a compound of Formula (I) wherein $R^7$ is H.

An additional embodiment of the invention is a compound of Formula (I) wherein $R^3$ is H, —$C_{1-5}$alkyl, and —$C_{1-5}$haloalkyl; $R^4$ is H, —CH$_3$, or F; and $R^5$ is H.

An additional embodiment of the invention is a compound of Formula (I) wherein $R^4$ is H; $R^3$ is H, halo, —$C_{1-5}$alkyl, —$C_{1-5}$haloalkyl, $C_{3-6}$cycloalkyl, or —$C_{1-5}$alkoxy; and $R^5$ is H, —CH$_3$, —CHF$_2$, —CH(CH$_3$)$_2$, —OH, —N(CH$_3$)CH$_2$CH$_2$F, —N(CH$_3$)$_2$, —O—CH$_2$CH$_2$F, —OCH$_3$, morpholinyl, or azetidinyl.

An additional embodiment of the invention is a compound of Formula (I) wherein $R^5$ is H; $R^4$ is H; and $R^3$ is H, —CH$_3$, —CH$_2$CH$_3$, —CH$_2$CH$_2$CH$_3$, —C(CH$_3$)$_3$, —CH(CH$_3$)$_2$, —CF$_3$, —CF$_2$H, or —CF$_2$CH$_3$.

An additional embodiment of the invention is a compound of Formula (I) wherein

X is N;

$R^1$ is H, $C_{1-5}$alkyl, $C_{1-5}$haloalkyl, $C_{1-5}$alkoxy, phenyl, or $C_{3-8}$cycloalkyl, wherein the cycloalkyl and phenyl are each independently optionally substituted with 1-3 halo substituents;

$R^2$ is

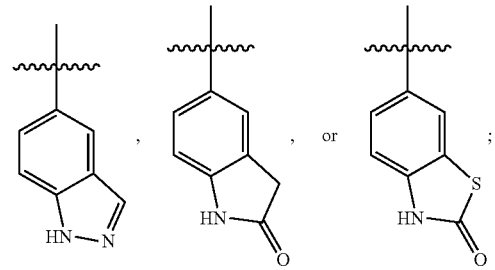 [SMILES: *c1ccc2[nH]ncc2c1 ; *c1ccc2c(c1)CC(=O)N2 ; *c1ccc2[nH]c(=O)sc2c1]

and $R^3$ is H, $C_{1-5}$alkyl, or $C_{1-5}$haloalkyl.

An additional embodiment of the invention is a compound of Formula (I) wherein

X is $CR^6$, where $R^6$ is H;

$R_1$ is H, $C_{1-5}$alkyl, $C_{1-5}$haloalkyl, $C_{1-5}$alkoxy, phenyl, or $C_{3-8}$cycloalkyl, wherein the cycloalkyl and phenyl are each independently optionally substituted with 1-3 halo substituents;

$R_2$ is

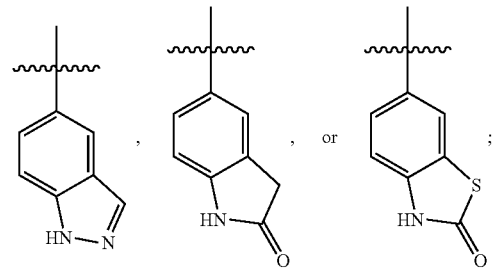 [SMILES: *c1ccc2[nH]ncc2c1 ; *c1ccc2c(c1)CC(=O)N2 ; *c1ccc2[nH]c(=O)sc2c1]

each $R^2$ is independently optionally substituted with halo, and —$C_{1-5}$alkyl;

$R^3$ is H, $C_{1-5}$alkyl, or $C_{1-5}$haloalkyl; and $R_4$ is H.

An additional embodiment of the invention is a compound of Formula (I) having the Formula (IA):

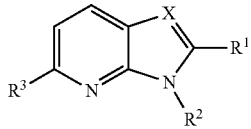
(IA)

wherein
R¹ is $C_{1-5}$alkyl, $C_{1-5}$haloalkyl, $C_{1-5}$alkoxy, phenyl, or $C_{3-8}$cycloalkyl, wherein the $C_{3-8}$cycloalkyl and phenyl are independently optionally substituted with 1-3 halo substituents;
R² is

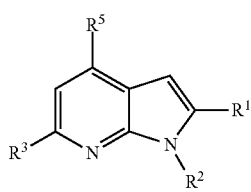

and
R³ is H, $C_{1-5}$alkyl, or $C_{1-5}$haloalkyl;
and pharmaceutically acceptable salts, N-oxides or solvates of compounds of Formula (IA).

An additional embodiment of the invention is a compound of Formula (I) having the Formula (IE):

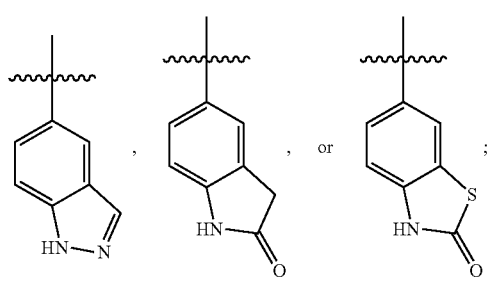 [SMILES: *c1ccc2[nH]ncc2c1 ; *c1ccc2c(c1)CC(=O)N2 ; *c1ccc2[nH]c(=O)sc2c1]
(IE)

wherein
R¹ is a member selected from the group consisting of:
H, —$C_{1-5}$alkyl, —$C_{1-5}$haloalkyl, —$(CH_2)_{1-3}$OH, —$(CH_2)_{1-2}$O—$C_{1-5}$alkyl, —$CH(CH_3)OCH_3$, or —C(=O)H, —$C_{3-8}$cycloalkyl, phenyl, and tetrahydrofuranyl, wherein the —$C_{3-8}$cycloalkyl, phenyl, and tetrahydrofuranyl rings are each independently optionally substituted with 1-3 halo substituents;

R² is selected from the group consisting of:

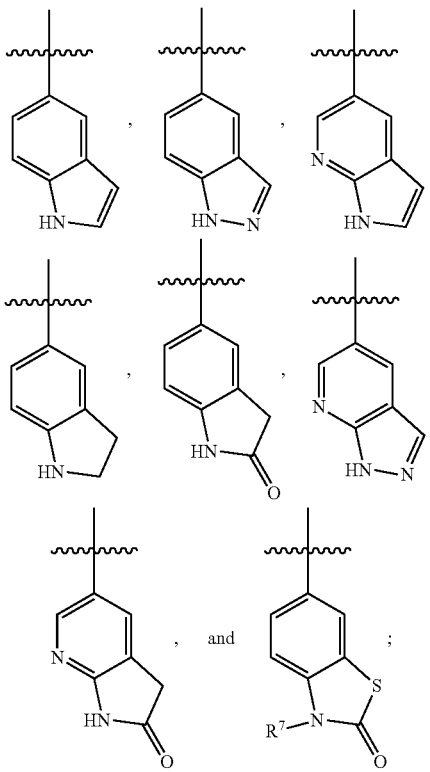

wherein each R² is independently optionally substituted with a member selected from the group consisting of: halo, and —$C_{1-5}$alkyl;
R³ is selected from the group consisting of: H, halo, —$C_{1-5}$alkyl, —$C_{1-5}$haloalkyl, and —$C_{1-5}$alkoxy;
R⁵ is selected from the group consisting of: H, —$C_{1-5}$alkyl, —$C_{1-5}$alkoxy, —$NR^{5a}R^{5b}$, azetidinyl, and morpholinyl; each $R^{5a}$ and $R^{5b}$ are independently —$C_{1-5}$alkyl; and
R⁷ is H;
and pharmaceutically acceptable salts, N-oxides or solvates of compounds of Formula (IE).

An additional embodiment of the invention is a compound of Formula (I) having the Formula (IE):
wherein:
R¹ is a member selected from the group consisting of:
—$C_{1-5}$alkoxy, —$(CH_2)_2C(=O)OCH_3$, —$C(CH_3)_2OCH_3$, —$CH_2SO_2CH_3$, —C(=O)H, —NH—$C_{1-5}$alkyl, —$N(C_{1-5}$alkyl$)_2$, —C(=O)N(H)$C_{1-5}$alkyl, or —C(=O)N($C_{1-5}$alkyl$)_2$, —$(CH_2)$—$C_{3-8}$cycloalkyl, —$CH(CH_3)$—$C_{3-8}$cycloalkyl, —NH—$C_{3-8}$cycloalkyl, —C(=O)NH-cyclopropyl, —C(=O)—NH-phenyl, —C(=O)-azetidinyl, —C(=O)-pyrrolidinyl, azetidinyl, phenyl, benzyl, oxetanyl, tetrahydrofuranyl, tetrahydropyranyl, —$CH_2$-pyrazinyl, furanyl, thienyl, or pyridinyl, wherein the —$C_{3-8}$cycloalkyl, phenyl, oxetanyl, azetidinyl, tetrahydrofuranyl, tetrahydropyranyl, pyridinyl, pyrazinyl, furanyl and thienyl rings are each independently optionally substituted with 1-3 substituents selected from the group consisting of: halo, —$C_{1-5}$alkyl, —$C_{1-5}$haloalkyl, —$C_{1-5}$haloalkoxy, —OH, and —C(=O)O$C_{1-5}$alkyl; and $R^2$ is selected from the group consisting of:

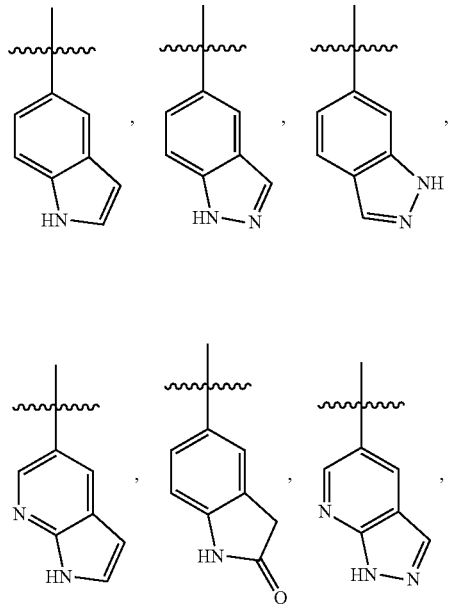

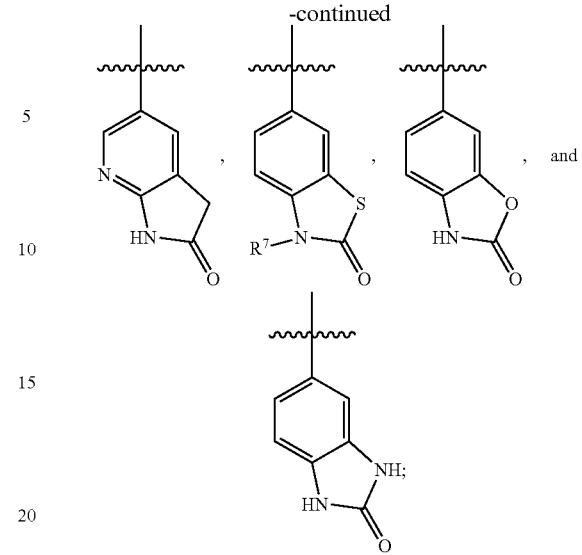

wherein each $R^2$ is independently optionally substituted with a member selected from the group consisting of: $^3H$, halo, —$C_{1-5}$alkyl, —$C_{1-5}$alkenyl, —CN, —OH, CH=CHCH$_2$OH, —(CH$_2$)$_3$COH and C(=O)OC$_{1-5}$alkyl.

A further embodiment of the current invention is a compound as shown below in Table 1.

TABLE 1

| Ex. # | Compound Name |
|---|---|
| 1 | 3-(1H-Indazol-5-yl)-2-phenyl-5-(trifluoromethyl)-3H-imidazo[4,5-b]pyridine; |
| 2 | 3-(1H-Indazol-5-yl)-2-phenyl-imidazo[4,5-b]pyridine; |
| 3 | 3-(1H-Indazol-5-yl)-5-methyl-2-phenyl-imidazo[4,5-b]pyridine; |
| 4 | 2-(4-Fluorophenyl)-3-(1H-indazol-5-yl)-5-methyl-imidazo[4,5-b]pyridine; |
| 5 | 2-(4-Fluorophenyl)-3-(1H-indol-5-yl)-5-methoxy-imidazo[4,5-b]pyridine; |
| 6 | 5-[2-(4-Fluorophenyl)-5-methoxy-imidazo[4,5-b]pyridin-3-yl]indolin-2-one; |
| 7 | 5-Chloro-2-(4-fluorophenyl)-3-(1H-indazol-5-yl)imidazo[4,5-b]pyridine; |
| 8 | 2-(2-Chlorophenyl)-3-(1H-indazol-5-yl)-5-methyl-imidazo[4,5-b]pyridine; |
| 9 | 3-(1H-Indazol-5-yl)-6-methyl-2-phenyl-imidazo[4,5-b]pyridine; |
| 10 | 5-Chloro-3-(1H-indazol-5-yl)-2-phenyl-imidazo[4,5-b]pyridine; |
| 11 | 5-Chloro-2-cyclopentyl-3-(1H-indazol-5-yl)imidazo[4,5-b]pyridine; |
| 12 | tert-Butyl 5-(5-methyl-2-phenyl-imidazo[4,5-b]pyridin-3-yl)indazole-1-carboxylate; |
| 13 | 3-(1H-Indol-5-yl)-2-phenyl-5-(trifluoromethyl)imidazo[4,5-b]pyridine; |
| 14 | 6-[2-Phenyl-5-(trifluoromethyl)imidazo[4,5-b]pyridin-3-yl]-3H-1,3-benzothiazol-2-one; |
| 15 | 6-(5-Fluoro-2-phenyl-imidazo[4,5-b]pyridin-3-yl)-3H-1,3-benzothiazol-2-one; |
| 16 | 6-[2-(4-Fluorophenyl)-5-(trifluoromethyl)imidazo[4,5-b]pyridin-3-yl]-3H-1,3-benzothiazol-2-one; |
| 17 | 6-(5-Methyl-2-phenyl-imidazo[4,5-b]pyridin-3-yl)-3H-1,3-benzothiazol-2-one; |
| 18 | 6-(5-Methoxy-2-phenyl-imidazo[4,5-b]pyridin-3-yl)-3H-1,3-benzothiazol-2-one; |
| 19 | 6-[2-tert-Butyl-5-(trifluoromethyl)imidazo[4,5-b]pyridin-3-yl]-3H-1,3-benzothiazol-2-one; |
| 20 | 6-[2-(4-Fluorophenyl)imidazo[4,5-b]pyridin-3-yl]-3H-1,3-benzothiazol-2-one; |
| 21 | 5-[2-(4-Fluorophenyl)imidazo[4,5-b]pyridin-3-yl]-1,3-dihydrobenzimidazol-2-one; |
| 22 | 2-(4-Fluorophenyl)-3-(1H-indazol-5-yl)imidazo[4,5-b]pyridine; |
| 23 | 5-[2-(4-Fluorophenyl)imidazo[4,5-b]pyridin-3-yl]indolin-2-one; |
| 24 | 6-[2-(4-Fluorophenyl)imidazo[4,5-b]pyridin-3-yl]-3H-1,3-benzoxazol-2-one; |
| 25 | 6-(2-Phenylimidazo[4,5-b]pyridin-3-yl)-3H-1,3-benzothiazol-2-one; |
| 26 | 3-(1H-Indol-5-yl)-2-phenyl-imidazo[4,5-b]pyridine; |
| 27 | 6-[2-(4-Fluorophenyl)-5-methyl-imidazo[4,5-b]pyridin-3-yl]-3H-1,3-benzothiazol-2-one; |
| 28 | 6-[2-(6-Fluoro-3-pyridyl)imidazo[4,5-b]pyridin-3-yl]-3H-1,3-benzothiazol-2-one; |
| 29 | 6-[2-(2-Fluoro-4-pyridyl)-5-methyl-imidazo[4,5-b]pyridin-3-yl]-3H-1,3-benzothiazol-2-one; |
| 30 | 6-[5-Chloro-2-(4-fluorophenyl)imidazo[4,5-b]pyridin-3-yl]-3H-1,3-benzothiazol-2-one; |

TABLE 1-continued

| Ex. # | Compound Name |
|---|---|
| 31 | 6-[2-(2-Fluoro-4-pyridyl)-5-(trifluoromethyl)imidazo[4,5-b]pyridin-3-yl]-3H-1,3-benzothiazol-2-one; |
| 32 | 6-(5-Bromo-2-phenyl-imidazo[4,5-b]pyridin-3-yl)-3H-1,3-benzothiazol-2-one; |
| 33 | 5-[2-(4-Fluorophenyl)-5-(trifluoromethyl)imidazo[4,5-b]pyridin-3-yl]indolin-2-one; |
| 34 | 5-(2-Phenylimidazo[4,5-b]pyridin-3-yl)indolin-2-one; |
| 35 | 5-[2-(4-Fluorophenyl)-5-methyl-imidazo[4,5-b]pyridin-3-yl]indolin-2-one; |
| 36 | 5-[2-Phenyl-5-(trifluoromethyl)imidazo[4,5-b]pyridin-3-yl]indolin-2-one; |
| 37 | 5-[5-Fluoro-2-(4-fluorophenyl)imidazo[4,5-b]pyridin-3-yl]indolin-2-one; |
| 38 | 5-[2-Isopropyl-5-(trifluoromethyl)imidazo[4,5-b]pyridin-3-yl]indolin-2-one; |
| 39 | 6-[2-Cyclopentyl-5-(trifluoromethyl)imidazo[4,5-b]pyridin-3-yl]-3H-1,3-benzothiazol-2-one; |
| 40 | 6-[2-Cyclohexyl-5-(trifluoromethyl)imidazo[4,5-b]pyridin-3-yl]-3H-1,3-benzothiazol-2-one; |
| 41 | 6-[2-Cyclopropyl-5-(trifluoromethyl)imidazo[4,5-b]pyridin-3-yl]-3H-1,3-benzothiazol-2-one; |
| 42 | 6-[2-Tetrahydropyran-4-yl-5-(trifluoromethyl)imidazo[4,5-b]pyridin-3-yl]-3H-1,3-benzothiazol-2-one; |
| 43 | 2-Cyclopropyl-3-(1H-indazol-5-yl)-5-(trifluoromethyl)imidazo[4,5-b]pyridine; |
| 44 | 6-[2-Ethyl-5-(trifluoromethyl)imidazo[4,5-b]pyridin-3-yl]-3H-1,3-benzothiazol-2-one; |
| 45 | 6-[2-Isopropyl-5-(trifluoromethyl)imidazo[4,5-b]pyridin-3-yl]-3H-1,3-benzothiazol-2-one; |
| 46 | 6-[2-Methyl-5-(trifluoromethyl)imidazo[4,5-b]pyridin-3-yl]-3H-1,3-benzothiazol-2-one; |
| 47 | 5-[2-Methyl-5-(trifluoromethyl)imidazo[4,5-b]pyridin-3-yl]indolin-2-one; |
| 48 | 5-[2-Cyclohexyl-5-(trifluoromethyl)imidazo[4,5-b]pyridin-3-yl]indolin-2-one; |
| 49 | 5-[2-Cyclobutyl-5-(trifluoromethyl)imidazo[4,5-b]pyridin-3-yl]indolin-2-one; |
| 50 | 5-[2-Tetrahydropyran-4-yl-5-(trifluoromethyl)imidazo[4,5-b]pyridin-3-yl]indolin-2-one; |
| 51 | 5-[2-Isobutyl-5-(trifluoromethyl)imidazo[4,5-b]pyridin-3-yl]indolin-2-one; |
| 52 | (racemic)-5-[2-Tetrahydrofuran-3-yl-5-(trifluoromethyl)imidazo[4,5-b]pyridin-3-yl]indolin-2-one; |
| 53 | 5-[5-(Trifluoromethyl)-2-(3,3,3-trifluoropropyl)imidazo[4,5-b]pyridin-3-yl]indolin-2-one; |
| 54 | 5-[2-(Cyclopentylmethyl)-5-(trifluoromethyl)imidazo[4,5-b]pyridin-3-yl]indolin-2-one; |
| 55 | 5-[2-Cyclopropyl-5-(trifluoromethyl)imidazo[4,5-b]pyridin-3-yl]indolin-2-one; |
| 56 | 5-[2-Benzyl-5-(trifluoromethyl)imidazo[4,5-b]pyridin-3-yl]indolin-2-one; |
| 57 | 5-[2-(Pyrazin-2-ylmethyl)-5-(trifluoromethyl)imidazo[4,5-b]pyridin-3-yl]indolin-2-one; |
| 58 | 2-Cyclopentyl-3-(1H-indol-5-yl)-5-(trifluoromethyl)imidazo[4,5-b]pyridine; |
| 59 | 2-tert-Butyl-3-(1H-indol-5-yl)-5-(trifluoromethyl)imidazo[4,5-b]pyridine; |
| 60 | 5-[2-Cyclopentyl-5-(trifluoromethyl)imidazo[4,5-b]pyridin-3-yl]indolin-2-one; |
| 61 | 5-[2-tert-Butyl-5-(trifluoromethyl)imidazo[4,5-b]pyridin-3-yl]indolin-2-one; |
| 62 | 4-[2-(4-Fluorophenyl)-3-(1H-indazol-5-yl)imidazo[4,5-b]pyridin-7-yl]morpholine; |
| 63 | 5-[2-(4-Fluorophenyl)-7-morpholino-imidazo[4,5-b]pyridin-3-yl]indolin-2-one; |
| 64 | 6-[2-Phenyl-5-(1-piperidyl)imidazo[4,5-b]pyridin-3-yl]-3H-1,3-benzothiazol-2-one; |
| 65 | 6-(5-Morpholino-2-phenyl-imidazo[4,5-b]pyridin-3-yl)-3H-1,3-benzothiazol-2-one; |
| 66 | 6-[5-(Dimethylamino)-2-phenyl-imidazo[4,5-b]pyridin-3-yl]-3H-1,3-benzothiazol-2-one; |
| 67 | 6-(5-(Difluoromethyl)-2-phenyl-3H-imidazo[4,5-b]pyridin-3-yl)benzo[d]thiazol-2(3H)-one; |
| 68 | 6-[2-[4-(Difluoromethyl)phenyl]imidazo[4,5-b]pyridin-3-yl]-3H-1,3-benzothiazol-2-one; |
| 69 | 6-[7-(Difluoromethyl)-2-phenyl-imidazo[4,5-b]pyridin-3-yl]-3H-1,3-benzothiazol-2-one; |
| 70 | 6-(7-Isopropyl-2-phenyl-imidazo[4,5-b]pyridin-3-yl)-3H-1,3-benzothiazol-2-one; |
| 71 | 6-(2-(4-Fluorophenyl)-5-(hydroxymethyl)-3H-imidazo[4,5-b]pyridin-3-yl)benzo[d]thiazol-2(3H)-one; |
| 72 | 6-(2-(4-Fluorophenyl)-7-hydroxy-5-methyl-3H-imidazo[4,5-b]pyridin-3-yl)benzo[d]thiazol-2(3H)-one; |
| 73 | 5-(2-(3-Hydroxypropyl)-5-(trifluoromethyl)-3H-imidazo[4,5-b]pyridin-3-yl)indolin-2-one; |
| 74 | 5-(2-Cyclobutyl-5-methyl-imidazo[4,5-b]pyridin-3-yl)indolin-2-one; |
| 75 | 5-(2-Ethyl-5-methyl-imidazo[4,5-b]pyridin-3-yl)indolin-2-one; |
| 76 | 5-[2-(3-Methyloxetan-3-yl)-5-(trifluoromethyl)imidazo[4,5-b]pyridin-3-yl]indolin-2-one; |
| 77 | 5-[2-(2-Methoxyethyl)-5-(trifluoromethyl)imidazo[4,5-b]pyridin-3-yl]indolin-2-one; |
| 78 | 2-Cyclobutyl-5-cyclopropyl-3-(1H-indazol-5-yl)imidazo[4,5-b]pyridine; |
| 79 | 5-Cyclopropyl-3-(1H-indazol-5-yl)-2-isopropyl-imidazo[4,5-b]pyridine; |
| 80 | 6-[2-Cyclobutyl-5-(trifluoromethyl)imidazo[4,5-b]pyridin-3-yl]-3H-1,3-benzoxazol-2-one; |
| 81 | Azetidin-1-yl-[3-(1H-indazol-5-yl)-5-(trifluoromethyl)imidazo[4,5-b]pyridin-2-yl]methanone; |

TABLE 1-continued

| Ex. # | Compound Name |
|---|---|
| 82 | 6-[5-Amino-2-(4-fluorophenyl)imidazo[4,5-b]pyridin-3-yl]-3H-1,3-benzothiazol-2-one; |
| 83 | 5-[2-(1-Ethylpropyl)-5-(trifluoromethyl)imidazo[4,5-b]pyridin-3-yl]indolin-2-one; |
| 84 | 5-(2-Isopropyl-5-methyl-imidazo[4,5-b]pyridin-3-yl)indolin-2-one; |
| 85 | 3-(1H-Indazol-5-yl)-N-phenyl-5-(trifluoromethyl)imidazo[4,5-b]pyridine-2-carboxamide; |
| 86 | 5-Cyclopropyl-2-(4-fluorophenyl)-3-(1H-indazol-5-yl)imidazo[4,5-b]pyridine; |
| 87 | 5-(2-Cyclopropyl-5-methyl-imidazo[4,5-b]pyridin-3-yl)indolin-2-one; |
| 88 | 5-[2,5-Bis(trifluoromethyl)imidazo[4,5-b]pyridin-3-yl]indolin-2-one; |
| 89 | 3-(1H-Indazol-5-yl)-2,5-bis(trifluoromethyl)imidazo[4,5-b]pyridine; |
| 90 | 2-(Difluoromethyl)-3-(1H-indazol-5-yl)-5-(trifluoromethyl)imidazo[4,5-b]pyridine; |
| 91 | 3-(1H-Indazol-5-yl)-2-(2-thienyl)-5-(trifluoromethyl)imidazo[4,5-b]pyridine; |
| 92 | 2-(2-Furyl)-3-(1H-indazol-5-yl)-5-(trifluoromethyl)imidazo[4,5-b]pyridine; |
| 93 | 5-[2-(1,1-Difluoroethyl)-5-(trifluoromethyl)imidazo[4,5-b]pyridin-3-yl]indolin-2-one; |
| 94 | 5-[2-(Difluoromethyl)-5-(trifluoromethyl)imidazo[4,5-b]pyridin-3-yl]indolin-2-one; |
| 95 | 5-(5-Chloro-2-cyclopropyl-imidazo[4,5-b]pyridin-3-yl)indolin-2-one; |
| 96 | (racemic)-5-[2-sec-Butyl-5-(trifluoromethyl)imidazo[4,5-b]pyridin-3-yl]indolin-2-one; |
| 97 | 5-[2-(2,2-Dimethylpropyl)-5-(trifluoromethyl)imidazo[4,5-b]pyridin-3-yl]indolin-2-one; |
| 98 | 3-(1H-Indazol-5-yl)-2-methyl-5-(trifluoromethyl)imidazo[4,5-b]pyridine; |
| 99 | 5-[2-Ethyl-5-(trifluoromethyl)imidazo[4,5-b]pyridin-3-yl]indolin-2-one; |
| 100 | (racemic)-3-(1H-Iindazol-5-yl)-2-tetrahydrofuran-3-yl-5-(trifluoromethyl)imidazo[4,5-b]pyridine; |
| 101 | 3-(1H-Indazol-5-yl)-2-isobutyl-5-(trifluoromethyl)imidazo[4,5-b]pyridine; |
| 102 | (racemic)-3-(1H-Indazol-5-yl)-2-sec-butyl-5-(trifluoromethyl)imidazo[4,5-b]pyridine; |
| 103 | 2-Cyclobutyl-3-(1H-indazol-5-yl)-5-(trifluoromethyl)imidazo[4,5-b]pyridine; |
| 104 | 2-Cyclopentyl-3-(1H-indazol-5-yl)-5-(trifluoromethyl)imidazo[4,5-b]pyridine; |
| 105 | 2-Ethyl-3-(1H-indazol-5-yl)-5-(trifluoromethyl)imidazo[4,5-b]pyridine; |
| 106 | 5-[2-Cyclopropyl-5-(trifluoromethyl)imidazo[4,5-b]pyridin-3-yl]-1,3-dihydrobenzimidazol-2-one; |
| 107 | 6-[2-Cyclopropyl-5-(trifluoromethyl)imidazo[4,5-b]pyridin-3-yl]-3H-1,3-benzoxazol-2-one; |
| 108 | 2-tert-Butyl-3-(1H-indazol-5-yl)-5-(trifluoromethyl)imidazo[4,5-b]pyridine; |
| 109 | 3-(1H-Indazol-5-yl)-2-isopropyl-5-(trifluoromethyl)imidazo[4,5-b]pyridine; |
| 110 | 2-(4-Fluorophenyl)-3-(1H-indazol-5-yl)-5-(trifluoromethyl)imidazo[4,5-b]pyridine; |
| 111 | 6-(5-Hydroxy-2-phenyl-imidazo[4,5-b]pyridin-3-yl)-3H-1,3-benzothiazol-2-one; |
| 112 | 2-(4-Fluorophenyl)-3-(1H-pyrazolo[3,4-b]pyridin-5-yl)imidazo[4,5-b]pyridine; |
| 113 | 3-(1H-Indazol-5-yl)-2-(2,2,2-trifluoroethyl)-5-(trifluoromethyl)imidazo[4,5-b]pyridine; |
| 114 | 2-Ethoxy-3-(1H-indazol-5-yl)-5-(trifluoromethyl)imidazo[4,5-b]pyridine; |
| 115 | 1-[3-(1H-Indazol-5-yl)-5-(trifluoromethyl)imidazo[4,5-b]pyridin-2-yl]cyclopropanol; |
| 116 | 2-(1,1-Difluoroethyl)-3-(1H-indazol-5-yl)-5-(trifluoromethyl)imidazo[4,5-b]pyridine; |
| 117 | (R/S)-2-(1-fluoroethyl)-3-(1H-indazol-5-yl)-5-(trifluoromethyl)imidazo[4,5-b]pyridine; |
| 118 | 5-tert-Butyl-2-(4-fluorophenyl)-3-(1H-indazol-5-yl)imidazo[4,5-b]pyridine; |
| 119 | 2-Cyclobutyl-3-(1H-indazol-5-yl)-5-isopropyl-imidazo[4,5-b]pyridine; |
| 120 | 2-(4-Fluorophenyl)-3-(1H-indazol-5-yl)-5-isopropyl-imidazo[4,5-b]pyridine; |
| 121 | 2-(4-Fluoro-3-methyl-phenyl)-3-(1H-indazol-5-yl)-5-(trifluoromethyl)imidazo[4,5-b]pyridine; |
| 122 | 3-(1H-Indazol-5-yl)-2-(m-tolyl)-5-(trifluoromethyl)imidazo[4,5-b]pyridine; |
| 123 | 3-(1H-Indazol-5-yl)-2-(p-tolyl)-5-(trifluoromethyl)imidazo[4,5-b]pyridine; |
| 124 | 3-(1H-Indazol-5-yl)-2-(4-pyridyl)-5-(trifluoromethyl)imidazo[4,5-b]pyridine; |
| 125 | 5-Cyclopropyl-3-(1H-indazol-5-yl)-2-(trifluoromethyl)imidazo[4,5-b]pyridine; |
| 126 | 3-(1H-Indazol-5-yl)-N,N-dimethyl-5-(trifluoromethyl)imidazo[4,5-b]pyridine-2-carboxamide; |
| 127 | 3-(1H-Indazol-5-yl)-N-methyl-5-(trifluoromethyl)imidazo[4,5-b]pyridine-2-carboxamide; |
| 128 | N-Cyclopropyl-3-(1H-indazol-5-yl)-5-(trifluoromethyl)imidazo[4,5-b]pyridine-2-carboxamide; |
| 129 | 3-(1H-Indazol-5-yl)-2-methoxy-5-(trifluoromethyl)imidazo[4,5-b]pyridine; |
| 130 | N-Ethyl-3-(1H-indazol-5-yl)-5-(trifluoromethyl)imidazo[4,5-b]pyridin-2-amine; |
| 131 | N-Cyclohexyl-3-(1H-indazol-5-yl)-5-(trifluoromethyl)imidazo[4,5-b]pyridin-2-amine; |
| 132 | 6-[2-Cyclobutyl-5-(trifluoromethyl)imidazo[4,5-b]pyridin-3-yl]-3H-1,3-benzothiazol-2-one; |
| 133 | 6-(2-Cyclobutyl-5-methyl-7-morpholino-imidazo[4,5-b]pyridin-3-yl)-3H-1,3-benzothiazol-2-one; |
| 134 | 6-[2,5-Bis(trifluoromethyl)imidazo[4,5-b]pyridin-3-yl]-3H-1,3-benzothiazol-2-one; |

TABLE 1-continued

| Ex. # | Compound Name |
|---|---|
| 135 | 6-(2-Cyclopropyl-7-methyl-imidazo[4,5-b]pyridin-3-yl)-3H-1,3-benzothiazol-2-one; |
| 136 | 6-(2-Cyclopropyl-5-methyl-7-morpholino-imidazo[4,5-b]pyridin-3-yl)-3H-1,3-benzothiazol-2-one; |
| 137 | 5-Chloro-2-cyclobutyl-3-(1H-indazol-5-yl)-7-methyl-imidazo[4,5-b]pyridine; |
| 138 | 3-(7-Bromo-1H-indazol-5-yl)-2-cyclobutyl-5-(trifluoromethyl)imidazo[4,5-b]pyridine; |
| 139 | 5-[5-Methyl-2-(trifluoromethyl)imidazo[4,5-b]pyridin-3-yl]indolin-2-one; |
| 140 | 5-[2-Cyclopropyl-5-(difluoromethyl)imidazo[4,5-b]pyridin-3-yl]indolin-2-one; |
| 141 | 5-[5-(Difluoromethyl)-2-isopropyl-imidazo[4,5-b]pyridin-3-yl]indolin-2-one; |
| 142 | 6-[5-Methyl-2-(trifluoromethyl)imidazo[4,5-b]pyridin-3-yl]-3H-1,3-benzothiazol-2-one; |
| 143 | 6-(2-Cyclopropyl-5-methyl-imidazo[4,5-b]pyridin-3-yl)-3H-1,3-benzothiazol-2-one; |
| 144 | 6-(2-Isopropyl-5-methyl-imidazo[4,5-b]pyridin-3-yl)-3H-1,3-benzothiazol-2-one; |
| 145 | 6-(2-Cyclobutyl-5-methyl-imidazo[4,5-b]pyridin-3-yl)-3H-1,3-benzothiazol-2-one; |
| 146 | 5-[2-(1,1-Difluoroethyl)-5-methyl-imidazo[4,5-b]pyridin-3-yl]indolin-2-one; |
| 147 | 2-Cyclopropyl-3-(1H-indazol-5-yl)-5-methyl-imidazo[4,5-b]pyridine; |
| 148 | 3-(1H-Indazol-5-yl)-2-isopropyl-5-methyl-imidazo[4,5-b]pyridine; |
| 149 | 2-Cyclobutyl-3-(1H-indazol-5-yl)-5-methyl-imidazo[4,5-b]pyridine; |
| 150 | 6-[2-(1,1-Difluoroethyl)-5-methyl-imidazo[4,5-b]pyridin-3-yl]-3H-1,3-benzothiazol-2-one; |
| 151 | 3-(1H-Indazol-5-yl)-5-methyl-2-(trifluoromethyl)imidazo[4,5-b]pyridine; |
| 152 | 2-(1,1-Difluoroethyl)-3-(1H-indazol-5-yl)-5-methyl-imidazo[4,5-b]pyridine; |
| 153 | 5-[5-(Difluoromethyl)-2-(trifluoromethyl)imidazo[4,5-b]pyridin-3-yl]indolin-2-one; |
| 154 | 5-[2-(1,1-Difluoroethyl)-5-(difluoromethyl)imidazo[4,5-b]pyridin-3-yl]indolin-2-one; |
| 155 | 2-(4-Fluorophenyl)-3-(1H-indol-5-yl)-5-methylsulfanyl-imidazo[4,5-b]pyridine; |
| 156 | 3-(1H-Indazol-5-yl)-2-phenyl-imidazo[4,5-b]pyridin-5-ol; |
| 157 | 2-Cyclopropyl-3-(1H-indazol-5-yl)-5-methoxy-imidazo[4,5-b]pyridine; |
| 158 | 6-[2-Ethyl-5-(trifluoromethyl)imidazo[4,5-b]pyridin-3-yl]-3H-1,3-benzoxazol-2-one; |
| 159 | 6-[2-Isopropyl-5-(trifluoromethyl)imidazo[4,5-b]pyridin-3-yl]-3H-1,3-benzoxazol-2-one; |
| 160 | 6-[2-Tetrahydropyran-4-yl-5-(trifluoromethyl)imidazo[4,5-b]pyridin-3-yl]-3H-1,3-benzoxazol-2-one; |
| 161 | (R/S)-6-[2-Tetrahydrofuran-3-yl-5-(trifluoromethyl)imidazo[4,5-b]pyridin-3-yl]-3H-1,3-benzoxazol-2-one; |
| 162 | 6-[2-(Ethoxymethyl)-5-(trifluoromethyl)imidazo[4,5-b]pyridin-3-yl]-3H-1,3-benzoxazol-2-one; |
| 163 | 6-[2-tert-Butyl-5-(trifluoromethyl)imidazo[4,5-b]pyridin-3-yl]-3H-1,3-benzoxazol-2-one; |
| 164 | 5-[2-(2-Fluoro-4-pyridyl)-5-(trifluoromethyl)imidazo[4,5-b]pyridin-3-yl]indolin-2-one; |
| 165 | 2-(2-Fluoro-4-pyridyl)-3-(1H-indazol-5-yl)-5-(trifluoromethyl)imidazo[4,5-b]pyridine; |
| 166 | 5-[2-(3-Fluorocyclobutyl)-5-(trifluoromethyl)imidazo[4,5-b]pyridin-3-yl]indolin-2-one; |
| 167 | (R)-3-(1H-Indazol-5-yl)-2-sec-butyl-5-(trifluoromethyl)imidazo[4,5-b]pyridine; |
| 168 | (S)-3-(1H-Indazol-5-yl)-2-sec-butyl-5-(trifluoromethyl)imidazo[4,5-b]pyridine; |
| 169 | 2-(5-Fluoro-2-pyridyl)-3-(1H-indazol-5-yl)-5-(trifluoromethyl)imidazo[4,5-b]pyridine; |
| 170 | 3-(1H-Indazol-5-yl)-5-isopropyl-2-(trifluoromethyl)imidazo[4,5-b]pyridine; |
| 171 | 5-tert-Butyl-3-(1H-indazol-5-yl)-2-(trifluoromethyl)imidazo[4,5-b]pyridine; |
| 172 | 3-(1H-Indazol-5-yl)-N-isopropyl-5-(trifluoromethyl)imidazo[4,5-b]pyridine-2-carboxamide; |
| 173 | [3-(1H-Indazol-5-yl)-5-(trifluoromethyl)imidazo[4,5-b]pyridin-2-yl]-pyrrolidin-1-yl-methanone; |
| 174 | 2-(4-Fluorophenyl)-3-(1H-indol-5-yl)imidazo[4,5-b]pyridine; |
| 175 | 4-[2-(4-Fluorophenyl)-3-(1H-indol-5-yl)imidazo[4,5-b]pyridin-7-yl]morpholine; |
| 176 | 3-(1H-Indazol-5-yl)-2-[4-(trifluoromethyl)phenyl]imidazo[4,5-b]pyridine; |
| 177 | 3-(1H-Indazol-5-yl)-2-[4-(trifluoromethoxy)phenyl]imidazo[4,5-b]pyridine; |
| 178 | 5-[2-[4-(Trifluoromethyl)phenyl]imidazo[4,5-b]pyridin-3-yl]indolin-2-one; |
| 179 | tert-Butyl 3-[3-(2-oxoindolin-5-yl)-5-(trifluoromethyl)imidazo[4,5-b]pyridin-2-yl]azetidine-1-carboxylate; |
| 180 | 5-[2-(Azetidin-3-yl)-5-(trifluoromethyl)imidazo[4,5-b]pyridin-3-yl]indolin-2-one; |
| 181 | 5-(2,5-Dimethylimidazo[4,5-b]pyridin-3-yl)indolin-2-one; |
| 182 | 2-Cyclopentyl-3-(1H-indol-5-yl)-5-piperazin-1-yl-imidazo[4,5-b]pyridine; |
| 183 | Methyl 3-[3-(2-oxoindolin-5-yl)-5-(trifluoromethyl)imidazo[4,5-b]pyridin-2-yl]propanoate; |
| 184 | 3-(7-Bromo-1H-indazol-5-yl)-2-isopropyl-5-(trifluoromethyl)imidazo[4,5-b]pyridine; |
| 185 | 6-(2-Cyclobutyl-5-(trifluoromethyl)-3H-imidazo[4,5-b]pyridin-3-yl)-3-methylbenzo[d]thiazol-2(3H)-one; |
| 186 | 3-(7-$^{3}$H-1H-indazol-5-yl)-2-isopropyl-5-(trifluoromethyl)-3H-imidazo[4,5-b]pyridine; |
| 187 | 3-(7-Bromo-1H-indazol-5-yl)-2,5-bis(trifluoromethyl)imidazo[4,5-b]pyridine; |

TABLE 1-continued

| Ex. # | Compound Name |
|---|---|
| 188 | 3-(7-Phenyl-1H-indazol-5-yl)-2,5-bis(trifluoromethyl)-3H-imidazo[4,5-b]pyridine; |
| 189 | 2,5-Bis(trifluoromethyl)-3-(7-vinyl-1H-indazol-5-yl)-3H-imidazo[4,5-b]pyridine; |
| 190 | 6-(5-(Trifluoromethyl)-3H-imidazo[4,5-b]pyridin-3-yl)benzo[d]thiazol-2(3H)-one; |
| 191 | 3-(3-Fluoro-1H-indazol-5-yl)-2-isopropyl-5-(trifluoromethyl)imidazo[4,5-b]pyridine; |
| 192 | 5-Chloro-3-(1H-indazol-5-yl)-2-(trifluoromethyl)imidazo[4,5-b]pyridine; |
| 193 | 5-Ethyl-3-(1H-indazol-5-yl)-2-(trifluoromethyl)imidazo[4,5-b]pyridine; |
| 194 | 3-(7-Methyl-1H-indazol-5-yl)-5-(trifluoromethyl)imidazo[4,5-b]pyridine; |
| 195 | 2-(4-Fluorophenyl)-3-(7-methyl-1H-indazol-5-yl)-5-(trifluoromethyl)imidazo[4,5-b]pyridine; |
| 196 | 2-Ethoxy-3-(3-fluoro-1H-indazol-5-yl)-5-(trifluoromethyl)imidazo[4,5-b]pyridine; |
| 197 | 2-Cyclopropyl-3-(3-fluoro-1H-indazol-5-yl)-5-(trifluoromethyl)imidazo[4,5-b]pyridine; |
| 198 | 2-Isopropyl-3-(7-methyl-1H-indazol-5-yl)-5-(trifluoromethyl)imidazo[4,5-b]pyridine; |
| 199 | 3-(7-Chloro-1H-indazol-5-yl)-2-(trifluoromethyl)imidazo[4,5-b]pyridine; |
| 200 | 3-(7-Chloro-1H-indazol-5-yl)-2-isopropyl-imidazo[4,5-b]pyridine; |
| 201 | 3-(1H-indazol-5-yl)-7-methyl-2-(trifluoromethyl)imidazo[4,5-b]pyridine; |
| 202 | 3-(7-Chloro-1H-indazol-5-yl)-7-methyl-2-(trifluoromethyl)imidazo[4,5-b]pyridine; |
| 203 | 7-Methyl-3-(7-methyl-1H-indazol-5-yl)-2-(trifluoromethyl)imidazo[4,5-b]pyridine; |
| 204 | 3-(1H-pyrazolo[3,4-b]pyridin-5-yl)-2,5-bis(trifluoromethyl)imidazo[4,5-b]pyridine; |
| 205 | 3-(7-Oxido-1H-pyrazolo[3,4-b]pyridin-7-ium-5-yl)-2,5-bis(trifluoromethyl)imidazo[4,5-b]pyridine; |
| 206 | 6-[5-(difluoromethyl)-2-(trifluoromethyl)imidazo[4,5-b]pyridin-3-yl]-3H-1,3-benzothiazol-2-one; |
| 207 | 3-(7-Chloro-1H-indazol-5-yl)-2,5-bis(difluoromethyl)imidazo[4,5-b]pyridine; |
| 208 | 5-Cyclobutyl-3-(1H-indazol-5-yl)-2-(trifluoromethyl)imidazo[4,5-b]pyridine; |
| 209 | 5-(2-Ethyl-5-methyl-imidazo[4,5-b]pyridin-3-yl)indoline-2,3-dione; |
| 210 | 5-(Difluoromethyl)-3-(1H-indazol-5-yl)-2-isopropyl-imidazo[4,5-b]pyridine; |
| 211 | 5-(1,1-Difluoroethyl)-3-(1H-indazol-5-yl)-2-isopropyl-imidazo[4,5-b]pyridine; |
| 212 | 2,5-Bis(difluoromethyl)-3-(7-methyl-1H-indazol-5-yl)imidazo[4,5-b]pyridine; |
| 213 | 2-(2-Fluoro-4-pyridyl)-5-methyl-3-(7-methyl-1H-indazol-5-yl)imidazo[4,5-b]pyridine; |
| 214 | N-(2-Fluoroethyl)-2-isopropyl-N-methyl-3-(7-methyl-1H-indazol-5-yl)-5-(trifluoromethyl)imidazo[4,5-b]pyridin-7-amine; |
| 215 | 5-[2-(2-Fluoro-4-pyridyl)-5-(trifluoromethyl)imidazo[4,5-b]pyridin-3-yl]indoline-2,3-dione; |
| 216 | Methyl 3-[3-(2,3-dioxoindolin-5-yl)-5-(trifluoromethyl)imidazo[4,5-b]pyridin-2-yl]propanoate; |
| 217 | 2-(2-Fluoro-4-pyridyl)-3-(7-methyl-1H-indazol-5-yl)-5-(trifluoromethyl)imidazo[4,5-b]pyridine; |
| 218 | 3-(7-Chloro-1H-indazol-5-yl)-7-(2-fluoroethoxy)-2,5-bis(trifluoromethyl)imidazo[4,5-b]pyridine; |
| 219 | (E)-3-(5-(2,5-Bis(trifluoromethyl)-3H-imidazo[4,5-b]pyridin-3-yl)-1H-indazol-7-yl)prop-2-en-1-ol; |
| 220 | 3-(5-(2,5-Bis(trifluoromethyl)-3H-imidazo[4,5-b]pyridin-3-yl)-1H-indazol-7-yl)propan-1-ol; |
| 221 | 3-(7-Propyl-1H-indazol-5-yl)-2,5-bis(trifluoromethyl)-3H-imidazo[4,5-b]pyridine; |
| 222 | (E)-3-(3-(7-Methyl-1H-indazol-5-yl)-2-(trifluoromethyl)-3H-imidazo[4,5-b]pyridin-5-yl)prop-2-en-1-ol; |
| 223 | 3-(3-(7-Methyl-1H-indazol-5-yl)-2-(trifluoromethyl)-3H-imidazo[4,5-b]pyridin-5-yl)propan-1-ol; |
| 224 | 3-(7-Methyl-1H-indazol-5-yl)-5-propyl-2-(trifluoromethyl)-3H-imidazo[4,5-b]pyridine; |
| 225 | 4-[3-(1H-Indazol-5-yl)-5-(trifluoromethyl)imidazo[4,5-b]pyridin-2-yl]pyridin-2-ol; |
| 226 | 3-(1H-Indazol-5-yl)-5-(trifluoromethyl)imidazo[4,5-b]pyridine; |
| 227 | 3-(7-Chloro-1H-indazol-5-yl)-2-cyclopropyl-5-(difluoromethyl)imidazo[4,5-b]pyridine; |
| 228 | 5-(Difluoromethyl)-2-(4-fluorophenyl)-3-(7-methyl-1H-indazol-5-yl)imidazo[4,5-b]pyridine; |
| 229 | 3-(7-Chloro-1H-indazol-5-yl)-5-(difluoromethyl)-2-(4-fluorophenyl)imidazo[4,5-b]pyridine; |
| 230 | 6-[7-Morpholino-2,5-bis(trifluoromethyl)imidazo[4,5-b]pyridin-3-yl]-3H-1,3-benzothiazol-2-one; |
| 231 | 4-[3-(1H-Indazol-5-yl)-2,5-bis(trifluoromethyl)imidazo[4,5-b]pyridin-7-yl]morpholine; |
| 232 | 2-(1,1-Difluoropropyl)-3-(1H-indazol-5-yl)-5-(trifluoromethyl)imidazo[4,5-b]pyridine; |
| 233 | 6-[2-(1,1,2,2,2-Pentafluoroethyl)-5-(trifluoromethyl)imidazo[4,5-b]pyridin-3-yl]-3H-1,3-benzothiazol-2-one; |
| 234 | 6-[2-(Difluoromethyl)-5-(trifluoromethyl)imidazo[4,5-b]pyridin-3-yl]-3H-1,3-benzothiazol-2-one; |
| 235 | 6-[2-(Difluoromethyl)-5-(trifluoromethyl)imidazo[4,5-b]pyridin-3-yl]-3H-1,3-benzoxazol-2-one; |

TABLE 1-continued

| Ex. # | Compound Name |
|---|---|
| 236 | 6-[2,5-Bis(trifluoromethyl)imidazo[4,5-b]pyridin-3-yl]-3H-1,3-benzoxazol-2-one; |
| 237 | 3-(3-Fluoro-1H-indazol-5-yl)-2,5-bis(trifluoromethyl)imidazo[4,5-b]pyridine; |
| 238 | 5-(Difluoromethyl)-3-(1H-indazol-5-yl)-2-(trifluoromethyl)imidazo[4,5-b]pyridine; |
| 239 | 6-[2-Methoxy-5-(trifluoromethyl)imidazo[4,5-b]pyridin-3-yl]-3H-1,3-benzothiazol-2-one; |
| 240 | 6-[2-Ethoxy-5-(trifluoromethyl)imidazo[4,5-b]pyridin-3-yl]-3H-1,3-benzothiazol-2-one; |
| 241 | 2-Methoxy-3-(7-methyl-1H-indazol-5-yl)-5-(trifluoromethyl)imidazo[4,5-b]pyridine; |
| 242 | 2-Ethoxy-3-(7-methyl-1H-indazol-5-yl)-5-(trifluoromethyl)imidazo[4,5-b]pyridine; |
| 243 | 5-[2-Ethoxy-5-(trifluoromethyl)imidazo[4,5-b]pyridin-3-yl]indolin-2-one; |
| 244 | 5-[2-Methoxy-5-(trifluoromethyl)imidazo[4,5-b]pyridin-3-yl]indolin-2-one; |
| 245 | 3-(1H-indazol-5-yl)-2-(methylsulfonylmethyl)-5-(trifluoromethyl)imidazo[4,5-b]pyridine; |
| 246 | 2-(3-Fluorocyclobutyl)-3-(7-methyl-1H-indazol-5-yl)-5-(trifluoromethyl)imidazo[4,5-b]pyridine; |
| 247 | 2-(3-Fluorocyclobutyl)-3-(7-methyl-1H-indazol-5-yl)-5-(trifluoromethyl)imidazo[4,5-b]pyridine; |
| 248 | 3-(7-Chloro-1H-indazol-5-yl)-2-(3-fluorocyclobutyl)-5-(trifluoromethyl)imidazo[4,5-b]pyridine; |
| 249 | 3-(7-Chloro-1H-indazol-5-yl)-2-(3-fluorocyclobutyl)-5-methyl-imidazo[4,5-b]pyridine; |
| 250 | 3-(7-Chloro-1H-indazol-5-yl)-2-(3-fluorocyclobutyl)-5-(trifluoromethyl)imidazo[4,5-b]pyridine; |
| 251 | 2-(1-Methoxy-1-methyl-ethyl)-3-(7-methyl-1H-indazol-5-yl)-5-(trifluoromethyl)imidazo[4,5-b]pyridine; |
| 252 | 2-(1,1-Difluoroethyl)-3-(7-methyl-1H-indazol-5-yl)-5-(trifluoromethyl)imidazo[4,5-b]pyridine; |
| 253 | 2-(1-Fluoro-1-methyl-ethyl)-3-(7-methyl-1H-indazol-5-yl)-5-(trifluoromethyl)imidazo[4,5-b]pyridine; |
| 254 | 3-(7-Chloro-1H-indazol-5-yl)-2-(1-fluoro-1-methyl-ethyl)-5-(trifluoromethyl)imidazo[4,5-b]pyridine; |
| 255 | 2-Cyclopropyl-3-(7-methyl-1H-indazol-5-yl)-5-(trifluoromethyl)imidazo[4,5-b]pyridine; |
| 256 | (*R)-2-(1-Fluoroethyl)-3-(7-methyl-1H-indazol-5-yl)-5-(trifluoromethyl)imidazo[4,5-b]pyridine; |
| 257 | (*S)-2-(1-Fluoroethyl)-3-(7-methyl-1H-indazol-5-yl)-5-(trifluoromethyl)imidazo[4,5-b]pyridine; |
| 258 | 3-(7-Chloro-1H-indazol-5-yl)-2-(1-fluorocyclopropyl)-5-(trifluoromethyl)imidazo[4,5-b]pyridine; |
| 259 | 2-(1-Fluorocyclopropyl)-3-(7-methyl-1H-indazol-5-yl)-5-(trifluoromethyl)imidazo[4,5-b]pyridine; |
| 260 | 3-(1H-Indazol-5-yl)-N-isopropyl-N-methyl-5-(trifluoromethyl)imidazo[4,5-b]pyridine-2-carboxamide; |
| 261 | 2-(2-Chloro-4-pyridyl)-3-(7-methyl-1H-indazol-5-yl)-5-(trifluoromethyl)imidazo[4,5-b]pyridine; |
| 262 | 2-(2-Bromo-4-pyridyl)-3-(7-methyl-1H-indazol-5-yl)-5-(trifluoromethyl)imidazo[4,5-b]pyridine; |
| 263 | 5-(Difluoromethyl)-2-(2-fluoro-4-pyridyl)-3-(7-methyl-1H-indazol-5-yl)imidazo[4,5-b]pyridine; |
| 264 | 3-(7-Chloro-1H-indazol-5-yl)-5-(difluoromethyl)-2-(2-fluoro-4-pyridyl)imidazo[4,5-b]pyridine; |
| 265 | 3-(4-Chloro-1H-indazol-6-yl)-2,5-bis(trifluoromethyl)imidazo[4,5-b]pyridine; |
| 266 | 6-[2-(1,1-Difluoroethyl)-5-(trifluoromethyl)imidazo[4,5-b]pyridin-3-yl]-3H-1,3-benzothiazol-2-one; |
| 267 | 3-(7-Chloro-1H-indazol-5-yl)-2-(1,1-difluoroethyl)-5-(trifluoromethyl)imidazo[4,5-b]pyridine; |
| 268 | 3-(7-Chloro-1H-indazol-5-yl)-5-methyl-2-(trifluoromethyl)imidazo[4,5-b]pyridine; |
| 269 | 3-(7-Chloro-1H-indazol-5-yl)-5-(difluoromethyl)-2-isopropyl-imidazo[4,5-b]pyridine; |
| 270 | 3-(7-Chloro-1H-indazol-5-yl)-2,5-bis(trifluoromethyl)imidazo[4,5-b]pyridine; |
| 271 | 5-[2,5-Bis(trifluoromethyl)imidazo[4,5-b]pyridin-3-yl]-7-chloro-indolin-2-one; |
| 272 | 7-Chloro-5-[2-(difluoromethyl)-5-(trifluoromethyl)imidazo[4,5-b]pyridin-3-yl]indolin-2-one; |
| 273 | 5-(Difluoromethyl)-2-isopropyl-3-(7-methyl-1H-indazol-5-yl)imidazo[4,5-b]pyridine; |
| 274 | 3-(7-Chloro-1H-indazol-5-yl)-5-(difluoromethyl)-2-methyl-imidazo[4,5-b]pyridine; |
| 275 | 5-[2,5-Bis(trifluoromethyl)imidazo[4,5-b]pyridin-3-yl]-7-methyl-indolin-2-one; |
| 276 | 5-[2-(1,1-Difluoroethyl)-5-(trifluoromethyl)imidazo[4,5-b]pyridin-3-yl]-7-methyl-indolin-2-one; |
| 277 | 3-(7-Chloro-1H-indazol-5-yl)-2-(difluoromethyl)-5-(trifluoromethyl)imidazo[4,5-b]pyridine; |
| 278 | 3-(7-Chloro-1H-indazol-5-yl)-2-(difluoromethyl)-5-methyl-imidazo[4,5-b]pyridine; |

TABLE 1-continued

| Ex. # | Compound Name |
|---|---|
| 279 | 3-(7-Chloro-1H-indazol-5-yl)-6-fluoro-2-(trifluoromethyl)imidazo[4,5-b]pyridine; |
| 280 | 3-(7-Bromo-1H-indazol-5-yl)-2-(difluoromethyl)-5-(trifluoromethyl)imidazo[4,5-b]pyridine; |
| 281 | 6-[2,5-Bis(trifluoromethyl)imidazo[4,5-b]pyridin-3-yl]-4-methyl-3H-1,3-benzothiazol-2-one; |
| 282 | 6-[2,5-Bis(trifluoromethyl)imidazo[4,5-b]pyridin-3-yl]-4-chloro-3H-1,3-benzothiazol-2-one; |
| 283 | 6-[2,5-Bis(trifluoromethyl)imidazo[4,5-b]pyridin-3-yl]-4-fluoro-3H-1,3-benzoxazol-2-one; |
| 284 | Methyl 5-[2,5-bis(trifluoromethyl)imidazo[4,5-b]pyridin-3-yl]-1H-indazole-7-carboxylate; |
| 285 | Methyl 5-[2-(difluoromethyl)-5-(trifluoromethyl)imidazo[4,5-b]pyridin-3-yl]-1H-indazole-7-carboxylate; |
| 286 | 2-(Difluoromethyl)-3-(7-methyl-1H-indazol-5-yl)-5-(trifluoromethyl)imidazo[4,5-b]pyridine; |
| 287 | 5-[2-(Difluoromethyl)-5-(trifluoromethyl)imidazo[4,5-b]pyridin-3-yl]-7-methyl-indolin-2-one; |
| 288 | 5-[2-(Difluoromethyl)-5-(trifluoromethyl)imidazo[4,5-b]pyridin-3-yl]-7-fluoro-indolin-2-one; |
| 289 | 3-(4-Methyl-1H-indazol-6-yl)-2,5-bis(trifluoromethyl)imidazo[4,5-b]pyridine; |
| 290 | 6-[2,5-Bis(trifluoromethyl)imidazo[4,5-b]pyridin-3-yl]-4-bromo-3H-1,3-benzoxazol-2-one; |
| 291 | 3-(1H-Indazol-6-yl)-2,5-bis(trifluoromethyl)imidazo[4,5-b]pyridine; |
| 292 | 5-[2,5-Bis(trifluoromethyl)imidazo[4,5-b]pyridin-3-yl]-1,3-dihydropyrrolo[2,3-b]pyridin-2-one; |
| 293 | 3-(1H-Pyrrolo[2,3-b]pyridin-5-yl)-2,5-bis(trifluoromethyl)imidazo[4,5-b]pyridine; |
| 294 | 3-(7-Methyl-1H-indazol-5-yl)-2,5-bis(trifluoromethyl)imidazo[4,5-b]pyridine; |
| 295 | 5-[2,5-Bis(trifluoromethyl)imidazo[4,5-b]pyridin-3-yl]-1H-indazole-3-carbonitrile; |
| 296 | 5-[2-(Difluoromethyl)-5-(trifluoromethyl)imidazo[4,5-b]pyridin-3-yl]-1H-indazol-3-ol; |
| 297 | 6-[2-Cyclopropyl-5-(trifluoromethyl)imidazo[4,5-b]pyridin-3-yl]indolin-2-one; |
| 298 | 3-(3-Bromo-1H-indazol-5-yl)-2-isopropyl-5-(trifluoromethyl)imidazo[4,5-b]pyridine; |
| 299 | 7-Chloro-5-[2-isopropyl-5-(trifluoromethyl)imidazo[4,5-b]pyridin-3-yl]indolin-2-one; |
| 300 | 3-(7-Chloro-1H-indazol-5-yl)-6-fluoro-2-isopropyl-imidazo[4,5-b]pyridine; |
| 301 | 5-[2-Isopropyl-5-(trifluoromethyl)imidazo[4,5-b]pyridin-3-yl]-1,3-dihydropyrrolo[2,3-b]pyridin-2-one; |
| 302 | 2-Isopropyl-3-(1H-pyrazolo[3,4-b]pyridin-5-yl)-5-(trifluoromethyl)imidazo[4,5-b]pyridine; |
| 303 | 2-Isopropyl-3-(1H-pyrrolo[2,3-b]pyridin-5-yl)-5-(trifluoromethyl)imidazo[4,5-b]pyridine; |
| 304 | 3-(7-Allyl-1H-indazol-5-yl)-2,5-bis(trifluoromethyl)-3H-imidazo[4,5-b]pyridine; |
| 305 | 3-(7-(Prop-1-en-2-yl)-1H-indazol-5-yl)-2,5-bis(trifluoromethyl)-3H-imidazo[4,5-b]pyridine; |
| 306 | 3-(7-Chloro-1H-indazol-5-yl)-5-(trifluoromethyl)imidazo[4,5-b]pyridine; |
| 307 | 3-(7-Chloro-1H-indazol-5-yl)-2-cyclopropyl-5-(trifluoromethyl)imidazo[4,5-b]pyridine; |
| 308 | 3-(7-Chloro-1H-indazol-5-yl)-2-cyclobutyl-5-(trifluoromethyl)imidazo[4,5-b]pyridine; |
| 309 | 7-Methyl-5-[2-methyl-5-(trifluoromethyl)imidazo[4,5-b]pyridin-3-yl]indolin-2-one; |
| 310 | 5-[2-Isopropyl-5-(trifluoromethyl)imidazo[4,5-b]pyridin-3-yl]-7-methyl-indolin-2-one; |
| 311 | 2-Isopropyl-3-(4-methyl-1H-indazol-6-yl)-5-(trifluoromethyl)imidazo[4,5-b]pyridine; |
| 312 | 3-(7-Chloro-1H-indazol-5-yl)-2-methyl-5-(trifluoromethyl)imidazo[4,5-b]pyridine; |
| 313 | 7-Chloro-5-[2-methyl-5-(trifluoromethyl)imidazo[4,5-b]pyridin-3-yl]indolin-2-one; |
| 314 | 3-(7-Chloro-1H-indazol-5-yl)-2-ethyl-5-(trifluoromethyl)imidazo[4,5-b]pyridine; |
| 315 | 2-Ethyl-3-(7-methyl-1H-indazol-5-yl)-5-(trifluoromethyl)imidazo[4,5-b]pyridine; |
| 316 | 3-(7-Chloro-1H-indazol-5-yl)-2-isopropyl-5-(trifluoromethyl)imidazo[4,5-b]pyridine; |
| 317 | 3-(7-Methyl-1H-indazol-5-yl)-2-(trifluoromethyl)imidazo[4,5-b]pyridine; |
| 318 | 7-Methyl-5-[2-(trifluoromethyl)imidazo[4,5-b]pyridin-3-yl]indolin-2-one; |
| 319 | 2-Methyl-3-(7-methyl-1H-indazol-5-yl)-5-(trifluoromethyl)imidazo[4,5-b]pyridine; |
| 320 | 3-(1H-Indazol-5-yl)-5-(2-pyridyl)-2-(trifluoromethyl)imidazo[4,5-b]pyridine; |
| 321 | 2-Cyclopropyl-5-(difluoromethyl)-3-(1H-indazol-5-yl)imidazo[4,5-b]pyridine; |
| 322 | 5-(Difluoromethyl)-2-(4-fluorophenyl)-3-(1H-indazol-5-yl)imidazo[4,5-b]pyridine; |
| 323 | 5-(Difluoromethyl)-3-(1H-indazol-5-yl)-2-phenyl-imidazo[4,5-b]pyridine; |
| 324 | 3-(7-Chloro-1H-indazol-5-yl)-5-(difluoromethyl)-2-(trifluoromethyl)imidazo[4,5-b]pyridine; |
| 325 | 5-[5-(Difluoromethyl)-2-(trifluoromethyl)imidazo[4,5-b]pyridin-3-yl]-7-fluoro-indolin-2-one; |

TABLE 1-continued

| Ex. # | Compound Name |
|---|---|
| 326 | 5-(Difluoromethyl)-3-(7-methyl-1H-indazol-5-yl)-2-(trifluoromethyl)imidazo[4,5-b]pyridine; |
| 327 | 3-(7-Chloro-1H-indazol-5-yl)-2-(2-fluoro-4-pyridyl)-5-methyl-imidazo[4,5-b]pyridine; |
| 328 | 3-(7-Bromo-1H-indazol-5-yl)-2-(2-fluoro-4-pyridyl)-5-(trifluoromethyl)imidazo[4,5-b]pyridine; |
| 329 | 5-(2-(Hydroxymethyl)-6-(trifluoromethyl)-1H-pyrrolo[2,3-b]pyridin-1-yl)-7-methylindolin-2-one; |
| 330 | (1-(1H-Indazol-5-yl)-6-(trifluoromethyl)-1H-pyrrolo[2,3-b]pyridin-2-yl)methanol; |
| 331 | 7-Methyl-5-(2-methyl-6-(trifluoromethyl)-1H-pyrrolo[2,3-b]pyridin-1-yl)indolin-2-one; |
| 332 | 5-(2-Isopropyl-1H-pyrrolo[2,3-b]pyridin-1-yl)-7-methyl-1H-indazole; |
| 333 | 1-(7-Chloro-1H-indazol-5-yl)-2-methyl-pyrrolo[2,3-b]pyridine; |
| 334 | 5-[6-(Difluoromethyl)-2-isopropyl-pyrrolo[2,3-b]pyridin-1-yl]-7-methyl-indolin-2-one; |
| 335 | 1-(1H-Indazol-5-yl)-2-isopropyl-6-(trifluoromethyl)pyrrolo[2,3-b]pyridine; |
| 336 | 5-[2-(Difluoromethyl)-6-(trifluoromethyl)pyrrolo[2,3-b]pyridin-1-yl]-7-methyl-indolin-2-one; |
| 337 | 6-[2-(Difluoromethyl)-6-(trifluoromethyl)pyrrolo[2,3-b]pyridin-1-yl]-3H-1,3-benzothiazol-2-one; |
| 338 | 7-Chloro-5-(2-methylpyrrolo[2,3-b]pyridin-1-yl)indolin-2-one; |
| 339 | 1-(7-Methyl-1H-indazol-5-yl)-6-(trifluoromethyl)pyrrolo[2,3-b]pyridin-3-ol; |
| 340 | 3-(Difluoromethyl)-1-(7-methyl-1H-indazol-5-yl)-6-(trifluoromethyl)pyrrolo[2,3-b]pyridine; |
| 341 | 6-Methyl-1-(7-methyl-1H-indazol-5-yl)pyrrolo[2,3-b]pyridine; |
| 342 | 5-(2-Isopropyl-6-methyl-pyrrolo[2,3-b]pyridin-1-yl)indolin-2-one; |
| 343 | 2-(4-Fluorophenyl)-1-(1H-indol-5-yl)-6-methoxy-pyrrolo[2,3-b]pyridine; |
| 344 | 2-(4-Fluorophenyl)-1-indolin-5-yl-pyrrolo[2,3-b]pyridine; |
| 345 | 2-(4-Fluorophenyl)-1-(1H-indol-5-yl)pyrrolo[2,3-b]pyridine; |
| 346 | 5-[3-Bromo-2-(4-fluorophenyl)pyrrolo[2,3-b]pyridin-1-yl]indolin-2-one; |
| 347 | 5-[2-(4-Fluorophenyl)pyrrolo[2,3-b]pyridin-1-yl]indolin-2-one; |
| 348 | 6-Fluoro-2-(4-fluorophenyl)-1-(1H-indol-5-yl)pyrrolo[2,3-b]pyridine; |
| 349 | 5-[3-Bromo-6-fluoro-2-(4-fluorophenyl)pyrrolo[2,3-b]pyridin-1-yl]indolin-2-one; |
| 350 | 5-[6-Fluoro-2-(4-fluorophenyl)pyrrolo[2,3-b]pyridin-1-yl]indolin-2-one; |
| 351 | 1-(1H-Indol-5-yl)-2-methyl-6-(trifluoromethyl)pyrrolo[2,3-b]pyridine; |
| 352 | 5-[2-Methyl-6-(trifluoromethyl)pyrrolo[2,3-b]pyridin-1-yl]indolin-2-one; |
| 353 | 7-Methyl-5-(2-methyl-1H-pyrrolo[2,3-b]pyridin-1-yl)indolin-2-one; |
| 354 | 5-(2-Methyl-6-(trifluoromethyl)-1H-pyrrolo[2,3-b]pyridin-1-yl)-1H-indazole; |
| 355 | 6-(2-Methyl-6-(trifluoromethyl)-1H-pyrrolo[2,3-b]pyridin-1-yl)benzo[d]thiazol-2(3H)-one; |
| 356 | 1-(7-Chloro-1H-indazol-5-yl)-2-isopropyl-pyrrolo[2,3-b]pyridine; |
| 357 | 7-Chloro-5-(2-isopropylpyrrolo[2,3-b]pyridin-1-yl)indolin-2-one; |
| 358 | 5-(2-Isopropylpyrrolo[2,3-b]pyridin-1-yl)-7-methyl-indolin-2-one; |
| 359 | 5-(2-Cyclopropylpyrrolo[2,3-b]pyridin-1-yl)-7-methyl-indolin-2-one; |
| 360 | 5-(2-Isopropyl-6-methyl-pyrrolo[2,3-b]pyridin-1-yl)-7-methyl-indolin-2-one; |
| 361 | 7-Fluoro-5-(2-isopropylpyrrolo[2,3-b]pyridin-1-yl)indolin-2-one; |
| 362 | 7-Fluoro-5-(2-isopropyl-6-methyl-pyrrolo[2,3-b]pyridin-1-yl)indolin-2-one; |
| 363 | 7-Fluoro-5-(2-methylpyrrolo[2,3-b]pyridin-1-yl)indolin-2-one; |
| 364 | 7-Fluoro-5-[2-methyl-6-(trifluoromethyl)pyrrolo[2,3-b]pyridin-1-yl]indolin-2-one; |
| 365 | (RS)-7-Fluoro-5-[2-tetrahydrofuran-3-yl-6-(trifluoromethyl)pyrrolo[2,3-b]pyridin-1-yl]indolin-2-one; |
| 366 | 7-Fluoro-5-[2-(methoxymethyl)-6-(trifluoromethyl)pyrrolo[2,3-b]pyridin-1-yl]indolin-2-one; |
| 367 | 5-[2-Isopropyl-6-(trifluoromethyl)pyrrolo[2,3-b]pyridin-1-yl]-7-methyl-indolin-2-one; |
| 368 | (RS)-5-[2-(1-Methoxyethyl)pyrrolo[2,3-b]pyridin-1-yl]-7-methyl-indolin-2-one; |
| 369 | 7-Fluoro-5-[2-isopropyl-6-(trifluoromethyl)pyrrolo[2,3-b]pyridin-1-yl]indolin-2-one; |
| 370 | 2-Isopropyl-1-(7-methyl-1H-indazol-5-yl)-6-(trifluoromethyl)pyrrolo[2,3-b]pyridine; |
| 371 | 2-(3-Fluoropropyl)-1-(7-methyl-1H-indazol-5-yl)-6-(trifluoromethyl)pyrrolo[2,3-b]pyridine; |
| 372 | 1-(7-Chloro-1H-indazol-5-yl)-2-(3-fluoropropyl)-6-(trifluoromethyl)pyrrolo[2,3-b]pyridine; |
| 373 | 2-Methyl-1-(7-methyl-1H-indazol-5-yl)-6-(trifluoromethyl)pyrrolo[2,3-b]pyridine; |
| 374 | 1-(7-Chloro-1H-indazol-5-yl)-2-methyl-6-(trifluoromethyl)pyrrolo[2,3-b]pyridine; |
| 375 | 2-Methyl-1-(7-methyl-1H-indazol-5-yl)pyrrolo[2,3-b]pyridine; |
| 376 | 5-[2-Isopropyl-6-(trifluoromethyl)pyrrolo[2,3-b]pyridin-1-yl]-1H-pyrazolo[3,4-b]pyridine; |
| 377 | 1-(7-Methyl-1H-indazol-5-yl)-6-(trifluoromethyl)pyrrolo[2,3-b]pyridine; |
| 378 | 7-Methyl-5-(6-methylpyrrolo[2,3-b]pyridin-1-yl)indolin-2-one; |
| 379 | 7-Fluoro-5-(6-methylpyrrolo[2,3-b]pyridin-1-yl)indolin-2-one; |
| 380 | 5-(2-Cyclopropyl-6-methyl-pyrrolo[2,3-b]pyridin-1-yl)indolin-2-one; |
| 381 | 2-(4-Fluorophenyl)-1-(1H-indol-5-yl)-6-methyl-pyrrolo[2,3-b]pyridine; |
| 382 | 5-[2-(4-Fluorophenyl)-6-methyl-pyrrolo[2,3-b]pyridin-1-yl]indolin-2-one; |
| 383 | 5-[6-Chloro-2-(4-fluorophenyl)pyrrolo[2,3-b]pyridin-1-yl]indolin-2-one; |
| 384 | 5-[2-(4-Fluorophenyl)-6-methoxy-pyrrolo[2,3-b]pyridin-1-yl]indolin-2-one; |
| 385 | 6-Chloro-2-(4-fluorophenyl)-1-(1H-indol-5-yl)pyrrolo[2,3-b]pyridine; |

TABLE 1-continued

| Ex. # | Compound Name |
|---|---|
| 386 | 6-tert-Butoxy-2-(4-fluorophenyl)-1-(1H-indol-5-yl)pyrrolo[2,3-b]pyridine; |
| 387 | 2-(4-Fluorophenyl)-1-(1H-indol-5-yl)-6-(trifluoromethyl)pyrrolo[2,3-b]pyridine; |
| 388 | 1-(1H-Indol-5-yl)-2-phenyl-6-(trifluoromethyl)pyrrolo[2,3-b]pyridine; |
| 389 | 5-[3-Bromo-2-cyclopropyl-6-(trifluoromethyl)pyrrolo[2,3-b]pyridin-1-yl]indolin-2-one; |
| 390 | 6-Methyl-2-phenyl-1-(1H-pyrrolo[2,3-b]pyridin-5-yl)pyrrolo[2,3-b]pyridine; |
| 391 | 2-Isopropyl-1-(1H-pyrrolo[2,3-b]pyridin-5-yl)-6-(trifluoromethyl)pyrrolo[2,3-b]pyridine; |
| 392 | 2-Methyl-1-(1H-pyrrolo[2,3-b]pyridin-5-yl)-6-(trifluoromethyl)pyrrolo[2,3-b]pyridine; |
| 393 | 5-(3-Bromo-6-methyl-2-phenyl-pyrrolo[2,3-b]pyridin-1-yl)-1,3-dihydropyrrolo[2,3-b]pyridin-2-one; |
| 394 | 5-[3-Bromo-2-isopropyl-6-(trifluoromethyl)pyrrolo[2,3-b]pyridin-1-yl]-1,3-dihydropyrrolo[2,3-b]pyridin-2-one; |
| 395 | 5-[3-Bromo-2-methyl-6-(trifluoromethyl)pyrrolo[2,3-b]pyridin-1-yl]-1,3-dihydropyrrolo[2,3-b]pyridin-2-one; |
| 396 | 5-[2-Isopropyl-6-(trifluoromethyl)pyrrolo[2,3-b]pyridin-1-yl]indolin-2-one; |
| 397 | 5-[2-Phenyl-6-(trifluoromethyl)pyrrolo[2,3-b]pyridin-1-yl]indolin-2-one; |
| 398 | 5-[2-(4-Fluorophenyl)-6-(trifluoromethyl)pyrrolo[2,3-b]pyridin-1-yl]indolin-2-one; |
| 399 | 5-[2-Cyclopropyl-6-(trifluoromethyl)pyrrolo[2,3-b]pyridin-1-yl]indolin-2-one; |
| 400 | 5-(6-Methyl-2-phenyl-pyrrolo[2,3-b]pyridin-1-yl)-1,3-dihydropyrrolo[2,3-b]pyridin-2-one; |
| 401 | 5-[2-Isopropyl-6-(trifluoromethyl)pyrrolo[2,3-b]pyridin-1-yl]-1,3-dihydropyrrolo[2,3-b]pyridin-2-one; |
| 402 | 5-[2-Methyl-6-(trifluoromethyl)pyrrolo[2,3-b]pyridin-1-yl]-1,3-dihydropyrrolo[2,3-b]pyridin-2-one; |
| 403 | 5-(2-Ethylpyrrolo[2,3-b]pyridin-1-yl)-7-methyl-indolin-2-one; |
| 404 | (*R)-2-(sec-Butyl)-3-(7-chloro-1H-indazol-5-yl)-5-(trifluoromethyl)-3H-imidazo[4,5-b]pyridine; |
| 405 | (*S)-2-(sec-Butyl)-3-(7-chloro-1H-indazol-5-yl)-5-(trifluoromethyl)-3H-imidazo[4,5-b]pyridine; |
| 406 | (*R)-2-(sec-Butyl)-3-(7-methyl-1H-indazol-5-yl)-5-(trifluoromethyl)-3H-imidazo[4,5-b]pyridine; |
| 407 | (*S)-2-(sec-Butyl)-3-(7-methyl-1H-indazol-5-yl)-5-(trifluoromethyl)-3H-imidazo[4,5-b]pyridine; |
| 408 | (*R)-3-(7-Chloro-1H-indazol-5-yl)-2-(1-fluoroethyl)-5-(trifluoromethyl)-3H-imidazo[4,5-b]pyridine; |
| 409 | (*S)-3-(7-Chloro-1H-indazol-5-yl)-2-(1-fluoroethyl)-5-(trifluoromethyl)-3H-imidazo[4,5-b]pyridine; |
| 410 | 3-(7-Chloro-1H-indazol-5-yl)-2-(1,1-difluoroethyl)-5-methyl-3H-imidazo[4,5-b]pyridine; |
| 411 | 3-(7-Chloro-1H-indazol-5-yl)-2-(cyclopropylmethyl)-5-(trifluoromethyl)-3H-imidazo[4,5-b]pyridine; |
| 412 | 3-(7-Chloro-1H-indazol-5-yl)-2-propyl-5-(trifluoromethyl)-3H-imidazo[4,5-b]pyridine; |
| 413 | 3-(7-Chloro-1H-indazol-5-yl)-2-(methoxymethyl)-5-(trifluoromethyl)-3H-imidazo[4,5-b]pyridine; |
| 414 | 3-(7-Chloro-1H-indazol-5-yl)-2-isobutyl-5-(trifluoromethyl)-3H-imidazo[4,5-b]pyridine; |
| 415 | 3-(7-Chloro-1H-indazol-5-yl)-5-methoxy-2-(trifluoromethyl)-3H-imidazo[4,5-b]pyridine; |
| 416 | 3-(7-Chloro-1H-indazol-5-yl)-2-(2,2,2-trifluoroethyl)-5-(trifluoromethyl)-3H-imidazo[4,5-b]pyridine; |
| 417 | 2-(1,1-Difluoropropyl)-3-(7-methyl-1H-indazol-5-yl)-5-(trifluoromethyl)-3H-imidazo[4,5-b]pyridine; |
| 418 | 3-(7-Methyl-1H-indazol-5-yl)-5-(trifluoromethyl)-2-(3,3,3-trifluoropropyl)-3H-imidazo[4,5-b]pyridine; |
| 419 | 3-(7-Chloro-1H-indazol-5-yl)-2,6-bis(trifluoromethyl)-3H-imidazo[4,5-b]pyridine; |
| 420 | 5-(5-Fluoro-2-isopropyl-1H-pyrrolo[2,3-b]pyridin-1-yl)-7-methylindolin-2-one; |
| 421 | 5-(6-(Difluoromethyl)-2-methyl-1H-pyrrolo[2,3-b]pyridin-1-yl)-7-methylindolin-2-one; |
| 422 | 1-(7-Methyl-2-oxoindolin-5-yl)-6-(trifluoromethyl)-1H-pyrrolo[2,3-b]pyridine-2-carbaldehyde; |
| 442 | 2-(2-Chloro-4-pyridyl)-3-(7-methyl-1H-indazol-5-yl)-5-(trifluoromethyl)imidazo[4,5-b]pyridine; |
| 443 | 2-(2-Bromo-4-pyridyl)-3-(7-methyl-1H-indazol-5-yl)-5-(trifluoromethyl)imidazo[4,5-b]pyridine; |
| 445 | 2-(2-[$^{19}$F]fluoro-4-pyridyl)-3-(7-methyl-1H-indazol-5-yl)-5-(trifluoromethyl)imidazo[4,5-b]pyridine; and |
| 446 | 2-(2-[$^{18}$F]fluoro-4-pyridyl)-3-(7-methyl-1H-indazol-5-yl)-5-(trifluoromethyl)imidazo[4,5-b]pyridine. |

A further embodiment of the current invention is a compound as shown below in Table 2.

TABLE 2

| Ex # | Compound Name |
|---|---|
| 423 | 3-(7-Ethyl-1H-indazol-5-yl)-2,5-bis(trifluoromethyl)-3H-imidazo[4,5-b]pyridine; |
| 424 | 3-(7-Isopropyl-1H-indazol-5-yl)-2,5-bis(trifluoromethyl)-3H-imidazo[4,5-b]pyridine; |
| 425 | 5-(2,5-Bis(trifluoromethyl)-3H-imidazo[4,5-b]pyridin-3-yl)-1H-indazole-7-carbonitrile; |
| 426 | 3-(7-Chloro-1H-indazol-5-yl)-2-isopropyl-6-(trifluoromethyl)-3H-imidazo[4,5-b]pyridine; |
| 427 | 3-(7-Chloro-1H-indazol-5-yl)-6-methyl-2-(trifluoromethyl)-3H-imidazo[4,5-b]pyridine; |
| 428 | 3-(7-Chloro-1H-indazol-5-yl)-7-methyl-2,5-bis(trifluoromethyl)-3H-imidazo[4,5-b]pyridine; |
| 429 | 7-Methyl-3-(7-methyl-1H-indazol-5-yl)-2,5-bis(trifluoromethyl)-3H-imidazo[4,5-b]pyridine; |
| 430 | 3-(7-Chloro-1H-indazol-5-yl)-2-isopropyl-7-methyl-5-(trifluoromethyl)-3H-imidazo[4,5-b]pyridine; |
| 431 | 3-(7-Chloro-1H-indazol-5-yl)-7-methoxy-2,5-bis(trifluoromethyl)-3H-imidazo[4,5-b]pyridine; |
| 432 | 3-(7-Chloro-1H-indazol-5-yl)-2-(1-cyclopropylethyl)-5-(trifluoromethyl)-3H-imidazo[4,5-b]pyridine; |
| 433 | 3-(7-Chloro-1H-indazol-5-yl)-2-(1-methylcyclopropyl)-5-(trifluoromethyl)-3H-imidazo[4,5-b]pyridine; |
| 434 | 3-(7-Methyl-1H-indazol-5-yl)-2-(1-methylcyclopropyl)-5-(trifluoromethyl)-3H-imidazo[4,5-b]pyridine; |
| 435 | 3-(7-Chloro-1H-indazol-5-yl)-2-(1-methoxyethyl)-5-(trifluoromethyl)-3H-imidazo[4,5-b]pyridine; |
| 436 | 6-Chloro-3-(7-chloro-1H-indazol-5-yl)-2-(trifluoromethyl)-3H-imidazo[4,5-b]pyridine; |
| 437 | 3-(7-Chloro-1H-indazol-5-yl)-5-(trifluoromethyl)-2-(1,1,1-trifluoropropan-2-yl)-3H-imidazo[4,5-b]pyridine; |
| 438 | 5-(4-(Dimethylamino)-2-methyl-1H-pyrrolo[2,3-b]pyridin-1-yl)-7-methylindolin-2-one; |
| 439 | 5-(4-(Azetidin-1-yl)-2-methyl-1H-pyrrolo[2,3-b]pyridin-1-yl)-7-methylindolin-2-one; |
| 440 | 5-(4-Methoxy-2-methyl-1H-pyrrolo[2,3-b]pyridin-1-yl)-7-methylindolin-2-one; |
| 441 | 5-(2,4-Dimethyl-1H-pyrrolo[2,3-b]pyridin-1-yl)-7-methylindolin-2-one; | and pharmaceutically acceptable salts, N-oxides, or solvates thereof.

An additional embodiment of the invention is a pharmaceutical composition comprising:

(A) an effective amount of at least one compound of Formula (I):

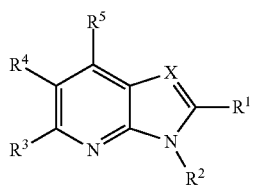

(I)

wherein
X is N or CR$^6$;
R$^1$ is a member selected from the group consisting of:
H, —C$_{1-5}$alkyl, —C$_{1-5}$haloalkyl, —C$_{1-5}$alkoxy, —(CH$_2$)$_2$C(=O)OCH$_3$, —(CH$_2$)$_{1-3}$OH, —(CH$_2$)$_{1-2}$O—C$_{1-5}$alkyl, —CH(CH$_3$)OCH$_3$, —C(CH$_3$)$_2$OCH$_3$, —CH$_2$SO$_2$CH$_3$, —C(=O)H, —NH—C$_{1-5}$alkyl, —N(C$_{1-5}$alkyl)$_2$, —C(=O)N(H)C$_{1-5}$alkyl, —C(=O)N(C$_{1-5}$alkyl)$_2$, —C$_{3-8}$cycloalkyl, —(CH$_2$)—C$_{3-5}$cycloalkyl, —CH(CH$_3$)—C$_{3-8}$cycloalkyl, —NH—C$_{3-8}$cycloalkyl, —C(=O)NH-cyclopropyl, —C(=O)—NH-phenyl, —C(=O)-azetidinyl, —C(=O)-pyrrolidinyl, azetidinyl, phenyl, benzyl, oxetanyl, tetrahydrofuranyl, tetrahydropyranyl, —CH$_2$-pyrazinyl, furanyl, thienyl, and pyridinyl, wherein the —C$_{3-8}$cycloalkyl, phenyl, oxetanyl, azetidinyl, tetrahydrofuranyl, tetrahydropyranyl, pyridinyl, pyrazinyl, furanyl and thienyl rings are each independently optionally substituted with 1-3 substituents selected from the group consisting of: halo, —C$_{1-5}$alkyl, —C$_{1-5}$haloalkyl, —C$_{1-5}$haloalkoxy, —OH, and —C(=O)OC$_{1-5}$alkyl;

R$^2$ is selected from the group consisting of:

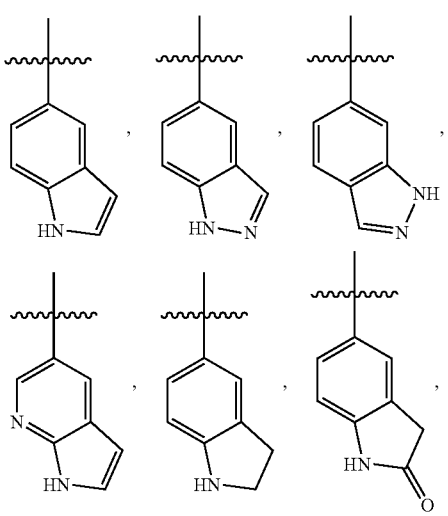

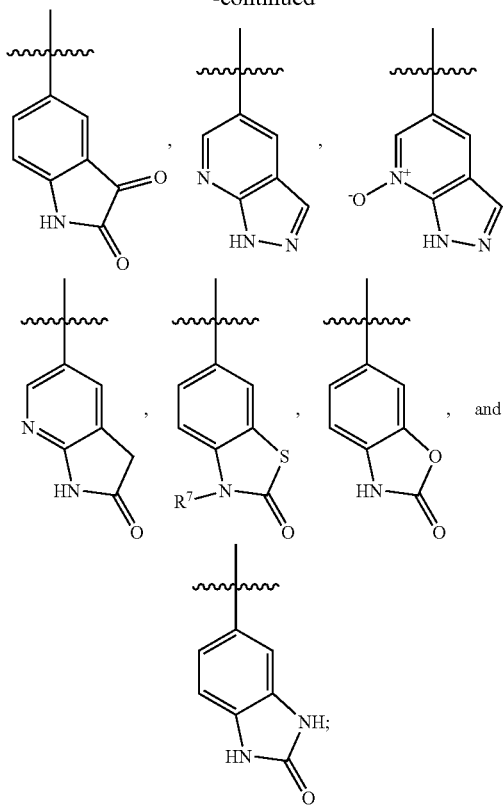

wherein each $R^2$ is independently optionally substituted with a member selected from the group consisting of: $^3H$, halo, —$C_{1-5}$alkyl, —$C_{1-5}$alkenyl, —CN, —OH, CH=CHCH$_2$OH, —(CH$_2$)$_3$COH, C(=O)OC$_{1-5}$alkyl, and phenyl;

$R^3$ is selected from the group consisting of: H, halo, —$C_{1-5}$alkyl, —S—$C_{1-5}$alkyl, —$C_{1-5}$haloalkyl, —$C_{1-5}$alkoxy, —NR$^{3a}$R$^{3b}$, —OH, —(CH$_2$)$_{1-3}$OH, —CH=CHCH$_2$OH, —$C_{3-8}$cycloalkyl, piperidinyl, piperazinyl, morpholinyl, and pyridyl;

each $R^{3a}$ and $R^{3b}$ are independently selected from the group consisting of H and $C_{1-5}$alkyl;

$R^4$ is selected from the group consisting of: H, halo, —CH$_3$, and —CF$_3$;

$R^5$ is selected from the group consisting of: H, —OH, —$C_{1-5}$alkyl, —$C_{1-5}$alkoxy, —$C_{1-5}$haloalkyl, —$C_{1-5}$haloalkoxy, —NR$^{5a}$R$^{5b}$, azetidinyl, and morpholinyl;

each $R^{5a}$ and $R^{5b}$ are independently selected from the group consisting of: —$C_{1-5}$alkyl, and —$C_{1-5}$haloalkyl;

$R^6$ is selected from the group consisting of: H, —OH, —CHF$_2$, and —Br; and $R^7$ is H or —$C_{1-5}$alkyl;

and pharmaceutically acceptable salts, N-oxides or solvates of compounds of Formula (I);

and (B) at least one pharmaceutically acceptable excipient.

An additional embodiment of the invention is a pharmaceutical composition comprising and effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising and effective amount of at least one compound of Formula (IE), as well as pharmaceutically acceptable salts, N-oxides or solvates of compounds of Formula (IE), pharmaceutically acceptable prodrugs of compounds of Formula (IE), and pharmaceutically active metabolites of Formula (IE); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

An additional embodiment of the invention is a pharmaceutical composition comprising and effective amount of at least one compound in Table 2, as well as pharmaceutically acceptable salts, N-oxides or solvates of compounds of Table 2, pharmaceutically acceptable prodrugs of compounds of Table 2, and pharmaceutically active metabolites of Table 2; and at least one pharmaceutically acceptable excipient.

Also within the scope of the invention are enantiomers and diastereomers of the compounds of Formula (I) (as well as Formulas (IA) and (IE)). Also within the scope of the invention are the pharmaceutically acceptable salts, N-oxides or solvates of the compounds of Formula (I) (as well as Formulas (IA) and (IE)). Also within the scope of the invention are the pharmaceutically acceptable prodrugs of compounds of Formula (I) (as well as Formulas (IA) and (IE)), and pharmaceutically active metabolites of the compounds of Formula (I) (as well as Formulas (IA) and (IE)).

Also within the scope of the invention are isotopic variations of compounds of Formula (I) (as well as Formulas (IA) and (IE)), such as, e.g., deuterated compounds of Formula (I). Also within the scope of the invention are the pharmaceutically acceptable salts, N-oxides or solvates of the isotopic variations of the compounds of Formula (I) (as well as Formulas (IA) and (IE)). Also within the scope of the invention are the pharmaceutically acceptable prodrugs of the isotopic variations of the compounds of Formula (I) (as well as Formulas (IA) and (IE)), and pharmaceutically active metabolites of the isotopic variations of the compounds of Formula (I) (as well as Formulas (IA) and (IE)).

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (I):

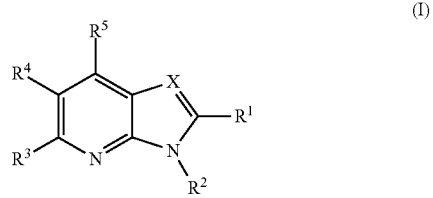

(I)

wherein

X is N or CR⁶;

R¹ is a member selected from the group consisting of:
H, —C₁₋₅alkyl, —C₁₋₅haloalkyl, —C₁₋₅alkoxy, —(CH₂)₂C(=O)OCH₃, —(CH₂)₁₋₃OH, —(CH₂)₁₋₂O—C₁₋₅alkyl, —CH(CH₃)OCH₃, —C(CH₃)₂OCH₃, —CH₂SO₂CH₃, —C(=O)H, —NH—C₁₋₅alkyl, —N(C₁₋₅alkyl)₂, —C(=O)N(H)C₁₋₅alkyl, —C(=O)N(C₁₋₅alkyl)₂, —C₃₋₈cycloalkyl, —(CH₂)—C₃₋₅cycloalkyl, —CH(CH₃)—C₃₋₈cycloalkyl, —NH—C₃₋₈cycloalkyl, —C(=O)NH-cyclopropyl, —C(=O)—NH-phenyl, —C(=O)-azetidinyl, —C(=O)-pyrrolidinyl, azetidinyl, phenyl, benzyl, oxetanyl, tetrahydrofuranyl, tetrahydropyranyl, —CH₂-pyrazinyl, furanyl, thienyl, and pyridinyl, wherein the —C₃₋₈cycloalkyl, phenyl, oxetanyl, azetidinyl, tetrahydrofuranyl, tetrahydropyranyl, pyridinyl, pyrazinyl, furanyl and thienyl rings are each independently optionally substituted with 1-3 substituents selected from the group consisting of: halo, —C₁₋₅alkyl, —C₁₋₅haloalkyl, —C₁₋₅haloalkoxy, —OH, and —C(=O)OC₁₋₅alkyl;

R² is selected from the group consisting of:

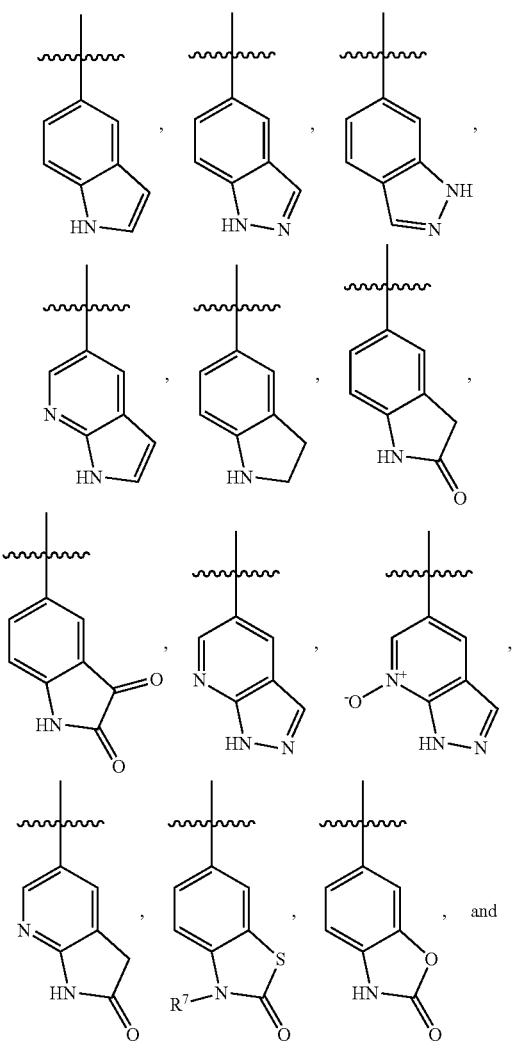

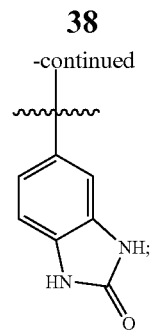

wherein each R² is independently optionally substituted with a member selected from the group consisting of: ³H, halo, —C₁₋₅alkyl, —C₁₋₅alkenyl, —CN, —OH, CH=CHCH₂OH, —(CH₂)₃COH, C(=O)OC₁₋₅ alkyl, and phenyl;

R³ is selected from the group consisting of: H, halo, —C₁₋₅alkyl, —S—C₁₋₅alkyl, —C₁₋₅haloalkyl, —C₁₋₅alkoxy, —NR³ᵃR³ᵇ, —OH, —(CH₂)₁₋₃OH, —CH=CHCH₂OH, —C₃₋₈cycloalkyl, piperidinyl, piperazinyl, morpholinyl, and pyridyl;
each R³ᵃ and R³ᵇ are independently selected from the group consisting of H and C₁₋₅alkyl;

R⁴ is selected from the group consisting of: H, halo, —CH₃, and —CF₃;

R⁵ is selected from the group consisting of: H, —OH, —C₁₋₅alkyl, —C₁₋₅alkoxy, —C₁₋₅haloalkyl, —C₁₋₅haloalkoxy, —NR⁵ᵃR⁵ᵇ, azetidinyl, and morpholinyl;
each R⁵ᵃ and R⁵ᵇ are independently selected from the group consisting of: —C₁₋₅alkyl, and —C₁₋₅haloalkyl;

R⁶ is selected from the group consisting of: H, —OH, —CHF₂, and —Br; and

R⁷ is H or —C₁₋₅alkyl;

and pharmaceutically acceptable salts, N-oxides, or solvates thereof, to a subject in need thereof.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. In their native environment, the pore-forming GluA tetramers directly or indirectly associate with numerous auxiliary proteins. The wide variety of proteins which can participate in AMPA receptor complexes vastly increases the ability of a neuron to tune the response characteristics of its synapses.

AMPA receptors mediate the majority of fast neurotransmission across synaptic gaps. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

In order to circumvent the problems with side-effects noted above, it is hereby proposed that selective modulation of TARP γ8-associated AMPA receptor complexes provides effective therapeutic agents which also avoid or reduce the side-effects associated with the administration of non-selective AMPA receptor modulators. TARP γ8 is primarily expressed in the hippocampus and the cortex, while TARP γ2 is primarily expressed in the cerebellum. In one aspect, selective modulation of TARP γ8 potentially avoids modulation of TARP γ2-associated AMPA receptor complexes, which are more prevalent in the cerebellum, thereby reducing side effects associated with general (non-TARP dependent/non-selective) AMPA antagonism.

For instance, selective modulation of TARP γ8-associated AMPA receptor complexes is contemplated as an effective anti-seizure/anti-epileptic therapeutic with reduced the side effects (e.g. sedation, ataxis, and/or dizziness) associated with general (non-TARP dependent/non-selective) AMPA antagonists. Similarly, reduction of hippocampal over-excitability, using selective modulation of TARP γ8-associated AMPA receptor complexes may lead to normalization of the symptoms of schizophrenia, and it may protect against the subsequent decline in hippocampal volume. In a further instance, selectively attenuating hippocampal excitability, via selective modulation of TARP γ8-associated AMPA receptor complexes, could provide therapeutic benefit to patients with bipolar disorder. Likewise, selective modulation of TARP γ8-associated AMPA receptor complexes within the hippocampus may provide an effective anxiolytic.

Accordingly, provided herein are compounds which are selective modulators of TARP γ8-associated AMPA receptor complexes. Compounds which are selective modulators of TARP γ8-associated AMPA receptor complexes ameliorate and/or eliminate the side effects (e.g. sedation, ataxis, and/or dizziness) of general (non-TARP dependent/non-selective) AMPA receptor modulators.

In some embodiments, provided herein are compounds which selectively modulate the activity of complexes comprising GluA1 receptors associated with the protein TARP γ8.

In one embodiment, selective modulation of TARP γ8-associated AMPA receptor complexes refers to selective antagonism of TARP γ8-associated AMPA receptor complexes. In another embodiment, selective modulation of TARP γ8-associated AMPA receptor complexes refers to selective partial inhibition of TARP γ8-associated AMPA receptor complexes. In a further embodiment, selective antagonism of TARP γ8-associated AMPA receptor complexes refers to negative allosteric modulation of TARP γ8-associated AMPA receptor complexes. The invention relates to methods of using the compounds described herein to treat subjects diagnosed with or suffering from a disease, disorder, or condition mediated by AMPA receptor activity. These methods are accomplished by administering to the subject a compound of the invention. In some embodiments, the compounds described herein are selective for modulation of TARP γ8 associated AMPA receptor complexes.

An AMPA receptor mediated disease, disorder or condition includes and is not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (for example, CNS lupus erythematodes, polyarteritis nodosa, Sjogren syndrome, sarcoidosis, isolated cerebral vasculitis, etc.), schizophrenia, depression, and bipolar disorder. In some embodiments, the AMPA mediated disease, disorder or condition is depression, anxiety disorders, anxious depression, post traumatic stress disorder, epilepsy, schizophrenia, prodromal schizophrenia, or a cognitive disorder.

In one group of embodiments, an AMPA receptor mediated disease, disorder or condition is a condition related to hippocampal hyperexcitability. In one embodiment, provided herein are methods to selectively dampen hippocampal activity in the brain comprising administration of compounds described herein to a subject in need thereof. In one embodiment, provided herein are methods for the treatment of an AMPA receptor mediated disease, disorder or condition which is depression comprising administration of compounds described herein to a subject in need thereof. As used herein, depression includes and is not limited to major depression, psychotic depression, persistent depressive disorder, post-partum depression, seasonal affective disorder, depression which is resistant to other anti-depressants, manic-depression associated with bipolar disorder, post traumatic stress disorder, and the like. In another embodiment, provided herein are methods for the treatment of an AMPA receptor mediated disease, disorder or condition which is post traumatic stress disorder (PTSD) comprising administration of compounds described herein to a subject in need thereof. In another embodiment, provided herein are methods for the treatment of an AMPA receptor mediated disease, disorder or condition which is epilepsy, schizophrenia, or prodromal schizophrenia comprising administration of compounds described herein to a subject in need thereof. In yet another embodiment, provided herein are methods for the treatment of an AMPA receptor mediated disease, disorder or condition which is a cognitive disorder comprising administration of compounds described herein to a subject in need thereof. As used herein, cognitive disorder includes and is not limited to mild cognitive impairment, amnesia, dementia, delirium, cognitive impairment associated with anxiety disorders, mood disorders, psychotic disorders and the like.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

Certain Definitions

As used herein, the terms "including", "containing" and "comprising" are used herein in their open, non-limiting sense.

The term "alkyl" refers to a straight- or branched-chain alkyl group having from 1 to 12 carbon atoms in the chain. In some embodiments, an alkyl group is a $C_1$-$C_6$alkyl group. In some embodiments, an alkyl group is a $C_1$-$C_4$alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_1$-$C_6$haloalkyl group. In some embodiments, a haloalkyl group is a $C_1$-$C_4$haloalkyl group. One exemplary substitutent is fluoro. Preferred substituted alkyl groups of the invention include trihalogenated alkyl groups such as trifluoromethyl groups. Haloalkyl includes and is not limited to —$CF_3$, —$CH_2F$, —$CHF_2$, —$CH_2Cl$, —$CH_2$—$CF_3$, and the like.

The term "cycloalkyl" refers to monocyclic, non-aromatic hydrocarbon groups having from 3 to 8 carbon atoms. Examples of cycloalkyl groups include, for example, cyclopropyl, cyclobutyl, cyclopentyl, cyclohexyl, and the like.

The term "alkoxy" includes a straight chain or branched alkyl group with a terminal oxygen linking the alkyl group to the rest of the molecule. In some embodiments, an alkoxy group is a $C_1$-$C_6$alkoxy group. In some embodiments, an alkoxy group is a $C_1$-$C_4$alkoxy group. Alkoxy includes methoxy, ethoxy, propoxy, isopropoxy, butoxy, t-butoxy, pentoxy and so on.

The term "haloalkoxy" includes a straight chain or branched alkyl group with a terminal oxygen linking the alkyl group to the rest of the molecule and having at least one of the hydrogens replaced with a halogen. In some embodiments, a haloalkoxy group is a $C_1$-$C_6$haloalkoxy group. In some embodiments, a haloalkoxy group is a $C_1$-$C_4$ haloalkoxy group. Haloalkoxy includes and is not limited to —$OCF_3$, —$OCH_2F$, —$OCHF_2$, —$OCH_2Cl$, —O—$CH_2$—$CF_3$, and the like.

The term "thiophenyl" and "thienyl" are used interchangeably.

The term "halogen" represents chlorine, fluorine, bromine, or iodine. The term "halo" represents chloro, fluoro, bromo, or iodo.

The term "benzyl" and —$CH_2$-phenyl are used interchangeably

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

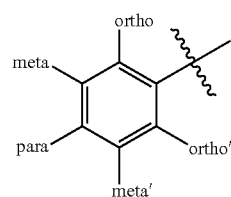

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

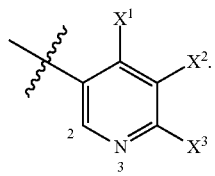

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, $5^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (-)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of t electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

Compounds of the invention may also exist as "rotamers," that is, conformational isomers that occur when the rotation leading to different conformations is hindered, resulting a rotational energy barrier to be overcome to convert from one conformational isomer to another.

The symbols ▬ and ▬ are used as meaning the same spatial arrangement in chemical structures shown herein. Analogously, the symbols ⁞⁞⁞ and ⁞⁞⁞ are used as meaning the same spatial arrangement in chemical structures shown herein.

A wavy line "∿" indicates the point of attachment to the rest of the molecule.

Additionally, any formula given herein is intended to refer also to hydrates, solvates, and polymorphs of such compounds, and mixtures thereof, even if such forms are not listed explicitly.

Certain compounds of Formula (I) (as well as Formulas (IA) and (IE)), or pharmaceutically acceptable salts of Formula (I) (as well as Formulas (IA) and (IE)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formulas (IA) and (IE)) or pharmaceutically acceptable salts of compounds of Formula (I) (as well as Formulas (IA) and (IE)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium or tritium (i.e., $^2H$, $^3H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^{2a}$, $R^3$, $R^{3a}$, $R^{3b}$, $R^{3c}$, $R^4$, $R^5$, $R^{5a}$, $R^{5b}$, $R^6$, $R^{6a}$, $R^7$, X, $X^1$, Y, $R^a$, $R^b$, $R^c$, $R^e$, $R^f$, $R^g$, HAL, and $HAL^3$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^{2a}$, $R^3$, $R^{3a}$, $R^{3b}$, $R^{3c}$, $R^4$, $R^5$, $R^{5a}$, $R^{5b}$, $R^6$, $R^{6a}$, $R^7$, X, $X^1$, Y, $R^a$, $R^b$, $R^c$, $R^e$, $R^f$, $R^g$, HAL, and $HAL^3$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies $n \leq N \leq m$, with $m > n$. Any disubstituent referred to herein is meant to encompass the various attachment possibilities when more than one of such possibilities are allowed. For example, reference to disubstituent -A-B-, where $A \neq B$, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (IA) and (IE)), preferably of those described above and of the specific compounds exemplified herein, and methods of treatment using such salts.

The term "pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formulas (IA) and (IE)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formulas (IA) and (IE)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (IA) and (IE)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (IA) and (IE)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of Formula (I) (as well as Formulas (IA) and (IE)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) (as well as Formulas (IA) and (IE). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (IA) and (IE)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (IA) and (IE)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (IA) and (IE)), which may also be used in the methods of the invention. A "pharmaceutically active metabolite" means a pharmacologically active product of metabolism in the body of a compound of Formula (I) (as well as Formulas (IA) and (IE) as applicable) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formulas (IA) and (IE)) and their pharmaceutically acceptable salts, pharmaceutically acceptable prodrugs, and pharmaceutically active metabolites of the present invention are useful as modulators of the AMPA receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the AMPA receptor expression or activity, and "activators" are compounds that increase, activate, facilitate, sensitize, or up-regulate AMPA receptor expression or activity.

The term "pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

The term "subject" includes humans. The terms "human," "patient," and "subject" are used interchangeably herein.

The term "treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 10 mg to about 2.5 g/day.

"Compounds of the present invention," and equivalent expressions, are meant to embrace compounds of the Formula (I) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 $\mu$·g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery. Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I), as well as Formulas (IA)-(IE). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

Table 3. Abbreviations and acronyms used herein include the following.

TABLE 3

| Term | Acronym/Abbreviation |
| --- | --- |
| 2-Methyltetrahydrofuran | 2-Me—THF |
| Acetic anhydride | $Ac_2O$ |
| Acetonitrile | ACN, MeCN |
| Acetic acid | AcOH |
| Azobisisobutyronitirile | AIBN |
| 2,2'-Bis(diphenylphosphino)-1,1'-binaphthyl | BINAP |
| 5-(Di-tert-butylphosphino)-1',3',5'-triphenyl-1'H-[1,4]bipyrazole | BippyPhos |
| tert-Butylcarbamoyl | BOC |
| Benzotriazol-1-yloxytris(dimethylamino)-phosphonium hexafluorophosphate | BOP |
| [2-(Di-1-adamantylphosphino)-2',4',6'-triisopropyl-3,6-dimethoxybiphenyl][2-(2'-amino-1,1'-biphenyl)]palladium(II) methanesulfonate | BrettPhos Pd third-generation pre-catalyst |
| 1,1'-Carbonyldiimidazole | CDI |
| Diatomaceous Earth | Celite 545, Celite ® |
| Copper(II) acetate | $Cu(OAc)_2$ |
| (Diethylamino)sulfur trifluoride | DAST |
| 2-Dicyclohexylphosphino-2'-(N,N-dimethylamino)biphenyl | DavePhos |
| Di-tert-butyl azodicarboxylate | DBAD |
| N,N'-Dicyclohexylcarbodiimide | DCC |
| Dichlorethane | DCE |
| Methylene chloride, dichloromethane | DCM |
| Bis(2-methoxyethyl)aminosulfur trifluoride | Deoxo-Fluor ® |
| 1,1,1-Triacetoxy-1,1-dihydro-1,2-benziodoxol-3(1H)-one | Dess-Martin periodinane |
| Diisobutylaluminium hydride | DIBAL, DIBAL-H |
| N,N-Diisopropylethylamine | DIPEA, DIEA, Hunig's base |
| N,N-Dimethylformamide | DMF |
| Dimethyl sulfoxide | DMSO |
| Deutero-dimethyl sulfoxide | $DMSO-d_6$ |
| Diphenylphosphino ferrocene | dppf |
| Di-tert-butylphosphino ferrocene | dtbpf |
| 1-Ethyl-3-(3-dimethylaminopropyl)carbodiimide | EDCI, EDC, EDAC |
| Electrospray Ionisation | ESI |
| Ethyl magnesium bromide | EtMgBr |
| Ethyl Acetate | EtOAc, or EA, or AcOEt |
| Ethanol | EtOH |
| Flash Column Chromatography | FCC |
| Diethyl 1,4-dihydro-2,6-dimethyl-3,5-pyridinecarboxylate | Hantzsch Ester |
| 2-(1H-9-Azobenzotriazole-1-yl)-1,1,3,3-tetramethylaminium hexafluorophosphate | HATU |
| Acetic Acid | HOAc |
| 1-Hydroxy-7-azabenzotriazole | HOAT, HOAt |
| 1-Hydroxy-benzotriazole | HOBt |
| High-pressure liquid chromatography | HPLC |
| Isopropyl Alcohol | IPA |
| Isopropyl magnesium bromide | i-PrMgBr |
| Potassium acetate | KOAc |
| Lithium aluminum hydride | LAH |
| Lithium hexamethyldisilylazide | LHMDS |
| meta-Chloroperoxybenzoic acid | mCPBA or MCPBA |
| Methyl magnesium bromide | MeMgBr |
| Deteromethanol | $MeOD-d_4$ |
| Methanol | MeOH |
| Mesyl chloride, Methanesulfonyl chloride | MsCl |
| Sodium dithionite | $Na_2S_2O_4$ |
| Sodium tert-butoxide | NaOtBu |
| N-Bromosuccinimide | NBS |
| N-Methylmorpholine | NMM |
| Tetrakis(triphenylphosphine)palladium(0) | $Pd(PPh_3)_4$ |
| Tris(dibenzylideneacetone)dipalladium (0) | $Pd_2(dba)_3$ |
| [1,1'-Bis(di-tert-butylphosphino)ferrocene]dichloropalladium(II) | $PdCl_2(dtbpf)$ |
| Palladium(II)bis(triphenylphosphine) dichloride, bis(triphenylphosphine)palladium(II) dichloride | $PdCl_2(PPh_3)_2$ |
| Phosphorous oxychloride | $POCl_3$ |
| Triphenylphosphine | $PPh_3$ |
| Precipitate | ppt |

TABLE 3-continued

| Term | Acronym/Abbreviation |
|---|---|
| p-Toluenesulfonic acid | p-TsOH, PTSA |
| Pyridinium tribromide | $Py^+Br_3^-$ |
| Sodium potassium L(+)-tartrate tetrahydrate | Rochelle salt |
| Room temperature | rt |
| 2-Dicyclohexylphosphino-2',6'-diisopropoxybiphenyl | Ru-Phos |
| N-Chloromethyl-N-fluorotriethylenediammonium bis(tetrafluoroborate) | Selectfluor ® |
| 2-(TriMethsilyl)-ethoxyMethyl chloride | SEM-Cl |
| [2-(Trimethylsilyl)ethoxy]methyl acetal | SEM |
| Supercritical Fluid Chromatography | SFC |
| Thionyl chloride | $SOCl_2$ |
| Tetrabutylammonium fluoride | TBAF |
| Triethyl amine | TEA |
| Trifluoroacetic acid | TFA |
| Trifluoroacetic anhydride | TFAA |
| Tetrahydrofuran | THF |
| Tetrahydropyran | THP |
| 4,5-bis(diphenylphosphino)-9,9-dimethylxanthene | XantPhos |
| 2-Dicyclohexylphosphino-2',4',6'-triisopropylbiphenyl | XPhos |

Preparative Examples

Exemplary compounds useful in methods of the invention will now be described by reference to the illustrative synthetic schemes for their general preparation below and the specific examples to follow.

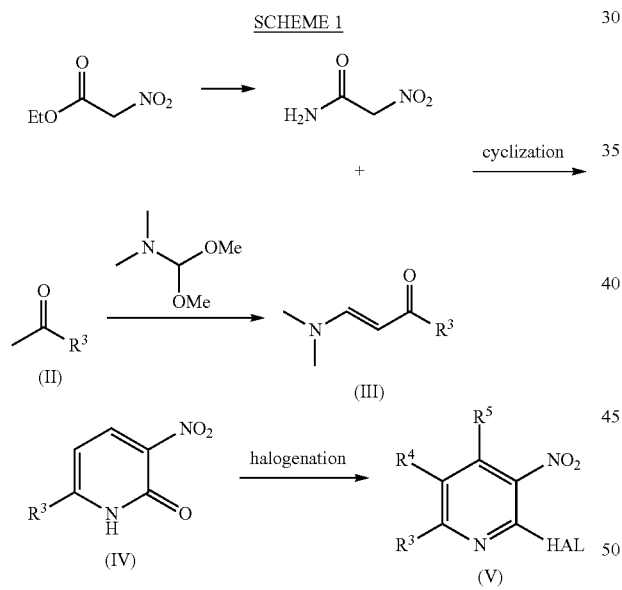

SCHEME 1

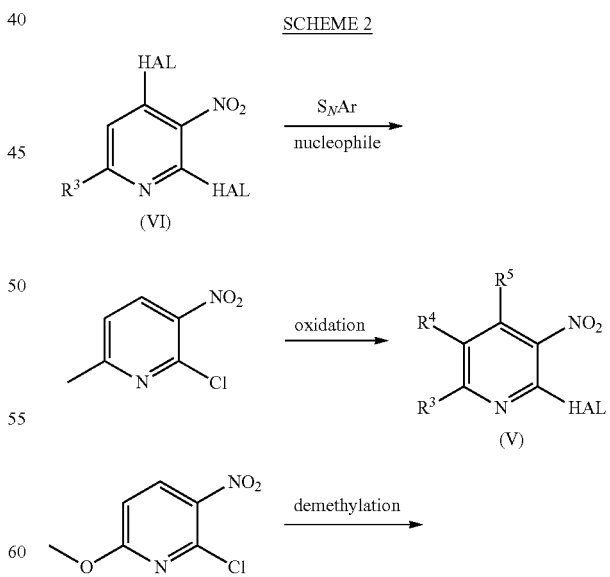

SCHEME 2

According to SCHEME 1, substituted 2-pyridones of formula (IV) or substituted halopyridines of formula (V) are commercially available or synthetically accessible. Addition of 2-nitroacetamide to an appropriate α,β-unsaturated carbonyl substrate of formula (III) provides a 2-pyridone compound of formula (IV). Ethyl 2-nitroacetate is reacted with ammonium hydroxide at room temperature for a period of 3-4 days to provide 2-nitroacetamide. An enamino ketone of formula (III), where $R^3$ is —$C_{3-8}$cycloalkyl, or $C_{1-5}$alkyl, is prepared by the reaction of 1,1-dimethoxy-N,N-dimethylmethanamine and an appropriately substituted commercially available or synthetically accessible ketone of formula (II), p-toluenesulfonic acid (p-TsOH), at temperatures ranging from 80-100° C., for a period of 12-24 h. In a preferred method 1,1-dimethoxy-N,N-dimethylmethanamine ketone is reacted with 1-cyclopropylethanone, p-toluenesulfonic acid at 100° C. for 16 h. A 2-pyridone compound of formula (IV) is prepared by the reaction of 2-nitroacetamide with an enamino ketone of formula (III), where $R^3$ is —$C_{3-8}$cycloalkyl, in the presence of piperidinium acetate, and the like, in a suitable solvent such as water, at room temperature for a period of 12-20 h. Halogenation of a 2-pyridone compound of formula (IV) is achieved under chlorination conditions known to one of skill in the art, providing a substituted chloropyridine of formula (V). For example, by the reaction of a compound of formula (IV) with a chlorinating agent such as $POCl_3$, $SOCl_2$, $PCl_5$ and the like, with or without a suitable solvent such as DMF, and the like, at temperatures ranging from 60-100° C., for a period of 12-20 h. In a preferred method, the chlorinating agent is $POCl_3$.

According to SCHEME 2, substituted halopyridines are modified to provide a compound of formula (V). In a specific example, 2,4-difluoro-3-nitropyridine is reacted with a suitable nucleophile such as an alkylamine or heterocycloalkylamine, in a suitable solvent such as DMF, THF, and the like, a temperatures ranging from 60-100° C., for a period of 12-20 h, to provide a compound of formula (V) where $R^5$ is $(-N(C_{1-5}alkyl)_2)$ or heterocycloalkylamine (morpholine) and $R^3$ is H. In a preferred method, the nucleophile is morpholine and the solvent is DMF. In another example, 2,4-dichloro-3-nitro-6-(trifluoromethyl)pyridine is reacted with a suitable nucleophile such as an alkylamine ($-N(C_{1-5}alkyl)_2$) or alcoholamine ($-N(CH_3)(CH_2CH_2OH)$), in a suitable solvent such as EtOH, and the like, at temperatures ranging from 0° C. to rt, to provide a compound of formula (V) where $R^5$ is $-N(C_{1-5}alkyl)_2$ or $-N(CH_3)(CH_2CH_2OH)$, and $R^3$ is $-C_{1-5}alkyl$, $-C_{1-5}haloalkyl$ or H. In a preferred method, the nucleophile is 2-(methylamino)ethan-1-ol and the solvent is EtOH. 2-Chloro-6-methyl-3-nitropyridine is oxidized with a suitable oxidizing agent such as sodium dichromate dehydrate in a solvent such as $H_2SO_4$, at temperatures ranging from room temperature to 50° C., for a period of 12-16 h, provide a compound of formula (V), where $R^3$ is $-CO_2H$, and one skilled in the art recognizes that the acid can be further transformed to an amide, ester or alkyl group. 2-Chloro-6-methoxy-3-nitropyridine is de-methylated, employing conditions known to one skilled in the art, to provide a compound of formula (V), where $R^3$ is $-OH$.

formula (IX), where $R^a$ is $-NO_2$ or $-Br$, is oxidized with an oxidizing agent such as Dess-Martin periodinane, in a solvent such as DCM, and the like, at room temperature, for a period of 1-3 h, to provide a compound of formula (X). A compound of formula (X), where $R^a$ is $-NO_2$ or $-Br$, is fluorinated with a fluorinating agent such as DAST, and the like, in a suitable solvent such as DCM, and the like, at temperatures ranging from −50-35° C., for a period of 30-90 minutes to provide a compound of formula (XI).

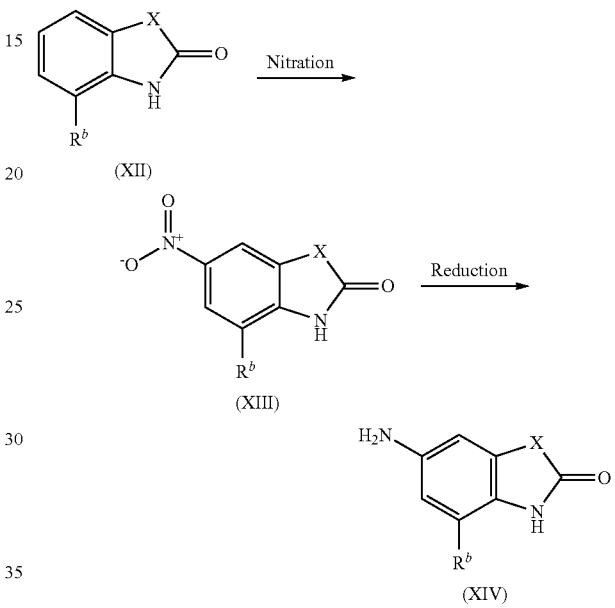

SCHEME 4

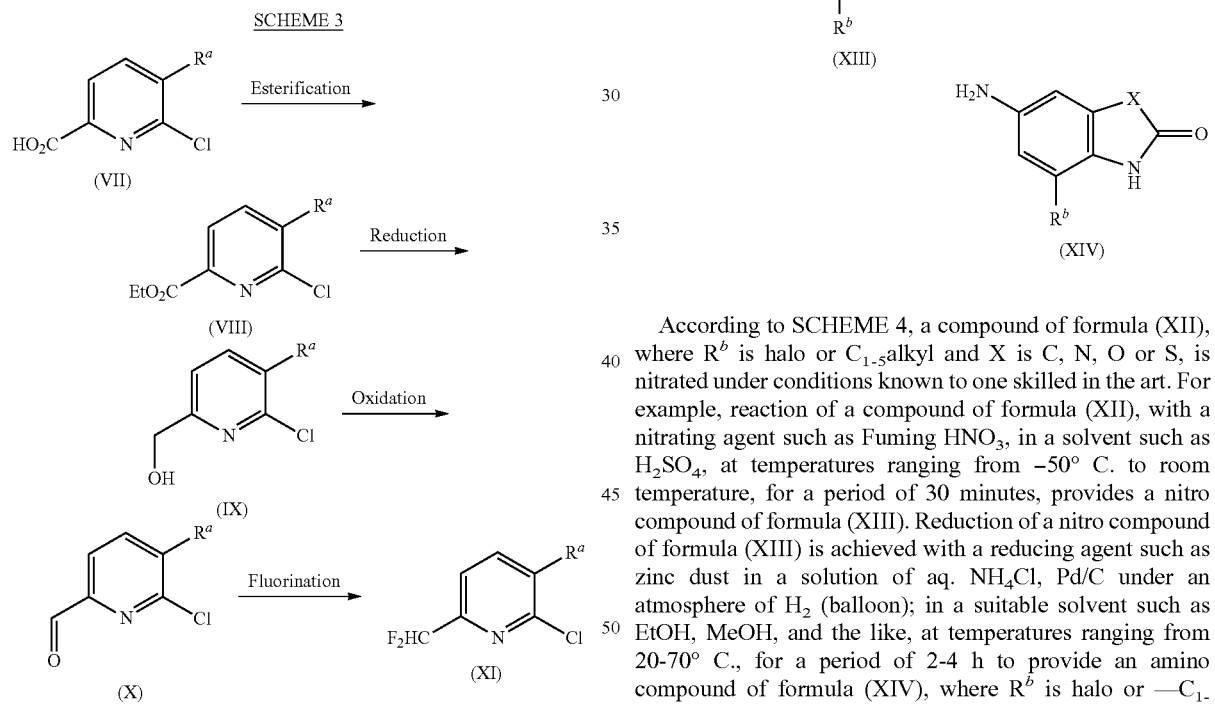

SCHEME 3

According to SCHEME 4, a compound of formula (XII), where $R^b$ is halo or $C_{1-5}alkyl$ and X is C, N, O or S, is nitrated under conditions known to one skilled in the art. For example, reaction of a compound of formula (XII), with a nitrating agent such as Fuming $HNO_3$, in a solvent such as $H_2SO_4$, at temperatures ranging from −50° C. to room temperature, for a period of 30 minutes, provides a nitro compound of formula (XIII). Reduction of a nitro compound of formula (XIII) is achieved with a reducing agent such as zinc dust in a solution of aq. $NH_4Cl$, Pd/C under an atmosphere of $H_2$ (balloon); in a suitable solvent such as EtOH, MeOH, and the like, at temperatures ranging from 20-70° C., for a period of 2-4 h to provide an amino compound of formula (XIV), where $R^b$ is halo or $-C_{1-5}alkyl$ and X is C, N, O or S. In some cases, a protecting group is installed on a compound of formula (XIII) before the nitro group is reduced.

According to SCHEME 3, a compound of formula (VII), where $R^a$ is $NO_2$, is esterified under conditions known to one skilled in the art, to provide a compound of formula (VIII). For example, reaction of 6-chloro-5-nitropicolinic acid with an acid such asp-toluenesulfonic acid, in a solvent such as EtOH, and the like, at temperatures ranging from 60-85° C., for a period of 12-24 h provides ethyl 6-chloro-5-nitropicolinate. A compound of formula (VIII), where $R^a$ is $NO_2$, is reduced with a reducing agent such as DIBAL, $NaBH_4$, and the like, in a suitable solvent such as THF and the like, at temperatures ranging from 0-30° C., for a period of 1-3 h, to provide a compound of formula (IX). In a preferred method, the reducing agent is DIBAL. A compound of

SCHEME 5

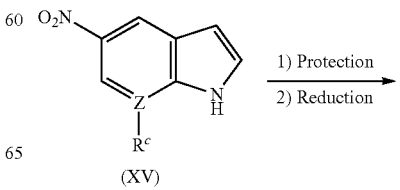

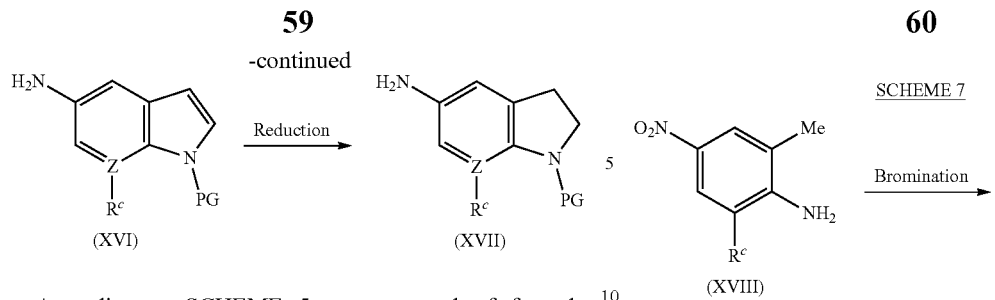

(XVI) → (XVII)

SCHEME 7

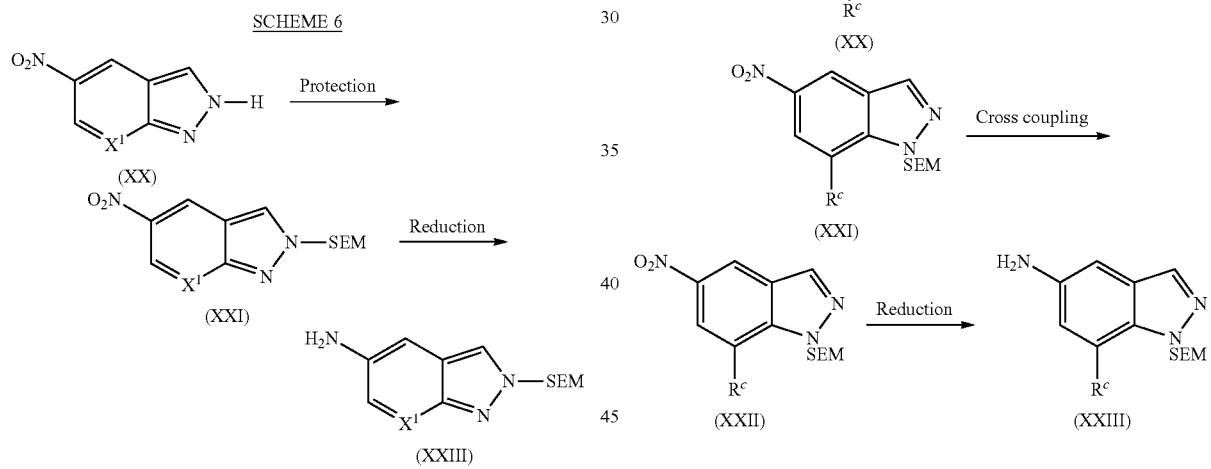

According to SCHEME 5, a compound of formula (XVII), where Z is C—$R^c$ or N, and $R^c$ is H, halo or $C_{1-5}$alkyl, is accessible from a compound of formula (XV). Protection of a compound formula (XV) with a suitable protecting group (PG) is achieved with $Boc_2O$, in a solvent such as THF, DMF, and the like, at temperatures ranging from 0-20° C., for a period of 1-3 h. Subsequent reduction of the nitro group with a reducing agent such as, Pd/C under an atmosphere of $H_2$ (balloon); in a suitable solvent such as THF, EtOH, MeOH, and the like, at room temperature, for a period of 12-24 h, provides an amino compound of formula (XVI). Access to the indoline compound of formula (XVII), where Z is C—$R^c$, and $R^c$ is H, halo or $C_{1-5}$alkyl, is achieved by further reduction, with a reducing agent such as Pd/C under an atmosphere of $H_2$ (balloon); in a suitable solvent such as EtOH, MeOH, and the like, at room temperature, for a period of 12-24 h.

According to SCHEME 6, a compound of formula (XXIII), where $X^1$ is C—$R^c$ or N, $R^c$ is H, —Cl, —$CH_3$, is accessible in two steps from a compound of formula (XX). In a first step, protection of a compound of formula (XX) with a suitable protecting group such as SEM, provides a compound of formula (XXI). For example, reaction of 5-nitro-1H-indazole with a base such as NaH, and a protecting group (PG) such as SEM-Cl, and the like, in a solvent such as DMF, and the like, at temperatures ranging from 0° C. to room temperature, for a period of 1-3 h provides 5-nitro-2-((2-(trimethylsilyl)ethoxy)methyl)-2H-indazole and 5-nitro-1-((2-(trimethylsilyl)ethoxy)methyl)-1H-indazole. In a second step, reduction of a nitro compound of formula (XXI) with a suitable reducing agent such as $Pd/C_{1-5}$, and the like, in a solvent such as EtOH, and the like, at room temperature, for a period of 12-24 h provides a compound of formula (XXIII). In the protection step, the SEM protecting group can go on either nitrogen in the 5-membered ring.

According to SCHEME 7, a compound of formula (XVIII), where $R^c$ is H, halo or $C_{1-5}$alkyl, is commercially available or synthetically accessible. A compound of formula (XXIII), where $R^c$ is $C_{1-5}$alkyl, is accessible from a compound of formula (XVIII), where $R^c$ is H. Bromination of a compound of formula (XVIII) with a brominating agent such as bromine, and the like, under acidic conditions, such as acetic acid, and the like, at temperatures ranging from 0° C. to room temperature, for a period of 30 minutes to 1 h provides an aniline compound of formula (XIX), where $R^c$ is Br. A commercially available or synthetically accessible compound of formula (XIX), where $R^c$ is H, halo or $C_{1-5}$alkyl, undergoes nitrosation followed by cyclization, under acidic conditions, such as acetic acid and sodium nitrite, in a solvent such as water, at temperatures ranging from 0-20° C., for a period of 30 min to 1 h to provide a compound of formula (XX). Protection, followed by reduction of a compound of formula (XX), as previously described, when $R^c$ is H, halo or $C_{1-4}$alkyl affords a compound of formula (XXIII).

In another example, a cross coupling step of a compound of formula (XX), where $R^c$ is halo, allows for introduction of a new substituent. For example, reaction of 7-bromo-5-nitro-1-((2-(trimethylsilyl)ethoxy)methyl)-1H-indazole under a metal mediated cross-coupling reaction with an alkyl boronic anhydride, such as trimethylboroxime, in the presence of a palladium catalyst such as Pd(PPh$_3$)$_4$, and the like, a base such as Cs$_2$CO$_3$, K$_2$CO$_3$, and the like, in a suitable solvent such as 1,4-dioxane, DMF, and the like at temperatures ranging from room temperature to 105° C., for a period of 16 h provides 7-methyl-5-nitro-1-((2-(trimethylsilyl)ethoxy)methyl)-1H-indazole, a compound of formula (XXII), where $R^c$ is —CH$_3$.

is —Br, —I, —OTf, is reacted under metal mediated cross coupling conditions with a terminal alkyne of formula (XXV) as described above to give a compound of formula (XXVI).

Alternatively, a compound of formula (XXIV), where $R^3$ is H, halo, C$_{1-5}$alkyl, C$_{1-5}$alkoxy, or C$_{1-5}$haloalkyl, HAL$^3$ is —Br or —Cl, and $R^g$ is —I, can undergo a Stille reaction to give a compound of formula (XXVI). For example, 2-chloro-3-iodo-6-(trifluoromethyl)pyridine, in the presence of a palladium catalyst such as Pd(PPh$_3$)$_4$ and the like, a co-catalyst such as CuI and the like, and an alkynyl stannane, such as tributyl(1-propynyl)tin, in a suitable solvent such as toluene, DMF and the like at temperatures ranging from 50 to 100° C., for a period of 16 h, to provide 2-chloro-3-(prop-1-yn-1-yl)-6-(trifluoromethyl)pyridine.

SCHEME 8

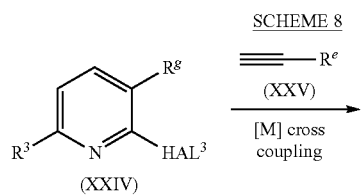

(XXIV)

SCHEME 9

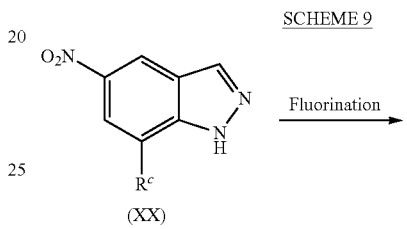

(XX)

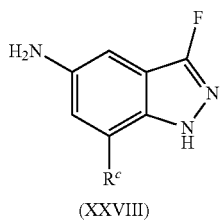

(XXVIII)

According to SCHEME 8, a commercially available or synthetically accessible compound of formula (XXIV) where $R^3$ is H, halo, C$_{1-5}$alkyl, C$_{1-5}$alkoxy, or C$_{1-5}$haloalkyl, $R^g$ is —Br or I, and HAL$^3$ is —Br or —Cl, is reacted in a metal mediated cross coupling reaction with a terminal alkyne of formula (XXV), where $R^e$ is C$_{1-5}$alkyl, C$_{1-5}$haloalkyl, —CH$_2$OCH$_3$, —CH(OCH$_3$)(CH$_3$), C$_{3-8}$cycloalkyl, tetrahydrofuran, —CH$_2$O-tetrahydropyran, or phenyl, 4-fluorophenyl, in the presence of a palladium catalyst such as PdCl$_2$(Ph$_3$)$_2$, Pd(PPh$_3$)$_4$, and the like, an amine base such as Et$_3$N, and the like, in a suitable solvent such as 1,4-dioxane, DMF, and the like, at temperatures ranging from 50 to 100° C., for a period of 16 to 40 h, to provide a compound of formula (XXVI), where $R^3$ is H, halo, C$_{1-5}$alkyl, C$_{1-5}$alkoxy, or C$_{1-5}$haloalkyl, $R^e$ is C$_{1-5}$alkyl, C$_{1-5}$haloalkyl, —CH$_2$OCH$_3$, —CH(OCH$_3$)(CH$_3$), C$_{3-8}$cycloalkyl, tetrahydrofuran, —CH$_2$O-tetrahydropyran, phenyl, or 4-fluorophenyl, and HAL$^3$ is —Br or —Cl.

A compound of formula (XXIV), where $R^3$ is H, halo, C$_{1-5}$alkyl, C$_{1-5}$alkoxy, or C$_{1-5}$haloalkyl, HAL$^3$ is —Br or —Cl, and $R^g$ is H or —OH, where $R^g$ is transformed to a halogen or triflate (OTf), by methods known to one skilled in the art, to a compound of formula (XXIV). A compound of formula (XXIV), where $R^3$ is H, halo, C$_{1-5}$alkyl, C$_{1-5}$alkoxy, or C$_{1-5}$haloalkyl, HAL$^3$ is —Br or —Cl, and $R^g$ According to SCHEME 9, a compound of formula (XX), where $R^c$ is H, is fluorinated, with an electrophilic fluorinating agent such as Selectfluor®, in a solvent such as acetic acid, with a co-colvent such as ACN, with microwave heating to 150° C., for a period of 30 min, to provide a compound of formula (XXVII). A nitro compound of formula (XXVII) is reduced under conditions known to one skilled in the art, and previously described, to provide a compound of formula (XXVIII), where $R^c$ is H.

SCHEME 10

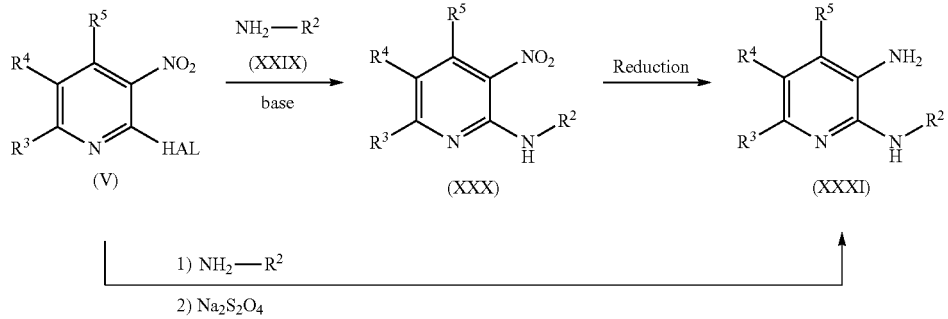

According to SCHEME 10, a commercially available or synthetically accessible substituted halopyridine of formula (V) is reacted with a commercially available or synthetically accessible amine of formula (XXIX) in the presence of a base such as DIEA, TEA, and the like, in a solvent such as EtOH, DMF, THF, and the like, at temperatures ranging from 70 to 110° C., employing microwave or conventional heating, to provide a compound of formula (XXX). As described in the schemes above, synthetically accessible amines of formula (XXIX) encompass amines of formula (XIV), (XVI), (XVII), (XXIII), and (XXVIII); all of which may or may not be protected with a protecting group such as BOC or SEM. Reduction of the nitro group of a compound of formula (XXX), employing methods previously described, provides a compound of formula (XXXI). In an alternate method, a substituted halopyridine of formula (V) is reacted with commercially available or synthetically accessible amine of formula (XXIX) in a solvent such as DMF, at a temperature of about 110° C., for a period of 3 h, followed by the addition of sodium dithionite, with additional heating at a temperature of about 110° C., for a period of 5 h, to provide a compound of formula (XXXI).

SCHEME 11

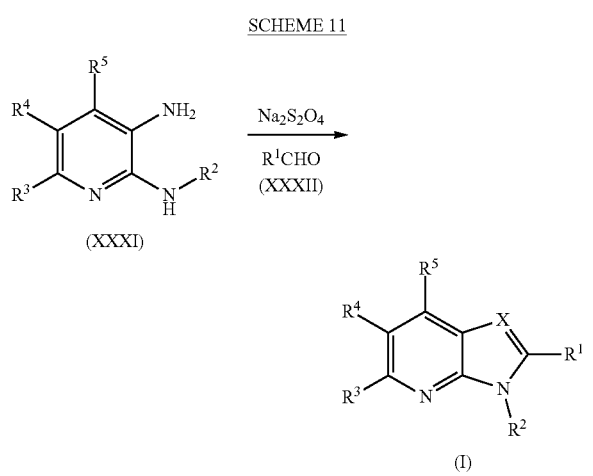

According to SCHEME 11, a compound of formula (XXXI), $R^3$ is H, halo, $C_{1-5}$alkyl, $C_{1-5}$haloalkyl, or $C_{1-5}$alkoxy, $R^4$ is H or $C_{1-5}$alkyl, and $R^5$ is H, is reacted with an aldehyde of formula (XXXII), where $R^1$ is —$CH_2CH_2CO_2CH_3$, $C_{1-5}$alkyl, phenyl, benzyl, 4-fluorophenyl, 2-chlorophenyl, $C_{3-8}$cycloalkyl, —$(CH_2)C_{3-8}$cycloalkyl, 6-fluoro-3-pyridyl, 2-fluoro-4-pyridyl, tetrahydropyran, tetrahydrofuran, pyrazin-2-ylmethyl, thienyl, 2-furyl, in the presence of sodium dithionite, in a suitable solvent such as DMF, and the like, at temperatures ranging from 80-120° C., for a period of 12-18 h to provide a compound of Formula (I), where X is N. In cases where the $NH_2$—$R^2$ group employs a protecting group, a deprotection step is added at the end to provide a compound of Formula (I), where X is N.

In a similar method, a compound of formula (XXXI), is reacted with an aldehyde of formula (XXXII) in the presence of a catalyst such as $Cu(OAc)_2$, in a solvent such as AcOH, at a temperature of about 40° C., for a period of about 2-5 h, to provide a compound of Formula (I), where X is N.

SCHEME 12

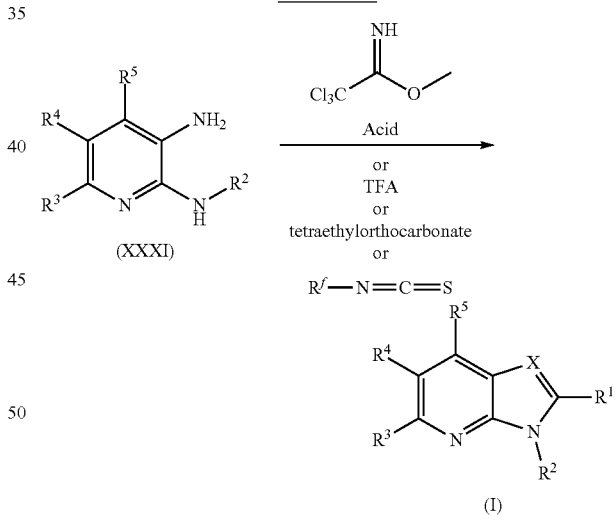

According to SCHEME 12, a compound of formula (XXXI), where $R^3$ is $C_{1-5}$haloalkyl, and $R^4$ and $R^5$ are H, is reacted with methyl 2,2,2-trichloroacetimidate, in a solvent such as AcOH, and the like, for a period of 12-18 h, at a temperature of about rt to 70° C., to provide a compound of Formula (I), where $R^1$ is —$CCl_3$, $R^3$ is $C_{1-5}$haloalkyl, and $R^5$ is H.

In a similar method, a compound of formula (XXXI), where $R^3$ is $C_{1-5}$haloalkyl, and $R^4$ and $R^5$ are H, is reacted with trifluoroacetic acid (TFA), 2,2-difluoropropanoic acid, 2,2-difluoroacetic acid, 3,3,3-trifluoropropanoic acid, and the like, with our without a solvent such as trifluoromethanesulfonic acid, at a temperature of about 70-120° C., for a period of 12-72 h, to provide a compound of Formula (I), where X is N, and $R^1$ is —$C_{1-5}$haloalkyl.

In a similar method, a compound of formula (XXXI), where $R^3$ is $C_{1-5}$haloalkyl, and $R^4$ and $R^5$ are H, is reacted with tetraethylorthocarbonate for a period of 12-18 h, at a temperature of about rt to 70° C., to provide a compound of Formula (I), where X is N, and $R^1$ is —$OCH_2CH_3$.

In a similar method, a compound of formula (XXXI), where $R^3$ is $C_{1-5}$haloalkyl, $R^4$ and $R^5$ are H, is reacted with an isocyanate compound of formula $R^f$—N=C=S, where $R^f$ is $C_{1-5}$alkyl or $C_{3-8}$cycloalkyl, a coupling agent such as dicyclohexyl carbodiimide, for a period of 12-18 h, at a temperature of about rt to 70° C., to provide a compound of Formula (I), where X is N, and $R^1$ is —NH($C_{1-5}$alkyl) or —NH($C_{3-8}$cycloalkyl).

SCHEME 13

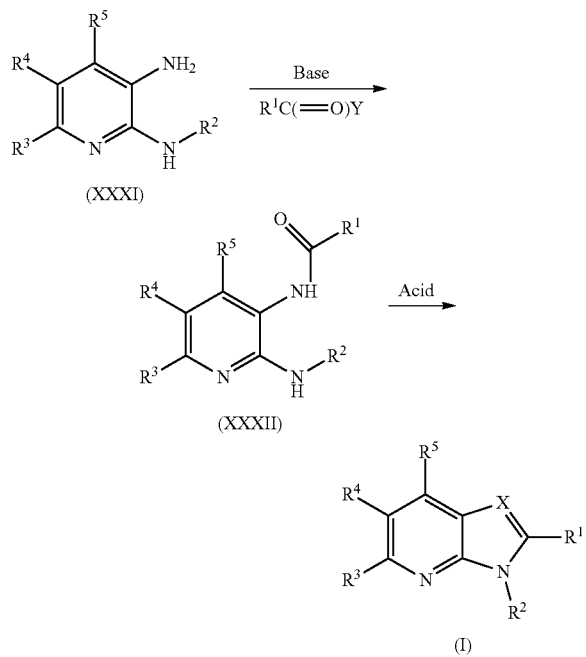

According to SCHEME 13, a substituted amino pyridine compound of formula (XXXI), where $R^3$ is $C_{1-5}$alkyl, $C_{1-5}$haloalkyl, $C_{3-8}$cycloalkyl, $R^4$ is H, and $R^5$ is H, or $C_{1-5}$alkyl, is acylated with a substituted activated acid of formula $R^1C(=O)Y$, where $R^1$ is $C_{1-5}$alkyl, $C_{1-5}$haloalkyl, $C_{3-5}$cycloalkyl, phenyl, or heteroaryl, and Y is —OH or —Cl. For example, a compound of formula (XXXI) is reacted with an acid of formula $R^1(C=O)Y$ in the presence of a dehydrating agent such as HOBt/EDAC, CDI, HATU, HOAT, propylphosphonic anhydride ($T_3P$), a suitably selected base such as DIPEA, TEA, and the like, in a solvent such as toluene, MeCN, EtOAc, DMF, THF, DCM, or a mixture thereof, to afford a compound of formula (XXXII). In a particularly preferred embodiment a compound of formula (XXXII) is obtained using the dehydrating agent HATU, the base TEA, and the solvent DMF. In another embodiment, a compound of formula (XXXI) is reacted with an acid of formula $R^1(C=O)Y$ in the presence of NaH in DMF at 60° C. Alternatively, a compound of formula (XXXI) is reacted with an acid chloride of formula $R^1(C=O)Y$ in the presence of base such as DIPEA, TEA, and the like, in an organic solvent such as toluene, MeCN, EtOAc, DMF, THF, DCM, and the like, to afford a compound of formula (XXXII). A compound of formula (XXXII) is cyclized to a compound of Formula (I), where X is N, in the presence of an acid, such as acetic acid, and the like, at 80° C. for 16 h.

SCHEME 14

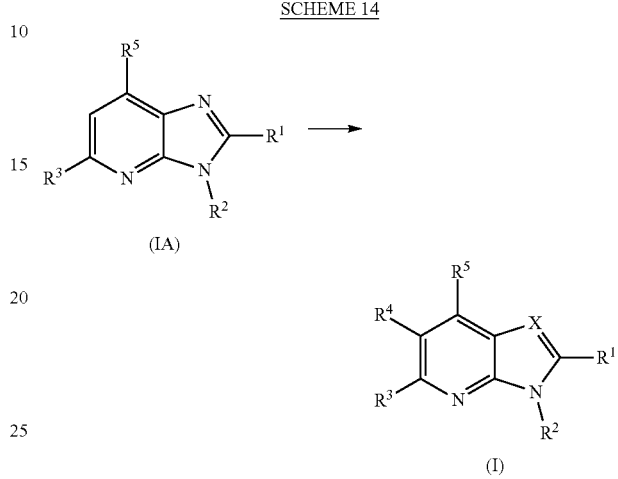

According to SCHEME 14, a compound of Formula (IA), where $R^3$ is $C_{1-5}$alkyl, and $R^5$ is H, is oxidized under conditions known to one skilled in the art, to afford a compound of Formula (I) where $R^5$ is —OH. For example, reaction of a compound of Formula (IA), where $R^1$ is 4-fluorophenyl, $R^2$ is benzo[d]thiazol-2(3H)-one, $R^3$ is —$CH^3$, $R^5$ is H, is oxidized with an oxidizing agent such as mCPBA, and the like, in a suitable solvent such as AcOH, and the like, at temperatures ranging from 100-130° C., employing microwave or conventional heating, provides a compound of Formula (I), where X is N, and $R^5$ is —OH.

A compound of Formula (IA), where $R^1$ is $C_{1-5}$haloalkyl, $R^3$ is halo, $R^5$ is H, is reacted in an iron-catalyzed cross coupling reaction, to provide a compound of Formula (I), where $R^3$ is $C_{1-5}$alkyl. For example, a compound of Formula (IA), where $R^3$ is —Cl, is reacted with a suitable iron catalyst such as iron (III) acetylacetonate (Fe(acac)$_3$), an alkylmagnesium reagent, an additive such as NMP, in a suitable solvent such as THF, and the like, to provide a compound of Formula (I), where X is N, $R^3$ is $C_{1-5}$alkyl. In a preferred method, the iron catalyst is Fe(acac)$_3$.

A compound of Formula (IA), where $R^3$ is halo, is reacted with a suitable amine in a nucleophilic displacement reaction under conditions known to one skilled in the art. For example, a compound of Formula (IA), where $R^3$ is —F, is reacted with a nucleophile such as piperidine, morpholine, —N(CH$_3$)$_2$, and the like, a base such as DIEA, and the like, in a suitable solvent such as DMSO, at temperatures ranging from 90-120° C., to provide a compound of Formula (I), where X is N, $R^3$ is piperidine.

A compound of Formula (IA), where $R^3$ and $R^5$ are H, and $R^1$ is phenyl, is difluoromethylated to provide a compound of Formula (I), where X is N, $R^3$ is —CHF$_2$, $R^5$ is H, and $R^1$ is phenyl; or where $R^3$ is H, $R^5$ is —CHF$_2$ and $R^1$ is phenyl; or where $R^3$ and $R^5$ are H and $R^1$ is 4-difluoromethylphenyl. For example, reaction of a compound of Formula (IA), where $R^3$ and $R^5$ are H, and $R^1$ is phenyl, with zinc difluoromethanesulfinate, tert-butyl hydroperoxide, in a suitable solvent such as DCE, DMSO, H$_2$O, or a mixture thereof, at a temperature of about 50-100° C., for a period of 24-73 h. In a similar method, a compound of Formula (IA) where $R^3$ and $R^5$ are H, and $R^1$ is phenyl, is alkylated using bis ((isopropylsulfinyl)oxy)zinc instead of zinc difluoromethanesulfinate, to provide a compound of Formula (I), where X is N, $R^3$ is H, $R^5$ is —CH(CH$_3$)$_2$ and $R^1$ is phenyl.

A compound of Formula (I) where X is N, $R^3$ is —CH$_2$OH, and $R^5$ is H, is prepared from a compound of Formula (IA), where $R^3$ is —CO$_2$H, and $R^5$ is H in two steps. Formula (IA), where $R^3$ is —CO$_2$H, and $R^5$ is H is first esterified, employing conditions known to one skilled in the art. For example, by reaction with a suitable acid, such asp-TsOH, H$_2$SO$_4$, and the like, in a suitable alcoholic solvent such as MeOH, EtOH and the like, at temperatures ranging from 50-80° C., to provide a compound of Formula (IA), where $R^3$ is —CO$_2$C$_{1-5}$alkyl, and $R^5$ is H. In a second step, reduction of an ester compound of Formula (IA), where $R^3$ is —CO$_2$C$_{1-5}$alkyl, and $R^5$ is H with a suitable reducing agent such as LAH, and the like, in a suitable solvent such as THF, and the like, provides a compound of Formula (I) where X is N, $R^3$ is —CH$_2$OH, and $R^5$ is H.

A compound of Formula (I) where X is N, $R^1$ is —CH$_2$CH$_2$CH$_2$OH, $R^3$ is —C$_{1-5}$haloalkyl, and $R^5$ is H, is prepared from a compound of Formula (IA), where $R^1$ is —CH$_2$CH$_2$CO$_2$CH$_3$, $R^3$ is —C$_{1-5}$haloalkyl, and $R^5$ is H, employing reduction conditions previously described. In a preferred method, the reducing agent is LAH and the solvent is THF.

A compound of Formula (I) where $R^1$ is —C(=O)NH(C$_{1-5}$alkyl), —C(=O)N(C$_{1-5}$alkyl)$_2$, —C(=O)azetidinyl, —C(=O)-pyrrolidinyl, or —C(=O)NH-phenyl, $R^3$ is —C$_{1-5}$haloalkyl, and $R^5$ is H is prepared from a compound of Formula (1A), where $R^1$ is C$_{1-5}$haloalkyl, $R^3$ is —C$_{1-5}$haloalkyl, and $R^5$ is H. For example, a compound of Formula (1A), where $R^1$ is —CCl$_3$, is reacted with an amine such as azetidine, aniline, —NH(C$_{1-5}$alkyl)$_2$, a base such as K$_2$CO$_3$, NaHCO$_3$, and the like, in a solvent such as ACN, THF, DMF, H$_2$O, or a mixture thereof, at temperatures ranging from 65-90° C., for a period of 12-24 h, to provide a compound of Formula (I), where X is N, $R^1$ is —C(=O)NH(C$_{1-5}$alkyl), —C(=O)N(C$_{1-5}$alkyl)$_2$, —C(=O)azetidinyl, —C(=O)-pyrrolidinyl, or —C(=O)NH-phenyl. In similar method, cyclopropyl amine was the amine, TEA is the base, and a coupling reagent such as HOBt is added.

A compound of Formula (1A) where $R^2$ is substituted with —Br, is reacted in a metal mediated cross coupling reaction to provide a compound of Formula (I), where $R^2$ is substituted with —C$_{1-5}$alkyl, —C$_{1-5}$alkenyl, —CH=CH—CH$_2$OH, and phenyl. For example, 3-(7-bromo-1H-indazol-5-yl)-2,5-bis(trifluoromethyl)-3H-imidazo[4,5-b]pyridine is reacted with a phenyl boronic acid, boronate ester, and the like, in the presence of a palladium catalyst such as PdCl$_2$(dtbpf), Pd(PPh$_3$)$_4$, and the like, a base such as K$_3$PO$_4$, aq. Na$_2$CO$_3$, and the like, in a suitable solvent such as 1,4-dioxane, DMF, and the like under microwave heating at 100° C., for a period of 30 min to provide a compound of Formula (I), specifically 3-(7-phenyl-1H-indazol-5-yl)-2,5-bis(trifluoromethyl)-3H-imidazo[4,5-b]pyridine. Where the boronate ester has a protecting group such as a THP installed, a deprotection step after the coupling step is necessary to afford a compound of Formula (I). In another example, 3-(7-bromo-1H-indazol-5-yl)-2,5-bis(trifluoromethyl)-3H-imidazo[4,5-b]pyridine can undergo a Stille reaction, with tributylvinyltin, and the like, in the presence of a palladium catalyst such as Pd(PPh$_3$)$_4$, and the like, in a suitable solvent such as toluene, and the like under microwave heating at 140° C., for a period of 45 min to provide a compound of Formula (I), specifically 2,5-bis(trifluoromethyl)-3-(7-vinyl-1H-indazol-5-yl)-3H-imidazo[4,5-b]pyridine.

A compound of Formula (IA), where $R^1$ and $R^3$ are C$_{1-5}$haloalkyl, $R^5$ is H, and $R^2$ is 1H-pyrazolo[3,4-b]pyridin-5-yl, is oxidized under conditions known to one skilled in the art, to provide the N-oxide compound of Formula (I), where X is N, $R^1$ and $R^3$ are C$_{1-5}$haloalkyl, $R^5$ is H, and $R^2$ is 1H-pyrazolo[3,4-b]pyridine 7-oxide. For example, 5-(2,5-bis(trifluoromethyl)-3H-imidazo[4,5-b]pyridin-3-yl)-1H-pyrazolo[3,4-b]pyridine is reacted with H$_2$O$_2$ and TFAA, in a solvent such as DCM, and the like, at temperatures ranging from 0° C. to room temperature, to provide 5-(2,5-bis(trifluoromethyl)-3H-imidazo[4,5-b]pyridin-3-yl)-1H-pyrazolo[3,4-b]pyridine 7-oxide.

A compound of Formula (IA), where $R^1$ is C$_{3-8}$cycloalkyl, $R^3$ is C$_{1-5}$haloalkyl, $R^5$ is H, and $R^2$ is benzo[d]thiazol-2(3H)-one is alkylated with an alkylating agent such as MeI, and the like, a base such as NaH, and the like, in a suitable solvent such as such as DMF, and the like, to provide a compound of Formula (I), where X is N, $R^1$ is C$_{3-8}$cycloalkyl, $R^3$ is C$_{1-5}$haloalkyl, $R^5$ is H, and $R^2$ is 3-methylbenzo[d]thiazol-2(3H)-one.

A compound of Formula (IA), where $R^1$ is C$_{1-5}$alkyl, $R^3$ is C$_{1-5}$haloalkyl, $R^5$ is H, and $R^2$ 1H-indazol-5-yl substituted with —Br, is tritiated, by reaction with Pd/C, $^3$H gas, in a suitable solvent such as EtOH, and the like, for a period of 8-12 h, to provide a compound of Formula (I), where X is N, $R^1$ is C$_{1-5}$alkyl, $R^3$ is C$_{1-5}$haloalkyl, $R^5$ is H, and $R^2$ 1H-indazol-5-yl substituted with $^3$H.

A compound of Formula (IA), where $R^1$ is C$_{1-5}$haloalkyl, $R^3$ is C$_{1-5}$haloalkyl, $R^5$ is H, and $R^2$ is substituted with —CH=CH—CH$_2$OH, is reduced, under hydrogenation conditions known to one skilled in the art, to provide a compound of Formula (I), where X is N, $R^1$ is C$_{1-5}$haloalkyl, $R^3$ is C$_{1-5}$haloalkyl, $R^5$ is H, and $R^2$ is substituted with —CH$_2$CH$_2$CH$_2$OH or —CH$_2$CH$_2$CH$_3$. In a preferred method, the reaction is performed in an H-Cube reactor, under 60 bar of H$_2$, in a suitable solvent such as MeOH or EtOH, and Pd/C as the catalyst. In a similar method, a compound of Formula (1A), where $R^1$ is C$_{1-5}$haloalkyl, $R^3$ is —CH=CH—CH$_2$OH, and $R^5$ is H is reduced to a compound of Formula (I) where X is N, $R^1$ is C$_{1-5}$haloalkyl, $R^3$ is —CH$_2$CH$_2$CH$_2$OH or —CH$_2$CH$_2$CH$_3$, and $R^5$ is H.

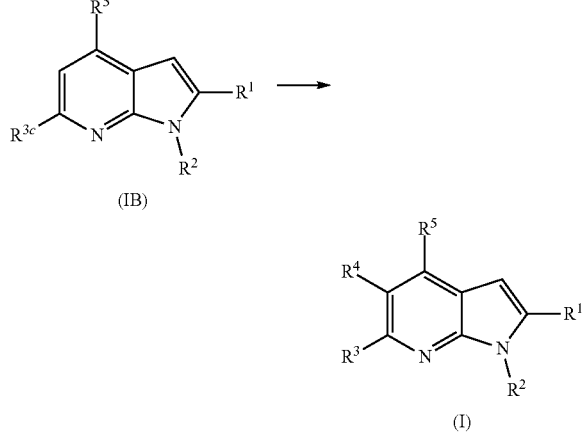

SCHEME 15

According to SCHEME 15, a compound of Formula (IB), where $R^{2a}$ is a trimethylsilyl protected 1H-indazole, benzo

[d]thiazol-2(3H)-one, 1H-pyrazolo[3,4-b]pyridinyl, where each $R^{2a}$ is optionally substituted with halo, or $C_{1-5}$alkyl, is deprotected with acid such as TFA, HCl, and the like, in a suitable solvent such as DCM, and the like, to provide a compound of Formula (I), where X is N and $R^2$ is 1H-indazole, benzo[d]thiazol-2(3H)-one, 1H-pyrazolo[3,4-b]pyridinyl, where each $R^2$ is optionally substituted with halo, or $C_{1-5}$alkyl.

A compound of Formula (IB), where $R^1$ is $C_{3-8}$cycloalkyl, $R^{3c}$ is —OH, $R^5$ is H, and $R^{2a}$ is a trimethylsilyl protected 1H-indazole, benzo[d]thiazol-2(3H)-one, 1H-pyrazolo[3,4-b]pyridinyl, where each $R^{2a}$ is optionally substituted with halo, or $C_{1-5}$alkyl, is alkylated under conditions known to one skilled in the art, for example, reaction with an alkylating agent such as MeI, and the like, a base such as NaH, LiH and the like, in a suitable solvent such as DMF, and the like, at temperatures ranging from 0° C. to room temperature, to provide a compound of Formula (IB) where $R^{3c}$ is —$C_{1-5}$alkoxy. Subsequent trimethylsilyl deprotection of a compound of Formula (IB), employing conditions previously described, provides a compound of Formula (I), where X is N, $R^1$ is $C_{3-5}$cycloalkyl, $R^3$ is —$C_{1-5}$alkoxy, $R^5$ is H, and $R^2$ is 1H-indazole, benzo[d]thiazol-2(3H)-one, or 1H-pyrazolo[3,4-b]pyridine each optionally substituted with halo, or $C_{1-5}$alkyl.

A compound of Formula (IB), where $R^1$ is $C_{1-5}$haloalkyl, $R^{3c}$ is halo, $R^5$ is H, and $R^{2a}$ is a trimethylsilyl protected 1H-indazole, is reacted in a metal mediated cross coupling reaction with an alkylzinc halide to provide a compound of Formula (IB), where $R^{3c}$ is $C_{3-8}$cycloalkyl. For example, reaction of a compound of Formula (IB), where $R^1$ is $C_{1-5}$haloalkyl, $R^{3c}$ is halo, $R^5$ is H, and $R^{2a}$ is a trimethylsilyl protected 1H-indazole with a palladium catalyst such as Pd(OAc)$_2$, a ligand such as Ru-Phos, and the like, in a suitable solvent such as THF, and the like, provides a compound of Formula (IB), where $R^1$ is $C_{1-5}$haloalkyl, $R^{3c}$ is $C_{3-8}$cycloalkyl, $R^5$ is H, and $R^{2a}$ is a trimethylsilyl protected 1H-indazole. Deprotection of the trimethylsilyl protecting group employing conditions previously described provides a compound of Formula (I), where X is N, $R^1$ is $C_{1-5}$haloalkyl, $R^3$ is $C_{3-8}$cycloalkyl, $R^5$ is H, and $R^2$ is 1H-indazole.

A compound of Formula (IB), where $R^1$ is $C_{1-5}$alkyl, $R^{2a}$ is a trimethylsilyl protected 1H-indazole, $R^{3c}$ is —C(=O)N(CH$_3$)OCH$_3$, and $R^5$ is H, is reacted with methylmagnesium bromide, in a solvent such as THF, at temperatures ranging from −45 to 0° C., to provide a compound of Formula (IB), where $R^1$ is $C_{1-5}$alkyl, $R^{2a}$ is a trimethylsilyl protected 1H-indazole, $R^{3c}$ is —C(=O)CH$_3$, and $R^5$ is H. A compound of Formula (IB), where $R^1$ is $C_{1-5}$alkyl, $R^{2a}$ is a trimethylsilyl protected 1H-indazole, $R^{3c}$ is —C(=O)CH$_3$, and $R^5$ is H, is fluorinated under conditions previously described to provide a compound of Formula (IB), where $R^1$ is $C_{1-5}$alkyl, $R^{2a}$ is a trimethylsilyl protected 1H-indazole, $R^{3c}$ is —CF$_2$CH$_3$, and $R^5$ is H. In a preferred method, the fluorinating agent is DAST. A compound of Formula (IB), where $R^1$ is $C_{1-5}$alkyl, $R^{2a}$ is a trimethylsilyl protected 1H-indazole, $R^{3c}$ is —CF$_2$CH$_3$, and $R^5$ is H is deprotected employing conditions previously described to provide a compound of Formula (I), where X is N, $R^1$ is $C_{1-5}$alkyl, $R^2$ is 1H-indazole, $R^3$ is —CF$_2$CH$_3$, and $R^5$ is H.

SCHEME 16

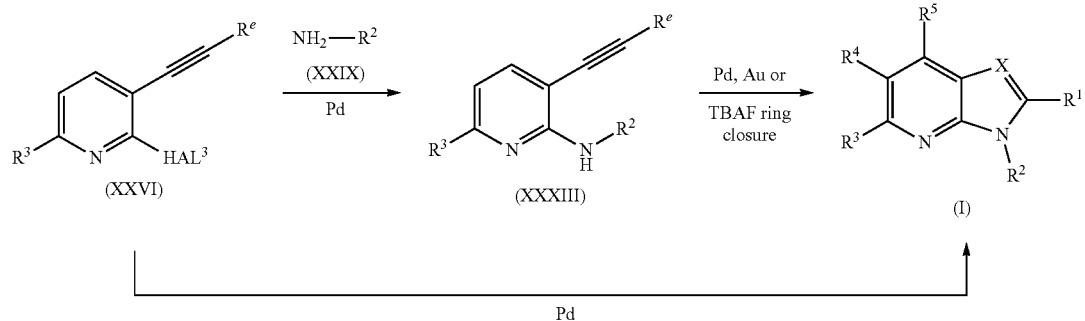

According to SCHEME 16, a compound of formula (XXVI), where $R^3$ is H, halo, $C_{1-5}$alkyl, $C_{1-5}$haloalkyl, or $C_{1-5}$alkoxy, and HAL$^3$ is —Br or —Cl, is reacted in a one-pot metal mediated $S_NAr$ with an amine compound of formula (XXIX), and cyclization of the intermediate amino alkynyl pyridine. A compound of formula (XXVI) in the presence of a palladium catalyst such as BrettPhos Pd third generation precatalyst, Pd$_2$(dba)$_3$, and the like, with or without a ligand such as XantPhos, XPhos, DavePhos, and the like, a base such as Cs$_2$CO$_3$, K$_2$CO$_3$ and the like, in a suitable solvent such as 1,4-dioxane, toluene, and the like at temperatures ranging from 100-110° C., for a period of 3 to 18 h, provides a compound of Formula (I), where $R^3$ is H, halo, $C_{1-5}$alkyl, $C_{1-5}$haloalkyl, or $C_{1-5}$alkoxy, and $R^1$ is $C_{1-5}$alkyl, $C_{1-5}$haloalkyl, —CH$_2$OCH$_3$, —CH(OCH$_3$)(CH$_3$), $C_{3-8}$cycloalkyl, tetrahydrofuran, —CH$_2$O-tetrahydropyran, phenyl, or 4-fluorophenyl.

Alternatively, in a two-step procedure, starting from a compound of formula (XXVI) affords a compound of Formula (I) through an alkynyl pyridine compound of formula (XXXIII). A compound of formula (XXXIII), is accessible from a compound of formula (XXIV) and a compound of formula (XXIX) NH$_2$—$R^2$, in the presence of a palladium catalyst such as BrettPhos Pd third generation precatalyst and the like, a base such as Cs$_2$CO$_3$, K$_2$CO$_3$ and the like, in a suitable solvent such as 1,4-dioxane, toluene, and the like at temperatures ranging from 100-120° C., for a period of 12 to 96 h, to provide a compound of formula (XXXIII). A compound of formula (XXXIII) undergoes a ring closure under the Pd mediated conditions above or in the presence of a gold catalyst such as AuCl$_3$, and the like, in a solvent such as EtOH, MeOH, and the like at 80° C., for a period of 30 min, to provide a compound of Formula (I), where X is CH. Ring closure can also be accomplished by the use of a reagent such as TBAF.

SCHEME 17

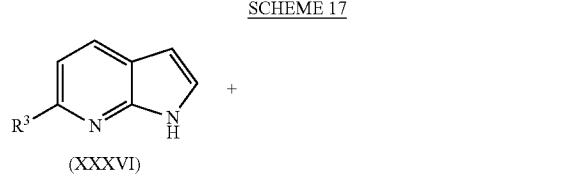

(XXXVI)

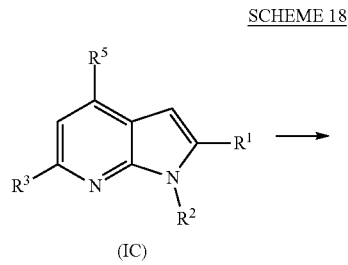

[M] Cross coupling

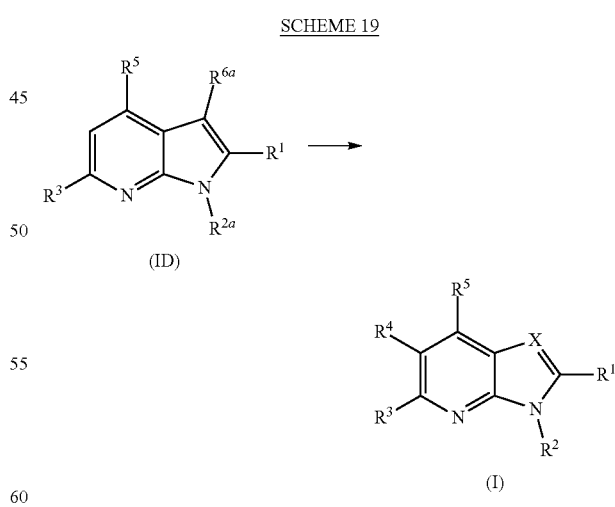

(ID)

According to SCHEME 17, a compound of Formula (1D) is accessible from a metal mediated cross-coupling reaction of a compound of formula (XXXVI), where $R^3$ is $C_{1-5}$alkyl or $C_{1-5}$haloalkyl, with, 5-bromo-7-methyl-1-((2-(trimethylsilyl)ethoxy)methyl)-1H-indazole or 5-bromo-7-methyl-2-((2-(trimethylsilyl)ethoxy)methyl)-2H-indazole, in the presence of a palladium catalyst such as [Pd(II)(n-Cinnamyl)Cl]$_2$ and the like, a ligand such as BippyPhos, a base such as NaOtBu, and the like, in a suitable solvent such as 1,4-dioxane, with microwave heating at 150-180° C., for a period of 30 min.

SCHEME 18

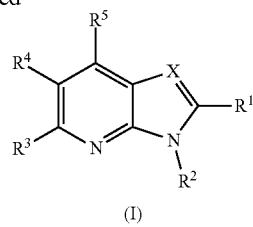

(I)

According to SCHEME 18, a hydroxymethyl compound of Formula (IC), where $R^1$ is $CH_2OH$, is mesylated, then reduced to provide a compound of Formula (I), where X is CH, $R^1$ is $C_{1-5}$alkyl, and $R^3$ is H, halo, $C_{1-5}$alkyl, $C_{1-5}$alkoxy, or $C_{1-5}$haloalkyl. In a preferred mesylation method, the mesylating agent is methanesulfonyl chloride, the base is DIEA, and the solvent is DCM. In a preferred reduction method, the reducing conditions are Pd/C, under an $H_2$ atmosphere, in a solvent such as MeOH.

A hydroxymethyl compound of Formula (IC) where $R^1$ is $CH_2OH$, is oxidized to an aldehyde of Formula (IC) where $R^1$ is CHO, employing oxidation conditions known to one skilled in the art, for example, DMP (Dess-Martin periodinane), $SO_3$-pyridine, Swern conditions [(COCl)$_2$, DMSO, Et$_3$N], PCC, and the like, in a solvent such as EtOAc, DMSO, DCM, and the like, at temperatures ranging from about –78° C. to room temperature. In a preferred method, a compound of Formula (IC) is oxidized with Dess-Martin periodinane, in DCM, at 20° C. for 1 h. A carbonyl compound of Formula (IC) where $R^1$ is CHO, is fluorinated with a fluorinating agent such as, DAST, XtalFluor®, Deoxo-Fluor®, and the like, in a suitable solvent such as DCM, and the like, at temperatures ranging from –78° C. to 50° C., for a period of 2-16 h. In a preferred method, a Formula (IC) where $R^1$ is CHO, is reacted with the a fluorinating agent such as DAST, in a solvent suitable solvent such as DCM, at 0 to 30° C., for 5 h, to provide a compound of Formula (I), where X is CH, and $R_1$ is $CHF_2$.

SCHEME 19

According to SCHEME 19. a compound of Formula (1D), where $R^3$ is $C_{1-5}$haloalkyl, $R^1$ and $R^{6a}$ are H, and $R^{2a}$ is a trimethylsilyl protected 1H-indazole optionally substituted with halo, or $C_{1-5}$alkyl, is reacted under Vilsmeier-Haack formylation conditions (POCl$_3$, DMF), to provide a compound of Formula (1D) where $R^1$ is H, $R^3$ is $C_{1-5}$haloalkyl, $R^{2a}$ is a trimethylsilyl protected 1H-indazole optionally substituted with halo or $C_{1-5}$alkyl, and $R^{6a}$ is C(=O)H. An additional product of the Vilsmeier-Haack reaction is a compound of Formula (I), where X is $CR^6$, $R^6$ is H, $R^1$ is H, $R^3$ is $C_{1-5}$haloalkyl, and $R^2$ is 1H-indazole optionally substituted with $C_{1-5}$alkyl. Deprotection of the trimethylsilyl protecting group of a compound of Formula (1D) employing conditions previously described provides a compound of Formula (1D) where $R^1$ is H, $R^3$ is $C_{1-5}$haloalkyl, $R^{2a}$ is 1H-indazole optionally substituted with halo or $C_{1-5}$alkyl, and $R^{6a}$ is C(=O)H. Baeyer-Villiger reaction of a compound of Formula (1D) where $R^1$ is H, $R^3$ is $C_{1-5}$haloalkyl, $R^{2a}$ is 1H-indazole optionally substituted with $C_{1-5}$alkyl, with mCPBA and removal of the resultant acetate group affords a compound of Formula (I), where X is $CR^6$, $R^6$ is —OH, $R^1$ is H, $R^3$ is $C_{1-5}$haloalkyl, and $R^2$ is 1H-indazole optionally substituted with $C_{1-5}$alkyl.

A compound of Formula (1D) where $R^1$ is H, $R^3$ is $C_{1-5}$haloalkyl, $R^{2a}$ is a trimethylsilyl protected 1H-indazole optionally substituted with halo or $C_{1-5}$alkyl, and $R^{6a}$ is C(=O)H. Alternatively, the aldehyde functionality in a compound of formula (XIII), is fluorinated with a fluorinating agent such as, DAST, XtalFluor®, Deoxo-Fluor®, and the like, in a suitable solvent such as DCM, and the like, at temperatures ranging from −78° C. to 50° C., for a period of 2-16 h. In a preferred method, a compound of Formula (1D) where $R^1$ is H, $R^3$ is $C_{1-5}$haloalkyl, $R^{2a}$ is a trimethylsilyl protected 1H-indazole optionally substituted with $C_{1-5}$alkyl, is reacted with the a fluorinating agent such as DAST, in a solvent suitable solvent such as DCM, at 0 to 50° C., for 16 h, to provide a compound of Formula (ID) where X is $CR^6$, $R^6$ is —$C_{1-5}$haloalkyl, $R^1$ is H, $R^3$ is $C_{1-5}$haloalkyl, $R^{2a}$ is a trimethylsilyl protected 1H-indazole optionally substituted with $C_{1-5}$alkyl. Deprotection of the trimethylsilyl protecting group of a compound of Formula (1D) employing conditions previously described provides a compound of Formula (1), X is $CR^6$, $R^6$ is —$C_{1-5}$haloalkyl, $R^1$ is H, $R^3$ is $C_{1-5}$haloalkyl, and $R^2$ is 1H-indazole optionally substituted with halo or $C_{1-5}$alkyl.

compound of formula (XXXIV) in two steps. In the first step, a compound of formula (XXXIV) is brominated to tribromo intermediate (XXXV), using pyridinium tribromide in tBuOH at 20° C. for 2-3 h. Intermediate (XXXV) is used directly in the second step without isolation. The tribromide intermediate (XXXV) can be reduced with a reducing agent, such as zinc dust, in a solvent such as acetic acid, and the like, at 20° C., for a period of 30 min to 1 h. In a preferred method, a compound of formula (XXXV) is reacted with zinc dust in acetic acid at 20° C. for 30 min to provide a compound of Formula (I), where X is C—$R^6$, $R^6$ is Br, $R^1$ is $C_{1-5}$alkyl, $C_{1-5}$haloalkyl, —$CH_2OCH_3$, —CH(OCH$_3$)(CH$_3$), $C_{3-8}$cycloalkyl, tetrahydrofuran, —$CH_2O$-tetrahydropyran, phenyl, or 4-fluorophenyl, $R^3$ is H, halo, $C_{1-5}$alkyl, $C_{1-5}$alkoxy, or $C_{1-5}$haloalkyl, and $R^2$ is indolin-2-one. In an alternate method, a compound of formula (XXXIV) is oxidized with pyridinium tribromide in a solvent such as water, AcOH, or a mixture thereof, at temperatures ranging from 80-90° C., for a period of 16-24 hr, to provide a compound of Formula (I), were X is C—$R^6$ and $R^6$ is H.

The incorporation of $^{18}F$ or $^{19}F$ in a compound of Formula (I), where $R^1$ is pyridinyl substituted with —Cl, —Br, —F, is carried out according to a method such as that described in Example 444 and 445. In a like manner, other compounds of Formula (I) can be prepared for use in PET studies.

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, $CH_3OH$, chloroform, or isopropanol to provide the corresponding salt form. Alternately, trifluoroacetic acid or formic acid salts are obtained as a result of reverse phase HPLC purification conditions. Cyrstalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

SCHEME 20

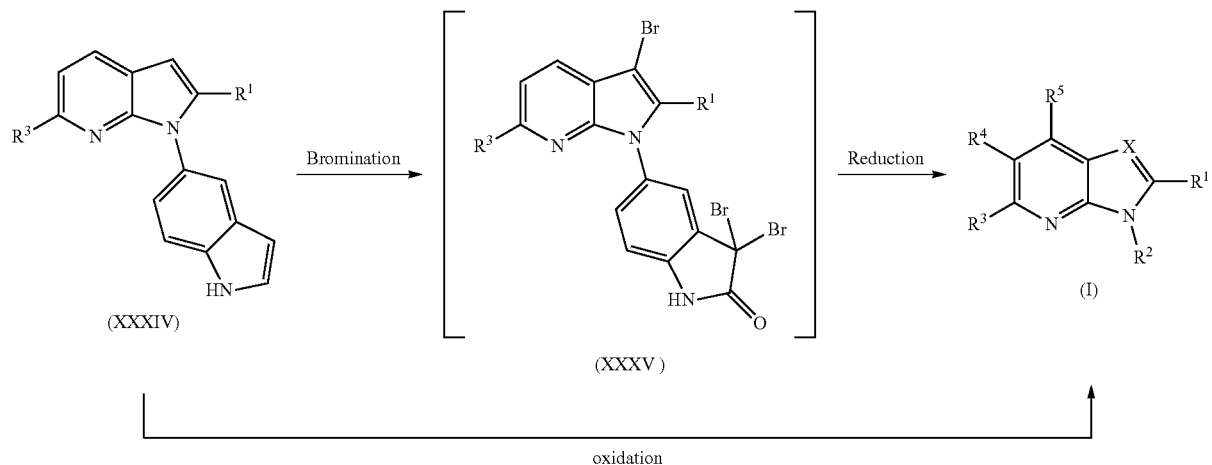

According to SCHEME 20, a compound of Formula (I), where $R^3$ is H, halo, $C_{1-5}$alkyl, $C_{1-5}$alkoxy, or $C_{1-5}$haloalkyl, $R^1$ is $C_{1-5}$alkyl, $C_{1-5}$haloalkyl, —$CH_2OCH_3$, —CH(OCH$_3$)(CH$_3$), $C_{3-5}$cycloalkyl, tetrahydrofuran, —$CH_2O$-tetrahydropyran, phenyl, or 4-fluorophenyl, is accessible from a Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE (PolyTetraFluoroEthylene) tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

Quality control testing includes identity, chemical, and radiochemical purity by HPLC using an XBridge C18 (5 μm, 4.6×250 mm) column eluted with a mixture of methanol/ammonium acetate 5 mM, 65/35, v/v at a flow rate of 1 mL/min equipped with serial UV (280 nm) and gamma detection.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

Intermediate 1:
2-Chloro-6-cyclopropyl-3-nitropyridine

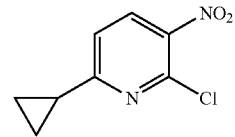 [SMILES: O=[N+]([O-])c1ccc(C2CC2)nc1Cl]

Step A: 2-Nitroacetamide

Ethyl nitroacetate (5.6 mL, 50.5 mmol) was added to ammonium hydroxide (28% in water, 34 mL, 505 mmol) and this was stirred for four days at rt. The reaction was cooled to 0° C. and acidified to pH=1 with concentrated HCl. This was extracted with EtOAc (×3) and the combined extracts were dried ($Na_2SO_4$), filtered, and concentrated in vacuo to give a white solid (3.95 g, 75%). $^1H$ NMR (500 MHz, DMSO-$d_6$) δ 7.84 (s, 1H), 7.62 (s, 1H), 5.28 (s, 2H).

Step B: (E)-1-Cyclopropyl-3-(dimethylamino)prop-2-en-1-one

1-Cyclopropylethanone (5.0 mL, 50.5 mmol) and 1,1-dimethoxy-N,N-dimethylmethanamine (6.7 mL, 50.5 mmol) were combined. p-Toluenesulfonic acid (87 mg, 0.505 mmol) was added and the reaction was stirred at 100° C. for 16 h. The reaction was concentrated and the crude material was carried on to the next step without purification. $^1$H NMR (500 MHz, CDCl$_3$) δ 7.56 (d, J=12.6 Hz, 1H), 5.20 (d, J=12.6 Hz, 1H), 3.45 (s, 6H), 1.80 (tt, J=7.9, 4.6 Hz, 1H), 1.06-0.95 (m, 2H), 0.75 (dt, J=7.9, 3.4 Hz, 2H).

Step C: 6-Cyclopropyl-3-nitropyridin-2(1H)-one

2-Nitroacetamide (3.95 g, 38.0 mmol) was taken up in water (4.4 mL, 244 mmol) and piperidinium acetate (2.2 g, 15.2 mmol). To this was added (E)-1-cyclopropyl-3-(dimethylamino)prop-2-en-1-one (5.28 g, 38.0 mmol) and the reaction was stirred at rt for 16 h. The precipitate was filtered and washed with water and hexanes to provide the title compound as a light yellow powder (1.06 g, 15.5%). The filtrate was then extracted with DCM (×3) and the combined organics were dried (Na$_2$SO$_4$), filtered, and concentrated. Purification (FCC, SiO$_2$, 0-100% EtOAc in hexanes) afforded the title compound (1.80 g, 26%). MS (ESI): mass calcd. for C$_8$H$_8$N$_2$O$_3$ 180.1, m/z found 181.0 [M+H]$^+$. $^1$H NMR (500 MHz, DMSO-d$_6$) δ 12.89 (s, 1H), 8.35 (d, J=8.3 Hz, 1H), 5.96 (d, J=8.3 Hz, 1H), 2.00 (tt, J=8.3, 5.0 Hz, 1H), 1.30-1.16 (m, 2H), 1.12-0.95 (m, 2H).

Step D: 2-Chloro-6-cyclopropyl-3-nitropyridine

6-Cyclopropyl-3-nitropyridin-2(1H)-one (0.99 g, 5.48 mmol) and phosphorus oxychloride (4.45 mL, 47.8 mmol) were stirred at 85° C. for 16 h. The reaction was concentrated then diluted with sat. aq. NaHCO$_3$ and extracted with EtOAc (×3). The combined organic extracts were dried (Na$_2$SO$_4$), filtered, and concentrated. Purification (FCC, SiO$_2$, 0-30% EtOAc in hexanes) afforded the title compound as a white solid (0.85 g, 78%). MS (ESI): mass calcd. for C$_8$H$_7$ClN$_2$O$_2$ 198.6, m/z found 199.0 [M+H]$^+$. $^1$H NMR (400 MHz, CDCl$_3$) δ 8.13 (d, J=8.3 Hz, 1H), 7.27 (d, J=8.3 Hz, 1H), 2.13 (ddd, J=12.7, 7.5, 5.4 Hz, 1H), 1.30-1.05 (m, 4H).

Intermediate 2:
6-(tert-Butyl)-2-chloro-3-nitropyridine

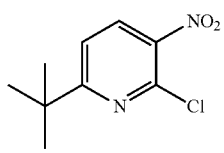

The title compound was prepared in a manner analogous to Intermediate 1. MS (ESI): mass calcd. for C$_9$H$_{11}$ClN$_2$O$_2$, 214.0, m/z found 215.0 [M+H]$^+$. $^1$H NMR (500 MHz, CDCl$_3$) δ 8.16 (d, J=8.3 Hz, 1H), 7.42 (d, J=8.3 Hz, 1H), 1.39 (s, 9H).

Intermediate 3:
2-Chloro-6-isopropyl-3-nitropyridine

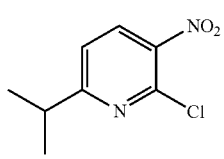

The title compound was prepared in a manner analogous to Intermediate 1. MS (ESI): mass calcd. for C$_8$H$_9$ClN$_2$O$_2$, 200.0, m/z found 201.0 [M+H]$^+$. $^1$H NMR (500 MHz, CDCl$_3$) δ 8.17 (d, J=8.2 Hz, 1H), 7.28 (d, J=8.3 Hz, 1H), 3.18-3.11 (m, 1H), 1.33 (d, J=6.9 Hz, 6H).

Intermediate 4: 6-Chloro-5-nitropyridin-2(1H)-one

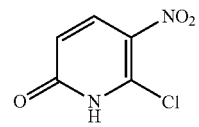 [SMILES: O=c1ccc([N+](=O)[O-])c(Cl)[nH]1]

A solution of 2-chloro-6-methoxy-3-nitropyridine (5.0 g, 26.5 mmol) in conc hydrochloric acid (40 mL) was heated at 120° C. for 6 h. The reaction was then cooled to rt and poured onto ice. When the ice has melted, dark brown solid was filtered, washed with water and air-dried on the filter for 2 h to give the title compound (2.8 g, 60%). MS (ESI): mass calcd. for C$_5$H$_3$ClN$_2$O$_3$, 174.5 m/z found, 175.5 [M+H]$^+$. $^1$H NMR (500 MHz, DMSO-d$_6$) δ 13.10 (s, 1H), 8.42 (d, J=8.8 Hz, 1H), 6.80 (d, J=8.9 Hz, 1H).

Intermediate 5: 6-Amino-4-chlorobenzo[d]thiazol-2(3H)-one

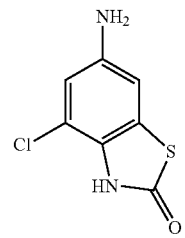 [SMILES: Nc1cc(Cl)c2[nH]c(=O)sc2c1]

Step A: 4-Chloro-6-nitrobenzo[d]thiazol-2(3H)-one

A solution of 4-chlorobenzo[d]thiazol-2(3H)-one (1.5 g, 8.1 mmol) in H$_2$SO$_4$ (10 mL) was cooled to −50° C. in an acetonitrile dry ice bath. Fuming HNO$_3$ (0.4 mL, 8.9 mmol) was added dropwise to the solution over several minutes and the reaction was allowed to warm to rt. The reaction was poured into ice water and let stir for 30 min. The resulting precipitate was filtered. Purification (FCC, SiO$_2$, EtOAc/hexanes) afforded the title compound (0.6 g, 32%). $^1$H NMR (400 MHz, DMSO-d$_6$) δ 13.06-12.73 (s, 1H), 8.71-8.64 (d, J=2.3 Hz, 1H), 8.33-8.18 (d, J=2.3 Hz, 1H).

Step B: 6-Amino-4-chlorobenzo[d]thiazol-2(3H)-one

To a solution of 4-chloro-6-nitrobenzo[d]thiazol-2(3H)-one (0.25 g, 1.1 mmol) in EtOH (50 mL) and sat. NHCl$_4$ (4 mL) was added Zinc dust (0.70 g, 11 mmol). The reaction was heated at 60° C. for 3 h then filtered through a pad of Celite® and washed with DCM. The filtrate was concentrated in vacuo and diluted with EtOAc and H$_2$O. The organic layer was separated, dried, and concentrated to give the desired product (0.075 g, 35%). MS (ESI): mass calcd. for C$_7$H$_5$ClN$_2$OS, 199.9 m/z found, 200.9 [M+H]$^+$.

Intermediate 6: 6-Amino-4-methylbenzo[d]thiazol-2(3H)-one

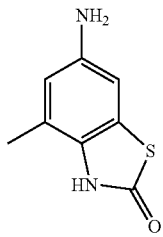

The title compound was prepared in a manner analogous to Intermediate 5. MS (ESI): mass calcd. for $C_8H_8N_2OS$, 180.04 m/z found, 181.0 $[M+H]^+$.

Intermediate 7: 6-Amino-4-bromobenzo[d]oxazol-2(3H)-one

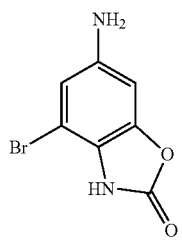

The title compound was prepared in a manner analogous to Intermediate 5. MS (ESI): mass calcd. for $C_7H_5BrN_2O_2$, 227.95 m/z found, 228.9 $[M+H]^+$.

Intermediate 8: 6-Amino-4-fluorobenzo[d]oxazol-2(3H)-one

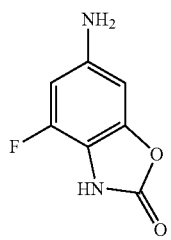 [SMILES: Nc1cc(F)c2[nH]c(=O)oc2c1]

The title compound was prepared in a manner analogous to Intermediate 5. MS (ESI): mass calcd. for $C_7H_5FN_2O_2$, 168.03 m/z found, 169.05 $[M+H]^+$.

Intermediate 9: 2-((2-(Trimethylsilyl)ethoxy)methyl)-2H-indazol-5-amine

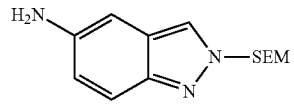 [SMILES: C[Si](C)(C)CCOCn1cc2cc(N)ccc2n1]

Step A: 5-Nitro-2-((2-(trimethylsilyl)ethoxy)methyl)-2H-indazole

NaH (60% dispersion in mineral oil, 3.2 g, 79 mmol) was added in one portion to a cooled solution of 5-nitro-1H-indazole (10 g, 61 mmol) in DMF (150 mL) at 0° C. under $N_2$. The resulting mixture was kept stirring at 0° C. for 10 minutes, then to it SEM-Cl (14.3 mL, 72.8 mmol) was added dropwise and the resulting mixture was stirred at 0° C. for 1 h. The mixture was allowed to warm to ambient temperature and stirred for 2 h. The reaction mixture was diluted with $H_2O$ and extracted with EtOAc (100 mL×3). The organic layer was dried ($Na_2SO_4$) and concentrated in vacuo to give the title compound and its regioisomer (31 g, 100%). MS (ESI): mass calcd. for $C_{13}H_{19}N_3O_3Si$, 293.1, m/z found, 294.0 $[M+H]^+$.

Step B: 2-((2-(Trimethylsilyl)ethoxy)methyl)-2H-indazol-5-amine

A solution of 5-nitro-2-((2-(trimethylsilyl)ethoxy)methyl)-2H-indazole (18 g, 61 mmol), 10% Pd/C (1.8 g) and EtOH (125 mL) in a 250 mL flask was placed under a $H_2$ balloon and stirred overnight. The reaction was filtered through Celite® and the resulting solution was concentrated in vacuo. Purification (FCC, $SiO_2$, EtOAc:DCM) afforded the title compound and its regioisomer (16.7 g, 92.8%). MS (ESI): mass calcd. for $C_{13}H_{21}N_3OSi$, 263.1; m/z found, 264.1 $[M+H]^+$.

Intermediate 10: 5-Amino-7-methylindolin-2-one

Step A: 7-Methyl-5-nitroindolin-2-one

A round bottom flask charged with 7-methyloxindole (2 g, 13.6 mmol) was suspended in concentrated sulfuric acid (27 mL) under ambient atmosphere with a drying tube installed, and the reaction mixture was cooled to −50° C. While stirring, a solution of fuming nitric acid (90% ACS reagent grade) (0.5 mL, 12 mmol) in concentrated sulfuric acid (7 mL) was added dropwise over 5 minutes. Upon completion of reagent addition, the cooling bath was removed, and the reaction was warmed to 20° C. with rapid stirring. The suspension was quenched by pouring onto ice (200 mL). The resulting light brown precipitate was collected over filter paper, washed with water, and dried under a gentle stream of air for 18 h to provide the title compound as a light tan solid (2.37 g, 91%). MS (ESI): mass calcd. for $C_9H_8N_2O_3$ 192.0, m/z found 193.1 $[M+H]^+$. $^1$H NMR (500 MHz, DMSO-$d_6$) δ 11.08 (s, 1H), 8.02-8.00 (dt, J=1.5, 0.8 Hz, 1H), 7.94 (s, 1H), 3.65 (s, 2H), 2.30 (s, 3H).

Step B: 5-Amino-7-methylindolin-2-one

To a flask containing 7-methyl-5-nitro-2-oxindole (2.37 g, 12.3 mmol) was added EtOH (123 mL), EtOAc (123 mL), and Pd/C (10%) (1.31 g). The suspension was placed under nitrogen atmosphere, then pressurized with hydrogen gas from a balloon and stirred vigorously at 20° C. After 2 hr at 20° C., all of the starting oxindole appeared to have dissolved. The reaction was placed under nitrogen gas and diluted with EtOAc (100 mL) and EtOH (100 mL). The resulting suspension was filtered through Celite® 545, and the organics were concentrated under reduced pressure to provide the title compound (1.02 g, 51%) as a powdery pink solid. MS (ESI): mass calcd. for $C_9H_{10}N_2O$ 192.0, m/z found 193.1 [M+H]$^+$. $^1$H NMR (500 MHz, DMSO-$d_6$) δ 9.96 (s, 1H), 6.32 (d, J=2.1 Hz, 1H), 6.20 (d, J=1.5 Hz, 1H), 4.56 (br. s., 2H), 3.30 (s, 2H), 2.05 (s, 3H).

Intermediate 11: tert-Butyl 5-amino-1H-indole-1-carboxylate

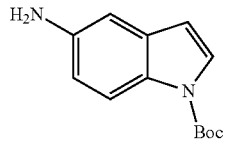

Step A: tert-Butyl 5-nitro-1H-indole-1-carboxylate

Di-tert-butyl dicarbonate (8.07 g, 37.0 mmol) was slowly added to a stirred solution of 5-nitroindole (6.00 g, 37.0 mmol) and 4-dimethylaminopyridine (226 mg, 1.85 mmol) in THF (60 mL) at 0° C. The mixture was then stirred for 3 h at 20° C. The reaction solution was concentrated in vacuo and the residue was dissolved in DCM (150 mL). The organic layer was washed with water, brine, dried (MgSO$_4$), filtered, and the solvent evaporated in vacuo to yield the title compound (9.60 g, 99%).

Step B: tert-Butyl 5-amino-1H-indole-1-carboxylate

A solution of tert-butyl 5-nitro-1H-indole-1-carboxylate (9.60 g, 36.6 mmol) in THF (125 mL) and EtOH (125 mL) was degassed by bubbling through nitrogen gas and 10% Pd/C (1.00 g, 0.94 mmol) was added. The resulting suspension was stirred at 20° C. under an atmosphere of hydrogen gas for 24 h. The suspension was filtered through a pad of Celite® 545, and the filtrate was concentrated in vacuo to give the title compound (8.45 g, 99%) as a thick yellow oil. MS (ESI): mass calcd. for $C_{13}H_{16}N_2O_2$ 232.1, m/z found 233 [M+H]$^+$.

Intermediate 12: tert-Butyl 5-aminoindoline-1-carboxylate

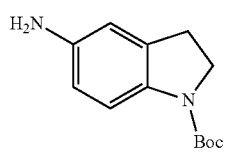

To a solution of tert-butyl 5-nitro-1H-indole-1-carboxylate (Step A, Intermediate 11, 1.49 g, 5.68 mmol) in methanol (30 mL) under nitrogen atmosphere was added 5% Pd/C (149 mg). The resulting suspension was stirred at 20° C. under an atmosphere of hydrogen gas for 24 hr. The suspension was filtered through a pad of Celite® 545, and the filtrate was concentrated in vacuo to give the title compound (1.3 g, 98%), which was used in the next step without further purification.

Intermediate 13: 5-Bromo-7-methyl-2-((2-(trimethylsilyl)ethoxy)methyl)-2H-indazole

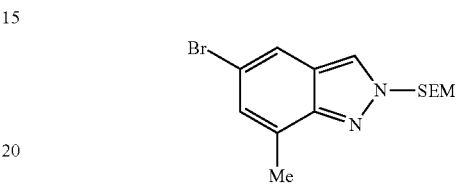

The title compound was prepared in a manner analogous to Intermediate 9, Step A using 5-bromo-7-methyl-1H-indazole. MS (ESI): mass calcd. for $C_{14}H_{21}BrN_2OSi$ 340.1, m/z found 341.1 [M+H]$^+$.

Intermediate 14: 7-Methyl-1-((2-(trimethylsilyl)ethoxy)methyl)-1H-indazol-5-amine

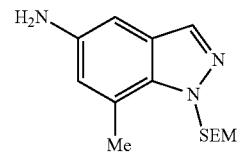 [SMILES: Cc1cc(N)cc2cnn(COCC[Si](C)(C)C)c12]

Method A:

Step A: 2-Bromo-6-methyl-4-nitroaniline

To a suspension of 2-methyl-4-nitroaniline (10.0 g, 65.7 mmol) in glacial acetic acid (100 mL) at 20° C. was added bromine (3.4 mL, 66 mmol) dropwise over 40 min. The mixture was stirred at 20° C. for another 30 min. Then water (100 mL) was added, and the resulting precipitate was collected by filtration and dried in vacuo at 80° C. for 6 h to yield the title compound (14.1 g, 99%) as a yellow solid. MS (ESI): mass calcd. for $C_7H_7BrN_2O_2$ 230.0, m/z found 231 [M+H]$^+$. $^1$H NMR (300 MHz, DMSO-$d_6$) δ 8.13 (d, J=2.2 Hz, 1H), 7.89 (d, J=1.5 Hz, 1H), 6.48 (s, 2H), 2.22 (s, 3H).

Step B: 7-Bromo-5-nitro-1H-indazole

To a solution of 2-bromo-6-methyl-4-nitroaniline (14.1 g, 61.0 mmol) in glacial acetic acid (162 mL) was added a solution of sodium nitrite (6.32 g, 91.5 mmol) in water (14 mL) dropwise over 10 min. During this time, the reaction solution was cooled in an ice bath to maintain an internal reaction temperature below 25° C. The reaction was stirred at 20° C. for 1 hr. The reaction solution was concentrated in vacuo, and the residue was triturated with 1:1 methanol: water. The resulting precipitate was collected by filtration, and dried in vacuo at 80° C. for 6 hr to afford the title compound (10.4 g, 49%) as a red solid. MS (ESI): mass calcd. for $C_7H_4BrN_3O_2$ 241.0, m/z found 242 $[M+H]^+$. $^1H$ NMR (300 MHz, DMSO-$d_6$) δ 8.84 (s, 1H), 8.53 (s, 1H), 8.37 (s, 1H).

Step C. 7-Bromo-5-nitro-1-((2-(trimethylsilyl) ethoxy)methyl)-1H-indazole

To a solution of 7-bromo-5-nitro-1H-indazole (2.00 g, 8.26 mmol) in DMF (60 mL) at 0° C. was added sodium hydride (60% dispersion in mineral oil, 413 mg, 10.3 mmol). The reaction mixture was allowed to warm to 20° C. and stirred for 15 min. Then the reaction was again cooled to 0° C. and SEM-Cl (1.6 mL, 9.1 mmol) was added dropwise. The reaction was again allowed to warm to 20° C. and stirred for 18 h. The reaction was quenched with water and extracted with EtOAc. The combined organic fractions were collected and dried (MgSO$_4$), filtered and concentrated in vacuo. Purification (FCC, SiO$_2$; 5:95 to 15:85 EtOAc/heptane afforded the title compound (1.09 g, 34%). $^1H$ NMR (300 MHz, CDCl$_3$) δ 8.67 (d, J=1.6 Hz, 1H), 8.52 (d, J=1.7 Hz, 1H), 8.25 (s, 1H), 6.10 (s, 2H), 3.76-3.45 (m, 2H), 0.98-0.79 (m, 2H), −0.07 (s, 9H).

Step D. 7-Methyl-5-nitro-1-((2-(trimethylsilyl) ethoxy)methyl)-1H-indazole

To a stirred solution of 7-bromo-5-nitro-1-((2-(trimethylsilyl)ethoxy)methyl)-1H-indazole (1.09 g, 2.93 mmol), Pd(PPh$_3$)$_4$ (169 mg, 0.146 mmol) and Cs$_2$CO$_3$ (1.91 g, 5.85 mmol) in 1,4-dioxane (50 mL), through which nitrogen gas was bubbling, was added trimethylboroxime (0.45 mL, 3.22 mmol). The reaction was stirred at 105° C. for 16 h. An aqueous sodium bicarbonate solution was added, and the mixture was then extracted with EtOAc. The organic phase was separated, dried (MgSO$_4$), filtered, and concentrated in vacuo. Purification (FCC, SiO$_2$; 5:95 to 30:70 EtOAc:heptanes) afforded the title compound (857 mg, 90%) as a red solid. $^1H$ NMR (300 MHz, CDCl$_3$) δ 8.54 (br s, 1H), 8.16 (s, 1H), 8.07 (d, J=0.7 Hz, 1H), 5.87 (s, 2H), 3.64-3.47 (m, 2H), 2.84 (s, 3H), 0.94-0.78 (m, 2H), 0.07 (s, 9H).

Step E. 7-Methyl-1-((2-(trimethylsilyl)ethoxy) methyl)-1H-indazol-5-amine

To a stirred solution of 7-methyl-5-nitro-1-((2-(trimethylsilyl)ethoxy)methyl)-1H-indazole (857 mg, 2.79 mmol) in methanol (25 mL), which had been previously purged with nitrogen, was added 10% Pd/C (59 mg). The reaction was placed under an atmosphere of hydrogen gas and stirred at 20° C. overnight. The suspension was filtered through a pad of Celite® 545, the resulting filter cake was washed with MeOH, and the combined organic phases concentrated in vacuo. Purification (FCC, SiO$_2$, 0:100 to 70:30 EtOAc:heptanes) afforded the title compound (620 mg, 76%) as a red solid. MS (ESI): mass calcd. for $C_{14}H_{23}N_3OSi$ 277.1, m/z found 278 $[M+H]^+$. $^1H$ NMR (300 MHz, DMSO-$d_6$) δ 7.73 (s, 1H), 6.59 (s, 2H), 5.68 (s, 2H), 4.77 (s, 2H), 3.42 (t, J=7.9 Hz, 2H), 2.56 (s, 3H), 0.77 (t, J=7.9 Hz, 2H), 0.05 (s, 9H).

Method B:

The title compound was prepared in a manner analogous to Intermediate 9.

Intermediate 15: 1H-Pyrrolo[2,3-b]pyridin-5-amine

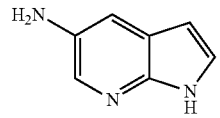

To a stirred solution of 5-nitro-7-azaindole (500 mg, 3.07 mmol) in methanol (125 mL) under nitrogen atmosphere was added 10% Pd/C (326 mg, 0.306 mmol). The reaction was placed under an atmosphere of hydrogen gas and stirred at 20° C. overnight. The suspension was filtered through a pad of Celite® 545, the resulting filter cake was washed with MeOH, and the combined organic phases concentrated in vacuo to afford the title compound (408 mg, 100%). MS (ESI): mass calcd. for $C_7H_7N_3$ 133.1, m/z found 133.9 $[M+H]^+$. $^1H$ NMR (300 MHz, DMSO-$d_6$) δ 11.04 (s, 1H), 7.70 (d, J=2.4 Hz, 1H), 7.27-7.18 (m, 1H), 7.08 (d, J=2.3 Hz, 1H), 6.22-6.06 (m, 1H), 4.62 (s, 2H).

Intermediate 16: 6-Amino-3-((2-(trimethylsilyl) ethoxy)methyl)benzo[d]thiazol-2(3H)-one

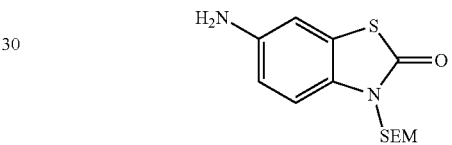

Step A: 6-Nitrobenzo[d]thiazol-2(3H)-one

To a solution of 2-hydroxybenzothiazole (1.0 g, 6.5 mmol) in concentrated sulfuric acid (26 mL) at 0° C. was added dropwise fuming nitric acid, 90% ACS reagent grade (0.42 mL, 6.5 mmol). The mixture was stirred at 0° C. for 30 min, and then the mixture was poured into ice (83 mL). A saturated aqueous solution of NaHCO$_3$ was added until pH~7 and the mixture was extracted with DCM. The organic layer was separated, dried (MgSO$_4$), filtered, and concentrated in vacuo to afford the title compound (1.11 g, 87%). MS (ESI): mass calcd. for $C_7H_4N_2O_3S$ 196.0, m/z found 197.0 $[M+H]^+$. $^1H$ NMR (300 MHz, DMSO-$d_6$) δ 12.56 (s, 1H), 8.65 (d, J=2.2 Hz, 1H), 8.18 (dd, J=8.8, 2.3 Hz, 1H), 7.28 (d, J=8.8 Hz, 1H).

Step B: 6-Nitro-3-((2-(trimethylsilyl)ethoxy)methyl) benzo[d]thiazol-2(3H)-one To a stirred solution of 6-nitrobenzo[d]thiazol-2(3H)-one (1.11 g, 5.66 mmol) in tetrahydrofuran (13 mL) at 0° C. was added sodium hydride (60% dispersion in mineral oil, 272 mg, 6.79 mmol). After 30 minutes, SEM-Cl (1.0 mL, 5.7 mmol) was added dropwise. The mixture was allowed to warm to 20° C. and stirred for 2 h. The reaction mixture was diluted with saturated aqueous NaHCO$_3$ and extracted with EtOAc. The organic phase was separated, dried (MgSO$_4$), filtered, and concentrated in vacuo. Purification (FCC, SiO$_2$; 0:100 to 80:20 EtOAc:heptanes) afforded the title compound (1.02 g, 55%). $^1H$ NMR (300 MHz, DMSO-$d_6$) δ 8.76 (d, J=2.3 Hz, 1H), 8.28 (dd, J=9.0, 2.3 Hz, 1H), 7.57 (d, J=9.0 Hz, 1H), 5.42 (s, 2H), 3.59 (t, J=8.0 Hz, 2H), 0.86 (t, J=8.0 Hz, 2H), 0.01 (s, 9H).

Step C: 6-Amino-3-((2-(trimethylsilyl)ethoxy)methyl)benzo[d]thiazol-2(3H)-one

To a stirred solution of 6-nitro-3-((2-(trimethylsilyl)ethoxy)methyl)benzo[d]thiazol-2(3H)-one (1.02 g, 3.13 mmol) in EtOAc (125 mL) under nitrogen atmosphere was added 10% Pd/C (125 mg, 0.585 mmol). The reaction was placed under an atmosphere of hydrogen gas and stirred at 20° C. overnight. Then, a second batch of 10% Pd/C (125 mg, 0.585 mmol) was added, and the reaction stirred at 20° C. overnight. The suspension was filtered through a pad of Celite® 545, and the resulting filter cake was washed with MeOH. The combined organic phases were concentrated in vacuo to afford the title compound (906 mg, 98%). MS (ESI): mass calcd. for $C_{13}H_{20}N_2O_2SSi$ 296.1, m/z found 297.0 [M+H]$^+$. $^1$H NMR (300 MHz, DMSO-d$_6$) δ 7.01 (d, J=8.6 Hz, 1H), 6.78 (d, J=2.0 Hz, 1H), 6.59 (dd, J=8.6, 2.1 Hz, 1H), 5.06 (s, 2H), 3.53 (t, J=7.9 Hz, 2H), 0.84 (t, J=7.9 Hz, 2H), 0.01 (d, J=6.0 Hz, 9H).

Intermediate 17: 5-Amino-7-fluoroindolin-2-one

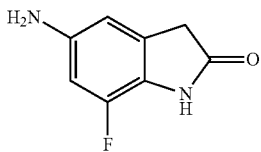 [SMILES: Nc1cc(F)c2c(c1)CC(=O)N2]

The title compound was prepared in a manner analogous to Intermediate 10. MS (ESI): mass calcd. for $C_8H_7FN_2O$ 166.1, m/z found 167.1 [M+H]$^+$. $^1$H NMR (400 MHz, DMSO-d$_6$) δ 10.33 (s, 1H), 6.36-6.30 (dd, J=1.8, 0.8 Hz, 1H), 6.28-6.20 (m, 1H), 4.94 (s, 2H), 3.39 (s, 3H). $^{19}$F NMR (376 MHz, DMSO-d$_6$) δ −133.21--133.30 (d, J=12.5 Hz).

Intermediate 18: 5-Amino-7-chloroindolin-2-one

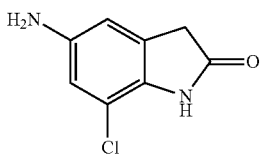 [SMILES: Nc1cc(Cl)c2c(c1)CC(=O)N2]

The title compound was prepared in a manner analogous to Intermediate 10. MS (ESI): mass calcd. for $C_8H_7ClN_2O$ 182.0, m/z found 183.0 [M+H]$^+$. $^1$H NMR (500 MHz, DMSO-d$_6$) δ 10.28 (s, 1H), 6.47 (d, J=1.7 Hz, 1H), 6.43 (d, J=2.0 Hz, 1H), 5.29 (s, 2H), 3.44 (s, 2H).

Intermediate 19: 7-Chloro-1-((2-(trimethylsilyl)ethoxy)methyl)-1H-indazol-5-amine

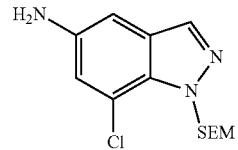 [SMILES: C[Si](C)(C)CCOCn1ncc2cc(N)cc(Cl)c21]

The title compound was prepared in a manner analogous to Intermediate 14, beginning with 2-chloro-6-methyl-4-nitroaniline, and omitting Steps A and D. $^1$H NMR (300 MHz, CDCl$_3$) δ 7.82 (s, 1H), 6.90 (d, J=1.7 Hz, 1H), 6.84 (d, J=1.7 Hz, 1H), 5.94 (s, 2H), 3.60-3.47 (m, 2H), 0.90-0.77 (m, 2H), 0.04 (s, 9H).

Intermediate 20: 1-((2-(Trimethylsilyl)ethoxy)methyl)-1H-pyrazolo[3,4-b]pyridin-5-amine

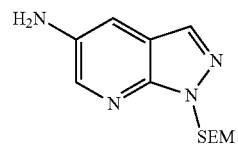 [SMILES: C[Si](C)(C)CCOCn1ncc2cc(N)cnc21]

The title compound was prepared in a manner analogous to Intermediate 9. MS (ESI): mass calcd. for $C_{12}H_{20}N_4OSi$ 264.1, m/z found 265.1 [M+H]$^+$. $^1$H NMR (300 MHz, DMSO-d$_6$) δ 8.09 (d, J=2.4 Hz, 1H), 7.90 (s, 1H), 7.21 (d, J=2.4 Hz, 1H), 5.64 (s, 2H), 5.14 (s, 2H), 3.55 (t, J=8.0 Hz, 2H), 0.79 (t, J=8.0 Hz, 2H), 0.1 (s, 9H).

Intermediate 21: 1-((2-(Trimethylsilyl)ethoxy)methyl)-1H-pyrrolo[2,3-b]pyridin-5-amine

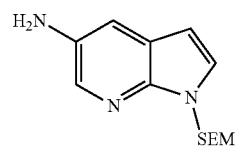 [SMILES: C[Si](C)(C)CCOCn1ccc2cc(N)cnc21]

The title compound was prepared in a manner analogous to Intermediate 9. MS (ESI): mass calcd. for $C_{13}H_{21}N_3OSi$ 263.1, m/z found 264.0 [M+H]$^+$. $^1$H NMR (300 MHz, CDCl$_3$) δ 7.94 (d, J=2.3 Hz, 1H), 7.27 (d, J=3.8 Hz, 2H), 6.35 (d, J=3.5 Hz, 1H), 5.61 (s, 2H), 3.62-3.42 (m, 4H), 0.95-0.86 (m, 2H), 0.05 (s, 9H).

Intermediate 22: 3-Fluoro-1H-indazol-5-amine

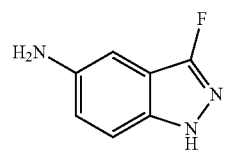 [SMILES: Nc1ccc2[nH]nc(F)c2c1]

Step A: 3-Fluoro-5-nitro-1H-indazole

To a solution of 5-nitro-1H-indazole (75 mg, 0.460 mmol) in acetonitrile (0.31 mL) was added Selectfluor® (162 mg, 0.460 mmol) and acetic acid (0.31 mL). The reaction mixture was heated in the microwave at 150° C. for 30 min. The reaction was quenched with water and extracted with EtOAc. The combined organic layers were dried ($Na_2SO_4$), filtered, and concentrated in vacuo. Purification (FCC, $SiO_2$, 20-100% EtOAc in hexanes) afforded the title compound (25 mg, 30%). $^1$H NMR (400 MHz, $CD_3OD$) δ 8.65 (d, J=2.2 Hz, 1H), 8.30-8.23 (m, 1H), 7.60-7.53 (m, 1H).

Step B: 3-Fluoro-1H-indazol-5-amine

A solution of 3-fluoro-5-nitro-1H-indazole (220 mg, 1.22 mmol) and 10% Pd/C (130 mg, 0.122 mmol) in EtOH (12 mL) was stirred under hydrogen at rt for 2 h. The reaction was filtered through Celite® with MeOH and the resulting solution was concentrated in vacuo. The product was carried on to the next step without further purification. $^1$H NMR (400 MHz, $CD_3OD$) δ 7.27-7.20 (m, 1H), 7.02 (dd, J=9.0, 2.0 Hz, 1H), 6.89 (d, J=1.9 Hz, 1H).

Intermediate 23: 2-Chloro-3-(3-((tetrahydro-2H-pyran-2-yl)oxy)prop-1-yn-1-yl)-6-(trifluoromethyl)pyridine

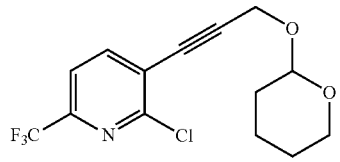 [SMILES: FC(F)(F)c1ccc(C#CCOC2CCCCO2)c(Cl)n1]

Step A: 2-Chloro-3-iodo-6-(trifluoromethyl)pyridine

A flask under nitrogen atmosphere was charged with anhydrous THF (240 mL) and cooled to −78° C. over 10 min while lithium diisopropylamide in THF/heptanes (60 mL, 2 µM, 121 mmol) was added. Then, a solution of 2-chloro-6-trifluoromethylpyridine (20 g, 110 mmol) in anhydrous THF (60 mL) was added slowly over 10 minutes, and the reaction was stirred at −78° C. for another 30 minutes. Then, a solution of iodine (30.7 g, 121 mmol) in anhydrous THF (60 mL) was added slowly over 10 minutes, and the reaction was stirred at −78° C. for another 35 minutes. The reaction was quenched by addition of saturated aqueous ammonium chloride (300 mL) at −78° C., and allowed to warm to 0-5° C. The reaction was extracted into EtOAc (360 mL) and the organic phase washed twice with 10% aqueous sodium thiosulfate (400 mL total) and brine (200 mL). The organics were combined, dried ($MgSO_4$), filtered, and concentrated under reduced pressure. Purification (FCC, $SiO_2$, 100:0 to 60:40 hexanes:DCM) afforded the title compound as a waxy white solid (20.3 g, 60%). $^1$H NMR (400 MHz, $CDCl_3$) δ 8.35 (dd, J=8.0, 0.8 Hz, 1H), 7.31 (d, J=8.0 Hz, 1H). $^{19}$F NMR (376 MHz, $CDCl_3$ δ −68.09 (s)

Step B: 2-Chloro-3-(3-((tetrahydro-2H-pyran-2-yl)oxy)prop-1-yn-1-yl)-6-(trifluoromethyl)pyridine To a sealed tube was added in order 2-chloro-3-iodo-6-(trifluoromethyl)pyridine (1 g, 3.2 mmol), anhydrous lithium chloride (344 mg, 8.13 mmol), DMF (13 mL) and TEA (1.4 mL, 9.8 mmol). The solution was degassed by bubbling through nitrogen gas for 5 min. Then, $PdCl_2$ $(PPh_3)_2$ (228 mg, 0.325 mmol) and tetrahydro-2-(2-propynyloxy)-2H-pyran (0.68 mL, 4.9 mmol) were added. The tube was immediately sealed under nitrogen atmosphere and stirred vigorously at 50° C. for 16 h. After removing from the heating bath and letting cool to 20° C., the reaction was poured into EtOAc (100 mL). The organic phase was washed with water (250 mL total), brine, dried ($MgSO_4$), filtered, and concentrated under reduced pressure. Purification (FCC, $SiO_2$, 0% to 20% EtOAc in hexanes) afforded the title compound as a yellow oil (915 mg, 88%). MS (ESI): mass calcd. for $C_{14}H_{13}ClF_3NO_2$ 319.1, m/z found 320.1 $[M+H]^+$. $^1$H NMR (400 MHz, $CDCl_3$) δ 7.94 (dd, J=7.9, 0.8 Hz, 1H), 7.58 (d, J=7.9 Hz, 1H), 4.92 (t, J=3.3 Hz, 1H), 4.57 (d, J=0.8 Hz, 2H), 3.89-3.82 (m, 1H), 3.66-3.51 (dd, J=11.1, 1.4 Hz, 1H), 1.95-1.57 (m, 6H). $^{19}$F NMR (376 MHz, $CDCl_3$) δ −68.04 (s).

Intermediate 24: 2-Chloro-3-(5-fluoropent-1-yn-1-yl)-6-(trifluoromethyl)pyridine

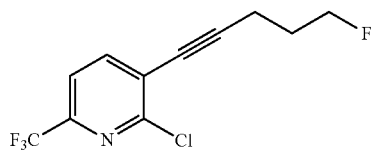 [SMILES: FCCCC#Cc1ccc(C(F)(F)F)nc1Cl]

Step A: Pent-4-yn-1-yl 4-methylbenzenesulfonate

To a solution of pent-4-yn-1-ol (15 g, 0.18 mol) and TEA (37 mL, 0.27 mol) in DCM (114 mL) at 0-4° C., was added a solution of toluenesulfonyl chloride (37.8 g, 0.21 mol) in DCM (25 mL) dropwise. After addition, the mixture was allowed to warm to rt and stirred overnight. A precipitate formed during the reaction and was removed by filtration. The filtrate was concentrated, diluted with diethyl ether (250 mL), and washed with brine (150 mL). The organics were combined, dried ($Na_2SO_4$), filtered, and concentrated under reduced pressure. Purification (FCC, $SiO_2$, 0-20% EtOAc in hexanes) afforded the title compound as a yellow oil (36 g, 85%). MS (ESI): mass calcd. for $C_{12}H_{14}O_4S$, 238.1, m/z found 239.1 $[M+H]^+$.

Step B: 5-Fluoropent-1-yne

To a 100-mL round bottom flask was added pent-4-yn-1-yl 4-methylbenzenesulfonate (20 g, 84 mmol) and TBAF (31 mL, 75% water solution, 84 mmol), and the mixture was stirred and heated at 45° C. for an hour. A distillation-condensing apparatus was installed, and the mixture was purified by distillation. The fraction that was volatile at 75-90° C. was collected to yield 5-fluoropent-1-yne as a colorless liquid (6.8 g, 94%). $^1$H NMR (500 MHz, $CDCl_3$) δ 4.56 (dtd, J=47.1, 5.8, 1.0 Hz, 2H), 2.36 (tdd, J=7.0, 2.7, 1.0 Hz, 2H), 1.99 (td, J=2.7, 0.7 Hz, 1H), 1.97-1.85 (m, 2H).

Step C: 2-Chloro-3-(5-fluoropent-1-yn-1-yl)-6-(trifluoromethyl)pyridine

3-Bromo-2-chloro-6-trifluoromethyl pyridine (700 mg, 2.67 mmol), $PdCl_2(PPh_3)_2$ (188 mg, 0.27 mmol), and anhydrous lithium chloride (228 mg, 5.38 mmol) were sealed in an oven dry reaction vessel with a septum seal. DMF (5.4 mL) and TEA (1.1 mL, 8.1 mmol) were added through syringes. The mixture was degassed with nitrogen, and 5-fluoropent-1-yne (300 mg, 3.50 mmol) was added via syringe. The reaction mixture was heated at 110° C. for 3 h. Upon completion, the reaction mixture was cooled to rt, diluted with EtOAc (100 mL), washed with sodium bicarbonate (50 mL) aqueous solution, and brine (50 mL). The organic layer was dried ($Na_2SO_4$), filtered, and concentrated under reduced pressure. Purification (FCC, $SiO_2$, 0-20% EtOAc in hexanes) afforded the title compound as a colorless oil (450 mg, 63%). MS (ESI): mass calcd. for $C_{11}H_8ClF_4N$, 265.1, m/z found 266.1 $[M+H]^+$. $^1$H NMR (400 MHz, $CDCl_3$) δ 7.92 (dd, J=7.9, 0.9 Hz, 1H), 7.60 (d, J=7.9 Hz, 1H), 4.68 (dt, J=47.1, 5.7 Hz, 2H), 2.73 (t, J=7.0 Hz, 2H), 2.09 (dtt, J=26.0, 6.9, 5.6 Hz, 2H).

Intermediate 25: 2-Chloro-3-(3-((tetrahydro-2H-pyran-2-yl)oxy)prop-1-yn-1-yl)pyridine

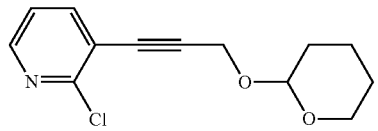

Step A: 2-Chloro-3-(3-((tetrahydro-2H-pyran-2-yl)oxy)prop-1-yn-1-yl)pyridine

To a sealed tube was added in order 2-chloro-3-iodopyridine (1.25 g, 5.22 mmol), anhydrous lithium chloride (553 mg, 13.05 mmol), DMF (13 mL), tetrahydro-2-(2-propynyloxy)-2H-pyran (0.8 mL, 5.7 mmol), and $PdCl_2(PPh_3)_2$ (183 mg, 0.261 mmol). The solution was degassed by bubbling through nitrogen gas for 5 min. Then TEA (2.2 mL, 15.7 mmol) was added, and the reaction mixture was degassed with nitrogen gas for 1 min. The reaction mixture was sealed and stirred vigorously at 50° C. for 15 h. Upon completion, the reaction mixture was cooled to 20° C. and poured into EtOAc (100 mL). The organic phase was washed five times with water (250 mL total), once with brine, dried ($MgSO_4$), filtered, and concentrated under reduced pressure. Purification (FCC, $SiO_2$, 0% to 20% EtOAc in hexanes) afforded the title compound as an orange oil (1.17 g, 89%). MS (ESI): mass calcd. for $C_{13}H_{14}ClNO_2$ 251.1, m/z found 252.1 $[M+H]^+$. $^1$H NMR (400 MHz, $CDCl_3$) δ 8.33 (dd, J=4.8, 2.0 Hz, 1H), 7.78 (dd, J=7.7, 1.9 Hz, 1H), 7.20 (dd, J=7.7, 4.8 Hz, 1H), 4.94 (t, J=3.4 Hz, 1H), 4.55 (d, J=0.6 Hz, 2H), 3.90 (ddd, J=11.5, 8.9, 3.1 Hz, 1H), 3.65-3.51 (m, 1H), 1.93-1.73 (m, 2H), 1.73-1.49 (m, 4H).

Intermediate 26: 2-Chloro-3-(prop-1-yn-1-yl)-6-(trifluoromethyl)pyridine

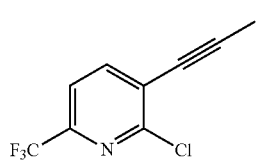

To a sealed tube containing a solution of 2-chloro-3-iodo-6-(trifluoromethyl)pyridine (obtained from Step A in Intermediate 23, 2.0 g, 6.44 mmol) in toluene (19 mL) was added $Pd(PPh_3)_4$ (506 mg, 0.438 mmol), copper(I) iodide (147 mg, 0.773 mmol) and tributyl(1-propynyl)tin (1.3 mL, 4.4 mmol) in order. The solution was degassed by bubbling through nitrogen for several minutes and stirred vigorously at 100° C. for 18 h. Upon completion the reaction mixture was cooled to 20° C., and the reaction was quenched by addition of aq. of 2M potassium fluoride. The resulting mixture was filtered to remove insolubles. The phases were separated, and the organic phase was dried ($MgSO_4$), filtered, and concentrated under reduced pressure. Purification (FCC, $SiO_2$, 0 to 15% EtOAc in hexanes) afforded the title compound (1.14 g, 64%). $^1$H NMR (300 MHz, $CDCl_3$) δ 7.87 (d, J=7.9 Hz, 1H), 7.54 (d, J=7.9 Hz, 1H), 2.16 (s, 3H).

Intermediate 27: 2-Chloro-3-(prop-1-yn-1-yl)pyridine

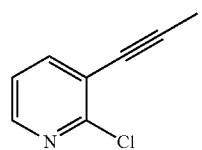

To a sealed tube was added in order 2-chloro-3-iodopyridine (1.0 g, 4.2 mmol), anhydrous lithium chloride (443 mg, 10.4 mmol), and DMF (10 mL). The vial was degassed by bubbling through nitrogen for 10 minutes. Then TEA (1.7 mL, 12.5 mmol), $PdCl_2(PPh_3)_2$ (293 mg, 0.418 mmol), and tributyl(1-propynyl)tin (1.3 mL, 4.4 mmol) were added in order. The tube was sealed under nitrogen atmosphere and stirred vigorously at 80° C. for 18 h. Upon completion, the reaction mixture was cooled to 20° C., and the reaction was poured into methanol (25 mL) and KF (50% on Celite®) was added (1.0 g). The resulting slurry was stirred vigorously at 20° C. for 1 hr, diluted with EtOAc (150 mL) and filtered to remove insolubles. The organic phase was washed water (5×400 mL total), brine (1×), dried ($MgSO_4$), filtered, and concentrated under reduced pressure. Purification (FCC, $SiO_2$, 0 to 10% EtOAc in hexanes) provided the title compound as a colorless oil (565 mg, 89%) which solidified upon standing overnight into colorless needles. MS (ESI): mass calcd. for $C_8H_6ClN$ 151.0, m/z found 152.1 $[M+H]^+$. $^1$H NMR (400 MHz, $CDCl_3$) δ 8.28 (dd, J=4.8, 1.9 Hz, 1H), 7.72 (dd, J=7.7, 2.0 Hz, 1H), 7.16 (dd, J=7.7, 4.8 Hz, 1H), 2.13 (s, 3H).

Intermediate 28: 2-Bromo-6-methyl-3-(3-methylbut-1-yn-1-yl)pyridine

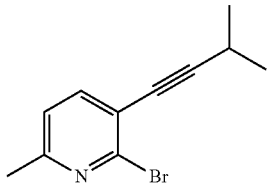

Step A: 2-Bromo-6-methylpyridin-3-yl trifluoromethanesulfonate

To a 20-mL glass microwave vial was added 2-bromo-3-hydroxy-5-methylpyridine (840 mg, 4.47 mmol), N,N-bis(trifluoromethanesulfonyl)aniline (1.76 g, 4.91 mmol), $K_2CO_3$ (679 mg, 4.94 mmol), and THF (9 mL), and the vial was sealed under an atmosphere of nitrogen gas. Then, the vial was warmed to 100° C. in a microwave reactor for 15 min. Upon completion, the reaction solution was diluted with EtOAc and poured into water. The organic phase was washed once with brine, dried ($MgSO_4$), filtered, and concentrated in vacuo to a colorless oily residue. Purification (FCC, $SiO_2$, 0:100 to 20:80, EtOAc/hexanes) afforded the title compound (1.31 g, 92%). MS (ESI): mass calcd. for $C_7H_5BrF_3NO_3S$ 318.9, m/z found 319.8 [M+H]$^+$. $^1$H NMR (400 MHz, $CDCl_3$) δ 7.57-7.50 (d, J=8.3 Hz, 1H), 7.23-7.16 (dd, J=8.3, 0.6 Hz, 1H), 2.59 (s, 3H). $^{19}$F NMR (376 MHz, $CDCl_3$) δ −73.16 (s).

Step B: 2-Bromo-6-methyl-3-(3-methylbut-1-yn-1-yl)pyridine

Into two separated glass sealed tubes were evenly divided the following reagents, in order: 2-bromo-6-methylpyridin-3-yl trifluoromethanesulfonate (695 mg, 2.17 mmol), anhydrous lithium chloride (304 mg, 7.17 mmol), DMF (22 mL), and TEA (0.91 mL, 6.5 mmol). The solutions were degassed by bubbling through nitrogen for 2 min, then the following reagents were evenly divided between the two tubes and added to the reaction mixture in order: $PdCl_2(PPh_3)_2$ (152 mg, 0.217 mmol), and 3-methyl-1-butyne (0.51 mL, 4.99 mmol). The tubes were sealed and heated with vigorous stirring at 50° C. for 40 h. Upon completion, the reaction mixtures were cooled to 20° C., and the reaction was poured into EtOAc (150 mL). The organic phase was washed four times with water (400 mL total), once with brine, dried ($MgSO_4$), filtered, and concentrated under reduced pressure. Purification (FCC, $SiO_2$, 0:100 to 20:80, EtOAc/hexanes) afforded the title compound (140 mg, 27%). MS (ESI): mass calcd. for $C_{11}H_{12}BrN$ 237.0, m/z found 238.0 [M+H]$^+$. $^1$H NMR (500 MHz, $CDCl_3$) δ 7.57-7.52 (d, J=7.8 Hz, 1H), 7.06-7.00 (dd, J=7.8, 0.7 Hz, 1H), 2.87-2.78 (hept, J=6.9 Hz, 1H), 2.52 (s, 3H), 1.32-1.27 (d, J=6.9 Hz, 6H).

Intermediate 29: 2-Chloro-6-(difluoromethyl)-3-(3-methylbut-1-yn-1-yl)pyridine

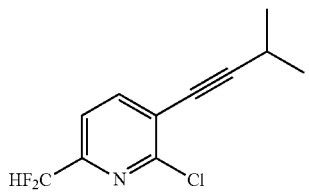

Step A: 5-Bromo-6-chloropicolinaldehyde

To a round bottom flask containing (5-bromo-6-chloropyridin-2-yl)methanol (405 mg, 1.82 mmol) was added 1,1,1-tris(acetyloxy)-1,1-dihydro-1,2-benziodoxol-3-(1H)-one (Dess-Martin periodinane) (811 mg, 1.91 mmol) and DCM (18 mL, 282 mmol), and the reaction mixture was stirred rapidly at 20° C. for 30 min. Upon completion, the reaction mixture was quenched with sat. aq. $NaHCO_3$ (10 mL) and 10% aqueous sodium thiosulfate (10 mL). The resultant biphasic mixture was stirred vigorously for 60 min, and the two phases separated. The organic phase was extracted once more with DCM. The combined organic phases were dried ($MgSO_4$), filtered, and concentrated under reduced pressure to afford the title compound (420 mg, 100%). $^1$H NMR (400 MHz, $CDCl_3$) δ 9.97 (d, J=0.9 Hz, 1H), 8.14 (dd, J=8.0, 0.9 Hz, 1H), 7.75 (d, J=8.0 Hz, 1H).

Step B. 3-Bromo-2-chloro-6-(difluoromethyl)pyridine

To a round bottom flask containing 5-bromo-6-chloropicolinaldehyde (420 mg, 1.91 mmol) under nitrogen atmosphere was added DCM (19 mL). The flask was cooled to −20° C. and DAST (0.6 mL, 4.2 mmol) was added. After 5 min, the flask was removed from the cooling bath and allowed to warm to 20° C. After 90 min, the reaction was quenched by pouring onto ice (50 mL), followed by the addition of sat. aq. $NaHCO_3$ (~10 mL) until pH~7 was reached. The phases were separated, and the aqueous phase extracted with DCM. The organics were combined, dried ($MgSO_4$), filtered, and concentrated under reduced pressure to provide the title compound (450 mg, 97%) as a cloudy orange oil. $^1$H NMR (400 MHz, $CDCl_3$) δ 8.09 (d, J=8.1 Hz, 1H), 7.46 (d, J=8.1 Hz, 1H), 6.56 (t, J=55.0 Hz, 1H). $^{19}$F NMR (376 MHz, $CDCl_3$) δ −115.85 (d, J=55.1 Hz).

Step C. 2-Chloro-6-(difluoromethyl)-3-(3-methylbut-1-yn-1-yl)pyridine

To a sealed tube was added in order 3-bromo-2-chloro-6-(difluoromethyl)pyridine (150 mg, 0.62 mmol), anhydrous lithium chloride (79 mg, 1.9 mmol), and DMF (3 mL). The solution was degassed by bubbling through nitrogen for 3 min. Then TEA (0.3 mL, 1.9 mmol) was added, followed by $PdCl_2(PPh_3)_2$ (43 mg, 0.062 mmol) and 3-methyl-1-butyne (0.08 mL, 0.7 mmol). The tube was immediately sealed under nitrogen atmosphere, and heated with vigorous stirring at 50° C. for 40 h. Upon completion the reaction mixture was cooled to 20° C. and the reaction was poured into EtOAc (50 mL). The organic phase was washed four times with water (200 mL total), once with brine, and the combined organics were dried ($MgSO_4$), filtered, and concentrated under reduced pressure. Purification (FCC, $SiO_2$, 0:100 to 10:90, EtOAc/hexanes) afforded the title compound (120 mg, 68%). MS (ESI): mass calcd. for $C_{11}H_{10}ClF_2N$ 229.0, m/z found 230.1 [M+H]$^+$. $^1$H NMR (400 MHz, $CDCl_3$) δ 7.85 (d, J=7.9 Hz, 1H), 7.50 (d, J=7.9 Hz, 1H), 6.56 (t, J=55.1 Hz, 1H), 2.95-2.76 (hept, J=6.7 Hz, 1H), 1.31 (d, J=6.9 Hz, 6H). $^{19}$F NMR (376 MHz, $CDCl_3$) δ −115.88 (d, J=55.1 Hz).

Intermediate 30: 2-Chloro-3-((tetrahydrofuran-3-yl)ethynyl)-6-(trifluoromethyl)pyridine

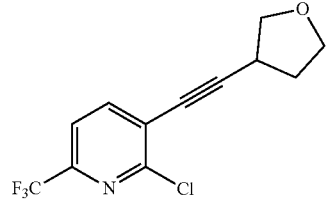 [SMILES: FC(F)(F)c1ccc(C#CC2CCOC2)c(Cl)n1]

The title compound was prepared in a manner analogous to Intermediate 23. MS (ESI): mass calcd. for $C_{12}H_9ClF_3NO$ 275.0, m/z found 276.0 [M+H]+. 1H NMR (400 MHz, CDCl3) δ 7.87 (d, J=8.3 Hz, 1H), 7.54 (d, J=7.9 Hz, 1H), 4.17-4.04 (dd, J=8.3, 7.4 Hz, 1H), 4.01-3.94 (m, 1H), 3.94-3.85 (ddd, J=8.5, 7.5, 6.2 Hz, 1H), 3.82-3.76 (dd, J=8.3, 6.6 Hz, 1H), 3.41-3.20 (ddd, J=13.7, 8.4, 6.7 Hz, 1H), 2.39-2.26 (dddd, J=12.3, 8.5, 7.4, 6.3 Hz, 1H), 2.20-2.05 (m, 1H).

Intermediate 31: 2-Chloro-3-(3-methoxyprop-1-yn-1-yl)-6-(trifluoromethyl)pyridine

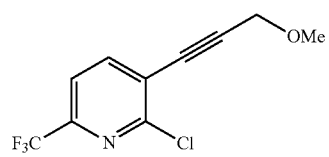 [SMILES: COCC#Cc1ccc(C(F)(F)F)nc1Cl]

The title compound was prepared in a manner analogous to Intermediate 23, using 3-methoxyprop-1-yne. MS (ESI): mass calcd. for $C_{10}H_7ClF_3NO$ 249.0, m/z found 249.9 [M+H]+. 1H NMR (400 MHz, CDCl3) δ 7.94 (dd, J=7.9, 0.8 Hz, 1H), 7.59 (d, J=7.9 Hz, 1H), 4.40 (s, 2H), 3.49 (s, 3H). 19F NMR (376 MHz, CDCl3) δ −68.06 (s).

Intermediate 32: 2-Chloro-3-(3-methylbut-1-yn-1-yl)-6-(trifluoromethyl)pyridine

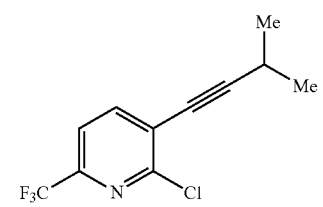 [SMILES: CC(C)C#Cc1ccc(C(F)(F)F)nc1Cl]

The title compound was prepared in a manner analogous to Intermediate 23. MS (ESI): mass calcd. for $C_{11}H_9ClF_3N$ 247.0, m/z found 247.9 [M+H]+. 1H NMR (500 MHz, CDCl3) δ 7.88-7.84 (dd, J=7.9, 0.8 Hz, 1H), 7.53 (d, J=7.9 Hz, 1H), 2.93-2.80 (hept, J=6.8 Hz, 1H), 1.31 (d, J=6.9 Hz, 6H). 19F NMR (376 MHz, CDCl3) δ −67.93 (s).

Intermediate 33: 2-Chloro-3-(phenylethynyl)-6-(trifluoromethyl)pyridine

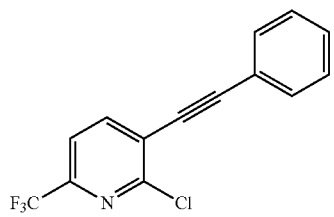 [SMILES: FC(F)(F)c1ccc(C#Cc2ccccc2)c(Cl)n1]

The title compound was prepared in a manner analogous to Intermediate 23. MS (ESI): mass calcd. for $C_{14}H_7ClF_3N$ 281.0, m/z found 281.8 [M+H]+. 1H NMR (300 MHz, DMSO-d6) δ 8.42 (d, J=7.9 Hz, 1H), 8.12 (d, J=12.7 Hz, 1H), 8.02 (d, J=8.0 Hz, 1H), 7.71-7.61 (m, 2H), 7.51 (d, J=6.1 Hz, 2H).

Intermediate 34: 2-Chloro-3-((4-fluorophenyl)ethynyl)-6-(trifluoromethyl)pyridine VILL_ssanchez_1284

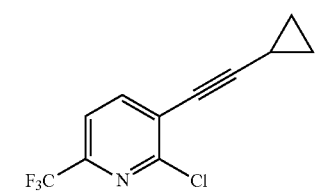 [SMILES: FC(F)(F)c1ccc(C#CC2CC2)c(Cl)n1]

The title compound was prepared in a manner analogous to Intermediate 23. MS (ESI): mass calcd. for $C_{11}H_7ClF_3N$ 245.0, m/z found 245.9 [M+H]+.

Intermediate 35: 2-Chloro-3-(3-methylbut-1-yn-1-yl)pyridine

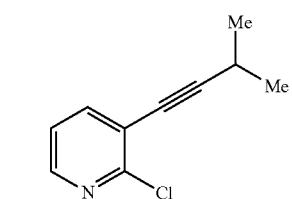 [SMILES: CC(C)C#Cc1cccnc1Cl]

The title compound was prepared in a manner analogous to Intermediate 25. MS (ESI): mass calcd. for $C_{10}H_{10}ClN$ 179.1, m/z found 180.0 [M+H]+. 1H NMR (400 MHz, CDCl3) δ 8.27 (dd, J=4.8, 1.9 Hz, 1H), 7.71 (dd, J=7.7, 1.9 Hz, 1H), 7.16 (dd, J=7.6, 4.8 Hz, 1H), 2.89-2.79 (hept, J=6.9 Hz, 1H), 1.29 (d, J=6.9 Hz, 6H).

Intermediate 36: 2-Chloro-3-(cyclopropylethynyl)pyridine

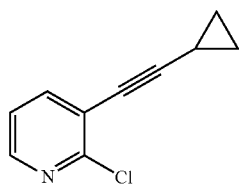 [SMILES: Clc1ncccc1C#CC1CC1]

The title compound was prepared in a manner analogous to Intermediate 25. MS (ESI): mass calcd. for $C_{10}H_5ClN$ 177.0, m/z found 178.1 [M+H]$^+$. 1H NMR (400 MHz, CDCl$_3$) δ 8.28-8.24 (dd, J=4.8, 1.9 Hz, 1H), 7.72-7.67 (dd, J=7.7, 1.9 Hz, 1H), 7.17-7.12 (dd, J=7.6, 4.8 Hz, 1H), 1.56-1.48 (m, 1H), 0.98-0.91 (m, 2H), 0.91-0.85 (m, 2H).

Intermediate 37: 2-Chloro-3-(3-methoxybut-1-yn-1-yl)pyridine

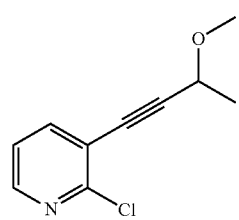

The title compound was prepared in a manner analogous to Intermediate 25. MS (ESI): mass calcd. for $C_{10}H_{10}ClNO$ 195.0, m/z found 196.1 [M+H]$^+$. 1H NMR (400 MHz, CDCl$_3$) δ 8.35-8.31 (dd, J=4.8, 1.9 Hz, 1H), 7.79-7.75 (dd, J=7.7, 1.9 Hz, 1H), 7.23-7.18 (dd, J=7.7, 4.8 Hz, 1H), 4.39-4.32 (q, J=6.6 Hz, 1H), 3.50 (s, 3H), 1.55 (d, J=6.6 Hz, 3H).

Intermediate 38: 3-(But-1-yn-1-yl)-2-chloropyridine

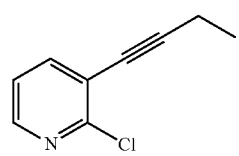

The title compound was prepared in a manner analogous to Intermediate 25. MS (ESI): mass calcd. for $C_9H_8ClN$ 165.0, m/z found 166.1 [M+H]$^+$. 1H NMR (500 MHz, CDCl$_3$) δ 8.29-8.26 (dd, J=4.8, 1.9 Hz, 1H), 7.74-7.70 (dd, J=7.7, 1.9 Hz, 1H), 7.19-7.14 (dd, J=7.6, 4.8 Hz, 1H), 2.49 (q, J=7.5 Hz, 2H), 1.27 (t, J=7.5 Hz, 3H).

Intermediate 39: 2-Bromo-3-(cyclopropylethynyl)-6-methylpyridine

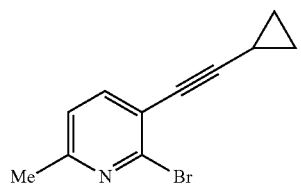 [SMILES: Cc1ccc(C#CC2CC2)c(Br)n1]

The title compound was prepared in a manner analogous to Intermediate 28. MS (ESI): mass calcd. for $C_{11}H_{10}BrN$ 235.0, m/z found 236.0 [M+H]$^+$.

Intermediate 40: 2-Bromo-3-((4-fluorophenyl)ethynyl)-6-methylpyridine

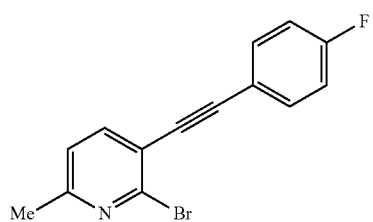 [SMILES: Cc1ccc(C#Cc2ccc(F)cc2)c(Br)n1]

The title compound was prepared in a manner analogous to Intermediate 28, using 1-ethynyl-4-fluorobenzene. MS (ESI): mass calcd. for $C_{14}H_9BrFN$ 289.0, m/z found 290 [M+H]$^+$.

Intermediate 41: 2-Bromo-6-methyl-3-(phenylethynyl)pyridine

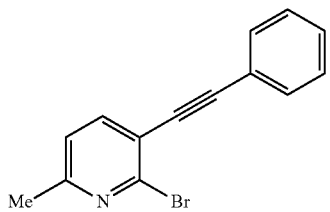 [SMILES: Cc1ccc(C#Cc2ccccc2)c(Br)n1]

The title compound was prepared in a manner analogous to Intermediate 28. MS (ESI): mass calcd. for $C_{14}H_{10}BrN$ 271.0, m/z found 273.8 [M+H]$^+$. $^1$H NMR (300 MHz, CDCl$_3$) δ 7.69 (d, J=7.8 Hz, 1H), 7.62-7.53 (m, 2H), 7.41-7.33 (m, 3H), 7.11 (d, J=7.8 Hz, 1H), 2.57 (s, 3H).

Intermediate 42: 2-Bromo-3-((4-fluorophenyl)ethynyl)pyridine

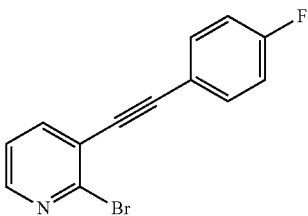 [SMILES: Fc1ccc(C#Cc2cccnc2Br)cc1]

The title compound was prepared in a manner analogous to Intermediate 28.

Intermediate 43: 2-Bromo-6-chloro-3-((4-fluorophenyl)ethynyl)pyridine

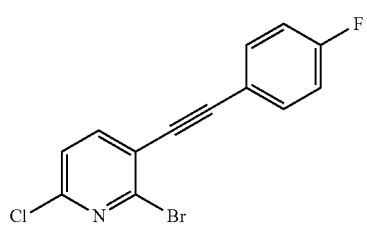 [SMILES: Fc1ccc(C#Cc2ccc(Cl)nc2Br)cc1]

The title compound was prepared in a manner analogous to Intermediate 28.

Intermediate 44: 2-Bromo-3-((4-fluorophenyl)ethynyl)-6-methoxypyridine

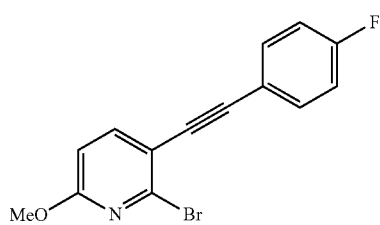 [SMILES: COc1ccc(C#Cc2ccc(F)cc2)c(Br)n1]

The title compound was prepared in a manner analogous to Intermediate 28.

Intermediate 45: 2-Bromo-6-fluoro-3-((4-fluorophenyl)ethynyl)pyridine

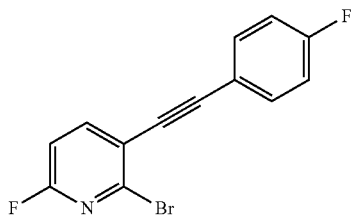 [SMILES: Fc1ccc(C#Cc2ccc(F)nc2Br)cc1]

The title compound was prepared in a manner analogous to Intermediate 28.

Intermediate 46: 5-((3-Amino-6-(trifluoromethyl)pyridin-2-yl)amino)indolin-2-one

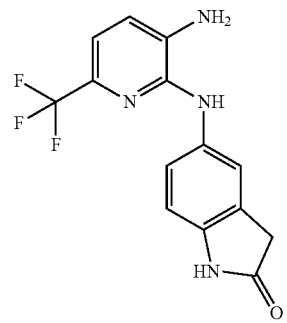 [SMILES: Nc1ccc(C(F)(F)F)nc1Nc1ccc2c(c1)CC(=O)N2]

Step A: 5-((3-Nitro-6-(trifluoromethyl)pyridin-2-yl)amino)indolin-2-one

A solution of 2-chloro-3-nitro-6-(trifluoromethyl)pyridine (27 g, 120 mmol), 5-aminoindolin-2-one (18 g, 120 mmol), and TEA (24 g, 240 mmol) in THF (250 mL) was refluxed at 90° C. for 12 h. The reaction was diluted with ether (200 mL) and stirred for 20 min where precipitate formed. The reaction was filtered and the solid was oven dried at 45° C. to give the title compound as a brown solid (21 g, 86%). MS (ESI): mass calcd. for $C_{14}H_9F_3N_4O_3$, 338.1; m/z found, 339.0 [M+H]$^+$.

Step B: 5-((3-Amino-6-(trifluoromethyl)pyridin-2-yl)amino)indolin-2-one

A solution of 5-((3-nitro-6-(trifluoromethyl)pyridin-2-yl)amino)indolin-2-one (20 g, 59 mmol), 10% Pd/C (10 g), and MeOH (1 L) was flushed with $H_2$ at 20 atm of pressure. The mixture was stirred at 50° C. for 16 h. The reaction was filtered and the resulting solution was concentrated in vacuo. The resulting solid was slurried with EtOH and oven dried at 45° C. to give the title compound as an off-white solid (12 g, 66%). MS (ESI): mass calcd. for $C_{14}H_{11}F_3N_4O$, 308.1 m/z found, 309.0 [M+H]$^+$.

Intermediate 47. N²-(1H-Indazol-5-yl)-6-(trifluoromethyl)pyridine-2,3-diamine

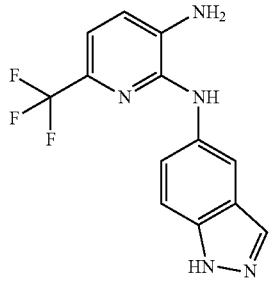 [SMILES: Nc1ccc(C(F)(F)F)nc1Nc1ccc2[nH]ncc2c1]

A solution of 2-chloro-3-nitro-6-(trifluoromethyl)pyridine (1.0 g, 4.4 mmol) and 1H-indazol-5-amine (0.58 g, 4.4 mmol) in DMF (22 mL) was heated at 110° C. After 3 h, sodium dithionite (3.0 g, 17.7 mmol) was added and the mixture was stirred at 110° C. for 5 h. The reaction was diluted with water (200 mL) and stirred for 20 min where a precipitate formed. The reaction was filtered and the solid was washed with H$_2$O and oven dried at 45° C. to give the title compound (0.78 g, 60%). MS (ESI): mass calcd. for C$_{13}$H$_{10}$F$_3$N$_5$, 293.1 m/z found, 294.0 [M+H]$^+$.

Intermediate 48: 5-((3-Amino-6-(difluoromethyl)pyridin-2-yl)amino)indolin-2-one

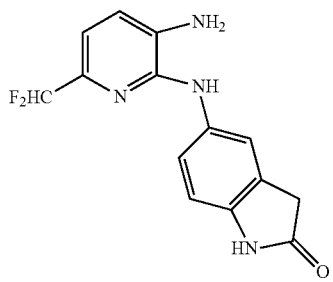 [SMILES: Nc1ccc(C(F)F)nc1Nc1ccc2c(c1)CC(=O)N2]

Step A: 6-Chloro-5-nitropicolinic acid

2-Chloro-6-methyl-3-nitropyridine (11.0 g, 63.7 mmol) was dissolved in conc. H$_2$SO$_4$ (30 mL) and the resulting solution was stirred for 10 min. to form a viscous yellowish solution. Sodium dichromate dihydrate (25.7 g, 86.4 mmol) was added to the resulting solution in batches slowly (caution: it was highly exothermic process). After 2 h stirring at rt, the reaction mixture was heated at 50° C. for 16 h. Ice (300 g) was added to the reaction mixture and stirred for 2 h. The mixture was cooled in freezer and the resulting precipitate was filtered, washed with ice cold water and dried under high vacuum to give a greenish solid as the title compound (10.1 g, 54.8%, 70% pure). MS (ESI): mass calcd. for C$_6$H$_3$ClN$_2$O$_4$, 202.0; m/z found, 202.9 [M+H]$^+$. $^1$H NMR (500 MHz, CDCl$_3$) δ 8.48-8.40 (m, 1H), 8.39-8.31 (m, 1H).

Step B: Ethyl 6-chloro-5-nitropicolinate

To a mixture of 6-chloro-5-nitropicolinic acid (6.0 g, 17.8 mmol) in EtOH (60 mL) was added p-TsOH (0.47 g, 2.5 mmol). The resulting mixture was heated at 85° C. overnight. The resulting greenish solution was concentrated under reduced pressure. Purification (FCC, SiO$_2$, EtOAc/hexanes) afforded the title compound as off-white solid (4.47 g, 92.7%). MS (ESI): mass calcd. for C$_8$H$_7$ClN$_2$O$_4$, 230.0; m/z found, 231.0 [M+H]$^+$.

Step C: (6-Chloro-5-nitropyridin-2-yl)methanol

To a solution of ethyl 6-chloro-5-nitropicolinate (4.5 g, 16.5 mmol) in DCM (50 mL) was added DIBAL (1.0 M in THF, 33.0 mL, 33.0 mmol) slowly. After 30 min, to the resulting solution was added another 2 eq. of DIBAL (1.0 M in THF, 33.0 mL, 33.0 mmol) slowly and stirred for 30 min. The resulting solution was added portion wise to the cold sat. Rochelle salt solution (100 mL) to avoid overheating and the resulting mixture was diluted with water (100 mL) and DCM (150 mL). The mixture was stirred overnight. The resulting mixture was further extracted with DCM (2×150 mL), dried (Na$_2$SO$_4$), filtered, and concentrated under reduced pressure. Purification (FCC, SiO$_2$, 0 to 50% EtOAc/Hexane) afforded the title compound as a yellowish wax (2.0 g, 40%). MS (ESI): mass calcd. for C$_6$H$_5$ClN$_2$O$_3$, 188.0; m/z found, 189.0 [M+H]$^+$. $^1$H NMR (500 MHz, CDCl$_3$) δ 8.28 (d, J=8.2 Hz, 1H), 7.62-7.44 (m, 1H), 4.87 (d, J=4.8 Hz, 2H), 2.74 (t, J=5.4 Hz, 1H).

Step D: 6-Chloro-5-nitropicolinaldehyde

To a solution of (6-chloro-5-nitropyridin-2-yl)methanol (1.14 g, 6.05 mmol) in DCM (100 mL) was added Dess-Martin periodinane (3.85 g, 9.07 mmol). The resulting cloudy brown mixture became clear solution after 30 minutes of stirring at ambient temperature. After 3 h, to the reaction mixture was added sat. NaHCO$_3$ solution (50 mL) slowly, then the resulting mixture was diluted with DCM (100 mL) and water (50 mL). The mixture was further extracted with DCM (2×100 mL). The combined extracts were dried (Na$_2$SO$_4$), filtered, concentrated under reduced pressure. Purification (FCC, SiO$_2$, 0 to 50% EtOAc/Hexane) afforded the title compound as a brown oil (0.83 g, 74%). MS (ESI): mass calcd. for C$_6$H$_3$ClN$_2$O$_3$, 186.0; m/z found, 186.9 [M+H]$^+$. $^1$H NMR (500 MHz, CDCl$_3$) δ 10.05 (d, J=0.9 Hz, 1H), 8.36 (dd, J=8.1, 0.9 Hz, 1H), 8.07 (d, J=8.1 Hz, 1H).

Step E: 2-Chloro-6-(difluoromethyl)-3-nitropyridine

To a solution of 6-chloro-5-nitropicolinaldehyde (0.834 g, 4.47 mmol) in anhydrous DCM (20 mL) at −50° C. was added DAST (1.18 mL, 8.94 mmol). The resulting mixture was allowed to warm to ambient temperature after 1 h. After another hour stirring, to the solution was added sat. NaHCO$_3$ solution (50 mL) slowly, and the resulting mixture was extracted with DCM (3×50 mL). The combined extracts were dried (Na$_2$SO$_4$), filtered, concentrated under reduced pressure. Purification (FCC, SiO$_2$, 0 to 20% EtOAc/Hexane) afforded the title compound as a brown oil (0.76 g, 82%). MS (ESI): mass calcd. for C$_6$H$_3$ClF$_2$N$_2$O$_2$, 208.0; m/z found, 209.0 [M+H]$^+$. $^1$H NMR (500 MHz, CDCl$_3$) δ 8.36 (d, J=8.0 Hz, 1H), 7.80 (d, J=8.2 Hz, 1H), 6.64 (t, J=54.6 Hz, 1H).

Step F: 5-((6-(Difluoromethyl)-3-nitropyridin-2-yl)amino)indolin-2-one

A mixture of 2-chloro-6-(difluoromethyl)-3-nitropyridine (1.8 mL, 1.0 M in benzene, 1.8 mmol), 5-aminoindolin-2- one (330 mg, 2.16 mmol), and Hunig's base (0.62 mL, 3.6 mmol) in EtOH (10 mL) was refluxed at 90° C. for 3 h. The reaction was cooled down and a precipitate formed. The mixture was filtered and the precipitate was washed with cold EtOH. The solid was dried under high vacuum to give the title compound as a brown solid (510 mg, 88%). MS (ESI): mass calcd. for $C_{14}H_{10}F_2N_4O_3$, 320.1; m/z found, 321.0 $[M+H]^+$.

Step G: 5-((3-Amino-6-(difluoromethyl)pyridin-2-yl)amino)indolin-2-one

A mixture of 5-((6-(difluoromethyl)-3-nitropyridin-2-yl)amino)indolin-2-one (510 mg, 1.6 mmol), 10% Pd/C (54 mg) in EtOH (13 mL) and THF (13 mL) in a 100 mL flask was placed under a $H_2$ balloon and stirred for 16 h. The reaction was filtered through Celite® and the resulting solution was concentrated in vacuo to give the desired compound as a grey solid (464 mg, 100%). MS (ESI): mass calcd. for $C_{14}H_{12}F_2N_4O$, 290.1 m/z found, 291.0 $[M+H]^+$.

Intermediate 49: 5-Amino-6-((1-((2-(trimethylsilyl)ethoxy)methyl)-1H-indazol-5-yl)amino)pyridin-2(1H)-one

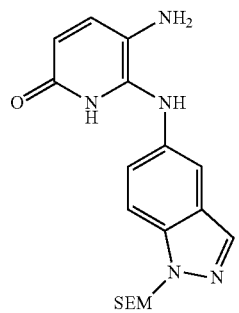 [SMILES: C[Si](C)(C)CCOCn1ncc2cc(Nc3[nH]c(=O)ccc3N)ccc21]

Step A: 5-Nitro-6-((1-((2-(trimethylsilyl)ethoxy)methyl)-1H-indazol-5-yl)amino)pyridin-2(1H)-one A solution of 6-chloro-5-nitropyridin-2(1H)-one (Intermediate 4, 500 mg, 2.86 mmol), 2-((2-(trimethylsilyl)ethoxy)methyl)-2H-indazol-5-amine (Intermediate 9, 755 mg, 2.86 mmol), and $Et_3N$ (0.5 mL, 2.86 mmol) in DMF (10.0 mL) was refluxed at 100° C. for 2 h. The reaction was diluted with water and extracted with EtOAc. The organic layers were combined, dried ($Na_2SO_4$), and concentrated in vacuo. The resulting residue was triturated in methanol to give the title compound as yellow solid (920 mg, 80%). MS (ESI): mass calcd. for $C_{18}H_{23}N_5O_4Si$, 401.5; m/z found, 402.5 $[M+H]^+$. $^1H$ NMR (500 MHz, DMSO-$d_6$) δ 10.80 (s, 1H), 8.36 (d, J=9.5 Hz, 1H), 8.23 (d, J=1.0 Hz, 1H), 8.13 (s, 1H), 7.85 (d, J=8.8 Hz, 1H), 7.59 (dd, J=8.8, 1.9 Hz, 1H), 6.08 (s, 1H), 5.85 (s, 2H), 3.67-3.57 (m, 2H), 0.99-0.85 (m, 2H), 0.04-0.01 (s, 9H).

Step B: 5-Amino-6-((1-((2-(trimethylsilyl)ethoxy)methyl)-1H-indazol-5-yl)amino)pyridin-2(1H)-one A solution of 5-nitro-6-((1-((2-(trimethylsilyl)ethoxy)methyl)-1H-indazol-5-yl)amino)pyridin-2(1H)-one (700 mg, 1.75 mmol), 10% Pd/C (295 mg), and MeOH-THF (2:1) (30.0 mL) in a 250 mL flask was flushed with $H_2$ at 20 atm of pressure. The mixture was stirred at rt for 1 h. The reaction was filtered through Celite® and the resulting solution was concentrated in vacuo. Purification (FCC, $SiO_2$, DCM/MeOH) afforded the title compound (357 mg, 55%). MS (ESI): mass calcd. for $C_{18}H_{25}N_5O_2Si$, 371.5 m/z found, 372.51 $[M+H]^+$. $^1H$ NMR (400 MHz, DMSO-$d_6$) δ 8.41 (dd, J=2.0, 0.7 Hz, 1H), 8.06 (d, J=0.8 Hz, 1H), 7.73-7.66 (m, 2H), 7.64-7.60 (m, 1H), 7.00 (d, J=8.0 Hz, 1H), 5.98 (d, J=8.0 Hz, 1H), 5.79 (s, 2H), 4.44 (s, 1H), 3.66-3.56 (m, 2H), 2.99 (s, 1H), 2.83 (d, J=0.6 Hz, 1H), 1.00-0.82 (m, 2H), 0.01 (s, 9H).

Intermediate 50: 5-((3-Amino-6-chloropyridin-2-yl)amino)indolin-2-one

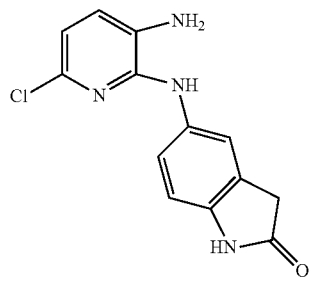 [SMILES: Nc1ccc(Cl)nc1Nc1ccc2c(c1)CC(=O)N2]

Step A: 5-((6-Chloro-3-nitropyridin-2-yl)amino)indolin-2-one

A solution of 2,6-dichloro-3-nitropyridine (1.0 g, 5.18 mmol), 5-aminoindolin-2-one (768 mg, 5.18 mol), and triethylamine (1.4 mL, 10.4 mmol) in THF (10 mL) was stirred 70° C. for 1 h. The reaction mixture was concentrated in vacuo to provide the title compound (1.95 g, 123%). MS (ESI): mass calcd. for $C_{13}H_9ClN_4O_3$ 304.0, m/z found 305.1 $[M+H]^+$.

Step B: 5-((3-Amino-6-chloropyridin-2-yl)amino)indolin-2-one

To a solution of 5-((6-chloro-3-nitropyridin-2-yl)amino)indolin-2-one (1.75 g, 5.74 mmol) in ethanol (35 mL) and water (7 mL) was added iron (1.28 g, 23.0 mmol) and ammonium chloride (35 mg, 0.66 mmol). The reaction was stirred at rt for 18 hours then refluxed for 3 hours. The reaction was cooled and filtered through Celite® and the resulting solution was concentrated in vacuo. The resulting solid was stirred in EtOAc (100 mL) and sat. aq. sodium carbonate. The organic layer was separated, washed with brine, dried ($Na_2SO_4$), filtered, and concentrated under reduced pressure. This provided the title compound as a dark grey solid (1.07 g, 68%). MS (ESI): mass calcd. for $C_{13}H_{11}ClN_4O$, 274.1 m/z found, 275.2 $[M+H]^+$. $^1H$ NMR (400 MHz, DMSO-$d_6$) δ 10.22 (s, 1H), 7.78 (s, 1H), 7.52 (s, 1H), 7.36 (dd, J=8.32, 2.08 Hz, 1H), 6.87 (d, J=7.86 Hz, 1H), 6.74 (d, J=8.32 Hz, 1H), 6.57 (d, J=7.86 Hz, 1H), 5.15 (s, 2H), 3.47 (s, 2H).

Intermediate 51: 6-Cyclopropyl-$N^2$-(1H-indazol-5-yl)pyridine-2,3-diamine

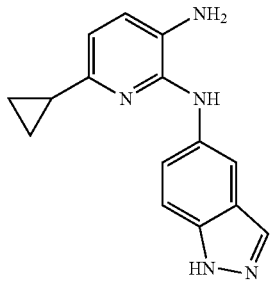 [SMILES: Nc1ccc(C2CC2)nc1Nc1ccc2[nH]ncc2c1]

Step A: N-(6-Cyclopropyl-3-nitropyridin-2-yl)-1H-indazol-5-amine

A solution of 2-chloro-6-cyclopropyl-3-nitropyridine (Intermediate 1, 427 mg, 2.15 mmol), 1H-indazol-5-amine (286 mg, 2.15 mmol), and $Et_3N$ (0.60 mL, 4.30 mmol) in THF (7.0 mL) was refluxed at 70° C. for 4 h. The reaction was diluted with EtOAc and water. The aqueous layer was extracted with EtOAc (×3), dried ($Na_2SO_4$), filtered, and concentrated in vacuo. The product was carried on assuming quantitative yield. MS (ESI): mass calcd. for $C_{15}H_{13}N_5O_2$ 295.3, m/z found 296.0 $[M+H]^+$.

Step B: 6-Cyclopropyl-$N^2$-(1H-indazol-5-yl)pyridine-2,3-diamine

A solution N-(6-cyclopropyl-3-nitropyridin-2-yl)-1H-indazol-5-amine (297 mg, 1.01 mmol) and 10% Pd/C (107 mg, 0.101 mmol) in EtOH/THF (1:1 v/v, 0.1 M) was stirred under hydrogen at rt for 5 h. The reaction was filtered through Celite® with MeOH and the resulting solution was concentrated in vacuo to provide the title compound in quantitative yield. MS (ESI): mass calcd. for $C_{15}H_{15}N_5$ 265.3, m/z found 266.1 $[M+H]^+$.

Intermediate 52: $N^2$-(3-Fluoro-1H-indazol-5-yl)-6-(trifluoromethyl)pyridine-2,3-diamine

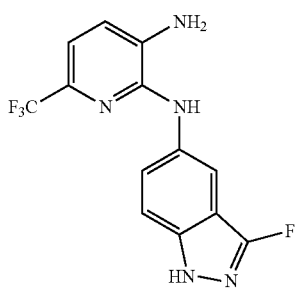 [SMILES: Nc1ccc(C(F)(F)F)nc1Nc1ccc2[nH]nc(F)c2c1]

The title compound was prepared in a manner analogous to Intermediate 52 using 3-fluoro-1H-indazol-5-amine (Intermediate 22) and 2-chloro-3-nitro-6-(trifluoromethyl)pyridine as starting materials. $^1$H NMR (400 MHz, $CD_3OD$) δ 8.25 (d, J=1.9 Hz, 1H), 7.63-7.58 (m, 1H), 7.38-7.32 (m, 1H), 7.04-6.98 (m, 2H).

Intermediate 53: 5-((3-Amino-6-methylpyridin-2-yl)amino)indolin-2-one

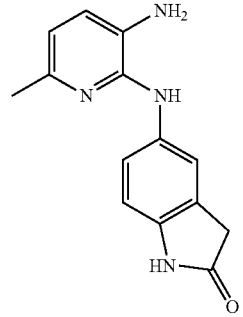 [SMILES: Cc1ccc(N)c(Nc2ccc3c(c2)CC(=O)N3)n1]

Step A: 5-((6-Methyl-3-nitropyridin-2-yl)amino)indolin-2-one

A solution of 2-chloro-6-methyl-3-nitropyridine (5.0 g, 5.9 mmol), 5-aminooxindole (5.3 g, 35 mmol), and Hunig's base (10 mL, 58 mmol) in EtOH (100 mL) was refluxed at 90° C. for 5 h. The reaction was filtered and the solid was washed with ethanol and vacuum dried to give the title compound as a black solid (6.2 g, 75%). MS (ESI): mass calcd. for $C_{14}H_{12}N_4O_3$, 284.1; m/z found, 285.0 $[M+H]^+$.

Step B: 5-((3-Amino-6-methylpyridin-2-yl)amino)indolin-2-one

A mixture of 5-((6-methyl-3-nitropyridin-2-yl)amino)indolin-2-one (6.15 g, 21.6 mmol), $SnCl_2$ dihydrate (14.6 g, 64.9 mmol), MeOH (50 mL) and EtOAc (200 mL) was stirred at ambient temperature for 10 minutes followed by heating at 85° C. for 4 h. The mixture was cooled down and to it another portion of $SnCl_2$ dihydrate (8.3 g, 32.5 mmol) was added and the resulting mixture was stirred at 85° C. for 5 h. The mixture was cooled down and concentrated in vacuo. To the residue was added MeOH (150 mL) and the resulting mixture was warmed to 50° C. The reaction mixture was filtered through Celite® and the precipitate was washed with MeOH. The grey solid was vacuum dried to give a grey solid (4.24 g, 77.3%). MS (ESI): mass calcd. for $C_{14}H_{14}N_4O$, 254.1 m/z found, 255.1 $[M+H]^+$.

Intermediate 54: $N^2$-(7-Bromo-1H-indazol-5-yl)-6-(trifluoromethyl)pyridine-2,3-diamine

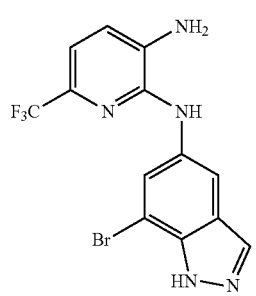 [SMILES: Nc1ccc(C(F)(F)F)nc1Nc1cc(Br)c2[nH]ncc2c1]

The title compound was prepared in a manner analogous to Intermediate 47. MS (ESI): mass calcd. for $C_{13}H_9BrF_3N_5$, 371.0 m/z found, 372.0 [M+H]⁺.

Intermediate 55: $N^2$-(7-Methyl-1H-indazol-5-yl)-6-(trifluoromethyl)pyridine-2,3-diamine

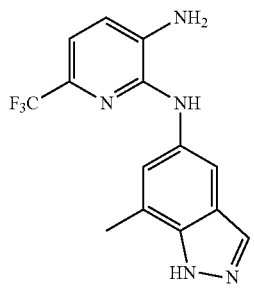 [SMILES: Cc1cc(Nc2nc(C(F)(F)F)ccc2N)cc2cn[nH]c12]

The title compound was prepared in a manner analogous to Intermediate 47. MS (ESI): mass calcd. for $C_{14}H_{12}F_3N_5$, 307.1; m/z found, 308.0 [M+H]⁺.

Intermediate 56: 6-((3-Amino-6-(difluoromethyl)pyridin-2-yl)amino)benzo[d]thiazol-2(3H)-one

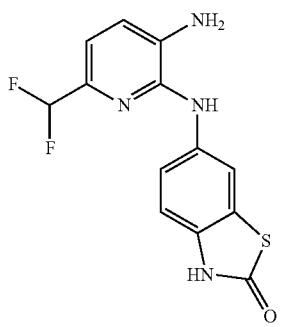 [SMILES: Nc1ccc(C(F)F)nc1Nc1ccc2[nH]c(=O)sc2c1]

The title compound was prepared in a manner analogous to Intermediate 48. MS (ESI): mass calcd. for $C_{13}H_{10}F_2N_4OS$, 308.0; m/z found, 309.0 [M+H]⁺. ¹H NMR (400 MHz, MeOD) δ 7.91 (d, J=2.1 Hz, 1H), 7.49-7.43 (m, 1H), 7.09-7.02 (m, 2H), 6.97-6.93 (m, 1H), 6.64-6.32 (m, 1H).

Intermediate 57: $N^2$-(7-Chloro-1H-indazol-5-yl)-6-(difluoromethyl)pyridine-2,3-diamine

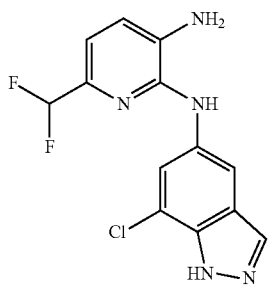 [SMILES: Nc1ccc(C(F)F)nc1Nc1cc(Cl)c2[nH]ncc2c1]

The title compound was prepared in a manner analogous to Intermediate 48. MS (ESI): mass calcd. for $C_{13}H_{10}ClF_2N_5$, 309.1; m/z found, 310.1 [M+H]⁺.

Intermediate 58: 6-((3-Amino-6-(trifluoromethyl)pyridin-2-yl)amino)benzo[d]oxazol-2(3H)-one

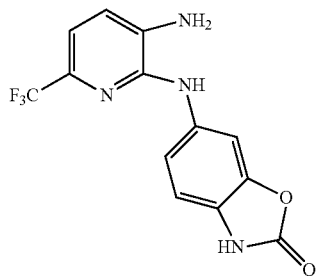 [SMILES: Nc1ccc(C(F)(F)F)nc1Nc1ccc2[nH]c(=O)oc2c1]

The title compound was prepared in a manner analogous to Intermediate 51. MS (ESI): mass calcd. for $C_{13}H_9F_3N_4O_2$, 310.1; m/z found, 311.0 [M+H]⁺. ¹H NMR (400 MHz, MeOD) δ 7.93 (d, J=2.1 Hz, 1H), 7.37-7.31 (m, 1H), 7.04-6.95 (m, 3H).

Intermediate 59: $N^2$-(1H-Indazol-5-yl)-6-isopropylpyridine-2,3-diamine

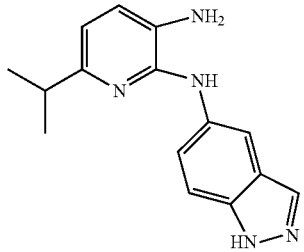 [SMILES: CC(C)c1ccc(N)c(Nc2ccc3[nH]ncc3c2)n1]

The title compound was prepared in a manner analogous to Intermediate 51. MS (ESI): mass calcd. for $C_{15}H_{11}N_5$ 267.1; m/z found 268.1 [M+H]⁺.

Intermediate 60: 6-(tert-Butyl)-$N^2$-(1H-indazol-5-yl)pyridine-2,3-diamine

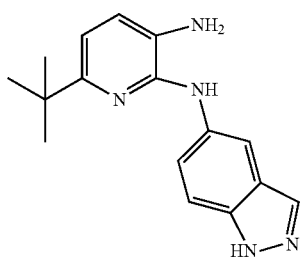 [SMILES: CC(C)(C)c1ccc(N)c(Nc2ccc3[nH]ncc3c2)n1]

The title compound was prepared in a manner analogous to Intermediate 51. MS (ESI): mass calcd. for $C_{16}H_{19}N_5$, 281.2; m/z found, 282.1 [M+H]⁺. ¹H NMR (400 MHz, MeOD) δ 8.21 (s, 1H), 7.93 (d, J=2.7 Hz, 1H), 7.58 (d, J=8.8 Hz, 1H), 7.46-7.38 (m, 1H), 6.97-6.90 (m, 1H), 6.68-6.61 (m, 1H), 1.32 (s, 9H).

Intermediate 61: 6-(Difluoromethyl)-N²-(7-methyl-1H-indazol-5-yl)pyridine-2,3-diamine

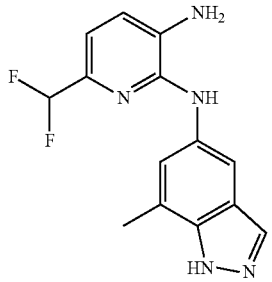 [SMILES: Cc1cc(Nc2nc(C(F)F)ccc2N)cc2cn[nH]c12]

The title compound was prepared in a manner analogous to Intermediate 48, using 2-chloro-6-(difluoromethyl)-3-nitropyridine (Intermediate 48, product from Step E) and 7-methyl-1H-indazol-5-amine. MS (ESI): mass calcd. for $C_{14}H_{13}F_2N_5$, 289.2 m/z found, [M+H]⁺=290.1.

Intermediate 62: 5-Bromo-3-(7-methyl-1H-indazol-5-yl)-2-(trifluoromethyl)-3H-imidazo[4,5-b]pyridine

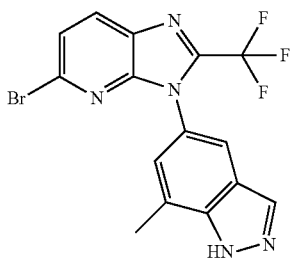 [SMILES: Cc1cc(-n2c(C(F)(F)F)nc3ccc(Br)nc32)cc2cn[nH]c12]

Step A: 6-Bromo-N²-(7-methyl-1H-indazol-5-yl)pyridine-2,3-diamine

To a solution of 2,6-dibromo-3-nitropyridine (564 mg, 2 mmol) and 7-methyl-1H-indazol-5-amine (280 mg, 1.9 mmol) in EtOH (10 mL) was added TEA (0.556 mL, 4 mmol). After 12 h the reaction was concentrated in vacuo and the resulting solid was dissolved in DMF (7.6 mL). Sodium dithionite (993 mg, 5.7 mmol) was then added in one portion and the reaction mixture heated to 100° C. After 2 h, the reaction was diluted with water (2 mL) and allowed to stir at rt. After 90 min, the solution was diluted with EtOAc (20 mL) and the organic layer washed with water (3×20 mL), dried (Na₂SO₄), filtered, and concentrated in vacuo to yield the title compound (450 mg) which was used without further purification.

Step C: 5-Bromo-3-(7-methyl-1H-indazol-5-yl)-2-(trifluoromethyl)-3H-imidazo[4,5-b]pyridine In a microwave vial, was added crude 6-bromo-N²-(7-methyl-1H-indazol-5-yl)pyridine-2,3-diamine (636 mg) and TFA (1 mL). The vial was capped and the reaction mixture heated at 100° C. for 60 min under microwave irradiation. The reaction mixture was then concentrated in vacuo and the resulting residue diluted with EtOAc/saturated sodium bicarbonate. The layers were separated and the organic layer was dried (Na₂SO₄), filtered, and concentrated in vacuo. Purification (FCC, SiO₂, 0-100% EtOAc in hexanes) afforded the title compound (135 mg). MS (ESI): mass calcd. for $C_{15}H_9BrF_3N_5$, 395.0; m/z found, 396.0 [M+H]⁺. ¹H NMR (400 MHz, CDCl₃) δ 8.16 (d, J=8.5 Hz, 1H), 8.05 (s, 1H), 7.63 (s, 1H), 7.60 (d, J=8.5 Hz, 1H), 7.08 (s, 1H), 2.55 (s, 3H).

Intermediate 63: 5-(2-(Hydroxymethyl)-1H-pyrrolo[2,3-b]pyridin-1-yl)-7-methylindolin-2-one

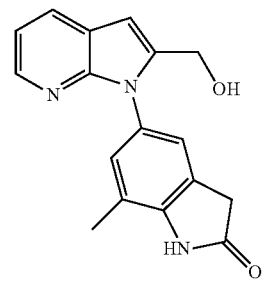 [SMILES: Cc1cc(-n2c(CO)cc3cccnc32)cc2c1NC(=O)C2]

Step A: 7-Methyl-5-((3-(3-((tetrahydro-2H-pyran-2-yl)oxy)prop-1-yn-1-yl)pyridin-2-yl)amino)indolin-2-one To a 20-mL microwave vial was added 2-chloro-3-(3-((tetrahydro-2H-pyran-2-yl)oxy)prop-1-yn-1-yl)pyridine (Intermediate 25, 250 mg, 0.993 mmol), 5-amino-7-methylindolin-2-one (Intermediate 10, 161 mg, 0.993 mmol), BrettPhos Pd third-generation pre-catalyst (90. mg, 0.099 mmol), Cs₂CO₃ (0.971 g, 2.98 mmol), and 1,4-dioxane (5.1 mL). The resulting suspension was degassed by bubbling through nitrogen gas while stirring for 5 min. The vial was sealed under nitrogen atmosphere and heated to 110° C. in an oil bath for 17.5 hr. Then, the reaction solution was partitioned between EtOAc (100 mL) and saturated aqueous ammonium chloride (25 mL). The aqueous phase was extracted twice more with EtOAc (50 mL total). The combined organic phases were washed once with brine, dried (MgSO₄), filtered, and concentrated. Purification (FCC, SiO₂, 0% to 5% methanol in DCM) afforded the title compound (64 mg, 17%) as a mixture with 7-methyl-5-(2-(((tetrahydro-2H-pyran-2-yl)oxy)methyl)-1H-pyrrolo[2,3-b]pyridin-1-yl)indolin-2-one (37 mg, 8%). MS (ESI): mass calcd. for $C_{22}H_{23}N_3O_3$ 377.2; m/z found 378.1 [M+H]⁺.

Step B: 7-Methyl-5-(2-(((tetrahydro-2H-pyran-2-yl)oxy)methyl)-1H-pyrrolo[2,3-b]pyridin-1-yl)indolin-2-one To a sealed tube containing a suspension of 7-methyl-5-((3-(3-(((tetrahydro-2H-pyran-2-yl)oxy)prop-1-yn-1-yl)pyridin-2-yl)amino)indolin-2-one (30 mg, 0.08 mmol) in anhydrous tetrahydrofuran (0.8 mL) was added TBAF (1 M in THF, 0.16 mL, 0.16 mmol). The reaction mixture was flushed briefly with nitrogen gas, sealed, and stirred at 100° C. (refluxing observed) for 1 hr. The reaction was diluted with EtOAc (15 mL), and the organic phase was washed three times with water (10 mL), once with brine (2 mL), dried ($MgSO_4$), filtered, and concentrated. Purification (FCC, $SiO_2$, 0% to 10% methanol in DCM) afforded the title compound (24 mg, 80%) as a brown glassy solid. MS (ESI): mass calcd. for $C_{22}H_{23}N_3O_3$ 377.2, m/z found 378.3 [M+H]$^+$. $^1$H NMR (400 MHz, $CD_3OD$) δ 8.13 (dd, J=4.8, 1.6 Hz, 1H), 8.03 (dd, J=7.8, 1.6 Hz, 1H), 7.21-7.08 (m, 3H), 6.67 (s, 1H), 4.72 (d, J=12.4 Hz, 1H), 4.55 (dd, J=6.5, 2.8 Hz, 1H), 4.46 (d, J=12.4 Hz, 1H), 3.61 (s, 2H), 3.59-3.48 (m, 1H), 3.39 (dt, J=11.0, 3.8 Hz, 1H), 2.32 (s, 3H), 1.85-1.38 (m, 6H).

Step C: 5-(2-(Hydroxymethyl)-1H-pyrrolo[2,3-b]pyridin-1-yl)-7-methylindolin-2-one To a suspension of 7-methyl-5-(2-(((tetrahydro-2H-pyran-2-yl)oxy)methyl)-1H-pyrrolo[2,3-b]pyridin-1-yl)indolin-2-one (22 mg, 0.058 mmol) in MeOH (0.58 mL, 0.058 mmol) was added concentrated hydrochloric acid (6.95 µL, 0.0641 mmol). The reaction was sealed under ambient atmosphere and stirred at 20° C. for 90 min. Upon completion, the reaction was partitioned between EtOAc (20 mL) and sat. aq. $NaHCO_3$ (2 mL). The aqueous phase was extracted twice more with EtOAc (10 mL total). The organics were combined, dried ($MgSO_4$), filtered, and concentrated to afford the title compound (16.7 mg, 98%). MS (ESI): mass calcd. for $C_{17}H_{15}N_3O_2$ 293.1, m/z found 294.1 [M+H]$^+$. $^1$H NMR (400 MHz, $CD_3OD$) δ 8.10 (dd, J=4.8, 1.5 Hz, 1H), 8.02 (dd, J=7.8, 1.6 Hz, 1H), 7.19-7.09 (m, 3H), 6.65 (s, 1H), 4.59 (s, 2H), 3.63 (s, 2H), 2.33 (s, 3H).

Intermediate 64: 1-(7-Methyl-2-((2-(trimethylsilyl)ethoxy)methyl)-2H-indazol-5-yl)-6-(trifluoromethyl)-1H-pyrrolo[2,3-b]pyridine-3-carbaldehyde

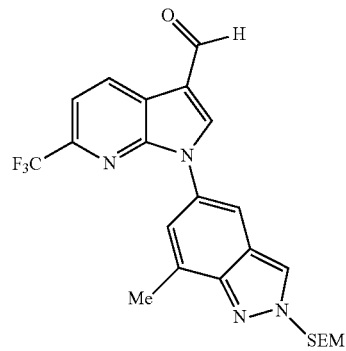 [SMILES: Cc1cc(-n2cc(C=O)c3ccc(C(F)(F)F)nc32)cc2cn(COCC[Si](C)(C)C)nc12]

Step A: 7-Methyl-5-(6-(trifluoromethyl)-1H-pyrrolo[2,3-b]pyridin-1-yl)-2-((2-(trimethylsilyl)ethoxy)methyl)-2H-indazole A mixture of 5-bromo-7-methyl-2-((2-(trimethylsilyl)ethoxy)methyl)-2H-indazole (Intermediate 13, 458 mg, 1.34 mmol), 6-(trifluoromethyl)-1H-pyrrolo[2,3-b]pyridine (250 mg, 1.34 mmol), [Pd(II)(η-Cinnamyl)Cl]2 (43.3 mg, 0.0806 mmol), BippyPhos (84 mg, 0.16 mmol) and sodium tert-butoxide (186 mg, 1.88 mmol) in 1,4-dioxane (9 mL) was heated in a microwave reactor at 150° C. for 30 minutes. The reaction mixture was diluted with $H_2O$ and extracted with EtOAc (25 mL×3). The organic layer was dried ($Na_2SO_4$), filtered and concentrated in vacuo. Purification (FCC, $SiO_2$, EtOAc/hexanes, 0:100 to 50:50) afforded the title compound (223 mg, 37%). MS (ESI): mass calcd. for $C_{22}H_{25}F_3N_4OSi$, 446.2; m/z found, 447.1 [M+H]$^+$.

Step B: 1-(7-Methyl-2-((2-(trimethylsilyl)ethoxy)methyl)-2H-indazol-5-yl)-6-(trifluoromethyl)-1H-pyrrolo[2,3-b]pyridine-3-carbaldehyde Phosphorus oxychloride (63.5 µL, 0.67 mmol) was added drop wise to DMF (1 mL) at 0° C. and stirred for 10 minutes. 7-Methyl-5-(6-(trifluoromethyl)-1H-pyrrolo[2,3-b]pyridin-1-yl)-2-((2-(trimethylsilyl)ethoxy)methyl)-2H-indazole (215 mg, 0.48 mmol) in DMF (1 mL) was added slowly to the resulting solution and the mixture was stirred at 50° C. for 3 h and then allowed to stir at ambient temperature overnight. The reaction mixture was added to a cooled, saturated solution of $NaHCO_3$ (10 mL) at 0° C. slowly. The biphasic mixture was then extracted with EtOAc (5 mL×3), and the combined organic layers dried ($Na_2SO_4$) and concentrated in vacuo. Purification (FCC, $SiO_2$, EtOAc:DCM, 0:100 to 50:50) afforded the title compound (124 mg, 54%). MS (ESI): mass calcd. for $C_{23}H_{25}F_3N_4O_2Si$, 474.2; m/z found, 475.1 [M+H]$^+$.

Intermediate 65: 2-Chloro-5-fluoro-3-(3-methylbut-1-yn-1-yl)pyridine

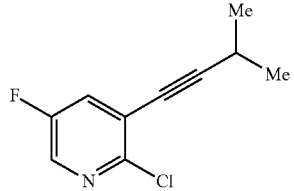 [SMILES: CC(C)C#Cc1cc(F)cnc1Cl]

The title compound was prepared in a manner analogous to 2-chloro-3-(3-((tetrahydro-2H-pyran-2-yl)oxy)prop-1-yn-1-yl)pyridine (Intermediate 25), using 3-bromo-2-chloro-5-fluoropyridine. MS (ESI): mass calcd. for $C_{10}H_9ClFN$, 197.0; m/z found, 198.0 [M+H]$^+$. 1H NMR (400 MHz, CDCl3) δ 8.14 (d, J=3.0 Hz, 1H), 7.48-7.43 (dd, J=8.1, 3.0 Hz, 1H), 2.91-2.78 (hept, J=6.9 Hz, 1H), 1.30 (d, J=6.9 Hz, 6H). 19F NMR (376 MHz, CDCl3) δ −130.32 (d, J=7.7 Hz).

Intermediate 66: 2-Chloro-6-(difluoromethyl)-3-(prop-1-yn-1-yl)pyridine

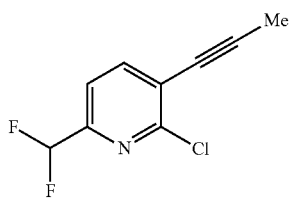 [SMILES: CC#Cc1ccc(C(F)F)nc1Cl]

The title compound was prepared in a manner analogous to 2-chloro-3-(prop-1-yn-1-yl)-6-(trifluoromethyl)pyridine (Intermediate 26), using 3-bromo-2-chloro-6-(difluoromethyl)pyridine (Intermediate 29, product from Step B). $^1$H NMR (500 MHz, CDCl3) δ 7.85 (d, J=7.9 Hz, 1H), 7.51 (d, J=7.9 Hz, 1H), 6.56 (t, J=55.1 Hz, 1H), 2.16 (s, 3H).

Example 1: 3-(1H-Indazol-5-yl)-2-phenyl-5-(trifluoromethyl)-3H-imidazo[4,5-b]pyridine

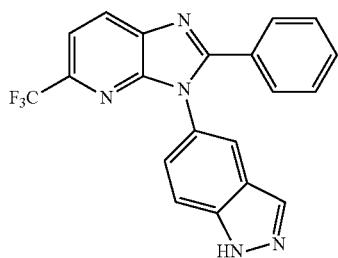

A solution of 2-chloro-3-nitro-6-(trifluoromethyl)pyridine (1.0 g, 4.4 mmol) and 1H-indazol-5-amine (0.59 g, 4.4 mmol) in DMF (20 mL) was heated at 100° C. for 3 h. Benzaldehyde (0.52 g, 4.9 mmol) was added to the mixture and the reaction was stirred for 30 min followed by addition of sodium dithionite (2.3 g, 13.2 mmol). After 12 h at 100° C. the reaction was cooled, diluted with EtOAc (100 mL), and washed with H$_2$O (50 mL×3). The organic layer was dried (Na$_2$SO$_4$) and concentrated in vacuo. Purification (FCC, SiO$_2$, EtOAc/hexanes) afforded the title compound (0.28 g, 16%). MS (ESI): mass calcd. for C$_{20}$H$_{12}$F$_3$N$_5$, 379.1; m/z found, 380.0 [M+H]$^+$. $^1$H NMR (500 MHz, DMSO-d6) δ 13.44 (br. s, 1H), 8.44 (d, J=8.2 Hz, 1H), 8.18 (s, 1H), 7.95-7.91 (m, 1H), 7.86 (d, J=8.3 Hz, 1H), 7.71 (d, J=8.7 Hz, 1H), 7.61-7.55 (m, 2H), 7.47-7.32 (m, 4H).

Example 2-Example 32 were made in a manner analogous to Example 1.

Example 2: 3-(1H-Indazol-5-yl)-2-phenyl-imidazo[4,5-b]pyridine

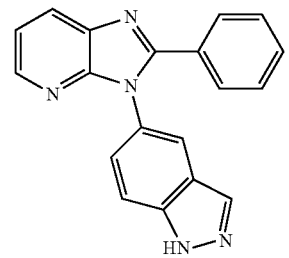 [SMILES: c1ccc(-c2nc3cccnc3n2-c2ccc3[nH]ncc3c2)cc1]

The title compound was prepared in a manner analogous to Example 1. MS (ESI): mass calcd. for C$_{19}$H$_{13}$N$_5$, 311.1; m/z found, 312.2 [M+H]$^+$. $^1$H NMR (500 MHz, CDCl$_3$) δ 11.04 (br s, 1H), 8.41 (dd, J=4.8, 1.5 Hz, 1H), 8.20 (dd, J=8.0, 1.5 Hz, 1H), 8.07 (d, J=1.0 Hz, 1H), 7.79 (dd, J=1.9, 0.8 Hz, 1H), 7.65-7.59 (m, 2H), 7.46 (d, J=8.7 Hz, 1H), 7.40-7.32 (m, 2H), 7.32-7.27 (m, 3H).

Example 3: 3-(1H-Indazol-5-yl)-5-methyl-2-phenyl-imidazo[4,5-b]pyridine

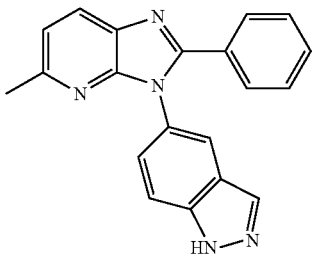 [SMILES: Cc1ccc2nc(-c3ccccc3)n(-c3ccc4[nH]ncc4c3)c2n1]

The title compound was prepared in a manner analogous to Example 1. MS (ESI): mass calcd. for C$_{20}$H$_{15}$N$_5$, 325.1; m/z found, 326.2 [M+H]$^+$. $^1$H NMR (500 MHz, DMSO-d$_6$) δ 13.37 (br s, 1H), 8.16 (s, 1H), 8.08 (d, J=8.1 Hz, 1H), 7.86 (dd, J=1.9, 0.7 Hz, 1H), 7.67 (d, J=8.7 Hz, 1H), 7.56-7.52 (m, 2H), 7.40-7.30 (m, 4H), 7.24 (d, J=8.2 Hz, 1H), 2.48 (s, 3H).

Example 4: 2-(4-Fluorophenyl)-3-(1H-indazol-5-yl)-5-methyl-imidazo[4,5-b]pyridine The title compound was prepared in a manner analogous to Example 1. MS (ESI): mass calcd. for $C_{20}H_{14}FN_5$, 343.1; m/z found, 344.2 [M+H]$^+$. $^1$H NMR (500 MHz, DMSO-d$_6$) δ 13.38 (br s, 1H), 8.18 (s, 1H), 8.07 (d, J=8.1 Hz, 1H), 7.88 (dd, J=1.9, 0.8 Hz, 1H), 7.68 (d, J=8.7 Hz, 1H), 7.60-7.54 (m, 2H), 7.32 (dd, J=8.7, 1.9 Hz, 1H), 7.24 (d, J=8.2 Hz, 1H), 7.22-7.15 (m, 2H), 2.48 (s, 3H).

Example 5: 2-(4-Fluorophenyl)-3-(1H-indol-5-yl)-5-methoxy-imidazo[4,5-b]pyridine

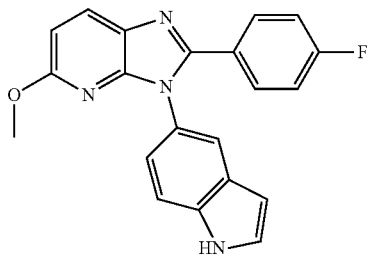 [SMILES: COc1ccc2nc(-c3ccc(F)cc3)n(-c3ccc4[nH]ccc4c3)c2n1]

The title compound was prepared in a manner analogous to Example 1. MS (ESI): mass calcd. for $C_{21}H_{15}FN_4O$, 358.1; m/z found, 359.2 [M+H]$^+$. $^1$H NMR (500 MHz, CDCl$_3$) δ 8.41 (br s, 1H), 8.01 (d, J=8.6 Hz, 1H), 7.66-7.63 (m, 1H), 7.59-7.53 (m, 2H), 7.46 (d, J=8.5 Hz, 1H), 7.33 (t, J=2.9 Hz, 1H), 7.11 (dd, J=8.5, 2.1 Hz, 1H), 6.99-6.90 (m, 2H), 6.74 (d, J=8.6 Hz, 1H), 6.63-6.59 (m, 1H), 3.83 (s, 3H).

Example 6: 5-[2-(4-Fluorophenyl)-5-methoxy-imidazo[4,5-b]pyridin-3-yl]indolin-2-one

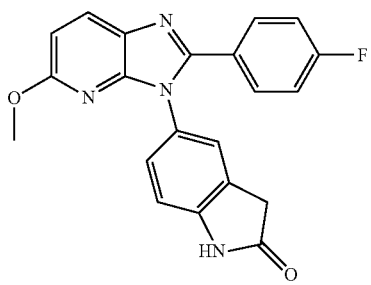 [SMILES: COc1ccc2nc(-c3ccc(F)cc3)n(-c3ccc4c(c3)CC(=O)N4)c2n1]

The title compound was prepared in a manner analogous to Example 1. MS (ESI): mass calcd. for $C_{21}H_{15}FN_4O_2$, 374.1; m/z found, 375.2 [M+H]$^+$. $^1$H NMR (500 MHz, CDCl$_3$) δ 8.27 (s, 1H), 8.05-7.97 (m, 1H), 7.59-7.52 (m, 2H), 7.23 (s, 1H), 7.22-7.17 (m, 1H), 7.07-6.99 (m, 2H), 6.95 (d, J=8.2 Hz, 1H), 6.76 (d, J=8.6 Hz, 1H), 3.87 (s, 3H), 3.60 (s, 2H).

Example 7: 5-Chloro-2-(4-fluorophenyl)-3-(1H-indazol-5-yl)imidazo[4,5-b]pyridine

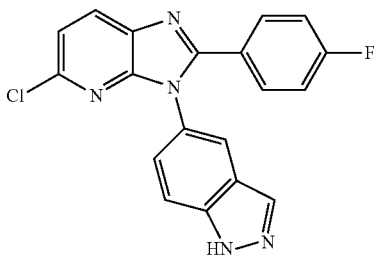 [SMILES: Fc1ccc(-c2nc3ccc(Cl)nc3n2-c2ccc3[nH]ncc3c2)cc1]

The title compound was prepared in a manner analogous to Example 1. MS (ESI): mass calcd. for $C_{19}H_{11}ClFN_5$, 363.1; m/z found, 364.1 [M+H]$^+$. $^1$H NMR (500 MHz, DMSO-d$_6$) δ 13.42 (s, 1H), 8.27 (d, J=8.3 Hz, 1H), 8.19 (s, 1H), 7.94 (d, J=2.0 Hz, 1H), 7.71 (d, J=8.7 Hz, 1H), 7.63-7.56 (m, 2H), 7.44 (d, J=8.3 Hz, 1H), 7.36 (dd, J=8.7, 2.0 Hz, 1H), 7.26-7.17 (m, 2H).

Example 8: 2-(2-Chlorophenyl)-3-(1H-indazol-5-yl)-5-methyl-imidazo[4,5-b]pyridine

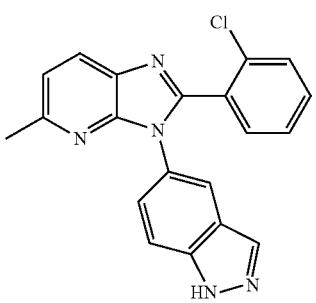 [SMILES: Cc1ccc2nc(-c3ccccc3Cl)n(-c3ccc4[nH]ncc4c3)c2n1]

The title compound was prepared in a manner analogous to Example 1. MS (ESI): mass calcd. for $C_{20}H_{14}ClN_5$, 359.1; m/z found, 360.1 [M+H]$^+$. $^1$H NMR (500 MHz, CDCl$_3$) δ 12.25 (br s, 1H), 8.12 (d, J=8.2 Hz, 1H), 7.82 (s, 1H), 7.54 (dd, J=1.9, 0.7 Hz, 1H), 7.49-7.45 (m, 1H), 7.33-7.20 (m, 4H), 7.15 (dd, J=8.8, 1.9 Hz, 1H), 7.06 (d, J=8.8 Hz, 1H), 2.71 (s, 3H).

Example 9: 3-(1H-Indazol-5-yl)-6-methyl-2-phenyl-imidazo[4,5-b]pyridine

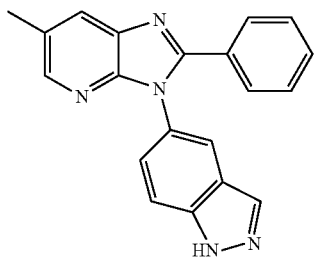 [SMILES: Cc1cnc2c(c1)nc(-c1ccccc1)n2-c1ccc2[nH]ncc2c1]

The title compound was prepared in a manner analogous to Example 1. MS (ESI): mass calcd. for $C_{20}H_{15}N_5$, 325.1; m/z found, 326.2 [M+H]$^+$. $^1$H NMR (500 MHz, CD$_3$OD) δ 8.19-8.17 (m, 1H), 8.13 (s, 1H), 8.04-8.00 (m, 1H), 7.87 (dd, J=2.0, 0.8 Hz, 1H), 7.68 (d, J=8.8 Hz, 1H), 7.61-7.54 (m, 2H), 7.45-7.31 (m, 4H), 2.53 (s, 3H).

Example 10: 5-Chloro-3-(1H-indazol-5-yl)-2-phenyl-imidazo[4,5-b]pyridine

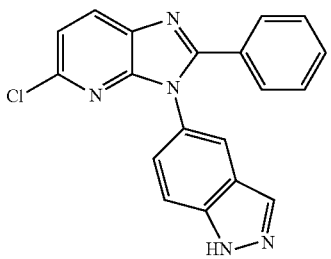 [SMILES: Clc1ccc2nc(-c3ccccc3)n(-c3ccc4[nH]ncc4c3)c2n1]

The title compound was prepared in a manner analogous to Example 1. MS (ESI): mass calcd. for $C_{19}H_{12}ClN_5$, 345.1; m/z found, 346.1 [M+H]$^+$. $^1$H NMR (400 MHz, DMSO-d$_6$) δ 13.43 (br s, 1H), 8.27 (d, J=8.3 Hz, 1H), 8.19 (s, 1H), 7.94-7.90 (m, 1H), 7.73-7.67 (m, 1H), 7.58-7.52 (m, 2H), 7.45 (d, J=8.3 Hz, 1H), 7.43-7.31 (m, 4H).

Example 11: 5-Chloro-2-cyclopentyl-3-(1H-indazol-5-yl)imidazo[4,5-b]pyridine

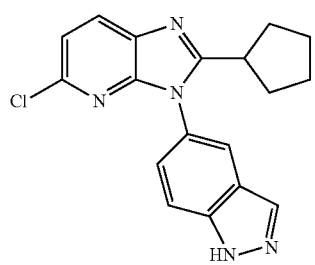 [SMILES: Clc1ccc2nc(C3CCCC3)n(-c3ccc4[nH]ncc4c3)c2n1]

The title compound was prepared in a manner analogous to Example 1. MS (ESI): mass calcd. for $C_{18}H_{16}ClN_5$, 337.1; m/z found, 338.1 [M+H]$^+$. $^1$H NMR (500 MHz, CDCl$_3$) δ 10.90 (s, 1H), 8.09 (d, J=1.0 Hz, 1H), 8.02 (d, J=8.3 Hz, 1H), 7.72 (dd, J=1.9, 0.8 Hz, 1H), 7.53-7.50 (m, 1H), 7.28-7.24 (m, 2H), 3.15-3.06 (m, 1H), 2.10-1.97 (m, 2H), 1.98-1.88 (m, 2H), 1.88-1.81 (m, 2H), 1.60-1.52 (m, 2H).

Example 12: tert-Butyl 5-(5-methyl-2-phenyl-imidazo[4,5-b]pyridin-3-yl)indazole-1-carboxylate

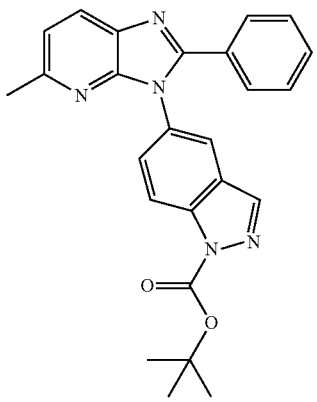 [SMILES: Cc1ccc2nc(-c3ccccc3)n(-c3ccc4c(cnn4C(=O)OC(C)(C)C)c3)c2n1]

The title compound was prepared in a manner analogous to Example 1. MS (ESI): mass calcd. for $C_{25}H_{23}N_5O_2$, 425.2; m/z found, 426.2 [M+H]$^+$. $^1$H NMR (400 MHz, CDCl$_3$) δ 8.29 (d, J=8.9 Hz, 1H), 8.20 (s, 1H), 8.03 (d, J=8.1 Hz, 1H), 7.76 (d, J=1.9 Hz, 1H), 7.56-7.49 (m, 3H), 7.39-7.33 (m, 1H), 7.32-7.25 (m, 2H), 7.17 (d, J=8.1 Hz, 1H), 2.59 (s, 3H), 1.74 (s, 9H).

Example 13: 3-(1H-Indol-5-yl)-2-phenyl-5-(trifluoromethyl)imidazo[4,5-b]pyridine

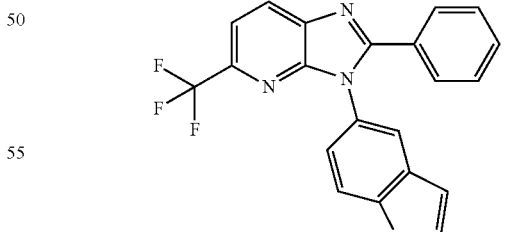

The title compound was prepared in a manner analogous to Example 1. MS (ESI): mass calcd. for $C_{21}H_{13}F_3N_4$, 378.1; m/z found, 379.1 [M+H]$^+$. $^1$H NMR (500 MHz, CDCl$_3$) δ 8.67 (s, 1H), 8.27 (d, J=8.2 Hz, 1H), 7.72 (d, J=8.3 Hz, 1H), 7.67-7.62 (m, 2H), 7.58 (d, J=2.0 Hz, 1H), 7.41-7.33 (m, 1H), 7.32-7.26 (m, 3H), 7.23-7.18 (m, 1H), 7.05 (dd, J=8.5, 2.1 Hz, 1H), 6.52-6.46 (m, 1H).

Example 14: 6-[2-Phenyl-5-(trifluoromethyl)imidazo[4,5-b]pyridin-3-yl]-3H-1,3-benzothiazol-2-one

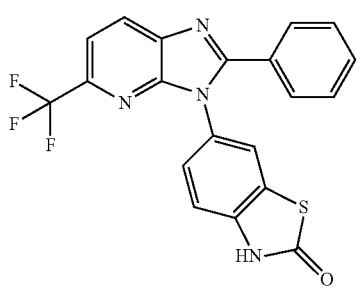

The title compound was prepared in a manner analogous to Example 1. MS (ESI): mass calcd. for $C_{20}H_{11}F_3N_4OS$, 412.1; m/z found, 413.1 [M+H]$^+$. $^1$H NMR (500 MHz, CDCl$_3$) δ 9.58 (s, 1H), 8.28 (d, J=8.2 Hz, 1H), 7.74 (d, J=8.2 Hz, 1H), 7.67-7.58 (m, 2H), 7.51-7.34 (m, 4H), 7.26-7.23 (m, 1H), 7.14 (d, J=8.4 Hz, 1H).

Example 15: 6-(5-Fluoro-2-phenyl-imidazo[4,5-b]pyridin-3-yl)-3H-1,3-benzothiazol-2-one

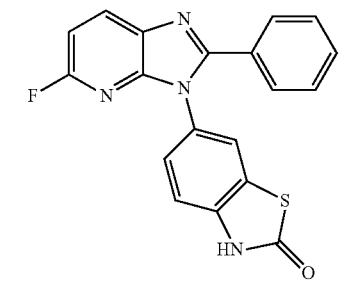 [SMILES: O=c1[nH]c2ccc(-n3c(-c4ccccc4)nc4ccc(F)nc43)cc2s1]

The title compound was prepared in a manner analogous to Example 1. MS (ESI): mass calcd. for $C_{19}H_{11}FN_4OS$, 362.1; m/z found, 363.1 [M+H]$^+$. $^1$H NMR (500 MHz, DMSO-d$_6$) δ 12.19 (s, 1H), 8.38 (dd, J=8.5, 7.2 Hz, 1H), 7.79 (d, J=2.2 Hz, 1H), 7.59-7.54 (m, 2H), 7.49-7.37 (m, 3H), 7.31 (dd, J=8.4, 2.2 Hz, 1H), 7.24 (d, J=8.4 Hz, 1H), 7.17-7.09 (m, 1H).

Example 16: 6-[2-(4-Fluorophenyl)-5-(trifluoromethyl)imidazo[4,5-b]pyridin-3-yl]-3H-1,3-benzothiazol-2-one

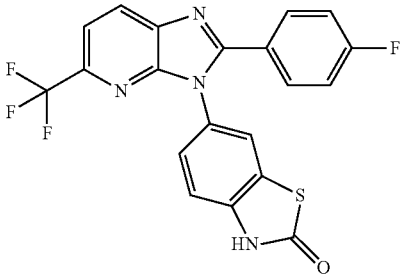 [SMILES: O=c1[nH]c2ccc(-n3c(-c4ccc(F)cc4)nc4ccc(C(F)(F)F)nc43)cc2s1]

The title compound was prepared in a manner analogous to Example 1. MS (ESI): mass calcd. for $C_{20}H_{10}F_4N_4OS$, 430.1; m/z found, 431.1 [M+H]$^+$. $^1$H NMR (500 MHz, DMSO-d$_6$) δ 12.24 (br s, 1H), 8.46 (d, J=8.2 Hz, 1H), 7.95 (s, 1H), 7.88 (d, J=8.3 Hz, 1H), 7.82 (d, J=2.1 Hz, 1H), 7.69-7.63 (m, 2H), 7.40 (dd, J=8.5, 2.2 Hz, 1H), 7.34-7.26 (m, 2H).

Example 17: 6-(5-Methyl-2-phenyl-imidazo[4,5-b]pyridin-3-yl)-3H-1,3-benzothiazol-2-one

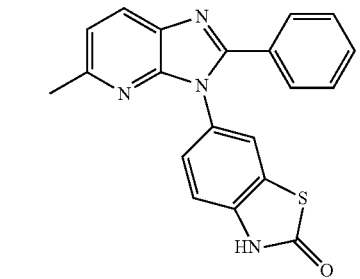 [SMILES: Cc1ccc2nc(-c3ccccc3)n(-c3ccc4[nH]c(=O)sc4c3)c2n1]

The title compound was prepared in a manner analogous to Example 1. MS (ESI): mass calcd. for $C_{20}H_{14}N_4OS$, 358.1; m/z found, 359.1 [M+H]$^+$. $^1$H NMR (500 MHz, DMSO-d$_6$) δ 12.20 (br s, 1H), 8.08 (d, J=8.1 Hz, 1H), 7.76 (d, J=2.1 Hz, 1H), 7.59-7.53 (m, 2H), 7.45-7.36 (m, 3H), 7.31-7.20 (m, 3H), 2.51 (s, 3H).

Example 18: 6-(5-Methoxy-2-phenyl-imidazo[4,5-b]pyridin-3-yl)-3H-1,3-benzothiazol-2-one

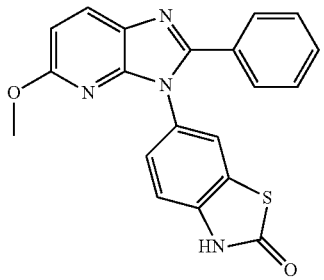

The title compound was prepared in a manner analogous to Example 1. MS (ESI): mass calcd. for $C_{20}H_{14}N_4O_2S$, 374.1; m/z found, 375.1 [M+H]$^+$. $^1$H NMR (400 MHz, DMSO-d$_6$) δ 12.18 (s, 1H), 8.11 (d, J=8.6 Hz, 1H), 7.75 (d, J=2.0 Hz, 1H), 7.54-7.48 (m, 2H), 7.43-7.34 (m, 3H), 7.31 (dd, J=8.4, 2.1 Hz, 1H), 7.23 (d, J=8.5 Hz, 1H), 6.81 (d, J=8.6 Hz, 1H), 3.77 (s, 3H).

Example 19: 6-[2-tert-Butyl-5-(trifluoromethyl)imidazo[4,5-b]pyridin-3-yl]-3H-1,3-benzothiazol-2-one

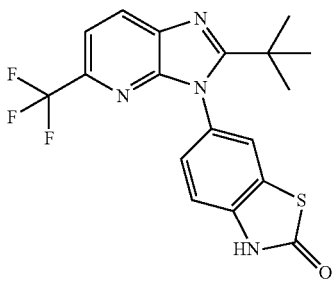

The title compound was prepared in a manner analogous to Example 1. MS (ESI): mass calcd. for $C_{18}H_{15}F_3N_4OS$, 392.1; m/z found, 393.0 [M+H]$^+$. $^1$H NMR (500 MHz, CDCl$_3$) δ 9.92 (br s, 1H), 8.22 (d, J=8.2 Hz, 1H), 7.70 (d, J=8.2 Hz, 1H), 7.49 (d, J=2.1 Hz, 1H), 7.15 (dd, J=8.4, 2.1 Hz, 1H), 7.00 (d, J=8.4 Hz, 1H), 1.40 (s, 9H).

Example 20: 6-[2-(4-Fluorophenyl)imidazo[4,5-b]pyridin-3-yl]-3H-1,3-benzothiazol-2-one

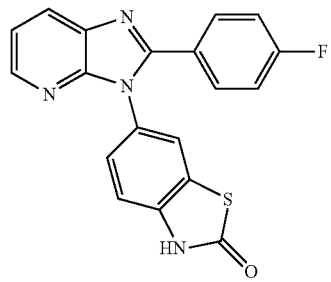 [SMILES: O=c1[nH]c2ccc(-n3c(-c4ccc(F)cc4)nc4cccnc43)cc2s1]

The title compound was prepared in a manner analogous to Example 1. MS (ESI): mass calcd. for $C_{19}H_{11}FN_4OS$, 362.1; m/z found, 363.1 [M+H]$^+$. $^1$H NMR (500 MHz, CDCl$_3$) δ 10.92 (br s, 1H), 8.39 (dd, J=4.8, 1.4 Hz, 1H), 8.18 (dd, J=8.0, 1.4 Hz, 1H), 7.66-7.58 (m, 2H), 7.46 (d, J=2.0 Hz, 1H), 7.34 (dd, J=8.0, 4.8 Hz, 1H), 7.12 (dd, J=8.4, 2.1 Hz, 1H), 7.08-6.97 (m, 3H).

Example 21: 5-[2-(4-Fluorophenyl)imidazo[4,5-b]pyridin-3-yl]-1,3-dihydrobenzimidazol-2-one

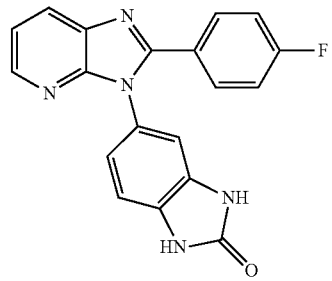 [SMILES: O=c1[nH]c2ccc(-n3c(-c4ccc(F)cc4)nc4cccnc43)cc2[nH]1]

The title compound was prepared in a manner analogous to Example 1. MS (ESI): mass calcd. for $C_{19}H_{12}FN_5O$, 345.1; m/z found, 346.0 [M+H]$^+$. $^1$H NMR (500 MHz, DMSO-d$_6$) δ 10.92 (br s, 1H), 10.86 (br s, 1H), 8.30 (dd, J=4.7, 1.5 Hz, 1H), 8.18 (dd, J=8.0, 1.5 Hz, 1H), 7.66-7.60 (m, 2H), 7.37 (dd, J=8.0, 4.8 Hz, 1H), 7.28-7.21 (m, 2H), 7.06 (d, J=2.0 Hz, 1H), 7.04 (d, J=8.2 Hz, 1H), 6.91 (dd, J=8.2, 2.0 Hz, 1H).

Example 22: 2-(4-Fluorophenyl)-3-(1H-indazol-5-yl)imidazo[4,5-b]pyridine

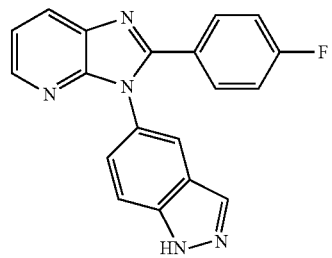 [SMILES: Fc1ccc(-c2nc3cccnc3n2-c2ccc3[nH]ncc3c2)cc1]

The title compound was prepared in a manner analogous to Example 1. MS (ESI): mass calcd. for $C_{19}H_{12}FN_5$, 329.1; m/z found, 330.2 [M+H]$^+$. $^1$H NMR (400 MHz, CDCl$_3$) δ 10.91 (br s, 1H), 8.41 (dd, J=4.8, 1.5 Hz, 1H), 8.18 (dd, J=8.1, 1.5 Hz, 1H), 8.09 (d, J=1.1 Hz, 1H), 7.79 (d, J=1.7 Hz, 1H), 7.66-7.57 (m, 2H), 7.51 (d, J=8.8 Hz, 1H), 7.34 (dd, J=8.0, 4.8 Hz, 1H), 7.29 (dd, J=8.7, 1.9 Hz, 1H), 7.03-6.95 (m, 2H).

Example 23: 5-[2-(4-Fluorophenyl)imidazo[4,5-b]pyridin-3-yl]indolin-2-one

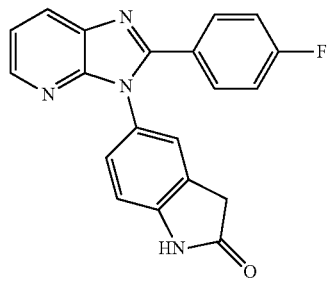 [SMILES: O=C1Cc2cc(-n3c(-c4ccc(F)cc4)nc4cccnc43)ccc2N1]

The title compound was prepared in a manner analogous to Example 1. MS (ESI): mass calcd. for $C_{20}H_{13}FN_4O$, 344.1; m/z found, 345.2 [M+H]$^+$. $^1$H NMR (500 MHz, CDCl$_3$) δ 8.38 (dd, J=4.8, 1.5 Hz, 1H), 8.31 (s, 1H), 8.14 (dd, J=8.0, 1.5 Hz, 1H), 7.70-7.58 (m, 2H), 7.36-7.28 (m, 2H), 7.20-7.14 (m, 1H), 7.09-7.02 (m, 2H), 6.97 (d, J=8.2 Hz, 1H), 3.63 (s, 2H).

Example 24: 6-[2-(4-Fluorophenyl)imidazo[4,5-b]pyridin-3-yl]-3H-1,3-benzoxazol-2-one

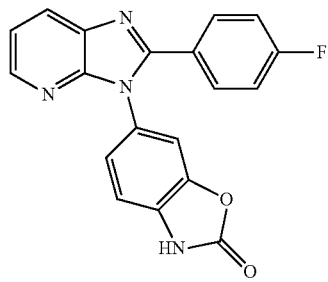 [SMILES: O=c1[nH]c2ccc(-n3c(-c4ccc(F)cc4)nc4cccnc43)cc2o1]

The title compound was prepared in a manner analogous to Example 1. MS (ESI): mass calcd. for $C_{19}H_{11}FN_4O_2$, 346.1; m/z found, 347.1 [M+H]$^+$. $^1$H NMR (500 MHz, DMSO-d$_6$) δ 11.91 (s, 1H), 8.32 (dd, J=4.7, 1.5 Hz, 1H), 8.20 (dd, J=8.0, 1.5 Hz, 1H), 7.66-7.61 (m, 2H), 7.57 (d, J=1.9 Hz, 1H), 7.39 (dd, J=8.0, 4.7 Hz, 1H), 7.30-7.22 (m, 2H), 7.21 (s, 1H), 7.17 (dd, J=8.2, 1.9 Hz, 1H).

Example 25: 6-(2-Phenylimidazo[4,5-b]pyridin-3-yl)-3H-1,3-benzothiazol-2-one

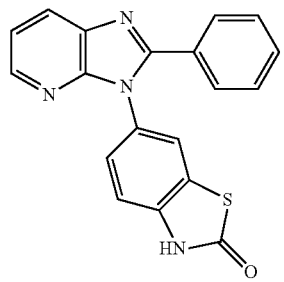 [SMILES: O=c1[nH]c2ccc(-n3c(-c4ccccc4)nc4cccnc43)cc2s1]

The title compound was prepared in a manner analogous to Example 1. MS (ESI): mass calcd. for $C_{19}H_{12}N_4OS$, 344.1; m/z found, 345.0 [M+H]$^+$. $^1$H NMR (500 MHz, CDCl$_3$) δ 10.48 (s, 1H), 8.40 (dd, J=4.8, 1.5 Hz, 1H), 8.20 (dd, J=8.0, 1.5 Hz, 1H), 7.63 (dd, J=8.4, 1.4 Hz, 2H), 7.47 (d, J=2.0 Hz, 1H), 7.45-7.39 (m, 1H), 7.39-7.32 (m, 3H), 7.16 (dd, J=8.4, 2.1 Hz, 1H), 7.04 (d, J=8.4 Hz, 1H).

Example 26: 3-(1H-Indol-5-yl)-2-phenyl-imidazo[4,5-b]pyridine

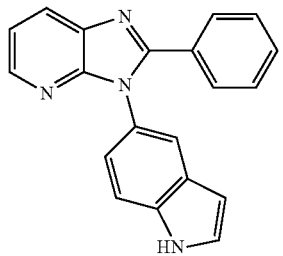 [SMILES: c1ccc(-c2nc3cccnc3n2-c2ccc3[nH]ccc3c2)cc1]

The title compound was prepared in a manner analogous to Example 1. MS (ESI): mass calcd. for $C_{20}H_{14}N_4$, 310.1; m/z found, 311.0 [M+H]$^+$. $^1$H NMR (500 MHz, CDCl$_3$) δ 8.50 (dd, J=5.0, 1.7 Hz, 2H), 8.45-8.37 (m, 1H), 7.73-7.63 (m, 3H), 7.52 (d, J=8.6 Hz, 1H), 7.49-7.40 (m, 2H), 7.40-7.29 (m, 3H), 7.13 (dd, J=8.5, 2.1 Hz, 1H), 6.62 (d, J=2.1 Hz, 1H).

Example 27: 6-[2-(4-Fluorophenyl)-5-methyl-imidazo[4,5-b]pyridin-3-yl]-3H-1,3-benzothiazol-2-one

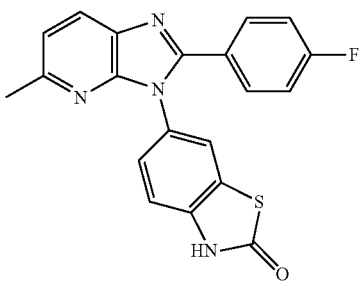 [SMILES: Cc1ccc2nc(-c3ccc(F)cc3)n(-c3ccc4[nH]c(=O)sc4c3)c2n1]

The title compound was prepared in a manner analogous to Example 1. MS (ESI): mass calcd. for $C_{20}H_{13}FN_4OS$, 376.1; m/z found, 377.0 [M+H]$^+$. $^1$H NMR (500 MHz, CDCl$_3$) δ 10.02 (s, 1H), 8.06 (d, J=8.1 Hz, 1H), 7.58 (dd, J=8.9, 5.3 Hz, 2H), 7.45 (d, J=2.1 Hz, 1H), 7.21 (d, J=8.2 Hz, 1H), 7.12 (dd, J=8.4, 2.1 Hz, 1H), 7.06-6.96 (m, 3H), 2.68 (s, 3H).

Example 28: 6-[2-(6-Fluoro-3-pyridyl)imidazo[4,5-b]pyridin-3-yl]-3H-1,3-benzothiazol-2-one

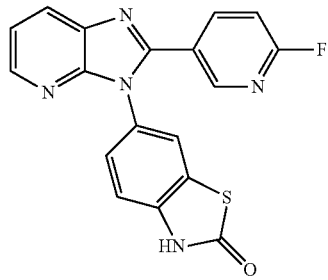 [SMILES: O=c1[nH]c2ccc(-n3c(-c4ccc(F)nc4)nc4cccnc43)cc2s1]

The title compound was prepared in a manner analogous to Example 1. MS (ESI): mass calcd. for $C_{18}H_{10}FN_5OS$, 363.1; m/z found, 364.0 [M+H]+. $^1$H NMR (400 MHz, CDCl$_3$/CD$_3$OD) δ 8.46 (d, J=2.5 Hz, 1H), 8.41 (dd, J=4.8, 1.5 Hz, 1H), 8.21 (dd, J=8.1, 1.5 Hz, 1H), 8.15-8.07 (m, 1H), 7.63 (s, 1H), 7.60-7.57 (m, 1H), 7.45 (dd, J=8.0, 4.8 Hz, 1H), 7.33-7.25 (m, 2H), 7.10 (dd, J=8.7, 2.7 Hz, 1H).

Example 29: 6-[2-(2-Fluoro-4-pyridyl)-5-methyl-imidazo[4,5-b]pyridin-3-yl]-3H-1,3-benzothiazol-2-one

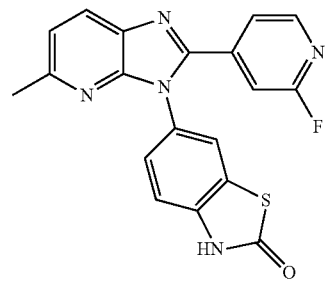 [SMILES: Cc1ccc2nc(-c3ccnc(F)c3)n(-c3ccc4[nH]c(=O)sc4c3)c2n1]

The title compound was prepared in a manner analogous to Example 1. MS (ESI): mass calcd. for $C_{19}H_{12}FN_5OS$, 377.1; m/z found, 378.0 [M+H]+. $^1$H NMR (400 MHz, CD$_3$OD/CDCl$_3$) δ 8.21 (d, J=5.3 Hz, 1H), 8.10 (d, J=8.2 Hz, 1H), 7.55 (s, 2H), 7.39-7.34 (m, 1H), 7.31 (d, J=8.4 Hz, 2H), 7.27-7.22 (m, 2H), 2.64 (s, 3H).

Example 30: 6-[5-Chloro-2-(4-fluorophenyl)imidazo[4,5-b]pyridin-3-yl]-3H-1,3-benzothiazol-2-one

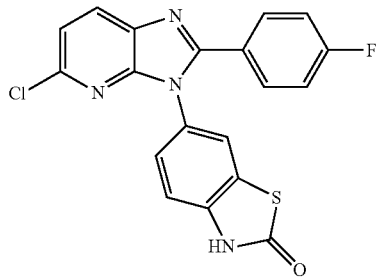 [SMILES: O=c1[nH]c2ccc(-n3c(-c4ccc(F)cc4)nc4ccc(Cl)nc43)cc2s1]

The title compound was prepared in a manner analogous to Example 1. MS (ESI): mass calcd. for $C_{19}H_{10}ClFN_4OS$, 396.0; m/z found, 396.9 [M+H]+. $^1$H NMR (500 MHz, CD$_3$OD) δ 8.09 (d, J=8.1 Hz, 1H), 7.78-7.68 (m, 1H), 7.63-7.56 (m, 2H), 7.54 (s, 1H), 7.39 (d, J=8.1 Hz, 1H), 7.28-7.17 (m, 2H), 7.16-7.05 (m, 2H).

Example 31: 6-[2-(2-Fluoro-4-pyridyl)-5-(trifluoromethyl)imidazo[4,5-b]pyridin-3-yl]-3H-1,3-benzothiazol-2-one

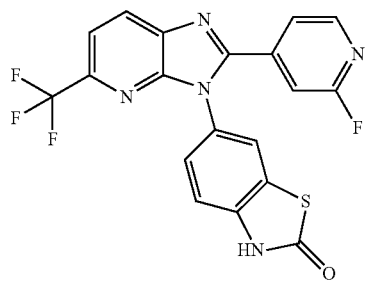 [SMILES: O=c1[nH]c2ccc(-n3c(-c4ccnc(F)c4)nc4ccc(C(F)(F)F)nc43)cc2s1]

The title compound was prepared in a manner analogous to Example 1. MS (ESI): mass calcd. for $C_{19}H_9F_4N_5OS$, 431.0; m/z found, 432.0 [M+H]+. $^1$H NMR (400 MHz, CDCl$_3$) δ 10.09 (br s, 1H), 8.36 (d, J=8.1 Hz, 1H), 8.27 (d, J=5.3 Hz, 1H), 7.79 (d, J=8.3 Hz, 1H), 7.49-7.47 (m, 1H), 7.39-7.34 (m, 1H), 7.26 (dd, J=2.8, 1.1 Hz, 3H).

Example 32: 6-(5-Bromo-2-phenyl-imidazo[4,5-b]pyridin-3-yl)-3H-1,3-benzothiazol-2-one

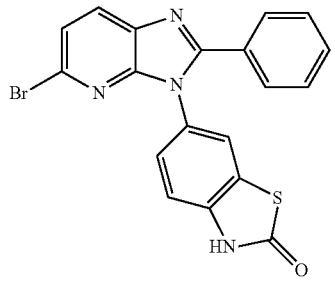 [SMILES: O=c1[nH]c2ccc(-n3c(-c4ccccc4)nc4ccc(Br)nc43)cc2s1]

The title compound was prepared in a manner analogous to Example 1. MS (ESI): mass calcd. for $C_{19}H_{11}BrN_4OS$, 422.0; m/z found, 422.9 [M+H]+. $^1$H NMR (400 MHz, CD$_3$OD) δ 8.00 (d, J=8.4 Hz, 1H), 7.59-7.53 (m, 2H), 7.49 (d, J=8.4 Hz, 1H), 7.48-7.34 (m, 4H), 7.23-7.17 (m, 2H).

Example 33: 5-[2-(4-Fluorophenyl)-5-(trifluoromethyl)imidazo[4,5-b]pyridin-3-yl]indolin-2-one

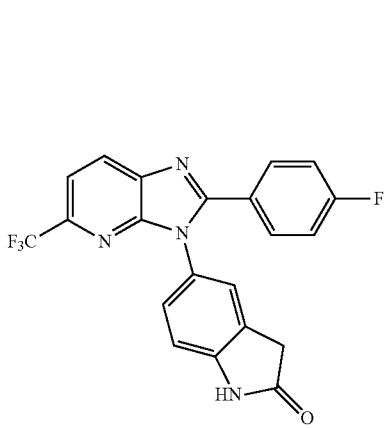 [SMILES: O=C1Cc2cc(-n3c(-c4ccc(F)cc4)nc4ccc(C(F)(F)F)nc43)ccc2N1]

Step A: tert-Butyl 5-(2-(4-fluorophenyl)-5-(trifluoromethyl)-3H-imidazo[4,5-b]pyridin-3-yl)-1H-indole-1-carboxylate A solution of 2-chloro-3-nitro-6-(trifluoromethyl)pyridine (1.0 g, 4.4 mmol) and tert-butyl 5-amino-1H-indole-1-carboxylate (0.59 g, 4.4 mmol) in DMF (20 mL) was heated at 100° C. for 3 h. 4-Fluorobenzaldehyde (0.60 g, 4.9 mmol) was added to the mixture and the reaction was stirred for 30 min followed by addition of sodium dithionite (2.3 g, 13.2 mmol). After 12 h at 100° C. the reaction was cooled, diluted with EtOAc (100 mL), and washed with $H_2O$ (50 mL×3). The organic layer was dried ($Na_2SO_4$), and concentrated in vacuo. Purification (FCC, $SiO_2$, EtOAc/hexanes) afforded the title compound (1.1 g, 50%). MS (ESI): mass calcd. for $C_{26}H_{20}F_4N_4O_2$, 496.1; m/z found, 497.0 [M+H]$^+$.

Step B: 5-[2-(4-Fluorophenyl)-5-(trifluoromethyl)imidazo[4,5-b]pyridin-3-yl]indolin-2-one To a solution of tert-butyl 5-(2-(4-fluorophenyl)-5-(trifluoromethyl)-3H-imidazo[4,5-b]pyridin-3-yl)-1H-indole-1-carboxylate (0.60 g, 1.2 mmol) in AcOH (30 mL) and $H_2O$ (6 mL) was added a solution of pyridinium tribromide (0.35 g, 1.1 mmol) in acetic acid (5 mL) and $H_2O$ (1 mL). The reaction mixture was heated at 80° C. After 24 h, the reaction was concentrated in vacuo, diluted with 1N NaOH (50 mL), and extracted with EtOAc (50 mL×3). The organic layers were combined, dried ($Na_2SO_4$), and concentrated in vacuo. Purification (FCC, $SiO_2$, EtOAc/hexanes) afforded the title compound (0.09 g, 17%). MS (ESI): mass calcd. for $C_{21}H_{12}F_4N_4O$, 412.1; m/z found 413.0 [M+H]$^+$. $^1$H NMR (500 MHz, CDCl$_3$) δ 8.51 (s, 1H), 8.24 (d, J=8.2 Hz, 1H), 7.71 (d, J=8.3 Hz, 1H), 7.67-7.62 (m, 2H), 7.24 (s, 1H), 7.21-7.14 (m, 1H), 7.11-7.04 (m, 2H), 6.96 (d, J=8.2 Hz, 1H), 3.59 (s, 2H).

Example 34-Example 37 were made according to Example 33.

Example 34: 5-(2-Phenylimidazo[4,5-b]pyridin-3-yl)indolin-2-one

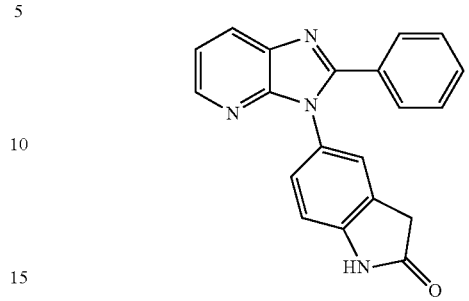

The title compound was prepared in a manner analogous to Example 33. MS (ESI): mass calcd. for $C_{20}H_{14}N_4O$, 326.1; m/z found, 327.2 [M+H]$^+$. $^1$H NMR (500 MHz, CDCl$_3$) δ 8.89 (s, 1H), 8.39-8.36 (m, 1H), 8.18-8.14 (m, 1H), 7.67-7.61 (m, 2H), 7.43-7.29 (m, 5H), 7.19-7.15 (m, 1H), 6.93 (d, J=8.2 Hz, 1H), 3.61 (s, 2H).

Example 35: 5-[2-(4-Fluorophenyl)-5-methyl-imidazo[4,5-b]pyridin-3-yl]indolin-2-one

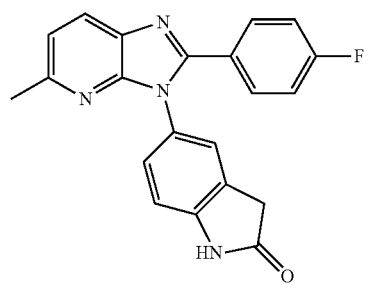 [SMILES: Cc1ccc2nc(-c3ccc(F)cc3)n(-c3ccc4c(c3)CC(=O)N4)c2n1]

The title compound was prepared in a manner analogous to Example 33. MS (ESI): mass calcd. for $C_{21}H_{15}FN_4O$, 358.1; m/z found, 359.2 [M+H]$^+$. $^1$H NMR (500 MHz, CDCl$_3$) δ 8.51 (s, 1H), 8.01 (d, J=8.2 Hz, 1H), 7.61-7.55 (m, 2H), 7.17 (d, J=8.2 Hz, 1H), 7.16-7.13 (m, 1H), 7.08-7.00 (m, 2H), 6.90 (d, J=8.2 Hz, 1H), 3.58 (s, 2H), 2.63 (s, 3H).

Example 36: 5-[2-Phenyl-5-(trifluoromethyl)imidazo[4,5-b]pyridin-3-yl]indolin-2-one

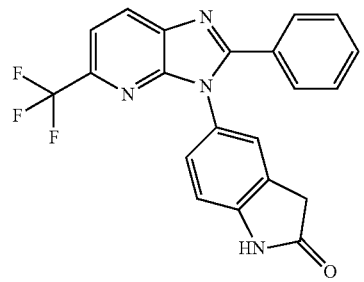 [SMILES: O=C1Cc2cc(-n3c(-c4ccccc4)nc4ccc(C(F)(F)F)nc43)ccc2N1]

The title compound was prepared in a manner analogous to Example 33. MS (ESI): mass calcd. for $C_{21}H_{13}F_3N_4O$, 394.1; m/z found, 395.1 [M+H]⁺. ¹H NMR (500 MHz, CDCl₃) δ 8.25 (d, J=8.2 Hz, 1H), 8.02 (s, 1H), 7.71 (d, J=8.3 Hz, 1H), 7.66-7.60 (m, 2H), 7.48-7.42 (m, 1H), 7.42-7.35 (m, 2H), 7.23-7.19 (m, 1H), 6.96 (d, J=8.2 Hz, 1H), 3.60 (s, 2H).

Example 37: 5-[5-Fluoro-2-(4-fluorophenyl)imidazo[4,5-b]pyridin-3-yl]indolin-2-one

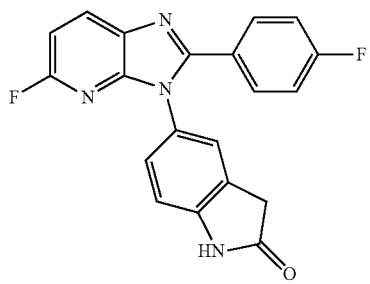

The title compound was prepared in a manner analogous to Example 33. MS (ESI): mass calcd. for $C_{20}H_{12}F_2N_4O$, 362.1; m/z found, 363.1 [M+H]⁺. ¹H NMR (500 MHz, CDCl₃) δ 8.19 (dd, J=8.5, 7.0 Hz, 1H), 8.08 (br s, 1H), 7.64-7.56 (m, 2H), 7.17-7.12 (m, 1H), 7.09-7.02 (m, 2H), 6.98-6.91 (m, 2H), 3.62 (s, 2H).

Example 38: 5-[2-Isopropyl-5-(trifluoromethyl)imidazo[4,5-b]pyridin-3-yl]indolin-2-one

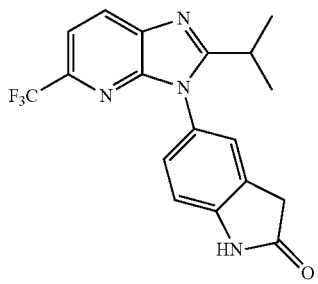 [SMILES: CC(C)c1nc2ccc(C(F)(F)F)nc2n1-c1ccc2c(c1)CC(=O)N2]

Step A: 5-((3-Nitro-6-(trifluoromethyl)pyridin-2-yl)amino)indolin-2-one

A solution of 2-chloro-3-nitro-6-(trifluoromethyl)pyridine (27 g, 120 mmol), 5-aminoindolin-2-one (18 g, 120 mmol), and Et₃N (24 g, 240 mmol) in THF (250 mL) was refluxed at 90° C. for 12 h. The reaction was diluted with ether (200 mL) and stirred for 20 min where precipitate formed. The reaction was filtered and the solid was oven dried at 45° C. to give the title compound as a brown solid (21 g, 86%). MS (ESI): mass calcd. for $C_{14}H_9F_3N_4O_3$, 338.1; m/z found, 339.0 [M+H]⁺.

Step B: 5-((3-Amino-6-(trifluoromethyl)pyridin-2-yl)amino)indolin-2-one

A solution of 5-((3-nitro-6-(trifluoromethyl)pyridin-2-yl)amino)indolin-2-one (20 g, 59 mmol), 10% Pd/C (10 g), and MeOH (1 L) was flushed with H₂ at 20 atm of pressure. The mixture was stirred at 50° C. for 16 h. The reaction was filtered and the resulting solution was concentrated in vacuo. The resulting solid was slurried with EtOH and oven dried at 45° C. to give the title compound as an off-white solid (12 g, 66%). MS (ESI): mass calcd. for $C_{14}H_{11}F_3N_4O$, 308.1; m/z found, 309.0 [M+H]⁺.

Step C. 5-(2-Isopropyl-5-(trifluoromethyl)-3H-imidazo[4,5-b]pyridin-3-yl)indolin-2-one To a solution of 5-((3-amino-6-(trifluoromethyl)pyridin-2-yl)amino)indolin-2-one (0.10 g, 0.32 mmol) and Cu(OAc)₂ (0.03 g, 0.16 mmol) in AcOH (16 mL) was added isobutryaldehyde (0.03 g, 0.36 mmol). The reaction was let stir for 2 h, concentrated in vacuo, diluted with 1N NaOH, and extracted with EtOAc (25 mL×3). The organic layers were combined, dried (Na₂SO₄), and concentrated in vacuo. Purification (FCC, SiO₂, EtOAc/hexanes) afforded the title compound (0.06 g, 48%). MS (ESI): mass calcd. for $C_{18}H_{15}F_3N_4O$, 360.1; m/z found, 361.1 [M+H]⁺. ¹H NMR (400 MHz, CDCl₃) δ 9.28 (s, 1H), 8.17 (d, J=8.2 Hz, 1H), 7.66 (d, J=8.3 Hz, 1H), 7.27 (d, J=1.9 Hz, 1H), 7.20 (dd, J=8.2, 2.1 Hz, 1H), 6.98 (d, J=8.1 Hz, 1H), 3.58 (s, 2H), 3.16 (hept, J=6.8 Hz, 1H), 1.38 (d, J=6.8 Hz, 6H).

Example 39: 6-[2-Cyclopentyl-5-(trifluoromethyl)imidazo[4,5-b]pyridin-3-yl]-3H-1,3-benzothiazol-2-one

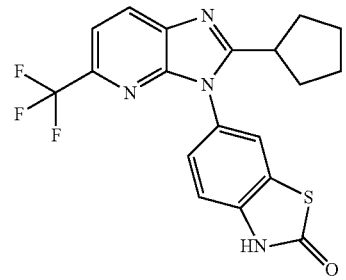 [SMILES: O=c1[nH]c2ccc(-n3c(C4CCCC4)nc4ccc(C(F)(F)F)nc43)cc2s1]

The title compound was prepared in a manner analogous to Example 38. MS (ESI): mass calcd. for $C_{19}H_{15}F_3N_4OS$, 404.1; m/z found 405.0 [M+H]⁺. ¹H NMR (600 MHz, CDCl₃) δ 10.17 (s, 1H), 8.19 (d, J=8.3 Hz, 1H), 7.69 (d, J=8.3 Hz, 1H), 7.51-7.43 (m, 1H), 7.18-7.13 (m, 1H), 7.06 (d, J=8.3 Hz, 1H), 3.19-3.11 (m, 1H), 2.09-2.02 (m, 2H), 2.01-1.94 (m, 2H), 1.92-1.86 (m, 2H), 1.67-1.59 (m, 2H).

Example 40: 6-[2-Cyclohexyl-5-(trifluoromethyl)imidazo[4,5-b]pyridin-3-yl]-3H-1,3-benzothiazol-2-one

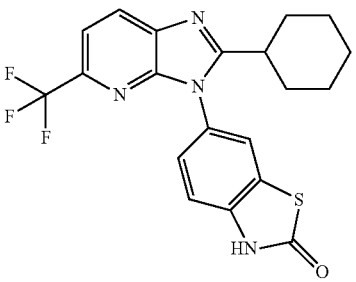 [SMILES: O=c1[nH]c2ccc(-n3c(C4CCCCC4)nc4ccc(C(F)(F)F)nc43)cc2s1]

The title compound was prepared in a manner analogous to Example 38. MS (ESI): mass calcd. for $C_{20}H_{17}F_3N_4OS$, 418.1; m/z found, 419.2 [M+H]+. 1H NMR (600 MHz, CDCl3) δ 9.89 (s, 1H), 8.20 (d, J=8.2 Hz, 1H), 7.70 (d, J=8.3 Hz, 1H), 7.46 (d, J=2.0 Hz, 1H), 7.18 (dd, J=8.3, 2.1 Hz, 1H), 7.11 (d, J=8.3 Hz, 1H), 2.79-2.71 (m, 1H), 1.97-1.88 (m, 2H), 1.87-1.69 (m, 5H), 1.38-1.18 (m, 3H).

Example 41: 6-[2-Cyclopropyl-5-(trifluoromethyl)imidazo[4,5-b]pyridin-3-yl]-3H-1,3-benzothiazol-2-one

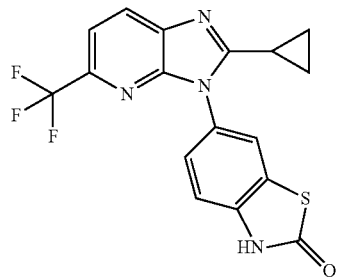

The title compound was prepared in a manner analogous to Example 38. MS (ESI): mass calcd. for $C_{17}H_{11}F_3N_4OS$, 376.1; m/z found, 377.0 [M+H]+. 1H NMR (400 MHz, CDCl3) δ 8.04 (d, J=8.1 Hz, 1H), 7.63 (d, J=8.3 Hz, 1H), 7.56 (d, J=2.1 Hz, 1H), 7.40 (dd, J=8.4, 2.1 Hz, 1H), 7.32 (d, J=8.5 Hz, 1H), 1.99-1.90 (m, 1H), 1.43-1.36 (m, 2H), 1.22-1.14 (m, 2H).

Example 42: 6-[2-Tetrahydropyran-4-yl-5-(trifluoromethyl)imidazo[4,5-b]pyridin-3-yl]-3H-1,3-benzothiazol-2-one

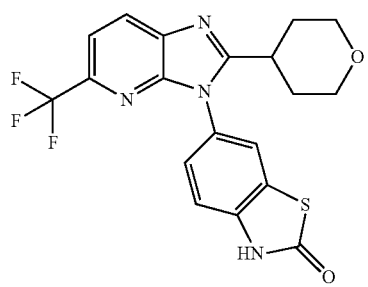 [SMILES: O=c1[nH]c2ccc(-n3c(C4CCOCC4)nc4ccc(C(F)(F)F)nc43)cc2s1]

The title compound was prepared in a manner analogous to Example 38. MS (ESI): mass calcd. for $C_{19}H_{15}F_3N_4O_2S$, 420.1; m/z found, 421.0 [M+H]+. 1H NMR (500 MHz, CDCl3) δ 9.89 (s, 1H), 8.23 (d, J=8.2 Hz, 1H), 7.72 (d, J=8.3 Hz, 1H), 7.48 (d, J=2.1 Hz, 1H), 7.18 (dd, J=8.4, 2.1 Hz, 1H), 7.09 (d, J=8.4 Hz, 1H), 4.07-4.02 (m, 2H), 3.44-3.36 (m, 2H), 3.09-3.00 (m, 1H), 2.23-2.11 (m, 2H), 1.82-1.75 (m, 2H).

Example 43: 2-Cyclopropyl-3-(1H-indazol-5-yl)-5-(trifluoromethyl)imidazo[4,5-b]pyridine

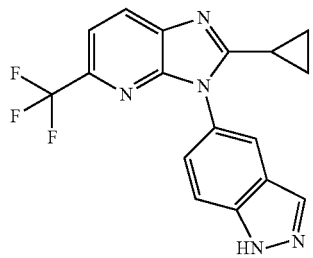 [SMILES: FC(F)(F)c1ccc2nc(C3CC3)n(-c3ccc4[nH]ncc4c3)c2n1]

The title compound was prepared in a manner analogous to Example 38. MS (ESI): mass calcd. for $C_{17}H_{12}F_3N_5$, 343.1; m/z found, 344.0 [M+H]+. 1H NMR (600 MHz, DMSO-d6) δ 13.46 (br s, 1H), 8.25 (s, 1H), 8.20 (d, J=8.0 Hz, 1H), 8.06 (dd, J=1.9, 0.7 Hz, 1H), 7.80 (d, J=8.7 Hz, 1H), 7.75 (d, J=8.3 Hz, 1H), 7.52 (dd, J=8.7, 1.9 Hz, 1H), 1.93-1.86 (m, 1H), 1.25-1.20 (m, 2H), 1.12-1.03 (m, 2H).

Example 44: 6-[2-Ethyl-5-(trifluoromethyl)imidazo[4,5-b]pyridin-3-yl]-3H-1,3-benzothiazol-2-one

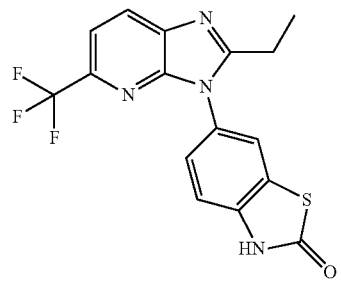 [SMILES: CCc1nc2ccc(C(F)(F)F)nc2n1-c1ccc2[nH]c(=O)sc2c1]

The title compound was prepared in a manner analogous to Example 38. MS (ESI): mass calcd. for $C_{16}H_{11}F_3N_4OS$, 364.1; m/z found, 365.0 [M+H]+. 1H NMR (400 MHz, CDCl3) δ 10.07 (br s, 1H), 8.20 (d, J=8.3 Hz, 1H), 7.69 (d, J=8.2 Hz, 1H), 7.46 (d, J=2.0 Hz, 1H), 7.19 (dd, J=8.4, 2.1 Hz, 1H), 7.11 (d, J=8.4 Hz, 1H), 2.85 (q, J=7.5 Hz, 2H), 1.40 (t, J=7.5 Hz, 3H).

Example 45: 6-[2-Isopropyl-5-(trifluoromethyl)imidazo[4,5-b]pyridin-3-yl]-3H-1,3-benzothiazol-2-one

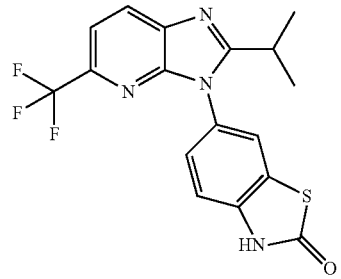 [SMILES: CC(C)c1nc2ccc(C(F)(F)F)nc2n1-c1ccc2[nH]c(=O)sc2c1]

The title compound was prepared in a manner analogous to Example 38. MS (ESI): mass calcd. for $C_{17}H_{13}F_3N_4OS$, 378.1; m/z found, 379.0 [M+H]$^+$. $^1$H NMR (400 MHz, CDCl$_3$) δ 10.11 (br s, 1H), 8.21 (d, J=8.3 Hz, 1H), 7.70 (d, J=8.2 Hz, 1H), 7.48 (d, J=2.2 Hz, 1H), 7.17 (dd, J=8.4, 2.2 Hz, 1H), 7.07 (d, J=8.4 Hz, 1H), 3.20-3.04 (m, 1H), 1.38 (d, J=6.9 Hz, 6H).

Example 46: 6-[2-Methyl-5-(trifluoromethyl)imidazo[4,5-b]pyridin-3-yl]-3H-1,3-benzothiazol-2-one

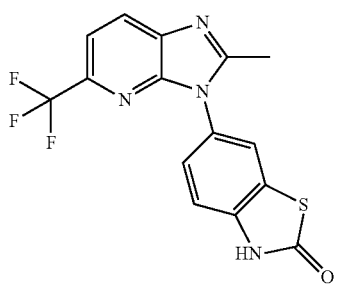

The title compound was prepared in a manner analogous to Example 38. MS (ESI): mass calcd. for $C_{15}H_9F_3N_4OS$, 350.0; m/z found 351.0 [M+H]$^+$. $^1$H NMR (500 MHz, CDCl$_3$) δ 10.08 (br s, 1H), 8.17 (d, J=8.2 Hz, 1H), 7.69 (d, J=8.2 Hz, 1H), 7.47 (d, J 2.1 Hz, 1H), 7.21 (dd, J 8.4, 2.1 Hz, 1H), 7.14 (d, J=8.4 Hz, 1H), 2.59 (s, 3H).

Example 47: 5-[2-Methyl-5-(trifluoromethyl)imidazo[4,5-b]pyridin-3-yl]indolin-2-one

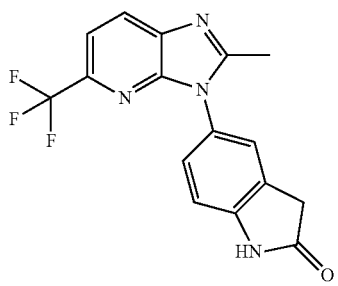

The title compound was prepared in a manner analogous to Example 38. MS (ESI): mass calcd. for $C_{16}H_{11}F_3N_4O$, 332.1; m/z found, 333.0 [M+H]$^+$. $^1$H NMR (400 MHz, CDCl$_3$) δ 8.92 (br s, 1H), 8.12 (d, J=8.1 Hz, 1H), 7.65 (d, J=8.2 Hz, 1H), 7.27 (s, 1H), 7.22 (dd, J=8.2, 2.2 Hz, 1H), 7.01 (d, J=8.2 Hz, 1H), 3.62 (s, 2H), 2.58 (s, 3H).

Example 48: 5-[2-Cyclohexyl-5-(trifluoromethyl)imidazo[4,5-b]pyridin-3-yl]indolin-2-one

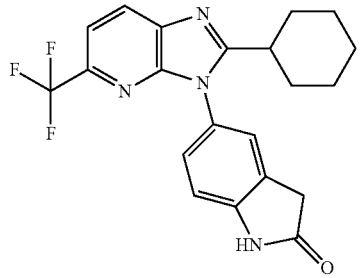 [SMILES: O=C1Cc2cc(-n3c(C4CCCCC4)nc4ccc(C(F)(F)F)nc43)ccc2N1]

The title compound was prepared in a manner analogous to Example 38. MS (ESI): mass calcd. for $C_{21}H_{19}F_3N_4O$, 400.2; m/z found, 401.2 [M+H]$^+$. $^1$H NMR (400 MHz, DMSO-d$_6$) δ 10.67 (s, 1H), 8.29 (d, J=8.3 Hz, 1H), 7.76 (d, J=8.3 Hz, 1H), 7.39 (s, 1H), 7.33 (dd, J=2.1, 8.1 Hz, 1H), 7.03 (d, J=8.1 Hz, 1H), 3.62 (s, 2H), 2.72 (tt, J=11.4, 3.4 Hz, 1H), 1.95-1.81 (m, 2H), 1.79-1.57 (m, 5H), 1.34-1.08 (m, 3H).

Example 49: 5-[2-Cyclobutyl-5-(trifluoromethyl)imidazo[4,5-b]pyridin-3-yl]indolin-2-one

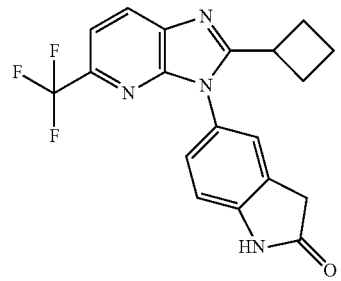 [SMILES: O=C1Cc2cc(-n3c(C4CCC4)nc4ccc(C(F)(F)F)nc43)ccc2N1]

The title compound was prepared in a manner analogous to Example 38. MS (ESI): mass calcd. for $C_{19}H_{15}F_3N_4O$, 372.1; m/z found, 373.1 [M+H]$^+$. $^1$H NMR (500 MHz, DMSO-d$_6$) δ 10.66 (s, 1H), 8.31 (d, J=8.2 Hz, 1H), 7.77 (d, J=8.2 Hz, 1H), 7.33 (s, 1H), 7.27 (dd, J=8.1, 2.2 Hz, 1H), 7.00 (d, J=8.1 Hz, 1H), 3.68-3.55 (m, 3H), 2.49-2.43 (m, 2H), 2.19-2.08 (m, 2H), 2.02-1.80 (m, 2H).

Example 50: 5-[2-Tetrahydropyran-4-yl-5-(trifluoromethyl)imidazo[4,5-b]pyridin-3-yl]indolin-2-one

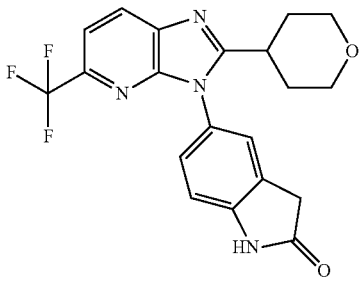 [SMILES: O=C1Cc2cc(-n3c(C4CCOCC4)nc4ccc(C(F)(F)F)nc43)ccc2N1]

The title compound was prepared in a manner analogous to Example 38. MS (ESI): mass calcd. for $C_{20}H_{17}F_3N_4O_2$, 402.1; m/z found, 403.1 [M+H]$^+$. $^1$H NMR (400 MHz, DMSO-d$_6$) δ 10.68 (s, 1H), 8.33 (d, J=8.1 Hz, 1H), 7.78 (d, J=8.3 Hz, 1H), 7.42 (br s, 1H), 7.36 (dd, J=8.3, 1.8 Hz, 1H), 7.03 (d, J=8.1 Hz, 1H), 3.92-3.84 (m, 2H), 3.62 (s, 2H), 3.29 (dt, J=11.3, 2.1 Hz, 2H), 3.03 (tt, J=3.8, 11.3 Hz, 1H), 1.96-1.82 (m, 2H), 1.80-1.71 (m, 2H).

Example 51: 5-[2-Isobutyl-5-(trifluoromethyl)imidazo[4,5-b]pyridin-3-yl]indolin-2-one

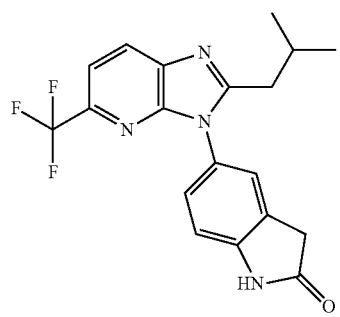 [SMILES: CC(C)Cc1nc2ccc(C(F)(F)F)nc2n1-c1ccc2c(c1)CC(=O)N2]

The title compound was prepared in a manner analogous to Example 38. MS (ESI): mass calcd. for $C_{19}H_{17}F_3N_4O$, 374.1; m/z found, 375.1 [M+H]$^+$. $^1$H NMR (400 MHz, CDCl$_3$) δ 8.14 (d, J=8.3 Hz, 1H), 7.97 (br s., 1H), 7.64 (d, J=8.3 Hz, 1H), 7.24 (br s., 1H), 7.21 (br. d., J=8.6 Hz, 1H), 7.03 (d, J=8.1 Hz, 1H), 3.66 (s, 2H), 2.72 (d, J=7.4 Hz, 2H), 2.25 (quind, J=13.6, 6.8 Hz, 1H), 0.95 (d, J=6.7 Hz, 6H).

Example 52: (racemic)-5-[2-Tetrahydrofuran-3-yl-5-(trifluoromethyl)imidazo[4,5-b]pyridin-3-yl]indolin-2-one

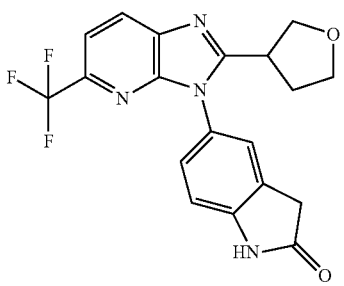 [SMILES: O=C1Cc2cc(-n3c(C4CCOC4)nc4ccc(C(F)(F)F)nc43)ccc2N1]

The title compound was prepared in a manner analogous to Example 38. MS (ESI): mass calcd. for $C_{19}H_{15}F_3N_4O_2$, 388.1; m/z found, 389.1 [M+H]$^+$. $^1$H NMR (500 MHz, DMSO-d$_6$) δ 10.69 (br s., 1H), 8.33 (d, J=8.4 Hz, 1H), 7.79 (d, J=8.1 Hz, 1H), 7.43 (s, 1H), 7.37 (dd, J=8.1, 2.3 Hz, 1H), 7.04 (d, J=8.1 Hz, 1H), 3.99-3.85 (m, 3H), 3.75 (q, J=7.2 Hz, 1H), 3.63 (s, 2H), 3.54 (quin, J=7.5 Hz, 1H), 2.37-2.29 (m, 1H), 2.18-2.09 (m, 1H).

Example 53: 5-[5-(Trifluoromethyl)-2-(3,3,3-trifluoropropyl)imidazo[4,5-b]pyridin-3-yl]indolin-2-one

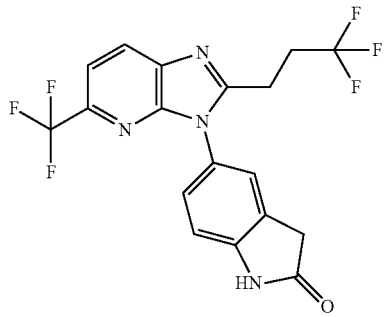 [SMILES: O=C1Cc2cc(-n3c(CCC(F)(F)F)nc4ccc(C(F)(F)F)nc43)ccc2N1]

The title compound was prepared in a manner analogous to Example 38. MS (ESI): mass calcd. for $C_{18}H_{12}F_6N_4O$, 414.1; m/z found, 415.1 [M+H]$^+$. $^1$H NMR (500 MHz, DMSO-d$_6$) δ 10.67 (br s., 1H), 8.35 (d, J=8.4 Hz, 1H), 7.80 (d, J=8.4 Hz, 1H), 7.43 (d, J=1.7 Hz, 1H), 7.37 (dd, J=8.1, 2.0 Hz, 1H), 7.04 (d, J=8.1 Hz, 1H), 3.62 (s, 2H), 3.04-2.99 (m, 2H), 2.94-2.82 (m, 2H).

Example 54: 5-[2-(Cyclopentylmethyl)-5-(trifluoromethyl)imidazo[4,5-b]pyridin-3-yl]indolin-2-one

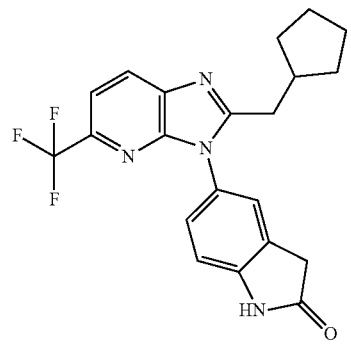 [SMILES: O=C1Cc2cc(-n3c(CC4CCCC4)nc4ccc(C(F)(F)F)nc43)ccc2N1]

The title compound was prepared in a manner analogous to Example 38. MS (ESI): mass calcd. for $C_{21}H_{19}F_3N_4O$, 400.2; m/z found, 401.2 [M+H]$^+$. $^1$H NMR (500 MHz, CDCl$_3$) δ 8.18-8.12 (m, 2H), 7.65 (d, J=8.1 Hz, 1H), 7.25 (s, 1H), 7.22 (br. d., J=8.4 Hz, 1H), 7.03 (d, J=8.1 Hz, 1H), 3.66 (s, 2H), 2.85 (d, J=7.5 Hz, 2H), 2.41 (spt, J=7.7 Hz, 1H), 1.86-1.77 (m, 2H), 1.66-1.50 (m, 4H), 1.23-1.12 (m, 2H).

Example 55: 5-[2-Cyclopropyl-5-(trifluoromethyl)imidazo[4,5-b]pyridin-3-yl]indolin-2-one

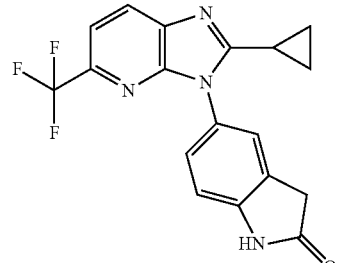

The title compound was prepared in a manner analogous to Example 38. MS (ESI): mass calcd. for $C_{18}H_{13}F_3N_4O$, 358.1; m/z found, 359.0 [M+H]$^+$. $^1$H NMR (500 MHz, CDCl$_3$) δ 8.87 (s, 1H), 8.04 (d, J=8.3 Hz, 1H), 7.61 (d, J=8.2 Hz, 1H), 7.38 (s, 1H), 7.36-7.32 (m, 1H), 7.02 (d, J=8.1 Hz, 1H), 3.62 (s, 2H), 1.97-1.88 (m, 1H), 1.43-1.36 (m, 2H), 1.20-1.11 (m, 2H).

Example 56: 5-[2-Benzyl-5-(trifluoromethyl)imidazo[4,5-b]pyridin-3-yl]indolin-2-one

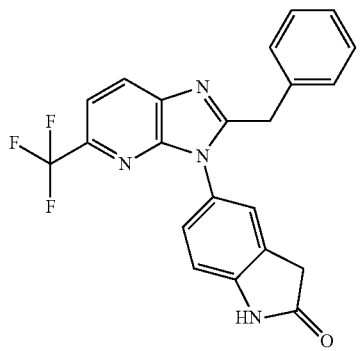 [SMILES: O=C1Cc2cc(-n3c(Cc4ccccc4)nc4ccc(C(F)(F)F)nc43)ccc2N1]

The title compound was prepared in a manner analogous to Example 38. MS (ESI): mass calcd. for $C_{22}H_{15}F_3N_4O$, 408.1; m/z found, 409.1 [M+H]$^+$. $^1$H NMR (500 MHz, CDCl$_3$) δ 8.38 (br s., 1H), 8.20 (d, J=8.4 Hz, 1H), 7.67 (d, J=8.4 Hz, 1H), 7.26-7.16 (m, 3H), 7.10-7.01 (m, 3H), 6.97 (s, 1H), 6.93 (d, J=8.4 Hz, 1H), 4.22 (s, 2H), 3.54 (s, 2H).

Example 57: 5-[2-(Pyrazin-2-ylmethyl)-5-(trifluoromethyl)imidazo[4,5-b]pyridin-3-yl]indolin-2-one

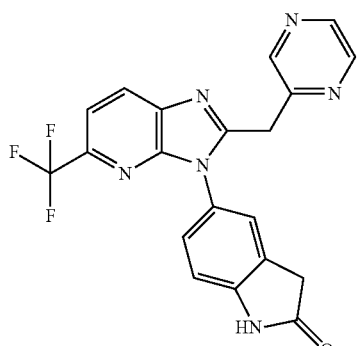

The title compound was prepared in a manner analogous to Example 38. MS (ESI): mass calcd. for $C_{20}H_{13}F_3N_6O$, 410.1; m/z found, 411.1 [M+H]$^+$. $^1$H NMR (400 MHz, DMSO-d$_6$) δ 10.65 (br s., 1H), 8.52 (br s, 1H), 8.51-8.46 (m, 2H), 8.30 (d, J=8.3 Hz, 1H), 7.79 (d, J=8.3 Hz, 1H), 7.32 (br s., 1H), 7.27 (dd, J=8.2, 2.2 Hz, 1H), 6.95 (d, J=8.3 Hz, 1H), 4.44 (s, 2H), 3.56 (s, 2H).

Example 58: 2-Cyclopentyl-3-(1H-indol-5-yl)-5-(trifluoromethyl)imidazo[4,5-b]pyridine

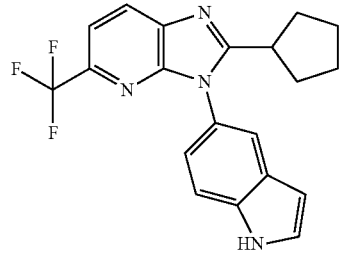 [SMILES: FC(F)(F)c1ccc2nc(C3CCCC3)n(-c3ccc4[nH]ccc4c3)c2n1]

The title compound was prepared in a manner analogous to Example 38. MS (ESI): mass calcd. for $C_{20}H_{17}F_3N_4$, 370.1; m/z found, 371.1 [M+H]$^+$. $^1$H NMR (500 MHz, CDCl$_3$) δ 8.69 (br s., 1H), 8.15 (d, J=8.4 Hz, 1H), 7.64 (d, J=8.4 Hz, 1H), 7.57 (s, 1H), 7.39 (d, J=8.7 Hz, 1H), 7.29-7.26 (m, 1H), 7.07 (dd, J=8.4, 1.7 Hz, 1H), 6.60-6.54 (m, 1H), 3.20 (quin, J=8.5 Hz, 1H), 2.10-2.00 (m, 2H), 2.00-1.91 (m, 2H), 1.91-1.81 (m, 2H), 1.62-1.51 (m, 2H).

Example 59: 2-tert-Butyl-3-(1H-indol-5-yl)-5-(trifluoromethyl)imidazo[4,5-b]pyridine

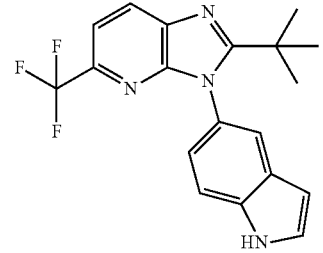 [SMILES: CC(C)(C)c1nc2ccc(C(F)(F)F)nc2n1-c1ccc2[nH]ccc2c1]

The title compound was prepared in a manner analogous to Example 38. MS (ESI): mass calcd. for $C_{19}H_{17}F_3N_4$, 358.1; m/z found, 359.1 [M+H]$^+$. $^1$H NMR (500 MHz, CDCl$_3$) δ 8.55 (br s., 1H), 8.16 (d, J=8.1 Hz, 1H), 7.61 (d, J=8.4 Hz, 1H), 7.60 (br. d, J=1.7 Hz, 1H), 7.41 (d, J=8.4 Hz, 1H), 7.30-7.27 (m, 1H), 7.08 (dd, J=8.5, 1.9 Hz, 1H), 6.58 (br. d., J=2.3 Hz, 1H), 1.37 (s, 9H).

Example 60: 5-[2-Cyclopentyl-5-(trifluoromethyl)imidazo[4,5-b]pyridin-3-yl]indolin-2-one

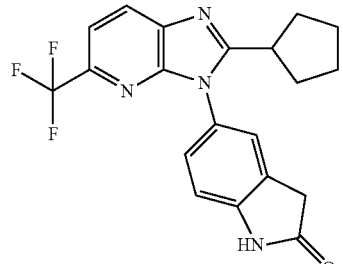

The title compound was prepared in a manner analogous to Example 38. MS (ESI): mass calcd. for $C_{20}H_{17}F_3N_4O$, 386.1; m/z found, 387.1 [M+H]+. 1H NMR (400 MHz, DMSO-d6) δ 10.67 (s, 1H), 8.29 (d, J=7.9 Hz, 1H), 7.77 (d, J=8.3 Hz, 1H), 7.39 (br s., 1H), 7.34 (dd, J=8.2, 2.2 Hz, 1H), 7.03 (d, J=8.3 Hz, 1H), 3.62 (s, 2H), 3.17 (quin, J=8.0 Hz, 1H), 2.04-1.82 (m, 4H), 1.82-1.69 (m, 2H), 1.64-1.49 (m, 2H).

Example 61: 5-[2-tert-Butyl-5-(trifluoromethyl)imidazo[4,5-b]pyridin-3-yl]indolin-2-one

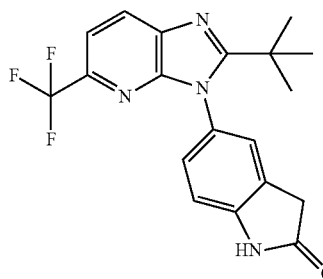

The title compound was prepared in a manner analogous to Example 38. MS (ESI): mass calcd. for C19H17F3N4O, 374.1; m/z found, 375.1 [M+H]+. 1H NMR (500 MHz, DMSO-d6) δ 10.70 (s, 1H), 8.31 (d, J=8.4 Hz, 1H), 7.77 (d, J=8.1 Hz, 1H), 7.40 (br s., 1H), 7.33 (dd, J=8.2, 2.2 Hz, 1H), 7.00 (d, J=8.1 Hz, 1H), 3.68-3.55 (m, 2H), 1.31 (s, 9H).

Example 62: 4-[2-(4-Fluorophenyl)-3-(1H-indazol-5-yl)imidazo[4,5-b]pyridin-7-yl]morpholine

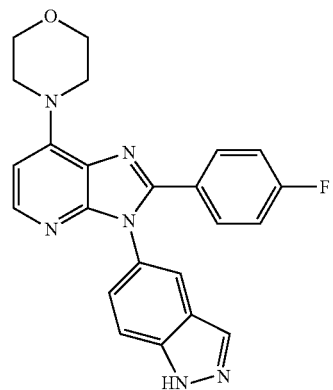 [SMILES: Fc1ccc(-c2nc3c(N4CCOCC4)ccnc3n2-c2ccc3[nH]ncc3c2)cc1]

Step A: 4-(2-Fluoro-3-nitropyridin-4-yl)morpholine

A solution of 2,4-difluoro-3-nitropyridine (0.5 g, 3.1 mmol) and morpholine (0.25 mg, 2.8 mmol) in DMF (15 mL) was heated at 90° C. After 2 h the reaction was diluted with EtOAc (50 mL) and washed with water (25 mL×3). The organics were dried (Na2SO4) and concentrated in vacuo. Purification (FCC, SiO2, EtOAc/hexanes) afforded the title compound (0.47 g, 66%). MS (ESI): mass calcd. for C9H10FN3O3, 227.1 m/z found, 228.1 [M+H]+.

Step B: 4-[2-(4-Fluorophenyl)-3-(1H-indazol-5-yl)imidazo[4,5-b]pyridin-7-yl]morpholine A solution of 4-(2-fluoro-3-nitropyridin-4-yl)morpholine (0.23 g, 1.0 mmol) and 5-aminoindazole (0.13 g, 1.0 mmol) in DMF (5 mL) was heated at 100° C. for 3 h. After cooling to rt, 4-fluorobenzaldehyde (0.12 g, 1.0 mmol) was added and the reaction was let stir. After 30 minutes, sodium dithionite (0.53 g, 3.0 mmol) was added and the reaction was again heated at 100° C. After 12 h, the reaction was diluted with EtOAc (50 mL) and washed with H2O (3×25 mL). The organic layer was dried (Na2SO4) and concentrated in vacuo. Purification (FCC, SiO2, Hex:EtOAc) afforded the title compound (0.12 g, 29%). MS (ESI): mass calcd. for C23H19FN6O, 414.1; m/z found, 415.2 [M+H]+. 1H NMR (500 MHz, DMSO-d6) δ 13.33 (s, 1H), 8.16 (s, 1H), 7.94 (d, J=5.7 Hz, 1H), 7.84-7.83 (m, 1H), 7.65 (d, J=8.7 Hz, 1H), 7.58-7.50 (m, 2H), 7.28 (dd, J=8.7, 1.9 Hz, 1H), 7.22-7.15 (m, 2H), 6.65 (d, J=5.8 Hz, 1H), 3.99-3.92 (m, 4H), 3.87-3.78 (m, 4H).

Example 63: 5-[2-(4-Fluorophenyl)-7-morpholino-imidazo[4,5-b]pyridin-3-yl]indolin-2-one

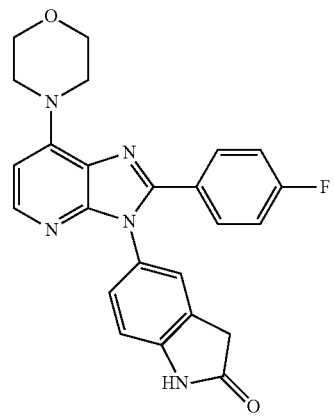 [SMILES: O=C1Cc2cc(-n3c(-c4ccc(F)cc4)nc4c(N5CCOCC5)ccnc43)ccc2N1]

The title compound was prepared in a manner analogous to Example 62 with the appropriate substitutions. MS (ESI): mass calcd. for C24H20FN5O2, 429.2; m/z found, 430.2 [M+H]+. 1H NMR (500 MHz, CDCl3) δ 8.67 (s, 1H), 8.07 (d, J=6.6 Hz, 1H), 7.61-7.51 (m, 2H), 7.24 (s, 1H), 7.13 (dd, J=8.2, 2.2 Hz, 1H), 7.05-7.00 (m, 2H), 6.96 (d, J=8.2 Hz, 1H), 6.57 (d, J=6.6 Hz, 1H), 4.22-4.14 (m, 4H), 3.99-3.93 (m, 4H), 3.56 (s, 2H).

Example 64: 6-[2-Phenyl-5-(1-piperidyl)imidazo[4,5-b]pyridin-3-yl]-3H-1,3-benzothiazol-2-one

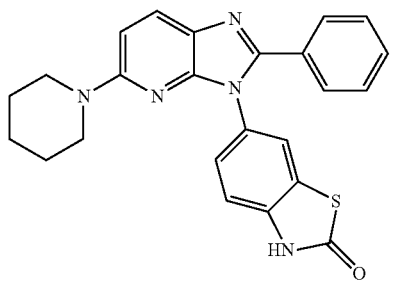 [SMILES: O=c1[nH]c2ccc(-n3c(-c4ccccc4)nc4ccc(N5CCCCC5)nc43)cc2s1]

Step A: 6-(5-Fluoro-2-phenyl-3H-imidazo[4,5-b]pyridin-3-yl)benzo[d]thiazol-2(3H)-one A solution of 2,6-difluoro-3-nitropyridine (0.20 g, 1.3 mmol) and 6-aminobenzo[d]thiazol-2(3H)-one (0.20 g, 1.2 mmol) in DMF (6 mL) was heated at 100° C. for 1 h. Benzaldehyde (0.15 g, 1.4 mmol) was added to the mixture and the reaction was let stir for 30 min followed by addition of sodium dithionite (0.65 g, 3.8 mmol). After 12 h at 100° C. the reaction was cooled, diluted with EtOAc (50 mL), and washed with $H_2O$ (25 mL×3). The organic layer was dried ($Na_2SO_4$) and concentrated in vacuo. Purification (FCC, $SiO_2$, EtOAc/hexanes) afforded the title compound (0.10 g, 22%). MS (ESI): mass calcd. for $C_{19}H_{11}FN_4OS$, 362.1; m/z found, 363.1 [M+H]+. 1H NMR (400 MHz, DMSO-$d_6$) δ 12.19 (br s, 1H), 8.39 (dd, J=8.5, 7.2 Hz, 1H), 7.79 (d, J=2.1 Hz, 1H), 7.60-7.53 (m, 2H), 7.48-7.37 (m, 3H), 7.31 (dd, J=8.4, 2.1 Hz, 1H), 7.24 (d, J=8.4 Hz, 1H), 7.14 (dd, J=8.5, 0.8 Hz, 1H).

Step B: 6-[2-Phenyl-5-(1-piperidyl)imidazo[4,5-b]pyridin-3-yl]-3H-1,3-benzothiazol-2-one A solution of 6-(5-fluoro-2-phenyl-3H-imidazo[4,5-b]pyridin-3-yl)benzo[d]thiazol-2(3H)-one (0.10 g, 0.28 mmol), piperidine (0.04 g, 0.41 mmol), and DIEA (0.7 mL, 0.41 mmol) in DMSO (3 mL) was heated in a sealed tube at 120° C. for 24 h. The reaction was diluted with EtOAc (15 mL) and washed with $H_2O$ (3×15 mL). The organic layer was dried ($Na_2SO_4$) and concentrated in vacuo. Purification (FCC, $SiO_2$, DCM:$NH_3$(MeOH) afforded the title compound (0.04 g, 30%). MS (ESI): mass calcd. for $C_{24}H_{21}N_5OS$, 427.2; m/z found, 428.2 [M+H]+. 1H NMR (500 MHz, CDCl$_3$) δ 10.51 (br s, 1H), 7.92 (d, J=8.9 Hz, 1H), 7.56-7.49 (m, 2H), 7.43 (d, J=2.1 Hz, 1H), 7.36-7.27 (m, 3H), 7.18 (dd, J=8.5, 2.1 Hz, 1H), 7.07 (d, J=8.5 Hz, 1H), 6.72 (d, J=8.9 Hz, 1H), 3.55-3.42 (m, 4H), 3.22-3.17 (m, 1H), 1.76-1.68 (m, 1H), 1.65-1.56 (m, 4H).

Example 65: 6-(5-Morpholino-2-phenyl-imidazo[4,5-b]pyridin-3-yl)-3H-1,3-benzothiazol-2-one

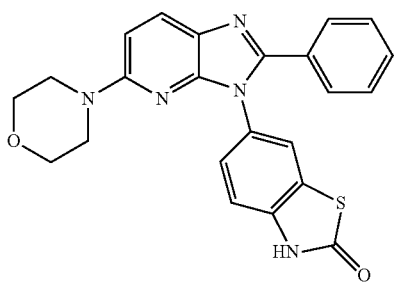 [SMILES: O=c1[nH]c2ccc(-n3c(-c4ccccc4)nc4ccc(N5CCOCC5)nc43)cc2s1]

The title compound was prepared in a manner analogous to Example 64. MS (ESI): mass calcd. for $C_{23}H_{19}N_5O_2S$, 429.1; m/z found, 430.1 [M+H]+. 1HNMR (500 MHz, DMSO-$d_6$) δ 7.96 (d, J=8.9 Hz, 1H), 7.63 (d, J=2.1 Hz, 2H), 7.52-7.44 (m, 2H), 7.40-7.31 (m, 3H), 7.28-7.17 (m, 2H), 6.87 (d, J=8.9 Hz, 1H), 3.66 (t, J=4.9 Hz, 4H), 3.37 (dd, J=5.8, 4.3 Hz, 4H).

Example 66: 6-[5-(Dimethylamino)-2-phenyl-imidazo[4,5-b]pyridin-3-yl]-3H-1,3-benzothiazol-2-one

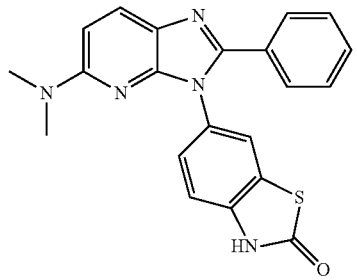 [SMILES: CN(C)c1ccc2nc(-c3ccccc3)n(-c3ccc4[nH]c(=O)sc4c3)c2n1]

The title compound was prepared in a manner analogous to Example 64. MS (ESI): mass calcd. for $C_{21}H_{17}N_5OS$, 387.1; m/z found, 388.1 [M+H]+. 1H NMR (500 MHz, CDCl$_3$) δ 10.56 (br s, 1H), 7.93 (d, J=8.9 Hz, 1H), 7.57-7.51 (m, 2H), 7.46 (d, J=2.0 Hz, 1H), 7.35-7.27 (m, 3H), 7.17 (dd, J=8.5, 2.1 Hz, 1H), 7.05 (d, J=8.5 Hz, 1H), 6.58 (d, J=8.9 Hz, 1H), 3.07 (s, 6H).

Example 67: 6-(5-(Difluoromethyl)-2-phenyl-3H-imidazo[4,5-b]pyridin-3-yl)benzo[d]thiazol-2(3H)-one

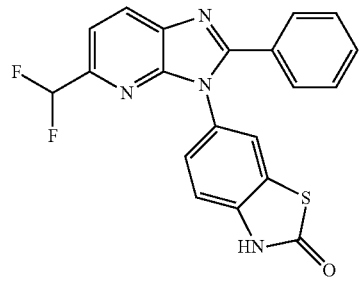 [SMILES: O=c1[nH]c2ccc(-n3c(-c4ccccc4)nc4ccc(C(F)F)nc43)cc2s1]

Step A: 6-(2-Phenyl-3H-imidazo[4,5-b]pyridin-3-yl)benzo[d]thiazol-2(3H)-one

The title compound was prepared in a manner analogous to Example 1, using 6-aminobenzo[d]thiazol-2(3H)-one and 2-chloro-3-nitropyridine. MS (ESI): mass calcd. for $C_{19}H_{12}N_4OS$, 344.1; m/z found, 345.1 [M+H]+. 1H NMR (500 MHz, CDCl$_3$) δ 10.48 (s, 1H), 8.40 (dd, J=4.8, 1.5 Hz, 1H), 8.20 (dd, J=8.0, 1.5 Hz, 1H), 7.63 (dd, J=8.4, 1.4 Hz, 2H), 7.47 (d, J=2.0 Hz, 1H), 7.45-7.39 (m, 1H), 7.39-7.32 (m, 3H), 7.16 (dd, J=8.4, 2.1 Hz, 1H), 7.04 (d, J=8.4 Hz, 1H).

Step B: 6-(5-(Difluoromethyl)-2-phenyl-3H-imidazo[4,5-b]pyridin-3-yl)benzo[d]thiazol-2(3H)-one To a mixture of 6-(2-phenyl-3H-imidazo[4,5-b]pyridin-3-yl)benzo[d]thiazol-2(3H)-one (100 mg, 0.29 mmol) and zinc difluoromethanesulfinate (190 mg, 0.58 mmol) in DCE (2 mL) and $H_2O$ (0.8 mL) was added tert-butyl hydroperoxide solution (161 μL, 1.16 mmol, 70%) dropwise and the resulting mixture was heated at 100° C. for 2 days. An additional aliquot of zinc difluoromethanesulfinate (190 mg, 0.58 mmol) and DMSO (0.4 mL) were added and the mixture was heated at 100° C. for another 2 days. The mixture was diluted with water and extracted with EtOAc, dried (Na$_2$SO$_4$), filtered, concentrated under reduced pressure. Purification (SiO$_2$, EtOAc/hexane gradient 0 to 100%) afforded the title compound which was further purified (prep HPLC, Agilent 1100 Series XBridge Prep $^{18}$C OBD 5 um, basic conditions (20 mM Ammonium Hydroxide in water/MeCN)) to give a yellowish solid. This solid was further purified (SFC, Stationary phase: Chiralpak IA 5 um 250×21 mm, Mobile phase: 25% EtOH, 75% CO$_2$) monitoring elution at 290 nm to give the title compound (4.5 mg, 3.9%). MS (ESI): mass calcd. for C$_{20}$H$_{12}$F$_2$N$_4$OS, 394.1; m/z found, 395.0 [M+H]$^+$. $^1$H NMR (600 MHz, CDCl$_3$) δ 9.75 (s, 1H), 8.28 (d, J=8.3 Hz, 1H), 7.69 (d, J=8.2 Hz, 1H), 7.62 (d, J=7.5 Hz, 2H), 7.53-7.41 (m, 2H), 7.38 (t, J=7.6 Hz, 2H), 7.22 (d, J=7.7 Hz, 1H), 7.16 (s, 1H), 6.70 (t, J=55.5 Hz, 1H).

Example 68: 6-[2-[4-(Difluoromethyl)phenyl]imidazo[4,5-b]pyridin-3-yl]-3H-1,3-benzothiazol-2-one

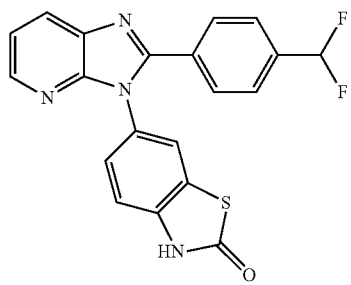 [SMILES: O=c1[nH]c2ccc(-n3c(-c4ccc(C(F)F)cc4)nc4cccnc43)cc2s1]

The title compound was prepared in manner analogous to Example 67, as a by-product. MS (ESI): mass calcd. for C$_{20}$H$_{12}$F$_2$N$_4$OS, 394.1; m/z found, 395.0 [M+H]$^+$. $^1$H NMR (500 MHz, CDCl$_3$) δ 8.43 (dd, J=4.8, 1.5 Hz, 1H), 8.21 (dd, J=8.0, 1.5 Hz, 1H), 7.73 (d, J=7.5 Hz, 2H), 7.55-7.47 (m, 3H), 7.37 (dd, J=8.1, 4.8 Hz, 2H), 7.22-7.16 (m, 1H), 7.15-7.09 (m, 1H), 6.66 (t, J=56.3 Hz, 1H).

Example 69: 6-[7-(Difluoromethyl)-2-phenyl-imidazo[4,5-b]pyridin-3-yl]-3H-1,3-benzothiazol-2-one

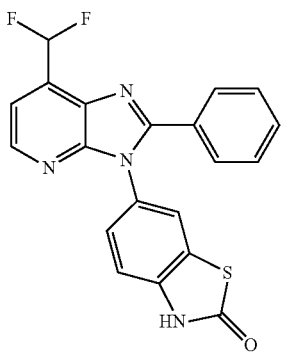 [SMILES: O=c1[nH]c2ccc(-n3c(-c4ccccc4)nc4c(C(F)F)ccnc43)cc2s1]

The title compound was prepared in manner analogous to Example 67, as a by-product. MS (ESI): mass calcd. for C$_{20}$H$_{12}$F$_2$N$_4$OS, 394.1; m/z found, 395.0 [M+H]$^+$. $^1$H NMR (600 MHz, DMSO-d$_6$) δ 12.22 (s, 1H), 8.48 (d, J=4.9 Hz, 1H), 7.84 (d, J=2.2 Hz, 1H), 7.76-7.52 (m, 4H), 7.51-7.46 (m, 1H), 7.46-7.39 (m, 2H), 7.35 (dd, J=8.2, 2.3 Hz, 1H), 7.25 (d, J=8.4 Hz, 1H).

Example 70: 6-(7-Isopropyl-2-phenyl-imidazo[4,5-b]pyridin-3-yl)-3H-1,3-benzothiazol-2-one

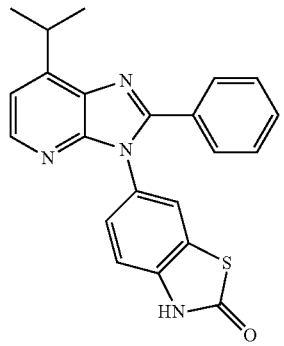 [SMILES: CC(C)c1ccnc2c1nc(-c1ccccc1)n2-c1ccc2[nH]c(=O)sc2c1]

The title compound was prepared in manner analogous to Example 67. MS (ESI): mass calcd. for C$_{22}$H$_{18}$N$_4$OS, 386.1; m/z found, 387.0 [M+H]$^+$. $^1$H NMR (500 MHz, CDCl$_3$) δ 9.93 (s, 1H), 8.32 (d, J=5.1 Hz, 1H), 7.61 (dd, J=8.4, 1.4 Hz, 2H), 7.45 (d, J=2.0 Hz, 1H), 7.42-7.37 (m, 1H), 7.37-7.31 (m, 2H), 7.21 (d, J=5.1 Hz, 1H), 7.14 (dd, J=8.4, 2.1 Hz, 1H), 7.00 (d, J=8.4 Hz, 1H), 3.88 (t, J=6.9 Hz, 1H), 1.49 (d, J=7.0 Hz, 6H).

Example 71: 6-(2-(4-Fluorophenyl)-5-(hydroxymethyl)-3H-imidazo[4,5-b]pyridin-3-yl)benzo[d]thiazol-2(3H)-one

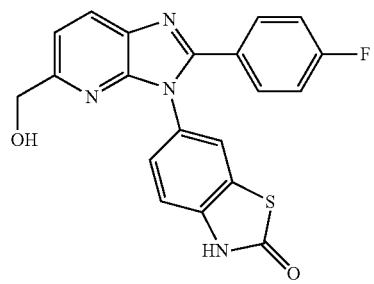 [SMILES: O=c1[nH]c2ccc(-n3c(-c4ccc(F)cc4)nc4ccc(CO)nc43)cc2s1]

Step A: 6-Chloro-5-nitropicolinic acid

2-Chloro-6-methyl-3-nitropyridine (11.0 g, 63.7 mmol) was dissolved in conc. H$_2$SO$_4$ (30 mL) and the resulting solution was stirred for 10 min. to form a viscous yellowish solution. Sodium dichromate dihydrate (25.7 g, 86.4 mmol) was added to the resulting solution in batches slowly (caution: it was highly exothermic process). After 2 h stirring at rt, the reaction mixture was heated at 50° C. for 16 h. Ice (300 g) was added the reaction mixture and stirred for 2 h, then the mixture was cooled in freezer. The precipitate was filtered, washed with ice cold water and dried under high vacuum to give a greenish solid as the title compound (10.1 g, 54.8%, 70% pure). MS (ESI): mass calcd. for C$_6$H$_3$ClN$_2$O$_4$, 202.0; m/z found, 202.9 [M+H]$^+$.

Step B: 5-Nitro-6-(2-oxo-2,3-dihydrobenzo[d]thi-azol-6-yl)picolinic acid

A solution of 6-chloro-5-nitropicolinic acid (1.0 g, 2.5 mmol, 50% pure), 6-amino-2(3H)-benzothiazolone (0.92 g, 5.6 mmol), and DIEA (1.3 mL, 7.4 mmol) in EtOH (10 mL) was refluxed at 80° C. for 16 h. To the reaction mixture was added another portion of 6-amino-2(3H)-benzothiazolone (102 mg, 0.61 mmol) and heated at 80° C. for 16 h. The resulting mixture was cooled in freezer. The precipitate was filtered, washed with cold EtOH and dried under high vacuum to give a dark brown solid (1.5 g, 91%, 50% pure). MS (ESI): mass calcd. for $C_{13}H_8N_4O_5S$, 332.0; m/z found, 332.9 [M+H]$^+$.

Step C: 5-Amino-6-(2-oxo-2,3-dihydrobenzo[d] thiazol-6-yl)picolinic acid

A mixture of 5-nitro-6-(2-oxo-2,3-dihydrobenzo[d]thiazol-6-yl)picolinic acid (400 mg, 1.20 mmol) and tin (II) chloride in EtOH (18 mL) was heated at 85° C. for 1.5 h. The reaction mixture was cooled, filtered through Celite®, and concentrated under reduced pressure to give brown oil which was used directly in the next step without further purification.

Step D: 2-(4-Fluorophenyl)-3-(2-oxo-2,3-dihyd-robenzo[d]thiazol-6-yl)-3H-imidazo[4,5-b]pyridine-5-carboxylic acid To a mixture of 5-amino-6-(2-oxo-2,3-dihydrobenzo[d] thiazol-6-yl)picolinic acid (360 mg, 1.19 mmol) and Cu(OAc)$_2$ (132 mg, 0.714 mmol) in AcOH (20 mL) was added 4-fluorobenzaldehyde (226 mg, 1.79 mmol). The reaction was let stir at 50° C. for 30 minutes then stirred at ambient temperature with open air for 16 h. The precipitate was washed with cold EtOAc and dried under high vacuum to give brown solid (381 mg, 63%, 80% pure). MS (ESI): mass calcd. for $C_{20}H_{11}FN_4O_3S$, 406.1; m/z found, 407.0 [M+H]$^+$.

Step E: Methyl 2-(4-fluorophenyl)-3-(2-oxo-2,3-dihydrobenzo[d]thiazol-6-yl)-3H-imidazo[4,5-b] pyridine-5-carboxylate To a solution of 2-(4-fluorophenyl)-3-(2-oxo-2,3-dihyd-robenzo[d]thiazol-6-yl)-3H-imidazo[4,5-b]pyridine-5-car-boxylic acid (500 mg, 1.23 mmol) in MeOH (3.0 mL) was added p-TsOH (58 mg, 0.31 mmol). The reaction was heated at 80° C. for 16 h. The reaction mixture was cooled, and concentrated under reduced pressure. Purification (FCC, SiO$_2$, 0 to 50% EtOAc:DCM) afforded the title compound (120 mg, 23.0%). MS (ESI): mass calcd. for $C_{21}H_{13}FN_4O_3S$, 420.1; m/z found, 420.9 [M+H]$^+$.

Step F: 6-(2-(4-Fluorophenyl)-5-(hydroxymethyl)-3H-imidazo[4,5-b]pyridin-3-yl)benzo[d]thiazol-2 (3H)-one To a solution of methyl 2-(4-fluorophenyl)-3-(2-oxo-2,3-dihydrobenzo[d]thiazol-6-yl)-3H-imidazo[4,5-b]pyridine-5-carboxylate (86 mg, 0.20 umol) in THF (2.0 mL) was added 1.0 M LAH in THF (0.51 mL, 0.51 mmol) slowly. The resulting mixture was stirred for 2 h. To the reaction mixture was added sat. Rochelle salt (5.0 mL) and stirred for 2 h. The mixture was diluted with water then extracted with EtOAc (×3), dried (Na$_2$SO$_4$), filtered, concentrated under reduced pressure. Purification (FCC, SiO$_2$, 0-100% EtOAc/DCM) afforded the title compound (8.3 mg, 10%). MS (ESI): mass calcd. for $C_{20}H_{13}FN_4O_2S$, 392.1; m/z found, 393.0 [M+H]. $^1$H NMR (500 MHz, CDCl$_3$) δ 8.14 (d, J=8.2 Hz, 1H), 7.66-7.55 (m, 2H), 7.44 (d, J=2.0 Hz, 1H), 7.30 (d, J=8.2 Hz, 1H), 7.16 (dd, J=8.4, 2.1 Hz, 1H), 7.11-7.00 (m, 3H), 4.86 (s, 2H).

Example 72: 6-(2-(4-Fluorophenyl)-7-hydroxy-5-methyl-3H-imidazo[4,5-b]pyridin-3-yl)benzo[d] thiazol-2(3H)-one

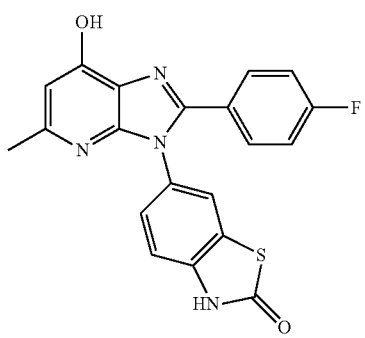 [SMILES: Cc1cc(O)c2nc(-c3ccc(F)cc3)n(-c3ccc4[nH]c(=O)sc4c3)c2n1]

Step A: 6-(2-(4-Fluorophenyl)-5-methyl-3H-imidazo [4,5-b]pyridin-3-yl)benzo[d]thiazol-2(3H)-one The title compound was prepared in a manner analogous to Example 1.

Step B: 6-(2-(4-Fluorophenyl)-7-hydroxy-5-methyl-3H-imidazo[4,5-b]pyridin-3-yl)benzo[d]thiazol-2 (3H)-one To a solution of 6-(2-(4-fluorophenyl)-5-methyl-3H-imidazo[4,5-b]pyridin-3-yl)benzo[d]thiazol-2(3H)-one (368 mg, 0.979 mmol) in AcOH (10 mL) was added mCPBA (676 mg, 3.92 mmol) and the resulting solution heated in a microwave reactor at 130° C. for 10 minutes. The reaction mixture was concentrated under reduced pressure. Purification (FCC, SiO$_2$, 0 to 5% 2M NH$_3$(MeOH):DCM) afforded oxidized compound (48.1 mg, 12.5%). To the oxidized compound (37 mg, 0.094 mmol) was added TFAA (0.5 mL, 3.6 mmol). The reaction mixture was heated at 50° C. for 2 h. The volatiles were removed under reduced pressure and the residue was diluted with water (adjusted pH=9 by addition of 1N NaOH) and extracted with DCM/IPA (3/1). The DCM/IPA layer was concentrated under reduced pressure and EtOAc (2 mL) was added to the residue. The solution was cooled in freezer, filtered, and the precipitate was washed with cold EtOAc. The resulting solid was dried under high vacuum to afford the title compound as an off-white solid (4.7 mg, 13%). MS (ESI): mass calcd. for $C_{20}H_{13}FN_4O_2S$, 392.1; m/z found, 393.0 [M+H]. $^1$H NMR (600 MHz, DMSO-d$_6$) δ 7.69 (t, J=1.4 Hz, 1H), 7.61-7.51 (m, 2H), 7.24 (t, J=8.9 Hz, 2H), 7.20 (d, J=1.3 Hz, 2H), 6.59 (s, 1H), 2.36 (s, 3H).

Example 73: 5-(2-(3-Hydroxypropyl)-5-(trifluoromethyl)-3H-imidazo[4,5-b]pyridin-3-yl)indolin-2-one

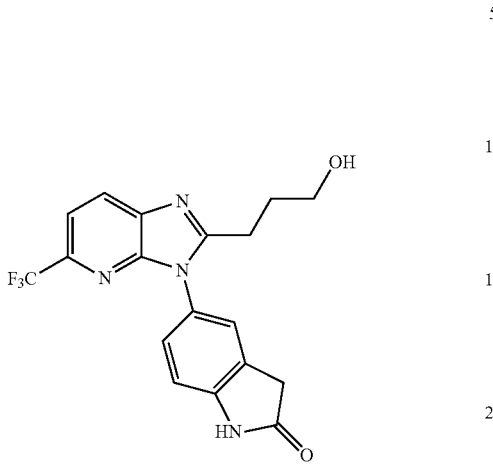

Step A: Methyl 3-(3-(2-oxoindolin-5-yl)-5-(trifluoromethyl)-3H-imidazo[4,5-b]pyridin-2-yl)propanoate A mixture of 5-((3-amino-6-(trifluoromethyl)pyridin-2-yl)amino)indolin-2-one (Intermediate 46, 154 mg, 0.5 mmol), methyl 4-oxobutanoate (69.6 mg, 0.6 mmol), and copper (II) acetate (45.4 mg, 0.25 mmol) in AcOH (4 mL) was stirred at 40° C. for 4 h. The reaction mixture was diluted with EtOAc (30 mL) and washed with saturated NaHCO₃ solution (3×30 mL). The organic layer was dried (Na₂SO₄) and concentrated under reduced pressure. Purification (FCC, SiO₂, EtOAc/Hexane) afforded the title compound as a brown wax (76 mg, 38%). MS (ESI): mass calcd. for $C_{19}H_{15}F_3N_4O_3$, 404.1 m/z found, 405.1 [M+H]⁺.

Step B: 5-(2-(3-Hydroxypropyl)-5-(trifluoromethyl)-3H-imidazo[4,5-b]pyridin-3-yl)indolin-2-one To methyl 3-(3-(2-oxoindolin-5-yl)-5-(trifluoromethyl)-3H-imidazo[4,5-b]pyridin-2-yl)propanoate (52 mg, 0.13 mmol) in THF (2 mL) at 0° C. was added dropwise an LAH solution (0.19 mL, 1 M in THF). The mixture was stirred at 0° C. for 20 min and quenched by addition of MeOH (0.5 mL). The reaction mixture was diluted with EtOAc (20 mL) and washed with water (2×20 mL), dried (Na₂SO₄), filtered and concentrated under reduced pressure. Purification (FCC, SiO₂, DCM/MeOH) afforded the title compound as a pale yellow solid (21 mg, 43%). MS (ESI): mass calcd. for $C_{18}H_{15}F_3N_4O_2$, 376.1 m/z found, 377.1 [M+H]⁺. ¹H NMR (400 MHz, CDCl₃) δ 9.01 (s, 1H), 8.12 (d, J=8.1 Hz, 1H), 7.65 (d, J=8.3 Hz, 1H), 7.27-7.17 (m, 2H), 6.98 (d, J=8.1 Hz, 1H), 3.77 (t, J=5.7 Hz, 2H), 3.58 (s, 2H), 2.98 (t, J=7.0 Hz, 2H), 2.16-2.05 (m, 2H).

Example 74: 5-(2-Cyclobutyl-5-methyl-imidazo[4,5-b]pyridin-3-yl)indolin-2-one

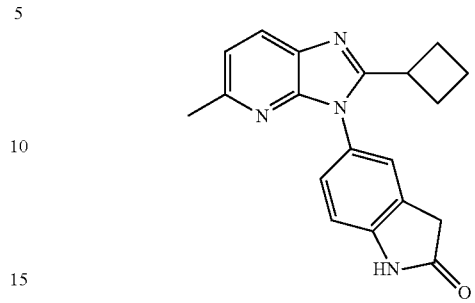

The title compound was prepared in a manner analogous to Example 38. MS (ESI): mass calcd. for $C_{19}H_{18}N_4O$, 318.1; m/z found, 319.1 [M+H]⁺. ¹H NMR (500 MHz, CDCl₃) δ 8.37 (s, 1H), 7.95 (d, J=8.1 Hz, 1H), 7.21 (d, J=1.9 Hz, 1H), 7.20-7.13 (m, 1H), 7.10 (d, J=8.1 Hz, 1H), 6.95 (d, J=8.2 Hz, 1H), 3.61 (s, 2H), 3.57 (td, J=9.1, 1.0 Hz, 1H), 2.68-2.52 (m, 5H), 2.32-2.14 (m, 2H), 2.09-1.88 (m, 2H).

Example 75: 5-(2-Ethyl-5-methyl-imidazo[4,5-b]pyridin-3-yl)indolin-2-one

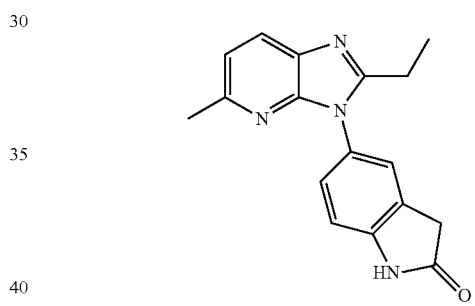

The title compound was prepared in a manner analogous to Example 38. MS (ESI): mass calcd. for $C_{17}H_{16}N_4O$, 292.1; m/z found, 293.1 [M+H]⁺. 1H NMR (500 MHz, CDCl₃) δ 8.46 (s, 1H), 7.92 (d, J=8.1 Hz, 1H), 7.26 (m, 1H), 7.24-7.17 (m, 1H), 7.09 (d, J=8.1 Hz, 1H), 6.97 (d, J=8.1 Hz, 1H), 3.61 (s, 2H), 2.79 (q, J=7.5 Hz, 2H), 2.59 (s, 3H), 1.36 (t, J=7.5 Hz, 3H).

Example 76: 5-[2-(3-Methyloxetan-3-yl)-5-(trifluoromethyl)imidazo[4,5-b]pyridin-3-yl]indolin-2-one

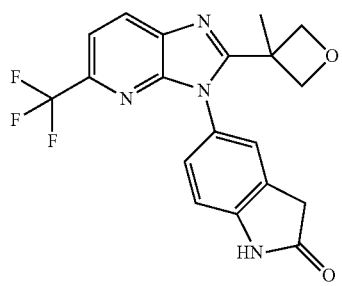 [SMILES: CC1(c2nc3ccc(C(F)(F)F)nc3n2-c2ccc3c(c2)CC(=O)N3)COC1]

The title compound was prepared in a manner analogous to Example 38. MS (ESI): mass calcd. for $C_{19}H_{15}F_3N_4O_2$, 388.1; m/z found, 389.1 [M+H]$^+$. $^1$H NMR (500 MHz, DMSO-d$_6$) δ 10.67 (s, 1H), 8.35 (d, J=8.3 Hz, 1H), 7.81 (d, J=8.3 Hz, 1H), 7.39 (s, 1H), 7.36-7.32 (m, 1H), 6.99 (d, J=8.1 Hz, 1H), 5.18 (d, J=5.7 Hz, 2H), 4.17 (d, J=5.8 Hz, 2H), 3.61 (s, 2H), 1.61 (s, 3H).

Example 77: 5-[2-(2-Methoxyethyl)-5-(trifluoromethyl)imidazo[4,5-b]pyridin-3-yl]indolin-2-one

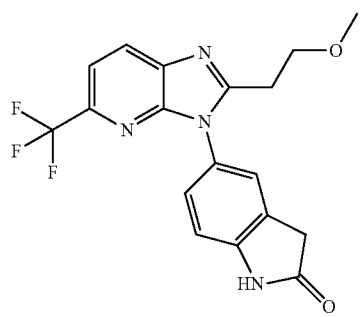 [SMILES: COCCc1nc2ccc(C(F)(F)F)nc2n1-c1ccc2c(c1)CC(=O)N2]

The title compound was prepared in a manner analogous to Example 38. MS (ESI): mass calcd. for $C_{18}H_{15}F_3N_4O_2$, 376.1; m/z found, 377.0 [M+H]$^+$. $^1$H NMR (500 MHz, DMSO-d$_6$) δ 10.67 (s, 1H), 8.30 (d, J=8.2 Hz, 1H), 7.78 (d, J=8.2 Hz, 1H), 7.39 (s, 1H), 7.35-7.30 (m, 1H), 7.03 (d, J=8.1 Hz, 1H), 3.76 (t, J=6.7 Hz, 2H), 3.62 (s, 2H), 3.19 (s, 3H), 3.01 (t, J=6.7 Hz, 2H).

Example 78: 2-Cyclobutyl-5-cyclopropyl-3-(1H-indazol-5-yl)imidazo[4,5-b]pyridine

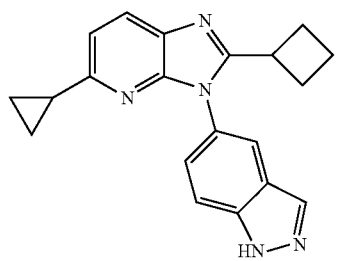 [SMILES: c1cc2[nH]ncc2cc1-n1c(C2CCC2)nc2ccc(C3CC3)nc21]

The title compound was prepared in a manner analogous to Step C of Example 38, from 6-cyclopropyl-N$^2$-(1H-indazol-5-yl)pyridine-2,3-diamine (Intermediate 52). MS (ESI): mass calcd. for $C_{20}H_{19}N_5$, 329.2; m/z found, 330.1 [M+H]$^+$. $^1$H NMR (400 MHz, CD$_3$OD) δ 8.19 (s, 1H), 7.89 (d, J=8.3 Hz, 1H), 7.82 (s, 1H), 7.74 (d, J=8.8 Hz, 1H), 7.35 (dd, J=8.8, 1.9 Hz, 1H), 7.12 (d, J=8.3 Hz, 1H), 3.76-3.64 (m, 1H), 2.57-2.42 (m, 2H), 2.23-1.86 (m, 5H), 0.93-0.86 (m, 2H), 0.86-0.80 (m, 2H).

Example 79: 5-Cyclopropyl-3-(1H-indazol-5-yl)-2-isopropyl-imidazo[4,5-b]pyridine

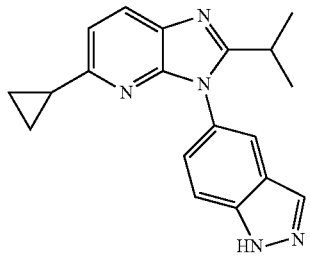 [SMILES: CC(C)c1nc2ccc(C3CC3)nc2n1-c1ccc2[nH]ncc2c1]

The title compound was prepared in a manner analogous to Step C of Example 38, from 6-cyclopropyl-N$^2$-(1H-indazol-5-yl)pyridine-2,3-diamine (Intermediate 52). MS (ESI): mass calcd. for $C_{19}H_{19}N_5$, 317.2; m/z found, 318.1 [M+H]$^+$. $^1$H NMR (400 MHz, CD$_3$OD) δ 8.20 (s, 1H), 7.90-7.84 (m, 2H), 7.76 (d, J=8.7 Hz, 1H), 7.38 (dd, J=8.8, 1.9 Hz, 1H), 7.11 (d, J=8.2 Hz, 1H), 3.20-3.09 (m, 1H), 2.13-2.03 (m, 1H), 1.32 (s, 3H), 1.31 (s, 3H), 0.92-0.84 (m, 2H), 0.84-0.79 (m, 2H).

Example 80: 6-[2-Cyclobutyl-5-(trifluoromethyl)imidazo[4,5-b]pyridin-3-yl]-3H-1,3-benzoxazol-2-one

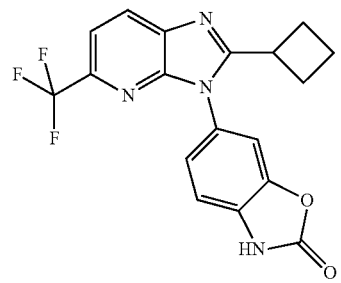 [SMILES: O=c1[nH]c2ccc(-n3c(C4CCC4)nc4ccc(C(F)(F)F)nc43)cc2o1]

The title compound was prepared in a manner analogous to Example 38. MS (ESI): mass calcd. for $C_{18}H_{13}F_3N_4O_2$, 374.1; m/z found, 375.0 [M+H]$^+$.

Example 81: Azetidin-1-yl-[3-(1H-indazol-5-yl)-5-(trifluoromethyl)imidazo[4,5-b]pyridin-2-yl]methanone

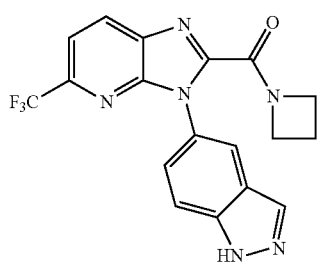 [SMILES: O=C(c1nc2ccc(C(F)(F)F)nc2n1-c1ccc2[nH]ncc2c1)N1CCC1]

Step A: 3-(1H-Indazol-5-yl)-2-(trichloromethyl)-5-(trifluoromethyl)-3H-imidazo[4,5-b]pyridine Methyl 2,2,2-trichloroacetimidate (106 µL, 0.853 mmol) was added to a solution of N²-(1H-indazol-5-yl)-6-(trifluoromethyl)pyridine-2,3-diamine (Intermediate 47, 250 mg, 0.853 mmol) in acetic acid (2.84 mL). The reaction mixture was stirred at rt for 16 h. The solution was neutralized with 4 N NaOH and the aqueous layer was extracted with EtOAc (5 mL×3). The combined organic layers were dried (Na$_2$SO$_4$), filtered, and concentrated in vacuo. Purification (FCC, SiO$_2$, 0-50% EtOAc/hexanes) afforded the title compound as a white solid (266 mg, 74%). MS (ESI): mass calcd. for C$_{15}$H$_7$C$_{13}$F$_3$N$_5$, 419.0 m/z found, 421.9 [M+H]$^+$. $^1$H NMR (400 MHz, CDCl$_3$) δ 8.41 (d, J=8.1 Hz, 1H), 8.19 (d, J=1.0 Hz, 1H), 7.97-7.93 (m, 1H), 7.78 (d, J=8.4 Hz, 1H), 7.67-7.62 (m, 1H), 7.44 (dd, J=8.8, 2.0 Hz, 1H).

Step B: Azetidin-1-yl-[3-(1H-indazol-5-yl)-5-(trifluoromethyl)imidazo[4,5-b]pyridin-2-yl]methanone To a solution of 3-(1H-indazol-5-yl)-2-(trichloromethyl)-5-(trifluoromethyl)-3H-imidazo[4,5-b]pyridine (70.0 mg, 0.166 mmol) in ACN (1.28 mL) and water (0.427 mL) was added azetidine (22.4 µL, 0.333 mmol) and 4 M K$_2$CO$_3$ (0.166 mL). The reaction mixture was heated to 85° C. for 18 h. The solution was cooled, diluted with water, and extracted with EtOAc (5 mL×3). The combined organic layers were dried (Na$_2$SO$_4$), filtered, and concentrated in vacuo. Purification (reverse phase HPLC, 5-95% ACN in 20 nM NH$_4$OH in water) afforded the title compound (2.10 mg, 3%). MS (ESI): mass calcd. for C$_{18}$H$_{13}$F$_3$N$_6$O, 386.1; m/z found, 387.0 [M+H]$^+$. $^1$H NMR (400 MHz, CD$_3$OD) δ 8.43 (d, J=8.3 Hz, 1H), 8.18 (s, 1H), 7.92 (s, 1H), 7.85 (d, J=8.4 Hz, 1H), 7.72 (d, J=8.7 Hz, 1H), 7.51-7.44 (m, 1H), 4.70 (t, J=7.8 Hz, 2H), 4.15 (t, J=7.8 Hz, 2H), 2.42 (p, J=7.8 Hz, 2H).

Example 82: 6-[5-Amino-2-(4-fluorophenyl)imidazo[4,5-b]pyridin-3-yl]-3H-1,3-benzothiazol-2-one

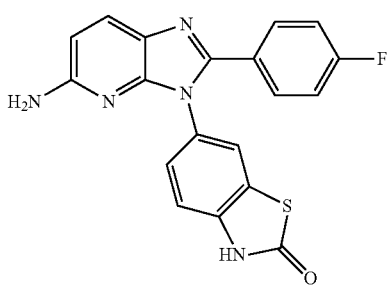 [SMILES: Nc1ccc2nc(-c3ccc(F)cc3)n(-c3ccc4[nH]c(=O)sc4c3)c2n1]

The title compound was prepared in a manner analogous to Example 38. MS (ESI): mass calcd. for C$_{19}$H$_{12}$FN$_5$OS, 377.1; m/z found, 378.0 [M+H]$^+$. $^1$H NMR (500 MHz, CD$_3$OD) δ 7.98 (s, 1H), 7.80 (d, J=8.7 Hz, 1H), 7.60 (d, J=2.0 Hz, 1H), 7.55-7.50 (m, 2H), 7.23 (d, J=8.5 Hz, 1H), 7.18 (dd, J=8.4, 2.1 Hz, 1H), 7.13-7.07 (m, 2H), 6.60 (d, J=8.7 Hz, 1H).

Example 83: 5-[2-(1-Ethylpropyl)-5-(trifluoromethyl)imidazo[4,5-b]pyridin-3-yl]indolin-2-one

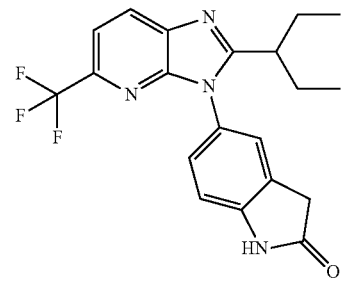 [SMILES: CCC(CC)c1nc2ccc(C(F)(F)F)nc2n1-c1ccc2c(c1)CC(=O)N2]

The title compound was prepared in a manner analogous to Example 38. MS (ESI): mass calcd. for C$_{20}$H$_{19}$F$_3$N$_4$O, 388.2; m/z found, 389.1 [M+H]$^+$. $^1$H NMR (500 MHz, DMSO-d$_6$) δ 10.68 (s, 1H), 8.31 (d, J=8.2 Hz, 1H), 7.77 (d, J=8.2 Hz, 1H), 7.33-7.30 (m, 1H), 7.28-7.24 (m, 1H), 7.04 (d, J=8.1 Hz, 1H), 3.62 (s, 2H), 2.69-2.61 (m, 1H), 1.86-1.75 (m, 2H), 1.73-1.60 (m, 2H), 0.75 (t, J=7.4 Hz, 6H).

Example 84: 5-(2-Isopropyl-5-methyl-imidazo[4,5-b]pyridin-3-yl)indolin-2-one

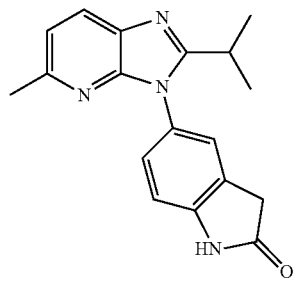 [SMILES: Cc1ccc2nc(C(C)C)n(-c3ccc4c(c3)CC(=O)N4)c2n1]

The title compound was prepared in a manner analogous to Example 38. MS (ESI): mass calcd. for C$_{18}$H$_{18}$N$_4$O, 306.1; m/z found, 307.1 [M+H]$^+$. $^1$H NMR (500 MHz, CDCl$_3$) δ 8.55 (s, 1H), 7.94 (d, J=8.1 Hz, 1H), 7.25 (s, 1H), 7.23-7.16 (m, 1H), 7.09 (d, J=8.1 Hz, 1H), 6.96 (d, J=8.1 Hz, 1H), 3.61 (s, 2H), 3.08 (dt, J=13.7, 6.8 Hz, 1H), 2.59 (s, 3H), 1.35 (d, J=6.9 Hz, 6H).

Example 85: 3-(1H-Indazol-5-yl)-N-phenyl-5-(trifluoromethyl)imidazo[4,5-b]pyridine-2-carboxamide

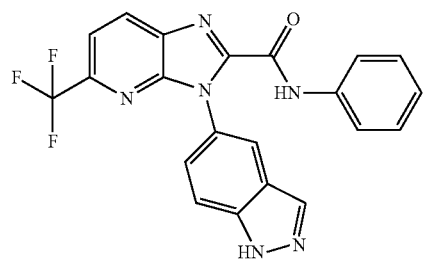 [SMILES: O=C(Nc1ccccc1)c1nc2ccc(C(F)(F)F)nc2n1-c1ccc2[nH]ncc2c1]

The title compound was prepared in a manner analogous to Example 81. MS (ESI): mass calcd. for $C_{21}H_{13}F_3N_6O$, 422.1; m/z found, 423.0 $[M+H]^+$. $^1H$ NMR (400 MHz, $CDCl_3$) δ 9.58 (s, 1H), 8.37 (d, J=8.4 Hz, 1H), 8.14 (s, 1H), 7.87-7.85 (m, 1H), 7.81 (d, J=8.4 Hz, 1H), 7.69-7.64 (m, 2H), 7.60 (d, J=8.7 Hz, 1H), 7.43 (dd, J=8.7, 1.9 Hz, 1H), 7.38-7.31 (m, 2H), 7.19-7.13 (m, 1H).

Example 86: 5-Cyclopropyl-2-(4-fluorophenyl)-3-(1H-indazol-5-yl)imidazo[4,5-b]pyridine

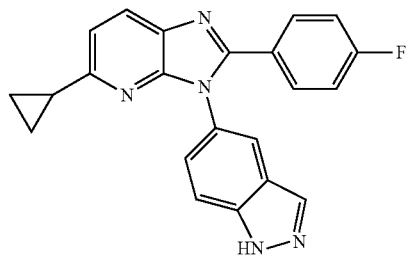 [SMILES: Fc1ccc(-c2nc3ccc(C4CC4)nc3n2-c2ccc3[nH]ncc3c2)cc1]

The title compound was prepared in a manner analogous to Step C of Example 38, from 6-cyclopropyl-$N^2$-(1H-indazol-5-yl)pyridine-2,3-diamine (Intermediate 52). MS (ESI): mass calcd. for $C_{22}H_{16}FN_5$, 369.1; m/z found, 370.1 $[M+H]^+$. $^1H$ NMR (400 MHz, $CDCl_3$) δ 8.10 (d, J=1.0 Hz, 1H), 8.00 (d, J=8.3 Hz, 1H), 7.73 (dd, J=1.8, 0.7 Hz, 1H), 7.59-7.48 (m, 3H), 7.30 (dd, J=8.8, 1.9 Hz, 1H), 7.12 (d, J=8.3 Hz, 1H), 7.01-6.93 (m, 2H), 2.19-2.10 (m, 1H), 0.98-0.91 (m, 4H).

Example 87: 5-(2-Cyclopropyl-5-methyl-imidazo[4,5-b]pyridin-3-yl)indolin-2-one

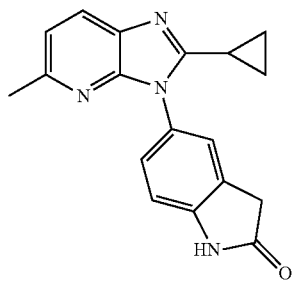 [SMILES: Cc1ccc2nc(C3CC3)n(-c3ccc4c(c3)CC(=O)N4)c2n1]

The title compound was prepared in a manner analogous to Example 38. MS (ESI): mass calcd. for $C_{18}H_{16}N_4O$, 304.1; m/z found, 305.1 $[M+H]^+$. $^1H$ NMR (500 MHz, $CDCl_3$) δ 7.89 (s, 1H), 7.83 (d, J=8.1 Hz, 1H), 7.39 (d, J=1.6 Hz, 1H), 7.38-7.32 (m, 1H), 7.06 (d, J=8.1 Hz, 1H), 7.01 (d, J=8.1 Hz, 1H), 3.65 (s, 2H), 2.58 (s, 3H), 1.96-1.79 (m, 1H), 1.40-1.24 (m, 2H), 1.05 (dd, J=8.2, 2.7 Hz, 2H).

Example 88: 5-[2,5-Bis(trifluoromethyl)imidazo[4,5-b]pyridin-3-yl]indolin-2-one

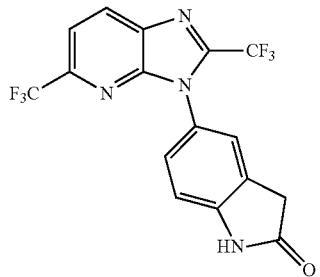 [SMILES: O=C1Cc2cc(-n3c(C(F)(F)F)nc4ccc(C(F)(F)F)nc43)ccc2N1]

Step A: 5-((3-Nitro-6-(trifluoromethyl)pyridin-2-yl)amino)indolin-2-one

A solution of 2-chloro-3-nitro-6-(trifluoromethyl)pyridine (27 g, 120 mmol), 5-aminoindolin-2-one (18 g, 120 mmol), and $Et_3N$ (24 g, 240 mmol) in THF (250 mL) was refluxed at 90° C. for 12 h. The reaction was diluted with ether (200 mL) and let stir for 20 min where precipitate formed. The reaction was filtered and the filtrate was slurried with $H_2O$ and oven dried at 45° C. to give the desired compound as a brown solid (21 g, 86%). MS (ESI): mass calcd. for $C_{14}H_9F_3N_4O_3$, 338.1; m/z found, 339.0 $[M+H]^+$.

Step B: 5-((3-amino-6-(trifluoromethyl)pyridin-2-yl)amino)indolin-2-one

A solution of 5-((3-nitro-6-(trifluoromethyl)pyridin-2-yl)amino)indolin-2-one (20 g, 59 mmol), 10% Pd/C (10 g), and MeOH (1 L) in a 2 L flask was flushed with $H_2$ at 20 atm of pressure. The mixture was stirred at 50° C. for 16 h. The reaction was filtered and the resulting solution was concentrated in vacuo. The resulting solid was slurried with EtOH and oven dried at 45° C. to give the desired compound as an off-white solid (12 g, 66%). MS (ESI): mass calcd. for $C_{14}H_{11}F_3N_4O$, 308.1; m/z found, 309.0 $[M+H]^+$.

Step C. 5-[2,5-bis(trifluoromethyl)imidazo[4,5-b]pyridin-3-yl]indolin-2-one

A solution of 5-((3-amino-6-(trifluoromethyl)pyridin-2-yl)amino)indolin-2-one (0.10 g, 0.32 mmol) in TFA (0.25 mL, 3.2 mmol) was stirred at 70° C. for 16 h. The reaction was concentrated in vacuo, diluted with 1 N $NaHCO_3$ (20 mL), and extracted with EtOAc (20 mL×3). The organic layers were dried ($Na_2SO_4$) and concentrated in vacuo. Purification (FCC, $SiO_2$, EtOAc/hexanes) afforded the title compound (0.09 g, 70%). MS (ESI): mass calcd. for $C_{16}H_8F_6N_4O$, 386.1; m/z found, 387.0 $[M+H]^+$. $^1H$ NMR (500 MHz, $CDCl_3$) δ 8.41 (d, J=8.4 Hz, 1H), 8.36 (s, 1H), 7.81 (d, J=8.4 Hz, 1H), 7.33-7.29 (m, 2H), 7.09-7.04 (m, 1H), 3.67 (s, 2H).

Example 89: 3-(1H-Indazol-5-yl)-2,5-bis(trifluoromethyl)imidazo[4,5-b]pyridine

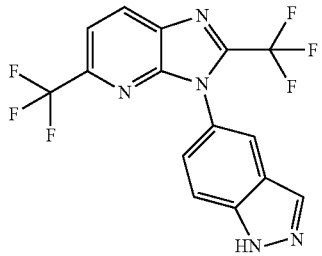 [SMILES: FC(F)(F)c1ccc2nc(C(F)(F)F)n(-c3ccc4[nH]ncc4c3)c2n1]

The title compound was made in a manner analogous to Step C of Example 88 from N²-(1H-indazol-5-yl)-6-(trifluoromethyl)pyridine-2,3-diamine (Intermediate 48). MS (ESI): mass calcd. for $C_{15}H_7F_6N_5$, 371.1; m/z found, 372.0 [M+H]⁺. ¹H NMR (400 MHz, CD₃OD) δ 8.53 (d, J=8.4 Hz, 1H), 8.22 (d, J=0.9 Hz, 1H), 8.03 (d, J=1.9 Hz, 1H), 7.92 (d, J=8.5 Hz, 1H), 7.78 (d, J=8.8 Hz, 1H), 7.51 (dd, J=8.8, 2.0 Hz, 1H).

Example 90: 2-(Difluoromethyl)-3-(1H-indazol-5-yl)-5-(trifluoromethyl)imidazo[4,5-b]pyridine

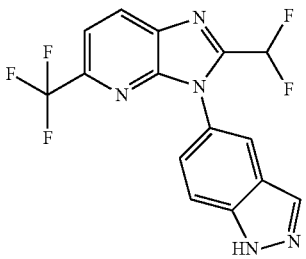 [SMILES: FC(F)c1nc2ccc(C(F)(F)F)nc2n1-c1ccc2[nH]ncc2c1]

The title compound was made in a manner analogous to Step C of Example 88 from N²-(1H-indazol-5-yl)-6-(trifluoromethyl)pyridine-2,3-diamine (Intermediate 48). MS (ESI): mass calcd. for $C_{15}H_8F_5N_5$, 353.1; m/z found, 354.0 [M+H]⁺. ¹H NMR (400 MHz, CD₃OD) δ 8.47 (d, J=8.4 Hz, 1H), 8.22 (s, 1H), 8.03 (s, 1H), 7.88 (d, J=8.4 Hz, 1H), 7.79 (d, J=8.9 Hz, 1H), 7.52 (d, J=8.8 Hz, 1H), 7.04 (t, J=52.0 Hz, 1H).

Example 91: 3-(1H-Indazol-5-yl)-2-(2-thienyl)-5-(trifluoromethyl)imidazo[4,5-b]pyridine

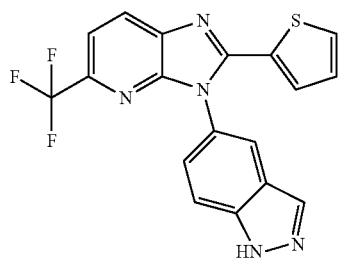 [SMILES: FC(F)(F)c1ccc2nc(-c3cccs3)n(-c3ccc4[nH]ncc4c3)c2n1]

The title compound was made in a manner analogous to Step C of Example 38 from N²-(1H-indazol-5-yl)-6-(trifluoromethyl)pyridine-2,3-diamine (Intermediate 48). MS (ESI): mass calcd. for $C_{18}H_{10}F_3N_5S$, 385.1; m/z found, 386.0 [M+H]⁺. ¹H NMR (400 MHz, CDCl₃) δ 10.64 (br s, 1H), 8.23 (d, J=8.3 Hz, 1H), 8.12 (d, J=1.0 Hz, 1H), 7.85 (dd, J=1.9, 0.7 Hz, 1H), 7.71 (d, J=8.3 Hz, 1H), 7.58 (d, J=8.7 Hz, 1H), 7.43 (dd, J=5.0, 1.1 Hz, 1H), 7.35 (dd, J=8.7, 1.9 Hz, 1H), 6.97 (dd, J=3.8, 1.2 Hz, 1H), 6.92 (dd, J=5.0, 3.8 Hz, 1H).

Example 92: 2-(2-Furyl)-3-(1H-indazol-5-yl)-5-(trifluoromethyl)imidazo[4,5-b]pyridine The title compound was made in a manner analogous to Step C of Example 38 from N²-(1H-indazol-5-yl)-6-(trifluoromethyl)pyridine-2,3-diamine (Intermediate 48). MS (ESI): mass calcd. for $C_{18}H_{10}F_3N_5O$, 369.1; m/z found, 370.0 [M+H]⁺. ¹H NMR (400 MHz, CD₃OD) δ 8.29 (d, J=8.3 Hz, 1H), 8.23 (d, J=1.0 Hz, 1H), 8.03-7.98 (m, 1H), 7.85-7.77 (m, 2H), 7.71 (d, J=1.6 Hz, 1H), 7.46 (dd, J=8.8, 2.0 Hz, 1H), 6.49 (dd, J=3.6, 1.8 Hz, 1H), 6.31 (d, J=3.5 Hz, 1H).

Example 93: 5-[2-(1,1-Difluoroethyl)-5-(trifluoromethyl)imidazo[4,5-b]pyridin-3-yl]indolin-2-one

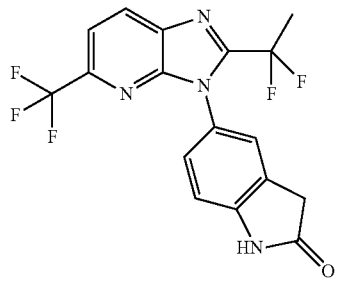 [SMILES: CC(F)(F)c1nc2ccc(C(F)(F)F)nc2n1-c1ccc2c(c1)CC(=O)N2]

The title compound was made in a manner analogous to Example 88. MS (ESI): mass calcd. for $C_{17}H_{11}F_5N_4O$, 382.1; m/z found, 383.0 [M+H]⁺. ¹H NMR (500 MHz, DMSO-d₆) δ 10.67 (br s, 1H), 8.57 (d, J=8.3 Hz, 1H), 7.93 (d, J=8.4 Hz, 1H), 7.40 (s, 1H), 7.35 (dd, J=8.2, 2.1 Hz, 1H), 6.99 (d, J=8.2 Hz, 1H), 3.60 (s, 2H), 2.13 (t, J=19.4 Hz, 3H).

Example 94: 5-[2-(Difluoromethyl)-5-(trifluoromethyl)imidazo[4,5-b]pyridin-3-yl]indolin-2-one

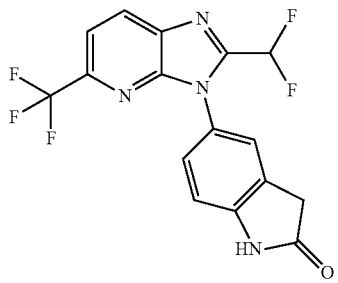

The title compound was made in a manner analogous to Example 88. MS (ESI): mass calcd. for $C_{16}H_9F_5N_4O$, 368.1; m/z found, 369.0 [M+H]$^+$. $^1$H NMR (500 MHz, DMSO-d$_6$) δ 10.72 (br s, 1H), 8.56 (d, J=8.3 Hz, 1H), 7.93 (d, J=8.4 Hz, 1H), 7.44 (s, 1H), 7.39 (dd, J=8.2, 2.2 Hz, 1H), 7.22 (t, J=51.7 Hz, 1H), 7.04 (d, J=8.1 Hz, 1H), 3.67 (s, 2H).

Example 95: 5-(5-Chloro-2-cyclopropyl-imidazo[4,5-b]pyridin-3-yl)indolin-2-one

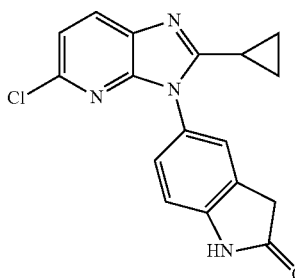

The title compound was prepared in a manner analogous to Example 38. MS (ESI): mass calcd. for $C_{17}H_{13}ClN_4O$, 324.1; m/z found, 325.0 [M+H]$^+$. $^1$H NMR (500 MHz, DMSO-d$_6$) δ 10.65 (s, 1H), 8.01 (d, J=8.3 Hz, 1H), 7.44-7.40 (m, 1H), 7.39-7.34 (m, 1H), 7.30 (d, J=8.3 Hz, 1H), 7.03 (d, J=8.2 Hz, 1H), 3.62 (s, 2H), 1.89-1.81 (m, 1H), 1.16-1.12 (m, 2H), 1.08-1.01 (m, 2H).

Example 96: (racemic)-5-[2-sec-Butyl-5-(trifluoromethyl)imidazo[4,5-b]pyridin-3-yl]indolin-2-one

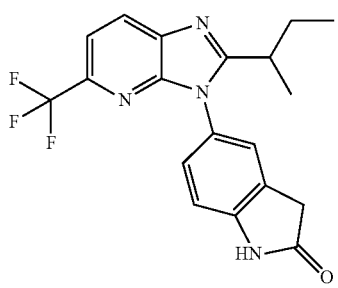 [SMILES: CCC(C)c1nc2ccc(C(F)(F)F)nc2n1-c1ccc2c(c1)CC(=O)N2]

The title compound was prepared in a manner analogous to Example 38. MS (ESI): mass calcd. for $C_{19}H_{17}F_3N_4O$, 374.1; m/z found, 375.1 [M+H]$^+$. $^1$H NMR (500 MHz, CDCl$_3$) δ 8.22 (s, 1H), 8.15 (d, J=8.2 Hz, 1H), 7.65 (d, J=8.2 Hz, 1H), 7.23 (s, 1H), 7.21-7.18 (m, 1H), 7.02 (d, J=8.1 Hz, 1H), 3.64 (s, 2H), 2.97-2.87 (m, 1H), 2.00-1.89 (m, 1H), 1.75-1.65 (m, 1H), 1.36 (d, J=6.9 Hz, 3H), 0.85 (t, J=7.4 Hz, 3H).

Example 97: 5-[2-(2,2-Dimethylpropyl)-5-(trifluoromethyl)imidazo[4,5-b]pyridin-3-yl]indolin-2-one

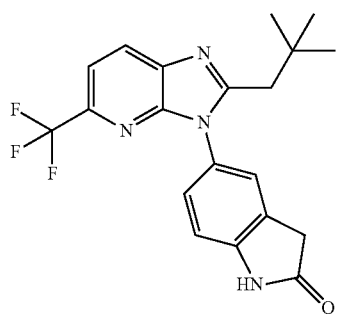 [SMILES: CC(C)(C)Cc1nc2ccc(C(F)(F)F)nc2n1-c1ccc2c(c1)CC(=O)N2]

The title compound was prepared in a manner analogous to Example 38. MS (ESI): mass calcd. for $C_{20}H_{19}F_3N_4O$, 388.2; m/z found, 389.1 [M+H]$^+$. $^1$H NMR (500 MHz, CDCl$_3$) δ 8.28 (s, 1H), 8.16 (d, J=8.2 Hz, 1H), 7.65 (d, J=8.2 Hz, 1H), 7.21 (s, 1H), 7.20-7.17 (m, 1H), 7.02 (d, J=8.1 Hz, 1H), 3.64 (s, 2H), 2.80 (s, 2H), 0.99 (s, 9H).

Example 98: 3-(1H-Indazol-5-yl)-2-methyl-5-(trifluoromethyl)imidazo[4,5-b]pyridine

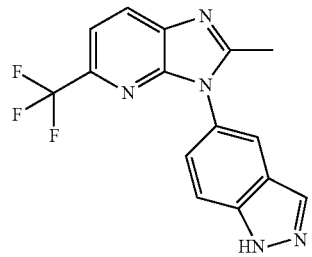 [SMILES: Cc1nc2ccc(C(F)(F)F)nc2n1-c1ccc2[nH]ncc2c1]

The title compound was made in a manner analogous to Step C of Example 38 from N$^2$-(1H-indazol-5-yl)-6-(trifluoromethyl)pyridine-2,3-diamine (Intermediate 48). MS (ESI): mass calcd. for $C_{15}H_{10}F_3N_5$, 317.1; m/z found, 318.0 [M+H]$^+$. $^1$H NMR (400 MHz, CDCl$_3$) δ 10.64 (br s, 1H), 8.16 (d, J=8.2 Hz, 1H), 8.12 (s, 1H), 7.76 (dd, J=1.9, 0.7 Hz, 1H), 7.68 (d, J=8.3 Hz, 1H), 7.59 (d, J=8.7 Hz, 1H), 7.33 (dd, J=8.8, 1.9 Hz, 1H), 2.58 (s, 3H).

Example 99: 5-[2-Ethyl-5-(trifluoromethyl)imidazo[4,5-b]pyridin-3-yl]indolin-2-one

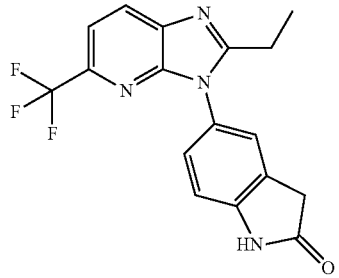

The title compound was prepared in a manner analogous to Example 38. MS (ESI): mass calcd. for $C_{17}H_{13}F_3N_4O$, 346.1; m/z found, 347.0 [M+H]$^+$. $^1$H NMR (500 MHz, CDCl$_3$) δ 8.94 (s, 1H), 8.15 (d, J=8.2 Hz, 1H), 7.65 (d, J=8.2 Hz, 1H), 7.21 (dd, J=8.2, 2.1 Hz, 1H), 6.99 (d, J=8.2 Hz, 1H), 3.60 (s, 2H), 2.85 (q, J=7.5 Hz, 2H), 1.75 (s, 1H), 1.39 (t, J=7.5 Hz, 3H).

Example 100: (racemic)-3-(1H-Indazol-5-yl)-2-tetrahydrofuran-3-yl-5-(trifluoromethyl)imidazo[4,5-b]pyridine

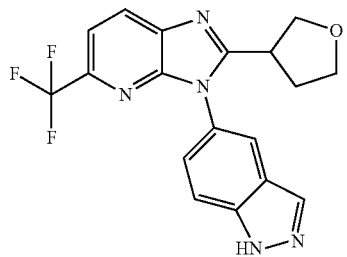 [SMILES: FC(F)(F)c1ccc2nc(C3CCOC3)n(-c3ccc4[nH]ncc4c3)c2n1]

The title compound was made in a manner analogous to Step C of Example 38 from N$^2$-(1H-indazol-5-yl)-6-(trifluoromethyl)pyridine-2,3-diamine (Intermediate 48). MS (ESI): mass calcd. for $C_{18}H_{14}F_3N_5O$, 373.1; m/z found, 374.0 [M+H]$^+$. $^1$H NMR (400 MHz, CDCl$_3$) δ 10.49 (br s, 1H), 8.20 (d, J=8.1 Hz, 1H), 8.15 (s, 1H), 7.77 (dd, J=2.0, 0.7 Hz, 1H), 7.68 (d, J=8.3 Hz, 1H), 7.63 (d, J=8.7 Hz, 1H), 7.32 (dd, J=8.8, 1.9 Hz, 1H), 4.15-3.99 (m, 3H), 3.93-3.84 (m, 1H), 3.64-3.52 (m, 1H), 2.56-2.43 (m, 1H), 2.30-2.18 (m, 1H).

Example 101: 3-(1H-Indazol-5-yl)-2-isobutyl-5-(trifluoromethyl)imidazo[4,5-b]pyridine

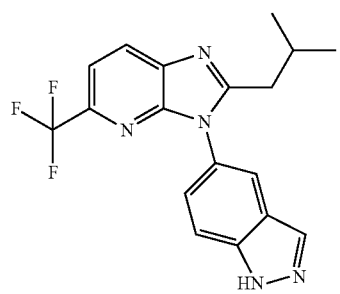 [SMILES: CC(C)Cc1nc2ccc(C(F)(F)F)nc2n1-c1ccc2[nH]ncc2c1]

The title compound was made in a manner analogous to Step C of Example 38 from N$^2$-(1H-indazol-5-yl)-6-(trifluoromethyl)pyridine-2,3-diamine (Intermediate 48). MS (ESI): mass calcd. for $C_{18}H_{16}F_3N_5$, 359.1; m/z found, 360.1 [M+H]$^+$. $^1$H NMR (400 MHz, CDCl$_3$) δ 10.84 (br s, 1H), 8.20 (d, J=8.3 Hz, 1H), 8.07 (s, 1H), 7.73-7.66 (m, 2H), 7.50 (d, J=8.7 Hz, 1H), 7.27-7.21 (m, 1H), 2.71 (d, J=7.3 Hz, 2H), 2.30-2.17 (m, 1H), 0.93 (s, 3H), 0.92 (s, 3H).

Example 102: (racemic)-3-(1H-Indazol-5-yl)-2-sec-butyl-5-(trifluoromethyl)imidazo[4,5-b]pyridine

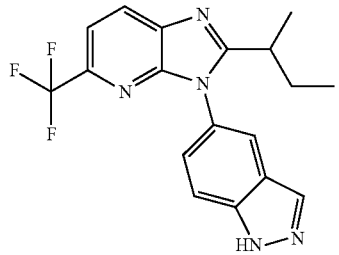 [SMILES: CCC(C)c1nc2ccc(C(F)(F)F)nc2n1-c1ccc2[nH]ncc2c1]

The title compound was made in a manner analogous to Step C of Example 38 from N$^2$-(1H-indazol-5-yl)-6-(trifluoromethyl)pyridine-2,3-diamine (Intermediate 48). MS (ESI): mass calcd. for $C_{18}H_{16}F_3N_5$, 359.1; m/z found, 360.0 [M+H]$^+$. $^1$H NMR (400 MHz, CDCl$_3$) δ 10.79 (br s, 1H), 8.21 (dd, J=8.3, 0.7 Hz, 1H), 8.07 (d, J=1.0 Hz, 1H), 7.73-7.65 (m, 2H), 7.51 (dt, J=8.6, 0.9 Hz, 1H), 7.28-7.21 (m, 1H), 2.98-2.83 (m, 1H), 2.05-1.88 (m, 1H), 1.68 (ddd, J=13.7, 7.5, 6.3 Hz, 1H), 1.36 (d, J=6.9 Hz, 3H), 0.84 (t, J=7.4 Hz, 3H).

Example 103: 2-Cyclobutyl-3-(1H-indazol-5-yl)-5-(trifluoromethyl)imidazo[4,5-b]pyridine

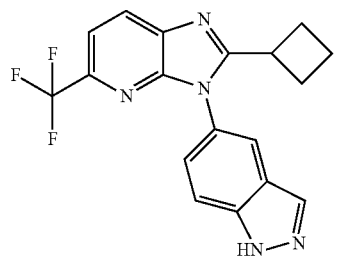 [SMILES: FC(F)(F)c1ccc2nc(C3CCC3)n(-c3ccc4[nH]ncc4c3)c2n1]

The title compound was made in a manner analogous to Step C of Example 38 from N$^2$-(1H-indazol-5-yl)-6-(trifluoromethyl)pyridine-2,3-diamine (Intermediate 48). MS (ESI): mass calcd. for $C_{18}H_{14}F_3N_5$, 357.1; m/z found, 358.0 [M+H]$^+$. $^1$H NMR (400 MHz, CDCl$_3$) δ 11.04 (br s, 1H), 8.23 (d, J=8.3 Hz, 1H), 8.01 (s, 1H), 7.70 (d, J=8.3 Hz, 1H), 7.63 (dd, J=2.0, 0.7 Hz, 1H), 7.42 (d, J=8.7 Hz, 1H), 7.18 (dd, J=8.7, 1.9 Hz, 1H), 3.67-3.56 (m, 1H), 2.68-2.55 (m, 2H), 2.26-2.13 (m, 2H), 2.05-1.92 (m, 2H).

Example 104: 2-Cyclopentyl-3-(1H-indazol-5-yl)-5-(trifluoromethyl)imidazo[4,5-b]pyridine

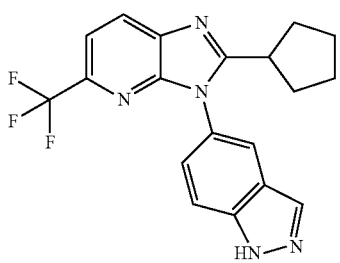 [SMILES: FC(F)(F)c1ccc2nc(C3CCCC3)n(-c3ccc4[nH]ncc4c3)c2n1]

The title compound was made in a manner analogous to Step C of Example 38 from $N^2$-(1H-indazol-5-yl)-6-(trifluoromethyl)pyridine-2,3-diamine (Intermediate 48). MS (ESI): mass calcd. for $C_{19}H_{16}F_3N_5$, 371.1; m/z found, 372.1 [M+H]$^+$. $^1$H NMR (400 MHz, CDCl$_3$) δ 11.20 (br s, 1H), 8.21 (d, J=8.2 Hz, 1H), 7.98 (d, J=1.1 Hz, 1H), 7.70 (d, J=8.3 Hz, 1H), 7.68 (d, J=1.8 Hz, 1H), 7.38 (d, J=8.7 Hz, 1H), 7.20 (dd, J=8.7, 1.9 Hz, 1H), 3.20-3.06 (m, 1H), 2.14-2.00 (m, 2H), 2.00-1.79 (m, 4H), 1.66-1.51 (m, 2H).

Example 105: 2-Ethyl-3-(1H-indazol-5-yl)-5-(trifluoromethyl)imidazo[4,5-b]pyridine

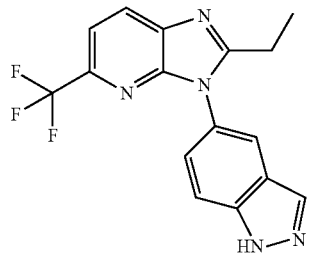 [SMILES: CCc1nc2ccc(C(F)(F)F)nc2n1-c1ccc2[nH]ncc2c1]

The title compound was made in a manner analogous to Step C of Example 38 from $N^2$-(1H-indazol-5-yl)-6-(trifluoromethyl)pyridine-2,3-diamine (Intermediate 48). MS (ESI): mass calcd. for $C_{16}H_{12}F_3N_5$, 331.1; m/z found, 332.1 [M+H]$^+$. $^1$H NMR (400 MHz, CDCl$_3$) δ 11.00 (br s, 1H), 8.22 (d, J=8.1 Hz, 1H), 8.01 (s, 1H), 7.74-7.66 (m, 2H), 7.43 (d, J=8.7 Hz, 1H), 7.22 (dd, J=8.7, 1.9 Hz, 1H), 2.84 (q, J=7.5 Hz, 2H), 1.38 (t, J=7.5 Hz, 3H).

Example 106: 5-[2-Cyclopropyl-5-(trifluoromethyl)imidazo[4,5-b]pyridin-3-yl]-1,3-dihydrobenzimidazol-2-one

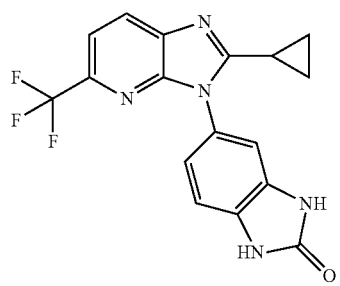

The title compound was prepared in a manner analogous to Example 38. MS (ESI): mass calcd. for $C_{17}H_{12}F_3N_5O$, 359.1; m/z found, 360.0 [M+H]$^+$. $^1$H NMR (400 MHz, DMSO-d$_6$) δ 10.97 (s, 1H), 10.93 (s, 1H), 8.17 (d, J=8.2 Hz, 1H), 7.72 (d, J=8.2 Hz, 1H), 7.19-7.11 (m, 3H), 1.94-1.86 (m, 1H), 1.25-1.17 (m, 2H), 1.13-1.05 (m, 2H).

Example 107: 6-[2-Cyclopropyl-5-(trifluoromethyl)imidazo[4,5-b]pyridin-3-yl]-3H-1,3-benzoxazol-2-one

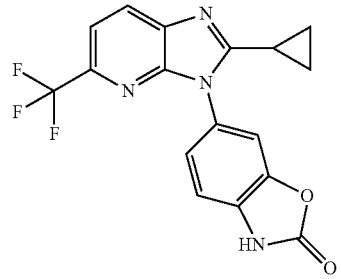

The title compound was prepared in a manner analogous to Example 38. MS (ESI): mass calcd. for $C_{17}H_{11}F_3N_4O_2$, 360.1; m/z found, 361.0 [M+H]$^+$. $^1$H NMR (400 MHz, CDCl$_3$) δ 8.04 (d, J=8.2 Hz, 1H), 7.64 (d, J=8.2 Hz, 1H), 7.39 (d, J=2.0 Hz, 1H), 7.35 (s, 1H), 7.32 (dd, J=8.2, 1.9 Hz, 1H), 7.26 (d, J=8.3 Hz, 1H), 2.00-1.91 (m, 1H), 1.42-1.36 (m, 2H), 1.22-1.15 (m, 2H).

Example 108: 2-tert-Butyl-3-(1H-indazol-5-yl)-5-(trifluoromethyl)imidazo[4,5-b]pyridine

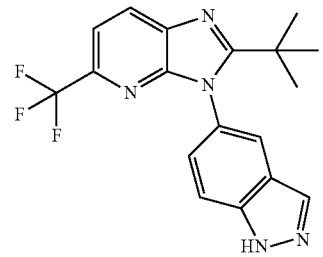 [SMILES: CC(C)(C)c1nc2ccc(C(F)(F)F)nc2n1-c1ccc2[nH]ncc2c1]

The title compound was prepared in a manner analogous to Example 38. MS (ESI): mass calcd. for $C_{18}H_{16}F_3N_5$, 359.1; m/z found, 360.1 [M+H]$^+$. $^1$H NMR (400 MHz, CDCl$_3$) δ 11.00 (br s, 1H), 8.22 (d, J=8.2 Hz, 1H), 8.00 (d, J=1.1 Hz, 1H), 7.73-7.71 (m, 1H), 7.68 (d, J=8.2 Hz, 1H), 7.39-7.34 (m, 1H), 7.21 (dd, J=8.7, 1.9 Hz, 1H), 1.36 (s, 9H).

Example 109: 3-(1H-Indazol-5-yl)-2-isopropyl-5-(trifluoromethyl)imidazo[4,5-b]pyridine

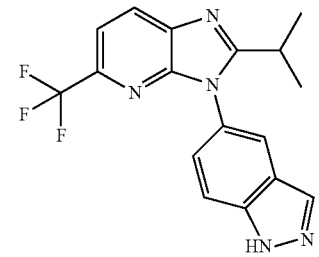 [SMILES: CC(C)c1nc2ccc(C(F)(F)F)nc2n1-c1ccc2[nH]ncc2c1]

Method A:
The title compound was prepared in a manner analogous to Example 38. MS (ESI): mass calcd. for $C_{17}H_{14}F_3N_5$, 345.1; m/z found, 346.0 [M+H]⁺. ¹H NMR (500 MHz, CDCl₃) δ 10.66 (br s, 1H), 8.20 (d, J=8.7 Hz, 1H), 8.11 (d, J=1.1 Hz, 1H), 7.75 (dd, J=1.9, 0.8 Hz, 1H), 7.67 (d, J=8.3 Hz, 1H), 7.60-7.54 (m, 1H), 7.31 (dd, J=8.7, 1.9 Hz, 1H), 3.20-3.12 (m, 1H), 1.38 (s, 3H), 1.36 (s, 3H).

Method B:

Step A: N²-(1H-Indazol-5-yl)-6-(trifluoromethyl)pyridine-2,3-diamine

A solution of 2-chloro-3-nitro-6-(trifluoromethyl)pyridine (1.0 g, 4.4 mmol) and 1H-indazol-5-amine (0.58 g, 4.4 mmol) in DMF (22 mL) was heated at 110° C. After 3 h, sodium dithionite (3.0 g, 17.7 mmol) was added to the mixture, and the reaction was stirred at 110° C. for 5 h. The reaction was diluted with water (200 mL) and stirred for 20 min. The resulting precipitate was filtered and washed with H₂O. The solid was dried at 45° C. to give the title compound as a solid (0.78 g, 60%). MS (ESI): mass calcd. for C₁₃H₁₀F₃N₅, 293.1; m/z found, 294.0 [M+H]⁺.

Step B. 3-(1H-indazol-5-yl)-2-isopropyl-5-(trifluoromethyl)-3H-imidazo[4,5-b]pyridine To a solution of N²-(1H-indazol-5-yl)-6-(trifluoromethyl)pyridine-2,3-diamine (0.20 g, 0.68 mmol) and Cu(OAc)₂ (0.06 g, 0.34 mmol) in AcOH (15 mL) was added isobutyraldehyde (0.06 g, 0.82 mmol). The reaction was stirred for 2 h. The reaction mixture was concentrated in vacuo, diluted with 1N NaOH, and extracted with EtOAc (50 mL×3). The organic layers were combined, dried (NaSO₄), and concentrated in vacuo. Purification (FCC, SiO₂, EtOAc/hexanes) afforded the title compound (0.15 g, 64%). MS (ESI): mass calcd. for C₁₇H₁₄F₃N₅, 345.1; m/z found, 346.0 [M+H]⁺. ¹H NMR (500 MHz, DMSO-d₆) δ 13.45 (s, 1H), 8.33 (dt, J=8.2, 0.6 Hz, 1H), 8.24 (d, J=1.0 Hz, 1H), 8.04 (dd, J=1.9, 0.8 Hz, 1H), 7.82-7.70 (m, 2H), 7.48 (dd, J=8.8, 1.9 Hz, 1H), 3.09 (dt, J=13.6, 6.8 Hz, 1H), 1.26 (d, J=6.8 Hz, 6H).

Example 110: 2-(4-Fluorophenyl)-3-(1H-indazol-5-yl)-5-(trifluoromethyl)imidazo[4,5-b]pyridine

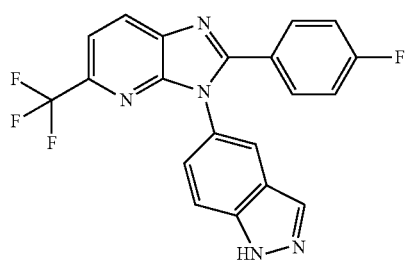 [SMILES: Fc1ccc(-c2nc3ccc(C(F)(F)F)nc3n2-c2ccc3[nH]ncc3c2)cc1]

The title compound was prepared in a manner analogous to Example 38. MS (ESI): mass calcd. for C₂₀H₁₁F₄N₅, 397.1; m/z found, 398.0 [M+H]⁺. ¹H NMR (500 MHz, DMSO-d₆) δ 13.44 (br s, 1H), 8.46 (d, J=8.3 Hz, 1H), 8.20 (s, 1H), 7.97 (dd, J=1.9, 0.7 Hz, 1H), 7.87 (d, J=8.3 Hz, 1H), 7.72 (d, J=8.7 Hz, 1H), 7.67-7.61 (m, 2H), 7.41 (dd, J=8.7, 1.9 Hz, 1H), 7.28-7.21 (m, 2H).

Example 111: 6-(5-Hydroxy-2-phenyl-imidazo[4,5-b]pyridin-3-yl)-3H-1,3-benzothiazol-2-one

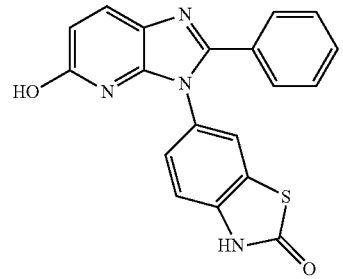 [SMILES: O=c1[nH]c2ccc(-n3c(-c4ccccc4)nc4ccc(O)nc43)cc2s1]

The title compound was prepared in a manner analogous to Example 1. MS (ESI): mass calcd. for C₁₉H₁₂N₄O₂S, 360.1; m/z found, 361.1 [M+H]⁺. ¹H NMR (400 MHz, DMSO-d₆) δ 10.86 (br s, 1H), 8.03 (d, J=8.6 Hz, 1H), 7.81 (d, J=2.0 Hz, 1H), 7.56-7.47 (m, 2H), 7.41-7.32 (m, 3H), 7.25 (dd, J=8.4, 2.1 Hz, 1H), 7.20 (d, J=8.4 Hz, 1H), 6.62 (d, J=8.5 Hz, 1H).

Example 112: 2-(4-Fluorophenyl)-3-(1H-pyrazolo[3,4-b]pyridin-5-yl)imidazo[4,5-b]pyridine

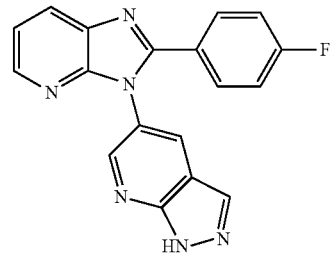 [SMILES: Fc1ccc(-c2nc3cccnc3n2-c2cnc3[nH]ncc3c2)cc1]

The title compound was prepared in a manner analogous to Example 38. MS (ESI): mass calcd. for C₁₈H₁₁FN₆, 330.1; m/z found, 331.1 [M+H]⁺. ¹H NMR (400 MHz, DMSO-d₆) δ 13.99 (br s, 1H), 8.55 (d, J=2.3 Hz, 1H), 8.45 (d, J=2.3 Hz, 1H), 8.33 (dd, J=4.8, 1.4 Hz, 1H), 8.27 (s, 1H), 8.25 (dd, J=7.9, 1.4 Hz, 1H), 7.67-7.59 (m, 2H), 7.42 (dd, J=8.0, 4.7 Hz, 1H), 7.30-7.21 (m, 2H).

Example 113: 3-(1H-Indazol-5-yl)-2-(2,2,2-trifluoroethyl)-5-(trifluoromethyl)imidazo[4,5-b]pyridine

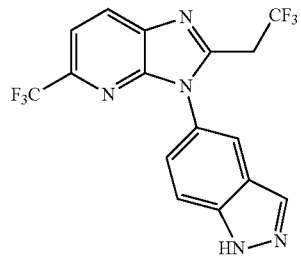 [SMILES: FC(F)(F)Cc1nc2ccc(C(F)(F)F)nc2n1-c1ccc2[nH]ncc2c1]

N²-(1H-indazol-5-yl)-6-(trifluoromethyl)pyridine-2,3-diamine (Intermediate 47, 20 mg, 0.068 mmol) was taken up in trifluoromethanesulfonic acid (0.5 mL, 5.65 mmol). 3,3,3-Trifluoropropanoic acid (6.0 µL, 0.068 mmol) was added and this was stirred at 120° C. for 72 h. The reaction was cooled to 0° C., neutralized with 4N NaOH, and the aqueous layer was extracted with EtOAc. The combined organic layers were dried (Na$_2$SO$_4$), filtered, and concentrated in vacuo. Purification (reverse phase HPLC, 5-95% ACN in 20 nM NH$_4$OH in water) afforded the title compound (9.5 mg, 36%). MS (ESI): mass calcd. for C$_{16}$H$_9$F$_6$N$_5$, 385.1; m/z found, 386.0 [M+H]$^+$. $^1$H NMR (400 MHz, CD$_3$OD) δ 8.35 (d, J=8.3 Hz, 1H), 8.24 (s, 1H), 7.97 (s, 1H), 7.82 (d, J=8.5 Hz, 2H), 7.45 (dd, J=8.9, 1.9 Hz, 1H), 3.94 (q, J=10.2 Hz, 2H).

Example 114: 2-Ethoxy-3-(1H-indazol-5-yl)-5-(trifluoromethyl)imidazo[4,5-b]pyridine

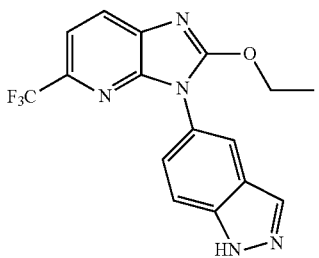 [SMILES: CCOc1nc2ccc(C(F)(F)F)nc2n1-c1ccc2[nH]ncc2c1]

To a solution of N$^2$-(1H-indazol-5-yl)-6-(trifluoromethyl)pyridine-2,3-diamine (Intermediate 47, 70 mg, 0.239 mmol) in acetic acid (0.2 mL) was added tetraethylorthocarbonate (1.0 mL, 4.77 mmol). The reaction mixture was heated at 70° C. for 2 h. The reaction was cooled and concentrated under reduced pressure. Purification (reverse phase HPLC, 5-95% ACN in 20 nM NH$_4$OH in water) afforded the title compound (15 mg, 18%). MS (ESI): mass calcd. for C$_{16}$H$_{12}$F$_3$N$_5$O, 347.1; m/z found, 348.0 [M+H]$^+$. $^1$H NMR (400 MHz, CD$_3$OD) δ 8.19 (d, J=1.0 Hz, 1H), 7.99 (dd, J=2.1, 0.7 Hz, 1H), 7.97 (d, J=8.0 Hz, 1H), 7.75-7.72 (m, 1H), 7.66 (d, J=8.2 Hz, 1H), 7.55 (dd, J=8.9, 2.0 Hz, 1H), 4.70 (q, J=7.1 Hz, 2H), 1.46 (t, J=7.1 Hz, 3H).

Example 115: 1-[3-(1H-Indazol-5-yl)-5-(trifluoromethyl)imidazo[4,5-b]pyridin-2-yl]cyclopropanol

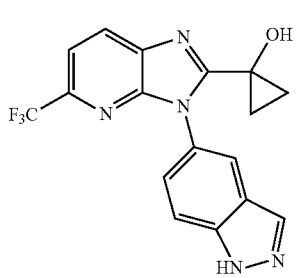 [SMILES: OC1(c2nc3ccc(C(F)(F)F)nc3n2-c2ccc3[nH]ncc3c2)CC1]

Step A: N-(2-(((1H-indazol-5-yl)amino)-6-(trifluoromethyl)pyridin-3-yl)-1-hydroxycyclopropanecarboxamide N$^2$-(1H-indazol-5-yl)-6-(trifluoromethyl)pyridine-2,3-diamine (Intermediate 47, 70 mg, 0.239 mmol) was dissolved in DMF (0.6 mL) in a dry vial. Sodium hydride (60% in mineral oil, 9.5 mg, 0.24 mmol) was added followed by the dropwise addition of ethyl 1-hydroxycyclopropanecarboxylate (28.8 µL, 0.24 mmol). This reaction was stirred at 60° C. for 16 h. The reaction was diluted with EtOAc and water and the aqueous layer was extracted with EtOAc (×3). The combined organic layers were combined, dried (Na$_2$SO$_4$), filtered, and concentrated in vacuo. The crude material was purified by reverse phase HPLC (5-95% ACN in 20 nM NH$_4$OH in water, 254 nm) to provide the title compound (19 mg, 21%). MS (ESI): mass calcd. for C$_{17}$H$_{14}$F$_3$N$_5$O$_2$ 377.3, m/z found 378.0 [M+H]$^+$. $^1$H NMR (400 MHz, CD$_3$OD) δ 8.11-8.06 (m, 1H), 7.96 (s, 1H), 7.84 (d, J=7.9 Hz, 1H), 7.56-7.45 (m, 2H), 7.19 (d, J=7.9 Hz, 1H), 1.38-1.32 (m, 2H), 1.15-1.09 (m, 2H).

Step B: 1-[3-(1H-indazol-5-yl)-5-(trifluoromethyl)imidazo[4,5-b]pyridin-2-yl]cyclopropanol N-(2-(((1H-indazol-5-yl)amino)-6-(trifluoromethyl)pyridin-3-yl)-1-hydroxycyclopropanecarboxamide (21 mg, 0.056 mmol) was heated in AcOH (0.56 mL) at 80° C. for 16 h. The reaction was diluted with EtOAc, neutralized with 4N NaOH, and the aqueous layer was extracted with EtOAc (×3). The combined organic layers were combined, dried (Na$_2$SO$_4$), filtered, and concentrated in vacuo. The crude material was purified by reverse phase HPLC (5-95% ACN in 20 nM NH$_4$OH in water) to provide the title compound (3.3 mg, 17%). MS (ESI): mass calcd. for C$_{17}$H$_{12}$F$_3$N$_5$O, 359.1; m/z found, 360.0 [M+H]$^+$. $^1$H NMR (400 MHz, CD$_3$OD) δ 8.22 (d, J=8.2 Hz, 1H), 8.19 (d, J=1.0 Hz, 1H), 8.01 (dd, J=2.0, 0.8 Hz, 1H), 7.78-7.69 (m, 2H), 7.56 (dd, J=8.8, 1.9 Hz, 1H), 1.41-1.35 (m, 2H), 1.12-1.05 (m, 2H).

Example 116: 2-(1,1-Difluoroethyl)-3-(1H-indazol-5-yl)-5-(trifluoromethyl)imidazo[4,5-b]pyridine

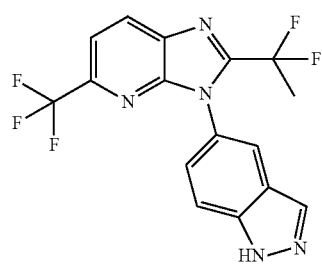 [SMILES: CC(F)(F)c1nc2ccc(C(F)(F)F)nc2n1-c1ccc2[nH]ncc2c1]

The title compound was prepared in a manner analogous to Step C of Example 88, from N$^2$-(1H-indazol-5-yl)-6-(trifluoromethyl)pyridine-2,3-diamine. MS (ESI): mass calcd. for C$_{16}$H$_{10}$F$_5$N$_5$, 367.1; m/z found, 368.0 [M+H]$^+$. $^1$H NMR (400 MHz, CD$_3$OD) δ 8.40 (d, J=8.3 Hz, 1H), 8.17 (d, J=1.1 Hz, 1H), 7.95 (dd, J=1.9, 0.8 Hz, 1H), 7.82 (d, J=8.3 Hz, 1H), 7.75-7.70 (m, 1H), 7.46 (dd, J=8.8, 2.0 Hz, 1H), 2.22-2.05 (m, 3H).

Example 117: (R/S)-2-(1-fluoroethyl)-3-(1H-inda-zol-5-yl)-5-(trifluoromethyl)imidazo[4,5-b]pyridine

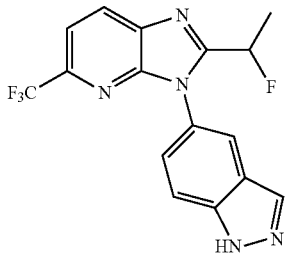 [SMILES: CC(F)c1nc2ccc(C(F)(F)F)nc2n1-c1ccc2[nH]ncc2c1]

Step A: N-(2-((1H-indazol-5-yl)amino)-6-(trifluo-romethyl)pyridin-3-yl)-2-fluoropropanamide $N^2$-(1H-indazol-5-yl)-6-(trifluoromethyl)pyridine-2,3-diamine (Intermediate 47, 25 mg, 0.085 mmol) and HATU (32 mg, 0.085 mmol) were dissolved in DMF (0.26 mL) in a dry flask under nitrogen. 2-Fluoropropanoic acid (6.6 μL, 0.085 mmol) was added followed by TEA (24 μL, 0.171 mmol). This reaction was stirred at rt for 16 h under nitrogen. The reaction was diluted with EtOAc and water and the aqueous layer was extracted with EtOAc (×3). The combined organic layers were combined, dried ($Na_2SO_4$), filtered, and concentrated in vacuo. The crude material was carried on to the next reaction without purification. MS (ESI): mass calcd. for $C_{16}H_{13}F_4N_5O$ 367.3, m/z found 368.0 [M+H]$^+$.

Step B: (R/S)-2-(1-Fluoroethyl)-3-(1H-indazol-5-yl)-5-(trifluoromethyl)imidazo[4,5-b]pyridine N-(2-((1H-indazol-5-yl)amino)-6-(trifluoromethyl)pyridin-3-yl)-2-fluoropropanamide (25 mg, 0.068 mmol) was taken up in AcOH (0.68 mL) and heated to 80° C. for 16 h. The reaction was diluted with EtOAc, neutralized with 4N NaOH, and the aqueous layer was extracted with EtOAc (×3). The combined organic layers were combined, dried ($Na_2SO_4$), filtered, and concentrated in vacuo. The crude material was purified by reverse phase HPLC (5-95% ACN in 20 nM $NH_4OH$ in water) to provide the title compound (13 mg, 55%). MS (ESI): mass calcd. for $C_{16}H_{11}F_4N_5$, 349.1; m/z found, 350.0 [M+H]$^+$. $^1$H NMR (500 MHz, $CD_3OD$) δ 8.36 (d, J=8.3 Hz, 1H), 8.21 (d, J=1.1 Hz, 1H), 7.99 (d, J=1.9 Hz, 1H), 7.81 (d, J=8.3 Hz, 1H), 7.80-7.76 (m, 1H), 7.49 (dd, J=8.8, 1.9 Hz, 1H), 5.89-5.74 (m, 1H), 1.81 (dd, J=23.9, 6.5 Hz, 3H).

Example 118: 5-tert-Butyl-2-(4-fluorophenyl)-3-(1H-indazol-5-yl)imidazo[4,5-b]pyridine

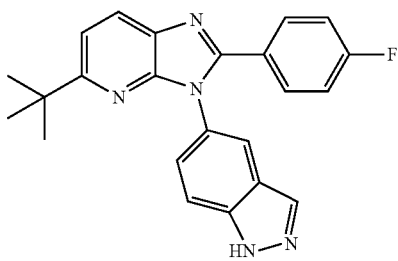 [SMILES: CC(C)(C)c1ccc2nc(-c3ccc(F)cc3)n(-c3ccc4[nH]ncc4c3)c2n1]

The title compound was prepared in a manner analogous to Example 1 from 6-(tert-butyl)-2-chloro-3-nitropyridine (Intermediate 2). MS (ESI): mass calcd. for $C_{23}H_{20}FN_5$, 385.2; m/z found, 386.1 [M+H]$^+$. $^1$H NMR (500 MHz, DMSO-$d_6$) δ 13.35 (s, 1H), 8.16 (s, 1H), 8.11 (d, J=8.4 Hz, 1H), 7.85 (d, J=1.5 Hz, 1H), 7.68 (d, J=8.8 Hz, 1H), 7.59-7.54 (m, 2H), 7.45 (d, J=8.4 Hz, 1H), 7.38-7.33 (m, 1H), 7.20 (t, J=8.9 Hz, 2H), 1.28 (s, 9H).

Example 119: 2-Cyclobutyl-3-(1H-indazol-5-yl)-5-isopropyl-imidazo[4,5-b]pyridine

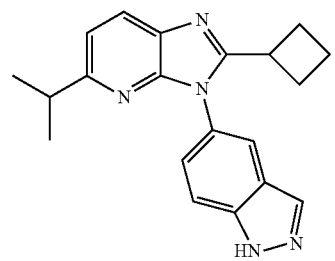 [SMILES: CC(C)c1ccc2nc(C3CCC3)n(-c3ccc4[nH]ncc4c3)c2n1]

The title compound was prepared in a manner analogous to Example 1. MS (ESI): mass calcd. for $C_{20}H_{21}N_5$, 331.2; m/z found, 332.1 [M+H]$^+$. $^1$H NMR (400 MHz, $CD_3OD$) δ 8.20 (d, J=1.0 Hz, 1H), 7.98 (d, J=8.3 Hz, 1H), 7.85 (dd, J=2.2, 0.6 Hz, 1H), 7.78-7.74 (m, 1H), 7.37 (dd, J=8.7, 1.9 Hz, 1H), 7.25 (d, J=8.3 Hz, 1H), 3.75-3.64 (m, 1H), 3.11-2.99 (m, 1H), 2.59-2.46 (m, 2H), 2.23-2.12 (m, 2H), 2.07-1.88 (m, 2H), 1.24 (d, J=7.0 Hz, 6H).

Example 120: 2-(4-Fluorophenyl)-3-(1H-indazol-5-yl)-5-isopropyl-imidazo[4,5-b]pyridine

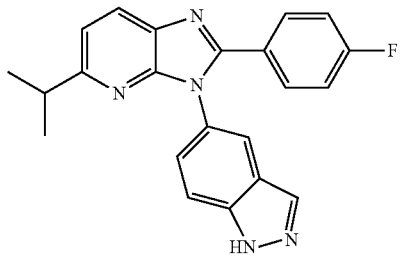 [SMILES: CC(C)c1ccc2nc(-c3ccc(F)cc3)n(-c3ccc4[nH]ncc4c3)c2n1]

The title compound was prepared in a manner analogous to Example 1 from 2-chloro-6-isopropyl-3-nitropyridine (Intermediate 3). MS (ESI): mass calcd. for $C_{22}H_{18}FN_5$, 371.2; m/z found, 372.1 [M+H]$^+$. $^1$H NMR (400 MHz, DMSO-$d_6$) δ 13.37 (s, 1H), 8.17 (s, 1H), 8.11 (d, J=8.2 Hz, 1H), 7.89-7.86 (m, 1H), 7.69 (d, J=8.8 Hz, 1H), 7.60-7.53 (m, 2H), 7.34 (dd, J=8.7, 2.0 Hz, 1H), 7.29 (d, J=8.2 Hz, 1H), 7.24-7.16 (m, 2H), 3.08-2.98 (m, 1H), 1.20 (d, J=6.9 Hz, 6H).

Example 121: 2-(4-Fluoro-3-methyl-phenyl)-3-(1H-indazol-5-yl)-5-(trifluoromethyl)imidazo[4,5-b]pyridine

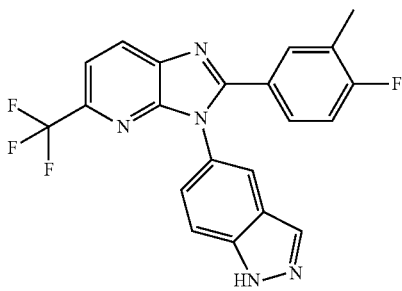 [SMILES: Cc1cc(-c2nc3ccc(C(F)(F)F)nc3n2-c2ccc3[nH]ncc3c2)ccc1F]

The title compound was prepared in a manner analogous to Example 1. MS (ESI): mass calcd. for $C_{21}H_{13}F_4N_5$, 411.1; m/z found, 412.0 [M+H]$^+$. $^1$H NMR (400 MHz, DMSO-d$_6$) δ 13.42 (s, 1H), 8.45 (d, J=8.3 Hz, 1H), 8.21 (s, 1H), 7.96 (d, J=1.6 Hz, 1H), 7.87 (d, J=8.2 Hz, 1H), 7.75-7.70 (m, 2H), 7.41 (dd, J=8.8, 1.9 Hz, 1H), 7.27-7.20 (m, 1H), 7.15-7.05 (m, 1H), 2.18 (d, J=1.9 Hz, 3H).

Example 122: 3-(1H-Indazol-5-yl)-2-(m-tolyl)-5-(trifluoromethyl)imidazo[4,5-b]pyridine

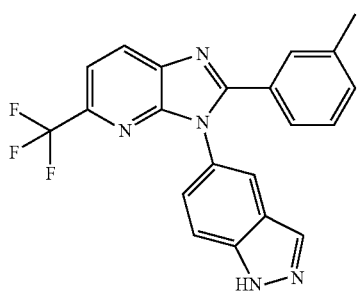 [SMILES: Cc1cccc(-c2nc3ccc(C(F)(F)F)nc3n2-c2ccc3[nH]ncc3c2)c1]

The title compound was prepared in a manner analogous to Example 1. MS (ESI): mass calcd. for $C_{21}H_{14}F_3N_5$, 393.1; m/z found, 394.0 [M+H]$^+$. $^1$H NMR (400 MHz, DMSO-d$_6$) δ 13.41 (s, 1H), 8.45 (d, J=8.2 Hz, 1H), 8.19 (s, 1H), 7.94 (dd, J=2.0, 0.7 Hz, 1H), 7.87 (d, J=8.3 Hz, 1H), 7.72 (d, J=8.8 Hz, 1H), 7.59 (s, 1H), 7.41 (dd, J=8.7, 1.9 Hz, 1H), 7.29-7.16 (m, 3H), 2.24 (s, 3H).

Example 123: 3-(1H-Indazol-5-yl)-2-(p-tolyl)-5-(trifluoromethyl)imidazo[4,5-b]pyridine

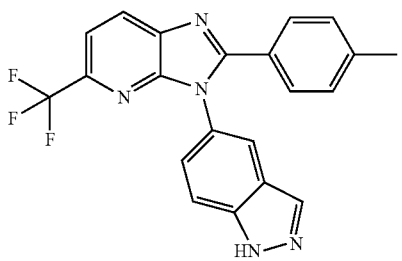 [SMILES: Cc1ccc(-c2nc3ccc(C(F)(F)F)nc3n2-c2ccc3[nH]ncc3c2)cc1]

The title compound was prepared in a manner analogous to Example 1. MS (ESI): mass calcd. for $C_{21}H_{14}F_3N_5$, 393.1; m/z found, 394.0 [M+H]$^+$. $^1$H NMR (400 MHz, DMSO-d$_6$) δ 13.41 (s, 1H), 8.44 (d, J=8.3 Hz, 1H), 8.19 (s, 1H), 7.94 (d, J=1.6 Hz, 1H), 7.85 (d, J=8.3 Hz, 1H), 7.72 (d, J=8.8 Hz, 1H), 7.51-7.46 (m, 2H), 7.40 (dd, J=8.8, 1.9 Hz, 1H), 7.21-7.13 (m, 2H), 2.28 (s, 3H).

Example 124: 3-(1H-Indazol-5-yl)-2-(4-pyridyl)-5-(trifluoromethyl)imidazo[4,5-b]pyridine

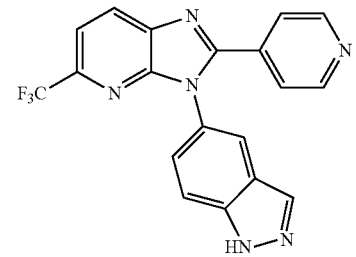 [SMILES: FC(F)(F)c1ccc2nc(-c3ccncc3)n(-c3ccc4[nH]ncc4c3)c2n1]

Step A: N-(2-((1H-Indazol-5-yl)amino)-6-(trifluoromethyl)pyridin-3-yl)isonicotinamide To a solution of isonicotinoyl chloride (35 mg, 0.247 mmol) in DMF (1.0 mL) was added N$^2$-(1H-indazol-5-yl)-6-(trifluoromethyl)pyridine-2,3-diamine (Intermediate 47, 69 mg, 0.235 mmol) and DIEA (0.16 mL, 1.18 mmol). The reaction was stirred at rt for 5 h. The reaction was diluted with EtOAc and water and the aqueous layer was extracted with EtOAc (×3). The combined organic layers were combined, dried (Na$_2$SO$_4$), filtered, and concentrated in vacuo. The crude material was carried on to the next reaction without purification. MS (ESI): mass calcd. for $C_{19}H_{13}F_3N_6O$ 398.4, m/z found 399.0 [M+H]$^+$.

Step B: 3-(1H-Indazol-5-yl)-2-(4-pyridyl)-5-(trifluoromethyl)imidazo[4,5-b]pyridine N-(2-((1H-indazol-5-yl)amino)-6-(trifluoromethyl)pyridin-3-yl)isonicotinamide (45 mg, 0.113 mmol) was taken up in AcOH (3.0 mL) and heated to 80° C. for 16 h. The reaction was diluted with EtOAc, neutralized with 4N NaOH, and the aqueous layer was extracted with EtOAc (×3). The combined organic layers were combined, dried (Na$_2$SO$_4$), filtered, and concentrated in vacuo. The crude material was purified by reverse phase HPLC (5-95% ACN in 20 nM NH$_4$OH in water) to provide the title compound (6.5 mg, 15%). MS (ESI): mass calcd. for $C_{19}H_{11}F_3N_6$, 380.1; m/z found, 381.0 [M+H]$^+$. $^1$H NMR (400 MHz, CD$_3$OD) δ 7.77-7.72 (m, 2H), 7.61 (d, J=8.3 Hz, 1H), 7.36 (d, J=0.9 Hz, 1H), 7.13 (d, J=1.9 Hz, 1H), 7.05 (d, J=8.3 Hz, 1H), 6.95-6.91 (m, 1H), 6.83-6.78 (m, 2H), 6.62 (dd, J=8.8, 1.9 Hz, 1H).

Example 125: 5-Cyclopropyl-3-(1H-indazol-5-yl)-2-(trifluoromethyl)imidazo[4,5-b]pyridine

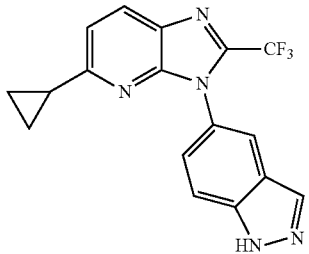 [SMILES: FC(F)(F)c1nc2ccc(C3CC3)nc2n1-c1ccc2[nH]ncc2c1]

A solution of 6-cyclopropyl-N²-(1H-indazol-5-yl)pyridine-2,3-diamine (Intermediate 52, 58 mg, 0.22 mmol) in TFA (0.17 mL, 2.2 mmol) was stirred at 70° C. for 7 h. The reaction was diluted with EtOAc and water and the pH was neutralized with 4N NaOH. The aqueous layer was extracted with EtOAc (×3) and the combined organic layers were dried (Na$_2$SO$_4$) and concentrated in vacuo. The resulting residue was purified by reverse phase HPLC (5-95% ACN in 20 nM NH$_4$OH in water) to give the title compound (10 mg, 13%). MS (ESI): mass calcd. for C$_{17}$H$_{12}$F$_3$N$_5$, 343.1; m/z found, 344.0 [M+H]$^+$. $^1$H NMR (500 MHz, CD$_3$OD) δ 8.20 (s, 1H), 8.10 (d, J=8.5 Hz, 1H), 7.94 (d, J=1.8 Hz, 1H), 7.74 (d, J=8.8 Hz, 1H), 7.43 (dd, J=8.8, 2.0 Hz, 1H), 7.35 (d, J=8.5 Hz, 1H), 2.20-2.12 (m, 1H), 0.98-0.92 (m, 2H), 0.89-0.84 (m, 2H).

Example 126: 3-(1H-Indazol-5-yl)-N,N-dimethyl-5-(trifluoromethyl)imidazo[4,5-b]pyridine-2-carboxamide

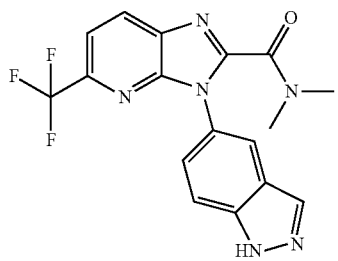 [SMILES: CN(C)C(=O)c1nc2ccc(C(F)(F)F)nc2n1-c1ccc2[nH]ncc2c1]

The title compound was prepared in a manner analogous to Example 128. MS (ESI): mass calcd. for C$_{17}$H$_{13}$F$_3$N$_6$O, 374.1; m/z found, 375.0 [M+H]$^+$. $^1$H NMR (400 MHz, CD$_3$OD) δ 8.42 (d, J=8.6 Hz, 1H), 8.21 (s, 1H), 7.99 (d, J=2.0 Hz, 1H), 7.87 (d, J=8.3 Hz, 1H), 7.75 (d, J=8.6 Hz, 1H), 7.54 (dd, J=8.9, 2.0 Hz, 1H), 3.07 (s, 3H), 3.01 (s, 3H).

Example 127: 3-(1H-Indazol-5-yl)-N-methyl-5-(trifluoromethyl)imidazo[4,5-b]pyridine-2-carboxamide

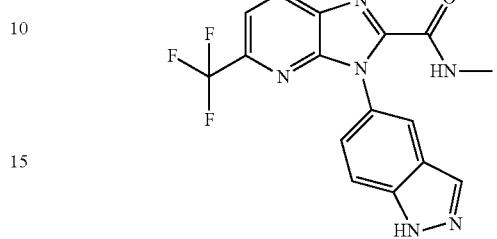

The title compound was prepared in a manner analogous to Example 128. MS (ESI): mass calcd. for C$_{16}$H$_{11}$F$_3$N$_6$O, 360.1; m/z found, 361.0 [M+H]$^+$. $^1$H NMR (400 MHz, CD$_3$OD) δ 8.42 (d, J=8.4 Hz, 1H), 8.18 (s, 1H), 7.89 (d, J=1.8 Hz, 1H), 7.84 (d, J=8.4 Hz, 1H), 7.71 (d, J=8.7 Hz, 1H), 7.49-7.40 (m, 1H), 2.88 (s, 3H).

Example 128: N-Cyclopropyl-3-(1H-indazol-5-yl)-5-(trifluoromethyl)imidazo[4,5-b]pyridine-2-carboxamide To a solution of 3-(1H-Indazol-5-yl)-2-(trichloromethyl)-5-(trifluoromethyl)-3H-imidazo[4,5-b]pyridine (Example 81, product from Step A, 50.0 mg, 0.119 mmol) in DMF (0.743 mL) was added hydroxybenzotriazole (19.3 mg, 0.143 mmol) and TEA dropwise (49.6 μL, 0.357 mmol). This solution was heated to 60° C. for 45 min. Cyclopropylamine (25.0 μL, 0.357 mmol) was added and the solution was stirred at 70° C. for 3 h. The solution was cooled, diluted with water, and extracted with EtOAc (5 mL×3). The combined organic layer was dried (Na$_2$SO$_4$), filtered, and concentrated in vacuo. The crude material was purified by reverse phase HPLC (5-95% ACN in 20 nM NH$_4$OH in water) to provide the title compound (8.40 mg, 18%). MS (ESI): mass calcd. for C$_{18}$H$_{13}$F$_3$N$_6$O, 386.1; m/z found, 387.0 [M+H]$^+$. $^1$H NMR (500 MHz, CD$_3$OD) δ 8.42 (dd, J=8.5, 0.7 Hz, 1H), 8.19 (d, J=1.0 Hz, 1H), 7.90 (dd, J=2.0, 0.8 Hz, 1H), 7.84 (d, J=8.4 Hz, 1H), 7.72 (dt, J=8.8, 0.9 Hz, 1H), 7.45 (dd, J=8.8, 1.9 Hz, 1H), 2.82-2.74 (m, 1H), 0.82-0.74 (m, 2H), 0.66-0.60 (m, 2H).

Example 129: 3-(1H-Indazol-5-yl)-2-methoxy-5-(trifluoromethyl)imidazo[4,5-b]pyridine

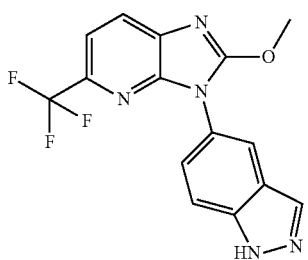 [SMILES: COc1nc2ccc(C(F)(F)F)nc2n1-c1ccc2[nH]ncc2c1]

The title compound was prepared in a manner analogous to Example 114. MS (ESI): mass calcd. for $C_{15}H_{10}F_3N_5O$, 333.1; m/z found, 334.0 [M+H]$^+$. $^1$H NMR (400 MHz, CD$_3$OD) δ 8.18 (s, 1H), 8.02-7.96 (m, 2H), 7.73 (d, J=8.8 Hz, 1H), 7.67 (d, J=8.2 Hz, 1H), 7.55 (dd, J=8.9, 2.0 Hz, 1H), 4.26 (s, 3H).

Example 130: N-Ethyl-3-(1H-indazol-5-yl)-5-(trifluoromethyl)imidazo[4,5-b]pyridin-2-amine

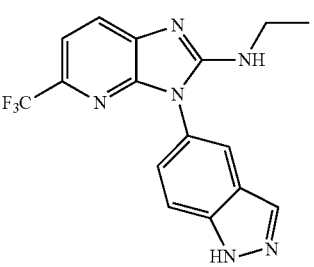 [SMILES: CCNc1nc2ccc(C(F)(F)F)nc2n1-c1ccc2[nH]ncc2c1]

$N^2$-(1H-Indazol-5-yl)-6-(trifluoromethyl)pyridine-2,3-diamine (Intermediate 47, 30 mg, 0.102 mmol) in THF (1.0 mL) was placed in a dry flask under a nitrogen atmosphere. Ethyl isothiocyanate (9.0 μL, 0.102 mmol) was added followed by dicyclohexyl carbodiimide (42 mg, 0.205 mmol). This was heated at 65° C. for 16 h. The reaction was diluted with EtOAc and water and the aqueous layer was extracted with EtOAc. The combined organic layers were dried (Na$_2$SO$_4$), filtered, and concentrated in vacuo. The crude material was purified by reverse phase HPLC (5-95% ACN in 20 nM NH$_4$OH in water) to provide the title compound (1.9 mg, 5%). MS (ESI): mass calcd. for $C_{16}H_{13}F_3N_6$, 346.1; m/z found, 347.0 [M+H]$^+$. $^1$H NMR (400 MHz, CD$_3$OD) δ 8.21 (s, 1H), 7.94 (d, J=1.9 Hz, 1H), 7.79 (d, J=8.8 Hz, 1H), 7.68 (d, J=8.0 Hz, 1H), 7.50 (d, J=8.0 Hz, 1H), 7.42 (dd, J=8.8, 1.9 Hz, 1H), 3.50 (q, J=7.2 Hz, 2H), 1.25 (t, J=7.2 Hz, 3H).

Example 131: N-Cyclohexyl-3-(1H-indazol-5-yl)-5-(trifluoromethyl)imidazo[4,5-b]pyridin-2-amine

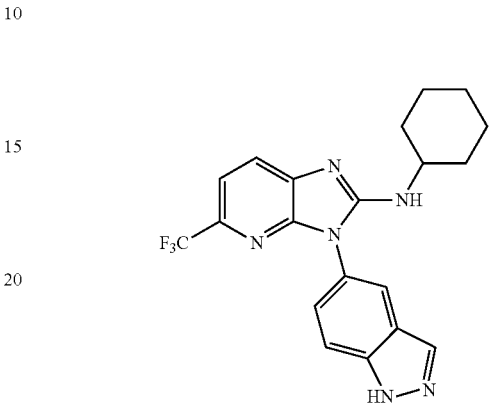

The title compound was prepared in a manner analogous to Example 130. MS (ESI): mass calcd. for $C_{20}H_{19}F_3N_6$, 400.2; m/z found, 401.0 [M+H]$^+$. $^1$H NMR (400 MHz, CD$_3$OD) δ 8.20 (d, J=0.9 Hz, 1H), 7.93 (dd, J=2.0, 0.7 Hz, 1H), 7.78 (dt, J=8.8, 1.0 Hz, 1H), 7.66 (d, J=7.9 Hz, 1H), 7.50 (d, J=8.1 Hz, 1H), 7.41 (dd, J=8.8, 1.9 Hz, 1H), 3.92-3.83 (m, 1H), 2.07-1.99 (m, 2H), 1.83-1.73 (m, 2H), 1.70-1.62 (m, 1H), 1.51-1.37 (m, 2H), 1.37-1.25 (m, 2H), 1.24-1.11 (m, 1H).

Example 132: 6-[2-Cyclobutyl-5-(trifluoromethyl)imidazo[4,5-b]pyridin-3-yl]-3H-1,3-benzothiazol-2-one

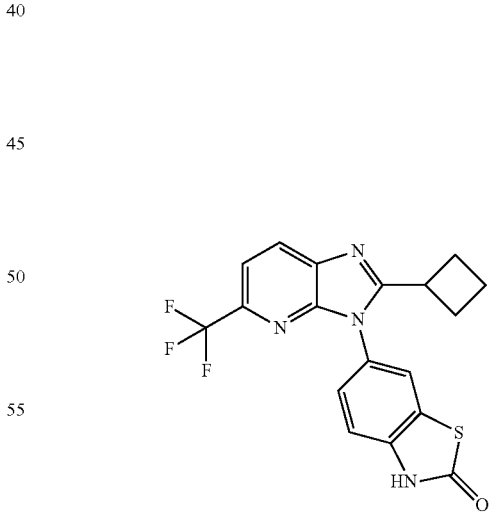

The title compound was prepared in a manner analogous to Example 38. MS (ESI): mass calcd. for $C_{18}H_{13}F_3N_4OS$, 390.1; m/z found, 391.0 [M+H]$^+$. $^1$H NMR (400 MHz, DMSO-d$_6$) δ 12.23 (s, 1H), 8.34 (d, J=7.9 Hz, 1H), 7.82-7.76 (m, 2H), 7.40 (dd, J=8.4, 2.1 Hz, 1H), 7.32 (d, J=8.4 Hz, 1H), 3.71-3.60 (m, 1H), 2.49-2.40 (m, 2H), 2.18-2.09 (m, 2H), 2.02-1.93 (m, 1H), 1.92-1.81 (m, 1H).

Example 133: 6-(2-Cyclobutyl-5-methyl-7-morpholino-imidazo[4,5-b]pyridin-3-yl)-3H-1,3-benzothiazol-2-one

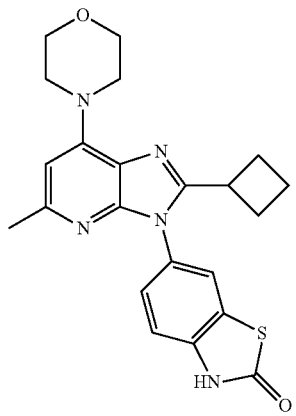 [SMILES: Cc1cc(N2CCOCC2)c2nc(C3CCC3)n(-c3ccc4[nH]c(=O)sc4c3)c2n1]

The title compound was prepared in a manner analogous to Example 62. MS (ESI): mass calcd. for $C_{22}H_{23}N_5O_2S$, 421.2; m/z found, 422.1 [M+H]$^+$. $^1$H NMR (400 MHz, CDCl$_3$) δ 7.27 (s, 1H), 6.94 (dd, J=8.3, 2.1 Hz, 1H), 6.84 (d, J=8.3 Hz, 1H), 6.36 (s, 1H), 4.12 (q, J=7.2 Hz, 1H), 4.0 (s, 4H), 3.49-3.32 (m, 1H), 2.61-2.44 (m, 4H), 2.16-2.05 (m, 2H), 1.93 (dt, J=18.0, 9.5 Hz, 2H), 1.66-1.42 (m, 4H).

Example 134: 6-[2,5-Bis(trifluoromethyl)imidazo[4,5-b]pyridin-3-yl]-3H-1,3-benzothiazol-2-one

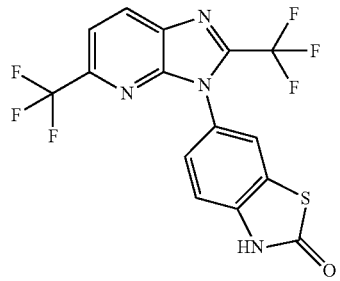

Method A:
The title compound was prepared in a manner analogous to Example 88.
Method B:

Step A: 6-((3-Amino-6-(trifluoromethyl)pyridin-2-yl)amino)benzo[d]thiazol-2(3H)-one A solution of 2-chloro-3-nitro-6-(trifluoromethyl)pyridine (2.0 g, 8.8 mmol) and 6-aminobenzo[d]thiazol-2(3H)-one (1.5 g, 8.8 mmol) in DMF (40 mL) was heated at 110° C. After 3 h, sodium dithionite (6.1 g, 35.3 mmol) was added to the mixture was let stir at 110° C. for 5 h. The reaction was diluted with water (320 mL) and let stir for 20 min where precipitate formed. The reaction was filtered and the solid was washed with H$_2$O and oven dried at 45° C. to give the desired compound as a solid (2.6 g, 90%). MS (ESI): mass calcd. for $C_{13}H_9F_3N_4OS$, 326.05 m/z found, 327.0 [M+H]$^+$.

Step B: 6-(2,5-Bis(trifluoromethyl)-3H-imidazo[4,5-b]pyridin-3-yl)benzo[d]thiazol-2(3H)-one A solution of 6-((3-amino-6-(trifluoromethyl)pyridin-2-yl)amino)benzo[d]thiazol-2(3H)-one (2.5 g, 7.7 mmol) in TFA (40 mL) was stirred at 70° C. for 16 h. The reaction was concentrated in vacuo, diluted with sat. NaHCO$_3$ (200 mL) and extracted with EtOAc (150 mL×3). The organic layers were combined, dried (Na$_2$SO$_4$) and concentrated in vacuo. Purification (FCC, SiO$_2$, EtOAc/hexanes) afforded the title compound (1.7 g, 55%). MS (ESI): mass calcd. for $C_{15}H_6F_6N_4OS$, 404.0; m/z found, 404.9 [M+H]$^+$. $^1$H NMR (500 MHz, DMSO-d$_6$) 12.32 (s, 1H), 8.72 (d, J=8.4 Hz, 1H), 8.04 (d, J=8.4 Hz, 1H), 7.96 (d, J=2.1 Hz, 1H), 7.59 (dd, J=8.5, 2.1 Hz, 1H), 7.35 (d, J=8.5 Hz, 1H).

Example 135: 6-(2-Cyclopropyl-7-methyl-imidazo[4,5-b]pyridin-3-yl)-3H-1,3-benzothiazol-2-one

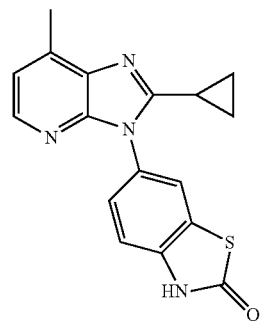 [SMILES: Cc1ccnc2c1nc(C1CC1)n2-c1ccc2[nH]c(=O)sc2c1]

The title compound was prepared in a manner analogous to Example 1. MS (ESI): mass calcd. for $C_{17}H_{14}N_4OS$, 322.1; m/z found, 323.0 [M+H]$^+$. $^1$H NMR (500 MHz, CDCl$_3$) δ 11.01 (s, 1H), 8.17 (d, J=5.0 Hz, 1H), 7.51 (d, J=2.1 Hz, 1H), 7.24 (dd, J=8.4, 2.1 Hz, 1H), 7.07 (dd, J=5.0, 0.8 Hz, 1H), 7.00 (d, J=8.3 Hz, 1H), 2.67 (s, 3H), 1.89-1.82 (m, 1H), 1.36-1.31 (m, 2H), 1.09-1.02 (m, 2H).

Example 136: 6-(2-Cyclopropyl-5-methyl-7-morpholino-imidazo[4,5-b]pyridin-3-yl)-3H-1,3-benzothiazol-2-one

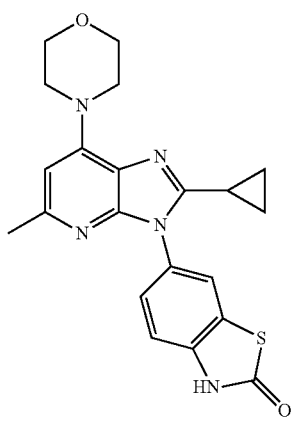 [SMILES: Cc1cc(N2CCOCC2)c2nc(C3CC3)n(-c3ccc4[nH]c(=O)sc4c3)c2n1]

The title compound was prepared in a manner analogous to Example 62. MS (ESI): mass calcd. for $C_{21}H_{21}N_5O_2S$, 407.1; m/z found, 408.0 [M+H]$^+$. $^1$H NMR (400 MHz, DMSO-d$_6$) δ 12.14 (s, 1H), 7.78 (d, J=2.0 Hz, 1H), 7.38 (dd, J=8.6, 2.1 Hz, 1H), 7.30 (d, J=8.4 Hz, 1H), 6.43 (s, 1H), 3.77 (s, 8H), 2.31 (s, 3H), 1.83-1.72 (m, 1H), 1.06-0.99 (m, 2H), 0.97-0.88 (m, 2H).

Example 137: 5-Chloro-2-cyclobutyl-3-(1H-indazol-5-yl)-7-methyl-imidazo[4,5-b]pyridine

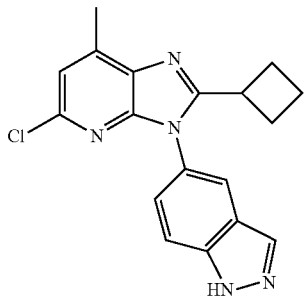 [SMILES: Cc1cc(Cl)nc2c1nc(C1CCC1)n2-c1ccc2[nH]ncc2c1]

The title compound was prepared in a manner analogous to Example 1. MS (ESI): mass calcd. for $C_{18}H_{16}ClN_5$, 337.1; m/z found, 338.0 [M+H]$^+$. $^1$H NMR (400 MHz, CDCl$_3$) δ 11.14 (br s, 1H), 8.02 (s, 1H), 7.61 (dd, J=2.0, 0.7 Hz, 1H), 7.41 (d, J=8.7 Hz, 1H), 7.14 (dd, J=8.7, 1.9 Hz, 1H), 7.11 (d, J=1.0 Hz, 1H), 3.61-3.49 (m, 1H), 2.74 (d, J=0.7 Hz, 3H), 2.66-2.53 (m, 2H), 2.19-2.08 (m, 2H), 1.99-1.87 (m, 2H).

Example 138: 3-(7-Bromo-1H-indazol-5-yl)-2-cyclobutyl-5-(trifluoromethyl)imidazo[4,5-b]pyridine

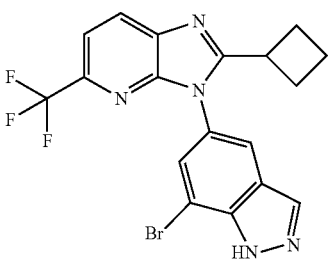 [SMILES: FC(F)(F)c1ccc2nc(C3CCC3)n(-c3cc(Br)c4[nH]ncc4c3)c2n1]

The title compound was prepared in a manner analogous to Example 1. MS (ESI): mass calcd. for $C_{18}H_{13}BrF_3N_5$, 435.0; m/z found, 436.0 [M+H]$^+$. $^1$H NMR (400 MHz, DMSO-d$_6$) δ 13.89 (s, 1H), 8.39 (s, 1H), 8.34 (d, J=8.1 Hz, 1H), 8.01 (d, J=1.6 Hz, 1H), 7.82 (d, J=1.6 Hz, 1H), 7.79 (d, J=8.2 Hz, 1H), 3.72-3.61 (m, 1H), 2.56-2.43 (m, 2H), 2.15-2.03 (m, 2H), 2.01-1.91 (m, 1H), 1.91-1.81 (m, 1H).

Example 139: 5-[5-Methyl-2-(trifluoromethyl)imidazo[4,5-b]pyridin-3-yl]indolin-2-one

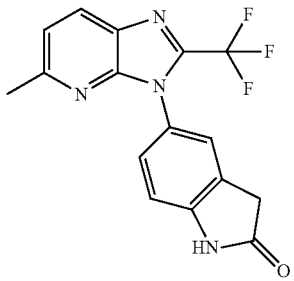

The title compound was prepared in a manner analogous to Example 88. MS (ESI): mass calcd. for $C_{16}H_{11}F_3N_4O$, 332.1; m/z found, 333.0 [M+H]$^+$. $^1$H NMR (500 MHz, CDCl$_3$) δ 8.11 (d, J=8.3 Hz, 1H), 7.99 (s, 1H), 7.33-7.28 (m, 2H), 7.27 (s, 1H), 7.02 (d, J=8.9 Hz, 1H), 3.65 (s, 2H), 2.63 (s, 3H).

Example 140: 5-[2-Cyclopropyl-5-(difluoromethyl)imidazo[4,5-b]pyridin-3-yl]indolin-2-one

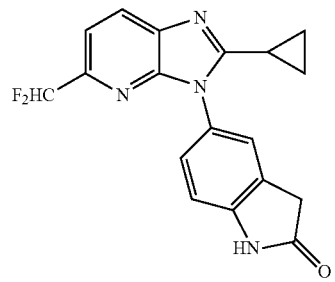 [SMILES: O=C1Cc2cc(-n3c(C4CC4)nc4ccc(C(F)F)nc43)ccc2N1]

Step A: 5-((6-(Difluoromethyl)-3-nitropyridin-2-yl)amino)indolin-2-one

A mixture of 2-chloro-6-(difluoromethyl)-3-nitropyridine (Intermediate 48, product from Step E, 1.8 mL, 1.0 M in benzene, 1.8 mmol), 5-aminoindolin-2-one (330 mg, 2.16 mmol), and DIEA (0.62 mL, 3.6 mmol) in EtOH (10 mL) was refluxed at 90° C. for 3 h. The reaction was cooled down and a precipitate formed. The mixture was filtered and the precipitate was washed with cold EtOH. The solid was dried under high vacuum to give the title compound as a brown solid (510 mg, 88%). MS (ESI): mass calcd. for $C_{14}H_{10}F_2N_4O_3$, 320.1; m/z found, 321.0 [M+H]$^+$.

Step B: 5-((3-Amino-6-(difluoromethyl)pyridin-2-yl)amino)indolin-2-one

A mixture of 5-((6-(difluoromethyl)-3-nitropyridin-2-yl)amino)indolin-2-one (510 mg, 1.6 mmol), 10% Pd/C (54 mg) in EtOH (13 mL) and THF (13 mL) in a 100 mL flask was placed under a H$_2$ balloon and stirred for 16 h. The reaction was filtered through Celite® and the resulting solution was concentrated in vacuo to give the desired compound as a grey solid (464 mg, 100%). MS (ESI): mass calcd. for $C_{14}H_{12}F_2N_4O$, 290.1 m/z found, 291.0 [M+H]$^+$.

Step C. 5-(2-Cyclopropyl-5-(difluoromethyl)-3H-imidazo[4,5-b]pyridin-3-yl)indolin-2-one To a solution of 5-((3-amino-6-(difluoromethyl)pyridin-2-yl)amino)indolin-2-one (0.10 g, 0.34 mmol) and Cu(OAc)$_2$ (0.03 g, 0.17 mmol) in AcOH (5.8 mL) was added cyclopropanecarboxaldehyde (39 μL, 0.52 mmol). The reaction was stirred for 1 h, then basified with 15% NaOH (6 mL). The reacting mixture was diluted with water (45 mL) and extracted with EtOAc (50 mL×3). The organic layers were combined, dried (Na$_2$SO$_4$), and concentrated in vacuo. Purification (FCC, SiO$_2$, EtOAc/hexanes) afforded the title compound (88 mg, 75%). MS (ESI): mass calcd. for C$_{18}$H$_{14}$F$_2$N$_4$O, 340.1; m/z found, 341.1 [M+H]$^+$. $^1$H NMR (500 MHz, CDCl$_3$) δ 8.33 (s, 1H), 8.05 (d, J=8.2 Hz, 1H), 7.57 (d, J=8.2 Hz, 1H), 7.45-7.31 (m, 2H), 7.07 (dd, J=8.1, 0.7 Hz, 1H), 6.63 (t, J=55.6 Hz, 1H), 3.74-3.61 (m, 2H), 1.99-1.83 (m, 1H), 1.45-1.33 (m, 2H), 1.13 (dd, J=8.2, 2.8 Hz, 2H).

Example 141: 5-[5-(Difluoromethyl)-2-isopropyl-imidazo[4,5-b]pyridin-3-yl]indolin-2-one

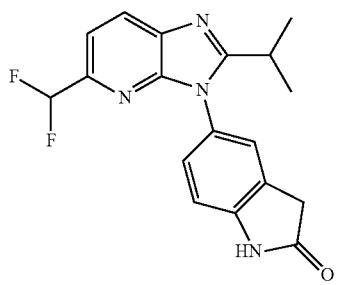

The title compound was prepared in a manner analogous to Example 140. MS (ESI): mass calcd. for C$_{18}$H$_{16}$F$_2$N$_4$O, 342.1; m/z found, 343.0 [M+H]$^+$. $^1$H NMR (500 MHz, CDCl$_3$) δ 8.48 (s, 1H), 8.16 (d, J=8.2 Hz, 1H), 7.60 (d, J=8.2 Hz, 1H), 7.25-7.22 (m, 1H), 7.05 (dd, J=8.1, 0.6 Hz, 1H), 6.63 (t, J=55.5 Hz, 1H), 3.66 (s, 2H), 3.19-3.09 (m, 1H), 1.37 (d, J=6.8 Hz, 6H).

Example 142: 6-[5-Methyl-2-(trifluoromethyl)imidazo[4,5-b]pyridin-3-yl]-3H-1,3-benzothiazol-2-one

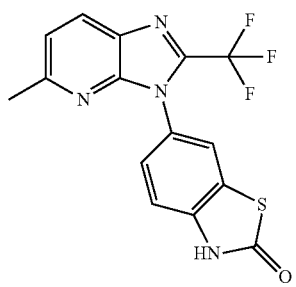 [SMILES: Cc1ccc2nc(C(F)(F)F)n(-c3ccc4[nH]c(=O)sc4c3)c2n1]

The title compound was prepared in a manner analogous to Example 88. MS (ESI): mass calcd. for C$_{15}$H$_9$F$_3$N$_4$OS, 350.0; m/z found, 351.0 [M+H]$^+$. $^1$H NMR (500 MHz, CDCl$_3$) δ 9.41 (s, 1H), 8.15 (d, J=8.3 Hz, 1H), 7.49 (d, J=2.1 Hz, 1H), 7.32-7.28 (m, 2H), 7.15 (d, J=8.4 Hz, 1H), 2.67 (s, 3H).

Example 143: 6-(2-Cyclopropyl-5-methyl-imidazo[4,5-b]pyridin-3-yl)-3H-1,3-benzothiazol-2-one

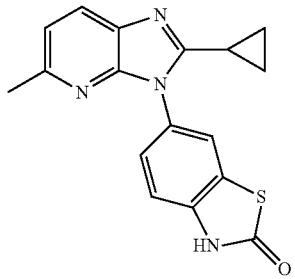 [SMILES: Cc1ccc2nc(C3CC3)n(-c3ccc4[nH]c(=O)sc4c3)c2n1]

The title compound was prepared in a manner analogous to Example 38. MS (ESI): mass calcd. for C$_{17}$H$_{14}$N$_4$OS, 322.1; m/z found, 323.0 [M+H]$^+$. $^1$H NMR (500 MHz, DMSO-d$_6$) δ 12.18 (s, 1H), 7.87-7.81 (m, 2H), 7.44 (dd, J=8.4, 2.2 Hz, 1H), 7.33 (d, J=8.3 Hz, 1H), 7.11 (d, J=8.2 Hz, 1H), 2.45 (s, 3H), 1.89-1.78 (m, 1H), 1.15-1.08 (m, 2H), 1.05-0.97 (m, 2H).

Example 144: 6-(2-Isopropyl-5-methyl-imidazo[4,5-b]pyridin-3-yl)-3H-1,3-benzothiazol-2-one

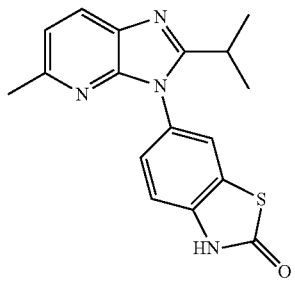

The title compound was prepared in a manner analogous to Example 38. MS (ESI): mass calcd. for C$_{17}$H$_{16}$N$_4$OS, 324.1; m/z found, 325.0 [M+H]$^+$. $^1$H NMR (500 MHz, DMSO-d$_6$) δ 12.19 (s, 1H), 7.92 (d, J=8.1 Hz, 1H), 7.80 (d, J=2.1 Hz, 1H), 7.38 (dd, J=8.4, 2.2 Hz, 1H), 7.31 (d, J=8.3 Hz, 1H), 7.14 (d, J=8.1 Hz, 1H), 3.07-2.97 (m, 1H), 2.45 (s, 3H), 1.23 (d, J=6.8 Hz, 6H).

Example 145: 6-(2-Cyclobutyl-5-methyl-imidazo[4,5-b]pyridin-3-yl)-3H-1,3-benzothiazol-2-one

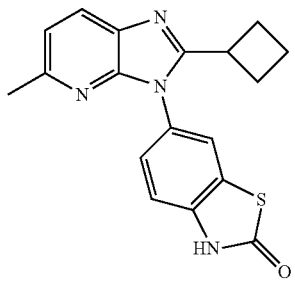

The title compound was prepared in a manner analogous to Example 38. MS (ESI): mass calcd. for $C_{18}H_{16}N_4OS$, 336.1; m/z found, 337.0 [M+H]$^+$. $^1$H NMR (500 MHz, DMSO-d$_6$) δ 12.17 (s, 1H), 7.94 (d, J=8.1 Hz, 1H), 7.72 (dd, J=1.9, 0.7 Hz, 1H), 7.34-7.26 (m, 2H), 7.14 (d, J=8.1 Hz, 1H), 3.63-3.52 (m, 1H), 2.45 (s, 3H), 2.44-2.37 (m, 2H), 2.15-2.05 (m, 2H), 2.00-1.90 (m, 1H), 1.90-1.80 (m, 1H).

Example 146: 5-[2-(1,1-Difluoroethyl)-5-methyl-imidazo[4,5-b]pyridin-3-yl]indolin-2-one

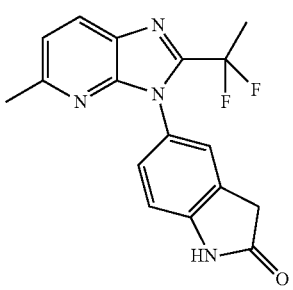 [SMILES: Cc1ccc2nc(C(C)(F)F)n(-c3ccc4c(c3)CC(=O)N4)c2n1]

The title compound was prepared in a manner analogous to Example 88. MS (ESI): mass calcd. for $C_{17}H_{14}F_2N_4O$, 328.1; m/z found, 329.0 [M+H]$^+$. $^1$H NMR (400 MHz, CDCl$_3$) δ 8.17 (s, 1H), 8.04 (d, J=8.2 Hz, 1H), 7.34-7.27 (m, 2H), 7.20 (d, J=8.3 Hz, 1H), 6.99-6.91 (m, 1H), 3.62 (s, 2H), 2.62 (s, 3H), 2.19 (t, J=18.9 Hz, 3H).

Example 147: 2-Cyclopropyl-3-(1H-indazol-5-yl)-5-methyl-imidazo[4,5-b]pyridine

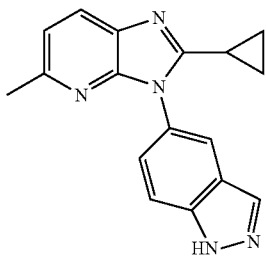 [SMILES: Cc1ccc2nc(C3CC3)n(-c3ccc4[nH]ncc4c3)c2n1]

The title compound was prepared in a manner analogous to Example 38. MS (ESI): mass calcd. for $C_{17}H_{15}N_5$, 289.1; m/z found, 290.1 [M+H]$^+$. $^1$H NMR (500 MHz, CDCl$_3$) δ 12.06 (s, 1H), 7.97 (t, J=1.0 Hz, 1H), 7.91 (d, J=8.1 Hz, 1H), 7.74 (d, J=1.9 Hz, 1H), 7.35-7.26 (m, 2H), 7.13 (d, J=8.2 Hz, 1H), 2.83-2.53 (m, 3H), 1.80 (s, 1H), 1.48-1.21 (m, 2H), 1.12-0.89 (m, 2H).

Example 148: 3-(1H-Indazol-5-yl)-2-isopropyl-5-methyl-imidazo[4,5-b]pyridine

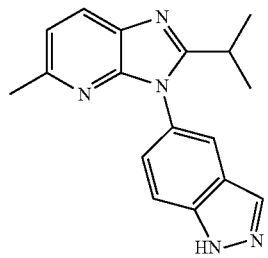 [SMILES: Cc1ccc2nc(C(C)C)n(-c3ccc4[nH]ncc4c3)c2n1]

The title compound was prepared in a manner analogous to Example 38. MS (ESI): mass calcd. for $C_{17}H_{17}N_5$, 291.1; m/z found, 292.1 [M+H]$^+$. $^1$H NMR (500 MHz, CDCl$_3$) δ 11.75 (s, 1H), 8.03-7.98 (m, 2H), 7.66 (dd, J=1.9, 0.8 Hz, 1H), 7.35 (d, J=8.5 Hz, 1H), 7.21-7.18 (m, 1H), 7.15 (d, J=8.2 Hz, 1H), 3.11-2.99 (m, 1H), 2.65 (s, 3H), 1.33 (d, J=6.9 Hz, 6H).

Example 149: 2-Cyclobutyl-3-(1H-indazol-5-yl)-5-methyl-imidazo[4,5-b]pyridine

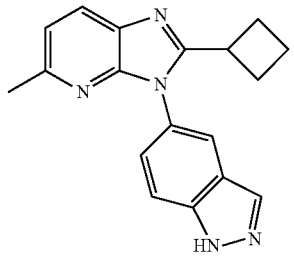 [SMILES: Cc1ccc2nc(C3CCC3)n(-c3ccc4[nH]ncc4c3)c2n1]

The title compound was prepared in a manner analogous to Example 38. MS (ESI): mass calcd. for $C_{18}H_{17}N_5$, 303.1; m/z found, 304.1 [M+H]$^+$. $^1$H NMR (500 MHz, CDCl$_3$) δ 12.29 (s, 1H), 8.04 (d, J=8.1 Hz, 1H), 7.93 (d, J=1.0 Hz, 1H), 7.56 (dd, J=1.9, 0.8 Hz, 1H), 7.22 (dd, J=8.7, 1.0 Hz, 1H), 7.17 (d, J=8.1 Hz, 1H), 7.08 (dd, J=8.7, 1.8 Hz, 1H), 3.60-3.50 (m, 1H), 2.69 (s, 3H), 2.66-2.52 (m, 2H), 2.15 (dddd, J=11.9, 9.5, 6.5, 4.2 Hz, 2H), 2.03-1.86 (m, 2H).

Example 150: 6-[2-(1,1-Difluoroethyl)-5-methyl-imidazo[4,5-b]pyridin-3-yl]-3H-1,3-benzothiazol-2-one

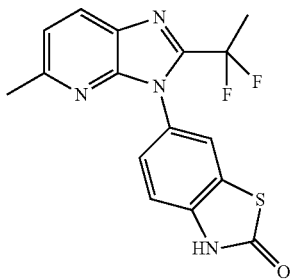

The title compound was prepared in a manner analogous to Example 88. MS (ESI): mass calcd. for $C_{16}H_{12}F_2N_4OS$, 346.1; m/z found, 347.0 [M+H]$^+$. $^1$H NMR (400 MHz, CDCl$_3$) δ 10.28 (s, 1H), 8.10 (d, J=8.2 Hz, 1H), 7.49 (d, J=2.0 Hz, 1H), 7.28-7.22 (m, 2H), 7.00 (d, J=8.5 Hz, 1H), 2.69 (s, 3H), 2.20 (t, J=18.9 Hz, 3H).

Example 151: 3-(1H-Indazol-5-yl)-5-methyl-2-(trifluoromethyl)imidazo[4,5-b]pyridine

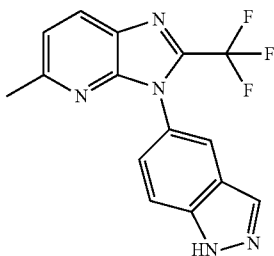 [SMILES: Cc1ccc2nc(C(F)(F)F)n(-c3ccc4[nH]ncc4c3)c2n1]

The title compound was prepared in a manner analogous to Example 88. MS (ESI): mass calcd. for $C_{15}H_{10}F_3N_5$, 317.1; m/z found, 318.0 [M+H]$^+$. $^1$H NMR (400 MHz, CDCl$_3$) δ 11.10 (s, 1H), 8.17 (d, J=8.3 Hz, 1H), 8.08 (d, J=1.0 Hz, 1H), 7.79 (d, J=1.8 Hz, 1H), 7.48-7.43 (m, 1H), 7.35-7.29 (m, 2H), 2.67 (s, 3H).

Example 152: 2-(1,1-Difluoroethyl)-3-(1H-indazol-5-yl)-5-methyl-imidazo[4,5-b]pyridine

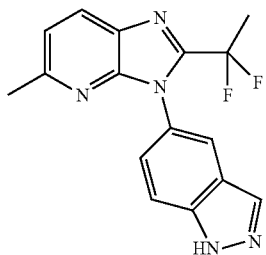 [SMILES: Cc1ccc2nc(C(C)(F)F)n(-c3ccc4[nH]ncc4c3)c2n1]

The title compound was prepared in a manner analogous to Example 88. MS (ESI): mass calcd. for $C_{16}H_{13}F_2N_5$, 313.1; m/z found, 314.0 [M+H]$^+$. $^1$H NMR (400 MHz, CDCl$_3$) δ 11.18 (s, 1H), 8.10 (d, J=8.2 Hz, 1H), 8.03 (d, J=1.0 Hz, 1H), 7.80-7.76 (m, 1H), 7.41-7.37 (m, 1H), 7.34-7.30 (m, 1H), 7.25 (d, J=8.4 Hz, 1H), 2.66 (s, 3H), 2.17 (t, J=18.8 Hz, 3H).

Example 153: 5-[5-(Difluoromethyl)-2-(trifluoromethyl)imidazo[4,5-b]pyridin-3-yl]indolin-2-one

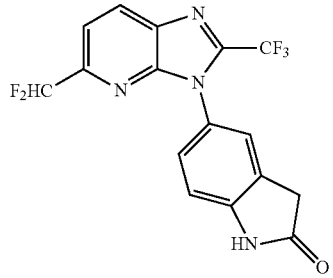 [SMILES: O=C1Cc2cc(-n3c(C(F)(F)F)nc4ccc(C(F)F)nc43)ccc2N1]

A solution of 5-((3-amino-6-(difluoromethyl)pyridin-2-yl)amino)indolin-2-one (Intermediate 48, product from Step G., 0.10 g, 0.34 mmol) in TFA (0.40 mL, 5.2 mmol) was stirred at 80° C. for 16 h. The reaction was concentrated in vacuo, diluted with sat. aq. NaHCO$_3$ (5 mL), and extracted with EtOAc (5 mL×3). The organic layers were combined, dried (Na$_2$SO$_4$), filtered, and concentrated in vacuo. Purification (FCC, SiO$_2$, EtOAc/hexanes) afforded the title compound (19 mg, 15%). MS (ESI): mass calcd. for $C_{16}H_9F_5N_4O$, 368.1; m/z found, 369.0 [M+H]$^+$. $^1$H NMR (500 MHz, CDCl$_3$) δ 8.39 (d, J=8.4 Hz, 1H), 8.21 (s, 1H), 7.78 (d, J=8.4 Hz, 1H), 7.34-7.28 (m, 2H), 7.07 (d, J=8.9 Hz, 1H), 6.64 (t, J=55.2 Hz, 1H), 3.68 (s, 2H).

Example 154: 5-[2-(1-Difluoroethyl)-5-(difluoromethyl)imidazo[4,5-b]pyridin-3-yl]indolin-2-one

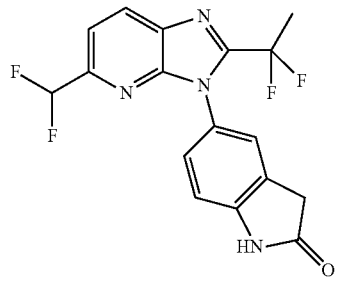 [SMILES: CC(F)(F)c1nc2ccc(C(F)F)nc2n1-c1ccc2c(c1)CC(=O)N2]

Example 154 was prepared in a manner analogous to Example 153. MS (ESI): mass calcd. for $C_{17}H_{12}F_4N_4O$, 364.1; m/z found, 365.0 [M+H]$^+$. $^1$H NMR (500 MHz, CDCl$_3$) δ 8.30 (d, J=8.3 Hz, 1H), 7.72 (d, J=8.3 Hz, 2H), 7.37-7.29 (m, 2H), 7.02 (d, J=8.9 Hz, 1H), 6.63 (t, J=55.3 Hz, 1H), 3.66 (s, 2H), 2.21 (t, J=19.0 Hz, 3H).

Example 155: 2-(4-Fluorophenyl)-3-(1H-indol-5-yl)-5-methylsulfanyl-imidazo[4,5-b]pyridine

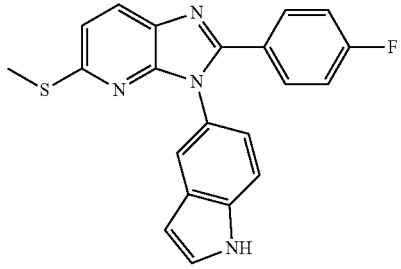 [SMILES: CSc1ccc2nc(-c3ccc(F)cc3)n(-c3ccc4[nH]ccc4c3)c2n1]

Example 155 was prepared in a manner analogous to Example 38. MS (ESI): mass calcd. for $C_{21}H_{15}FN_4S$, 374.1; m/z found, 375.0 [M+H]$^+$. $^1$H NMR (400 MHz, DMSO-d$_6$) δ 2.41 (s, 3H) 6.51 (t, J=2.1 Hz, 1H) 7.08 (dd, J=8.6, 2.1 Hz, 1H) 7.14-7.21 (m, 2H) 7.24 (d, J=8.6 Hz, 1H) 7.49 (t, J=2.8 Hz, 1H) 7.53 (d, J=8.6 Hz, 1H) 7.55-7.60 (m, 2H) 7.62 (d, J=2.1 Hz, 1H) 8.06 (d, J=8.6 Hz, 1H) 11.42 (br s, 1H).

Example 156: 3-(1H-Indazol-5-yl)-2-phenyl-imidazo[4,5-b]pyridin-5-ol

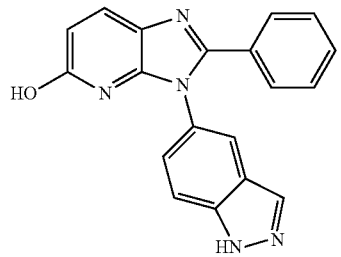 [SMILES: Oc1ccc2nc(-c3ccccc3)n(-c3ccc4[nH]ncc4c3)c2n1]

A solution of 6-chloro-5-nitropyridin-2(1H)-one (Intermediate 4, 150 mg, 0.86 mmol) and 1H-indazol-5-amine (115 mg, 0.86 mmol) in DMF (2.5 mL) was heated at 100° C. for 3 h. Benzaldehyde (90 mg, 0.86 mmol) was added to the mixture and the reaction was let stir for 30 min followed by addition of sodium dithionite (150 mg, 0.86 mmol). After 12 h at 100° C. the reaction was allowed to cool, diluted with EtOAc (100 mL), and washed with H$_2$O (50 mL×3). The organic layer was dried (Na$_2$SO$_4$), filtered, and concentrated in vacuo. Purification (FCC, SiO$_2$, EtOAc/hexanes) afforded the title compound (25 mg, 10%). MS (ESI): mass calcd. for $C_{19}H_{13}N_5O$, 327.1; m/z found, 328.0 [M+H]$^+$. $^1$H NMR (500 MHz, DMSO-d$_6$) δ 13.33 (s, 1H), 10.76 (s, 1H), 8.16 (s, 1H), 8.03 (d, J=8.5 Hz, 1H), 7.90 (dd, J=1.9, 0.7 Hz, 1H), 7.66 (d, J=8.7 Hz, 1H), 7.52-7.48 (m, 2H), 7.36-7.27 (m, 4H), 6.62 (d, J=8.5 Hz, 1H).

Example 157: 2-Cyclopropyl-3-(1H-indazol-5-yl)-5-methoxy-imidazo[4,5-b]pyridine

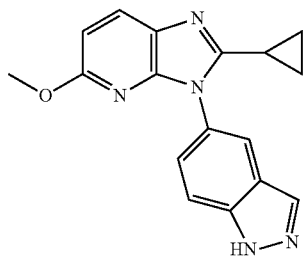 [SMILES: COc1ccc2nc(C3CC3)n(-c3ccc4[nH]ncc4c3)c2n1]

Step A: 2-Cyclopropyl-3-(1-((2-(trimethylsilyl) ethoxy)methyl)-1H-indazol-5-yl)-3H-imidazo[4,5-b] pyridin-5(4H)-one To a solution of 5-amino-6-((1-((2-(trimethylsilyl)ethoxy) methyl)-1H-indazol-5-yl)amino)pyridin-2(1H)-one (Intermediate 49, 350 mg, 0.94 mmol) in DMF (12.0 mL) was added cyclopropanecarbaldehyde (0.24 mL, 1.8 mmol) and sodium dithionite (538 mg, 2.83 mmol). The resulting mixture was heated 85° C. for 1 hr. The reaction was allowed to cool, diluted with EtOAc and washed with H$_2$O. The organic layer was dried (Na$_2$SO$_4$) and concentrated in vacuo. The resulting residue was triturated in DCM to give the title compound (225 mg, 56%). MS (ESI): mass calcd. for $C_{22}H_{27}N_5O_2Si$, 421.6; m/z found, 422.6 [M+H]$^+$. $^1$H NMR (400 MHz, DMSO-d$_6$) δ 10.57 (s, 1H), 8.40-8.29 (m, 1H), 8.14-8.06 (m, 1H), 8.06-7.98 (m, 1H), 7.89 (d, J=8.5 Hz, 1H), 7.64 (dt, J=8.8, 2.8 Hz, 1H), 6.56 (d, J=8.5 Hz, 1H), 5.91 (s, 2H), 3.71-3.58 (m, 2H), 1.83 (ddd, J=13.0, 6.8, 3.3 Hz, 1H), 1.14 (ddd, J=6.2, 3.8, 2.1 Hz, 2H), 0.99 (ddd, J=8.3, 6.3, 3.4 Hz, 2H), 0.96-0.86 (m, 2H), 0.06-0.01 (s, 9H).

Step B: 2-Cyclopropyl-5-methoxy-3-(1-((2-(trimethylsilyl)ethoxy)methyl)-1H-indazol-5-yl)-3H-imidazo[4,5-b]pyridine A solution of 2-cyclopropyl-3-(1-((2-(trimethylsilyl) ethoxy)methyl)-1H-indazol-5-yl)-3H-imidazo[4,5-b]pyridin-5(4H)-one (215 mg, 0.51 mmol) in DMF (6.0 mL) was added lithium hydride (10.6 mg, 1.53 mmol) portionwise at 0° C. The mixture was stirred at this temperature for 30 minutes. Methyl iodide (0.07 mL, 1.12 mmol) was added. The resulting mixture was stirred at 0° C. for another 10 minutes, and then warmed to rt and stirred for 3 h. The reaction mixture was quenched with sat aq. NH$_4$Cl and diluted with EtOAc and water. The combined organic layers were dried (Na$_2$SO$_4$), filtered, and concentrated under reduced pressure. Purification (FCC, SiO$_2$, Hex/EtOAc) afforded the title compound (72 mg, 32%). MS (ESI): mass calcd. for $C_{23}H_{29}N_5O_2Si$, 435.6 m/z found, 436.6 [M+H]$^+$. $^1$H NMR (400 MHz, DMSO-d$_6$) δ 8.38 (d, J=0.9 Hz, 1H), 8.14 (dd, J=2.0, 0.7 Hz, 1H), 8.07 (dt, J=8.8, 0.9 Hz, 1H), 8.00 (d, J=8.6 Hz, 1H), 7.72 (dd, J=8.8, 1.9 Hz, 1H), 6.78 (d, J=8.5 Hz, 1H), 5.94 (s, 2H), 3.79 (s, 3H), 3.72-3.63 (m, 2H), 1.94 (tt, J=8.2, 4.8 Hz, 1H), 1.24-1.15 (m, 2H), 1.06 (m, J=8.2, 6.6, 3.7 Hz, 2H), 1.00-0.86 (m, 2H), 0.03--0.04 (m, 9H).

Step C: 2-Cyclopropyl-3-(1H-indazol-5-yl)-5-methoxy-imidazo[4,5-b]pyridine

A solution of 2-cyclopropyl-5-methoxy-3-(1-((2-(trimethylsilyl)ethoxy)methyl)-1H-indazol-5-yl)-3H-imidazo[4,5-b] pyridine (70 mg, 0.16 mmol) in DCM (1.0 mL) was added TFA (1.0 mL) and the mixture was stirred for 30 minutes. The solvent was concentrated in vacuo to give the intermediate (5-(2-cyclopropyl-5-methoxy-3H-imidazo[4,5-b]pyridin-3-yl)-1H-indazol-1-yl)methanol which was further dissolved in 2M NH$_3$ in methanol. After stirring the mixture for another 30 minutes, the solvent was concentrated in vacuo and the crude residue was purified by reverse-phase HPLC using a XBridge $^{18}$C column (5 m, 100×4.6 mm), mobile phase of 10-100% ACN in 20 mM NH$_4$OH, to afford the title compound as white solid (24 mg, 48%). MS (ESI): mass calcd. for $C_{17}H_{15}N_5O$, 305.1; m/z found, 306.0 [M+H]$^+$. $^1$H NMR (400 MHz, DMSO-d$_6$) δ 13.41 (br s, 1H), 8.22 (d, J=1.1 Hz, 1H), 8.01-7.98 (m, 1H), 7.89 (d, J=8.5 Hz, 1H), 7.79-7.74 (m, 1H), 7.50 (dd, J=8.8, 1.9 Hz, 1H), 6.67 (d, J=8.5 Hz, 1H), 3.69 (s, 3H), 1.91-1.79 (m, 1H), 1.13-1.07 (m, 2H), 1.00-0.92 (m, 2H).

Example 158: 6-[2-Ethyl-5-(trifluoromethyl)imidazo[4,5-b]pyridin-3-yl]-3H-1,3-benzoxazol-2-one

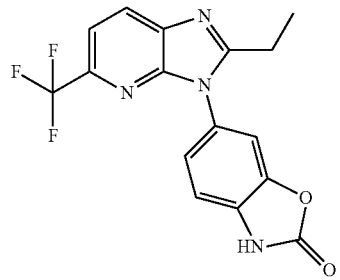

Step A: N-(2-((2-Oxo-2,3-dihydrobenzo[d]oxazol-6-yl)amino)-6-(trifluoromethyl)pyridin-3-yl)tetrahydro-2H-pyran-4-carboxamide A solution of 6-((3-amino-6-(trifluoromethyl)pyridin-2-yl)amino)benzo[d]oxazol-2(3H)-one (Intermediate 58, 50 mg, 0.16 mmol) and Et₃N (0.045 mmol, 0.32 mmol) in DCM at 0° C. was treated with tetrahydro-2H-pyran-4-carbonyl chloride (26 mg, 0.18 mmol) and the reaction stirred at rt for 2 h. The mixture was washed with water, and the organic layer dried (MgSO₄). Purification (FCC, SiO₂, with a gradient of 0 to 45% ethyl acetate/hexanes) afforded the title compound (32 mg, 46%).

Step B: 6-[2-Ethyl-5-(trifluoromethyl)imidazo[4,5-b]pyridin-3-yl]-3H-1,3-benzoxazol-2-one A solution of N-(2-((2-oxo-2,3-dihydrobenzo[d]oxazol-6-yl)amino)-6-(trifluoromethyl)pyridin-3-yl)tetrahydro-2H-pyran-4-carboxamide (321 mg, 0.76 mmol) in propionic acid (1 mL) was heated to 100° C. for 1 h. To the reaction mixture was added HCl (0.0046 mL, 0.15 mmol) and the reaction was further heated at 100° C. for 1 h. The reaction was quenched with NaHCO₃ and extracted with DCM. The organic layer was separated, dried (MgSO₄), filtered and the solvents evaporated in vacuo. Purification (reverse phase chromatography, 75% [25 mM NH₄HCO₃]-25% [ACN: MeOH 1:1] to 38% [25 mM NH₄HCO₃]-62% [ACN: MeOH 1:1]) afforded the title compound instead of the desired pyran (3.26 mg, 1.2%). MS (ESI): mass calcd. for $C_{16}H_{11}F_3N_4O_2$, 348.1; m/z found, 349.0 [M+H]⁺. ¹H NMR (300 MHz, DMSO-d₆): δ 11.99 (br s, 1H), 8.31 (d, J=8.2 Hz, 1H), 7.78 (d, J=8.2 Hz, 1H), 7.63 (s, 1H), 7.41-7.17 (m, 2H), 2.78 (d, J=7.5 Hz, 2H), 1.27 (t, J=7.5 Hz, 3H).

Example 159: 6-[2-Isopropyl-5-(trifluoromethyl)imidazo[4,5-b]pyridin-3-yl]-3H-1,3-benzoxazol-2-one

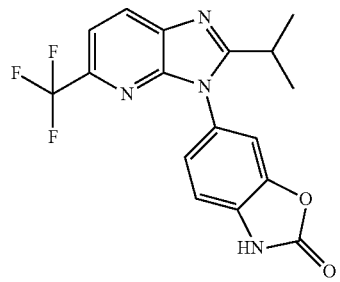

A solution of 6-((3-amino-6-(trifluoromethyl)pyridin-2-yl)amino)benzo[d]oxazol-2(3H)-one (Intermediate 58, 100 mg, 0.32 mmol), and isobutyryl chloride (0.037 mL, 0.35 mmol) in toluene (4 mL) was heated to 100° C. for 2 h. The reaction was treated with HCl (15 µL), and heated at 120° C. for 2 h, followed by the addition of p-toluenesulfonic acid (12 mg, 0.064 mmol) and heated an additional 2 h at 120° C. The reaction was cooled to rt and washed with water. The organics were combined, dried (MgSO₄), filtered and concentrated under reduced pressure. Purification (FCC, SiO₂, with a gradient of 0 to 45% ethyl acetate/hexanes) afforded the title compound (30 mg, 25%). MS (ESI): mass calcd. for $C_{17}H_{13}F_3N_4O_2$, 362.1; m/z found, 363.0 [M+H]⁺. ¹H NMR (300 MHz, DMSO-d₆) δ 12.00 (br s, 1H), 8.32 (d, J=8.2 Hz, 1H), 7.78 (d, J=8.2 Hz, 1H), 7.68 (d, J=1.5 Hz, 1H), 7.37 (dd, J=8.2, 1.7 Hz, 1H), 7.31 (d, J=8.2 Hz, 1H), 3.14-2.99 (m, 1H), 1.26 (d, J=6.8 Hz, 6H).

Example 160: 6-[2-Tetrahydropyran-4-yl-5-(trifluoromethyl)imidazo[4,5-b]pyridin-3-yl]-3H-1,3-benzoxazol-2-one

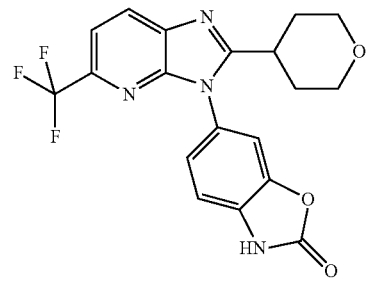 [SMILES: O=c1[nH]c2ccc(-n3c(C4CCOCC4)nc4ccc(C(F)(F)F)nc43)cc2o1]

The title compound was prepared in a manner analogous to Example 159. MS (ESI): mass calcd. for $C_{19}H_{15}F_3N_4O_3$, 404.1; m/z found, 405.0 [M+H]⁺. ¹H NMR (300 MHz, DMSO-d₆) δ 12.01 (br s, 1H), 8.38 (d, J=8.2 Hz, 1H), 7.84 (d, J=8.2 Hz, 1H), 7.68 (d, J=1.5 Hz, 1H), 7.38 (dd, J=8.2, 1.7 Hz, 1H), 7.31 (d, J=8.2 Hz, 1H), 3.99-3.63 (m, 2H), 3.30-3.23 (m, 2H), 3.21-2.82 (m, 1H), 2.03-1.82 (m, 2H), 1.82-1.61 (m, 2H).

Example 161: (R/S)-6-[2-Tetrahydrofuran-3-yl-5-(trifluoromethyl)imidazo[4,5-b]pyridin-3-yl]-3H-1,3-benzoxazol-2-one

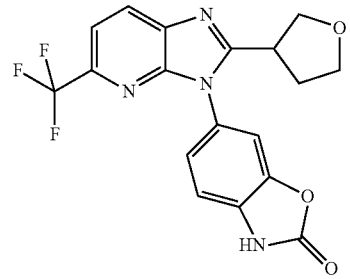 [SMILES: O=c1[nH]c2ccc(-n3c(C4CCOC4)nc4ccc(C(F)(F)F)nc43)cc2o1]

The title compound was prepared in a manner analogous to Example 159. MS (ESI): mass calcd. for $C_{18}H_{13}F_3N_4O_3$, 390.1; m/z found, 391.0 [M+H]$^+$. $^1$H NMR (300 MHz, DMSO-d$_6$) δ 12.01 (br s, 1H), 8.34 (d, J=8.2 Hz, 1H), 7.80 (d, J=8.2 Hz, 1H), 7.67 (s, 1H), 7.38 (d, J=8.3 Hz, 1H), 7.32 (d, J=8.2 Hz, 1H), 4.03-3.93 (m, 1H), 3.92-3.81 (m, 2H), 3.80-3.66 (m, 1H), 3.65-3.50 (m, 1H), 2.40-2.21 (m, 1H), 2.20-2.01 (m, 1H).

Example 162: 6-[2-(Ethoxymethyl)-5-(trifluoromethyl)imidazo[4,5-b]pyridin-3-yl]-3H-1,3-benzoxazol-2-one

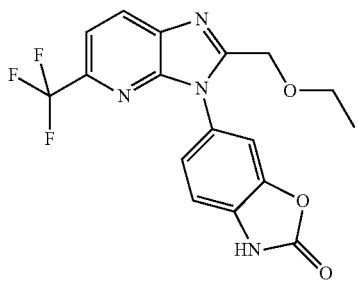 [SMILES: CCOCc1nc2ccc(C(F)(F)F)nc2n1-c1ccc2[nH]c(=O)oc2c1]

The title compound was prepared in a manner analogous to Example 159. MS (ESI): mass calcd. for $C_{17}H_{13}F_3N_4O_3$, 378.1; m/z found, 379.0 [M+H]$^+$. $^1$H NMR (300 MHz, DMSO-d$_6$) δ 12.00 (s, 1H), 8.41 (d, J=8.1 Hz, 1H), 7.84 (d, J=8.1 Hz, 1H), 7.64 (d, J=1.6 Hz, 1H), 7.38 (dd, J=8.3, 1.8 Hz, 1H), 7.31 (d, J=8.2 Hz, 1H), 4.65 (s, 2H), 3.42 (q, J=7.0 Hz, 2H), 1.00 (t, J=7.0 Hz, 3H).

Example 163: 6-[2-tert-Butyl-5-(trifluoromethyl)imidazo[4,5-b]pyridin-3-yl]-3H-1,3-benzoxazol-2-one

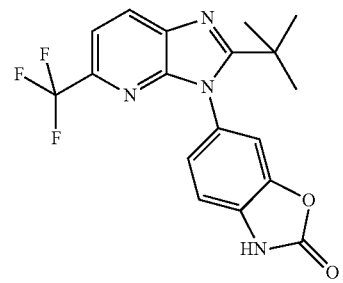 [SMILES: CC(C)(C)c1nc2ccc(C(F)(F)F)nc2n1-c1ccc2[nH]c(=O)oc2c1]

The title compound was prepared in a manner analogous to Example 159. MS (ESI): mass calcd. for $C_{18}H_{15}F_3N_4O_2$, 376.1; m/z found, 377.0 [M+H]$^+$. $^1$H NMR (300 MHz, DMSO-d$_6$) δ 12.04 (s, 1H), 8.29 (d, J=8.2 Hz, 1H), 7.77 (d, J=8.2 Hz, 1H), 7.67 (d, J=1.4 Hz, 1H), 7.36 (dd, J=8.2, 1.6 Hz, 1H), 7.28 (d, J=8.2 Hz, 1H), 1.30 (s, 9H).

Example 164: 5-[2-(2-Fluoro-4-pyridyl)-5-(trifluoromethyl)imidazo[4,5-b]pyridin-3-yl]indolin-2-one

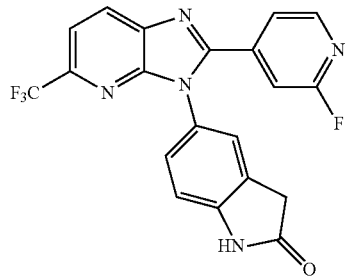 [SMILES: O=C1Cc2cc(-n3c(-c4ccnc(F)c4)nc4ccc(C(F)(F)F)nc43)ccc2N1]

A mixture of 5-((3-amino-6-(trifluoromethyl)pyridin-2-yl)amino)indolin-2-one (Intermediate 46, 308 mg, 1 mmol), 2-fluoroisonicotinaldehyde (150 mg, 1.2 mmol), and copper (II) acetate (90.7 mg, 0.5 mmol) in 5 mL of AcOH was stirred at rt for 15 h in a loosely capped vial. The vial cap was removed and the reaction was stirred in open air for 15 h. The crude mixture was filtered and purified (semi-prep HPLC with TFA (0.05%) buffered water and ACN). The purified product was re-dissolved in EtOAc (20 mL), washed with NaHCO$_3$ (sat. 2×20 mL), then water (20 mL). The organics were dried (Na$_2$SO$_4$), filtered, and concentrated under reduced pressure to afford the title compound as a brown solid (40 mg, 10%). MS (ESI): mass calcd. for $C_{20}H_{11}F_4N_5O$, 413.1; m/z found, 414.0 [M+H]$^+$. $^1$H NMR (400 MHz, CD$_3$OD) δ 8.41 (d, J=8.2 Hz, 1H), 8.26 (d, J=5.0 Hz, 1H), 7.85 (d, J=8.3 Hz, 1H), 7.52-7.46 (m, 1H), 7.38 (d, J=23.3 Hz, 2H), 7.30 (d, J=8.4 Hz, 1H), 7.08 (d, J=8.3 Hz, 1H), 3.65 (s, 2H).

Example 165: 2-(2-Fluoro-4-pyridyl)-3-(1H-indazol-5-yl)-5-(trifluoromethyl)imidazo[4,5-b]pyridine

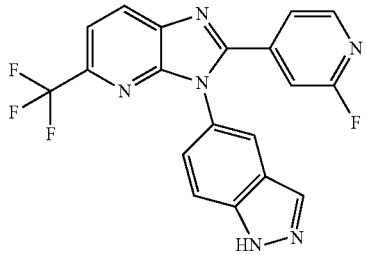 [SMILES: Fc1cc(-c2nc3ccc(C(F)(F)F)nc3n2-c2ccc3[nH]ncc3c2)ccn1]

The title compound was prepared in a manner analogous to Example 1. $^1$H NMR (400 MHz, CD$_3$OD) δ 8.44 (d, J=8.2 Hz, 1H), 8.21-8.17 (m, 2H), 7.96 (dd, J=2.0, 0.8 Hz, 1H), 7.87 (d, J=8.3 Hz, 1H), 7.76 (dt, J=8.7, 0.9 Hz, 1H), 7.45 (dd, J=8.8, 1.9 Hz, 1H), 7.42 (dt, J=5.3, 1.6 Hz, 1H), 7.32-7.29 (m, 1H).

Example 166: 5-[2-(3-Fluorocyclobutyl)-5-(trifluoromethyl)imidazo[4,5-b]pyridin-3-yl]indolin-2-one

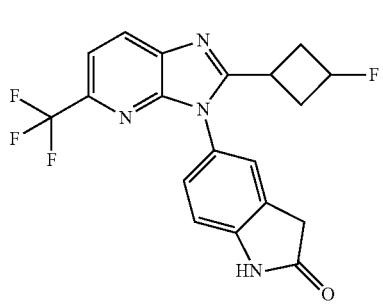 [SMILES: O=C1Cc2cc(-n3c(C4CC(F)C4)nc4ccc(C(F)(F)F)nc43)ccc2N1]

Step A: 3-Fluorocyclobutanecarbonyl chloride

To a solution of 3-fluorocyclobutanecarboxylic acid (118 mg, 1 mmol) in DMF (5 μL) and DCM (1 mL) was added oxalyl dichloride (127 mg, 1 mmol) dropwise at rt. The reaction mixture was stirred for 3 h. The crude 3-fluorocyclobutanecarbonyl chloride solution was used directly without further purification in the next step.

Step B: 3-Fluoro-N-(2-((2-oxoindolin-5-yl)amino)-6-(trifluoromethyl)pyridin-3-yl)cyclobutanecarboxamide A cooled (0° C.) solution of 5-((3-amino-6-(trifluoromethyl)pyridin-2-yl)amino)indolin-2-one (Intermediate 46, 285 mg, 0.92 mmol) in THF (4 mL) and Et$_3$N (0.51 mL, 3.7 mmol) was added dropwise to 3-fluorocyclobutanecarbonyl chloride. The reaction was stirred at 0° C. for 2 h. Solvent was removed under reduced pressure. Purification (FCC, SiO$_2$, hexane/EtOAc) afforded the title compound (105 mg, 28%). $^1$H NMR (400 MHz, CD$_3$OD) δ 7.85 (d, J=7.8 Hz, 1H), 7.57 (d, J=2.1 Hz, 1H), 7.45 (dd, J=8.5, 2.2 Hz, 1H), 7.13 (d, J=7.9 Hz, 1H), 6.83 (d, J=8.4 Hz, 1H), 5.38-5.11 (m, 1H), 3.53 (s, 2H), 3.42-3.35 (m, 1H), 2.75-2.61 (m, 2H), 2.62-2.44 (m, 2H).

Step C: 5-[2-(3-Fluorocyclobutyl)-5-(trifluoromethyl)imidazo[4,5-b]pyridin-3-yl]indolin-2-one A solution of 3-fluoro-N-(2-((2-oxoindolin-5-yl)amino)-6-(trifluoromethyl)pyridin-3-yl)cyclobutanecarboxamide (80 mg, 0.19 mmol) in acetic acid (8 mL) was heated in a microwave reactor at 120° C. for 20 min. The reaction mixture was concentrated under reduced pressure. The reaction mixture was diluted with EtOAc (20 mL) and washed with NaHCO$_3$ (sat. 3×20 mL). The organics were dried (Na$_2$SO$_4$), filtered, and concentrated under reduced pressure. Purification (FCC, SiO$_2$, hexane/EtOAc, 5% to 35%) afforded the title compound (35 mg, 46%). $^1$H NMR (400 MHz, CDCl$_3$) δ 9.10 (s, 1H), 8.20 (d, J=8.2 Hz, 1H), 7.68 (d, J=8.3 Hz, 1H), 7.21 (s, 1H), 7.15 (dd, J=8.1, 2.1 Hz, 1H), 6.98 (d, J=8.2 Hz, 1H), 5.10-4.85 (m, 1H), 3.59 (s, 2H), 3.10-2.99 (m, 1H), 2.91-2.74 (m, 2H), 2.74-2.62 (m, 2H).

Example 167: (R)-3-(1H-Indazol-5-yl)-2-sec-butyl-5-(trifluoromethyl)imidazo[4,5-b]pyridine

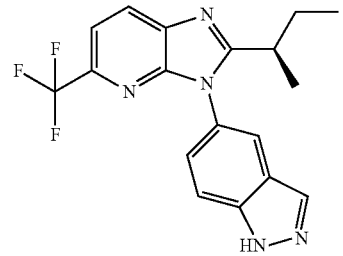 [SMILES: CC[C@@H](C)c1nc2ccc(C(F)(F)F)nc2n1-c1ccc2[nH]ncc2c1]

Resolved enantiomer of Example 102. MS (ESI): mass calcd. for C$_{18}$H$_{16}$F$_3$N$_5$, 359.1; m/z found, 360.0 [M+H]$^+$. $^1$H NMR (400 MHz, CD$_3$OD) δ 8.25-8.19 (m, 2H), 7.93 (d, J=1.7 Hz, 1H), 7.80 (d, J=8.7 Hz, 1H), 7.75 (d, J=8.3 Hz, 1H), 7.44-7.39 (m, 1H), 3.03-2.92 (m, 1H), 1.99-1.87 (m, 1H), 1.75-1.64 (m, 1H), 1.37 (d, J=6.9 Hz, 3H), 0.87-0.79 (m, 3H).

Example 168: (S)-3-(1H-Indazol-5-yl)-2-sec-butyl-5-(trifluoromethyl)imidazo[4,5-b]pyridine

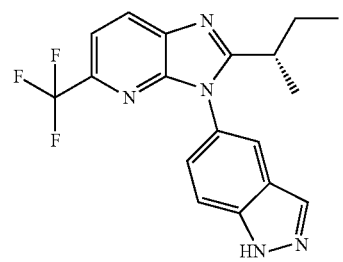 [SMILES: CC[C@H](C)c1nc2ccc(C(F)(F)F)nc2n1-c1ccc2[nH]ncc2c1]

Resolved enantiomer of Example 102. MS (ESI): mass calcd. for C$_{18}$H$_{16}$F$_3$N$_5$, 359.1; m/z found, 360.0 [M+H]$^+$. $^1$H NMR (400 MHz, CD$_3$OD) δ 8.25-8.20 (m, 2H), 7.95-7.91 (m, 1H), 7.80 (d, J=8.8 Hz, 1H), 7.75 (d, J=8.3 Hz, 1H), 7.44-7.39 (m, 1H), 3.04-2.91 (m, 1H), 1.99-1.86 (m, 1H), 1.75-1.63 (m, 1H), 1.37 (d, J=6.8 Hz, 3H), 0.88-0.79 (m, 3H).

Example 169: 2-(5-Fluoro-2-pyridyl)-3-(1H-indazol-5-yl)-5-(trifluoromethyl)imidazo[4,5-b]pyridine

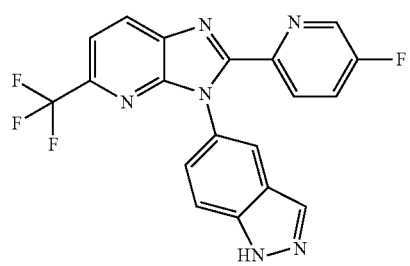 [SMILES: Fc1ccc(-c2nc3ccc(C(F)(F)F)nc3n2-c2ccc3[nH]ncc3c2)nc1]

The title compound was prepared in a manner analogous to Example 1. MS (ESI): mass calcd. for C$_{19}$H$_{10}$F$_4$N$_6$, 398.1; m/z found, 399.0 [M+H]$^+$. $^1$H NMR (400 MHz, CD$_3$OD) δ 8.39 (d, J=8.2 Hz, 1H), 8.29 (d, J=2.9 Hz, 1H), 8.18 (dd, J=8.8, 4.4 Hz, 1H), 8.13 (s, 1H), 7.87-7.81 (m, 2H), 7.76-7.69 (m, 1H), 7.66 (d, J=8.8 Hz, 1H), 7.37 (dd, J=8.8, 1.9 Hz, 1H).

Example 170: 3-(1H-Indazol-5-yl)-5-isopropyl-2-(trifluoromethyl)imidazo[4,5-b]pyridine

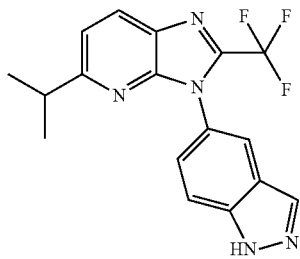 [SMILES: CC(C)c1ccc2nc(C(F)(F)F)n(-c3ccc4[nH]ncc4c3)c2n1]

The title compound was prepared in a manner analogous to Example 125. MS (ESI): mass calcd. for C$_{17}$H$_{14}$F$_3$N$_5$, 345.1; m/z found, 346.0 [M+H]$^+$. $^1$H NMR (400 MHz, CD$_3$OD) δ 8.24-8.17 (m, 2H), 7.98 (d, J=1.8 Hz, 1H), 7.79-7.74 (m, 1H), 7.47 (dd, J=8.9, 1.9 Hz, 1H), 7.43 (d, J=8.5 Hz, 1H), 3.16-3.06 (m, 1H), 1.25 (s, 3H), 1.23 (s, 3H).

Example 171: 5-tert-Butyl-3-(1H-indazol-5-yl)-2-(trifluoromethyl)imidazo[4,5-b]pyridine

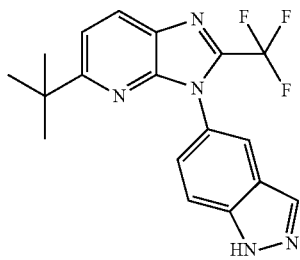 [SMILES: CC(C)(C)c1ccc2nc(C(F)(F)F)n(-c3ccc4[nH]ncc4c3)c2n1]

The title compound was prepared in a manner analogous to Example 125. MS (ESI): mass calcd. for C$_{18}$H$_{16}$F$_3$N$_5$, 359.1; m/z found, 360.0 [M+H]$^+$. $^1$H NMR (400 MHz, CD$_3$OD) δ 8.22 (d, J=1.0 Hz, 1H), 8.18 (d, J=8.6 Hz, 1H), 7.97 (d, J=1.8 Hz, 1H), 7.78-7.74 (m, 1H), 7.61 (d, J=8.6 Hz, 1H), 7.50-7.45 (m, 1H), 1.30 (s, 9H).

Example 172: 3-(1H-Indazol-5-yl)-N-isopropyl-5-(trifluoromethyl)imidazo[4,5-b]pyridine-2-carboxamide

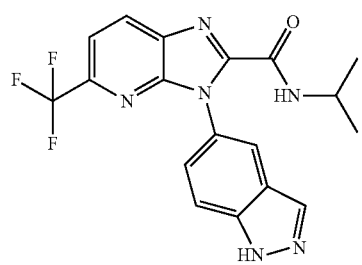 [SMILES: CC(C)NC(=O)c1nc2ccc(C(F)(F)F)nc2n1-c1ccc2[nH]ncc2c1]

The title compound was prepared in a manner analogous to Example 128. MS (ESI): mass calcd. for C$_{18}$H$_{15}$F$_3$N$_6$O, 388.1; m/z found, 389.0 [M+H]$^+$. $^1$H NMR (400 MHz, CD$_3$OD) δ 8.42 (d, J=8.3 Hz, 1H), 8.18 (d, J=1.1 Hz, 1H), 7.92-7.89 (m, 1H), 7.85 (d, J=8.4 Hz, 1H), 7.74-7.69 (m, 1H), 7.46 (dd, J=8.8, 1.9 Hz, 1H), 4.11-4.00 (m, 1H), 1.21 (s, 3H), 1.19 (s, 3H).

Example 173: [3-(1H-Indazol-5-yl)-5-(trifluoromethyl)imidazo[4,5-b]pyridin-2-yl]-pyrrolidin-1-yl-methanone

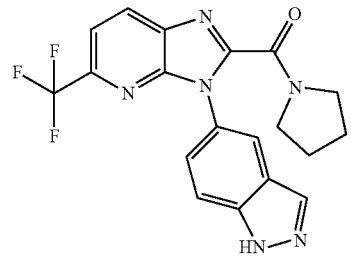 [SMILES: O=C(c1nc2ccc(C(F)(F)F)nc2n1-c1ccc2[nH]ncc2c1)N1CCCC1]

The title compound was prepared in a manner analogous to Example 128. MS (ESI): mass calcd. for C$_{19}$H$_{15}$F$_3$N$_6$O, 400.1; m/z found, 401.0 [M+H]$^+$. $^1$H NMR (500 MHz, CD$_3$OD) δ 8.44-8.40 (m, 1H), 8.19 (d, J=1.1 Hz, 1H), 7.99-7.96 (m, 1H), 7.86 (d, J=8.5 Hz, 1H), 7.76-7.72 (m, 1H), 7.55-7.51 (m, 1H), 3.67 (t, J=6.8 Hz, 2H), 3.52-3.46 (m, 2H), 1.96-1.88 (m, 4H).

Example 174: 2-(4-Fluorophenyl)-3-(1H-indol-5-yl)imidazo[4,5-b]pyridine

The title compound was prepared in a manner analogous to Example 33. MS (ESI): mass calcd. for C$_{20}$H$_{13}$FN$_4$, 328.1; m/z found, 329.1 [M+H]$^+$. $^1$H NMR (500 MHz, CDCl$_3$) δ 8.51 (s, 1H), 8.38 (dd, J=4.8, 1.5 Hz, 1H), 8.15 (dd, J=8.0, 1.5 Hz, 1H), 7.69-7.62 (m, 3H), 7.50-7.45 (m, 1H), 7.33-7.27 (m, 2H), 7.12 (dd, J=8.5, 2.0 Hz, 1H), 7.01-6.93 (m, 2H), 6.62-6.57 (m, 1H).

Example 175: 4-[2-(4-Fluorophenyl)-3-(1H-indol-5-yl)imidazo[4,5-b]pyridin-7-yl]morpholine

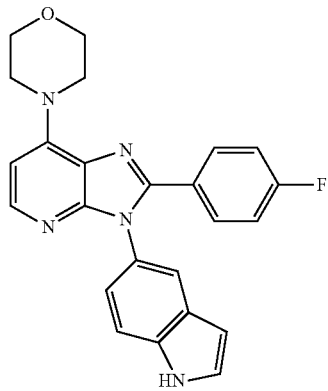 [SMILES: Fc1ccc(-c2nc3c(N4CCOCC4)ccnc3n2-c2ccc3[nH]ccc3c2)cc1]

The title compound was prepared in a manner analogous to Example 62. MS (ESI): mass calcd. for $C_{24}H_{20}FN_5O$, 413.2; m/z found, 414.2 [M+H]⁺.

Example 176: 3-(1H-Indazol-5-yl)-2-[4-(trifluoromethyl)phenyl]imidazo[4,5-b]pyridine

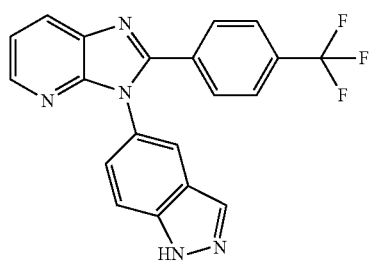 [SMILES: FC(F)(F)c1ccc(-c2nc3cccnc3n2-c2ccc3[nH]ncc3c2)cc1]

The title compound was prepared in a manner analogous to Example 1. MS (ESI): mass calcd. for $C_{20}H_{12}F_3N_5$, 379.1; m/z found, 380.1[M+H]⁺. ¹H NMR (500 MHz, CDCl₃) δ 11.43 (s, 1H), 8.47 (dd, J=4.8, 1.5 Hz, 1H), 8.24 (dd, J=8.1, 1.5 Hz, 1H), 8.06 (d, J=1.1 Hz, 1H), 7.79-7.73 (m, 3H), 7.58-7.52 (m, 2H), 7.45-7.41 (m, 1H), 7.38 (dd, J=8.0, 4.8 Hz, 1H), 7.27-7.24 (m, 1H).

Example 177: 3-(1H-Indazol-5-yl)-2-[4-(trifluoromethoxy)phenyl]imidazo[4,5-b]pyridine

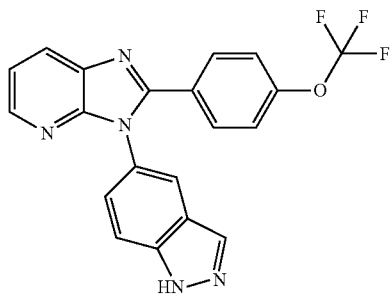 [SMILES: FC(F)(F)Oc1ccc(-c2nc3cccnc3n2-c2ccc3[nH]ncc3c2)cc1]

The title compound was prepared in a manner analogous to Example 1. MS (ESI): mass calcd. for $C_{20}H_{12}F_3N_5O$, 395.1; m/z found, 396.1 [M+H]⁺. ¹H NMR (500 MHz, CDCl₃) δ 10.68 (s, 1H), 8.42 (dd, J=4.8, 1.5 Hz, 1H), 8.19 (dd, J=8.0, 1.5 Hz, 1H), 8.12 (d, J=1.1 Hz, 1H), 7.82 (dd, J=1.9, 0.8 Hz, 1H), 7.70-7.63 (m, 2H), 7.59-7.53 (m, 1H), 7.35 (dd, J=8.1, 4.8 Hz, 1H), 7.31 (dd, J=8.7, 1.9 Hz, 1H), 7.16-7.12 (m, 2H).

Example 178: 5-[2-[4-(Trifluoromethyl)phenyl]imidazo[4,5-b]pyridin-3-yl]indolin-2-one

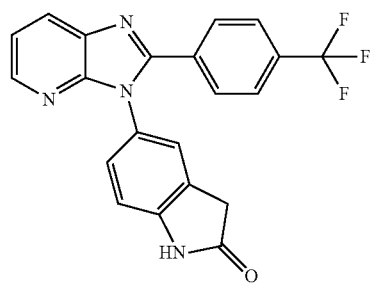 [SMILES: O=C1Cc2cc(-n3c(-c4ccc(C(F)(F)F)cc4)nc4cccnc43)ccc2N1]

The title compound was prepared in a manner analogous to Example 33. MS (ESI): mass calcd. for $C_{21}H_{13}F_3N_4O$, 394.1; m/z found, 395.1 [M+H]⁺. ¹H NMR (500 MHz, CDCl₃) δ 8.44 (s, 1H), 8.42 (dd, J=4.8, 1.5 Hz, 1H), 8.19 (dd, J=8.0, 1.5 Hz, 1H), 7.80-7.76 (m, 2H), 7.65-7.59 (m, 2H), 7.35 (dd, J=8.0, 4.8 Hz, 1H), 7.32 (s, 1H), 7.20-7.15 (m, 1H), 6.98 (d, J=8.2 Hz, 1H), 3.63 (s, 2H).

Example 179: tert-Butyl 3-[3-(2-oxoindolin-5-yl)-5-(trifluoromethyl)imidazo[4,5-b]pyridin-2-yl]azetidine-1-carboxylate

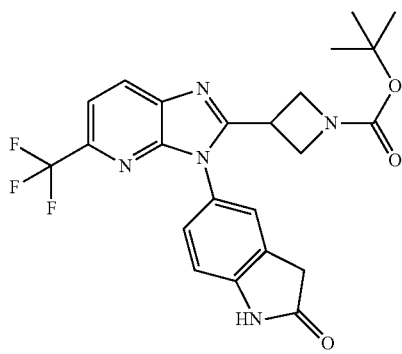 [SMILES: CC(C)(C)OC(=O)N1CC(c2nc3ccc(C(F)(F)F)nc3n2-c2ccc3c(c2)CC(=O)N3)C1]

The title compound was prepared in a manner analogous to Example 38. MS (ESI): mass calcd. for $C_{23}H_{22}F_3N_5O_3$, 473.2; m/z found, 474.1 [M+H]⁺. ¹H NMR (500 MHz, DMSO-d₆) δ 10.67 (s, 1H), 8.38 (dd, J=8.2, 0.7 Hz, 1H), 7.81 (d, J=8.3 Hz, 1H), 7.37-7.35 (m, 1H), 7.32-7.28 (m, 1H), 7.01 (d, J=8.2 Hz, 1H), 4.29-4.18 (m, 2H), 4.09-3.97 (m, 2H), 3.95-3.87 (m, 1H), 3.61 (s, 2H), 1.38 (s, 9H).

Example 180: 5-[2-(Azetidin-3-yl)-5-(trifluoromethyl)imidazo[4,5-b]pyridin-3-yl]indolin-2-one

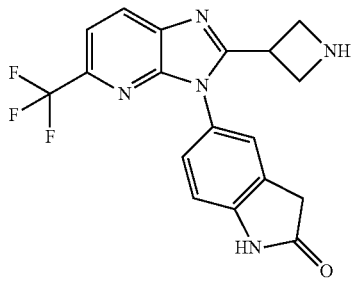 [SMILES: O=C1Cc2cc(-n3c(C4CNC4)nc4ccc(C(F)(F)F)nc43)ccc2N1]

The title compound was prepared in a manner analogous to Example 38. MS (ESI): mass calcd. for $C_{18}H_{14}F_3N_5O$, 373.1; m/z found, 374.0 $[M+H]^+$. $^1H$ NMR (500 MHz, DMSO) δ 10.89-10.62 (m, 1H), 8.92 (d, J=50.0 Hz, 1H), 8.52-8.31 (m, 1H), 7.91-7.61 (m, 1H), 7.49-7.24 (m, 1H), 7.05 (dt, J=8.4, 4.5 Hz, 1H), 5.01 (d, J=86.4 Hz, 1H), 3.60 (s, 1H), 2.56 (d, J=3.0 Hz, 1H), 2.32-2.24 (m, 3H).

Example 181: 5-(2,5-Dimethylimidazo[4,5-b]pyridin-3-yl)indolin-2-one

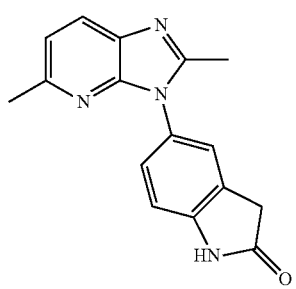 [SMILES: Cc1ccc2nc(C)n(-c3ccc4c(c3)CC(=O)N4)c2n1]

The title compound was prepared in a manner analogous to Example 38. MS (ESI): mass calcd. for $C_{16}H_{14}N_4O$, 278.1; m/z found, 279.1 $[M+H]^+$. $^1H$ NMR (500 MHz, CDCl$_3$) δ 8.11 (s, 1H), 7.88 (d, J=8.1 Hz, 1H), 7.29-7.27 (m, 1H), 7.25-7.20 (m, 1H), 7.09 (d, J=8.1 Hz, 1H), 7.00 (d, J=8.1 Hz, 1H), 3.63 (s, 2H), 2.59 (s, 3H), 2.50 (s, 3H).

Example 182: 2-Cyclopentyl-3-(1H-indol-5-yl)-5-piperazin-1-yl-imidazo[4,5-b]pyridine

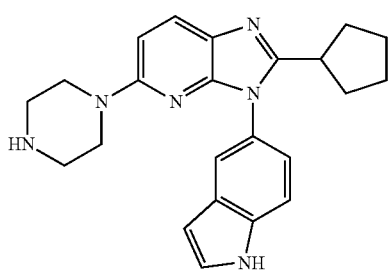 [SMILES: c1cc2cc(-n3c(C4CCCC4)nc4ccc(N5CCNCC5)nc43)ccc2[nH]1]

The title compound was prepared in a manner analogous to Example 38. $^1H$ NMR (500 MHz, DMSO-d$_6$) δ 1.42-1.51 (m, 2H) 1.65-1.80 (m, 4H) 1.82-1.91 (m, 2H) 2.21 (br s, 1H) 2.66-2.72 (m, 4H) 3.08 (quin, J=8.1 Hz, 1H) 3.19-3.24 (m, 4H) 6.53 (ddd, J=3.0, 2.0, 0.9 Hz, 1H) 6.69 (d, J=9.0 Hz, 1H) 7.06 (dd, J=8.7, 2.0 Hz, 1H) 7.49 (t, J=2.7 Hz, 1H) 7.53-7.56 (m, 1H) 7.57 (s, 1H) 7.77 (d, J=8.7 Hz, 1H) 11.39 (br s, 1H).

Example 183: Methyl 3-[3-(2-oxoindolin-5-yl)-5-(trifluoromethyl)imidazo[4,5-b]pyridin-2-yl]propanoate

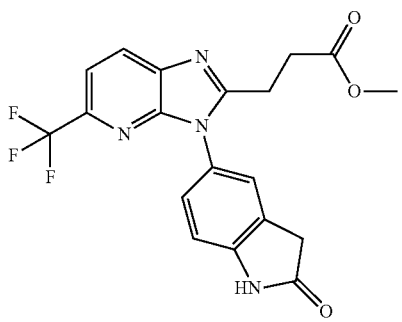 [SMILES: COC(=O)CCc1nc2ccc(C(F)(F)F)nc2n1-c1ccc2c(c1)CC(=O)N2]

The title compound was prepared in a manner analogous to Example 73 Step A. MS (ESI): mass calcd. for $C_{19}H_{15}F_3N_4O_3$, 404.1; m/z found, 405.0 $[M+H]^+$. $^1H$ NMR (400 MHz, CDCl$_3$) δ 8.64 (s, 1H), 8.13 (d, J=8.3 Hz, 1H), 7.64 (d, J=8.2 Hz, 1H), 7.32-7.26 (m, 2H), 7.01 (d, J=8.1 Hz, 1H), 3.68 (s, 3H), 3.62 (s, 2H), 3.14-3.06 (m, 2H), 3.05-2.97 (m, 2H).

Example 184: 3-(7-Bromo-1H-indazol-5-yl)-2-isopropyl-5-(trifluoromethyl)imidazo[4,5-b]pyridine

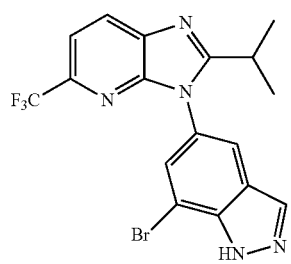 [SMILES: CC(C)c1nc2ccc(C(F)(F)F)nc2n1-c1cc(Br)c2[nH]ncc2c1]

The title compound was made in a manner analogous to Example 109, Method B. MS (ESI): mass calcd. for $C_{17}H_{13}BrF_3N_5$, 423.0; m/z found, 424.0 $[M+H]^+$. $^1H$ NMR (500 MHz, DMSO-d$_6$) δ 13.92 (s, 1H), 8.40 (s, 1H), 8.33 (dd, J=8.2, 0.7 Hz, 1H), 8.11 (d, J=1.7 Hz, 1H), 7.92 (d, J=1.7 Hz, 1H), 7.79 (d, J=8.2 Hz, 1H), 3.12-3.01 (m, 1H), 1.26 (d, J=6.8 Hz, 6H).

Example 185: 6-(2-Cyclobutyl-5-(trifluoromethyl)-3H-imidazo[4,5-b]pyridin-3-yl)-3-methylbenzo[d]thiazol-2(3H)-one

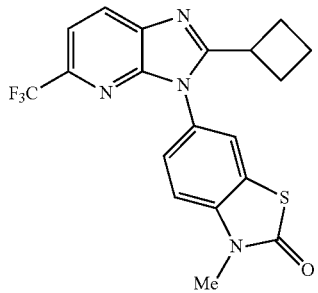 [SMILES: Cn1c(=O)sc2cc(-n3c(C4CCC4)nc4ccc(C(F)(F)F)nc43)ccc21]

To a solution of 6-(2-cyclobutyl-5-(trifluoromethyl)-3H-imidazo[4,5-b]pyridin-3-yl)benzo[d]thiazol-2(3H)-one (Example 132, 0.03 g, 0.077 mmol) in DMF (3 mL) was added NaH (0.003 g, 0.077 mmol). The reaction was stirred for 30 minutes then MeI (0.005 mL, 0.077 mmol) was added to the mixture. After 1 h the reaction was diluted with EtOAc and washed with water (5 mL×3). The organics were dried and concentrated in vacuo. Purification (FCC, SiO$_2$, EtOAc/hexanes) afforded the title compound (0.02 g, 74%). MS (ESI): mass calcd. for C$_{19}$H$_{15}$F$_3$N$_4$OS, 404.1; m/z found, 405.0 [M+H]$^+$. $^1$H NMR (500 MHz, CDCl$_3$) δ 8.20-8.14 (m, 1H), 7.65 (d, J=8.2 Hz, 1H), 7.43 (d, J=2.1 Hz, 1H), 7.32 (dd, J=8.5, 2.1 Hz, 1H), 7.23 (d, J=8.5 Hz, 1H), 3.70-3.59 (m, 1H), 3.54 (s, 3H), 2.69-2.53 (m, 2H), 2.34-2.20 (m, 2H), 2.09-1.95 (m, 2H).

Example 186: 3-(7-$^3$H-1H-indazol-5-yl)-2-isopropyl-5-(trifluoromethyl)-3H-imidazo[4,5-b]pyridine

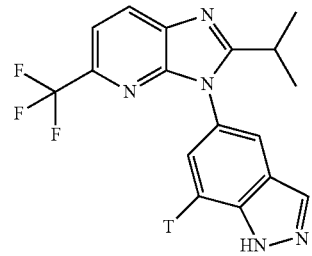

To a solution of 3-(7-bromo-1H-indazol-5-yl)-2-isopropyl-5-(trifluoromethyl)imidazo[4,5-b]pyridine (Example 184, 5 mg) in ethanol (1 mL), was added Pd/C (10%, 2.5 mg), and $^3$H gas (760 mmHg). The reaction was stirred at room temperature for 8 hours. The crude product was filtered and the labile tritium was removed by rotovap. This was repeated 2 additional times. The crude material was purified (HPLC-$^{18}$C-column, mobile phase gradient A: 0.1% TFA, B: 100% CH$_3$CN, A to B 100% B in 60 min, U.V. 280 nm, flow 6 mL/min) to afford the title compound.

Example 187: 3-(7-Bromo-1H-indazol-5-yl)-2,5-bis(trifluoromethyl)imidazo[4,5-b]pyridine

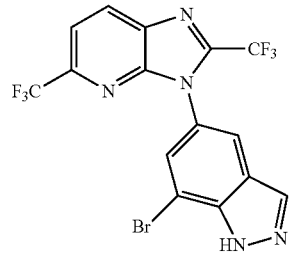 [SMILES: FC(F)(F)c1ccc2nc(C(F)(F)F)n(-c3cc(Br)c4[nH]ncc4c3)c2n1]

The title compound was made in a manner analogous to Example 134 using 2-chloro-3-nitro-6-(trifluoromethyl)pyridine and 7-bromo-1H-indazol-5-amine. MS (ESI): mass calcd. for C$_{15}$H$_6$BrF$_6$N$_5$, 449.0; m/z found, 449.8 [M+H]+. 1H NMR (500 MHz, DMSO-d$_6$) δ 13.98 (s, 1H), 8.73 (d, J=8.4 Hz, 1H), 8.44 (s, 1H), 8.22 (d, J=1.6 Hz, 1H), 8.04 (d, J=8.4 Hz, 1H), 8.02 (s, 1H).

Example 188: 3-(7-Phenyl-1H-indazol-5-yl)-2,5-bis(trifluoromethyl)-3H-imidazo[4,5-b]pyridine

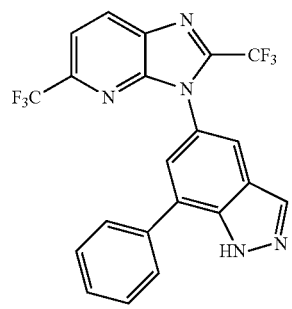 [SMILES: FC(F)(F)c1ccc2nc(C(F)(F)F)n(-c3cc(-c4ccccc4)c4[nH]ncc4c3)c2n1]

A solution of 3-(7-bromo-1H-indazol-5-yl)-2,5-bis(trifluoromethyl)-3H-imidazo[4,5-b]pyridine (Example 187, 0.04 g, 0.09 mmol), phenyl boronic acid (0.01 g, 0.09 mmol), PdCl$_2$(dtbpf) (0.03 g, 0.004 mmol), and K$_3$PO$_4$ (0.06 g, 0.27 mmol) in 1,4 dioxane (2 mL) and H$_2$O (1 mL) was irradiated for 30 minutes at 100° C. The reaction was concentrated in vacuo. Purification (FCC, SiO$_2$, EtOAc/hexanes) afforded the title compound (0.02 g, 50%). MS (ESI): mass calcd. for C$_{21}$H$_{11}$F$_6$N$_5$, 447.1; m/z found, 448.1 [M+H]$^+$. $^1$H NMR (400 MHz, CDCl$_3$) δ 10.93-10.77 (s, 1H), 8.52-8.34 (dd, J=8.6, 0.8 Hz, 1H), 8.29-8.16 (s, 1H), 7.94-7.78 (m, 2H), 7.78-7.64 (s, 2H), 7.61-7.37 (m, 4H).

Example 189: 2,5-Bis(trifluoromethyl)-3-(7-vinyl-1H-indazol-5-yl)-3H-imidazo[4,5-b]pyridine

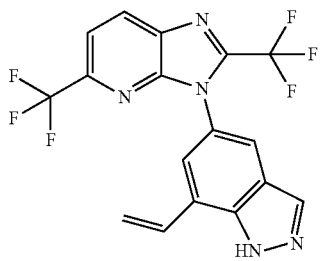 [SMILES: C=Cc1cc(-n2c(C(F)(F)F)nc3ccc(C(F)(F)F)nc32)cc2cn[nH]c12]

A solution of 3-(7-bromo-1H-indazol-5-yl)-2,5-bis(trifluoromethyl)-3H-imidazo[4,5-b]pyridine (Example 187, 0.025 g, 0.056), tributylvinyltin (0.2 g, 0.06 mmol), and Pd(PPh$_3$)$_4$ (0.006 g, 0.006 mmol) in toluene (2 mL) was irradiated in a microwave apparatus for 45 min at 140° C. The reaction was concentrated in vacuo. Purification (FCC, SiO$_2$, EtOAc:Hex) afforded the title compound (0.005 g, 23%). MS (ESI): mass calcd. for C$_{17}$H$_9$F$_6$N$_5$, 397.1; m/z found, 398.1 [M+H]$^+$. $^1$H NMR (500 MHz, CDCl$_3$) δ10.95-10.65 (s, 1H), 8.55-8.40 (d, J=8.4 Hz, 1H), 8.24-8.09 (s, 1H), 7.90-7.81 (d, J=8.4 Hz, 1H), 7.81-7.68 (d, J=1.8 Hz, 1H), 7.44-7.33 (d, J=1.7 Hz, 1H), 7.03-6.89 (m, 1H), 6.02-5.81 (d, J=17.7 Hz, 1H), 5.76-5.52 (d, J=11.2 Hz, 1H), 4.22-3.97 (q, J=7.1 Hz, 6H).

Example 190: 6-(5-(Trifluoromethyl)-3H-imidazo[4,5-b]pyridin-3-yl)benzo[d]thiazol-2(3H)-one

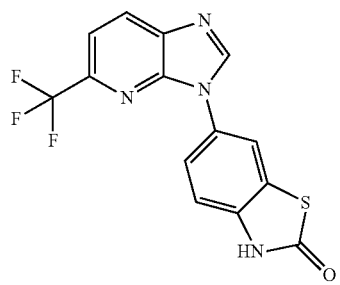 [SMILES: O=c1[nH]c2ccc(-n3cnc4ccc(C(F)(F)F)nc43)cc2s1]

A solution of 6-((3-amino-6-(trifluoromethyl)pyridin-2-yl)amino)benzo[d]thiazol-2(3H)-one (Example 134, Method B, product from Step A, 0.10 g, 0.31 mmol) in triethyl orthoformate (15 mL, 3.1 mmol) was heated at 145° C. for 18 h. The reaction was concentrated in vacuo. Purification (FCC, SiO$_2$, petrol ether/EtOAc, 1:1 to 0:1) afforded the title compound (0.06 g, 62%). MS (ESI): mass calcd. for C$_{14}$H$_7$F$_3$N$_4$OS, 336.0; m/z found, 337.0, [M+H]$^+$. $^1$H NMR (500 MHz, DMSO-d$_6$) δ 9.08-8.98 (s, 1H), 8.52-8.41 (d, J=8.2 Hz, 1H), 8.10-8.03 (d, J=2.2 Hz, 1H), 7.93-7.84 (d, J=8.1 Hz, 1H), 7.80-7.66 (dd, J=8.4, 2.0 Hz, 1H), 7.41-7.27 (d, J=8.5 Hz, 1H).

Example 191: 3-(3-Fluoro-1H-indazol-5-yl)-2-isopropyl-5-(trifluoromethyl)imidazo[4,5-b]pyridine

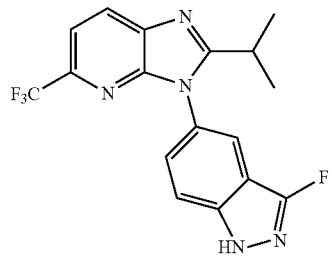 [SMILES: CC(C)c1nc2ccc(C(F)(F)F)nc2n1-c1ccc2[nH]nc(F)c2c1]

To a solution of N$^2$-(3-fluoro-1H-indazol-5-yl)-6-(trifluoromethyl)pyridine-2,3-diamine (Intermediate 53, 85 mg, 0.273 mmol) in AcOH (1.1 mL) was added copper (II) acetate (24.8 mg, 0.137 mmol) and isobutyraldehyde (37.4 μL, 0.410 mmol). This was stirred at rt for 1.5 h. The reaction was quenched to pH=7 with 4N NaOH and extracted with EtOAc. The combined organic layers were dried (Na$_2$SO$_4$), filtered, and concentrated in vacuo. Purification (FCC, SiO$_2$, 0-100% EtOAc in hexanes) then recrystallization out of EtOH afforded the title compound (22 mg, 22%). MS (ESI): mass calcd. for C$_{17}$H$_{13}$F$_4$N$_5$, 363.1; m/z found, 364.0 [M+H]$^+$. $^1$H NMR (400 MHz, DMSO-d$_6$) δ 12.97 (s, 1H), 8.33 (d, J=8.3 Hz, 1H), 8.09 (d, J=1.7 Hz, 1H), 7.79 (d, J=8.2 Hz, 1H), 7.76-7.72 (m, 1H), 7.61-7.57 (m, 1H), 3.14-3.05 (m, 1H), 1.26 (d, J=6.8 Hz, 6H).

Example 192: 5-Chloro-3-(1H-indazol-5-yl)-2-(trifluoromethyl)imidazo[4,5-b]pyridine

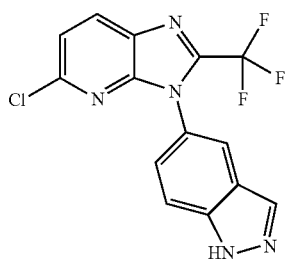 [SMILES: FC(F)(F)c1nc2ccc(Cl)nc2n1-c1ccc2[nH]ncc2c1]

The title compound was prepared in a manner analogous to Example 125. MS (ESI): mass calcd. for C$_{14}$H$_7$ClF$_3$N$_5$, 337.0; m/z found, 338.0 [M+H]$^+$. $^1$H NMR (400 MHz, CD$_3$OD) δ 8.30 (d, J=8.5 Hz, 1H), 8.22 (d, J=1.0 Hz, 1H), 8.00 (d, J=1.9 Hz, 1H), 7.79-7.75 (m, 1H), 7.53 (d, J=8.5 Hz, 1H), 7.50-7.45 (m, 1H).

Example 193: 5-Ethyl-3-(1H-indazol-5-yl)-2-(trifluoromethyl)imidazo[4,5-b]pyridine

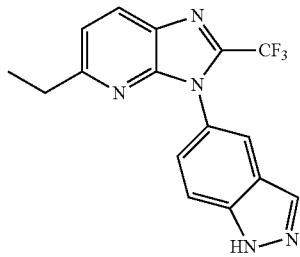 [SMILES: CCc1ccc2nc(C(F)(F)F)n(-c3ccc4[nH]ncc4c3)c2n1]

In an oven dried flask under nitrogen, 5-chloro-3-(1H-indazol-5-yl)-2-(trifluoromethyl)-3H-imidazo[4,5-b]pyridine (Example 192, 50 mg, 0.148 mmol), iron (III) acetylacetonate (2.6 mg, 0.007 mmol), and N-methyl-2-pyrrolidone (92 μL, 0.962 mmol) were stirred in THF (0.75 mL). Ethylmagnesium bromide (0.2 mL, 3.0 M in diethyl ether) was added to this solution dropwise. The reaction mixture was stirred at rt for 30 min. The reaction was quenched with brine and extracted with EtOAc. The combined organic layers were dried (Na$_2$SO$_4$), filtered, and concentrated in vacuo. Purification (reverse phase HPLC, 5-95% ACN in 20 nM NH$_4$OH in water) afforded the title compound (16.7 mg, 34%). MS (ESI): mass calcd. for C$_{16}$H$_{12}$F$_3$N$_5$, 331.1; m/z found, 332.0 [M+H]$^+$. $^1$H NMR (400 MHz, CD$_3$OD) δ 8.24-8.18 (m, 2H), 7.98 (d, J=1.8 Hz, 1H), 7.76 (d, J=8.7 Hz, 1H), 7.49-7.44 (m, 1H), 7.42 (d, J=8.4 Hz, 1H), 2.89-2.80 (m, 2H), 1.28-1.20 (m, 3H).

Example 194: 3-(7-Methyl-1H-indazol-5-yl)-5-(trifluoromethyl)imidazo[4,5-b]pyridine

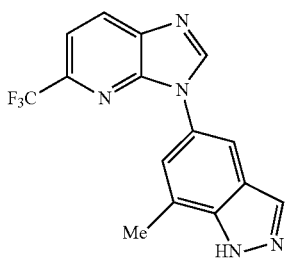

N$^2$-(7-methyl-1H-indazol-5-yl)-6-(trifluoromethyl)pyridine-2,3-diamine (Intermediate 55, 50 mg, 0.163 mmol) was taken up in ethanol (1.9 mL). To this was added trimethoxymethane (0.18 mL, 1.63 mmol) and hydrochloric acid (6 N, 95 μL). This was heated in the microwave at 120° C. for 30 min. The solvent was evaporated and the residue was basified with sat. aq. NaHCO$_3$ and extracted with EtOAc. The combined organic layers were dried (Na$_2$SO$_4$), filtered, and concentrated in vacuo. This crude material was purified by reverse phase HPLC (5-95% ACN in 20 nM NH$_4$OH in water) to provide the title compound (16 mg, 31%). MS (ESI): mass calcd. for C$_{15}$H$_{10}$F$_3$N$_5$, 317.1; m/z found, 318.1 [M+H]$^+$. $^1$H NMR (400 MHz, CD$_3$OD) δ 8.88 (s, 1H), 8.34 (d, J=8.3 Hz, 1H), 8.19 (s, 1H), 8.04 (d, J=1.9 Hz, 1H), 7.82 (d, J=8.4 Hz, 1H), 7.61-7.56 (m, 1H), 2.68 (s, 3H).

Example 195: 2-(4-Fluorophenyl)-3-(7-methyl-1H-indazol-5-yl)-5-(trifluoromethyl)imidazo[4,5-b]pyridine

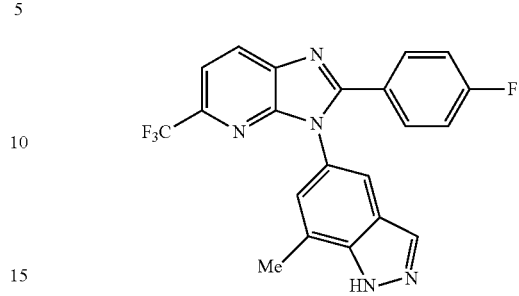

Step A: 2-(4-Fluorophenyl)-3-(7-methyl-1H-indazol-5-yl)-5-(trifluoromethyl)-2,3-dihydro-1H-imidazo[4,5-b]pyridine To a solution of N$^2$-(7-methyl-1H-indazol-5-yl)-6-(trifluoromethyl)pyridine-2,3-diamine (Intermediate 55, 80 mg, 0.260 mmol) in acetic acid (1.3 mL) was added copper (II) acetate (24 mg, 0.130 mmol) and 4-fluorobenzaldehyde (28 μL, 0.260 mmol). This reaction was stirred at rt for 2 h before it was quenched with water and extracted with EtOAc. The combined organic layers were dried (Na$_2$SO$_4$), filtered, and concentrated in vacuo. Purification (reverse phase HPLC, 5-95% ACN in 20 nM NH$_4$OH in water) afforded the title compound (43 mg, 40%). MS (ESI): mass calcd. for C$_{21}$H$_{15}$F$_4$N$_5$, 413.1; m/z found, 414.0 [M+H]$^+$.

Step B: 2-(4-Fluorophenyl)-3-(7-methyl-1H-indazol-5-yl)-5-(trifluoromethyl)imidazo[4,5-b]pyridine To a solution of 2-(4-fluorophenyl)-3-(7-methyl-1H-indazol-5-yl)-5-(trifluoromethyl)-2,3-dihydro-1H-imidazo[4,5-b]pyridine (43 mg, 0.104 mmol) in acetonitrile (1.0 mL) was added copper (II) acetate (19 mg, 0.104 mmol). This reaction was stirred at 50° C. for 5 h. The reaction was quenched with water and extracted with EtOAc. The combined organic layers were dried (Na$_2$SO$_4$), filtered, and concentrated in vacuo. This crude material was purified by reverse phase HPLC (5-95% ACN in 20 nM NH$_4$OH in water) to provide the title compound (2.7 mg, 6%). MS (ESI): mass calcd. for C$_{21}$H$_{13}$F$_4$N$_5$, 411.1; m/z found, 412.0 [M+H]$^+$. $^1$H NMR (500 MHz, CD$_3$OD) δ 8.32 (d, J=8.3 Hz, 1H), 8.14 (s, 1H), 7.81 (d, J=8.3 Hz, 1H), 7.71-7.69 (m, 1H), 7.69-7.64 (m, 2H), 7.20-7.17 (m, 1H), 7.14-7.08 (m, 2H), 2.60 (d, J=0.8 Hz, 3H).

Example 196: 2-Ethoxy-3-(3-fluoro-1H-indazol-5-yl)-5-(trifluoromethyl)imidazo[4,5-b]pyridine

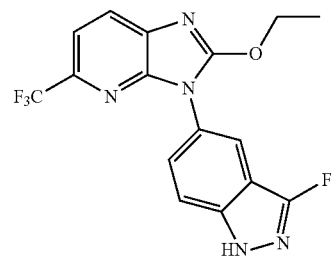 [SMILES: CCOc1nc2ccc(C(F)(F)F)nc2n1-c1ccc2[nH]nc(F)c2c1]

Step A: 2,2-Diethoxy-3-(3-fluoro-1H-indazol-5-yl)-5-(trifluoromethyl)-2,3-dihydro-1H-imidazo[4,5-b]pyridine A solution of N²-(3-fluoro-1H-indazol-5-yl)-6-(trifluoromethyl)pyridine-2,3-diamine (Intermediate 52, 40 mg, 0.129 mmol) and acetic acid (0.1 mL) in tetraethylorthocarbonate (0.54 mL, 2.57 mmol) was heated to 70° C. for 2 h. Purification (reverse phase HPLC, 5-95% ACN in 20 nM NH$_4$OH in water) afforded the title compound (23 mg, 44%). MS (ESI): mass calcd. for C$_{18}$H$_{17}$F$_4$N$_5$O$_2$, 411.1; m/z found, 412.2 [M+H]$^+$.

Step B: 2-Ethoxy-3-(3-fluoro-1H-indazol-5-yl)-5-(trifluoromethyl)imidazo[4,5-b]pyridine To a solution of 2,2-diethoxy-3-(3-fluoro-1H-indazol-5-yl)-5-(trifluoromethyl)-2,3-dihydro-1H-imidazo[4,5-b]pyridine (23 mg, 0.056 mmol) in ethanol (0.28 mL) was added p-toluenesulfonic acid (2.0 mg, 0.011 mmol). The reaction was stirred at 70° C. for 30 min. The solvent was removed under reduced pressure. Purification (reverse phase HPLC, 5-95% ACN in 20 nM NH$_4$OH in water) afforded the title compound (15 mg, 73%). MS (ESI): mass calcd. for C$_{16}$H$_{11}$F$_4$N$_5$O, 365.1; m/z found, 366.1 [M+H]$^+$. $^1$H NMR (600 MHz, DMSO-d$_6$) δ 12.90 (s, 1H), 8.09 (d, J=8.1 Hz, 1H), 8.00 (d, J=1.8 Hz, 1H), 7.74-7.69 (m, 2H), 7.63-7.60 (m, 1H), 4.69-4.62 (m, 2H), 1.41-1.35 (m, 3H).

Example 197: 2-Cyclopropyl-3-(3-fluoro-1H-indazol-5-yl)-5-(trifluoromethyl)imidazo[4,5-b]pyridine

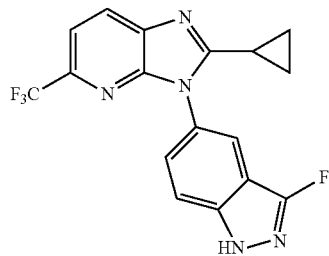 [SMILES: Fc1n[nH]c2ccc(-n3c(C4CC4)nc4ccc(C(F)(F)F)nc43)cc12]

To a solution of N²-(3-fluoro-1H-indazol-5-yl)-6-(trifluoromethyl)pyridine-2,3-diamine (Intermediate 52, 55 mg, 0.177 mmol) in DMF (1.7 mL) was added cyclopropane carboxaldehyde (26 µL, 0.363 mmol) and sodium metabisulfite (100 mg, 0.530 mmol). This was heated to 85° C. for 16 h. An additional aliquot of cyclopropane carboxaldehyde was added and the solution was reacted in the microwave at 120° C. for 20 min. The reaction mixture was quenched with water and extracted with EtOAc. The combined organic layers were dried (Na$_2$SO$_4$), filtered, and concentrated in vacuo. The crude material was purified by reverse phase HPLC (5-95% ACN in 20 nM NH$_4$OH in water) to provide the title compound (43 mg, 67%). MS (ESI): mass calcd. for C$_{17}$H$_{11}$F$_4$N$_5$, 361.1; m/z found, 362.1 [M+H]$^+$. $^1$H NMR (500 MHz, CD$_3$OD) δ 8.11 (d, J=8.2 Hz, 1H), 7.96-7.93 (m, 1H), 7.73-7.69 (m, 2H), 7.60-7.57 (m, 1H), 2.03-1.96 (m, 1H), 1.36-1.31 (m, 2H), 1.20-1.15 (m, 2H).

Example 198: 2-Isopropyl-3-(7-methyl-1H-indazol-5-yl)-5-(trifluoromethyl)imidazo[4,5-b]pyridine

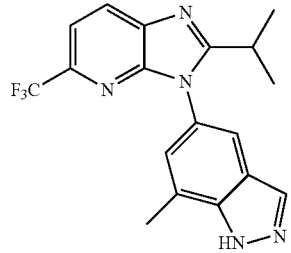 [SMILES: Cc1cc(-n2c(C(C)C)nc3ccc(C(F)(F)F)nc32)cc2cn[nH]c12]

A solution of N²-(7-methyl-1H-indazol-5-yl)-6-(trifluoromethyl)pyridine-2,3-diamine (Intermediate 55, 80 mg, 0.260 mmol) and isobutyric anhydride (52 µL, 0.312 mmol) in isobutyric acid (0.65 mL) was reacted in the microwave at 120° C. for 40 min. The solvent was evaporated and the crude material was purified by FCC (SiO$_2$, 0-70-100% EtOAc in hexanes). This yielded the title compound (56 mg, 60%). MS (ESI): mass calcd. for C$_{18}$H$_{16}$F$_3$N$_5$, 359.1; m/z found, 360.1 [M+H]$^+$. $^1$H NMR (600 MHz, CDCl$_3$) δ 8.25 (d, J=8.3 Hz, 1H), 7.91 (s, 1H), 7.74 (d, J=8.3 Hz, 1H), 7.48-7.46 (m, 1H), 6.94-6.92 (m, 1H), 3.06 (sex, J=6.6 Hz, 1H), 2.44 (s, 3H), 1.35 (d, J=6.8 Hz, 6H).

Example 199: 3-(7-Chloro-1H-indazol-5-yl)-2-(trifluoromethyl)imidazo[4,5-b]pyridine

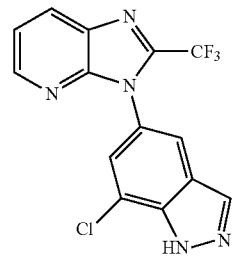 [SMILES: FC(F)(F)c1nc2cccnc2n1-c1cc(Cl)c2[nH]ncc2c1]

Step A: N²-(7-Chloro-1H-indazol-5-yl)pyridine-2,3-diamine

A solution of 2-fluoro-3-nitropyridine (85 mg, 0.597 mmol) and 7-chloro-1H-indazol-5-amine (100 mg, 0.597 mmol) in DMF (1.2 mL) was heated at 110° C. for 1 h. Sodium dithionite (416 mg, 2.39 mmol) was added and the reaction was held at 110° C. for an additional 2.5 h. The reaction was allowed to cool and the solids were filtered off. The filtrate was concentrated and purified by reverse phase HPLC (5-95% ACN in 20 nM NH$_4$OH in water) to provide the title compound (46 mg, 30%). MS (ESI): mass calcd. for C$_{12}$H$_{10}$ClN$_5$, 259.1; m/z found, 260.1 [M+H]$^+$. $^1$H NMR (400 MHz, CD$_3$OD) δ 7.99 (s, 1H), 7.66 (d, J=1.7 Hz, 1H), 7.55-7.51 (m, 1H), 7.49 (d, J=1.8 Hz, 1H), 7.08-7.03 (m, 1H), 6.74-6.68 (m, 1H).

Step B: 3-(7-Chloro-1H-indazol-5-yl)-2-(trifluoromethyl)imidazo[4,5-b]pyridine N²-(7-chloro-1H-indazol-5-yl)pyridine-2,3-diamine (22 mg, 0.085 mmol) was stirred in trifluoroacetic acid (0.2 mL, 2.54 mmol) at 70° C. for 16 h. The reaction was neutralized with 4 N NaOH and extracted with EtOAc. The combined organic layers were dried (Na$_2$SO$_4$), filtered, and concentrated in vacuo. Purification (reverse phase HPLC, 5-95% ACN in 20 nM NH$_4$OH in water) afforded the title compound (19 mg, 66%). MS (ESI): mass calcd. for C$_{14}$H$_7$ClF$_3$N$_5$, 337.0; m/z found, 338.1 [M+H]$^+$. $^1$H NMR (400 MHz, CD$_3$OD) δ 8.53-8.48 (m, 1H), 8.38-8.33 (m, 1H), 8.30 (s, 1H), 8.00 (d, J=1.8 Hz, 1H), 7.63 (d, J=1.7 Hz, 1H), 7.58-7.52 (m, 1H).

Example 200: 3-(7-Chloro-1H-indazol-5-yl)-2-isopropyl-imidazo[4,5-b]pyridine

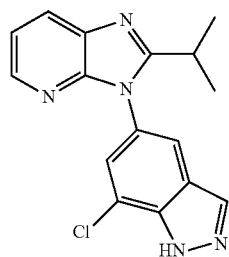 [SMILES: CC(C)c1nc2cccnc2n1-c1cc(Cl)c2[nH]ncc2c1]

The title compound was prepared in a manner analogous to Example 191 from the product of Example 199, Step A. MS (ESI): mass calcd. for C$_{16}$H$_{14}$ClN$_5$, 311.1; m/z found, 312.1 [M+H]$^+$. $^1$H NMR (400 MHz, CD$_3$OD) δ 8.29 (s, 1H), 8.25-8.20 (m, 1H), 8.12-8.07 (m, 1H), 7.95-7.91 (m, 1H), 7.59-7.55 (m, 1H), 7.39-7.33 (m, 1H), 3.23-3.11 (m, 1H), 1.37 (s, 3H), 1.35 (s, 3H).

Example 201: 3-(1H-indazol-5-yl)-7-methyl-2-(trifluoromethyl)imidazo[4,5-b]pyridine

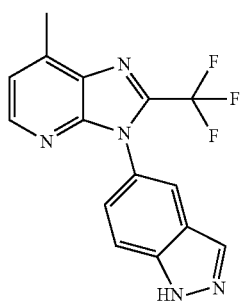 [SMILES: Cc1ccnc2c1nc(C(F)(F)F)n2-c1ccc2[nH]ncc2c1]

Step A: 7-Chloro-N-(4-methyl-3-nitropyridin-2-yl)-1H-indazol-5-amine

A solution of 7-chloro-1H-indazol-5-amine (100 mg, 0.597 mmol) and 2-fluoro-4-methyl-3-nitropyridine (93 mg, 0.597 mmol) in DMF (1.5 mL) was reacted in the microwave at 150° C. for 2 h. The reaction was diluted with water and EtOAc and extracted with EtOAc. The combined organic layers were dried (Na$_2$SO$_4$), filtered, and concentrated in vacuo. Purification (FCC, SiO$_2$, 0-70-100% EtOAc in hexanes) afforded the title compound (38 mg, 21%). $^1$H NMR (400 MHz, CDCl$_3$) δ 9.20 (s, 1H), 8.19 (d, J=4.8 Hz, 1H), 8.09 (s, 1H), 7.83 (d, J=1.7 Hz, 1H), 7.56 (d, J=1.7 Hz, 1H), 6.72-6.67 (m, 1H), 2.60 (s, 3H).

Step B: N$^2$-(7-Chloro-1H-indazol-5-yl)-4-methylpyridine-2,3-diamine and N$^2$-(1H-indazol-5-yl)-4-methylpyridine-2,3-diamine A solution of 7-chloro-N-(4-methyl-3-nitropyridin-2-yl)-1H-indazol-5-amine (38 mg, 0.125 mmol) and 10% Pd/C (13 mg, 0.013 mmol) in EtOH/THF (1:1 v/v, 0.1 M) was stirred under hydrogen at rt for 2 h. The reaction was filtered through Celite® with MeOH and the resulting solution was concentrated in vacuo. This material with mixed products was carried on to the next reaction without purification.

Step C: 3-(7-Chloro-1H-indazol-5-yl)-7-methyl-2-(trifluoromethyl)imidazo[4,5-b]pyridine and 3-(1H-Indazol-5-yl)-7-methyl-2-(trifluoromethyl)imidazo[4,5-b]pyridine N$^2$-(7-Chloro-1H-indazol-5-yl)-4-methylpyridine-2,3-diamine and N$^2$-(1H-indazol-5-yl)-4-methylpyridine-2,3-diamine (34 mg) were taken up in trifluoroacetic acid (0.28 mL) and heated at 70° C. for 16 h. The reaction was neutralized with 4 N NaOH and extracted with EtOAc. The combined organic layers were dried (Na$_2$SO$_4$), filtered, and concentrated in vacuo. The crude material was purified by reverse phase HPLC (5-95% ACN in 20 nM NH$_4$OH in water) to provide 3-(7-chloro-1H-indazol-5-yl)-7-methyl-2-(trifluoromethyl)imidazo[4,5-b]pyridine (Example 202, 15 mg, 34%) and the title compound (12 mg, 30%). MS (ESI): mass calcd. for C$_{15}$H$_{10}$F$_3$N$_5$, 317.1; m/z found, 318.0 [M+H]$^+$. $^1$H NMR (500 MHz, CD$_3$OD) δ 8.31 (d, J=4.9 Hz, 1H), 8.21 (d, J=1.0 Hz, 1H), 7.99 (d, J=1.9 Hz, 1H), 7.78-7.74 (m, 1H), 7.48-7.44 (m, 1H), 7.36-7.33 (m, 1H), 2.77 (s, 3H).

Example 202: 3-(7-Chloro-1H-indazol-5-yl)-7-methyl-2-(trifluoromethyl)imidazo[4,5-b]pyridine

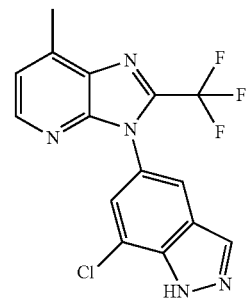 [SMILES: Cc1ccnc2c1nc(C(F)(F)F)n2-c1cc(Cl)c2[nH]ncc2c1]

The title compound was isolated as a product from Example 201. MS (ESI): mass calcd. for C$_{15}$H$_9$ClF$_3$N$_5$, 351.0; m/z found, 352.0 [M+H]$^+$. $^1$H NMR (400 MHz, CD$_3$OD) δ 8.35-8.27 (m, 2H), 8.01-7.95 (m, 1H), 7.63-7.58 (m, 1H), 7.38-7.32 (m, 1H), 2.77 (s, 3H).

Example 203: 7-Methyl-3-(7-methyl-1H-indazol-5-yl)-2-(trifluoromethyl)imidazo[4,5-b]pyridine

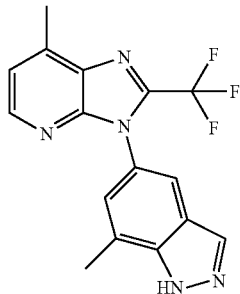 [SMILES: Cc1ccnc2c1nc(C(F)(F)F)n2-c1cc(C)c2[nH]ncc2c1]

The title compound was prepared in a manner analogous to Example 201. MS (ESI): mass calcd. for $C_{16}H_{12}F_3N_5$, 331.1; m/z found, 332.1 [M+H]$^+$. $^1$H NMR (400 MHz, CD$_3$OD) δ 8.30 (d, J=4.9 Hz, 1H), 8.19 (s, 1H), 7.80 (d, J=1.8 Hz, 1H), 7.33 (d, J=5.1 Hz, 1H), 7.24 (d, J=1.7 Hz, 1H), 2.77 (s, 3H), 2.68-2.63 (m, 3H).

Example 204: 3-(1H-pyrazolo[3,4-b]pyridin-5-yl)-2,5-bis(trifluoromethyl)imidazo[4,5-b]pyridine

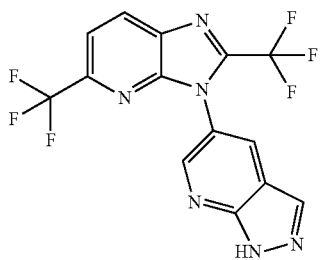 [SMILES: FC(F)(F)c1ccc2nc(C(F)(F)F)n(-c3cnc4[nH]ncc4c3)c2n1]

The title compound was prepared in a manner analogous to Example 134, Method B. MS (ESI): mass calcd. for $C_{14}H_6F_6N_6$, 372.1; m/z found, 373.1 [M+H]$^+$. $^1$H NMR (400 MHz, CD$_3$OD) δ 8.69 (d, J=2.3 Hz, 1H), 8.57 (d, J=8.4 Hz, 1H), 8.54 (d, J=2.3 Hz, 1H), 8.30 (s, 1H), 7.95 (d, J=8.4 Hz, 1H).

Example 205: 3-(7-Oxido-1H-pyrazolo[3,4-b]pyridin-7-ium-5-yl)-2,5-bis(trifluoromethyl)imidazo[4,5-b]pyridine

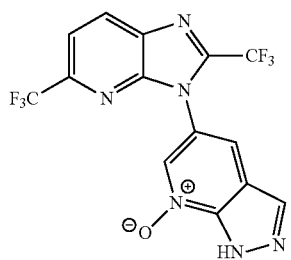 [SMILES: [O-][n+]1cc(-n2c(C(F)(F)F)nc3ccc(C(F)(F)F)nc32)cc2cn[nH]c21]

3-(1H-pyrazolo[3,4-b]pyridin-5-yl)-2,5-bis(trifluoromethyl)imidazo[4,5-b]pyridine (Example 204, 12 mg, 0.032 mmol) was taken up in DCM (0.32 mL) and cooled to 0° C. To this was added urea hydrogen peroxide (6.2 mg, 0.066 mmol) and trifluoroacetic anhydride (9.0 μL, 0.065 mmol) dropwise. The reaction was allowed to warm to rt and stir for 1 h. The reaction was neutralized with sat. aq. NaHCO$_3$ and extracted with EtOAc. The combined organic layers were dried (Na$_2$SO$_4$), filtered, and concentrated in vacuo. This crude material was purified by reverse phase HPLC (5-95% ACN in 20 nM NH$_4$OH in water) to provide the title compound (4.1 mg, 33%). MS (ESI): mass calcd. for $C_{14}H_6F_6N_6O$, 388.1; m/z found, 389.0 [M+H]$^+$. $^1$H NMR (400 MHz, CD$_3$OD) δ 8.85 (d, J=1.6 Hz, 1H), 8.58 (d, J=8.5 Hz, 1H), 8.51 (s, 1H), 8.37 (d, J=1.6 Hz, 1H), 7.97 (d, J=8.4 Hz, 1H).

Example 206: 6-[5-(difluoromethyl)-2-(trifluoromethyl)imidazo[4,5-b]pyridin-3-yl]-3H-1,3-benzothiazol-2-one

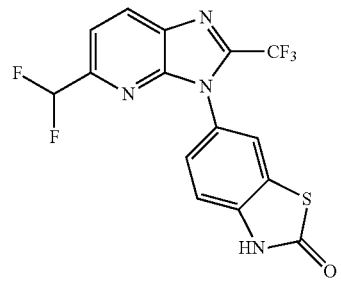 [SMILES: O=c1[nH]c2ccc(-n3c(C(F)(F)F)nc4ccc(C(F)F)nc43)cc2s1]

To a solution of 6-((3-amino-6-(difluoromethyl)pyridin-2-yl)amino)benzo[d]thiazol-2(3H)-one (Intermediate 56, 50 mg, 0.162 mmol) in EtOAc (0.81 mL) was added trifluoroacetic anhydride (34 μL, 0.243 mmol). The reaction mixture was stirred at 50° C. for 45 min. The reaction was concentrated in vacuo and purified by reverse phase HPLC (5-95% ACN in 20 nM NH$_4$OH in water) to provide the title compound (15 mg, 24%). MS (ESI): mass calcd. for $C_{15}H_7F_5N_4OS$, 386.0; m/z found, 387.0 [M+H]$^+$. $^1$H NMR (500 MHz, CD$_3$OD) δ 8.48 (d, J=8.4 Hz, 1H), 7.84 (d, J=8.4 Hz, 1H), 7.75 (d, J=2.1 Hz, 1H), 7.48-7.45 (m, 1H), 7.36 (d, J=8.5 Hz, 1H), 6.86-6.61 (m, 1H).

Example 207: 3-(7-Chloro-1H-indazol-5-yl)-2,5-bis(difluoromethyl)imidazo[4,5-b]pyridine

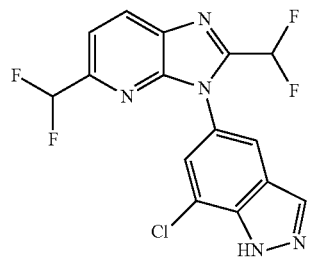 [SMILES: FC(F)c1ccc2nc(C(F)F)n(-c3cc(Cl)c4[nH]ncc4c3)c2n1]

To a solution of N$^2$-(7-chloro-1H-indazol-5-yl)-6-(difluoromethyl)pyridine-2,3-diamine (Intermediate 57, 50 mg, 0.161 mmol) in benzene (0.81 mL) was added difluoroacetic anhydride (28 μL, 0.242 mmol). This was stirred at 50° C. for 30 min. The reaction was quenched with water and extracted with EtOAc. The combined organic layers were dried (Na₂SO₄), filtered, and concentrated in vacuo. The crude material was purified by reverse phase HPLC (5-95% ACN in 20 nM NH₄OH in water) to provide the title compound (35 mg, 59%). MS (ESI): mass calcd. for C₁₅H₅ClF₄N₅, 369.0; m/z found, 370.0 [M+H]⁺. ¹H NMR (400 MHz, CD₃OD) δ 8.44 (d, J=8.4 Hz, 1H), 8.32 (s, 1H), 8.01 (d, J=1.8 Hz, 1H), 7.81 (d, J=8.4 Hz, 1H), 7.65 (d, J=1.7 Hz, 1H), 7.21-6.92 (m, 1H), 6.89-6.57 (m, 1H).

Example 208: 5-Cyclobutyl-3-(1H-indazol-5-yl)-2-(trifluoromethyl)imidazo[4,5-b]pyridine

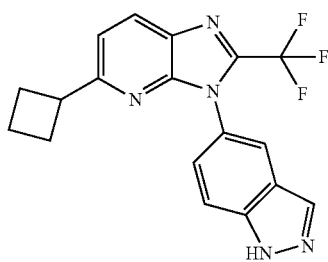 [SMILES: FC(F)(F)c1nc2ccc(C3CCC3)nc2n1-c1ccc2[nH]ncc2c1]

Step A: 5-Chloro-2-(trifluoromethyl)-3-(1-((2-(trimethylsilyl)ethoxy)methyl)-1H-indazol-5-yl)-3H-imidazo[4,5-b]pyridine The title compound was prepared in a manner analogous to Intermediate 9, Step A, starting with 5-chloro-3-(1H-indazol-5-yl)-2-(trifluoromethyl)imidazo[4,5-b]pyridine (Example 192). MS (ESI): mass calcd. for C₂₀H₂₁ClF₃N₅OSi, 467.1 m/z found, 468.2 [M+H]⁺

Step B: 5-Cyclobutyl-2-(trifluoromethyl)-3-(1-((2-(trimethylsilyl)ethoxy)methyl)-1H-indazol-5-yl)-3H-imidazo[4,5-b]pyridine A solution of 5-chloro-2-(trifluoromethyl)-3-(1-((2-(trimethylsilyl)ethoxy)methyl)-1H-indazol-5-yl)-3H-imidazo[4,5-b]pyridine (150 mg, 0.321 mmol), Pd(OAc)₂ (7 mg, 0.032 mmol), and Ru-Phos (30 mg, 0.064 mmol) in THF (3.3 mL) was placed in a syringe and cyclobutylzinc bromide (3.3 mL, 0.34 M) was placed in another syringe. The solutions were pumped through a Sigma Aldrich flow reactor and a 2 mL coil at rt, with a flowrate of 0.5 mL/min for each solution (RT=3 min). Once collected, the solvent was evaporated in vacuo, and the crude mixture was quenched with sat. aq. NH₄Cl and extracted with EtOAc. The combined organic layers were dried (Na₂SO₄), filtered, and concentrated. The crude material was taken forward without further purification (138 mg, 88%). MS (ESI): mass calcd. for C₂₄H₂₈F₃N₅OSi, 487.2; m/z found, 488.2 [M+H]⁺.

Step C: 5-Cyclobutyl-3-(1H-indazol-5-yl)-2-(trifluoromethyl)imidazo[4,5-b]pyridine 5-Cyclobutyl-2-(trifluoromethyl)-3-(1-((2-(trimethylsilyl)ethoxy)methyl)-1H-indazol-5-yl)-3H-imidazo[4,5-b]pyridine (138 mg, 0.285 mmol) was taken up in trifluoroacetic acid (1.5 mL) and stirred at rt for 30 min. The reaction was cooled to 0° C., diluted with THF (13 mL), and sat. aq. NaOH was added until pH~10. The reaction mixture was stirred at rt for 30 min. After this time, the reaction was quenched with sat. aq. ammonium chloride and extracted with EtOAc. The combined organic layers were dried (Na₂SO₄), filtered, and concentrated in vacuo. Purification (FCC, SiO₂, 0-50% EtOAc in heptane) afforded the title compound as a white solid (36 mg, 35%). MS (ESI): mass calcd. for C₁₈H₁₄F₃N₅, 357.1; m/z found, 358.1 [M+H]⁺. ¹H NMR (400 MHz, CDCl₃) δ 10.98 (s, 1H), 8.19 (d, J=8.4 Hz, 1H), 8.10 (s, 1H), 7.81 (s, 1H), 7.49-7.44 (m, 1H), 7.36-7.34 (m, 2H), 3.79 (quin, J=8.7 Hz, 1H), 2.35-2.25 (m, 4H), 2.05-1.95 (m, 1H), 1.87-1.79 (m, 1H).

Example 209: 5-(2-Ethyl-5-methyl-imidazo[4,5-b]pyridin-3-yl)indoline-2,3-dione

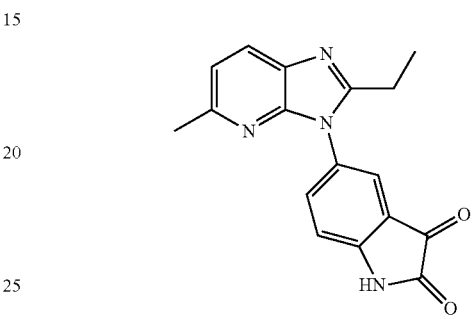

To a mixture of 5-((3-amino-6-methylpyridin-2-yl)amino)indolin-2-one (Intermediate 53, 200 mg, 0.629 mmol) and propionaldehyde (68.7 µL, 0.944 mmol) in AcOH (6 mL) was added Cu(OAc)₂ (57 mg, 0.315 mmol) and the resulting mixture was stirred in open air at ambient temperature overnight. The mixture was basified by addition of 3.75 N NaOH (6 mL) then diluted with water (50 mL). The reaction was extracted with EtOAc (50 mL×3) and concentrated in vacuo. Purification (FCC, SiO₂, 2M NH₃MeOH:DCM) afforded the title compound (96.4 mg, 50.0%). MS (ESI): mass calcd. for C₁₇H₁₄N₄O₂, 306.1; m/z found, 307.1 [M+H]⁺. ¹H NMR (400 MHz, CDCl₃) δ 9.07 (s, 1H), 7.94 (d, J=8.1 Hz, 1H), 7.66 (dd, J=2.1, 0.6 Hz, 1H), 7.59 (dd, J=8.3, 2.2 Hz, 1H), 7.13 (d, J=8.1 Hz, 1H), 7.07 (dd, J=8.3, 0.6 Hz, 1H), 2.82 (q, J=7.5 Hz, 2H), 2.59 (s, 3H), 1.39 (t, J=7.5 Hz, 3H).

Example 210: 5-(Difluoromethyl)-3-(1H-indazol-5-yl)-2-isopropyl-imidazo[4,5-b]pyridine

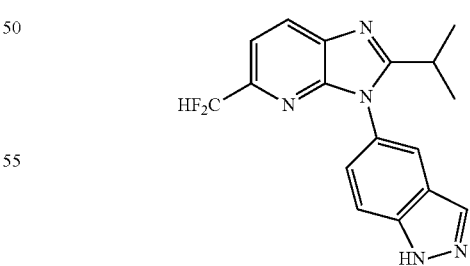

Step A: 5-(Difluoromethyl)-2-isopropyl-3-(2-((2-(trimethylsilyl)ethoxy)methyl)-2H-indazol-5-yl)-3H-imidazo[4,5-b]pyridine A solution of 2-chloro-6-(difluoromethyl)-3-nitropyridine (Intermediate 48, product from Step E, 127 µL, 0.96 mmol)

and 2-((2-(trimethylsilyl)ethoxy)methyl)-2H-indazol-5-amine (Intermediate 9, 316 mg, 1.2 mmol) in DMF (4.5 mL) was heated at 100° C. for 2 h. The reaction mixture was cooled and isobutyraldehyde (131 µL, 1.4 mmol) was added to the mixture and the reaction was let stir at ambient temperature for 45 min followed by addition of sodium dithionite (626 mg, 3.6 mmol). After 16 h at 100° C. the reaction was allowed to cool, diluted with H$_2$O (25 mL), and extracted with EtOAc (25 mL×3). The organic layer was dried (Na$_2$SO$_4$) and concentrated in vacuo. Purification (FCC, SiO$_2$, EtOAc/hexanes) afforded the title compound (118 mg, 27%). MS (ESI): mass calcd. for C$_{23}$H$_{29}$F$_2$N$_5$OSi, 457.2; m/z found, 458.1 [M+H]$^+$.

Step B: 5-(Difluoromethyl)-3-(1H-indazol-5-yl)-2-isopropyl-imidazo[4,5-b]pyridine A solution of 5-(difluoromethyl)-2-isopropyl-3-(2-((2-(trimethylsilyl)ethoxy)methyl)-2H-indazol-5-yl)-3H-imidazo[4,5-b]pyridine (73 mg, 0.16 mmol) in TFA (1 mL) and DCM (1 mL) was stirred for 1.5 h. Volatiles were removed by evaporation and the residue was basified by sat. NaHCO$_3$ solution (5 mL) followed by extraction with EtOAc (5 mL×3). The organic layer was dried (Na$_2$SO$_4$) and concentrated in vacuo. To the resulting residue was added 2M NH$_3$ in MeOH (0.5 mL) and the solution was stirred for 1 h. The volatiles were removed in vacuo. Purification (FCC, SiO$_2$, EtOAc:DCM) afforded the title compound (24.7 mg, 47.5%). MS (ESI): mass calcd. for C$_{17}$H$_{15}$F$_2$N$_5$, 327.1; m/z found, 328.1 [M+H]$^+$. $^1$H NMR (400 MHz, CDCl$_3$) δ 10.91 (s, 1H), 8.20 (d, J=8.2 Hz, 1H), 8.12 (d, J=1.0 Hz, 1H), 7.76 (dd, J=1.9, 0.8 Hz, 1H), 7.62 (d, J=8.2 Hz, 1H), 7.59-7.53 (m, 1H), 7.30 (dd, J=8.7, 1.9 Hz, 1H), 6.66 (t, J=55.6 Hz, 1H), 3.29-2.95 (m, 1H), 1.37 (d, J=6.8 Hz, 6H).

Example 211: 5-(1,1-Difluoroethyl)-3-(1H-indazol-5-yl)-2-isopropyl-imidazo[4,5-b]pyridine

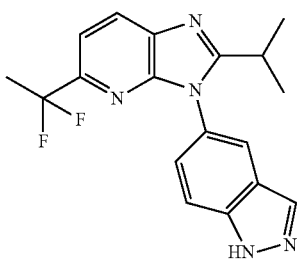 [SMILES: CC(C)c1nc2ccc(C(C)(F)F)nc2n1-c1ccc2[nH]ncc2c1]

Step A:
6-Chloro-N-methoxy-N-methyl-5-nitropicolinamide

A solution of 6-chloro-5-nitropicolinic acid (Intermediate 48, product from Step A, 3.6 g, 11 mmol), N,O-dimethylhydroxylamine hydrochloride (1.4 g, 14 mmol), TEA (4.6 mL, 33 mmol) and HATU (4.6 g, 12 mmol) in DCM (50 mL) was stirred for 4 h. The reaction was quenched with saturated NH$_4$Cl (50 mL) then extracted with DCM (50 mL×3). The organic layer was dried (Na$_2$SO$_4$) and concentrated in vacuo. Purification (FCC, SiO$_2$, EtOAc/hexanes) afforded the title compound (2.37 g, 87.6%). MS (ESI): mass calcd. for C$_8$H$_5$ClN$_3$O$_4$, 245.0; m/z found, 245.9 [M+H]$^+$. $^1$H NMR (500 MHz, CDCl$_3$) δ 8.30 (d, J=8.1 Hz, 1H), 7.73 (s, 1H), 3.82 (s, 3H), 3.37 (s, 3H).

Step B: 2-Isopropyl-N-methoxy-N-methy-3-(2-((2-(trimethylsilyl)ethoxy)methyl)-2H-indazol-5-yl)-3H-imidazo[4,5-b]pyridine-5-carboxamide A solution of 6-chloro-N-methoxy-N-methyl-5-nitropicolinamide (200 mg, 0.81 mmol) and 2-((2-(trimethylsilyl)ethoxy)methyl)-2H-indazol-5-amine (Intermediate 9, 268 mg, 1.0 mmol) in DMF (3 mL) was heated at 100° C. for 3 h. The reaction mixture was cooled down and isobutyraldehyde (111 µL, 1.2 mmol) was added to the mixture and the reaction was let stir at ambient temperature for 45 min followed by addition of sodium dithionite (532 mg, 3.05 mmol). After 16 h at 100° C., the reaction was allowed to cool, diluted with H$_2$O (25 mL), and extracted with EtOAc (25 mL×3). The organic layer was dried (Na$_2$SO$_4$) and concentrated in vacuo. Purification (FCC, SiO$_2$, EtOAc/hexanes) afforded the title compound (76 mg, 18.9%). MS (ESI): mass calcd. for C$_{21}$H$_{28}$N$_6$O$_5$Si, 494.2; m/z found, 495.1 [M+H]$^+$.

Step C: 1-(2-Isopropyl-3-(2-((2-(trimethylsilyl)ethoxy)methyl)-2H-indazol-5-yl)-3H-imidazo[4,5-b]pyridin-5-yl)ethan-1-one To a cooled solution of 2-isopropyl-N-methoxy-N-methyl-3-(2-((2-(trimethylsilyl)ethoxy)methyl)-2H-indazol-5-yl)-3H-imidazo[4,5-b]pyridine-5-carboxamide (76 mg, 0.15 mmol) in anhydrous THF (4.5 mL) at −45° C. in an acetonitrile/dry ice bath methylmagnesium bromide (3M in ether, 76.8 µL, 0.23 mmol) was added drop wise. The resulting mixture was stirred at −45° C. for 20 min. then warmed to 0° C. To the reaction mixture was added another portion of methylmagnesium bromide (3M in ether, 76.8 µL, 0.23 mmol) and the resulting solution was stirred at 0° C. for 1 h. The reaction was quenched with saturated NH$_4$Cl (5 mL) then extracted with EtOAc (5 mL×3). The organic layer was dried (Na$_2$SO$_4$) and concentrated in vacuo to give the title compound (65.8 mg, 95%).

Step D: 5-(1,1-Difluoroethyl)-2-isopropyl-3-(2-((2-(trimethylsilyl)ethoxy)methyl)-2H-indazol-5-yl)-3H-imidazo[4,5-b]pyridine To a solution of 1-(2-isopropyl-3-(2-((2-(trimethylsilyl)ethoxy)methyl)-2H-indazol-5-yl)-3H-imidazo[4,5-b]pyridin-5-yl)ethan-1-one (65 mg, 0.14 mmol) in anhydrous DCM (2 mL) at −50° C. was added DAST (38 µL, 0.29 mmol) and the resulting mixture was allowed to warm to ambient temperature after 1 h. Then another portion of DAST (76 µL 0.58 mmol) was added followed by addition of EtOH (1.7 µL, 0.029 mmol) and the resulting mixture was heated in a sealed tube at 50° C. for 2 days. The reaction mixture was concentrated in vacuo. Purification (FCC, SiO$_2$, EtOAc/hexanes) afforded the title compound (10 mg, 15%). MS (ESI): mass calcd. for C$_{24}$H$_{31}$F$_2$N$_5$OSi, 471.2; m/z found, 472.1 [M+H]$^+$.

Step E: 5-(1,1-Difluoroethyl)-3-(1H-indazol-5-yl)-2-isopropyl-3H-imidazo[4,5-b]pyridine A solution of 5-(1,1-difluoroethyl)-2-isopropyl-3-(2-((2-(trimethylsilyl)ethoxy)methyl)-2H-indazol-5-yl)-3H-imidazo[4,5-b]pyridine (10 mg, 0.021 mmol) in TFA (0.5 mL) and DCM (0.5 mL) was stirred for 1 h. Volatiles were removed by evaporation and the residue was basified by 2M NH₃ in MeOH (1 mL). The resulting solution was stirred for 1 h and volatiles were removed in vacuo. Purification (FCC, SiO₂, EtOAc:DCM) afforded the title compound (1.4 mg, 19%). MS (ESI): mass calcd. for $C_{18}H_{17}F_2N_5$, 341.1; m/z found, 342.1 [M+H]⁺. ¹H NMR (400 MHz, CDCl₃) δ 10.51 (s, 1H), 8.19-8.09 (m, 2H), 7.77 (dd, J=1.9, 0.8 Hz, 1H), 7.69-7.57 (m, 2H), 7.35 (dd, J=8.8, 1.9 Hz, 1H), 3.34-3.03 (m, 1H), 1.93 (t, J=18.5 Hz, 3H), 1.36 (d, J=6.8 Hz, 6H).

Example 212: 2,5-Bis(difluoromethyl)-3-(7-methyl-1H-indazol-5-yl)imidazo[4,5-b]pyridine

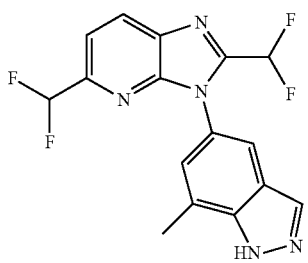 [SMILES: Cc1cc(-n2c(C(F)F)nc3ccc(C(F)F)nc32)cc2cn[nH]c12]

A solution of 6-(difluoromethyl)-N²-(7-methyl-1H-indazol-5-yl)pyridine-2,3-diamine (Intermediate 61, 50 mg, 0.17 mmol) and difluoroacetic anhydride (73 µL, 0.62 mmol) in benzene (2 mL) was stirred at 50° C. for 1 h. The reaction was basified with saturated NaHCO₃ (5 mL) and extracted with EtOAc (5 mL×3). The organic layers were dried (Na₂SO₄), filtered and concentrated in vacuo. Purification (FCC, SiO₂, EtOAc/hexanes) afforded the title compound (33 mg, 55%). MS (ESI): mass calcd. for $C_{16}H_{11}F_4N_5$, 349.1; m/z found, 350.1 [M+H]⁺. ¹H NMR (500 MHz, CDCl₃) δ 8.36 (d, J=8.4 Hz, 1H), 8.18 (s, 1H), 7.75 (d, J=8.4 Hz, 1H), 7.73 (d, J=2.1 Hz, 1H), 7.23 (dd, J=1.8, 1.0 Hz, 1H), 6.96-6.49 (m, 2H), 2.73-2.48 (m, 3H).

Example 213: 2-(2-Fluoro-4-pyridyl)-5-methyl-3-(7-methyl-1H-indazol-5-yl)imidazo[4,5-b]pyridine

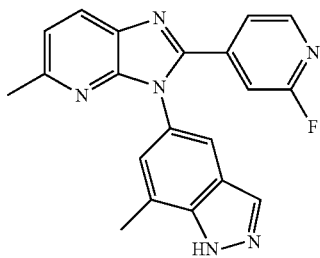 [SMILES: Cc1ccc2nc(-c3ccnc(F)c3)n(-c3cc(C)c4[nH]ncc4c3)c2n1]

The title compound was prepared in a manner analogous to Example 1. MS (ESI): mass calcd. for $C_{20}H_{15}FN_6$, 358.1; m/z found, 359.1 [M+H]⁺. ¹H NMR (400 MHz, CDCl₃) δ 8.15 (d, J=8.2 Hz, 1H), 8.11 (d, J=5.3 Hz, 1H), 7.98 (s, 1H), 7.54-7.51 (m, 1H), 7.33 (dt, J=5.3, 1.6 Hz, 1H), 7.29 (d, J=8.3 Hz, 1H), 7.16 (d, J=0.6 Hz, 1H), 7.02 (dd, J=1.8, 1.0 Hz, 1H), 2.75 (s, 3H), 2.48 (s, 3H).

Example 214: N-(2-Fluoroethyl)-2-isopropyl-N-methyl-3-(7-methyl-1H-indazol-5-yl)-5-(trifluoromethyl)imidazo[4,5-b]pyridin-7-amine

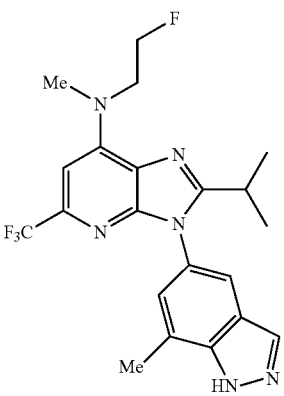 [SMILES: Cc1cc(-n2c(C(C)C)nc3c(N(C)CCF)cc(C(F)(F)F)nc32)cc2cn[nH]c12]

Step A. 2-((2-Chloro-3-nitro-6-(trifluoromethyl)pyridin-4-yl)(methyl)amino)ethanol To 2,4-dichloro-3-nitro-6-(trifluoromethyl)pyridine (261 mg, 1 mmol) in EtOH (5 mL) at 0° C. was added drop-wise a solution of 2-(methylamino)ethanol (90 mg, 1.2 mmol) in EtOH (1 mL). The mixture was stirred at 0° C. for 20 min followed by the addition of TEA (0.3 mL). The reaction mixture was concentrated under reduced pressure. Purification (FCC, SiO₂, 0 to 50% EtOAc in hexanes) afforded the title compound as an orange thick oil (203 mg, 68%). MS (ESI): mass calcd. for $C_9H_9ClF_3N_3O_3$, 299.0; m/z found, 300.1 [M+H]⁺.

Step B. 2-Chloro-N-(2-fluoroethyl)-N-methyl-3-nitro-6-(trifluoromethyl)pyridin-4-amine To 2-((2-chloro-3-nitro-6-(trifluoromethyl)pyridin-4-yl)(methyl)amino)ethanol (236 mg, 0.79 mmol) in CH₂Cl₂ (4 mL) at −78° C. was added dropwise a solution of DAST (0.193 mL) in CH₂Cl₂ (1 mL). The reaction was allowed to warm to rt and the stirring was continued for 15 h at rt. To the reaction mixture was added a solution of TEA (0.45 mL) in CH₂Cl₂ (2 mL). The mixture was concentrated under reduced pressure. Purification (FCC, SiO₂, 0 to 50% EtOAc in hexanes) afforded the title compound as a yellow wax (162 mg, 68%). MS (ESI): mass calcd. for $C_9H_5ClF_4N_3O_2$, 301.0; m/z found, 302.1 [M+H]⁺.

Step C. N⁴-(2-Fluoroethyl)-N⁴-methyl-N²-(7-methyl-1H-indazol-5-yl)-3-nitro-6-(trifluoromethyl)pyridine-2,4-diamine A mixture of 2-chloro-N-(2-fluoroethyl)-N-methyl-3-nitro-6-(trifluoromethyl)pyridin-4-amine (70 mg, 0.23 mmol), 7-methyl-1H-indazol-5-amine (51 mg, 0.35 mmol), Cs₂CO₃ (113 mg, 0.35 mmol), and BrettPhos Palladacycle 3rd Generation (21 mg, 0.023 mmol) in 1,4-dioxane in a vial was flushed with N₂ and sealed. It was heated at 120° C. for 2 h and diluted with EtOAc (30 mL), washed with water (2×30 mL), dried (Na₂SO₄) and concentrated under reduced pressure. Purification (CFF, SiO₂, 0 to 70% EtOAc in hexanes)

afforded the title compound an orange solid (54 mg, 56%). MS (ESI): mass calcd. for $C_{17}H_{16}F_4N_6O_2$, 412.1; m/z found, 413.2 $[M+H]^+$.

Step D. $N^4$-(2-Fluoroethyl)-$N^4$-methyl-$N^2$-(7-methyl-1H-indazol-5-yl)-6-(trifluoromethyl)pyridine-2,3,4-triamine To a solution of $N^4$-(2-Fluoroethyl)-$N^4$-methyl-$N^2$-(7-methyl-1H-indazol-5-yl)-3-nitro-6-(trifluoromethyl)pyridine-2,4-diamine (120 mg, 0.29 mmol) in methanol was added 10% Pd/C (34 mg, 0.03 mmol). The flask was purged by hydrogen three times. The mixture was stirred under hydrogen atmosphere for 1 h (hydrogen balloon). The reaction mixture was filtered and the filtrate was collected and concentrated under reduced pressure to afford the title compound as a light yellow wax (105 mg, 94%). MS (ESI): mass calcd. for $C_{17}H_{18}F_4N_6$, 382.2; m/z found, 383.3 $[M+H]^+$.

Step E. N-(2-Fluoroethyl)-2-isopropyl-N-methyl-3-(7-methyl-1H-indazol-5-yl)-5-(trifluoromethyl)-3H-imidazo[4,5-b]pyridin-7-amine A mixture of $N^4$-(2-Fluoroethyl)-$N^4$-methyl-$N^2$-(7-methyl-1H-indazol-5-yl)-6-(trifluoromethyl)pyridine-2,3,4-triamine (17 mg, 0.044 mmol), isobutyric anhydride (50 mg, 0.31 mmol), and isobutyric acid (0.5 mL) was heated at 120° C. for 30 min in a microwave reactor. The crude product was subjected to $C_{18}$ HPLC purification (0.05% TFA buffer, 5% to 95% MeCN in water) to afford the title compound as a white solid (4 mg, 21%). MS (ESI): mass calcd. for $C_{21}H_{22}F_4N_6$, 434.2; m/z found, 435.2 $[M+H]^+$. $^1$H NMR (400 MHz, $CD_3OD$) δ 7.97 (s, 1H), 7.47 (s, 1H), 6.96-6.91 (m, 1H), 6.56 (s, 1H), 4.53 (t, J=4.8 Hz, 1H), 4.43 (t, J=4.8 Hz, 1H), 4.37 (t, J=4.8 Hz, 1H), 2.85 (dt, J=13.6, 6.8 Hz, 1H), 2.45 (d, J=0.9 Hz, 3H), 1.73 (s, 2H), 1.06 (d, J=6.8 Hz, 6H).

Example 215: 5-[2-(2-Fluoro-4-pyridyl)-5-(trifluoromethyl)imidazo[4,5-b]pyridin-3-yl]indoline-2,3-dione

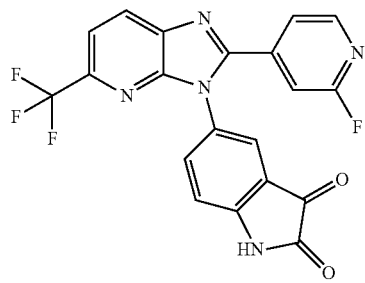 [SMILES: O=C1Nc2ccc(-n3c(-c4ccnc(F)c4)nc4ccc(C(F)(F)F)nc43)cc2C1=O]

A mixture of 5-((3-amino-6-(trifluoromethyl)pyridin-2-yl)amino)indolin-2-one (Intermediate 46, 100 mg, 0.32 mmol), 2-fluoroisonicotinaldehyde (48.7 mg, 0.39 mmol), copper(II) acetate (29 mg, 0.162 mmol), and acetic acid (4 mL) was stirred at 40° C. for 15 h. The volatiles were removed under reduced pressure and the residue was diluted with 30 mL of EtOAc. It was washed with saturated aqueous $NaHCO_3$ (2×30 mL), dried ($Na_2SO_4$), and concentrated under reduced pressure. The crude product was purified by silica chromatography (0 to 90% EtOAc in hexanes) to afford the title compound as brown solid (14 mg, 10%). MS (ESI): mass calcd. for $C_{20}H_9F_4N_5O_2$, 427.1; m/z found, 428.1 $[M+H]^+$. $^1$H NMR (400 MHz, $CDCl_3$) δ 8.41 (dd, J=8.4, 2.5 Hz, 1H), 8.27 (dd, J=5.2, 2.1 Hz, 1H), 7.89-7.82 (m, 1H), 7.74-7.62 (m, 1H), 7.53-7.32 (m, 3H), 7.10 (dd, J=18.9, 8.2 Hz, 1H).

Example 216: Methyl 3-[3-(2,3-dioxoindolin-5-yl)-5-(trifluoromethyl)imidazo[4,5-b]pyridin-2-yl]propanoate

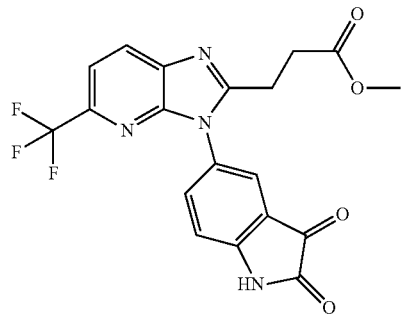 [SMILES: COC(=O)CCc1nc2ccc(C(F)(F)F)nc2n1-c1ccc2c(c1)C(=O)C(=O)N2]

A mixture of 5-((3-amino-6-(trifluoromethyl)pyridin-2-yl)amino)indolin-2-one (Intermediate 46, 154 mg, 0.5 mmol), methyl 4-oxobutanoate (69.6 mg, 0.6 mmol), copper (II) acetate (45.4 mg, 0.25 mmol), and acetic acid (4 mL) was stirred at rt for 24 h. The volatiles were removed under reduced pressure and the residue was diluted with 30 mL of EtOAc. It was washed with saturated aqueous $NaHCO_3$ (2×30 mL) and dried ($Na_2SO_4$). Purification (FCC, $SiO_2$, 0 to 90% EtOAc in hexanes) afforded the title compound as brown solid (38 mg, 18%). MS (ESI): mass calcd. for $C_{19}H_{13}F_3N_4O_4$, 418.1; m/z found, 419.1$[M+H]^+$. $^1$H NMR (400 MHz, $CDCl_3$) δ 9.48 (s, 1H), 8.15 (d, J=8.3 Hz, 1H), 7.79-7.57 (m, 3H), 7.14 (d, J=8.3 Hz, 1H), 3.66 (s, 3H), 3.24-2.94 (m, 4H).

Example 217: 2-(2-Fluoro-4-pyridyl)-3-(7-methyl-1H-indazol-5-yl)-5-(trifluoromethyl)imidazo[4,5-b]pyridine

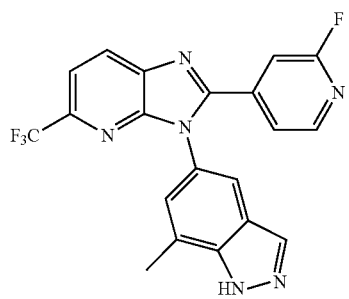 [SMILES: Cc1cc(-n2c(-c3ccnc(F)c3)nc3ccc(C(F)(F)F)nc32)cc2cn[nH]c12]

Step A: 2-Fluoro-N-(2-((7-methyl-1H-indazol-5-yl)amino)-6-(trifluoromethyl)pyridin-3-yl)isonicotinamide To a solution of $N^2$-(7-methyl-1H-indazol-5-yl)-6-(trifluoromethyl)pyridine-2,3-diamine (Intermediate 55, 150 mg, 0.49 mmol) in a mixture of DCM (1.5 mL) and THF (1.5 mL) and cooled to 0° C. was added 2-fluoroisonicotinoyl chloride (1.4 mL, 0.35 M in DCM, 0.49 mmol) to produce a dark brown solution. After 70 minutes, the reaction was diluted with $H_2O$ followed by sat. aq. $NaHCO_3$ and the aqueous layer was extracted with DCM (×3). The organic layers were combined, dried with $MgSO_4$, filtered, and concentrated in vacuo to produce a brown foam (147 mg) which was used without further purification. MS (ESI): mass calcd. for $C_{20}H_{14}F_4N_6O$, 430.1 m/z found, 431.1 [M+H]$^+$.

Step B. 2-(2-Fluoro-4-pyridyl)-3-(7-methyl-1H-indazol-5-yl-5-(trifluoromethyl)imidazo[4,5-b]pyridine Crude 2-fluoro-N-(2-((7-methyl-1H-indazol-5-yl)amino)-6-(trifluoromethyl)pyridin-3-yl)isonicotinamide (129 mg) was dissolved in AcOH (3.5 mL) and heated to 80° C. After 100 minutes, the reaction was concentrated in vacuo, and the residue dissolved in DCM. Saturated $NaHCO_3$ solution was then added and the aqueous layer was extracted with DCM (×3). The combined organic layers dried with $MgSO_4$, filtered, and concentrated in vacuo to produce a light orange film (111 mg). The resulting residue was purified by reverse phase chromatography (0.05% TFA in $H_2O$/MeCN) to provide a colourless solid which was free based (DCM/saturated $NaHCO_3$ solution) to yield the compound (8.2 mg). MS (ESI): mass calcd. for $C_{20}H_{12}F_4N_6$, 412.1; m/z found, 412.9 [M+H]$^+$. $^1$H NMR (400 MHz, CDCl$_3$) δ 10.84 (br s, 1H), 8.38 (d, J=8.4 Hz, 1H), 8.17 (d, J=5.3 Hz, 1H), 8.04 (s, 1H), 7.81 (d, J=8.3 Hz, 1H), 7.58-7.56 (m, 1H), 7.32-7.29 (m, 1H), 7.24-7.22 (m, 1H), 7.08-7.05 (m, 1H), 2.54 (s, 3H). $^{19}$F NMR (376 MHz, CDCl$_3$) δ −65.54 (s, 3F), −65.58−−65.60 (m, 1F).

Example 218: 3-(7-Chloro-1H-indazol-5-yl)-7-(2-fluoroethoxy)-2,5-bis(trifluoromethyl)imidazo[4,5-b]pyridine

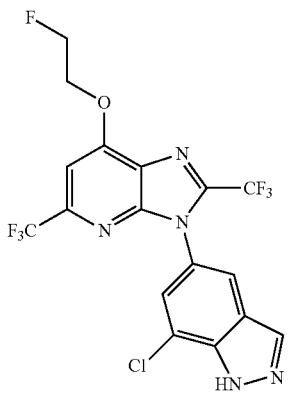 [SMILES: FCCOc1cc(C(F)(F)F)nc2c1nc(C(F)(F)F)n2-c1cc(Cl)c2[nH]ncc2c1]

Step A. 2-Chloro-4-(2-fluoroethoxy)-3-nitro-6-(trifluoromethyl)pyridine

To a solution of 2-fluoroethan-1-ol (22.5 μL, 0.38 mmol) in DMF (1 mL) was added NaH (24.5 mg, 0.61 mmol, 60% in mineral oil). After two minutes, 2,4-dichloro-3-nitro-6-(trifluoromethyl)pyridine (100 mg, 0.38 mmol) was added in a single portion and the reaction mixture left to stir at ambient temperature. After 80 minutes, the reaction was quenched with saturated $NH_4Cl$ solution and extracted with EtOAc (×4). The combined organic layers were dried with $MgSO_4$, filtered, and concentrated in vacuo to produce the title compound (117 mg) which was used without further purification.

Step B. 3-(7-Chloro-1H-indazol-5-yl)-7-(2-fluoroethoxy)-2,5-bis(trifluoromethyl)imidazo[4,5-b]pyridine To a solution of 2-chloro-4-(2-fluoroethoxy)-3-nitro-6-(trifluoromethyl)pyridine (55 mg) in DMF (2 mL) was added 7-chloro-1H-indazol-5-amine (48 mg, 0.29 mmol) and the reaction was heated to 80° C. for 85 min. DIEA (0.05 mL) was then added and the heating continued for an additional 85 min. before $Na_2O_4S_2$ (150 mg, 0.86 mmol) and $H_2O$ (0.5 mL) were added. After 70 minutes, the reaction was allowed to cool to ambient temperature. The reaction was diluted with $H_2O$ and the aqueous layer extracted with EtOAc (×3). The organic layers were combined, washed with 5% LiCl solution, brine, dried with $MgSO_4$, filtered, and concentrated in vacuo. The resulting residue was dissolved in TFA (4 mL) and heated to reflux overnight. The reaction mixture was then concentrated in vacuo and the residue dissolved in EtOAc. Saturated $NaHCO_3$ solution/solid $NaHCO_3$ was then added and the aqueous layer was extracted with EtOAc (×3). The combined organic layers were washed with brine, dried with $MgSO_4$, filtered, and concentrated in vacuo. Purification (FCC, $SiO_2$, 0-50% EtOAc in hexanes) afforded the title compound (3.3 mg). MS (ESI): mass calcd. for $C_{17}H_9ClF_7N_5O$, 467.0; m/z found, 468.0 [M+H]$^+$. $^1$H NMR (400 MHz, CDCl$_3$) δ 8.18 (s, 1H), 7.73 (d, J=1.6 Hz, 1H), 7.39 (d, J=1.7 Hz, 1H), 7.32 (s, 1H), 5.08-5.05 (m, 1H), 5.01-4.96 (m, 2H), 4.88-4.84 (m, 1H).

Example 219: (E)-3-(5-(2,5-Bis(trifluoromethyl)-3H-imidazo[4,5-b]pyridin-3-yl)-1H-indazol-7-yl)prop-2-en-1-ol

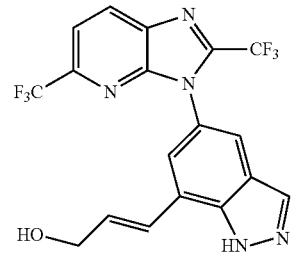 [SMILES: OC/C=C/c1cc(-n2c(C(F)(F)F)nc3ccc(C(F)(F)F)nc32)cc2cn[nH]c12]

Step A. (E)-3-(7-(3-((tetrahydro-2H-pyran-2-yl)oxy)prop-1-en-1-yl)-1H-indazol-5-yl)-2,5-bis(trifluoromethyl)-3H-imidazo[4,5-b]pyridine In a microwave vial, was added 3-(7-bromo-1H-indazol-5-yl)-2,5-bis(trifluoromethyl)-3H-imidazo[4,5-b]pyridine (Example 187, 358 mg, 0.80 mmol), 4,4,5,5-tetramethyl-2-(3-((tetrahydro-2H-pyran-2-yl)oxy)prop-1-en-1-yl)-1,3,2-dixoaborolane (320 mg, 1.19 mmol), Pd(PPh$_3$)$_4$ (92 mg, 0.080 mmol), 1M $Na_2CO_3$ solution (3.2 mL), and dioxane (4.8 mL). The vial was capped and the reaction mixture heated at 105° C. for 30 min under microwave irradiation.

The reaction mixture was then concentrated in vacuo and the resulting residue diluted with EtOAc/water. The layers were separated and the organic layer was washed with brine, dried with Na$_2$SO$_4$, filtered, and concentrated in vacuo to produce the title compound which was used without further purification.

Step B. (E)-3-(5-(2,5-Bis(trifluoromethyl)-3H-imidazo[4,5-b]pyridin-3-yl)-1H-indazol-7-yl)prop-2-en-1-ol Crude (E)-3-(7-(3-((tetrahydro-2H-pyran-2-yl)oxy)prop-1-en-1-yl)-1H-indazol-5-yl)-2,5-bis(trifluoromethyl)-3H-imidazo[4,5-b]pyridine from Step A was dissolved in MeOH (6 mL) and 6M HCl (0.6 mL) was added. After 10 min, the reaction was concentrated in vacuo and the resulting residue was diluted with EtOAc/saturated NaHCO$_3$ solution. The layers were separated and the organic layer was washed with brine, dried with Na$_2$SO$_4$, filtered and concentrated in vacuo. Purification (FCC, SiO$_2$, 0-100% EtOAc in hexanes) afforded the title compound (105 mg, 0.25 mmol, 31%). MS (ESI): mass calcd. for C$_{18}$H$_{11}$F$_6$N$_5$O, 427.1; m/z found, 428.1 [M+H]$^+$. $^1$H NMR (400 MHz, CDCl$_3$) δ 11.15 (br.s, 1H), 8.45 (d, J=8.4 Hz, 1H), 8.18 (s, 1H), 7.84 (d, J=8.4 Hz, 1H), 7.75-7.72 (m, 1H), 7.37 (d, J=1.8 Hz, 1H), 6.98-6.91 (m, 1H), 6.55 (dt, J=16.0, 5.1 Hz, 1H), 4.45 (dd, J=5.5, 1.6 Hz, 2H).

Example 220: 3-(5-(2,5-Bis(trifluoromethyl)-3H-imidazo[4,5-b]pyridin-3-yl)-1H-indazol-7-yl)propan-1-ol

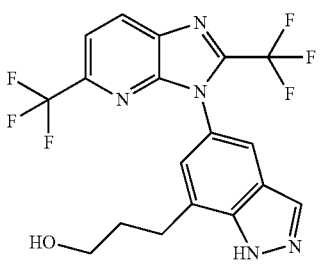 [SMILES: OCCCc1cc(-n2c(C(F)(F)F)nc3ccc(C(F)(F)F)nc32)cc2cn[nH]c12]

A solution of (E)-3-(5-(2,5-bis(trifluoromethyl)-3H-imidazo[4,5-b]pyridin-3-yl)-1H-indazol-7-yl)prop-2-en-1-ol (Example 219, 18 mg, 0.04 mmol) in MeOH (1.2 mL) was subjected to H-Cube hydrogenation (10% Pd/C, H$_2$ 60 bar) at ambient temperature and a flow rate of 1 mL/min. After a single pass the solvent was removed in vacuo. Purification (FCC, SiO$_2$, 0-100% EtOAc in hexanes) afforded the title compound (9 mg, 0.02 mmol, 50%) MS (ESI): mass calcd. for C$_{18}$H$_{13}$F$_6$N$_5$O, 429.1; m/z found, 430.1 [M+H]$^+$. $^1$H NMR (400 MHz, CDCl$_3$) δ 8.42 (d, J=8.4 Hz, 1H), 8.22 (br.s, 1H), 7.81 (d, J=8.4 Hz, 1H), 7.74 (d, J=1.5 Hz, 1H), 7.21-7.19 (m, 1H), 3.78 (t, J=5.7 Hz, 2H), 3.16 (t, J=6.9 Hz, 2H), 2.10-2.02 (m, 2H) and 3-(7-propyl-1H-indazol-5-yl)-2,5-bis(trifluoromethyl)-3H-imidazo[4,5-b]pyridine (Example 221, 3 mg, 0.007 mmol, 17%).

Example 221: 3-(7-Propyl-1H-indazol-5-yl)-2,5-bis(trifluoromethyl)-3H-imidazo[4,5-b]pyridine

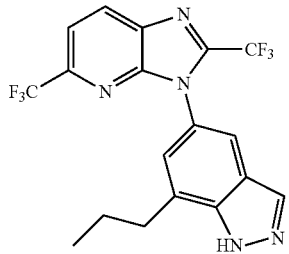 [SMILES: CCCc1cc(-n2c(C(F)(F)F)nc3ccc(C(F)(F)F)nc32)cc2cn[nH]c12]

The title compound was prepared as a by-product in Example 220. MS (ESI): mass calcd. for C$_{18}$H$_{13}$F$_6$N$_5$, 413.1; m/z found, 414.1 [M+H]$^+$. $^1$H NMR (400 MHz, CDCl$_3$) δ 10.51 (br s, 1H), 8.44 (d, J=8.4 Hz, 1H), 8.16 (s, 1H), 7.82 (d, J=8.4 Hz, 1H), 7.70 (d, J=1.8 Hz, 1H), 7.19-7.14 (m, 1H), 2.89 (t, J=7.5 Hz, 2H), 1.81 (h, J=7.4 Hz, 2H), 1.01 (t, J=7.3 Hz, 3H).

Example 222: (E)-3-(3-(7-Methyl-1H-indazol-5-yl)-2-(trifluoromethyl)-3H-imidazo[4,5-b]pyridin-5-yl)prop-2-en-1-ol

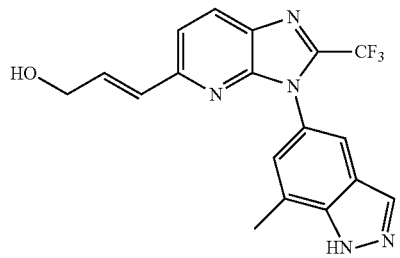 [SMILES: Cc1cc(-n2c(C(F)(F)F)nc3ccc(/C=C/CO)nc32)cc2cn[nH]c12]

Step A. (E)-3-(7-Methyl-1H-indazol-5-yl)-5-(3-((tetrahydro-2H-pyran-2-yl)oxy)prop-1-en-1-yl)-2-(trifluoromethyl)-3H-imidazo[4,5-b]pyridine In a microwave vial, was added 5-bromo-3-(7-methyl-1H-indazol-5-yl)-2-(trifluoromethyl)-3H-imidazo[4,5-b]pyridine (Intermediate 62, 65 mg, 0.16 mmol), 4,4,5,5-tetramethyl-2-(3-((tetrahydro-2H-pyran-2-yl)oxy)prop-1-en-1-yl)-1,3,2-dixoaborolane (66 mg, 0.25 mmol), Pd(PPh$_3$)$_4$ (19 mg, 0.016 mmol), 1M Na$_2$CO$_3$ solution (0.7 mL), and dioxane (1 mL). The vial was capped and the reaction mixture heated at 105° C. for 30 min under microwave irradiation. The reaction mixture was then concentrated in vacuo and the resulting residue diluted with EtOAc/H$_2$O. The layers were separated and the organic layer was washed with brine, dried with Na$_2$SO$_4$, filtered, and concentrated in vacuo. Purification (FCC, SiO$_2$, 0-100% EtOAc in hexanes) afforded the title compound (50 mg, 67%).

Step B. (E)-3-(3-(7-Methyl-1H-indazol-5-yl)-2-(trifluoromethyl)-3H-imidazo[4,5-b]pyridin-5-yl)prop-2-en-1-ol (E)-3-(7-methyl-1H-indazol-5-yl)-5-(3-((tetrahydro-2H-pyran-2-yl)oxy)prop-1-en-1-yl)-2-(trifluoromethyl)-3H- imidazo[4,5-b]pyridine (50 mg) was dissolved in MeOH (3.6 mL) and 6M HCl (0.4 mL) was added. After 2 h the reaction was concentrated in vacuo and the resulting residue was diluted with EtOAc/saturated NaHCO$_3$ solution. The layers were separated and the organic layer was washed with brine, dried with Na$_2$SO$_4$, filtered and concentrated in vacuo to yield the title compound (38 mg). MS (ESI): mass calcd. for $C_{18}H_{14}F_3N_5O$, 373.1; m/z found, 374.1 [M+H]$^+$. $^1$H NMR (400 MHz, CDCl$_3$) δ 10.41 (br s, 1H), 8.21-8.15 (m, 2H), 7.71-7.68 (m, 1H), 7.46 (d, J=8.4 Hz, 1H), 7.19 (s, 1H), 6.80-6.76 (m, 2H), 4.35-4.33 (m, 2H), 2.62 (s, 3H).

Example 223: 3-(3-(7-Methyl-1H-indazol-5-yl)-2-(trifluoromethyl)-3H-imidazo[4,5-b]pyridin-5-yl)propan-1-ol

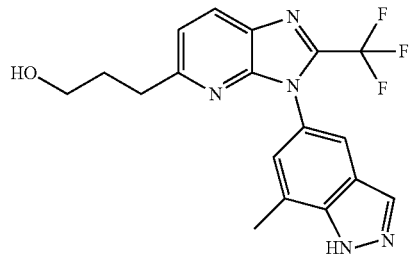 [SMILES: Cc1cc(-n2c(C(F)(F)F)nc3ccc(CCCO)nc32)cc2cn[nH]c12]

A solution of (E)-3-(3-(7-methyl-1H-indazol-5-yl)-2-(trifluoromethyl)-3H-imidazo[4,5-b]pyridin-5-yl)prop-2-en-1-ol (Example 222, 36 mg, 0.09 mmol) in MeOH (2.6 mL) was subjected to H-Cube hydrogenation (10% Pd/C, H$_2$ 60 bar) at ambient temperature and a flow rate of 1 mL/min. After a single pass the solvent was removed in vacuo and the resulting residue was purified via reverse phase chromatography (0.05% TFA in H$_2$O/MeCN). The desired fractions were concentrated in vacuo and the resulting solids were free based (EtOAc/saturated NaHCO$_3$ solution) to yield (16 mg, 44%) of the title compound. MS (ESI): mass calcd. for $C_{18}H_{16}F_3N_5O$, 375.1; m/z found, 376.1 [M+H]$^+$. $^1$H NMR (400 MHz, CDCl$_3$) δ 8.21 (d, J=8.4 Hz, 1H), 8.16-8.11 (m, 1H), 7.70-7.66 (m, 1H), 7.34 (d, J=8.3 Hz, 1H), 7.14 (s, 1H), 3.65 (t, J=5.7 Hz, 2H), 3.09 (t, J=6.7 Hz, 2H), 2.46 (s, 3H), 2.02-1.94 (m, 2H). and 3-(7-methyl-1H-indazol-5-yl)-5-propyl-2-(trifluoromethyl)-3H-imidazo[4,5-b]pyridine (Example 224, 5 mg, 14%).

Example 224: 3-(7-Methyl-1H-indazol-5-yl)-5-propyl-2-(trifluoromethyl)-3H-imidazo[4,5-b]pyridine

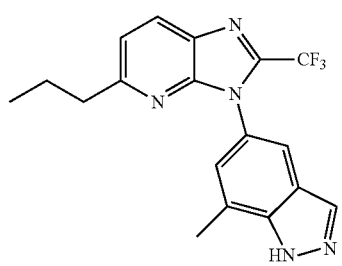 [SMILES: CCCc1ccc2nc(C(F)(F)F)n(-c3cc(C)c4[nH]ncc4c3)c2n1]

The title compound was prepared as a by-product in Example 223. MS (ESI): mass calcd. for $C_{18}H_{16}F_3N_5$, 359.1; m/z found, 360.1 [M+H]$^+$. $^1$H NMR (400 MHz, CDCl$_3$) δ 8.19 (d, J=8.3 Hz, 1H), 8.05 (br s, 1H), 7.63-7.59 (m, 1H), 7.32 (d, J=8.3 Hz, 1H), 7.10 (br s, 1H), 2.96-2.85 (m, 2H), 2.53 (s, 3H), 1.82-1.70 (m, 2H), 0.94 (t, J=7.4 Hz, 3H).

Example 225: 4-[3-(1H-Indazol-5-yl)-5-(trifluoromethyl)imidazo[4,5-b]pyridin-2-yl]pyridin-2-ol

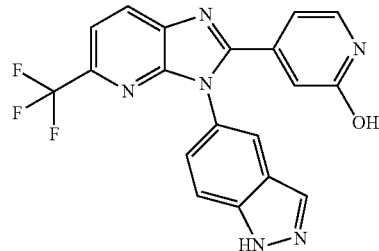 [SMILES: Oc1cc(-c2nc3ccc(C(F)(F)F)nc3n2-c2ccc3[nH]ncc3c2)ccn1]

The title compound was obtained as a by-product from the synthesis of 2-(2-fluoro-4-pyridyl)-3-(1H-indazol-5-yl)-5-(trifluoromethyl)imidazo[4,5-b]pyridine (Example 165). (11 mg, 6.8%). MS (ESI): mass calcd. for $C_{19}H_{11}F_3N_6O$, 396.1; m/z found, 397.1 [M+H]$^+$. $^1$H NMR (400 MHz, CDCl$_3$) δ 8.36 (d, J=8.3 Hz, 1H), 8.19 (d, J=5.3 Hz, 1H), 8.15 (s, 1H), 7.82-7.76 (m, 2H), 7.65 (d, J=8.6 Hz, 1H), 7.37-7.29 (m, 2H), 7.22 (s, 1H).

Example 226: 3-(1H-Indazol-5-yl)-5-(trifluoromethyl)imidazo[4,5-b]pyridine

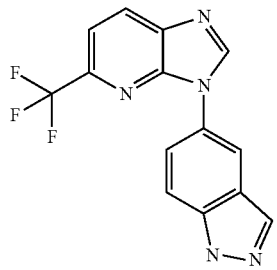 [SMILES: FC(F)(F)c1ccc2ncn(-c3ccc4[nH]ncc4c3)c2n1]

The title compound was recovered as a by-product in synthesis of Example 165, when using N, N-dimethylformamide as the reaction solvent. MS(ESI): mass calcd. for $C_{14}H_8F_3N_5$, 303.1; m/z found, 304.1, [M+H]$^+$. $^1$H NMR (400 MHz, Acetonitrile-d$_3$) δ 8.67 (s, 1H), 8.40-8.33 (m, 1H), 8.23-8.12 (m, 2H), 7.86-7.72 (m, 3H).

Example 227: 3-(7-Chloro-1H-indazol-5-yl)-2-cyclopropyl-5-(difluoromethyl)imidazo[4,5-b]pyridine

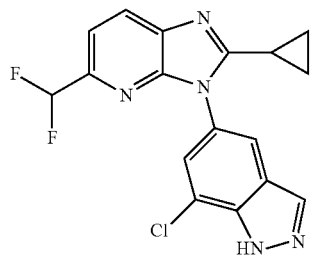 [SMILES: FC(F)c1ccc2nc(C3CC3)n(-c3cc(Cl)c4[nH]ncc4c3)c2n1]

The title compound was prepared in a manner analogous to Example 1. MS (ESI): mass calcd. for $C_{17}H_{12}ClF_2N_5$, 359.1; m/z found, 360.1 [M+H]+. 1H NMR (400 MHz, CDCl3) δ 11.04 (s, 1H), 8.13 (s, 1H), 8.10 (d, J=8.2 Hz, 1H), 7.76 (d, J=1.6 Hz, 1H), 7.62 (d, J=8.2 Hz, 1H), 7.46 (d, J=1.7 Hz, 1H), 6.89-6.56 (m, 1H), 1.91-1.80 (m, 1H), 1.44-1.36 (m, 2H), 1.17-1.06 (m, 2H).

Example 228: 5-(Difluoromethyl)-2-(4-fluorophenyl)-3-(7-methyl-1H-indazol-5-yl)imidazo[4,5-b]pyridine

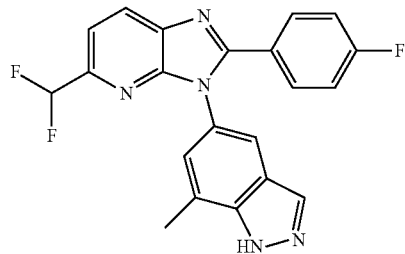 [SMILES: Cc1cc(-n2c(-c3ccc(F)cc3)nc3ccc(C(F)F)nc32)cc2cn[nH]c12]

The title compound was prepared in a manner analogous to Example 1, using 2-chloro-6-(difluoromethyl)-3-nitropyridine (Intermediate 48, product from Step E). MS (ESI): mass calcd. for $C_{21}H_{14}F_3N_5$, 393.1; m/z found, 394.1 [M+H]+. 1H NMR (500 MHz, CDCl3) δ 10.45 (s, 1H), 8.26 (d, J=8.2 Hz, 1H), 8.10 (s, 1H), 7.69 (d, J=8.3 Hz, 1H), 7.66-7.56 (m, 3H), 7.11 (dd, J=1.9, 1.0 Hz, 1H), 7.00 (dd, J=9.0, 8.3 Hz, 2H), 6.68 (t, J=55.5 Hz, 1H), 2.73-2.41 (m, 3H).

Example 229: 3-(7-Chloro-1H-indazol-5-yl)-5-(difluoromethyl)-2-(4-fluorophenyl)imidazo[4,5-b]pyridine

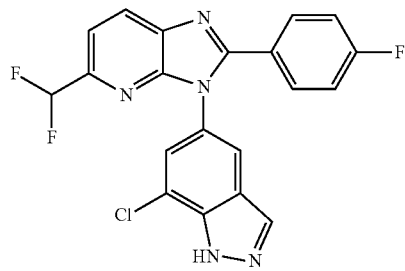 [SMILES: Fc1ccc(-c2nc3ccc(C(F)F)nc3n2-c2cc(Cl)c3[nH]ncc3c2)cc1]

The title compound was prepared in a manner analogous to Example 1, using 2-chloro-6-(difluoromethyl)-3-nitropyridine (Intermediate 48, product from Step E). MS (ESI): mass calcd. for $C_{20}H_{11}ClF_3N_5$, 413.1; m/z found, 414.1 [M+H]+. 1H NMR (400 MHz, CDCl3) δ 10.43 (s, 1H), 8.26 (d, J=8.3 Hz, 1H), 8.19 (s, 1H), 7.75-7.57 (m, 3H), 7.40 (d, J=1.7 Hz, 1H), 7.10-6.97 (m, 2H), 6.65 (t, J=55.4 Hz, 1H).

Example 230: 6-[7-Morpholino-2,5-bis(trifluoromethyl)imidazo[4,5-b]pyridin-3-yl]-3H-1,3-benzothiazol-2-one

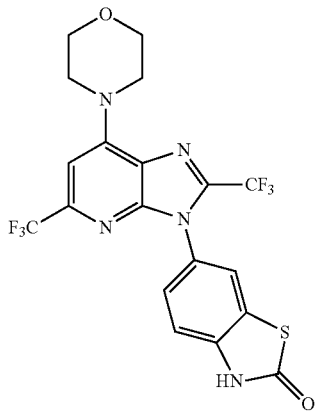 [SMILES: O=c1[nH]c2ccc(-n3c(C(F)(F)F)nc4c(N5CCOCC5)cc(C(F)(F)F)nc43)cc2s1]

The title compound was made in a manner analogous to Example 62. MS (ESI): mass calcd. for $C_{19}H_{13}F_6N_5O_2S$, 489.1; m/z found, 490.0 [M+H]+. 1H NMR (500 MHz, DMSO-d6) δ 12.28 (s, 1H), 7.88 (d, J=2.1 Hz, 1H), 7.48 (dd, J=8.4, 2.2 Hz, 1H), 7.31 (d, J=8.5 Hz, 1H), 7.12 (s, 1H), 4.13-4.05 (m, 4H), 3.85-3.77 (m, 4H).

Example 231: 4-[3-(1H-Indazol-5-yl)-2,5-bis(trifluoromethyl)imidazo[4,5-b]pyridin-7-yl]morpholine

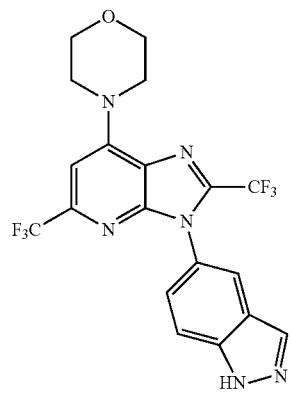 [SMILES: FC(F)(F)c1cc(N2CCOCC2)c2nc(C(F)(F)F)n(-c3ccc4[nH]ncc4c3)c2n1]

The title compound was made in a manner analogous to Example 62. MS (ESI): mass calcd. for $C_{19}H_{14}F_6N_6O$, 456.1; m/z found, 457.1 [M+H]+. 1H NMR (500 MHz, CDCl3) δ 7.92 (d, J=1.0 Hz, 1H), 7.67 (d, J=1.8 Hz, 1H), 7.29-7.27 (m, 1H), 7.17 (dd, J=8.7, 1.9 Hz, 1H), 6.92 (s, 1H), 4.15-4.12 (m, 4H), 3.98-3.94 (m, 4H).

Example 232: 2-(1,1-Difluoropropyl)-3-(1H-indazol-5-yl)-5-(trifluoromethyl)imidazo[4,5-b]pyridine

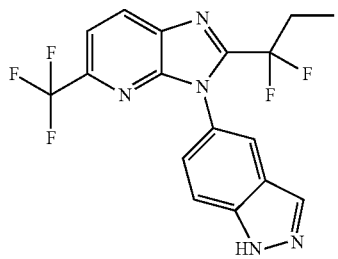 [SMILES: CCC(F)(F)c1nc2ccc(C(F)(F)F)nc2n1-c1ccc2[nH]ncc2c1]

The title compound was made in a manner analogous to Example 88. MS (ESI): mass calcd. for $C_{17}H_{12}F_5N_5$, 381.1; m/z found, 382.0 [M+H]$^+$. $^1$H NMR (400 MHz, CD$_3$OD) δ 8.43 (d, J=8.4 Hz, 1H), 8.20 (d, J=1.0 Hz, 1H), 7.96 (d, J=2.0 Hz, 1H), 7.85 (d, J=8.3 Hz, 1H), 7.74 (d, J=8.8 Hz, 1H), 7.49-7.44 (m, 1H), 2.51-2.33 (m, 2H), 1.08 (t, J=7.5 Hz, 3H).

Example 233: 6-[2-(1,1,2,2,2-Pentafluoroethyl)-5-(trifluoromethyl)imidazo[4,5-b]pyridin-3-yl]-3H-1,3-benzothiazol-2-one

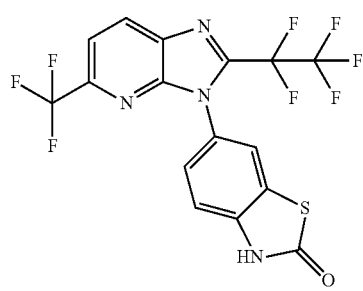 [SMILES: O=c1[nH]c2ccc(-n3c(C(F)(F)C(F)(F)F)nc4ccc(C(F)(F)F)nc43)cc2s1]

The title compound was prepared in a manner analogous to Example 88. MS (ESI): mass calcd. for $C_{16}H_6F_8N_4OS$, 454.0; m/z found, 454.9 [M+H]$^+$. $^1$H NMR (400 MHz, CD$_3$OD) δ 8.53 (d, J=8.5 Hz, 1H), 7.91 (d, J=8.4 Hz, 1H), 7.73 (d, J=2.1 Hz, 1H), 7.48-7.42 (m, 1H), 7.38-7.33 (m, 1H).

Example 234: 6-[2-(Difluoromethyl)-5-(trifluoromethyl)imidazo[4,5-b]pyridin-3-yl]-3H-1,3-benzothiazol-2-one

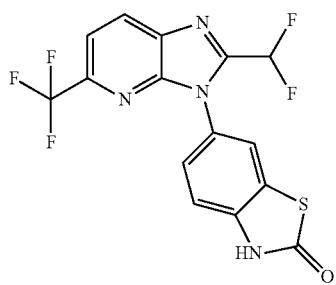

The title compound was prepared in a manner analogous to Example 88. MS (ESI): mass calcd. for $C_{15}H_7F_5N_4OS$, 386.0; m/z found, 386.9 [M+H]$^+$. $^1$H NMR (400 MHz, CD$_3$OD) δ 8.45 (d, J=8.4 Hz, 1H), 7.87 (d, J=8.4 Hz, 1H), 7.72 (d, J=2.1 Hz, 1H), 7.49-7.42 (m, 1H), 7.40-7.33 (m, 1H), 7.21-6.90 (m, 1H).

Example 235: 6-[2-(Difluoromethyl)-5-(trifluoromethyl)imidazo[4,5-b]pyridin-3-yl]-3H-1,3-benzoxazol-2-one

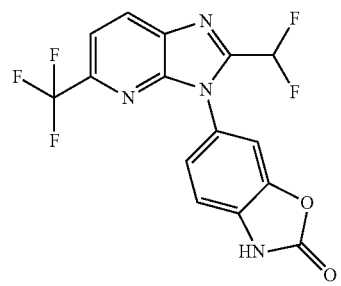 [SMILES: O=c1[nH]c2ccc(-n3c(C(F)F)nc4ccc(C(F)(F)F)nc43)cc2o1]

The title compound was prepared in a manner analogous to Example 88. MS (ESI): mass calcd. for $C_{15}H_7F_5N_4O_2$, 370.0; m/z found, 371.0 [M+H]$^+$. $^1$H NMR (400 MHz, DMSO-d$_6$) δ 12.05 (s, 1H), 8.61 (d, J=8.3 Hz, 1H), 7.96 (d, J=8.4 Hz, 1H), 7.70 (d, J=1.9 Hz, 1H), 7.46-7.15 (m, 3H).

Example 236: 6-[2,5-Bis(trifluoromethyl)imidazo[4,5-b]pyridin-3-yl]-3H-1,3-benzoxazol-2-one The title compound was prepared in a manner analogous to Example 88. MS (ESI): mass calcd. for $C_{15}H_6F_6N_4O_2$, 388.0; m/z found, 389.0 [M+H]$^+$. $^1$H NMR (400 MHz, DMSO-d$_6$) δ 12.08 (s, 1H), 8.71 (d, J=8.4 Hz, 1H), 8.03 (d, J=8.4 Hz, 1H), 7.74 (d, J=1.9 Hz, 1H), 7.52-7.46 (m, 1H), 7.33 (d, J=8.2 Hz, 1H).

Example 237: 3-(3-Fluoro-1H-indazol-5-yl)-2,5-bis(trifluoromethyl)imidazo[4,5-b]pyridine

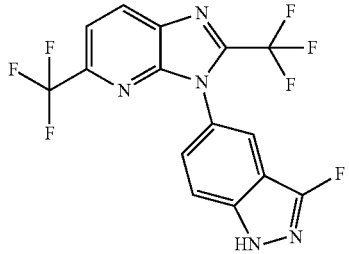 [SMILES: Fc1n[nH]c2ccc(-n3c(C(F)(F)F)nc4ccc(C(F)(F)F)nc43)cc12]

The title compound was prepared in a manner analogous to 125 from N²-(3-fluoro-1H-indazol-5-yl)-6-(trifluoromethyl)pyridine-2,3-diamine (Intermediate 53). MS (ESI): mass calcd. for C₁₅H₆F₇N₅, 389.1; m/z found, 390.1 [M+H]⁺. ¹H NMR (500 MHz, CD₃OD) δ 8.53 (d, J=8.4 Hz, 1H), 7.96 (d, J=1.8 Hz, 1H), 7.93 (d, J=8.4 Hz, 1H), 7.71-7.66 (m, 1H), 7.58-7.54 (m, 1H).

Example 238: 5-(Difluoromethyl)-3-(1H-indazol-5-yl)-2-(trifluoromethyl)imidazo[4,5-b]pyridine

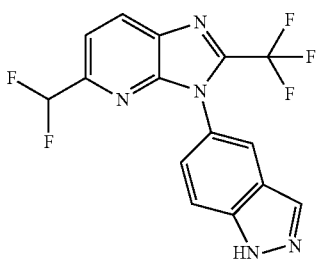 [SMILES: FC(F)c1ccc2nc(C(F)(F)F)n(-c3ccc4[nH]ncc4c3)c2n1]

The title compound was prepared in a manner analogous to Example 88, using 2-chloro-6-(difluoromethyl)-3-nitropyridine (Intermediate 48, product from Step E). MS (ESI): mass calcd. for C₁₅H₈F₅N₅, 353.1; m/z found, 354.1 [M+H]⁺. ¹H NMR (500 MHz, CDCl₃) δ 8.42 (d, J=8.4 Hz, 1H), 8.22 (d, J=1.1 Hz, 1H), 7.88 (d, J=1.8 Hz, 1H), 7.79 (d, J=8.4 Hz, 1H), 7.75-7.65 (m, 1H), 7.42 (dd, J=8.8, 1.9 Hz, 1H), 6.61 (t, J=55.2 Hz, 1H).

Example 239: 6-[2-Methoxy-5-(trifluoromethyl)imidazo[4,5-b]pyridin-3-yl]-3H-1,3-benzothiazol-2-one

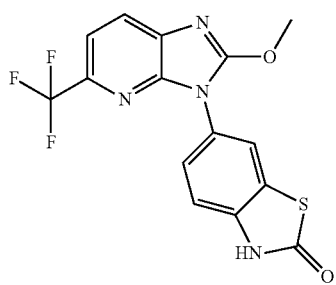

The title compound was made in a manner analogous to Example 114. MS (ESI): mass calcd. for C₁₅H₉F₃N₄O₂S, 366.0; m/z found, 367.0 [M+H]⁺. ¹H NMR (400 MHz, CD₃OD) δ 7.97 (d, J=8.2 Hz, 1H), 7.71 (d, J=2.1 Hz, 1H), 7.66 (d, J=8.1 Hz, 1H), 7.50-7.46 (m, 1H), 7.33-7.29 (m, 1H), 4.25 (s, 3H).

Example 240: 6-[2-Ethoxy-5-(trifluoromethyl)imidazo[4,5-b]pyridin-3-yl]-3H-1,3-benzothiazol-2-one

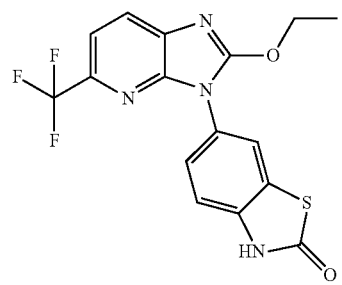 [SMILES: CCOc1nc2ccc(C(F)(F)F)nc2n1-c1ccc2[nH]c(=O)sc2c1]

The title compound was made in a manner analogous to Example 114. MS (ESI): mass calcd. for C₁₆H₁₁F₃N₄O₂S, 380.1; m/z found, 381.0 [M+H]⁺. ¹H NMR (400 MHz, CD₃OD) δ 7.95 (d, J=8.2 Hz, 1H), 7.71 (d, J=2.1 Hz, 1H), 7.65 (d, J=8.2 Hz, 1H), 7.50-7.46 (m, 1H), 7.31 (d, J=8.5 Hz, 1H), 4.73-4.64 (m, 2H), 1.46 (t, J=7.1 Hz, 3H).

Example 241: 2-Methoxy-3-(7-methyl-1H-indazol-5-yl)-5-(trifluoromethyl)imidazo[4,5-b]pyridine

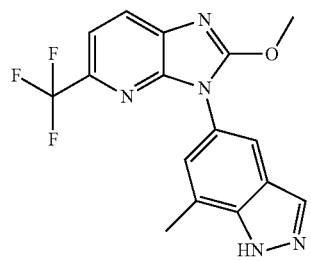 [SMILES: COc1nc2ccc(C(F)(F)F)nc2n1-c1cc(C)c2[nH]ncc2c1]

The title compound was prepared in a manner analogous to Example 114. MS (ESI): mass calcd. for C₁₆H₁₂F₃N₅O, 347.1; m/z found, 348.0 [M+H]⁺. ¹H NMR (500 MHz, CD₃OD) δ 8.16 (s, 1H), 7.98 (d, J=8.2 Hz, 1H), 7.82-7.76 (m, 1H), 7.66 (d, J=8.2 Hz, 1H), 7.34-7.27 (m, 1H), 4.25 (s, 3H), 2.65 (s, 3H).

Example 242: 2-Ethoxy-3-(7-methyl-1H-indazol-5-yl)-5-(trifluoromethyl)imidazo[4,5-b]pyridine

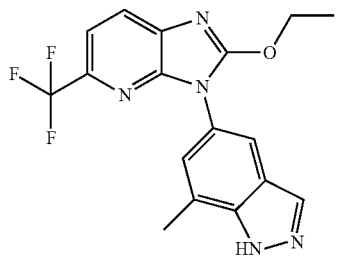 [SMILES: CCOc1nc2ccc(C(F)(F)F)nc2n1-c1cc(C)c2[nH]ncc2c1]

The title compound was prepared in a manner analogous to Example 114 from $N^2$-(7-methyl-1H-indazol-5-yl)-6-(trifluoromethyl)pyridine-2,3-diamine (Intermediate 56). MS (ESI): mass calcd. for $C_{17}H_{14}F_3N_5O$, 361.1; m/z found, 362.0 [M+H]$^+$. $^1$H NMR (400 MHz, CD$_3$OD) δ 8.16 (s, 1H), 7.95 (d, J=8.1 Hz, 1H), 7.79 (d, J=1.9 Hz, 1H), 7.64 (d, J=8.2 Hz, 1H), 7.30 (d, J=1.5 Hz, 1H), 4.72-4.63 (m, 2H), 2.64 (s, 3H), 1.49-1.40 (m, 3H).

Example 243: 5-[2-Ethoxy-5-(trifluoromethyl)imidazo[4,5-b]pyridin-3-yl]indolin-2-one

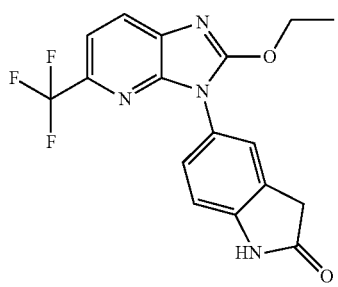 [SMILES: CCOc1nc2ccc(C(F)(F)F)nc2n1-c1ccc2c(c1)CC(=O)N2]

The title compound was prepared in a manner analogous to Example 114. MS (ESI): mass calcd. for $C_{17}H_{13}F_3N_4O_2$, 362.1; m/z found, 363.0 [M+H]$^+$. $^1$H NMR (400 MHz, DMSO-d$_6$) δ 10.61 (s, 1H), 8.03 (d, J=8.2 Hz, 1H), 7.68 (d, J=8.1 Hz, 1H), 7.41 (d, J=2.0 Hz, 1H), 7.39-7.34 (m, 1H), 7.01 (d, J=8.2 Hz, 1H), 4.70-4.60 (m, 2H), 3.60 (s, 2H), 1.44-1.35 (m, 3H).

Example 244: 5-[2-Methoxy-5-(trifluoromethyl)imidazo[4,5-b]pyridin-3-yl]indolin-2-one

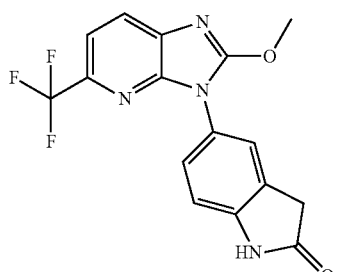

The title compound was prepared in a manner analogous to Example 114. MS (ESI): mass calcd. for $C_{16}H_{11}F_3N_4O_2$, 348.1; m/z found, 349.1 [M+H]$^+$. $^1$H NMR (400 MHz, DMSO-d$_6$) δ 10.62 (s, 1H), 8.07 (d, J=8.1 Hz, 1H), 7.71 (d, J=8.1 Hz, 1H), 7.40 (d, J=2.0 Hz, 1H), 7.39-7.33 (m, 1H), 6.99 (d, J=8.2 Hz, 1H), 4.17 (s, 3H), 3.59 (s, 2H).

Example 245: 3-(1H-indazol-5-yl)-2-(methylsulfonylmethyl)-5-(trifluoromethyl)imidazo[4,5-b]pyridine

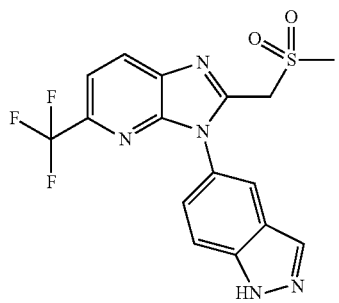 [SMILES: CS(=O)(=O)Cc1nc2ccc(C(F)(F)F)nc2n1-c1ccc2[nH]ncc2c1]

The title compound was made in a manner analogous to Example 117. MS (ESI): mass calcd. for $C_{16}H_{12}F_3N_5O_2S$, 395.1; m/z found, 396.0 [M+H]$^+$. $^1$H NMR (600 MHz, DMSO-d$_6$) δ 13.49 (s, 1H), 8.50 (d, J=8.3 Hz, 1H), 8.27 (s, 1H), 8.03-8.00 (m, 1H), 7.90 (d, J=8.3 Hz, 1H), 7.80 (d, J=8.7 Hz, 1H), 7.47 (dd, J=8.7, 2.0 Hz, 1H), 4.82 (s, 2H), 3.26 (s, 3H).

Example 246: 2-(3-Fluorocyclobutyl)-3-(7-methyl-1H-indazol-5-yl)-5-(trifluoromethyl)imidazo[4,5-b]pyridine

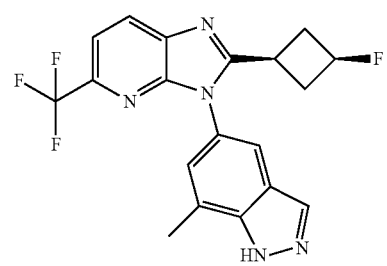 [SMILES: Cc1cc(-n2c3nc(C(F)(F)F)ccc3nc2[C@H]2C[C@@H](F)C2)cc2cn[nH]c12]

The title compound was prepared in a manner analogous to Example 117 with a chiral separation. MS (ESI): mass calcd. for $C_{19}H_{15}F_4N_5$, 389.1; m/z found, 390.1 [M+H]$^+$. $^1$H NMR (400 MHz, CDCl$_3$) δ 11.33 (s, 1H), 8.28 (d, J=8.2 Hz, 1H), 7.93 (s, 1H), 7.75 (d, J=8.3 Hz, 1H), 7.42 (d, J=1.7 Hz, 1H), 6.89 (s, 1H), 5.03-4.76 (m, 1H), 3.01-2.89 (m, 1H), 2.89-2.72 (m, 2H), 2.69-2.55 (m, 2H), 2.46 (s, 3H).

Example 247: 2-(3-Fluorocyclobutyl)-3-(7-methyl-1H-indazol-5-yl)-5-(trifluoromethyl)imidazo[4,5-b]pyridine

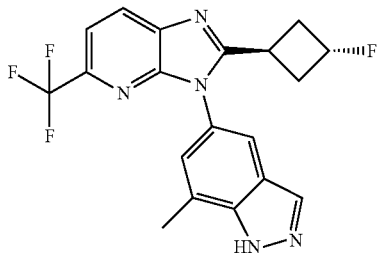 [SMILES: Cc1cc(-n2c3nc(C(F)(F)F)ccc3nc2[C@H]2C[C@H](F)C2)cc2cn[nH]c12]

The title compound was prepared in a manner analogous to Example 117 with a chiral separation, from $N^2$-(7-methyl-1H-indazol-5-yl)-6-(trifluoromethyl)pyridine-2,3-diamine (Intermediate 56). MS (ESI): mass calcd. for $C_{19}H_{15}F_4N_5$, 389.1; m/z found, 390.1 [M+H]$^+$. $^1$H NMR (400 MHz, CDCl$_3$) δ 8.25 (d, J=8.3 Hz, 1H), 7.90 (s, 1H), 7.75 (d, J=8.3 Hz, 1H), 7.40 (d, J=1.7 Hz, 1H), 6.87-6.84 (m, 1H), 5.55-5.32 (m, 1H), 3.70-3.58 (m, 1H), 2.96-2.81 (m, 2H), 2.63-2.47 (m, 2H), 2.43 (s, 3H).

Example 248: 3-(7-Chloro-1H-indazol-5-yl)-2-(3-fluorocyclobutyl)-5-(trifluoromethyl)imidazo[4,5-b]pyridine

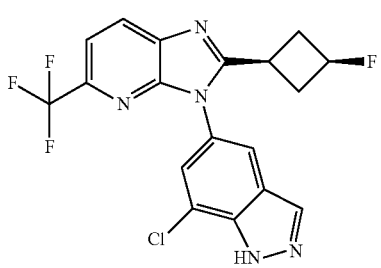 [SMILES: FC(F)(F)c1ccc2nc([C@H]3C[C@@H](F)C3)n(-c3cc(Cl)c4[nH]ncc4c3)c2n1]

The title compound was prepared in a manner analogous to Example 117 with a chiral separation. MS (ESI): mass calcd. for $C_{18}H_{12}ClF_4N_5$, 409.1; m/z found, 410.1 [M+H]$^+$. $^1$H NMR (400 MHz, CDCl$_3$) δ 8.29 (d, J=8.2 Hz, 1H), 8.02 (s, 1H), 7.76 (d, J=8.3 Hz, 1H), 7.55 (d, J=1.7 Hz, 1H), 7.21 (d, J=1.7 Hz, 1H), 5.04-4.80 (m, 1H), 3.03-2.92 (m, 1H), 2.91-2.75 (m, 2H), 2.72-2.59 (m, 2H).

Example 249: 3-(7-Chloro-1H-indazol-5-yl)-2-(3-fluorocyclobutyl)-5-methyl-imidazo[4,5-b]pyridine

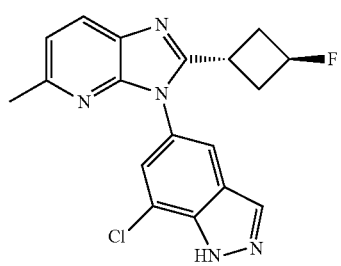 [SMILES: Cc1ccc2nc([C@H]3C[C@H](F)C3)n(-c3cc(Cl)c4[nH]ncc4c3)c2n1]

The title compound was prepared in a manner analogous to Example 117 with a chiral separation. MS (ESI): mass calcd. for $C_{18}H_{15}ClFN_5$, 355.1; m/z found, 356.1 [M+H]$^+$. $^1$H NMR (400 MHz, CDCl$_3$) δ 12.67 (s, 1H), 8.03 (d, J=8.2 Hz, 1H), 7.95 (s, 1H), 7.45 (d, J=1.6 Hz, 1H), 7.21 (d, J=8.2 Hz, 1H), 7.18 (d, J=1.7 Hz, 1H), 5.52-5.30 (m, 1H), 3.66-3.55 (m, 1H), 2.95-2.80 (m, 2H), 2.73 (s, 3H), 2.61-2.44 (m, 2H).

Example 250: 3-(7-Chloro-1H-indazol-5-yl)-2-(3-fluorocyclobutyl)-5-(trifluoromethyl)imidazo[4,5-b]pyridine

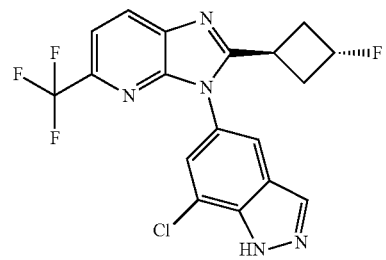 [SMILES: FC(F)(F)c1ccc2nc([C@H]3C[C@H](F)C3)n(-c3cc(Cl)c4[nH]ncc4c3)c2n1]

The title compound was prepared in a manner analogous to Example 117 with a chiral separation. MS (ESI): mass calcd. for $C_{18}H_{12}ClF_4N_5$, 409.1; m/z found, 410.1 [M+H]$^+$. $^1$H NMR (400 MHz, CDCl$_3$) δ 8.23 (d, J=8.3 Hz, 1H), 8.11 (s, 1H), 7.73 (d, J=8.2 Hz, 1H), 7.58 (d, J=1.7 Hz, 1H), 7.26 (d, J=1.8 Hz, 1H), 5.56-5.32 (m, 1H), 3.74-3.63 (m, 1H), 2.98-2.83 (m, 2H), 2.68-2.51 (m, 2H).

Example 251: 2-(1-Methoxy-1-methyl-ethyl)-3-(7-methyl-1H-indazol-5-yl)-5-(trifluoromethyl)imidazo[4,5-b]pyridine

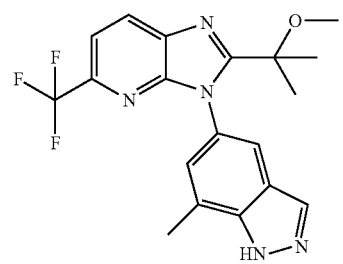 [SMILES: COC(C)(C)c1nc2ccc(C(F)(F)F)nc2n1-c1cc(C)c2[nH]ncc2c1]

The title compound was prepared in a manner analogous to Example 117, from $N^2$-(7-methyl-1H-indazol-5-yl)-6-(trifluoromethyl)pyridine-2,3-diamine (Intermediate 56). MS (ESI): mass calcd. for $C_{19}H_{18}F_3N_5O$, 389.1; m/z found, 390.1 [M+H]$^+$. $^1$H NMR (400 MHz, CD$_3$OD) δ 8.27 (d, J=8.2 Hz, 1H), 8.17 (s, 1H), 7.77-7.72 (m, 2H), 7.22-7.19 (m, 1H), 3.13 (s, 3H), 2.65 (s, 3H), 1.61 (s, 6H).

Example 252: 2-(1,1-Difluoroethyl)-3-(7-methyl-1H-indazol-5-yl)-5-(trifluoromethyl)imidazo[4,5-b]pyridine

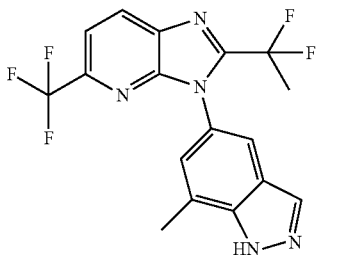

The title compound was prepared in a manner analogous to Example 117, from $N^2$-(7-methyl-1H-indazol-5-yl)-6-(trifluoromethyl)pyridine-2,3-diamine (Intermediate 56). MS (ESI): mass calcd. for $C_{17}H_{12}F_5N_5$, 381.1; m/z found, 382.1 [M+H]+. $^1$H NMR (400 MHz, CDCl$_3$) δ 11.01 (s, 1H), 8.37 (d, J=8.3 Hz, 1H), 7.99 (s, 1H), 7.80 (d, J=8.4 Hz, 1H), 7.62 (d, J=1.9 Hz, 1H), 7.10-7.06 (m, 1H), 2.47 (s, 3H), 2.24-2.11 (m, 3H).

Example 253: 2-(1-Fluoro-1-methyl-ethyl)-3-(7-methyl-1H-indazol-5-yl)-5-(trifluoromethyl)imidazo[4,5-b]pyridine

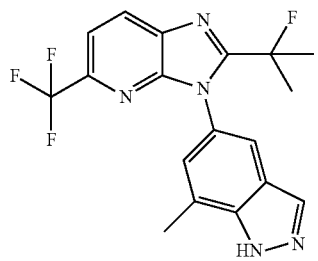 [SMILES: Cc1cc(-n2c(C(C)(C)F)nc3ccc(C(F)(F)F)nc32)cc2cn[nH]c12]

The title compound was prepared in a manner analogous to Example 117, from $N^2$-(7-methyl-1H-indazol-5-yl)-6-(trifluoromethyl)pyridine-2,3-diamine (Intermediate 56). MS (ESI): mass calcd. for $C_{18}H_{15}F_4N_5$, 377.1; m/z found, 378.1 [M+H]+. $^1$H NMR (400 MHz, CDCl$_3$) δ 10.77 (s, 1H), 8.27 (d, J=8.3 Hz, 1H), 8.02 (s, 1H), 7.74 (d, J=8.3 Hz, 1H), 7.59 (s, 1H), 7.08 (d, J=1.0 Hz, 1H), 2.49 (s, 3H), 1.80 (d, J=21.4 Hz, 6H).

Example 254: 3-(7-Chloro-1H-indazol-5-yl)-2-(1-fluoro-1-methyl-ethyl)-5-(trifluoromethyl)imidazo[4,5-b]pyridine

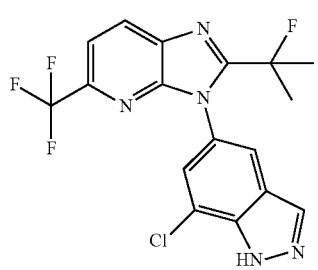

The title compound was prepared in a manner analogous to Example 117. MS (ESI): mass calcd. for $C_{17}H_{12}ClF_4N_5$, 397.1; m/z found, 398.1 [M+H]+. $^1$H NMR (400 MHz, CDCl$_3$) δ 10.65 (s, 1H), 8.29 (d, J=8.3 Hz, 1H), 8.08 (s, 1H), 7.76 (d, J=8.3 Hz, 1H), 7.72-7.67 (m, 1H), 7.42-7.36 (m, 1H), 1.82 (d, J=21.5 Hz, 6H).

Example 255: 2-Cyclopropyl-3-(7-methyl-1H-indazol-5-yl)-5-(trifluoromethyl)imidazo[4,5-b]pyridine

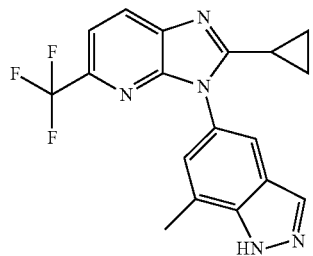 [SMILES: Cc1cc(-n2c(C3CC3)nc3ccc(C(F)(F)F)nc32)cc2cn[nH]c12]

The title compound was prepared in a manner analogous to Example 117, from $N^2$-(7-methyl-1H-indazol-5-yl)-6-(trifluoromethyl)pyridine-2,3-diamine (Intermediate 56). MS (ESI): mass calcd. for $C_{18}H_{14}F_3N_5$, 357.1; m/z found, 358.0 [M+H]+. $^1$H NMR (500 MHz, CDCl$_3$) δ 11.16 (s, 1H), 8.12-8.09 (m, 1H), 7.99 (s, 1H), 7.68 (d, J=8.2 Hz, 1H), 7.61-7.59 (m, 1H), 7.10-7.07 (m, 1H), 2.51 (s, 3H), 1.87-1.81 (m, 1H), 1.41-1.36 (m, 2H), 1.12-1.07 (m, 2H).

Example 256: (*R)-2-(1-Fluoroethyl)-3-(7-methyl-1H-indazol-5-yl)-5-(trifluoromethyl)imidazo[4,5-b]pyridine

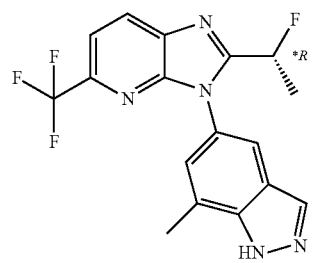 [SMILES: Cc1cc(-n2c([C@@H](C)F)nc3ccc(C(F)(F)F)nc32)cc2cn[nH]c12]

The title compound was prepared in a manner analogous to Example 117, with a chiral separation, from $N^2$-(7-methyl-1H-indazol-5-yl)-6-(trifluoromethyl)pyridine-2,3-diamine (Intermediate 56). MS (ESI): mass calcd. for $C_{17}H_{13}F_4N_5$, 363.1; m/z found, 364.1 [M+H]+. $^1$H NMR (400 MHz, CDCl$_3$) δ 11.29 (s, 1H), 8.37 (d, J=8.3 Hz, 1H), 7.97 (s, 1H), 7.79 (d, J=8.3 Hz, 1H), 7.59 (d, J=1.7 Hz, 1H), 7.08-7.03 (m, 1H), 5.67 (dq, J=6.4, 47.2 Hz, 1H), 2.48 (s, 3H), 1.86 (dd, J=6.4, 24.0 Hz, 3H).

Example 257: (*S)-2-(1-Fluoroethyl)-3-(7-methyl-1H-indazol-5-yl)-5-(trifluoromethyl)imidazo[4,5-b]pyridine

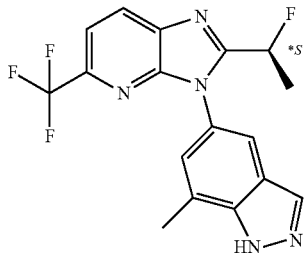 [SMILES: Cc1cc(-n2c([C@H](C)F)nc3ccc(C(F)(F)F)nc32)cc2cn[nH]c12]

The title compound was prepared in a manner analogous to Example 117, with a chiral separation, from N²-(7-methyl-1H-indazol-5-yl)-6-(trifluoromethyl)pyridine-2,3-diamine (Intermediate 56). MS (ESI): mass calcd. for $C_{17}H_{13}F_4N_5$, 363.1; m/z found, 364.1 [M+H]⁺. ¹H NMR (400 MHz, CDCl₃) δ 11.35 (s, 1H), 8.37 (d, J=8.3 Hz, 1H), 7.96 (s, 1H), 7.79 (d, J=8.3 Hz, 1H), 7.59 (d, J=1.8 Hz, 1H), 7.07-7.03 (m, 1H), 5.67 (dq, J=6.4, 47.2 Hz, 1H), 2.47 (s, 3H), 1.86 (dd, J=23.8, 6.5 Hz, 3H).

Example 258: 3-(7-Chloro-1H-indazol-5-yl)-2-(1-fluorocyclopropyl)-5-(trifluoromethyl)imidazo[4,5-b]pyridine

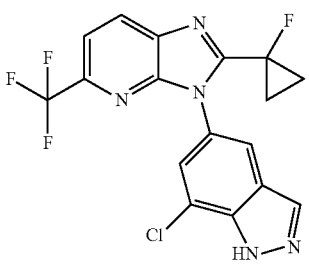

The title compound was prepared in a manner analogous to Example 117. MS (ESI): mass calcd. for $C_{17}H_{10}ClF_4N_5$, 395.1; m/z found, 396.1 [M+H]⁺. ¹H NMR (400 MHz, CDCl₃) δ 11.10 (s, 1H), 8.26 (d, J=8.2 Hz, 1H), 8.12 (s, 1H), 7.78 (d, J=1.7 Hz, 1H), 7.76 (d, J=8.3 Hz, 1H), 7.49-7.45 (m, 1H), 1.53-1.43 (m, 4H).

Example 259: 2-(1-Fluorocyclopropyl)-3-(7-methyl-1H-indazol-5-yl)-5-(trifluoromethyl)imidazo[4,5-b]pyridine

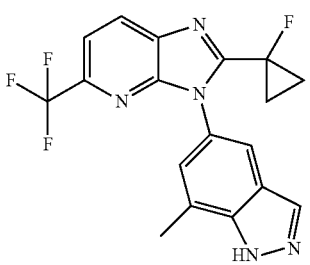 [SMILES: Cc1cc(-n2c(C3(F)CC3)nc3ccc(C(F)(F)F)nc32)cc2cn[nH]c12]

The title compound was prepared in a manner analogous to Example 117, from N²-(7-methyl-1H-indazol-5-yl)-6-(trifluoromethyl)pyridine-2,3-diamine (Intermediate 56). MS (ESI): mass calcd. for $C_{18}H_{13}F_4N_5$, 375.1; m/z found, 376.1 [M+H]⁺. ¹H NMR (500 MHz, CDCl₃) δ 11.15 (s, 1H), 8.28-8.24 (m, 1H), 7.97 (s, 1H), 7.76 (d, J=8.3 Hz, 1H), 7.63 (d, J=1.7 Hz, 1H), 7.14-7.10 (m, 1H), 2.48 (s, 3H), 1.49-1.38 (m, 4H).

Example 260: 3-(1H-Indazol-5-yl)-N-isopropyl-N-methyl-5-(trifluoromethyl)imidazo[4,5-b]pyridine-2-carboxamide

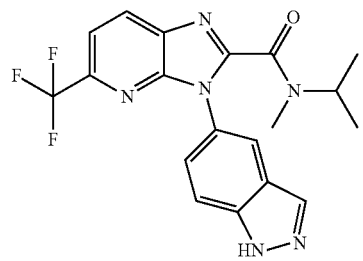 [SMILES: CC(C)N(C)C(=O)c1nc2ccc(C(F)(F)F)nc2n1-c1ccc2[nH]ncc2c1]

The title compound was prepared in a manner analogous to Example 128. MS (ESI): mass calcd. for $C_{19}H_{17}F_3N_6O$, 402.1; m/z found, 403.0 [M+H]⁺. ¹H NMR (400 MHz, CD₃OD) δ 8.40 (dd, J=8.3, 3.3 Hz, 1H), 8.20 (d, J=1.1 Hz, 1H), 8.02-7.97 (m, 1H), 7.89-7.84 (m, 1H), 7.79-7.73 (m, 1H), 7.59-7.53 (m, 1H), 4.72-4.60 (m, 0.46H), 3.99-3.88 (m, 0.54H), 2.84 (s, 3H), 1.10-0.99 (m, 6H).

Example 261: 2-(2-Chloro-4-pyridyl)-3-(7-methyl-1H-indazol-5-yl)-5-(trifluoromethyl)imidazo[4,5-b]pyridine

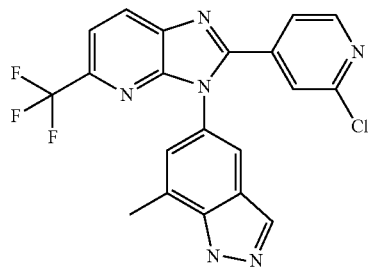 [SMILES: Cc1cc(-n2c(-c3ccnc(Cl)c3)nc3ccc(C(F)(F)F)nc32)cc2cn[nH]c12]

The title compound was prepared in a manner analogous to Example 166. MS (ESI): mass calcd. for $C_{20}H_{12}ClF_3N_6$, 428.1; m/z found, 429.1, [M+H]⁺. ¹H NMR (500 MHz, Acetonitrile-d₃) δ 8.42 (dd, J=8.3, 0.8 Hz, 1H), 8.33 (dd, J=5.2, 0.7 Hz, 1H), 8.15 (s, 1H), 7.86 (d, J=8.3 Hz, 1H), 7.73 (dd, J=1.7, 0.8 Hz, 1H), 7.64 (dd, J=1.5, 0.7 Hz, 1H), 7.43 (dd, J=5.2, 1.5 Hz, 1H), 7.22 (dd, J=1.9, 1.0 Hz, 1H), 2.62 (s, 3H).

Example 262: 2-(2-Bromo-4-pyridyl)-3-(7-methyl-1H-indazol-5-yl)-5-(trifluoromethyl)imidazo[4,5-b]pyridine

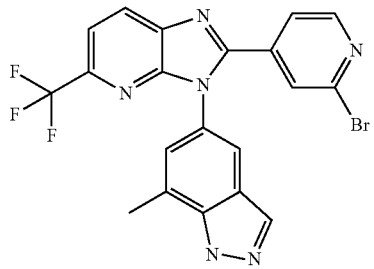

The title compound was prepared in a manner analogous to Example 166. MS (ESI): mass calcd. for $C_{20}H_{12}BrF_3N_6$, 472.0; m/z found, 473.1, [M+H]$^+$. $^1$H NMR (500 MHz, Acetonitrile-d$_3$) δ 8.42 (dd, J=8.4, 0.8 Hz, 1H), 8.31 (dd, J=5.2, 0.8 Hz, 1H), 8.15 (s, 1H), 7.86 (d, J=8.3 Hz, 1H), 7.79 (dd, J=1.5, 0.7 Hz, 1H), 7.73 (dd, J=1.7, 0.8 Hz, 1H), 7.46 (dd, J=5.2, 1.5 Hz, 1H), 7.22 (dt, J=2.0, 1.0 Hz, 1H), 2.63 (s, 3H).

Example 263: 5-(Difluoromethyl)-2-(2-fluoro-4-pyridyl)-3-(7-methyl-1H-indazol-5-yl)imidazo[4,5-b]pyridine

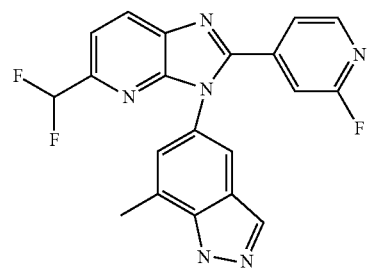 [SMILES: Cc1cc(-n2c(-c3ccnc(F)c3)nc3ccc(C(F)F)nc32)cc2cn[nH]c12]

The title compound was prepared in a manner analogous to Example 166. MS (ESI): mass calcd. for $C_{20}H_{13}F_3N_6$, 394.1; m/z found, 395.1, [M+H]$^+$. $^1$H NMR (400 MHz, Acetonitrile-d3) δ 8.38 (d, J=8.3 Hz, 1H), 8.21-8.08 (m, 2H), 7.80-7.68 (m, 2H), 7.42 (ddd, J=5.3, 1.9, 1.3 Hz, 1H), 7.23 (dd, J=1.9, 1.0 Hz, 2H), 6.74 (t, J=55.3 Hz, 1H), 2.62 (s, 3H).

Example 264: 3-(7-Chloro-1H-indazol-5-yl)-5-(difluoromethyl)-2-(2-fluoro-4-pyridyl)imidazo[4,5-b]pyridine

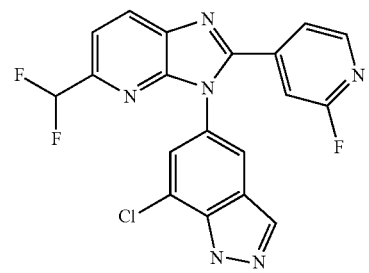 [SMILES: Fc1cc(-c2nc3ccc(C(F)F)nc3n2-c2cc(Cl)c3[nH]ncc3c2)ccn1]

The title compound was prepared in a manner analogous to Example 166. MS (ESI): mass calcd. for $C_{19}H_{10}ClF_3N_6$, 414.1; m/z found, 415.1, [M+H]$^+$. $^1$H NMR (400 MHz, Acetonitrile-d$_3$) δ 8.40 (d, J=8.3 Hz, 1H), 8.24 (s, 1H), 8.18 (dt, J=5.3, 0.7 Hz, 1H), 7.86 (d, J=1.7 Hz, 1H), 7.76 (d, J=8.3 Hz, 1H), 7.57 (d, J=1.7 Hz, 1H), 7.38 (dt, J=5.2, 1.6 Hz, 1H), 7.29 (t, J=1.7 Hz, 1H), 6.76 (t, J=55.3 Hz, 1H).

Example 265: 3-(4-Chloro-1H-indazol-6-yl)-2,5-bis(trifluoromethyl)imidazo[4,5-b]pyridine

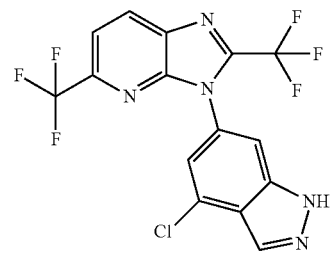 [SMILES: FC(F)(F)c1ccc2nc(C(F)(F)F)n(-c3cc(Cl)c4cn[nH]c4c3)c2n1]

The title compound was prepared in a manner analogous to Example 134, Method B. MS (ESI): mass calcd. for $C_{15}H_6ClF_6N_5$, 405.0; m/z found, 406.0 [M+H]$^+$. $^1$H NMR (400 MHz, CD$_3$OD) δ 8.58 (d, J=8.4 Hz, 1H), 7.96 (d, J=8.4 Hz, 1H), 7.93-7.89 (m, 1H), 7.76-7.73 (m, 1H), 7.46 (d, J=1.5 Hz, 1H).

Example 266: 6-[2-(1,1-Difluoroethyl)-5-(trifluoromethyl)imidazo[4,5-b]pyridin-3-yl]-3H-1,3-benzothiazol-2-one

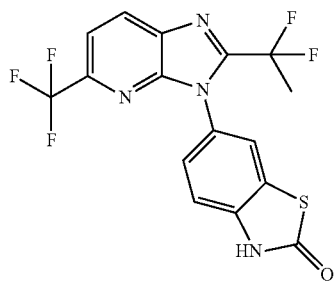 [SMILES: CC(F)(F)c1nc2ccc(C(F)(F)F)nc2n1-c1ccc2[nH]c(=O)sc2c1]

The title compound was prepared in a manner analogous to Example 134, Method B. MS (ESI): mass calcd. for $C_{16}H_9F_5N_4OS$, 400.0; m/z found, 401.0 [M+H]$^+$. $^1$H NMR (400 MHz, CDCl$_3$) δ 10.19 (s, 1H), 8.36 (d, J=8.3 Hz, 1H), 7.78 (d, J=8.3 Hz, 1H), 7.55 (d, J=2.0 Hz, 1H), 7.33-7.28 (m, 1H), 7.16 (d, J=8.4 Hz, 1H), 2.30-2.15 (m, 3H).

Example 267: 3-(7-Chloro-1H-indazol-5-yl)-2-(1,1-difluoroethyl)-5-(trifluoromethyl)imidazo[4,5-b]pyridine

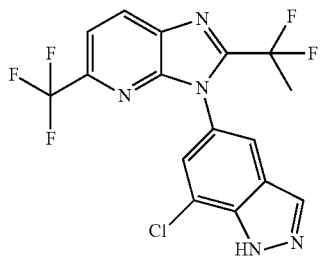

The title compound was prepared in a manner analogous to Example 134, Method B. MS (ESI): mass calcd. for $C_{16}H_9ClF_5N_5$, 401.0; m/z found, 402.0 [M+H]$^+$. $^1$H NMR (400 MHz, CDCl$_3$) δ 10.87 (s, 1H), 8.35 (d, J=8.3 Hz, 1H), 8.19 (s, 1H), 7.80-7.76 (m, 2H), 7.45 (d, J=1.7 Hz, 1H), 2.28-2.15 (m, 3H).

Example 268: 3-(7-Chloro-1H-indazol-5-yl)-5-methyl-2-(trifluoromethyl)imidazo[4,5-b]pyridine

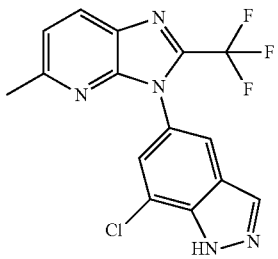 [SMILES: Cc1ccc2nc(C(F)(F)F)n(-c3cc(Cl)c4[nH]ncc4c3)c2n1]

The title compound was prepared in a manner analogous to Example 134, Method B. MS (ESI): mass calcd. for $C_{15}H_9ClF_3N_5$, 351.0; m/z found, 352.0 [M+H]$^+$. $^1$H NMR (500 MHz, DMSO-d$_6$) δ 14.05 (s, 1H), 8.38 (s, 1H), 8.28 (d, J=8.3 Hz, 1H), 8.08 (d, J=1.6 Hz, 1H), 7.79 (d, J=1.7 Hz, 1H), 7.41 (d, J=8.3 Hz, 1H), 2.52 (s, 3H).

Example 269: 3-(7-Chloro-1H-indazol-5-yl)-5-(difluoromethyl)-2-isopropyl-imidazo[4,5-b]pyridine

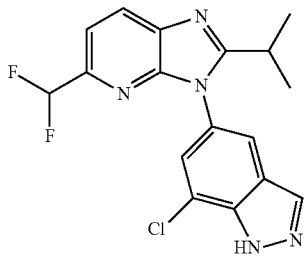 [SMILES: CC(C)c1nc2ccc(C(F)F)nc2n1-c1cc(Cl)c2[nH]ncc2c1]

The title compound was prepared in a manner analogous to Example 1. MS (ESI): mass calcd. for $C_{17}H_{14}ClF_2N_5$, 361.1; m/z found, 362.1 [M+H]$^+$. $^1$H NMR (500 MHz, CD$_3$OD) δ 8.29 (s, 1H), 8.19 (d, J=8.2 Hz, 1H), 7.93 (d, J=1.7 Hz, 1H), 7.66 (d, J=8.3 Hz, 1H), 7.58 (d, J=1.7 Hz, 1H), 6.77-6.53 (m, 1H), 3.24-3.14 (m, 1H), 1.37 (d, J=6.9 Hz, 6H).

Example 270: 3-(7-Chloro-1H-indazol-5-yl)-2,5-bis(trifluoromethyl)imidazo[4,5-b]pyridine

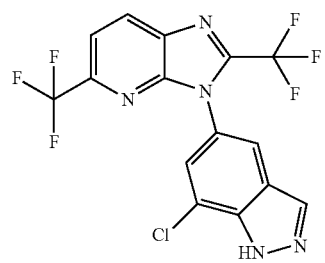

The title compound was prepared in a manner analogous to Example 134, Method B. MS (ESI): mass calcd. for $C_{15}H_6ClF_6N_5$, 405.0; m/z found, 406.0 [M+H]$^+$. $^1$H NMR (400 MHz, DMSO-d$_6$) δ 14.09 (s, 1H), 8.73 (d, J=8.4 Hz, 1H), 8.41 (d, J=1.5 Hz, 1H), 8.19 (d, J=1.6 Hz, 1H), 8.04 (d, J=8.4 Hz, 1H), 7.90 (d, J=1.7 Hz, 1H).

Example 271: 5-[2,5-Bis(trifluoromethyl)imidazo[4,5-b]pyridin-3-yl]-7-chloro-indolin-2-one

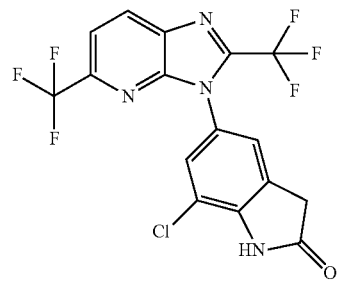 [SMILES: O=C1Cc2cc(-n3c(C(F)(F)F)nc4ccc(C(F)(F)F)nc43)cc(Cl)c2N1]

The title compound was prepared in a manner analogous to Example 134, Method B. MS (ESI): mass calcd. for $C_{16}H_7ClF_6N_4O$, 420.0; m/z found, 421.0 [M+H]$^+$. $^1$H NMR (500 MHz, CDCl$_3$) δ 8.42 (d, J=8.4 Hz, 1H), 7.82 (d, J=8.4 Hz, 1H), 7.36 (d, J=1.8 Hz, 1H), 7.23 (d, J=1.9 Hz, 1H), 3.76 (s, 2H).

Example 272: 7-Chloro-5-[2-(difluoromethyl)-5-(trifluoromethyl)imidazo[4,5-b]pyridin-3-yl]indolin-2-one

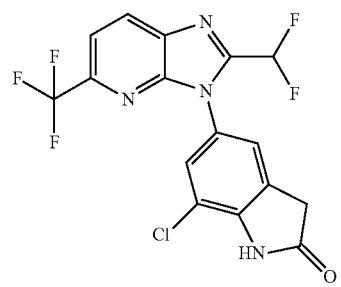 [SMILES: O=C1Cc2cc(-n3c(C(F)F)nc4ccc(C(F)(F)F)nc43)cc(Cl)c2N1]

The title compound was prepared in a manner analogous to Example 134, Method B. MS (ESI): mass calcd. for $C_{16}H_5ClF_5N_4O$, 402.0; m/z found, 403.0 [M+H]$^+$. $^1$H NMR (500 MHz, CDCl$_3$) δ 8.35 (d, J=8.4 Hz, 1H), 8.11 (s, 1H), 7.79 (d, J=8.4 Hz, 1H), 7.41 (d, J=1.8 Hz, 1H), 7.28 (d, J=1.9 Hz, 1H), 6.98-6.74 (m, 1H), 3.76 (s, 2H).

Example 273: 5-(Difluoromethyl)-2-isopropyl-3-(7-methyl-1H-indazol-5-yl)imidazo[4,5-b]pyridine

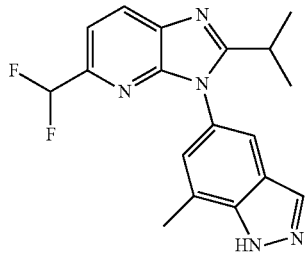 [SMILES: Cc1cc(-n2c(C(C)C)nc3ccc(C(F)F)nc32)cc2cn[nH]c12]

The title compound was prepared in a manner analogous to Example 1. MS (ESI): mass calcd. for $C_{18}H_{17}F_2N_5$, 341.1; m/z found, 342.1 [M+H]$^+$. $^1$H NMR (400 MHz, CDCl$_3$) δ 10.90 (s, 1H), 8.20 (d, J=8.2 Hz, 1H), 8.08 (s, 1H), 7.62 (d, J=8.2 Hz, 1H), 7.57 (d, J=1.7 Hz, 1H), 7.07-7.05 (m, 1H), 6.69 (t, J=55.5 Hz, 1H), 3.17-3.05 (m, 1H), 2.57 (s, 3H), 1.36 (d, J=6.9 Hz, 6H).

Example 274: 3-(7-Chloro-1H-indazol-5-yl)-5-(difluoromethyl)-2-methyl-imidazo[4,5-b]pyridine

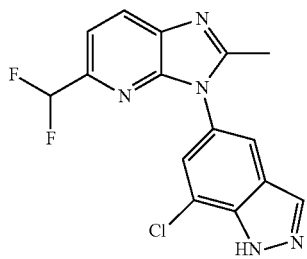 [SMILES: Cc1nc2ccc(C(F)F)nc2n1-c1cc(Cl)c2[nH]ncc2c1]

The title compound was prepared in a manner analogous to Example 1. MS (ESI): mass calcd. for $C_{15}H_{10}ClF_2N_5$, 333.1; m/z found, 334.0 [M+H]$^+$. $^1$H NMR (400 MHz, CDCl$_3$) δ 10.74 (s, 1H), 8.21 (s, 1H), 8.15 (d, J=8.2 Hz, 1H), 7.72 (d, J=1.7 Hz, 1H), 7.64 (d, J=8.3 Hz, 1H), 7.41 (d, J=1.7 Hz, 1H), 6.81-6.49 (m, 1H), 2.58 (s, 3H).

Example 275: 5-[2,5-Bis(trifluoromethyl)imidazo[4,5-b]pyridin-3-yl]-7-methyl-indolin-2-one

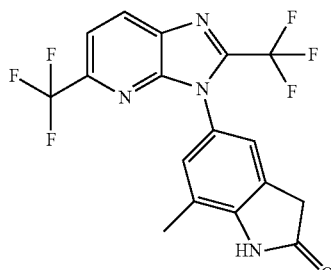

The title compound was prepared in a manner analogous to Example 134, Method B. MS (ESI): mass calcd. for $C_{17}H_{10}F_6N_4O$, 400.1; m/z found, 401.1 [M+H]$^+$. $^1$H NMR (500 MHz, CDCl$_3$) δ 8.88 (s, 1H), 8.44-8.37 (m, 1H), 7.80 (d, J=8.4 Hz, 1H), 7.14 (d, J=8.2 Hz, 2H), 3.68 (s, 2H), 2.38 (s, 3H).

Example 276: 5-[2-(1,1-Difluoroethyl)-5-(trifluoromethyl)imidazo[4,5-b]pyridin-3-yl]-7-methyl-indolin-2-one

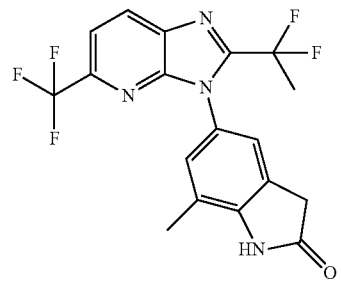 [SMILES: Cc1cc(-n2c(C(C)(F)F)nc3ccc(C(F)(F)F)nc32)cc2c1NC(=O)C2]

The title compound was prepared in a manner analogous to Example 134, Method B. MS (ESI): mass calcd. for $C_{18}H_{13}F_5N_4O$, 396.1; m/z found, 397.2 [M+H]$^+$. $^1$H NMR (400 MHz, CDCl$_3$) δ 8.74 (s, 1H), 8.30 (d, J=8.3 Hz, 1H), 7.74 (d, J=8.3 Hz, 1H), 7.14 (d, J=5.4 Hz, 2H), 3.65 (s, 2H), 2.35 (s, 3H), 2.27-2.14 (m, 3H).

Example 277: 3-(7-Chloro-1H-indazol-5-yl)-2-(difluoromethyl)-5-(trifluoromethyl)imidazo[4,5-b]pyridine

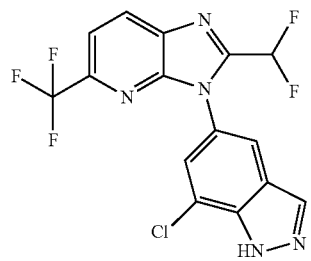 [SMILES: FC(F)c1nc2ccc(C(F)(F)F)nc2n1-c1cc(Cl)c2[nH]ncc2c1]

The title compound was prepared in a manner analogous to Example 134, Method B. MS (ESI): mass calcd. for $C_{15}H_7ClF_5N_5$, 387.0; m/z found, 388.0 [M+H]$^+$. $^1$H NMR (400 MHz, DMSO-d$_6$) δ 14.05 (s, 1H), 8.62 (d, J=8.3 Hz, 1H), 8.44-8.38 (m, 1H), 8.12 (d, J=1.7 Hz, 1H), 7.97 (d, J=8.4 Hz, 1H), 7.82 (d, J=1.6 Hz, 1H), 7.46-7.17 (m, 1H).

Example 278: 3-(7-Chloro-1H-indazol-5-yl)-2-(difluoromethyl)-5-methyl-imidazo[4,5-b]pyridine

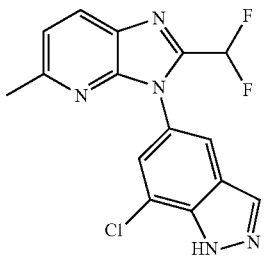 [SMILES: Cc1ccc2nc(C(F)F)n(-c3cc(Cl)c4[nH]ncc4c3)c2n1]

The title compound was prepared in a manner analogous to Example 134, Method B. MS (ESI): mass calcd. for $C_{15}H_{10}ClF_2N_5$, 333.1; m/z found, 334.1 [M+H]$^+$. $^1$H NMR (400 MHz, CDCl$_3$) δ 8.17 (d, J=8.2 Hz, 1H), 7.98 (s, 1H), 7.64 (d, J=1.6 Hz, 1H), 7.37 (d, J=1.6 Hz, 1H), 7.33 (d, J=8.3 Hz, 1H), 6.94-6.64 (m, 1H), 2.77 (s, 3H).

Example 279: 3-(7-Chloro-1H-indazol-5-yl)-6-fluoro-2-(trifluoromethyl)imidazo[4,5-b]pyridine

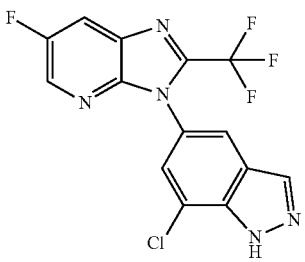 [SMILES: Fc1cnc2c(c1)nc(C(F)(F)F)n2-c1cc(Cl)c2[nH]ncc2c1]

The title compound was prepared in a manner analogous to Example 134, Method B. MS (ESI): mass calcd. for $C_{14}H_6ClF_4N_5$, 355.0; m/z found, [M+H]=356.0 [M+H]$^+$. $^1$H NMR (500 MHz, CDCl$_3$) δ 10.65 (s, 1H), 8.44 (dd, J=2.7, 1.5 Hz, 1H), 8.23 (s, 1H), 8.00 (dd, J=8.0, 2.6 Hz, 1H), 7.80 (d, J=1.6 Hz, 1H), 7.45 (d, J=1.7 Hz, 1H).

Example 280: 3-(7-Bromo-1H-indazol-5-yl)-2-(difluoromethyl)-5-(trifluoromethyl)imidazo[4,5-b]pyridine

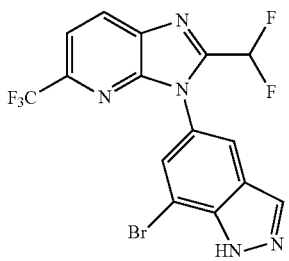 [SMILES: FC(F)c1nc2ccc(C(F)(F)F)nc2n1-c1cc(Br)c2[nH]ncc2c1]

The title compound was made in a manner analogous to Example 134, using 2-chloro-3-nitro-6-(trifluoromethyl)pyridine and 7-bromo-1H-indazol-5-amine, and substituting 2,2-difluoroacetic acid in Step B. MS (ESI): mass calcd. for $C_{15}H_7BrF_5N_5$, 431.0; m/z found, 432.0 [M+H]$^+$. $^1$H NMR (500 MHz, DMSO-d$_6$) δ 13.94 (s, 1H), 8.62 (d, J=8.3 Hz, 1H), 8.42 (s, 1H), 8.15 (d, J=1.6 Hz, 1H), 7.97 (d, J=8.4 Hz, 1H), 7.94 (s, 1H), 7.31 (t, J=51.5 Hz, 1H).

Example 281: 6-[2,5-Bis(trifluoromethyl)imidazo[4,5-b]pyridin-3-yl]-4-methyl-3H-1,3-benzothiazol-2-one

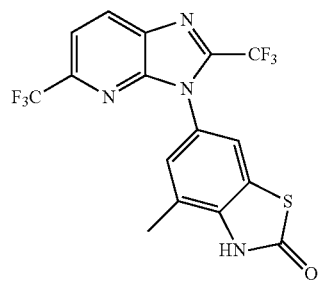 [SMILES: Cc1cc(-n2c(C(F)(F)F)nc3ccc(C(F)(F)F)nc32)cc2sc(=O)[nH]c12]

The title compound was prepared analogous to Example 134 using 2-chloro-3-nitro-6-(trifluoromethyl)pyridine and 6-amino-4-methylbenzo[d]thiazol-2(3H)-one. MS (ESI): mass calcd. for $C_{16}H_8F_6N_4OS$, 418.0; m/z found, 419.0 [M+H]$^+$. $^1$H NMR (400 MHz, CDCl$_3$) δ 9.95-9.86 (s, 1H), 8.47-8.40 (dd, J=8.3, 0.7 Hz, 1H), 7.87-7.79 (d, J=8.4 Hz, 1H), 7.42-7.31 (d, J=2.0 Hz, 1H), 7.24-7.16 (m, 1H), 2.10-2.00 (s, 3H).

Example 282: 6-[2,5-Bis(trifluoromethyl)imidazo[4,5-b]pyridin-3-yl]-4-chloro-3H-1,3-benzothiazol-2-one

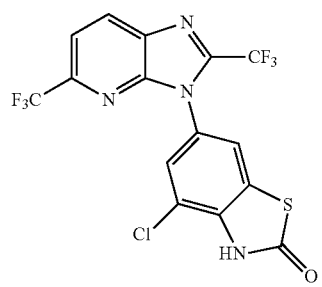 [SMILES: O=c1[nH]c2c(Cl)cc(-n3c(C(F)(F)F)nc4ccc(C(F)(F)F)nc43)cc2s1]

The title compound was prepared analogous to Example 134 using 2-chloro-3-nitro-6-(trifluoromethyl)pyridine and 6-amino-4-chlorobenzo[d]thiazol-2(3H)-one. MS (ESI): mass calcd. for $C_{15}H_5ClF_6N_4OS$, 438.0; m/z found, 439.0 [M+H]$^+$. $^1$H NMR (600 MHz, DMSO-d$_6$) δ 12.73-12.56 (s, 1H), 8.80-8.65 (d, J=8.4 Hz, 1H), 8.09-8.01 (d, J=8.4 Hz, 1H), 8.01-7.94 (d, J=2.0 Hz, 1H), 7.91-7.78 (m, 1H).

Example 283: 6-[2,5-Bis(trifluoromethyl)imidazo[4,5-b]pyridin-3-yl]-4-fluoro-3H-1,3-benzoxazol-2-one

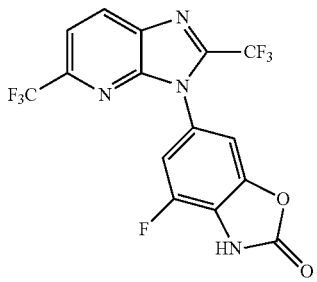 [SMILES: O=c1[nH]c2c(F)cc(-n3c(C(F)(F)F)nc4ccc(C(F)(F)F)nc43)cc2o1]

The title compound was prepared analogous to Example 134 using 2-chloro-3-nitro-6-(trifluoromethyl)pyridine and 6-amino-4-fluorobenzo[d]oxazol-2(3H)-one. MS (ESI): mass calcd. for $C_{15}H_5F_7N_4O_2$, 406.0; m/z found, 407.1 [M+H]$^+$. $^1$H NMR (500 MHz, DMSO-d$_6$) δ 12.86-12.61 (s, 1H), 8.78-8.66 (d, J=8.4 Hz, 1H), 8.12-7.98 (d, J=8.4 Hz, 1H), 7.77-7.55 (m, 2H).

Example 284: Methyl 5-[2,5-bis(trifluoromethyl)imidazo[4,5-b]pyridin-3-yl]-1H-indazole-7-carboxylate

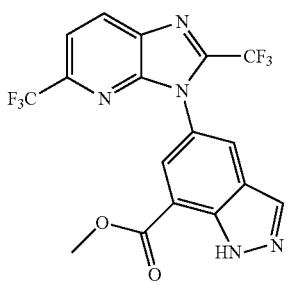 [SMILES: COC(=O)c1cc(-n2c(C(F)(F)F)nc3ccc(C(F)(F)F)nc32)cc2cn[nH]c12]

The title compound was prepared analogous to Example 134 using 2-chloro-3-nitro-6-(trifluoromethyl)pyridine and methyl 5-amino-1H-indazole-7-carboxylate. MS (ESI): mass calcd. for $C_{17}H_9F_6N_5O_2$, 429.1; m/z found, 430.1 [M+H]$^+$. $^1$H NMR (500 MHz, DMSO-d$_6$) δ 13.79-13.62 (s, 1H), 8.81-8.65 (d, J=8.4 Hz, 1H), 8.57-8.40 (m, 2H), 8.40-8.24 (d, J=1.9 Hz, 1H), 8.10-7.94 (d, J=8.4 Hz, 1H), 4.11-3.86 (s, 3H).

Example 285: Methyl 5-[2-(difluoromethyl)-5-(trifluoromethyl)imidazo[4,5-b]pyridin-3-yl]-1H-indazole-7-carboxylate

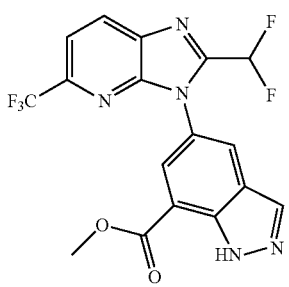 [SMILES: COC(=O)c1cc(-n2c(C(F)F)nc3ccc(C(F)(F)F)nc32)cc2cn[nH]c12]

The title compound was prepared analogous to Example 134 using 2-chloro-3-nitro-6-(trifluoromethyl)pyridine and methyl 5-amino-1H-indazole-7-carboxylate, substituting 2,2-difluoroacetic acid in Step B. MS (ESI): mass calcd. for $C_{17}H_{10}F_5N_5O_2$, 411.1; m/z found, 412.1 [M+H]$^+$. $^1$H NMR (500 MHz, DMSO-d$_6$) δ 13.80-13.56 (s, 1H), 8.75-8.56 (d, J=8.3 Hz, 1H), 8.52-8.36 (m, 2H), 8.36-8.19 (d, J=1.9 Hz, 1H), 8.07-7.84 (d, J=8.4 Hz, 1H), 7.52-7.09 (m, 1H), 4.13-3.84 (s, 3H).

Example 286: 2-(Difluoromethyl)-3-(7-methyl-1H-indazol-5-yl)-5-(trifluoromethyl)imidazo[4,5-b]pyridine

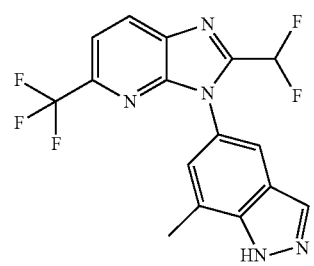 [SMILES: Cc1cc(-n2c(C(F)F)nc3ccc(C(F)(F)F)nc32)cc2cn[nH]c12]

The title compound was prepared analogous to Example 134 using 2-chloro-3-nitro-6-(trifluoromethyl)pyridine and 7-methyl-1H-indazol-5-amine, and substituting 2,2-difluoroacetic acid in Step B. MS (ESI): mass calcd. for $C_{16}H_{10}F_5N_5$, 367.1; m/z found, 368.0 [M+H]$^+$. $^1$H NMR (500 MHz, DMSO-d$_6$) δ 13.57 (s, 1H), 8.61 (d, J=8.4 Hz, 1H), 8.24 (s, 1H), 7.95 (d, J=8.4 Hz, 1H), 7.91-7.88 (m, 1H), 7.39-7.15 (m, 2H), 2.60 (s, 3H).

Example 287: 5-[2-(Difluoromethyl)-5-(trifluoromethyl)imidazo[4,5-b]pyridin-3-yl]-7-methyl-indolin-2-one

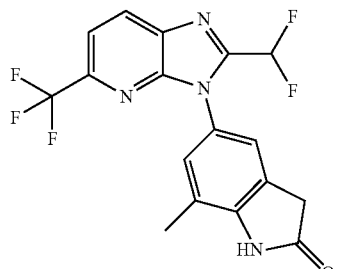

The title compound was prepared analogous to Example 134 using 2-chloro-3-nitro-6-(trifluoromethyl)pyridine and 5-amino-7-methylindolin-2-one, and substituting 2,2-difluoroacetic acid in Step B. MS (ESI): mass calcd. for $C_{17}H_{11}F_5N_4O$, 382.1; m/z found, 383.1 [M+H]$^+$. $^1$H NMR (400 MHz, CD$_3$OD) δ 8.43 (d, J=8.4 Hz, 1H), 7.86 (d, J=8.4 Hz, 1H), 7.28-7.21 (m, 2H), 7.01 (t, J=52.0 Hz, 1H), 2.36 (s, 3H).

Example 288: 5-[2-(Difluoromethyl)-5-(trifluoromethyl)imidazo[4,5-b]pyridin-3-yl]-7-fluoro-indolin-2-one

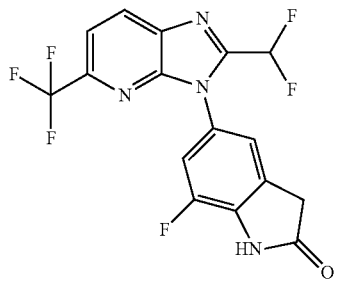

The title compound was prepared analogous to Example 134 using 2-chloro-3-nitro-6-(trifluoromethyl)pyridine and 5-amino-7-fluoroindolin-2-one, and substituting 2,2-difluoroacetic acid in Step B. MS (ESI): mass calcd. for $C_{16}H_8F_6N_4O$, 386.1; m/z found, 387.1 [M+H]$^+$. $^1$H NMR (400 MHz, CD$_3$OD) δ 8.44 (d, J=8.4 Hz, 1H), 7.87 (d, J=8.3 Hz, 1H), 7.38-7.30 (m, 2H), 7.20-6.91 (m, 1H).

Example 289: 3-(4-Methyl-1H-indazol-6-yl)-2,5-bis(trifluoromethyl)imidazo[4,5-b]pyridine

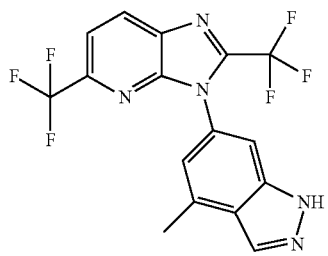 [SMILES: Cc1cc(-n2c(C(F)(F)F)nc3ccc(C(F)(F)F)nc32)cc2[nH]ncc12]

The title compound was prepared analogous to Example 134 using 2-chloro-3-nitro-6-(trifluoromethyl)pyridine and 4-methyl-1H-indazol-6-amine. MS (ESI): mass calcd. for $C_{16}H_9F_6N_5$, 385.1; m/z found, 386.1 [M+H]$^+$. $^1$H NMR (500 MHz, CD$_3$OD) δ 8.52 (d, J=8.4 Hz, 1H), 8.27 (s, 1H), 7.92 (d, J=8.4 Hz, 1H), 7.62 (s, 1H), 7.06 (s, 1H), 2.70 (d, J=0.8 Hz, 3H).

Example 290: 6-[2,5-Bis(trifluoromethyl)imidazo[4,5-b]pyridin-3-yl]-4-bromo-3H-1,3-benzoxazol-2-one

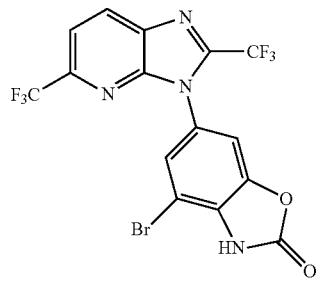 [SMILES: O=c1[nH]c2c(Br)cc(-n3c(C(F)(F)F)nc4ccc(C(F)(F)F)nc43)cc2o1]

The title compound was prepared analogous to Example 134 using 2-chloro-3-nitro-6-(trifluoromethyl)pyridine and 6-amino-4-bromobenzo[d]oxazol-2(3H)-one. MS (ESI): mass calcd. for $C_{15}H_5BrF_6N_4O_2$, 466.0; m/z found, 467.4 [M+H]$^+$. $^1$H NMR (600 MHz, DMSO-d$_6$) δ 12.61-12.46 (s, 1H), 8.77-8.64 (d, J=8.4 Hz, 1H), 8.11-7.95 (d, J=8.4 Hz, 1H), 7.91-7.68 (dd, J=27.7, 1.8 Hz, 2H).

Example 291: 3-(1H-Indazol-6-yl)-2,5-bis(trifluoromethyl)imidazo[4,5-b]pyridine

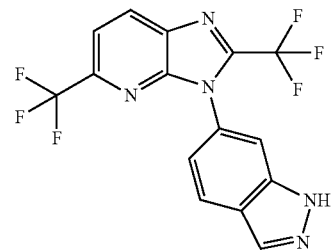 [SMILES: FC(F)(F)c1ccc2nc(C(F)(F)F)n(-c3ccc4cn[nH]c4c3)c2n1]

The title compound was prepared analogous to Example 134 using 2-chloro-3-nitro-6-(trifluoromethyl)pyridine and 1H-indazol-6-amine. MS (ESI): mass calcd. for $C_{15}H_7F_6N_5$, 371.1; m/z found, 372.0 [M+H]$^+$. $^1$H NMR (400 MHz, CD$_3$OD) δ 8.54 (d, J=8.4 Hz, 1H), 8.24 (d, J=1.0 Hz, 1H), 8.03 (d, J=8.5 Hz, 1H), 7.93 (d, J=8.5 Hz, 1H), 7.82 (s, 1H), 7.31-7.26 (m, 1H).

Example 292: 5-[2,5-Bis(trifluoromethyl)imidazo[4,5-b]pyridin-3-yl]-1,3-dihydropyrrolo[2,3-b]pyridin-2-one

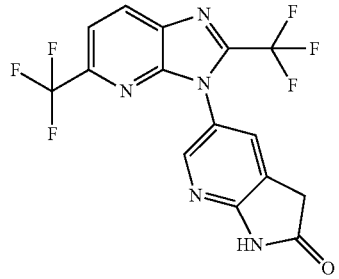 [SMILES: O=C1Cc2cc(-n3c(C(F)(F)F)nc4ccc(C(F)(F)F)nc43)cnc2N1]

The title compound was prepared analogous to Example 134 using 2-chloro-3-nitro-6-(trifluoromethyl)pyridine and 5-amino-1H-pyrrolo[2,3-b]pyridin-2(3H)-one. MS (ESI): mass calcd. for $C_{15}H_7F_6N_5O$, 387.1; m/z found, 388.0 [M+H]$^+$. $^1$H NMR (400 MHz, CD$_3$OD) δ 8.54 (d, J=8.4 Hz, 1H), 8.29 (d, J=2.7 Hz, 1H), 7.98-7.91 (m, 1H), 7.85-7.79 (m, 1H).

Example 293: 3-(1H-Pyrrolo[2,3-b]pyridin-5-yl)-2,5-bis(trifluoromethyl)imidazo[4,5-b]pyridine

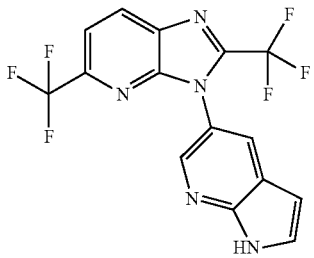 [SMILES: FC(F)(F)c1ccc2nc(C(F)(F)F)n(-c3cnc4[nH]ccc4c3)c2n1]

The title compound was prepared analogous to Example 134 using 2-chloro-3-nitro-6-(trifluoromethyl)pyridine and 1H-pyrrolo[2,3-b]pyridin-5-amine. MS (ESI): mass calcd. for $C_{15}H_7F_6N_5$, 371.1; m/z found, 372.1 [M+H]$^+$. $^1$H NMR (400 MHz, CD$_3$OD) δ 8.55 (d, J=8.4 Hz, 1H), 8.34 (d, J=2.3 Hz, 1H), 8.21 (d, J=2.4 Hz, 1H), 7.93 (d, J=8.5 Hz, 1H), 7.61 (d, J=3.5 Hz, 1H), 6.67 (d, J=3.5 Hz, 1H).

Example 294: 3-(7-Methyl-1H-indazol-5-yl)-2,5-bis(trifluoromethyl)imidazo[4,5-b]pyridine

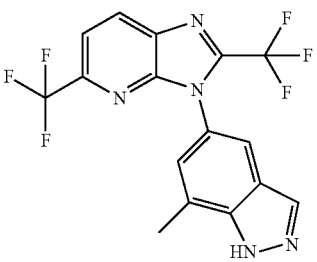 [SMILES: Cc1cc(-n2c(C(F)(F)F)nc3ccc(C(F)(F)F)nc32)cc2cn[nH]c12]

The title compound was prepared analogous to Example 134 using 2-chloro-3-nitro-6-(trifluoromethyl)pyridine and 7-methyl-1H-indazol-5-amine. MS (ESI): mass calcd. for $C_{16}H_9F_6N_5$, 385.1; m/z found, 386.1 [M+H]$^+$. $^1$H NMR (600 MHz, CDCl$_3$) δ 10.98 (s, 1H), 8.47 (d, J=8.4 Hz, 1H), 8.05 (s, 1H), 7.86 (d, J=8.4 Hz, 1H), 7.67-7.64 (m, 1H), 7.10 (d, J=1.5 Hz, 1H), 2.52 (s, 3H).

Example 295: 5-[2,5-Bis(trifluoromethyl)imidazo[4,5-b]pyridin-3-yl]-1H-indazole-3-carbonitrile

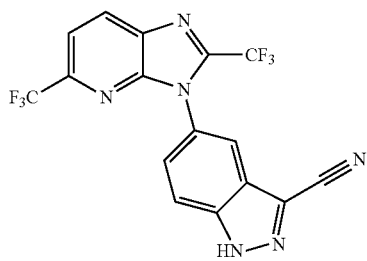 [SMILES: N#Cc1n[nH]c2ccc(-n3c(C(F)(F)F)nc4ccc(C(F)(F)F)nc43)cc12]

The title compound was prepared analogous to Example 134 using 2-chloro-3-nitro-6-(trifluoromethyl)pyridine and 5-amino-1H-indazole-3-carbonitrile. MS (ESI): mass calcd. for $C_{16}H_6F_6N_6$, 396.1; m/z found, 397.0 [M+H]$^+$. $^1$H NMR (400 MHz, DMSO-d$_6$) δ 14.95-14.71 (s, 1H), 8.89-8.62 (d, J=8.4 Hz, 1H), 8.47-8.32 (d, J=1.7 Hz, 1H), 8.13-7.95 (m, 2H), 7.92-7.71 (dd, J=8.9, 1.8 Hz, 1H).

Example 296: 5-[2-(Difluoromethyl)-5-(trifluoromethyl)imidazo[4,5-b]pyridin-3-yl]-1H-indazol-3-ol

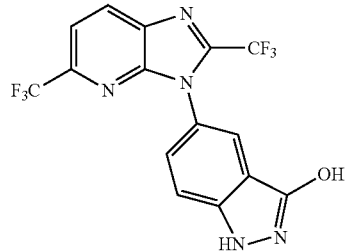 [SMILES: Oc1n[nH]c2ccc(-n3c(C(F)(F)F)nc4ccc(C(F)(F)F)nc43)cc12]

The title compound was prepared analogous to Example 134 using 2-chloro-3-nitro-6-(trifluoromethyl)pyridine and 5-amino-1H-indazol-3-ol, and substituting 2,2-difluoroacetic acid in Step B. MS (ESI): mass calcd. for $C_{15}H_8F_5N_5O$, 369.1; m/z found, 370.1 [M+H]$^+$. $^1$H NMR (600 MHz, DMSO-d$_6$) δ 10.92-10.71 (s, 1H), 8.67-8.53 (d, J=8.4 Hz, 1H), 8.00-7.91 (d, J=8.4 Hz, 1H), 7.91-7.83 (dd, J=2.0, 0.8 Hz, 1H), 7.54-7.43 (m, 2H), 12.16-11.94 (m, 1H), 7.39-7.14 (m, 1H).

Example 297: 6-[2-Cyclopropyl-5-(trifluoromethyl)imidazo[4,5-b]pyridin-3-yl]indolin-2-one

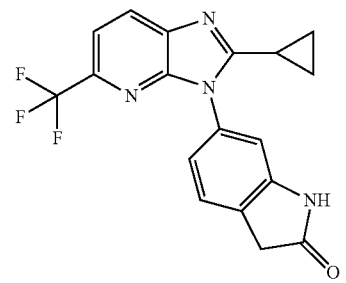 [SMILES: O=C1Cc2ccc(-n3c(C4CC4)nc4ccc(C(F)(F)F)nc43)cc2N1]

The title compound was made in a manner analogous to Example 109, Method B using 2-chloro-3-nitro-6-(trifluoromethyl)pyridine and 6-aminoindolin-2-one. MS (ESI): mass calcd. for $C_{18}H_{13}F_3N_4O$, 358.1; m/z found, 359.0 [M+H]$^+$. $^1$H NMR (300 MHz, DMSO-d$_6$) δ 10.63 (s, 1H), 8.19 (d, J=8.2 Hz, 1H), 7.74 (d, J=8.2 Hz, 1H), 7.47 (d, J=7.8 Hz, 1H), 7.15 (d, J=7.8 Hz, 1H), 7.04 (s, 1H), 3.62 (s, J=5.4 Hz, 2H), 2.08-1.84 (m, 1H), 1.27-1.18 (m, 2H), 1.16-1.07 (m, 2H).

Example 298: 3-(3-Bromo-1H-indazol-5-yl)-2-isopropyl-5-(trifluoromethyl)imidazo[4,5-b]pyridine

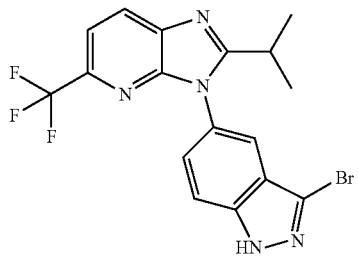 [SMILES: CC(C)c1nc2ccc(C(F)(F)F)nc2n1-c1ccc2[nH]nc(Br)c2c1]

The title compound was made in a manner analogous to Example 109, Method B using 3-bromo-1H-indazol-5-amine and 2-chloro-3-nitro-6-(trifluoromethyl)pyridine. MS (ESI): mass calcd. for C$_{17}$H$_{3}$BrF$_{3}$N$_{5}$, 423.0; m/z found, 424.0 [M+H]$^{+}$. $^{1}$H NMR (400 MHz, DMSO-d$_{6}$) δ 13.82 (s, 1H), 8.33 (d, J=8.3 Hz, 1H), 7.95-7.90 (m, 1H), 7.86-7.75 (m, 2H), 7.60 (dd, J=8.7, 2.0 Hz, 1H), 3.12-3.02 (m, 1H), 1.26 (d, J=6.9 Hz, 6H).

Example 299: 7-Chloro-5-[2-isopropyl-5-(trifluoromethyl)imidazo[4,5-b]pyridin-3-yl]indolin-2-one

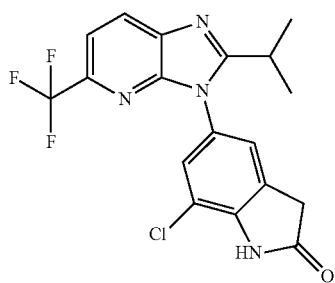

The title compound was prepared in a manner analogous to Example 109, Method B. MS (ESI): mass calcd. for C$_{18}$H$_{14}$ClF$_{3}$N$_{4}$O, 394.1; m/z found, 395.1 [M+H]$^{+}$. $^{1}$H NMR (400 MHz, CDCl$_{3}$) δ 8.20-8.14 (m, 2H), 7.65 (d, J=8.3 Hz, 1H), 7.30-7.28 (m, 1H), 7.18 (d, J=1.7 Hz, 1H), 3.74 (s, 2H), 3.21-3.09 (m, 1H), 1.39 (d, J=6.8 Hz, 6H).

Example 300: 3-(7-Chloro-1H-indazol-5-yl)-6-fluoro-2-isopropyl-imidazo[4,5-b]pyridine

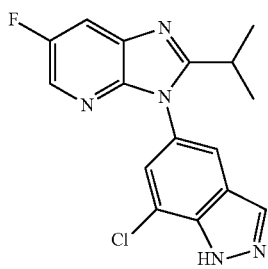 [SMILES: CC(C)c1nc2cc(F)cnc2n1-c1cc(Cl)c2[nH]ncc2c1]

The title compound was prepared in a manner analogous to Example 109, Method B. MS (ESI): mass calcd. for C$_{16}$H$_{13}$ClFN$_{5}$, 329.1; m/z found, 330.0 [M+H]$^{+}$. $^{1}$H NMR (500 MHz, CDCl$_{3}$) δ 8.22 (dd, J=2.6, 1.5 Hz, 1H), 8.17 (s, 1H), 7.82 (dd, J=8.8, 2.5 Hz, 1H), 7.69 (d, J=1.7 Hz, 1H), 7.37 (d, J=1.7 Hz, 1H), 3.27-2.90 (m, 1H), 1.38 (d, J=6.8 Hz, 6H).

Example 301: 5-[2-Isopropyl-5-(trifluoromethyl)imidazo[4,5-b]pyridin-3-yl]-1,3-dihydropyrrolo[2,3-b]pyridin-2-one

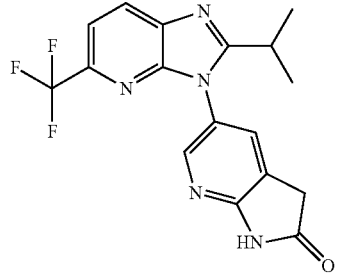 [SMILES: CC(C)c1nc2ccc(C(F)(F)F)nc2n1-c1cnc2c(c1)CC(=O)N2]

The title compound was made in a manner analogous to Example 109, Method B using 2-chloro-3-nitro-6-(trifluoromethyl)pyridine and 5-amino-1H-pyrrolo[2,3-b]pyridin-2(3H)-one. MS (ESI): mass calcd. for C$_{17}$H$_{14}$F$_{3}$N$_{5}$O, 361.1; m/z found, 362.2 [M+H]$^{+}$. $^{1}$H NMR (400 MHz, CD$_{3}$OD) δ 8.26-8.19 (m, 2H), 7.79-7.73 (m, 2H), 3.25-3.16 (m, 1H), 1.39 (s, 3H), 1.37 (s, 3H).

Example 302: 2-Isopropyl-3-(1H-pyrazolo[3,4-b]pyridin-5-yl)-5-(trifluoromethyl)imidazo[4,5-b]pyridine

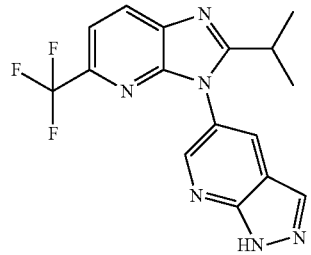 [SMILES: CC(C)c1nc2ccc(C(F)(F)F)nc2n1-c1cnc2[nH]ncc2c1]

The title compound was made in a manner analogous to Example 109, Method B. MS (ESI): mass calcd. for C$_{16}$H$_{13}$F$_{3}$N$_{6}$, 346.1; m/z found, 347.1 [M+H]$^{+}$. $^{1}$H NMR (400 MHz, CD$_{3}$OD) δ 8.64 (d, J=2.3 Hz, 1H), 8.47 (d, J=2.3 Hz, 1H), 8.28 (s, 1H), 8.25 (d, J=8.3 Hz, 1H), 7.77 (d, J=8.2 Hz, 1H), 3.24-3.15 (m, 1H), 1.39 (s, 3H), 1.37 (s, 3H).

Example 303: 2-Isopropyl-3-(1H-pyrrolo[2,3-b]pyridin-5-yl)-5-(trifluoromethyl)imidazo[4,5-b]pyridine

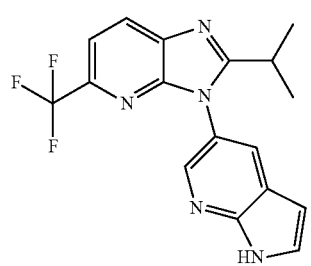 [SMILES: CC(C)c1nc2ccc(C(F)(F)F)nc2n1-c1cnc2[nH]ccc2c1]

The title compound was made in a manner analogous to Example 109, Method B. MS (ESI): mass calcd. for $C_{17}H_{14}F_3N_5$, 345.1; m/z found, 346.2 [M+H]$^+$. $^1$H NMR (400 MHz, CD$_3$OD) δ 8.28 (d, J=2.1 Hz, 1H), 8.23 (d, J=8.1 Hz, 1H), 8.15 (d, J=2.3 Hz, 1H), 7.75 (d, J=8.3 Hz, 1H), 7.60 (d, J=3.5 Hz, 1H), 6.67 (d, J=3.5 Hz, 1H), 3.23-3.15 (m, 1H), 1.38 (s, 3H), 1.37 (s, 3H).

Example 304: 3-(7-Allyl-1H-indazol-5-yl)-2,5-bis(trifluoromethyl)-3H-imidazo[4,5-b]pyridine

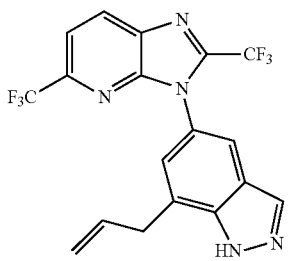

The title compound was prepared in a manner analogous to Example 189. MS (ESI): mass calcd. for $C_{18}H_{11}F_6N_5$, 411.1; m/z found, 412.1 [M+H]$^+$. $^1$H NMR (500 MHz, CDCl$_3$) δ 8.49-8.36 (d, J=8.4 Hz, 1H), 8.18-8.04 (d, J=1.0 Hz, 1H), 7.89-7.74 (m, 2H), 6.17-6.00 (m, 1H), 7.66-7.55 (dt, J=8.9, 0.9 Hz, 1H), 7.44-7.36 (dd, J=8.8, 2.0 Hz, 1H), 5.18-5.02 (dt, J=5.9, 1.5 Hz, 2H).

Example 305: 3-(7-(Prop-1-en-2-yl)-1H-indazol-5-yl)-2,5-bis(trifluoromethyl)-3H-imidazo[4,5-b]pyridine

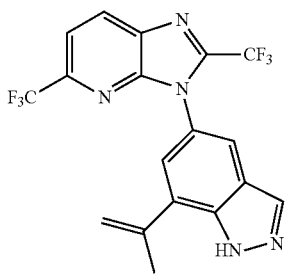 [SMILES: C=C(C)c1cc(-n2c(C(F)(F)F)nc3ccc(C(F)(F)F)nc32)cc2cn[nH]c12]

The title compound was prepared in a manner analogous to Example 189. MS (ESI): mass calcd. for $C_{18}H_{11}F_6N_5$, 411.1; m/z found, 412.1 [M+H]$^+$. $^1$H NMR (500 MHz, CDCl$_3$) δ 8.43 (d, J=8.3 Hz, 1H), 7.84-7.73 (m, 2H), 7.56 (s, 1H), 7.49-7.38 (s, 1H), 7.38-7.28 (m, 1H), 5.65-5.54 (m, 2H), 2.34-2.20 (s, 3H).

Example 306: 3-(7-Chloro-1H-indazol-5-yl)-5-(trifluoromethyl)imidazo[4,5-b]pyridine

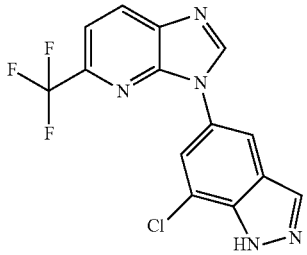 [SMILES: FC(F)(F)c1ccc2ncn(-c3cc(Cl)c4[nH]ncc4c3)c2n1]

The title compound was prepared in a manner analogous to Example 194. MS (ESI): mass calcd. for $C_{14}H_7ClF_3N_5$, 337.0; m/z found, 338.1 [M+H]$^+$. $^1$H NMR (400 MHz, CD$_3$OD) δ 8.94 (s, 1H), 8.37 (d, J=8.3 Hz, 1H), 8.30 (s, 1H), 8.22 (d, J=1.7 Hz, 1H), 7.97 (d, J=1.7 Hz, 1H), 7.84 (d, J=8.3 Hz, 1H).

Example 307: 3-(7-Chloro-1H-indazol-5-yl)-2-cyclopropyl-5-(trifluoromethyl)imidazo[4,5-b]pyridine

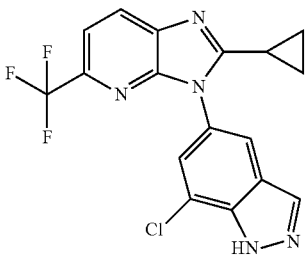 [SMILES: FC(F)(F)c1ccc2nc(C3CC3)n(-c3cc(Cl)c4[nH]ncc4c3)c2n1]

The title compound was prepared in a manner analogous to Example 197. MS (ESI): mass calcd. for $C_{17}H_{11}ClF_3N_5$, 377.1; m/z found, 378.0 [M+H]$^+$. $^1$H NMR (400 MHz, DMSO-d$_6$) δ 8.38 (s, 1H), 8.21 (d, J=8.2 Hz, 1H), 8.08 (s, 1H), 7.80-7.74 (m, 2H), 1.96-1.87 (m, 1H), 1.26-1.20 (m, 2H), 1.13-1.04 (m, 2H).

Example 308: 3-(7-Chloro-1H-indazol-5-yl)-2-cyclobutyl-5-(trifluoromethyl)imidazo[4,5-b]pyridine

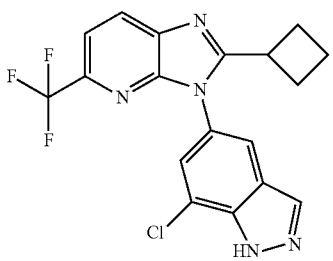 [SMILES: FC(F)(F)c1ccc2nc(C3CCC3)n(-c3cc(Cl)c4[nH]ncc4c3)c2n1]

The title compound was prepared in a manner analogous to Example 197. MS (ESI): mass calcd. for $C_{18}H_{13}ClF_3N_5$, 391.1; m/z found, 392.1 [M+H]$^+$. $^1$H NMR (500 MHz, CDCl$_3$) δ 8.27-8.23 (m, 1H), 8.07 (s, 1H), 7.73 (d, J=8.3 Hz, 1H), 7.57 (d, J=1.7 Hz, 1H), 7.25 (d, J=1.7 Hz, 1H), 3.62-3.53 (m, 1H), 2.67-2.56 (m, 2H), 2.25-2.16 (m, 2H), 2.06-1.95 (m, 2H).

Example 309: 7-Methyl-5-[2-methyl-5-(trifluoromethyl)imidazo[4,5-b]pyridin-3-yl]indolin-2-one

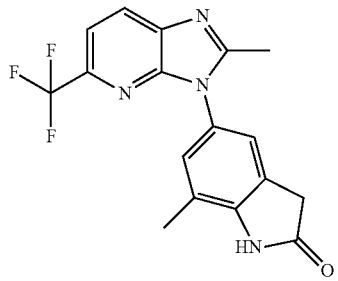

The title compound was prepared in a manner analogous to Example 198. MS (ESI): mass calcd. for $C_{17}H_{13}F_3N_4O$, 346.1; m/z found, 347.1 [M+H]$^+$. $^1$H NMR (400 MHz, CD$_3$OD) δ 8.16 (d, J=8.2 Hz, 1H), 7.72 (d, J=8.2 Hz, 1H), 7.22-7.15 (m, 2H), 3.65 (s, 2H), 2.55 (s, 3H), 2.36 (s, 3H).

Example 310: 5-[2-Isopropyl-5-(trifluoromethyl)imidazo[4,5-b]pyridin-3-yl]-7-methyl-indolin-2-one

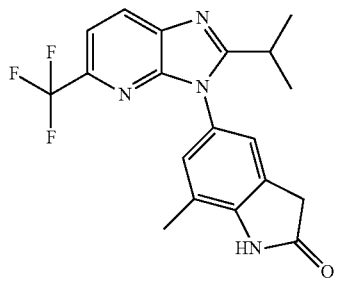

The title compound was prepared in a manner analogous to Example 198. MS (ESI): mass calcd. for $C_{19}H_{17}F_3N_4O$, 374.1; m/z found, 375.1 [M+H]$^+$. $^1$H NMR (500 MHz, CD$_3$OD) δ 8.20-8.16 (m, 1H), 7.72 (d, J=8.3 Hz, 1H), 7.21-7.14 (m, 2H), 3.23-3.15 (m, 1H), 2.36 (s, 3H), 1.36 (s, 3H), 1.35 (s, 3H).

Example 311: 2-Isopropyl-3-(4-methyl-1H-indazol-6-yl)-5-(trifluoromethyl)imidazo[4,5-b]pyridine

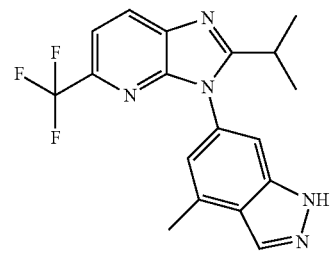 [SMILES: Cc1cc(-n2c(C(C)C)nc3ccc(C(F)(F)F)nc32)cc2[nH]ncc12]

The title compound was prepared in a manner analogous to Example 198. MS (ESI): mass calcd. for $C_{18}H_{16}F_3N_5$, 359.1; m/z found, 360.2 [M+H]$^+$. $^1$H NMR (400 MHz, CD$_3$OD) δ 8.28 (d, J=1.1 Hz, 1H), 8.22 (d, J=8.3 Hz, 1H), 7.75 (d, J=8.2 Hz, 1H), 7.53 (s, 1H), 6.99 (d, J=2.3 Hz, 1H), 3.28-3.20 (m, 1H), 2.72 (s, 3H), 1.38 (s, 3H), 1.36 (s, 3H).

Example 312: 3-(7-Chloro-1H-indazol-5-yl)-2-methyl-5-(trifluoromethyl)imidazo[4,5-b]pyridine

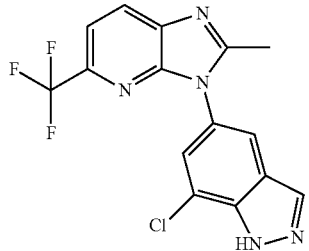 [SMILES: Cc1nc2ccc(C(F)(F)F)nc2n1-c1cc(Cl)c2[nH]ncc2c1]

The title compound was prepared in a manner analogous to Example 198. MS (ESI): mass calcd. for $C_{15}H_9ClF_3N_5$, 351.0; m/z found, 352.0 [M+H]$^+$. $^1$H NMR (500 MHz, CD$_3$OD) δ 8.29 (s, 1H), 8.20 (d, J=8.2 Hz, 1H), 7.95 (d, J=1.7 Hz, 1H), 7.75 (d, J=8.3 Hz, 1H), 7.61 (d, J=1.7 Hz, 1H), 2.59 (s, 3H).

Example 313: 7-Chloro-5-[2-methyl-5-(trifluoromethyl)imidazo[4,5-b]pyridin-3-yl]indolin-2-one

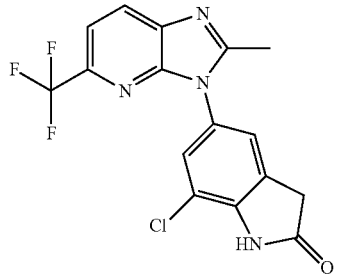 [SMILES: Cc1nc2ccc(C(F)(F)F)nc2n1-c1cc(Cl)c2c(c1)CC(=O)N2]

The title compound was prepared in a manner analogous to Example 198. MS (ESI): mass calcd. for $C_{16}H_{10}ClF_3N_4O$, 366.0; m/z found, 367.0 [M+H]$^+$. $^1$H NMR (500 MHz, CDCl$_3$) δ 8.20 (s, 1H), 8.13-8.10 (m, 1H), 7.66 (d, J=8.2 Hz, 1H), 7.31-7.29 (m, 1H), 7.22-7.19 (m, 1H), 3.74 (s, 2H), 2.59 (s, 3H).

Example 314: 3-(7-Chloro-1H-indazol-5-yl)-2-ethyl-5-(trifluoromethyl)imidazo[4,5-b]pyridine

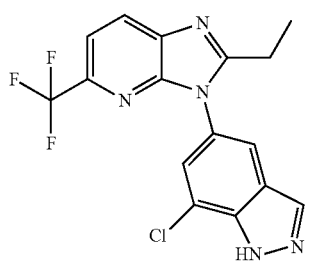 [SMILES: CCc1nc2ccc(C(F)(F)F)nc2n1-c1cc(Cl)c2[nH]ncc2c1]

The title compound was prepared in a manner analogous to Example 198. MS (ESI): mass calcd. for $C_{16}H_{11}ClF_3N_5$, 365.1; m/z found, 366.1 [M+H]+. 1H NMR (400 MHz, CD3OD) δ 8.32 (s, 1H), 8.24 (d, J=8.4 Hz, 1H), 7.96 (d, J=1.7 Hz, 1H), 7.78 (d, J=8.3 Hz, 1H), 7.62 (d, J=1.7 Hz, 1H), 2.98-2.89 (m, 2H), 1.42-1.35 (m, 3H).

Example 315: 2-Ethyl-3-(7-methyl-1H-indazol-5-yl)-5-(trifluoromethyl)imidazo[4,5-b]pyridine

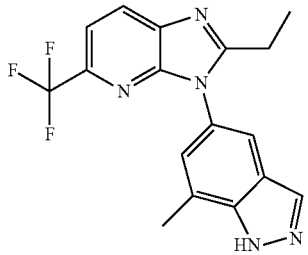 [SMILES: CCc1nc2ccc(C(F)(F)F)nc2n1-c1cc(C)c2[nH]ncc2c1]

The title compound was prepared in a manner analogous to Example 198 from N2-(7-methyl-1H-indazol-5-yl)-6-(trifluoromethyl)pyridine-2,3-diamine (Intermediate 56). MS (ESI): mass calcd. for $C_{17}H_{14}F_3N_5$, 345.1; m/z found, 346.2 [M+H]+. 1H NMR (400 MHz, CDCl3) δ 10.51 (s, 1H), 8.23 (d, J=8.3 Hz, 1H), 7.97 (s, 1H), 7.72 (d, J=8.3 Hz, 1H), 7.49 (d, J=1.7 Hz, 1H), 6.96 (d, J=1.8 Hz, 1H), 2.84-2.76 (m, 2H), 2.48 (s, 3H), 1.39-1.33 (m, 3H).

Example 316: 3-(7-Chloro-1H-indazol-5-yl)-2-isopropyl-5-(trifluoromethyl)imidazo[4,5-b]pyridine

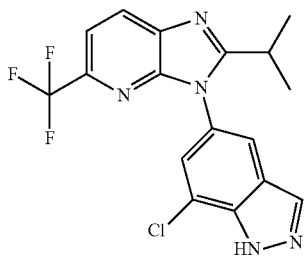 [SMILES: CC(C)c1nc2ccc(C(F)(F)F)nc2n1-c1cc(Cl)c2[nH]ncc2c1]

The title compound was prepared in a manner analogous to Example 198. MS (ESI): mass calcd. for $C_{17}H_{13}ClF_3N_5$, 379.1; m/z found, 380.1 [M+H]+. 1H NMR (400 MHz, CD3OD) δ 8.32 (s, 1H), 8.24 (d, J=8.3 Hz, 1H), 7.96 (d, J=1.8 Hz, 1H), 7.77 (d, J=8.3 Hz, 1H), 7.61 (d, J=1.7 Hz, 1H), 3.27-3.18 (m, 1H), 1.39 (d, J=6.9 Hz, 6H).

Example 317: 3-(7-Methyl-1H-indazol-5-yl)-2-(trifluoromethyl)imidazo[4,5-b]pyridine

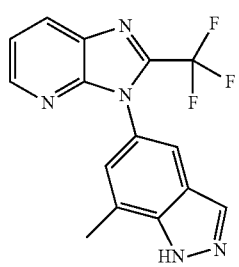 [SMILES: Cc1cc(-n2c(C(F)(F)F)nc3cccnc32)cc2cn[nH]c12]

The title compound was prepared in a manner analogous to Example 199. MS (ESI): mass calcd. for $C_{15}H_{10}F_3N_5$, 317.1; m/z found, 318.1 [M+H]+. 1H NMR (400 MHz, CD3OD) δ 8.52-8.46 (m, 1H), 8.38-8.32 (m, 1H), 8.20 (s, 1H), 7.82 (d, J=1.8 Hz, 1H), 7.57-7.50 (m, 1H), 7.27 (s, 1H), 2.66 (s, 3H).

Example 318: 7-Methyl-5-[2-(trifluoromethyl)imidazo[4,5-b]pyridin-3-yl]indolin-2-one

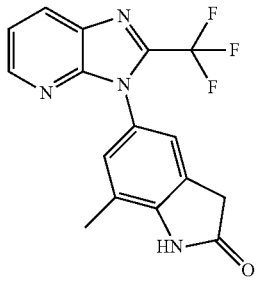 [SMILES: Cc1cc(-n2c(C(F)(F)F)nc3cccnc32)cc2c1NC(=O)C2]

The title compound was prepared in a manner analogous to Example 199. MS (ESI): mass calcd. for $C_{16}H_{11}F_3N_4O$, 332.1; m/z found, 333.1 [M+H]+. 1H NMR (500 MHz, CD3OD) d 8.51-8.47 (m, 1H), 8.32 (dd, J=8.2, 1.4 Hz, 1H), 7.55-7.50 (m, 1H), 7.24 (d, J=2.0 Hz, 1H), 7.20 (d, J=2.0 Hz, 1H), 2.35 (s, 3H).

Example 319: 2-Methyl-3-(7-methyl-1H-indazol-5-yl)-5-(trifluoromethyl)imidazo[4,5-b]pyridine

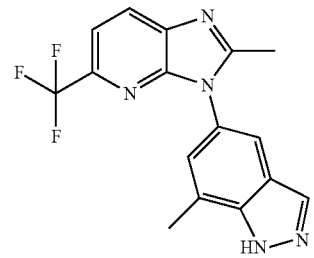 [SMILES: Cc1cc(-n2c(C)nc3ccc(C(F)(F)F)nc32)cc2cn[nH]c12]

The title compound was made in a manner analogous to Example 198. MS (ESI): mass calcd. for $C_{16}H_{12}F_3N_5$, 331.1; m/z found, 332.1 [M+H]+. 1H NMR (400 MHz, CD3OD) δ 8.22-8.16 (m, 2H), 7.77 (d, J=1.8 Hz, 1H), 7.73 (d, J=8.3 Hz, 1H), 7.27-7.22 (m, 1H), 2.67 (s, 3H), 2.56 (s, 3H).

Example 320: 3-(1H-Indazol-5-yl)-5-(2-pyridyl)-2-(trifluoromethyl)imidazo[4,5-b]pyridine

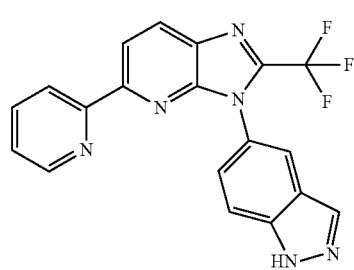 [SMILES: FC(F)(F)c1nc2ccc(-c3ccccn3)nc2n1-c1ccc2[nH]ncc2c1]

The title compound was prepared in a manner analogous to Example 208, using pyridin-2-ylzinc(II) bromide in Step B. MS (ESI): mass calcd. for $C_{19}H_{11}F_3N_6$, 380.1; m/z found, 380.2 [M+H]$^+$. $^1$HNMR (400 MHz, DMSO-d$_6$) δ 8.60 (d, J=4.6 Hz, 1H), 8.50 (d, J=8.0 Hz, 1H), 8.45 (d, J=8.0 Hz, 1H), 8.19 (s, 1H), 8.06 (s, 1H), 7.98 (d, J=7.9 Hz, 1H), 7.70-7.78 (m, 2H), 7.52 (dd, J=8.8, 1.6 Hz, 1H), 7.32-7.36 (m, 1H).

Example 321: 2-Cyclopropyl-5-(difluoromethyl)-3-(1H-indazol-5-yl)imidazo[4,5-b]pyridine

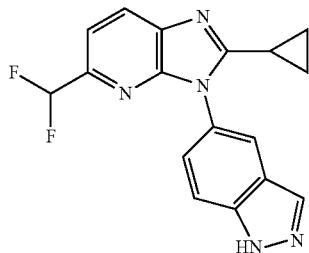 [SMILES: FC(F)c1ccc2nc(C3CC3)n(-c3ccc4[nH]ncc4c3)c2n1]

The title compound was prepared in a manner analogous to Example 210. MS (ESI): mass calcd. for $C_{17}H_{13}F_2N_5$, 325.1; m/z found, 326.1 [M+H]$^+$. $^1$H NMR (500 MHz, CDCl$_3$) δ 8.24-8.13 (m, 1H), 8.07 (d, J=8.3 Hz, 1H), 7.91 (d, J=2.0 Hz, 1H), 7.72 (d, J=8.5 Hz, 1H), 7.60 (d, J=8.2 Hz, 1H), 7.48 (dd, J=8.7, 2.0 Hz, 1H), 6.62 (t, J=55.4 Hz, 1H), 2.00-1.76 (m, 1H), 1.39 (dd, J=4.5, 2.6 Hz, 2H), 1.13 (dd, J=8.2, 2.9 Hz, 2H).

Example 322: 5-(Difluoromethyl)-2-(4-fluorophenyl)-3-(1H-indazol-5-yl)imidazo[4,5-b]pyridine

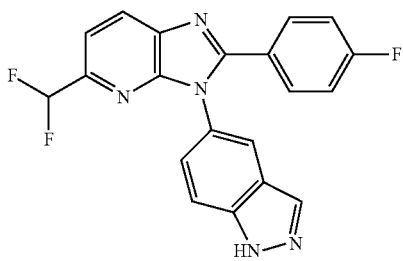 [SMILES: Fc1ccc(-c2nc3ccc(C(F)F)nc3n2-c2ccc3[nH]ncc3c2)cc1]

The title compound was prepared in a manner analogous to Example 210. MS (ESI): mass calcd. for $C_{20}H_{12}F_3N_5$, 379.1; m/z found, 380.0 [M+H]$^+$. $^1$H NMR (500 MHz, CDCl$_3$) δ 8.27 (d, J=8.2 Hz, 1H), 8.12 (d, J=1.1 Hz, 1H), 7.79 (dd, J=2.0, 0.8 Hz, 1H), 7.70 (d, J=8.3 Hz, 1H), 7.65-7.58 (m, 2H), 7.56 (dt, J=8.8, 0.9 Hz, 1H), 7.31 (dd, J=8.8, 1.9 Hz, 1H), 7.00 (dd, J=8.9, 8.4 Hz, 2H), 6.67 (t, J=55.5 Hz, 1H).

Example 323: 5-(Difluoromethyl)-3-(1H-indazol-5-yl)-2-phenyl-imidazo[4,5-b]pyridine

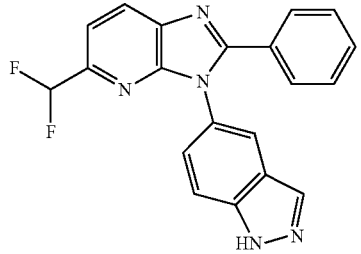 [SMILES: FC(F)c1ccc2nc(-c3ccccc3)n(-c3ccc4[nH]ncc4c3)c2n1]

The title compound was prepared in a manner analogous to Example 210. MS (ESI): mass calcd. for $C_{20}H_{13}F_2N_5$, 361.1; m/z found, 362.0 [M+H]$^+$. $^1$H NMR (500 MHz, CDCl$_3$) δ 8.28 (d, J=8.1 Hz, 1H), 8.14 (t, J=1.1 Hz, 1H), 7.81 (d, J=2.0 Hz, 1H), 7.69 (d, J=8.2 Hz, 1H), 7.66-7.53 (m, 3H), 7.44-7.37 (m, 1H), 7.37-7.28 (m, 3H), 6.66 (t, J=55.5 Hz, 1H).

Example 324: 3-(7-Chloro-1H-indazol-5-yl)-5-(difluoromethyl)-2-(trifluoromethyl)imidazo[4,5-b]pyridine

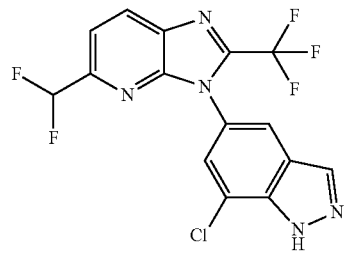

The title compound was prepared in a manner analogous to Example 212. MS (ESI): mass calcd. for $C_{15}H_7ClF_5N_5$, 387.0; m/z found, 388.1 [M+H]$^+$. $^1$H NMR (500 MHz, CDCl$_3$) δ 10.85 (s, 1H), 8.44 (d, J=8.4 Hz, 1H), 8.22 (d, J=0.7 Hz, 1H), 7.81 (d, J=8.4 Hz, 1H), 7.78 (d, J=1.6 Hz, 1H), 7.44 (d, J=1.6 Hz, 1H), 6.67 (t, J=55.1 Hz, 1H).

Example 325: 5-[5-(Difluoromethyl)-2-(trifluoromethyl)imidazo[4,5-b]pyridin-3-yl]-7-fluoro-indolin-2-one

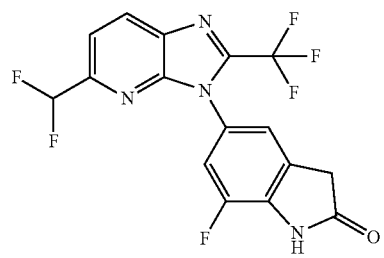 [SMILES: O=C1Cc2cc(-n3c(C(F)(F)F)nc4ccc(C(F)F)nc43)cc(F)c2N1]

The title compound was prepared in a manner analogous to Example 212. MS (ESI): mass calcd. for $C_{16}H_8F_6N_4O$, 386.1; m/z found, 387.1 [M+H]+. 1H NMR (400 MHz, CDCl3) δ 8.40 (d, J=8.4 Hz, 1H), 8.03 (s, 1H), 7.79 (d, J=8.4 Hz, 1H), 7.23-7.09 (m, 2H), 6.64 (t, J=55.2 Hz, 1H), 3.72 (t, J=1.0 Hz, 2H).

Example 326: 5-(Difluoromethyl)-3-(7-methyl-1H-indazol-5-yl)-2-(trifluoromethyl)imidazo[4,5-b]pyridine

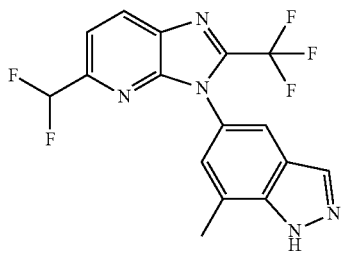 [SMILES: Cc1cc(-n2c(C(F)(F)F)nc3ccc(C(F)F)nc32)cc2cn[nH]c12]

The title compound was prepared in a manner analogous to Example 212. MS (ESI): mass calcd. for $C_{16}H_{10}F_5N_5$, 367.1; m/z found, 368.1 [M+H]+. 1H NMR (500 MHz, CDCl3) δ 8.41 (d, J=8.4 Hz, 1H), 8.19 (s, 1H), 7.79 (d, J=8.4 Hz, 1H), 7.73-7.62 (m, 1H), 7.18 (s, 1H), 6.63 (t, J=55.2 Hz, 1H), 2.73-2.52 (m, 3H).

Example 327: 3-(7-Chloro-1H-indazol-5-yl)-2-(2-fluoro-4-pyridyl)-5-methyl-imidazo[4,5-b]pyridine

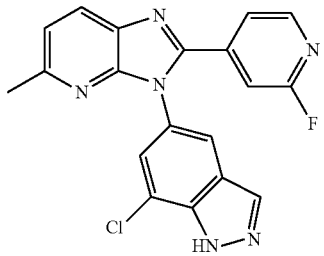 [SMILES: Cc1ccc2nc(-c3ccnc(F)c3)n(-c3cc(Cl)c4[nH]ncc4c3)c2n1]

The title compound was prepared in a manner analogous to Example 213. The title compound was obtained as an off-white solid (9 mg, 4.7%). MS (ESI): mass calcd. for $C_{19}H_{12}ClFN_6$, 378.1; m/z found, 379.1 [M+H]+. 1H NMR (500 MHz, CD3OD) δ 8.22 (s, 1H), 8.17 (d, J=5.3 Hz, 1H), 8.12 (d, J=8.2 Hz, 1H), 7.80 (d, J=1.7 Hz, 1H), 7.49 (d, J=1.7 Hz, 1H), 7.35-7.30 (m, 2H), 7.25 (d, J=0.7 Hz, 1H), 2.63 (s, 3H).

Example 328: 3-(7-Bromo-1H-indazol-5-yl)-2-(2-fluoro-4-pyridyl)-5-(trifluoromethyl)imidazo[4,5-b]pyridine

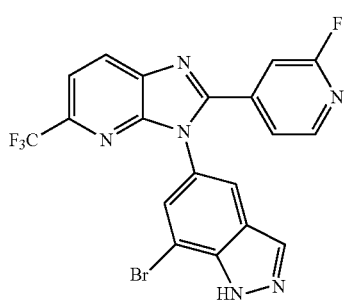 [SMILES: Fc1cc(-c2nc3ccc(C(F)(F)F)nc3n2-c2cc(Br)c3[nH]ncc3c2)ccn1]

The title compound was prepared in a manner analogous to Example 217 using $N^2$-(7-bromo-1H-indazol-5-yl)-6-(trifluoromethyl)pyridine-2,3-diamine (Intermediate 54) in Step A. MS (ESI): mass calcd. for $C_{19}H_9BrF_4N_6$, 476.0; m/z found, 477.0 [M+H]+. 1H NMR (400 MHz, Acetonitrile-d3) δ 11.77 (br s, 1H), 8.41 (d, J=8.2 Hz, 1H), 8.25 (s, 1H), 8.16 (d, J=5.2 Hz, 1H), 7.90 (d, J=1.7 Hz, 1H), 7.85 (d, J=8.3 Hz, 1H), 7.69 (d, J=1.7 Hz, 1H), 7.35 (dt, J=5.3, 1.7 Hz, 1H), 7.28-7.25 (m, 1H).

Example 329: 5-(2-(Hydroxymethyl)-6-(trifluoromethyl)-1H-pyrrolo[2,3-b]pyridin-1-yl)-7-methylindolin-2-one

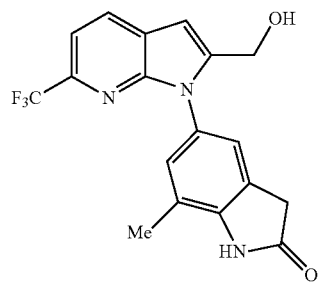 [SMILES: Cc1cc(-n2c(CO)cc3ccc(C(F)(F)F)nc32)cc2c1NC(=O)C2]

Step A. 7-Methyl-5-((3-(3-((tetrahydro-2H-pyran-2-yl)oxy)prop-1-yn-1-yl)-6-(trifluoromethyl)pyridin-2-yl)amino)indolin-2-one To a 20-mL glass microwave vial was added 2-chloro-3-(3-((tetrahydro-2H-pyran-2-yl)oxy)prop-1-yn-1-yl)-6-(trifluoromethyl)pyridine (Intermediate 23, 250 mg, 0.78 mmol), amino-7-methylindolin-2-one (Intermediate 10, 127 mg, 0.782 mmol), BrettPhos Pd third-generation pre-catalyst (70.9 mg, 0.0782 mmol), $Cs_2CO_3$ (764 mg, 2.35 mmol), and 1,4-dioxane (4 mL). The resulting suspension was degassed by bubbling through nitrogen gas while stirring for 5 min. The vial was sealed under nitrogen atmosphere and heated to 110° C. for 4.5 hr. The reaction mixture was removed from the heating bath and cooled to 20° C., and then the reaction was partitioned between EtOAc and saturated aqueous ammonium chloride. The organics were washed with brine, dried ($MgSO_4$), filtered, and concentrated under reduced pressure. Purification (FCC, $SiO_2$, 0% to 5% methanol in DCM) afforded the title compound (155 mg, 45%). 1H NMR (400 MHz, CD3OD) δ 7.78 (d, J=7.7 Hz, 1H), 7.55 (s, 1H), 7.37 (d, J=2.1 Hz, 1H), 7.05 (d, J=7.7 Hz, 1H), 4.92 (t, J=3.3 Hz, 1H), 4.61 (s, 2H), 3.92 (ddd, J=11.7, 8.7, 3.1 Hz, 1H), 3.61-3.49 (m, 3H), 2.26 (s, 3H), 1.90-1.49 (m, 6H).

Step B: 7-Methyl-5-(2-(((tetrahydro-2H-pyran-2-yl)oxy)methyl)-6-(trifluoromethyl)-1H-pyrrolo[2,3-b]pyridin-1-yl)indolin-2-one To a glass sealed tube containing a suspension of 7-methyl-5-((3-(3-((tetrahydro-2H-pyran-2-yl)oxy)prop-1-yn-1-yl)-6-(trifluoromethyl)pyridin-2-yl)amino)indolin-2-one (150 mg, 0.337 mmol) in anhydrous THF (3.5 mL) was added TBAF (1 M in THF, 0.67 mL, 0.67 mmol). The tube was flushed briefly with nitrogen gas and sealed under nitrogen atmosphere. The tube was stirred at 100° C. (refluxing observed) for 15 min. The reaction solution was partitioned between EtOAc (50 mL) and water. The organic phase was washed twice more with water, then once with brine, dried (MgSO$_4$), filtered, and concentrated in vacuo. Purification (FCC, SiO$_2$, 0% to 5% methanol in DCM) afforded the title compound (45 mg, 30%). $^1$HNMR (400 MHz, CD$_3$OD) δ 8.14 (dd, J=8.1, 0.8 Hz, 1H), 7.50 (d, J=8.1 Hz, 1H), 7.15 (dd, J=2.1, 0.6 Hz, 1H), 7.12 (dd, J=2.0, 0.8 Hz, 1H), 6.75 (s, 1H), 4.74 (d, J=12.7 Hz, 1H), 4.56 (t, J=3.4 Hz, 1H), 4.48 (d, J=12.7 Hz, 1H), 3.55 (ddd, J=11.1, 9.3, 3.2 Hz, 1H), 3.40 (dt, J=10.1, 3.8 Hz, 1H), 2.32 (s, 3H), 1.83-1.36 (m, 6H). $^{19}$F NMR (376 MHz, CD$_3$OD) δ −67.23 (s).

Step C. 5-(2-(Hydroxymethyl)-6-(trifluoromethyl)-1H-pyrrolo[2,3-b]pyridin-1-yl)-7-methylindolin-2-one To a suspension of 7-methyl-5-(2-(((tetrahydro-2H-pyran-2-yl)oxy)methyl)-6-(trifluoromethyl)-1H-pyrrolo[2,3-b]pyridin-1-yl)indolin-2-one (45 mg, 0.10 mmol) in MeOH (0.5 mL) was added concentrated hydrochloric acid (12 μL, 0.11 mmol). The reaction was sealed under ambient atmosphere and stirred at 20° C. for 90 min. The reaction mixture was partitioned between EtOAc (20 mL) and sat. aq. NaHCO$_3$ (5 mL), and the aqueous layer was extracted with EtOAc (5 mL total). The combined organics were dried (MgSO$_4$), filtered, and concentrated under reduced pressure to afford the title compound (39 mg, 100%) as an off-white powdery solid. MS (ESI): mass calcd. for C$_{18}$H$_{14}$F$_3$N$_3$O$_2$, 361.1; m/z found, 362.1 [M+H]$^+$. $^{19}$F NMR (376 MHz, CD$_3$OD) δ −67.28 (s). $^1$H NMR (400 MHz, CD$_3$OD) δ 8.13 (d, J=8.1 Hz, 1H), 7.50 (dd, J=8.1, 1.1 Hz, 1H), 7.16 (s, 1H), 7.12 (d, J=2.1 Hz, 1H), 6.74 (s, 1H), 4.62 (s, 2H), 2.34 (s, 3H).

Example 330: (1-(1H-Indazol-5-yl)-6-(trifluoromethyl)-1H-pyrrolo[2,3-b]pyridin-2-yl)methanol

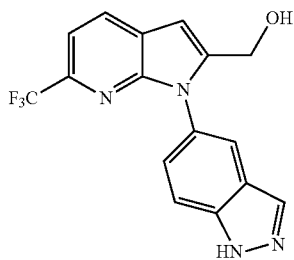

Step A: N-(3-(3-((Tetrahydro-2H-pyran-2-yl)oxy)prop-1-yn-1-yl)-6-(trifluoromethyl)pyridin-2-yl)-1-((2-(trimethylsilyl)ethoxy)methyl)-1H-indazol-5-amine To a solution of 2-chloro-3-(3-((tetrahydro-2H-pyran-2-yl)oxy)prop-1-yn-1-yl)-6-(trifluoromethyl)pyridine (Intermediate 23, 1.66 g, 2.59 mmol) in anhydrous toluene (55 mL) was added Pd$_2$(dba)$_3$ (474 mg, 0.518 mmol), XantPhos (600 mg, 1.04 mmol) and Cs$_2$CO$_3$ (4.73 g, 14.5 mmol) under N$_2$. After 10 min, 2-((2-(trimethylsilyl)ethoxy)methyl)-2H-indazol-5-amine (Intermediate 9, 1.37 g, 5.19 mmol) was added and the mixture was stirred at 20° C. for 10 min. Then, the mixture was heated at 100° C. for 3 hr. EtOAc and water were added. The organic phase was separated and dried (MgSO$_4$), filtered and concentrated. Purification (FCC, SiO$_2$, 0:100 to 5:95 EtOAc/heptane) afforded the title compound (942 mg, 33%). MS (ESI): mass calcd. for C$_{27}$H$_{33}$F$_3$N$_4$O$_3$Si 546.2; m/z found 547.2 [M+H]$^+$. $^1$H NMR (300 MHz, DMSO-d$_6$) δ 8.64 (s, 1H), 8.10 (s, 1H), 8.05 (s, 1H), 7.94 (d, J=7.7 Hz, 1H), 7.72 (d, J=8.9 Hz, 1H), 7.62 (d, J=9.1 Hz, 1H), 7.17 (d, J=7.7 Hz, 1H), 5.74 (s, 2H), 4.87 (s, 1H), 4.63 (d, J=16.2 Hz, 1H), 4.55 (d, J=16.2 Hz, 1H), 3.56-3.48 (m, 2H), 1.79-1.60 (m, 2H), 1.59-1.42 (m, 4H), 0.81 (t, J=8.0 Hz, 2H), −0.11 (s, 9H).

Step B. (1-(1H-indazol-3-yl)-6-(trifluoromethyl)-1H-pyrrolo[2,3-b]pyridin-2-yl)methanol The title compound was prepared in a manner analogous to Example 329, Steps B and C. $^1$H NMR (300 MHz, DMSO-d$_6$) δ 13.34 (s, 1H), 8.27 (d, J=8.1 Hz, 1H), 8.19 (s, 1H), 7.90 (s, 1H), 7.71 (d, J=8.8 Hz, 1H), 7.60 (d, J=8.1 Hz, 1H), 7.39 (dd, J=8.7, 1.7 Hz, 1H), 6.78 (s, 1H), 5.38 (t, J=5.4 Hz, 1H), 4.52 (d, J=5.3 Hz, 2H).

Example 331: 7-Methyl-5-(2-methyl-6-(trifluoromethyl)-1H-pyrrolo[2,3-b]pyridin-1-yl)indolin-2-one

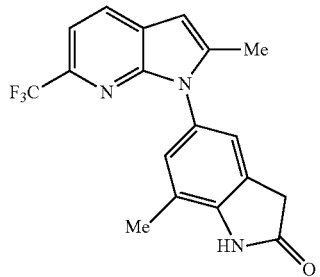

Step A: 5-(2-(Chloromethyl)-6-(trifluoromethyl)-1H-pyrrolo[2,3-b]pyridin-1-yl)-7-methylindolin-2-one To a glass vial was added 5-(2-(hydroxymethyl)-6-(trifluoromethyl)-1H-pyrrolo[2,3-b]pyridin-1-yl)-7-methylindolin-2-one (Example 329, 52 mg, 0.14 mmol), DCM (1.4 mL), N,N-diisopropylethylamine (50 μL, 0.29 mmol), and methanesulfonyl chloride (33 mg, 0.29 mmol). The reaction was sealed under ambient atmosphere and stirred at 20° C. After 60 min, additional methanesulfonyl chloride (16 mg, 0.14 mmol) was added. After stirring at 20° C. for another 60 min, the reaction was diluted with DCM (25 mL). The organic phase was washed once with sat. aq. NaHCO$_3$ (1 mL). The organic phase was dried (MgSO$_4$), filtered and concentrated to provide the title compound (85 mg) as a brown powdery solid. MS (ESI): mass calcd. for C$_{18}$H$_{13}$ClF$_3$N$_3$O, 379.1; m/z found, 380.1 [M+H]$^+$.

Step B: 7-Methyl-5-(2-methyl-6-(trifluoromethyl)-1H-pyrrolo[2,3-b]pyridin-1-yl)indolin-2-one To a round bottom flask containing 5-(2-(chloromethyl)-6-(trifluoromethyl)-1H-pyrrolo[2,3-b]pyridin-1-yl)-7-methylindolin-2-one (85 mg, 0.22 mmol) under nitrogen atmosphere was added 10% Pd/C (24 mg, 0.022 mmol), then MeOH (4.5 mL). The flask was stirred under hydrogen atmosphere at 20° C. for 16 h. Upon completion, the reaction vessel was purged with nitrogen, and the suspension was filtered through a pad of Celite® 545 to remove insolubles, and washed with methanol (50 mL total). The resulting filtrate was concentrated under reduced pressure. Purification (FCC, SiO$_2$, 0 to 5% methanol in DCM) afforded the title compound (36 mg, 47%). MS (ESI): mass calcd. for C$_{18}$H$_{14}$F$_3$N$_3$O, 345.1; m/z found, 346.2 [M+H]$^+$. $^{19}$F NMR (376 MHz, CD$_3$OD) δ −67.11 (s). $^1$H NMR (400 MHz, CD$_3$OD) δ 8.02 (d, J=8.1 Hz, 1H), 7.45 (d, J=8.0 Hz, 1H), 7.09 (d, J=2.0 Hz, 1H), 7.08-7.01 (m, 1H), 6.49 (d, J=1.0 Hz, 1H), 2.34 (s, 3H), 2.33 (s, 3H).

Example 332: 5-(2-Isopropyl-1H-pyrrolo[2,3-b]pyridin-1-yl)-7-methyl-1H-indazole

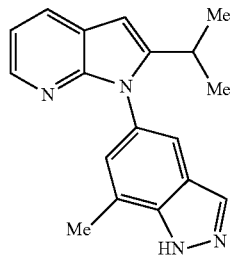

Step A. 7-Methyl-N-(3-(3-methylbut-1-yn-1-yl)pyridin-2-yl)-1H-indazol-5-amine

To a glass sealed tube was added 2-chloro-3-(3-methylbut-1-yn-1-yl)pyridine (Intermediate 35, 220 mg, 1.23 mmol), 7-methyl-1H-indazol-5-amine (180 mg, 1.23 mmol), BrettPhos Pd third-generation pre-catalyst (111 mg, 0.122 mmol), Cs$_2$CO$_3$ (1.20 g, 3.67 mmol), and 1,4-dioxane (6 mL). The resulting suspension was degassed by bubbling through nitrogen gas while stirring for 6 min. The tube was sealed under nitrogen atmosphere and heated to 120° C. in an oil bath for 48 h. The tube was cooled to 20° C., and additional BrettPhos Pd third-generation pre-catalyst (111 mg, 0.122 mmol) was added. The resulting suspension was again degassed by bubbling through nitrogen gas while stirring for 6 min before resealing and heating at 120° C. for another 48 h. The reaction mixture was then cooled to 20° C. and partitioned between EtOAc (150 mL) and aqueous ammonium chloride (50 mL). The resulting mixture was extracted with EtOAc (50 mL). The combined organics were dried (MgSO$_4$), filtered, and concentrated under reduced pressure. Purification (FCC, SiO$_2$, 0% to 5% methanol in DCM) afforded the title compound (132 mg, 37%). MS (ESI): mass calcd. for C$_{18}$H$_{18}$N$_4$, 290.2; m/z found, 291.1 [M+H]$^+$.

Step B: 5-(2-Isopropyl-1H-pyrrolo[2,3-b]pyridin-1-yl)-7-methyl-1H-indazole

To a vial was added 7-methyl-N-(3-(3-methylbut-1-yn-1-yl)pyridin-2-yl)-1H-indazol-5-amine (235 mg, 0.809 mmol), gold(III) chloride (24 mg, 0.081 mmol), and EtOH (16 mL) in order. The vial was sealed under ambient atmosphere and stirred at 80° C. for 30 min. The reaction mixture was filtered thru a 0.45 m Teflon membrane and concentrated under reduced pressure. Purification (FCC, SiO$_2$, 0 to 10% methanol in DCM) afforded the title compound, which was further purified by preparative reverse-phase HPLC (95:5 to 5:95 water:acetonitrile with 20 mM ammonium hydroxide aqueous modifier) to provide the title compound (21 mg, 8%) as an off-white solid. MS (ESI): mass calcd. for C$_{18}$H$_{18}$N$_4$, 290.2; m/z found, 291.1 [M+H]$^+$. $^1$H NMR (400 MHz, CD$_3$OD) δ 8.15 (s, 1H), 8.00 (dd, J=4.9, 1.5 Hz, 1H), 7.96 (dd, J=7.8, 1.5 Hz, 1H), 7.64 (d, J=1.7 Hz, 1H), 7.16-7.05 (m, 2H), 6.46 (s, 1H), 3.06-2.93 (m, 1H), 2.64 (d, J=0.9 Hz, 3H), 1.22 (d, J=6.8 Hz, 6H).

Example 333: 1-(7-Chloro-1H-indazol-5-yl)-2-methyl-pyrrolo[2,3-b]pyridine

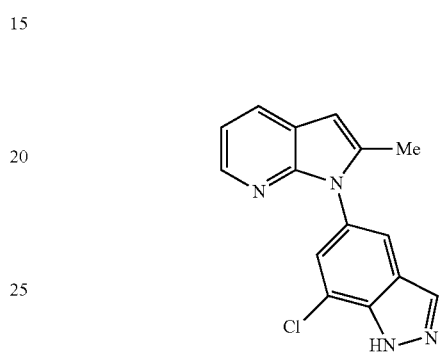

Step A. 7-Chloro-5-(2-methyl-1H-pyrrolo[2,3-b]pyridin-1-yl)-1-((2-(trimethylsilyl)ethoxy)methyl)-1H-indazole The title compound was prepared in a manner analogous to Example 332, following Steps A and B. In Step A, using 7-chloro-1-((2-(trimethylsilyl)ethoxy)methyl)-1H-indazol-5-amine (Intermediate 19) and 2-chloro-3-(prop-1-yn-1-yl)pyridine (Intermediate 27). MS (ESI): mass calcd. for C$_{21}$H$_{25}$ClN$_4$OSi, 412.1; m/z found, 413.0 [M+H]$^+$. $^1$H NMR (300 MHz, CDCl$_3$) δ 8.21 (d, J=4.5 Hz, 1H), 8.10 (s, 1H), 7.87 (d, J=7.6 Hz, 1H), 7.70 (d, J=1.4 Hz, 1H), 7.44 (d, J=1.6 Hz, 1H), 7.12-7.05 (m, 1H), 6.38 (s, 1H), 6.08 (s, 2H), 3.66-3.57 (m, 2H), 2.33 (s, 3H), 0.99-0.94 (m, 2H), 0.03 (s, 9H).

Step B. 1-(7-Chloro-1H-indazol-5-yl)-2-methyl-pyrrolo[2,3-b]pyridine

To a sealed tube containing a suspension of 7-chloro-5-(2-methyl-1H-pyrrolo[2,3-b]pyridin-1-yl)-1-((2-(trimethylsilyl)ethoxy)methyl)-1H-indazole (70 mg, 0.17 mmol) in anhydrous THF (1.4 mL) was added TBAF (1 M in THF, 0.34 mL, 0.34 mmol). The tube was flushed briefly with nitrogen gas, sealed and stirred at 100° C. (refluxing observed) for 16 h. The reaction solution was partitioned between EtOAc (50 mL) and sat. aq. NaHCO$_3$. The organic phase was dried (MgSO$_4$), filtered, and concentrated in vacuo. The residue was triturated with diethyl ether to afford the title compound (7.1 mg, 15%). MS (ESI): mass calcd. for C$_{15}$H$_{11}$ClN$_4$, 282.1; m/z found, 283.0 [M+H]$^+$. $^1$H NMR (300 MHz, CDCl$_3$) δ 12.36 (br s, 1H), 8.32 (d, J=4.7 Hz, 1H), 7.97 (s, 1H), 7.91 (d, J=7.8 Hz, 1H), 7.54 (d, J=1.1 Hz, 1H), 7.27 (s, 1H), 7.14 (dd, J=7.7, 4.9 Hz, 1H), 6.38 (s, 1H), 2.29 (s, 3H).

Example 334: 5-[6-(Difluoromethyl)-2-isopropyl-pyrrolo[2,3-b]pyridin-1-yl]-7-methyl-indolin-2-one

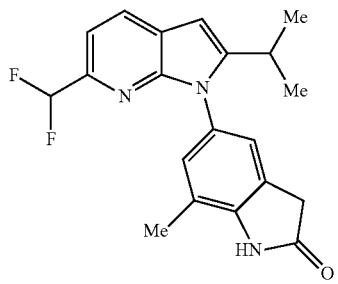 [SMILES: Cc1cc(-n2c(C(C)C)cc3ccc(C(F)F)nc32)cc2c1NC(=O)C2]

Step A: 5-((6-(Difluoromethyl)-3-(3-methylbut-1-yn-1-yl)pyridin-2-yl)amino)-7-methylindolin-2-one To a sealed tube was added 2-chloro-6-(difluoromethyl)-3-(3-methylbut-1-yn-1-yl)pyridine (Intermediate 29, 91 mg, 0.396 mmol), 5-amino-7-methylindolin-2-one (Intermediate 10, 64 mg, 0.396 mmol), BrettPhos Pd third-generation pre-catalyst (36 mg, 0.0396 mmol), $Cs_2CO_3$ (387 mg, 1.19 mmol), 1,4-dioxane (4.1 mL) in order. The resulting suspension was degassed by bubbling through nitrogen gas while stirring for 4 min. The tube was sealed under nitrogen atmosphere and heated to 110° C. in an oil bath for 12 h. The reaction mixture was cooled to 20° C., and partitioned between EtOAc (20 mL) and aqueous ammonium chloride (20 mL). The aqueous phase was extracted with EtOAc (4×80 mL). The combined organics were dried ($MgSO_4$), filtered, and concentrated. Purification (FCC, $SiO_2$, 0% to 5% methanol in DCM) afforded the title compound (40 mg, 28%). MS (ESI): mass calcd. for $C_{20}H_{19}F_2N_3O$, 355.2; m/z found, 356.1 $[M+H]^+$.

Step B: 5-[6-(Difluoromethyl)-2-isopropyl-pyrrolo[2,3-b]pyridin-1-yl]-7-methyl-indolin-2-one To a glass sealed tube containing a suspension of 5-((6-(difluoromethyl)-3-(3-methylbut-1-yn-1-yl)pyridin-2-yl)amino)-7-methylindolin-2-one (50 mg, 0.14 mmol) in anhydrous tetrahydrofuran (2.5 mL) was added TBAF (1 M in THF, 0.28 mL, 0.28 mmol). The tube was flushed briefly with nitrogen gas, sealed and stirred at 100° C. (refluxing observed) for 30 min. The reaction solution was partitioned between EtOAc (40 mL) and saturated aqueous ammonium chloride (10 mL). The organic phase was dried ($MgSO_4$), filtered, and concentrated in vacuo. Purification (FCC, $SiO_2$, 0% to 10% methanol in DCM) afforded the title compound (15.5 mg, 29%). MS (ESI): mass calcd. for $C_{20}H_{19}F_2N_3O$, 355.1; m/z found, 356.1 $[M+H]^+$. $^1H$ NMR (400 MHz, $CD_3OD$) δ 8.02 (d, J=8.0 Hz, 1H), 7.38 (d, J=8.0 Hz, 1H), 7.09 (s, 1H), 7.04 (s, 1H), 6.57 (t, J=55.7 Hz, 1H), 6.48 (d, J=0.8 Hz, 1H), 3.63 (s, 2H), 3.07-2.93 (hept, J=6.8 Hz, 1H), 2.33 (s, 3H), 1.23 (d, J=6.8 Hz, 6H). $^{19}F$ NMR (376 MHz, $CD_3OD$) δ −112.87 (d, J=55.7 Hz).

Example 335: 1-(1H-Indazol-5-yl)-2-isopropyl-6-(trifluoromethyl)pyrrolo[2,3-b]pyridine

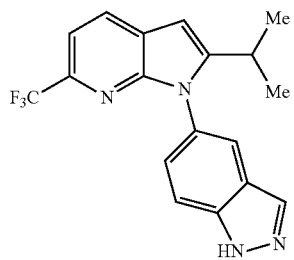 [SMILES: CC(C)c1cc2ccc(C(F)(F)F)nc2n1-c1ccc2[nH]ncc2c1]

Step A: N-(3-(3-Methylbut-1-yn-1-yl)-6-(trifluoromethyl)pyridin-2-yl)-1-((2-(trimethylsilyl)ethoxy)methyl)-1H-indazol-5-amine Tris(dibenzylideneacetone)dipalladium(0) (214 mg, 0.234 mmol), XantPhos (270 mg, 0.468 mmol) and $Cs_2CO_3$ (2.13 g, 6.546 mmol) were added to a solution of 2-chloro-3-(3-methylbut-1-yn-1-yl)-6-(trifluoromethyl)pyridine (Intermediate 32, 597 mg, 1.205 mmol) in anhydrous toluene (25 mL) while nitrogen was bubbling. After 10 min, 2-((2-(trimethylsilyl)ethoxy)methyl)-2H-indazol-5-amine (Intermediate 9, 615 mg, 2.338 mmol) was added and the mixture was stirred at 20° C. for 10 min. Then, the mixture was heated at 100° C. for 3 hr. EtOAc and water were added. The organic phase was separated, dried ($MgSO_4$), filtered and concentrated under reduced pressure. Purification (FCC, $SiO_2$; 0:100 to 5:95 EtOAc/heptane) afforded the title compound (597 mg, 52%). MS (ESI): mass calcd. for $C_{24}H_{29}F_3N_4OSi$, 474.2; m/z found, 474.9 $[M+H]^+$.

Step B: 1-(1H-Indazol-5-yl)-2-isopropyl-6-(trifluoromethyl)pyrrolo[2,3-b]pyridine To a glass sealed tube containing a suspension of N-(3-(3-methylbut-1-yn-1-yl)-6-(trifluoromethyl)pyridin-2-yl)-1-((2-(trimethylsilyl)ethoxy)methyl)-1H-indazol-5-amine (597 mg, 0.629 mmol) in anhydrous tetrahydrofuran (10.3 mL) was added TBAF (1 M in THF, 2.5 mL, 2.5 mmol). The tube was sealed under nitrogen atmosphere and stirred at 110° C. overnight. The reaction solution was partitioned between EtOAc and sat. aq. $NaHCO_3$. The organic phase was dried ($MgSO_4$), filtered, and concentrated in vacuo. Purification (FCC, $SiO_2$, 0% to 35% EtOAc/hexanes) afforded the title compound (79 mg, 36%). MS (ESI): mass calcd. for $C_{18}H_{15}F_3N_4$, 344.1; m/z found, 345.1 $[M+H]^+$. $^1H$ NMR (300 MHz, DMSO-$d_6$) δ 13.38 (s, 1H), 8.23-8.15 (m, 2H), 7.90 (s, 1H), 7.73 (d, J=8.7 Hz, 1H), 7.57 (d, J=8.1 Hz, 1H), 7.35 (dd, J=8.7, 1.6 Hz, 1H), 6.65 (s, 1H), 2.97 (hept, J=6.8 Hz, 1H), 1.17 (d, J=6.8 Hz, 6H).

Example 336: 5-[2-(Difluoromethyl)-6-(trifluoromethyl)pyrrolo[2,3-b]pyridin-1-yl]-7-methyl-indolin-2-one

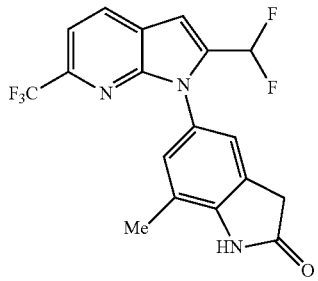 [SMILES: Cc1cc(-n2c(C(F)F)cc3ccc(C(F)(F)F)nc32)cc2c1NC(=O)C2]

Step A: 1-(7-Methyl-2-oxoindolin-5-yl)-6-(trifluoromethyl)-1H-pyrrolo[2,3-b]pyridine-2-carbaldehyde To a round bottom flask containing 5-(2-(hydroxymethyl)-6-(trifluoromethyl)-1H-pyrrolo[2,3-b]pyridin-1-yl)-7-methylindolin-2-one (Example 329, 310 mg, 0.858 mmol) was added Dess-Martin periodinane (728 mg, 1.72 mmol) followed by DCM (6 mL). The flask was sealed under ambient atmosphere and stirred rapidly at 20° C. for 60 min. The reaction was quenched by adding sat. aq. NaHCO$_3$ (25 mL) and 10% aqueous sodium thiosulfate (25 mL). The biphasic mixture was stirred vigorously for 2 h, the phases separated, and the aqueous phase extracted once more with DCM. The combined organic phases were washed once with sat. aq. NaHCO$_3$, dried (MgSO$_4$), filtered, and concentrated to give the title compound (295 mg, 96%), as a light brown solid, which was carried forward to the next step without further purification. MS (ESI): mass calcd. for C$_{18}$H$_{12}$F$_3$N$_3$O$_2$, 359.1; m/z found, 360.0 [M+H]$^+$. $^1$H NMR (400 MHz, DMSO-d$_6$) δ 10.67 (s, 1H), 9.90 (s, 1H), 8.60 (d, J=8.3 Hz, 1H), 7.75 (d, J=8.2 Hz, 1H), 7.69 (s, 1H), 7.18 (s, 1H), 7.14 (s, 1H), 3.59 (s, 2H), 2.26 (s, 3H). $^{19}$F NMR (376 MHz, DMSO-d$_6$) δ −64.88 (s).

Step B: 5-[2-(Difluoromethyl)-6-(trifluoromethyl)pyrrolo[2,3-b]pyridin-1-yl]-7-methyl-indolin-2-one To a flask containing 1-(7-methyl-2-oxoindolin-5-yl)-6-(trifluoromethyl)-1H-pyrrolo[2,3-b]pyridine-2-carbaldehyde (60 mg, 0.17 mmol) under nitrogen atmosphere was added anhydrous DCM (3 mL), and the reaction mixture was degassed. The flask was cooled to 0° C. and DAST (0.11 mL, 0.84 mmol) was added slowly dropwise over 30 seconds. After 1 min, the flask was removed from the cooling bath and allowed to warm to 20° C. under nitrogen atmosphere. After 2 hr, the flask was warmed to 30° C. in a water bath for an additional 3 hr. The reaction was quenched by pouring onto ice (20 mL) and extracted into DCM (10 mL total). The combined organics were dried (MgSO$_4$), filtered, and concentrated. Purification (FCC, SiO$_2$, 0 to 5% MeOH in DCM), afforded the title compound which was further purified (preparative silica gel TLC, two 20 cm×20 cm plates, 0.5 mm thickness, 95:5 DCM/MeOH) to afford the title compound (11 mg, 17%) as a light tan solid. MS (ESI): mass calcd. for C$_{18}$H$_{12}$F$_5$N$_3$O, 381.1; m/z found, 382.0 [M+H]$^+$. $^{19}$F NMR (376 MHz, CD$_3$OD) δ −67.66 (s), −114.82 (d, J=52.7 Hz). $^1$H NMR (400 MHz, CD$_3$OD) δ 8.31 (s, 1H), 7.60 (d, J=10.2 Hz, 1H), 7.17-7.09 (m, 3H), 6.87 (t, J=54.0 Hz, 1H), 3.63 (s, 2H), 2.34 (s, 3H).

Example 337: 6-[2-(Difluoromethyl)-6-(trifluoromethyl)pyrrolo[2,3-b]pyridin-1-yl]-3H-1,3-benzothiazol-2-one

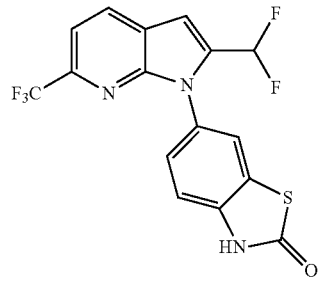 [SMILES: O=c1[nH]c2ccc(-n3c(C(F)F)cc4ccc(C(F)(F)F)nc43)cc2s1]

Step A: 6-((3-(3-(((Tetrahydro-2H-pyran-2-yl)oxy)prop-1-yn-1-yl)-6-(trifluoromethyl)pyridin-2-yl)amino)-3-((2-(trimethylsilyl)ethoxy)methyl)benzo[d]thiazol-2(3H)-one To a solution of 2-chloro-3-(3-((tetrahydro-2H-pyran-2-yl)oxy)prop-1-yn-1-yl)-6-(trifluoromethyl)pyridine (Intermediate 23, 595 mg, 1.75 mmol) in anhydrous toluene (19 mL) was added Pd(dba)$_3$ (160 mg, 0.175 mmol), XantPhos (203 mg, 0.350 mmol) and Cs$_2$CO$_3$ (1.60 g, 4.90 mmol) under nitrogen. After 10 min, 6-amino-3-((2-(trimethylsilyl)ethoxy)methyl)benzo[d]thiazol-2(3H)-one (Intermediate 16, 519 mg, 1.75 mmol) was added and the mixture was stirred at 20° C. for 10 min. Then, the mixture was heated at 100° C. for 3 hr. Upon completion, EtOAc and water were added to the reaction mixture. The organic phase was separated, dried (MgSO$_4$), filtered, and concentrated. Purification (FCC, SiO$_2$; 0:100 to 5:95 EtOAc/heptane) afforded the title compound (971 mg, 71%). MS (ESI): mass calcd. for C$_{27}$H$_{32}$F$_3$N$_3$O$_4$SSi 579.2, m/z found 580.0 [M+H]$^+$. $^1$H NMR (300 MHz, CDCl$_3$) δ 8.06 (d, J=1.9 Hz, 1H), 7.71 (d, J=7.6 Hz, 1H), 7.60 (s, 1H), 7.57 (dd, J=8.8, 2.1 Hz, 1H), 7.23 (d, J=8.7 Hz, 1H), 7.06 (d, J=7.7 Hz, 1H), 5.36 (s, 2H), 4.94 (s, 1H), 4.60 (s, 2H), 3.68-3.56 (m, 4H), 1.88-1.75 (m, 2H), 1.74-1.62 (m, 4H), 0.97-0.89 (m, 2H), 0.02 (s, 9H).

Step B: 6-(2-(Hydroxymethyl)-6-(trifluoromethyl)-1H-pyrrolo[2,3-b]pyridin-1-yl)benzo[d]thiazol-2(3H)-one The title compound was prepared in a manner analogous to Intermediate 63, Steps B and C. MS (ESI): mass calcd. for C$_{16}$H$_{10}$F$_3$N$_3$O$_2$S 365.0, m/z found 365.9 [M+H]$^+$.

Step C: 1-(2-Oxo-2,3-dihydrobenzo[d]thiazol-6-yl)-6-(trifluoromethyl)-1H-pyrrolo[2,3-b]pyridine-2-carbaldehyde The title compound was prepared in a manner analogous to Example 336, Step A. MS (ESI): mass calcd. for C$_{16}$H$_8$F$_3$N$_3$O$_2$S, 363.0; m/z found, 363.7 [M+H]$^+$. $^1$H NMR (300 MHz, CDCl$_3$) δ 9.97 (s, 1H), 8.89 (s, 1H), 8.33 (d, J=8.2 Hz, 1H), 7.63 (d, J=8.3 Hz, 1H), 7.49 (s, 2H), 7.32 (dd, J=8.5, 1.9 Hz, 1H), 7.17 (d, J=8.4 Hz, 1H).

Step D: 6-[2-(Difluoromethyl)-6-(trifluoromethyl)pyrrolo[2,3-b]pyridin-1-yl]-3H-1,3-benzothiazol-2-one To a solution of 1-(2-oxo-2,3-dihydrobenzo[d]thiazol-6-yl)-6-(trifluoromethyl)-1H-pyrrolo[2,3-b]pyridine-2-carbaldehyde (65 mg, 0.14 mmol) in anhydrous DCM (1.4 mL) at 0° C. was added Deoxo-Fluor® (50% solution in toluene, 0.16 mL, 0.35 mmol). After 1 min, the cold bath was removed and reaction mixture was stirred at 40° C. for 2 hr. The reaction temperature was then raised to 40° C., and additional Deoxo-Fluor® (50% solution in toluene, 0.16 mL, 0.35 mmol) was added in batches every 12 to 16 hr until all starting material was consumed. The mixture was diluted with sat. aq. NaHCO$_3$ and extracted with DCM. The organic layer was washed with water, dried (MgSO$_4$), filtered, and concentrated in vacuo. Purification (FCC, SiO$_2$, 0:100 to 70:30, EtOAc/heptanes) afforded the title compound (16 mg, 28%). MS (ESI): mass calcd. for C$_{16}$H$_8$F$_5$N$_3$OS, 385.0; m/z found, 385.9 [M+H]$^+$. $^1$HNMR (300 MHz, CDCl$_3$) δ 9.08 (s, 1H), 8.22 (d, J=8.2 Hz, 1H), 7.61 (d, J=8.2 Hz, 1H), 7.51 (s, 1H), 7.32 (dd, J=8.4, 1.4 Hz, 1H), 7.16 (d, J=8.4 Hz, 1H), 7.04 (s, 1H), 6.68 (t, J=53.6 Hz, 1H).

Example 338: 7-Chloro-5-(2-methylpyrrolo[2,3-b]pyridin-1-yl)indolin-2-one

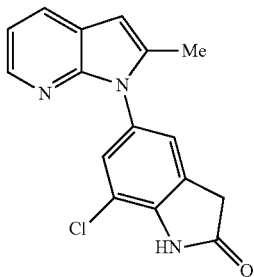 [SMILES: Cc1cc2cccnc2n1-c1cc(Cl)c2c(c1)CC(=O)N2]

The title compound was prepared in a manner analogous to Example 332, Step A, using 2-chloro-3-(prop-1-yn-1-yl)pyridine (Intermediate 27) and 5-amino-7-chloroindolin-2-one (Intermediate 18). MS (ESI): mass calcd. for C$_{16}$H$_{12}$ClN$_3$O, 297.1; m/z found, 298.0 [M+H]$^+$. $^1$H NMR (400 MHz, CD$_3$OD) δ 8.05 (dd, J=3.9, 2.3 Hz, 1H), 7.92 (s, 1H), 7.30 (d, J=3.6 Hz, 1H), 7.22 (d, J=3.6 Hz, 1H), 7.14-7.09 (m, 1H), 6.42 (d, J=2.7 Hz, 1H), 3.70 (s, 1H), 2.32 (s, 3H).

Example 339: 1-(7-Methyl-1H-indazol-5-yl)-6-(trifluoromethyl)pyrrolo[2,3-b]pyridin-3-ol

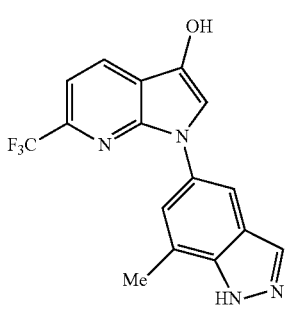 [SMILES: Cc1cc(-n2cc(O)c3ccc(C(F)(F)F)nc32)cc2cn[nH]c12]

Step A: 1-(7-Methyl-1H-indazol-5-yl)-6-(trifluoromethyl)-1H-pyrrolo[2,3-b]pyridine-3-carbaldehyde 1-(7-methyl-2-((2-(trimethylsilyl)ethoxy)methyl)-2H-indazol-5-yl)-6-(trifluoromethyl)-1H-pyrrolo[2,3-b]pyridine-3-carbaldehyde (Intermediate 64, 124 mg, 0.261 mmol) was dissolved in DCM (2 mL) and TFA (1 mL), and the resulting solution was stirred at ambient temperature for 2 h. The volatiles were removed under reduced pressure. Purification (FCC, SiO$_2$, 0:100 to 100:0, EtOAc:Hex) afforded the title compound as an off-white solid (61 mg, 68%). MS (ESI): mass calcd. for C$_{17}$H$_{11}$F$_3$N$_4$O, 344.1; m/z found, 345.1 [M+H]$^+$.

Step B: 1-(7-Methyl-1H-indazol-5-yl)-6-(trifluoromethyl)-1H-pyrrolo[2,3-b]pyridin-3-yl formate To a solution of 1-(7-methyl-1H-indazol-5-yl)-6-(trifluoromethyl)-1H-pyrrolo[2,3-b]pyridine-3-carbaldehyde (68 mg, 0.20 mmol) in DCM (4 mL) was added mCPBA (85 mg, 0.49 mmol) in one portion, and the resulting mixture was stirred at ambient temperature overnight. An additional portion of mCPBA (85 mg, 0.49 mmol) was added and the reaction mixture was stirred for 4 h. Then the reaction was diluted with 10% Na$_2$SO$_3$ (5 mL) and extracted with EtOAc (5 mL×3). The organic layer was dried (Na$_2$SO$_4$) and concentrated in vacuo to give the title compound (49 mg, 68%), which was used in the next step without further purification. MS (ESI): mass calcd. for C$_{17}$H$_{11}$F$_3$N$_4$O$_2$, 360.1; m/z found, 361.1 [M+H]$^+$.

Step C: 1-(7-Methyl-1H-indazol-5-yl)-6-(trifluoromethyl)pyrrolo[2,3-b]pyridin-3-ol To a solution of 1-(7-methyl-1H-indazol-5-yl)-6-(trifluoromethyl)-1H-pyrrolo[2,3-b]pyridin-3-yl formate (40 mg, 0.11 mmol) in MeOH (1 mL) was added Na$_2$CO$_3$ (12 mg, 0.11 mmol) and the resulting mixture was stirred for 2 minutes. The mixture was quenched with 2% citric acid (5 mL) and extracted with EtOAc (5 mL×3). The organic layer was dried (Na$_2$SO$_4$) and concentrated in vacuo. Purification (FCC, SiO$_2$, 0:100 to 50:50, EtOAc:DCM) afforded the title compound (18.5 mg, 28%). MS (ESI): mass calcd. for C$_{16}$H$_{11}$F$_3$N$_4$O, 332.1; m/z found, 333.1 [M+H]$^+$. $^1$H NMR (400 MHz, CD$_3$OD) δ 8.19 (d, J=8.3 Hz, 1H), 8.13-7.95 (m, 1.5H), 7.95-7.75 (m, 1.5H), 7.61 (t, J=1.6 Hz, 0.5H), 7.48 (d, J=8.2 Hz, 1H), 7.35 (s, 1H), 7.22 (d, J=7.7 Hz, 0.5H), 2.64 (s, 3H).

Example 340: 3-(Difluoromethyl)-1-(7-methyl-1H-indazol-5-yl)-6-(trifluoromethyl)pyrrolo[2,3-b]pyridine

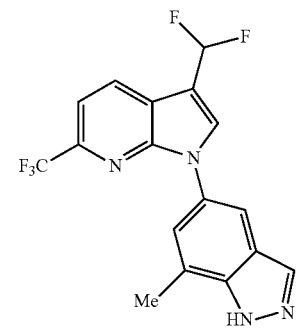 [SMILES: Cc1cc(-n2cc(C(F)F)c3ccc(C(F)(F)F)nc32)cc2cn[nH]c12]

Step A: 5-(3-(Difluoromethyl)-6-(trifluoromethyl)-1H-pyrrolo[2,3-b]pyridin-1-yl)-7-methyl-2-((2-(trimethylsilyl)ethoxy)methyl)-2H-indazole To a solution of 1-(7-methyl-2-((2-(trimethylsilyl)ethoxy)methyl)-2H-indazol-5-yl)-6-(trifluoromethyl)-1H-pyrrolo[2,3-b]pyridine-3-carbaldehyde (Intermediate 64, 50 mg, 0.10 mmol) in anhydrous DCM (20 mL) was added DAST (105 µL, 0.78 mmol) and the resulting mixture was heated at 50° C. for 2 h followed by stirring at ambient temperature for 16 h. The mixture was cooled to 0° C. and slowly quenched with sat. aq. NaHCO$_3$ (5 mL). The resulting mixture was extracted with DCM (3×5 mL), dried (Na$_2$SO$_4$), filtered, and concentrated under reduced pressure. Purification (FCC, SiO$_2$, 0:100 to 25:75, EtOAc:Hex) afforded the title compound (31 mg, 59%). MS (ESI): mass calcd. for C$_{23}$H$_{25}$F$_5$N$_4$OSi, 496.2; m/z found, 497.1 [M+H]$^+$.

Step B: 3-(Difluoromethyl)-1-(7-methyl-1H-indazol-5-yl)-6-(trifluoromethyl)pyrrolo[2,3-b]pyridine A solution of 5-(3-(difluoromethyl)-6-(trifluoromethyl)-1H-pyrrolo[2,3-b]pyridin-1-yl)-7-methyl-2-((2-(trimethylsilyl)ethoxy)methyl)-2H-indazole (31 mg, 0.062 mmol) in TBAF (1.0 M in THF, 0.25 mL) was stirred at 65° C. for 5 h. The reaction mixture was cooled to room temperature, diluted with brine (5 mL) and extracted with EtOAc (3×5 mL). The organic layers were dried (Na$_2$SO$_4$) and concentrated in vacuo. Purification (FCC, SiO$_2$, 0:100 to 50:50, EtOAc/hexanes) afforded the title compound (7.5 mg, 33%). MS (ESI): mass calcd. for C$_{17}$H$_{11}$F$_5$N$_4$, 366.1; m/z found, 367.1 [M+H]$^+$. $^1$H NMR (500 MHz, CDCl$_3$) δ 10.39 (s, 1H), 8.31 (d, J=8.2 Hz, 1H), 8.15 (d, J=1.0 Hz, 1H), 7.92-7.79 (m, 2H), 7.64 (dd, J=8.2, 1.0 Hz, 1H), 7.47 (dt, J=1.9, 1.0 Hz, 1H), 7.01 (dd, J=56.6, 55.4 Hz, 1H), 2.87-2.37 (m, 3H).

Example 341: 6-Methyl-1-(7-methyl-1H-indazol-5-yl)pyrrolo[2,3-b]pyridine

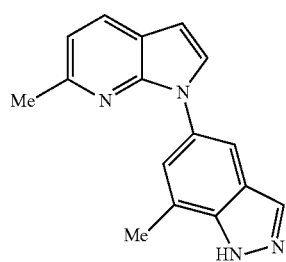 [SMILES: Cc1ccc2ccn(-c3cc(C)c4[nH]ncc4c3)c2n1]

Step A: 7-Methyl-5-(6-methyl-1H-pyrrolo[2,3-b]pyridin-1-yl)-2-((2-(trimethylsilyl)ethoxy)methyl)-2H-indazole A mixture of 5-bromo-7-methyl-2-((2-(trimethylsilyl)ethoxy)methyl)-2H-indazole (Intermediate 13, 0.25 mL, 0.76 mmol), 6-methyl-1H-pyrrolo[2,3-b]pyridine (100 mg, 0.76 mmol), [Pd(II)(π-cinnamyl)Cl]2 (24 mg, 0.045 mmol), BippyPhos (47 mg, 0.091 mmol), and sodium tert-butoxide (105 mg, 1.06 mmol) in 1,4-dioxane (5 mL) was heated in a microwave reactor at 180° C. for 20 minutes. The reaction mixture was diluted with H$_2$O and extracted with EtOAc (5 mL×3). The organic layer was dried (Na$_2$SO$_4$) and concentrated in vacuo. Purification (FCC, SiO$_2$, 0:100 to 20:80, EtOAc:Hex) afforded the title compound (251 mg, 85%). MS (ESI): mass calcd. for C$_{22}$H$_{28}$N$_4$OSi, 392.2; m/z found, 393.2 [M+H]$^+$.

Step B: 6-Methyl-1-(7-methyl-1H-indazol-5-yl)pyrrolo[2,3-b]pyridine

A solution of 7-methyl-5-(6-methyl-1H-pyrrolo[2,3-b]pyridin-1-yl)-2-((2-(trimethylsilyl)ethoxy)methyl)-2H-indazole (250 mg, 0.637 mmol) in TFA (1 mL) and DCM (2 mL) was stirred for 3 h. Volatiles were removed by evaporation and the residue was basified by 2M NH$_3$ in MeOH (2 mL). The resulting solution was stirred for 1 h and volatiles were removed in vacuo. Purification (FCC, SiO$_2$, 0:100 to 100:0, EtOAc:Hex) afforded the title compound (39.5 mg, 24%). MS (ESI): mass calcd. for C$_{16}$H$_{14}$N$_4$, 262.1; m/z found, 263.1 [M+H]$^+$. $^1$H NMR (400 MHz, CDCl$_3$) δ 10.86 (s, 1H), 8.04 (s, 1H), 7.89 (d, J=8.0 Hz, 1H), 7.76 (dd, J=1.7, 0.8 Hz, 1H), 7.41 (dd, J=1.9, 1.0 Hz, 1H), 7.37 (d, J=3.6 Hz, 1H), 7.03 (d, J=8.0 Hz, 1H), 6.57 (d, J=3.5 Hz, 1H), 2.68 (s, 3H), 2.55 (t, J=0.8 Hz, 3H).

Example 342: 5-(2-Isopropyl-6-methyl-pyrrolo 2,3-b pyridin-1-yl)indolin-2-one

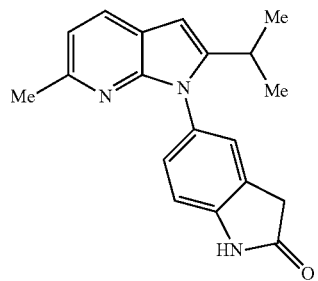 [SMILES: Cc1ccc2cc(C(C)C)n(-c3ccc4c(c3)CC(=O)N4)c2n1]

Step A: 1-(1H-Indol-5-yl)-2-isopropyl-6-methyl-1H-pyrrolo[2,3-b]pyridine

To a solution of 2-bromo-6-methyl-3-(3-methylbut-1-yn-1-yl)pyridine (Intermediate 28, 630 mg, 2.65 mmol), tert-butyl 5-amino-1H-indole-1-carboxylate (Intermediate 11, 799 mg, 3.44 mmol), [Pd(II)(π-cinnamyl)Cl]2 (27 mg, 0.053 mmol), and potassium tert-butoxide (890 mg, 7.94 mmol) in anhydrous toluene (31 mL) was added DavePhos (26 mg, 0.066 mmol). The solution was refluxed at 110° C. for 18 hr, then allowed to cool to 20° C. The reaction was diluted with EtOAc, filtered through a pad of Celite® 545, and concentrated in vacuo. Purification (FCC, SiO$_2$, 0% to 60% EtOAc/heptanes) afforded the title compound (170 mg, 22%) as a yellow oil.

Step B: 5-(2-Isopropyl-6-methyl-pyrrolo[2,3-b]pyridin-1-yl)indolin-2-one

To a solution of 1-(1H-indol-5-yl)-2-isopropyl-6-methyl-1H-pyrrolo[2,3-b]pyridine (170 mg, 0.59 mmol) in deionized water (0.5 mL) and glacial acetic acid (5 mL) was added pyridinium tribromide (188 mg, 0.587 mmol). The solution was stirred at 80° C. for 24 h, then allowed to cool to 20° C. The solution was poured into sat. aq. NaHCO$_3$ (50 mL) and extracted with EtOAc. The organic layer was washed with water, brine, dried (MgSO$_4$), filtered and concentrated in vacuo. Purification (FCC, SiO$_2$, 0 to 80% EtOAc/heptanes) afforded the title compound which was re-purified (preparative reverse-phase HPLC, gradient from 57% 10 mM NH$_4$CO$_3$H pH 9 solution in water, 43% CH$_3$CN to 40% 10 mM NH$_4$CO$_3$H pH 9 solution in water, 60% CH$_3$CN) to afford the title compound (16 mg, 9%) as a white powdery solid. MS (ESI): mass calcd. for C$_{19}$H$_{19}$N$_3$O, 305.2; m/z found, 306.2 [M+H]$^+$. $^1$H NMR (500 MHz, DMSO-d$_6$) δ 10.58 (br. s, 1H), 7.79 (d, J=7.80 Hz, 1H), 7.20 (s, 1H), 7.16 (dd, J=8.09, 2.02 Hz, 1H), 6.97 (d, J=8.09 Hz, 1H), 6.95 (d, J=7.80 Hz, 1H), 6.34 (s, 1H), 3.59 (s, 2H), 2.89 (hept, J=6.9 Hz, 1H), 2.34-2.45 (m, 3H), 1.15 (d, J=6.94 Hz, 6H).

Example 343: 2-(4-Fluorophenyl)-1-(1H-indol-5-yl)-6-methoxy-pyrrolo[2,3-b]pyridine

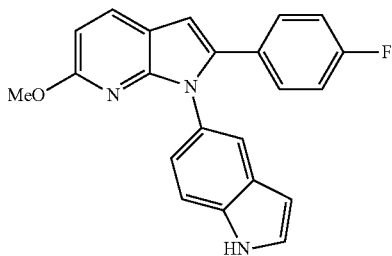 [SMILES: COc1ccc2cc(-c3ccc(F)cc3)n(-c3ccc4[nH]ccc4c3)c2n1]

To a solution of 2-bromo-3-((4-fluorophenyl)ethynyl)-6-methoxypyridine (Intermediate 44, 531 mg, 0.867 mmol) in anhydrous toluene (9 mL) was added XPhos (83 mg, 0.17 mmol), Pd$_2$(dba)$_3$ (79 mg, 0.088 mmol), and potassium tert-butoxide (292 mg, 2.60 mmol). After 10 min, tert-butyl 5-amino-1H-indole-1-carboxylate (Intermediate 11, 201 mg, 0.867 mmol) was added. The resulting solution was refluxed at 100° C. for 3 hr, then allowed to cool to 20° C. The reaction was partitioned between EtOAc and water. The organic phase was separated, dried (MgSO$_4$), filtered, and concentrated in vacuo, no deprotection necessary. Purification (FCC, SiO$_2$, 0% to 30% EtOAc/heptanes) afforded the title compound (60 mg, 19%) as a yellow solid. MS (ESI): mass calcd. for C$_{22}$H$_{16}$FN$_3$O, 357.1; m/z found, 358 [M+H]$^+$. $^1$H NMR (300 MHz, DMSO-d$_6$) δ 11.36 (s, 1H), 7.53-7.42 (m, 3H), 7.41-7.30 (m, 3H), 7.11 (t, J=8.8 Hz, 2H), 6.92 (d, J=8.5 Hz, 1H), 6.85 (s, 1H), 6.57 (d, J=8.8 Hz, 1H), 6.47 (s, 1H), 3.90 (s, 3H).

Example 344: 2-(4-Fluorophenyl)-1-indolin-5-yl-pyrrolo[2,3-b]pyridine

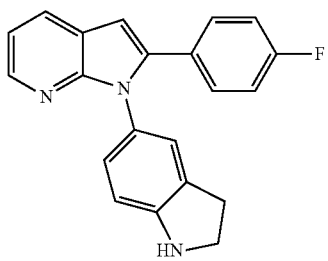 [SMILES: Fc1ccc(-c2cc3cccnc3n2-c2ccc3c(c2)CCN3)cc1]

Step A: tert-Butyl 5-(2-(4-fluorophenyl)-1H-pyrrolo[2,3-b]pyridin-1-yl)indoline-1-carboxylate To a solution of 2-bromo-3-((4-fluorophenyl)ethynyl) pyridine (Intermediate 42, 340 mg, 1.23 mmol) in anhydrous toluene (15 mL) was added Pd$_2$(dba)$_3$ (113 mg, 0.123 mmol), XPhos (117 mg, 0.246 mmol) and potassium tert-butoxide (414 mg, 3.69 mmol) under N$_2$. After 10 min, tert-butyl 5-aminoindoline-1-carboxylate (Intermediate 12, 519 mg, 1.75 mmol) was added and the mixture was stirred at 20° C. for 10 min. Then, the mixture was heated at 100° C. for 3 hr. EtOAc and water were added. The organic phase was separated and dried (MgSO$_4$), filtered and concentrated. Purification (FCC, SiO$_2$; 0:100 to 30:70, EtOAc/heptane) afforded the title compound (330 mg, 62%).

Step B: 2-(4-Fluorophenyl)-1-indolin-5-yl-pyrrolo[2,3-b]pyridine

To a flask charged with tert-butyl 5-(2-(4-fluorophenyl)-1H-pyrrolo[2,3-b]pyridin-1-yl)indoline-1-carboxylate (330 mg, 0.77 mmol) was added HCl (4 M solution in 1,4-dioxane, 2 mL, 8 mmol). The mixture was stirred at 20° C. for 15 min. The reaction was concentrated in vacuo, azeotroping with toluene several times. The residue was treated with an aqueous NaHCO$_3$ solution until pH>7, then extracted with DCM. The organic phases were combined, dried (MgSO$_4$), filtered and concentrated in vacuo. Purification (FCC, SiO$_2$, 0% to 10% EtOAc/heptanes) afforded the title compound (157 mg, 63%) as a white solid. MS (ESI): mass calcd. for C$_{21}$H$_{16}$FN$_3$, 329.1; m/z found, 330 [M+H]$^+$. $^1$H NMR (300 MHz, CDCl$_3$) δ 8.36-8.27 (m, 1H), 7.93 (dd, J=7.7, 1.3 Hz, 1H), 7.31 (dd, J=8.7, 5.4 Hz, 2H), 7.10 (dd, J=7.8, 4.7 Hz, 1H), 7.05 (s, 1H), 6.97 (t, J=8.7 Hz, 2H), 6.87 (d, J=8.1 Hz, 1H), 6.65 (s, 1H), 6.62 (d, J=8.2 Hz, 1H), 3.61 (t, J=8.4 Hz, 2H), 3.05 (t, J=8.4 Hz, 2H).

Example 345: 2-(4-Fluorophenyl)-1-(1H-indol-5-yl)pyrrolo[2,3-b]pyridine

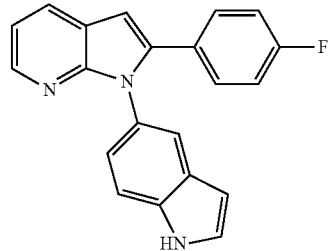 [SMILES: Fc1ccc(-c2cc3cccnc3n2-c2ccc3[nH]ccc3c2)cc1]

To a solution of 2-(4-fluorophenyl)-1-indolin-5-yl-pyrrolo[2,3-b]pyridine (Example 344, 150 mg, 0.46 mmol) in toluene (10 mL) was added manganese dioxide (79 mg, 0.91 mmol). The suspension was stirred at 80° C. for 3 hr, then allowed to cool to 20° C. The suspension was filtered through a pad of Celite® 545 and concentrated in vacuo. Purification (FCC, SiO$_2$, 0 to 20% EtOAc in DCM), afforded the title compound which was triturated with diisopropyl ether to give the title compound (57 mg, 36%) as a brown solid. MS (ESI): mass calcd. for C$_{21}$H$_{14}$FN$_3$, 327.1; m/z found, 328 [M+H]$^+$. $^1$H NMR (300 MHz, DMSO-d$_6$) δ 11.27 (s, 1H), 8.21-8.13 (m, 1H), 8.10-8.01 (m, 1H), 7.51 (s, 1H), 7.47-7.31 (m, 4H), 7.21-7.05 (m, 3H), 6.91 (dd, J=8.5, 1.6 Hz, 1H), 6.85 (s, 1H), 6.46 (s, 1H).

Example 346: 5-[3-Bromo-2-(4-fluorophenyl)pyrrolo[2,3-b]pyridin-1-yl]indolin-2-one

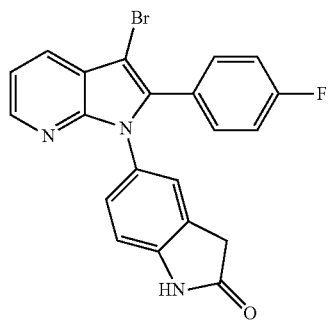 [SMILES: O=C1Cc2cc(-n3c(-c4ccc(F)cc4)c(Br)c4cccnc43)ccc2N1]

Step A: 3,3-Dibromo-5-(3-bromo-2-(4-fluorophenyl)-1H-pyrrolo[2,3-b]pyridin-1-yl)indolin-2-one To a solution of 2-(4-fluorophenyl)-1-(1H-indol-5-yl)pyrrolo[2,3-b]pyridine (Example 345, 157 mg, 0.480 mmol) in t-BuOH (14 mL) was added pyridinium tribromide (512 mg, 1.44 mmol) portionwise. The resulting solution was stirred at 20° C. for 2.5 hr. The reaction was concentrated in vacuo and the residue diluted with EtOAc and washed with water. The aqueous phase was again extracted with EtOAc, and the combined organic phases were washed with brine, dried (MgSO$_4$), filtered, and concentrated in vacuo to give the title compound (278 mg, 100%), which was used in the next step without further purification.

Step B. 5-[3-Bromo-2-(4-fluorophenyl)pyrrolo[2,3-b]pyridin-1-yl]indolin-2-one

To a solution of 3,3-dibromo-5-(3-bromo-2-(4-fluorophenyl)-1H-pyrrolo[2,3-b]pyridin-1-yl)indolin-2-one (278 mg, 0.48 mmol) in glacial acetic acid (5 mL) under a nitrogen atmosphere was added zinc dust (314 mg, 4.8 mmol). The resulting suspension was stirred at 20° C. for 30 min, then filtered through a pad of Celite® 545 and concentrated in vacuo. The residue was diluted with EtOAc and washed with sat. aq. NaHCO$_3$. The organic phase was separated, dried (MgSO$_4$), filtered, and concentrated in vacuo. Purification (FCC, SiO$_2$, 0 to 50% EtOAc/heptanes) afforded the title compound (88 mg, 43%). MS (ESI): mass calcd. for C$_{21}$H$_{13}$BrFN$_3$O, 421.0; m/z found, 422 [M+H]$^+$. $^1$H NMR (300 MHz, DMSO-d$_6$) δ 10.49 (s, 1H), 8.35-8.26 (m, 1H), 7.98 (dd, J=7.9, 1.3 Hz, 1H), 7.45 (dd, J=8.6, 5.6 Hz, 2H), 7.32 (dd, J=7.9, 4.7 Hz, 1H), 7.29-7.20 (m, 3H), 7.00 (d, J=6.7 Hz, 1H), 6.77 (d, J=8.2 Hz, 1H), 3.49 (s, 2H).

Example 347: 5-[2-(4-Fluorophenyl)pyrrolo[2,3-b]pyridin-1-yl]indolin-2-one

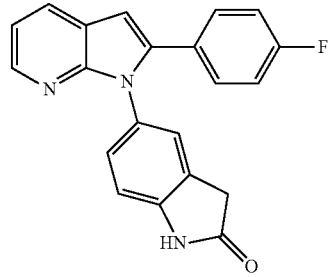 [SMILES: O=C1Cc2cc(-n3c(-c4ccc(F)cc4)cc4cccnc43)ccc2N1]

To a solution of 5-[3-bromo-2-(4-fluorophenyl)pyrrolo[2,3-b]pyridin-1-yl]indolin-2-one (Example 346, 81 mg, 0.19 mmol) in MeOH (5 mL) and TEA (27 μL, 0.19 mmol) under nitrogen atmosphere was added 10% Pd/C (10 mg). The flask was stirred under hydrogen atmosphere at 20° C. After 16 hr, the reaction was purged with nitrogen gas. The suspension was filtered through a pad of Celite®545, and the resulting filtrate was concentrated. The residue was treated with sat. aq. NaHCO$_3$ and extracted with DCM. The organic phase was separated, dried (MgSO$_4$), filtered, and concentrated in vacuo. The residue was recrystallized in acetonitrile to give the title compound (26 mg, 39%) as a brown solid. MS (ESI): mass calcd. for C$_{21}$H$_{14}$FN$_3$O, 343.1; m/z found, 344 [M+H]$^+$. $^1$H NMR (300 MHz, DMSO-d$_6$) δ 10.51 (s, 1H), 8.25-8.16 (m, 1H), 8.05 (d, J=7.8 Hz, 1H), 7.38 (dd, J=8.6, 5.6 Hz, 2H), 7.29-7.12 (m, 4H), 6.98 (d, J=8.2 Hz, 1H), 6.88-6.79 (m, 2H), 3.53 (s, 2H).

Example 348: 6-Fluoro-2-(4-fluorophenyl)-1-(1H-indol-5-yl)pyrrolo[2,3-b]pyridine

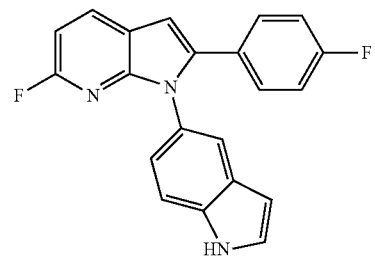 [SMILES: Fc1ccc(-c2cc3ccc(F)nc3n2-c2ccc3[nH]ccc3c2)cc1]

Step A: N-(6-Fluoro-3-((4-fluorophenyl)ethynyl)pyridin-2-yl)-1H-indol-5-amine

To a solution of 2-bromo-6-fluoro-3-((4-fluorophenyl)ethynyl)pyridine (Intermediate 45, 484 mg, 1.23 mmol) in anhydrous toluene (51 mL) was added Pd$_2$(dba)$_3$ (2.80 g, 4.76 mmol), XPhos (454 mg, 0.952 mmol) and Cs$_2$CO$_3$ (4.65 g, 14.3 mmol) under nitrogen gas. After 10 min, tert-butyl 5-amino-1H-indole-1-carboxylate (Intermediate 11, 1.11 g, 4.76 mmol) was added and the mixture was stirred at 20° C. for 10 min. Then, the mixture was heated at 100° C. for 3 hr. Upon completion, the reaction mixture was cooled to room temperature and EtOAc and water were added. The organic phase was separated, dried (MgSO$_4$), filtered, and concentrated, Purification (FCC, SiO$_2$; 0:100 to 10:90 EtOAc/heptane) afforded the title compound (1.60 g, 75%).

Step B: 6-Fluoro-2-(4-fluorophenyl)-1-(1H-indol-5-yl)pyrrolo[2,3-b]pyridine

To a sealed tube containing a suspension of N-(6-fluoro-3-((4-fluorophenyl)ethynyl)pyridin-2-yl)-1H-indol-5-amine (1.60 g, 3.59 mmol) in anhydrous THF (29 mL) was added TBAF (1 M in THF, 7.2 mL, 7.2 mmol). The tube was flushed briefly with nitrogen gas and sealed under nitrogen atmosphere. The tube was stirred at 110° C. for 90 min. The reaction solution was partitioned between EtOAc and sat. aq. NaHCO$_3$. The organic phase was dried (MgSO$_4$), filtered, and concentrated in vacuo. Purification (FCC, SiO$_2$, 0% to 20% EtOAc/heptanes) afforded the title compound (344 mg, 28%). MS (ESI): mass calcd. for C$_{21}$H$_{13}$F$_2$N$_3$, 345.1; m/z found, 346 [M+H]$^+$. $^1$H NMR (300 MHz, DMSO-d$_6$) δ 11.31 (s, 1H), 8.22 (t, J=8.2 Hz, 1H), 7.51 (d, J=1.3 Hz, 1H), 7.47-7.39 (m, 2H), 7.34 (dd, J=8.7, 5.6 Hz, 2H), 7.11 (t, J=8.9 Hz, 2H), 6.97-6.86 (m, 3H), 6.47 (d, J=2.5 Hz, 1H).

Example 349: 5-[3-Bromo-6-fluoro-2-(4-fluorophenyl)pyrrolo[2,3-b]pyridin-1-yl]indolin-2-one

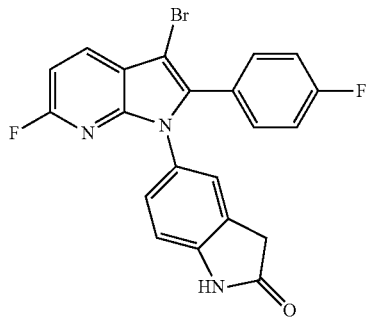 [SMILES: O=C1Cc2cc(-n3c(-c4ccc(F)cc4)c(Br)c4ccc(F)nc43)ccc2N1]

Step A: 3,3-Dibromo-5-(3-bromo-6-fluoro-2-(4-fluorophenyl)-1H-pyrrolo[2,3-b]pyridin-1-yl)indolin-2-one To a solution of 6-fluoro-2-(4-fluorophenyl)-1-(1H-indol-5-yl)pyrrolo[2,3-b]pyridine (Example 348, 100 mg, 0.290 mmol) in tert-butanol (2.8 mL) was added pyridinium tribromide (309 mg, 0.869 mmol) portionwise. The resulting solution was stirred at 20° C. for 15 hr. The reaction was concentrated in vacuo and the residue diluted with EtOAc and washed with water. The aqueous phase was again extracted with EtOAc, and the combined organic phases were washed with brine, dried (MgSO$_4$), filtered, and concentrated in vacuo to give the title compound (173 mg, 100%), which was used in the next step without further purification.

Step B: 5-(3-Bromo-6-fluoro-2-(4-fluorophenyl)-1H-pyrrolo[2,3-b]pyridin-1-yl)indolin-2-one To a solution of 3,3-dibromo-5-(3-bromo-6-fluoro-2-(4-fluorophenyl)-1H-pyrrolo[2,3-b]pyridin-1-yl)indolin-2-one (173 mg, 0.48 mmol) in glacial acetic acid (3 mL) under a nitrogen atmosphere was added zinc dust (190 mg, 2.90 mmol). The resulting suspension was stirred at 20° C. for 60 min, then filtered through a pad of Celite® 545 and concentrated in vacuo. The residue was diluted with EtOAc and washed with sat. aq. NaHCO$_3$. The organic phase was separated, dried (MgSO$_4$), filtered, and concentrated in vacuo. Purification (FCC, SiO$_2$, 0 to 50% EtOAc/heptanes) afforded the title compound (53 mg, 42%) as a white solid. MS (ESI): mass calcd. for C$_{21}$H$_{12}$BrF$_2$N$_3$O, 439.0; m/z found, 440.0 [M+H]$^+$. $^1$H NMR (300 MHz, DMSO-d$_6$) δ 10.52 (s, 1H), 8.16 (t, J=8.0 Hz, 1H), 7.50-7.36 (m, 2H), 7.31-7.17 (m, 3H), 7.08 (d, J=8.4 Hz, 1H), 7.04 (d, J=8.4 Hz, 1H), 6.79 (d, J=8.2 Hz, 1H), 3.49 (s, 2H).

Example 350: 5-[6-Fluoro-2-(4-fluorophenyl)pyrrolo[2,3-b]pyridin-1-yl]indolin-2-one

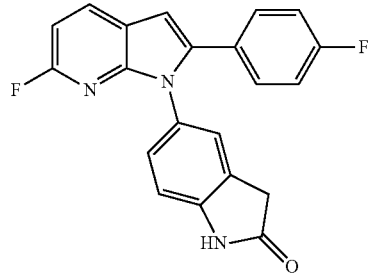 [SMILES: O=C1Cc2cc(-n3c(-c4ccc(F)cc4)cc4ccc(F)nc43)ccc2N1]

The title compound was prepared in a manner analogous to Example 347, using 5-(3-bromo-6-fluoro-2-(4-fluorophenyl)-1H-pyrrolo[2,3-b]pyridin-1-yl)indolin-2-one (Example 349). MS (ESI): mass calcd. for C$_{21}$H$_{13}$F$_2$N$_3$O, 361.1; m/z found, 362 [M+H]$^+$. $^1$H NMR (300 MHz, DMSO-d$_6$) δ 10.54 (s, 1H), 8.22 (t, J=8.2 Hz, 1H), 7.35 (dd, J=8.6, 5.6 Hz, 2H), 7.25-7.11 (m, 3H), 7.01 (d, J=8.2 Hz, 1H), 6.94 (d, J=8.3 Hz, 1H), 6.89 (s, 1H), 6.85 (d, J=8.2 Hz, 1H), 3.53 (s, 2H).

Example 351: 1-(1H-Indol-5-yl)-2-methyl-6-(trifluoromethyl)pyrrolo[2,3-b]pyridine

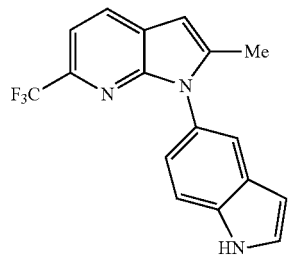 [SMILES: Cc1cc2ccc(C(F)(F)F)nc2n1-c1ccc2[nH]ccc2c1]

Step A: (1-(1H-Indol-5-yl)-6-(trifluoromethyl)-1H-pyrrolo[2,3-b]pyridin-2-yl)methanol The title compound was prepared in a manner analogous to Example 337, Steps A-B, starting with 2-chloro-3-(3-((tetrahydro-2H-pyran-2-yl)oxy)prop-1-yn-1-yl)-6-(trifluoromethyl)pyridine (Intermediate 23) and tert-butyl 5-amino-1H-indole-1-carboxylate (Intermediate 11). MS (ESI): mass calcd. for C$_{17}$H$_{12}$F$_3$N$_3$O 331.1; m/z found 331.9 [M+H]$^+$. $^1$H NMR (300 MHz, DMSO-d$_6$) δ 11.39 (s, 1H), 8.24 (d, J=8.0 Hz, 1H), 7.64-7.45 (m, 4H), 7.10 (dd, J=8.5, 1.8 Hz, 1H), 6.75 (s, 1H), 6.53 (s, 1H), 5.36 (t, J=5.5 Hz, 1H), 4.50 (d, J=5.4 Hz, 2H).

Step B: 1-(1H-Indol-5-yl)-2-methyl-6-(trifluoromethyl)pyrrolo[2,3-b]pyridine

The title compound was prepared in a manner analogous to Example 331, Steps A-B. MS (ESI): mass calcd. for $C_{17}H_{12}F_3N_3$, 315.1; m/z found, 316.1 [M+H]$^+$. $^1$H NMR (300 MHz, DMSO-$d_6$) δ 11.40 (s, 1H), 8.15 (d, J=8.0 Hz, 1H), 7.60-7.47 (m, 4H), 7.06 (dd, J=8.5, 1.8 Hz, 1H), 6.60 (s, 1H), 6.54 (s, 1H), 2.30 (s, 3H).

Example 352: 5-[2-Methyl-6-(trifluoromethyl)pyrrolo[2,3-b]pyridin-1-yl]indolin-2-one

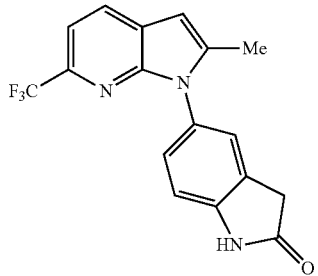 [SMILES: Cc1cc2ccc(C(F)(F)F)nc2n1-c1ccc2c(c1)CC(=O)N2]

Step A: 3,3-Dibromo-5-(3-bromo-2-methyl-6-(trifluoromethyl)-1H-pyrrolo[2,3-b]pyridin-1-yl)indolin-2-one To a solution of 1-(1H-indol-5-yl)-2-methyl-6-(trifluoromethyl)pyrrolo[2,3-b]pyridine (Example 351, 120 mg, 0.320 mmol) in t-butanol (10 mL) was added pyridinium tribromide (341 mg, 0.959 mmol) portionwise. The resulting solution was stirred at 20° C. for 2.5 hr. The reaction was concentrated in vacuo and the residue diluted with EtOAc and washed with water. The aqueous phase was again extracted with EtOAc, and the combined organic phases were washed with brine, dried (MgSO$_4$), filtered, and concentrated in vacuo to give the title compound (182 mg, 100%), which was used in the next step without further purification.

Step B: 5-(3-Bromo-2-methyl-6-(trifluoromethyl)-1H-pyrrolo[2,3-b]pyridin-1-yl)indolin-2-one To a solution of 3,3-dibromo-5-(3-bromo-2-methyl-6-(trifluoromethyl)-1H-pyrrolo[2,3-b]pyridin-1-yl)indolin-2-one (181 mg, 0.319 mmol) in glacial acetic acid (3.3 mL) under a nitrogen atmosphere was added zinc dust (208 mg, 3.19 mmol). The resulting suspension was stirred at 20° C. for 30 min, then filtered through a pad of Celite® 545 and concentrated in vacuo. The residue was diluted with EtOAc and washed with sat. aq. NaHCO$_3$. The organic phase was separated, dried (MgSO$_4$), filtered, and concentrated in vacuo. Purification (FCC, SiO$_2$, 0 to 40% EtOAc/heptanes) afforded the title compound (27 mg, 21%) as a white solid.

Step C: 5-[2-Methyl-6-(trifluoromethyl)pyrrolo[2,3-b]pyridin-1-yl]indolin-2-one

To a round bottom flask containing a solution of 5-(3-bromo-2-methyl-6-(trifluoromethyl)-1H-pyrrolo[2,3-b]pyridin-1-yl)indolin-2-one (27 mg, 0.066 mmol) in methanol (1.7 mL) and TEA (9.2 μL, 0.066 mmol) under nitrogen atmosphere was added 10% Pd/C (3.5 mg). The flask was stirred under hydrogen atmosphere at 20° C. After 16 hr, the reaction was purged with nitrogen gas. The suspension was filtered through a pad of Celite® 545, and the resulting filtrate was concentrated. The residue was treated with sat. aq. NaHCO$_3$ and extracted with DCM. The organic phase was separated, dried (MgSO$_4$), filtered, and concentrated in vacuo. Purification (FCC, SiO$_2$, 0 to 70% EtOAc/heptanes) afforded the title compound (11.5 mg, 52%). MS (ESI): mass calcd. for $C_{17}H_{12}F_3N_3O$, 331.1; m/z found, 332.1 [M+H]$^+$. $^1$H NMR (300 MHz, DMSO-$d_6$) δ 10.61 (s, 1H), 8.15 (d, J=8.1 Hz, 1H), 7.55 (d, J=8.0 Hz, 1H), 7.28 (s, 1H), 7.23 (d, J=9.8 Hz, 1H), 6.99 (d, J=8.2 Hz, 1H), 6.59 (s, 1H), 3.59 (s, 2H), 2.31 (s, 3H).

Example 353: 7-Methyl-5-(2-methyl-1H-pyrrolo[2,3-b]pyridin-1-yl)indolin-2-one

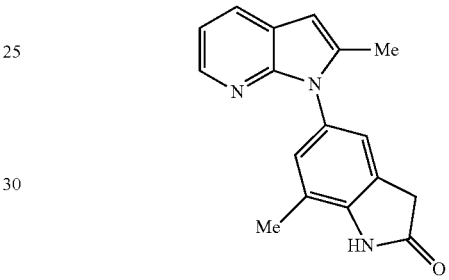

The title compound was prepared in a manner analogous to Example 331, beginning with 5-(2-(hydroxymethyl)-1H-pyrrolo[2,3-b]pyridin-1-yl)-7-methylindolin-2-one (Intermediate 63). MS (ESI): mass calcd. for $C_{17}H_{15}N_3O$, 277.1; m/z found, 278.1 [M+H]$^+$. $^1$H NMR (400 MHz, CD$_3$OD) δ 8.01 (dd, J=4.9, 1.5 Hz, 1H), 7.91 (dd, J=7.8, 1.5 Hz, 1H), 7.12-7.07 (m, 2H), 7.04 (d, J=1.8 Hz, 1H), 6.39 (d, J=1.1 Hz, 1H), 3.63 (s, 1H), 2.34 (s, 3H), 2.29 (s, 3H).

Example 354: 5-(2-Methyl-6-(trifluoromethyl)-1H-pyrrolo[2,3-b]pyridin-1-yl)-1H-indazole

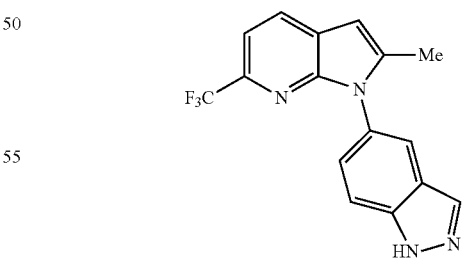

The title compound was prepared in a manner analogous to Example 331, using (1-(1H-indazol-5-yl)-6-(trifluoromethyl)-1H-pyrrolo[2,3-b]pyridin-2-yl)methanol (Example 330). $^1$H NMR (300 MHz, DMSO-$d_6$) δ 13.36 (s, 1H), 8.19 (s, 1H), 8.18 (d, J=9.2 Hz, 1H), 7.88 (d, J=1.0 Hz, 1H), 7.73 (d, J=8.7 Hz, 1H), 7.56 (d, J=8.1 Hz, 1H), 7.36 (dd, J=8.7, 1.5 Hz, 1H), 6.63 (s, 1H), 2.33 (s, 3H).

Example 355: 6-(2-Methyl-6-(trifluoromethyl)-1H-pyrrolo[2,3-b]pyridin-1-yl)benzo[d]thiazol-2(3H)-one

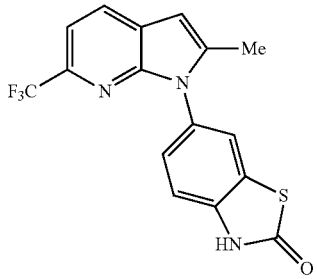

The title compound was prepared in a manner analogous to Example 331, using 6-(2-(hydroxymethyl)-6-(trifluoromethyl)-1H-pyrrolo[2,3-b]pyridin-1-yl)benzo[d]thiazol-2(3H)-one (Example 337, product from Step B). $^1$H NMR (300 MHz, DMSO-$d_6$) δ 12.16 (s, 1H), 8.17 (d, J=8.0 Hz, 1H), 7.76 (d, J=1.5 Hz, 1H), 7.57 (d, J=8.1 Hz, 1H), 7.38-7.27 (m, 2H), 6.62 (s, 1H), 2.33 (s, 3H).

Example 356: 1-(7-Chloro-1H-indazol-5-yl)-2-isopropyl-pyrrolo[2,3-b]pyridine

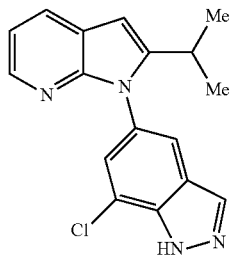 [SMILES: CC(C)c1cc2cccnc2n1-c1cc(Cl)c2[nH]ncc2c1]

The title compound was prepared in a manner analogous to Example 332. In Step A, using 2-chloro-3-(3-methylbut-1-yn-1-yl)pyridine (Intermediate 35) and 7-chloro-1H-indazol-5-amine. MS (ESI): mass calcd. for $C_{17}H_{15}ClN_4$, 310.1; m/z found, 311.1 [M+H]$^+$. 1H NMR (500 MHz, CD$_3$OD) δ 8.25 (s, 1H), 8.03 (dd, J=4.8, 1.5 Hz, 1H), 7.98 (dd, J=7.8, 1.5 Hz, 1H), 7.81 (d, J=1.6 Hz, 1H), 7.43 (d, J=1.6 Hz, 1H), 7.13 (dd, J=7.8, 4.8 Hz, 1H), 6.49 (d, J=0.8 Hz, 1H), 3.06-2.96 (hept, J=6.9 Hz, 1H), 1.24 (d, J=6.8 Hz, 6H).

Example 357: 7-Chloro-5-(2-isopropylpyrrolo[2,3-b]pyridin-1-yl)indolin-2-one

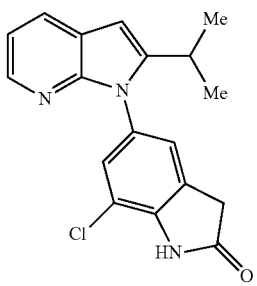 [SMILES: CC(C)c1cc2cccnc2n1-c1cc(Cl)c2c(c1)CC(=O)N2]

The title compound was prepared in a manner analogous to Example 332. In Step A using 2-chloro-3-(3-methylbut-1-yn-1-yl)pyridine (Intermediate 35) and 5-amino-7-chloroindolin-2-one (Intermediate 18). MS (ESI): mass calcd. for $C_{18}H_{16}ClN_3O$, 325.1; m/z found, 326.1 [M+H]$^+$. $^1$H NMR (500 MHz, CD$_3$OD) δ 8.04 (dd, J=4.8, 1.5 Hz, 1H), 7.93 (dd, J=7.8, 1.5 Hz, 1H), 7.27 (d, J=1.8 Hz, 1H), 7.20 (d, J=1.7 Hz, 1H), 7.09 (dd, J=7.8, 4.8 Hz, 1H), 6.44 (s, 1H), 3.70 (s, 2H), 3.04-2.94 (hept, J=6.7 Hz, 1H), 1.23 (d, J=6.8 Hz, 6H).

Example 358: 5-(2-Isopropylpyrrolo[2,3-b]pyridin-1-yl)-7-methyl-indolin-2-one

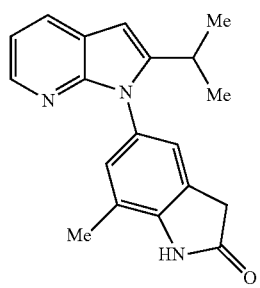 [SMILES: Cc1cc(-n2c(C(C)C)cc3cccnc32)cc2c1NC(=O)C2]

The title compound was prepared in a manner analogous to Example 332. In Step A, using 2-chloro-3-(3-methylbut-1-yn-1-yl)pyridine (Intermediate 35) and 5-amino-7-methylindolin-2-one (Intermediate 10). MS (ESI): mass calcd. for $C_{19}H_{19}N_3O$, 305.2; m/z found, 306.1 [M+H]$^+$. $^1$H NMR (400 MHz, CD$_3$OD) δ 8.01 (dd, J=4.9, 1.5 Hz, 1H), 7.93 (dd, J=7.8, 1.5 Hz, 1H), 7.09-7.06 (m, 2H), 7.04 (s, 1H), 6.41 (s, 1H), 3.62 (s, 2H), 3.06-2.93 (hept, J=6.8 Hz, 1H), 2.33 (s, 3H), 1.22 (d, J=6.8 Hz, 6H).

Example 359: 5-(2-Cyclopropylpyrrolo[2,3-b]pyridin-1-yl)-7-methyl-indolin-2-one

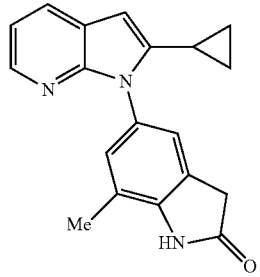 [SMILES: Cc1cc(-n2c(C3CC3)cc3cccnc32)cc2c1NC(=O)C2]

The title compound was prepared in a manner analogous to Example 332. In Step A, using 2-chloro-3-(cyclopropylethynyl)pyridine (Intermediate 36) and 5-amino-7-methylindolin-2-one (Intermediate 10). MS (ESI): mass calcd. for $C_{19}H_{17}N_3O$, 303.1; m/z found, 304.2 [M+H]$^+$. $^1$H NMR (500 MHz, CD$_3$OD) δ 8.03-7.99 (dd, J=4.9, 1.6 Hz, 1H), 7.91-7.85 (dd, J=7.8, 1.5 Hz, 1H), 7.15 (s, 1H), 7.11 (d, J=2.0 Hz, 1H), 7.09-7.04 (dd, J=7.8, 4.8 Hz, 1H), 6.18 (d, J=0.9 Hz, 1H), 3.62 (d, J=1.0 Hz, 2H), 2.33 (s, 3H), 1.76-1.68 (m, 1H), 0.93-0.87 (ddd, J=8.3, 6.5, 4.1 Hz, 2H), 0.82-0.76 (m, 2H).

Example 360: 5-(2-Isopropyl-6-methyl-pyrrolo[2,3-b]pyridin-1-yl)-7-methyl-indolin-2-one

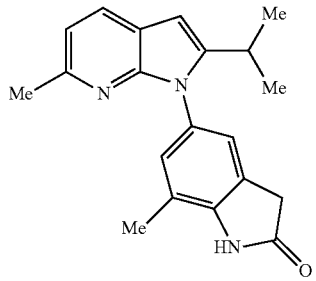

The title compound was prepared in a manner analogous to Example 332. In Step A, using 2-bromo-6-methyl-3-(3-methylbut-1-yn-1-yl)pyridine (Intermediate 28) and 5-amino-7-methylindolin-2-one (Intermediate 10). MS (ESI): mass calcd. for $C_{20}H_{21}N_3O$, 319.2; m/z found, 320.3 [M+H]$^+$. $^1$H NMR (400 MHz, CD$_3$OD) δ 7.78 (d, J=7.9 Hz, 1H), 7.05 (s, 1H), 7.01 (s, 1H), 6.94 (d, J=7.9 Hz, 1H), 6.33 (s, 1H), 3.62 (s, 2H), 2.99-2.85 (hept, J=6.8 Hz, 1H), 2.46 (s, 3H), 2.33 (s, 3H), 1.19 (d, J=6.8 Hz, 6H).

Example 361: 7-Fluoro-5-(2-isopropylpyrrolo[2,3-b]pyridin-1-yl)indolin-2-one

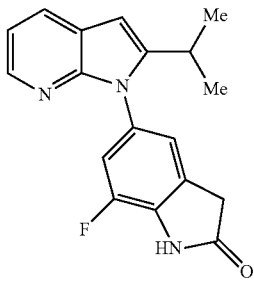 [SMILES: CC(C)c1cc2cccnc2n1-c1cc(F)c2c(c1)CC(=O)N2]

The title compound was prepared in a manner analogous to Example 332. In Step A, using 5-amino-7-fluoroindolin-2-one (Intermediate 17) and 2-chloro-3-(3-methylbut-1-yn-1-yl)pyridine (Intermediate 35). MS (ESI): mass calcd. for $C_{18}H_{16}FN_3O$, 309.1; m/z found, 310.2 [M+H]$^+$. $^{19}$F NMR (376 MHz, CD$_3$OD) δ −134.17 (d, J=10.6 Hz). $^1$H NMR (400 MHz, CD$_3$OD) δ 8.04 (dd, J=4.8, 1.6 Hz, 1H), 7.94 (dd, J=7.8, 1.6 Hz, 1H), 7.14 (d, J=1.9 Hz, 1H), 7.12-7.06 (m, 2H), 6.45 (d, J=0.8 Hz, 1H), 3.10-2.95 (m, 1H), 1.24 (d, J=6.8 Hz, 6H).

Example 362: 7-Fluoro-5-(2-isopropyl-6-methyl-pyrrolo[2,3-b]pyridin-1-yl)indolin-2-one

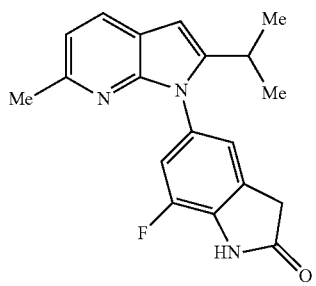 [SMILES: Cc1ccc2cc(C(C)C)n(-c3cc(F)c4c(c3)CC(=O)N4)c2n1]

The title compound was prepared in a manner analogous to Example 332. In Step A, using 5-amino-7-fluoroindolin-2-one (Intermediate 17) and 2-bromo-6-methyl-3-(3-methylbut-1-yn-1-yl)pyridine (Intermediate 28). MS (ESI): mass calcd. for $C_{19}H_{18}FN_3O$, 323.1; m/z found, 324.1 [M+H]$^+$. $^{19}$F NMR (376 MHz, CD$_3$OD) δ −134.38 (d, J=10.7 Hz). $^1$H NMR (400 MHz, CD$_3$OD) δ 7.80 (d, J=7.9 Hz, 1H), 7.16-7.06 (m, 2H), 6.97 (d, J=7.9 Hz, 1H), 6.36 (s, 1H), 3.03-2.90 (hept, J=6.9 Hz, 1H), 2.47 (s, 3H), 1.22 (d, J=6.8 Hz, 6H).

Example 363: 7-Fluoro-5-(2-methylpyrrolo[2,3-b]pyridin-1-yl)indolin-2-one

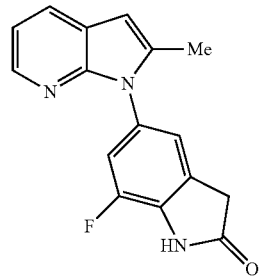 [SMILES: Cc1cc2cccnc2n1-c1cc(F)c2c(c1)CC(=O)N2]

The title compound was prepared in a manner analogous to Example 332. In Step A, using 5-amino-7-fluoroindolin-2-one (Intermediate 17) and 2-chloro-3-(prop-1-yn-1-yl)pyridine (Intermediate 27). MS (ESI): mass calcd. for $C_{16}H_{12}FN_3O$, 281.1; m/z found, 282.0 [M+H]$^+$. $^1$H NMR (300 MHz, CDCl$_3$) δ 8.21 (dd, J=3.9, 0.6 Hz, 1H), 7.84 (dd, J=7.7, 1.3 Hz, 1H), 7.12-7.02 (m, 3H), 6.35 (d, J=0.7 Hz, 1H), 3.66 (s, 2H), 2.33 (s, 3H).

Example 364: 7-Fluoro-5-[2-methyl-6-(trifluoromethyl)pyrrolo[2,3-b]pyridin-1-yl]indolin-2-one

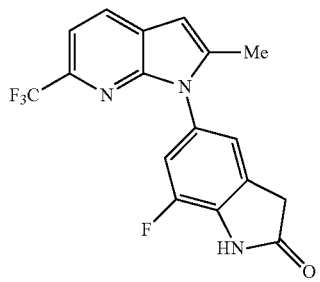 [SMILES: Cc1cc2ccc(C(F)(F)F)nc2n1-c1cc(F)c2c(c1)CC(=O)N2]

The title compound was prepared in a manner analogous to Example 332. In Step A, using 2-chloro-3-(prop-1-yn-1-yl)-6-(trifluoromethyl)pyridine (Intermediate 26) and 5-amino-7-fluoroindolin-2-one (Intermediate 17). MS (ESI): mass calcd. for $C_{17}H_{11}F_4N_3O$, 349.1; m/z found, 350.0 [M+H]$^+$. $^1$H NMR (300 MHz, CDCl$_3$) δ 7.66 (d, J=7.8 Hz, 1H), 7.64 (br s, 1H), 7.59 (br s, 1H), 7.34 (s, 1H), 7.33 (s, 1H), 7.05 (d, J=7.7 Hz, 1H), 3.59 (s, 2H), 2.21 (s, 3H).

Example 365: (RS)-7-Fluoro-5-[2-tetrahydrofuran-3-yl-6-(trifluoromethyl)pyrrolo[2,3-b]pyridin-1-yl]indolin-2-one

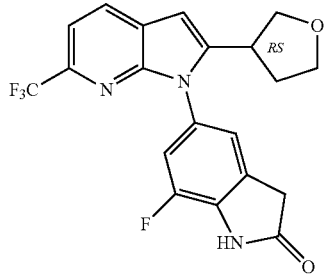 [SMILES: O=C1Cc2cc(-n3c(C4CCOC4)cc4ccc(C(F)(F)F)nc43)cc(F)c2N1]

The title compound was prepared in a manner analogous to Example 334. In Step A, using 2-chloro-3-((tetrahydrofuran-3-yl)ethynyl)-6-(trifluoromethyl)pyridine (Intermediate 30) and 5-amino-7-fluoroindolin-2-one (Intermediate 17). MS (ESI): mass calcd. for $C_{20}H_{15}F_4N_3O_2$, 405.1; m/z found, 406.0 [M+H]$^+$. $^{19}$F NMR (376 MHz, CDCl$_3$) δ −65.69 (s), −131.48 (d, J=10.0 Hz). $^1$H NMR (400 MHz, CDCl$_3$) δ 8.17 (s, 1H), 7.99 (dd, J=8.1, 0.7 Hz, 1H), 7.49 (d, J=8.0 Hz, 1H), 7.11-7.02 (m, 2H), 6.53 (d, J=0.8 Hz, 1H), 4.07-3.99 (td, J=8.3, 5.3 Hz, 1H), 4.00-3.92 (dd, J=8.4, 7.3 Hz, 1H), 3.92-3.83 (dt, J=8.6, 7.3 Hz, 1H), 3.83-3.74 (dd, J=8.4, 6.8 Hz, 1H), 3.65-3.64 (m, 1H), 3.52-3.38 (dt, J=14.9, 7.7 Hz, 1H), 2.33-2.19 (m, 1H), 2.14-2.02 (dq, J=12.4, 7.5 Hz, 1H).

Example 366: 7-Fluoro-5-[2-(methoxymethyl)-6-(trifluoromethyl)pyrrolo[2,3-b]pyridin-1-yl]indolin-2-one

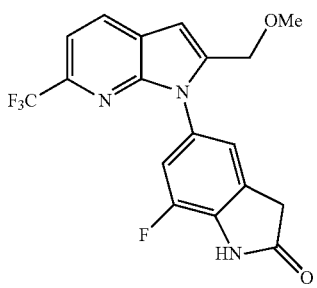 [SMILES: COCc1cc2ccc(C(F)(F)F)nc2n1-c1cc(F)c2c(c1)CC(=O)N2]

The title compound was prepared in a manner analogous to Example 334, in Step A, using 5-amino-7-fluoroindolin-2-one (Intermediate 17) and 2-chloro-3-(3-methoxyprop-1-yn-1-yl)-6-(trifluoromethyl)pyridine (Intermediate 31). MS (ESI): mass calcd. for $C_{18}H_{13}F_4N_3O_2$, 379.1; m/z found, 380.1 [M+H]$^+$. $^{19}$F NMR (376 MHz, CD$_3$OD) δ −67.43 (s), −134.62 (d, J=10.7 Hz). $^1$H NMR (400 MHz, CD$_3$OD) δ 8.18 (dd, J=8.0, 0.8 Hz, 1H), 7.54 (d, J=8.2 Hz, 1H), 7.27-7.18 (m, 2H), 6.80 (s, 1H), 4.51 (s, 2H), 3.67 (br. s., 1H), 3.31 (s, 3H).

Example 367: 5-[2-Isopropyl-6-(trifluoromethyl)pyrrolo[2,3-b]pyridin-1-yl]-7-methyl-indolin-2-one

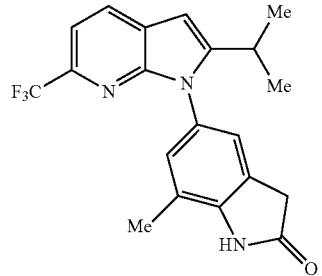

The title compound was prepared in a manner analogous to Example 334. In Step A, using 2-chloro-3-(3-methylbut-1-yn-1-yl)-6-(trifluoromethyl)pyridine (Intermediate 32) and 5-amino-7-methylindolin-2-one (Intermediate 10). MS (ESI): mass calcd. for $C_{20}H_{18}F_3N_3O$, 373.1; m/z found, 374.3 [M+H]$^+$. $^{19}$F NMR (376 MHz, DMSO-d$_6$) δ −63.84 (s). $^1$H NMR (400 MHz, DMSO-d$_6$) δ 10.67 (s, 1H), 8.21-8.12 (d, J=8.1 Hz, 1H), 7.59-7.51 (d, J=8.1 Hz, 1H), 7.10 (s, 1H), 7.07 (s, 1H), 6.60 (s, 1H), 3.60 (s, 2H), 2.96-2.87 (m, 1H), 2.27 (s, 3H), 1.22-1.15 (d, J=6.8 Hz, 6H).

Example 368: (RS)-5-[2-(1-Methoxyethyl)pyrrolo[2,3-b]pyridin-1-yl]-7-methyl-indolin-2-one

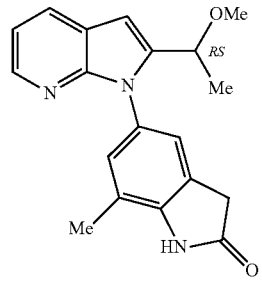 [SMILES: COC(C)c1cc2cccnc2n1-c1cc(C)c2c(c1)CC(=O)N2]

The title compound was prepared in a manner analogous to Example 334. In Step A, using 2-chloro-3-(3-methoxybut-1-yn-1-yl)pyridine (Intermediate 37) and 5-amino-7-methylindolin-2-one (Intermediate 10). MS (ESI): mass calcd. for $C_{19}H_{19}N_3O_2$, 321.1; m/z found, 322.2 [M+H]$^+$. $^1$H NMR (500 MHz, CD$_3$OD) δ 8.12-8.07 (dd, J=4.8, 1.6 Hz, 1H), 8.05-8.01 (dd, J=7.8, 1.5 Hz, 1H), 7.16-7.09 (dd, J=7.8, 4.8 Hz, 1H), 7.10 (s, 1H), 7.07 (s, 1H), 6.64 (d, J=0.7 Hz, 1H), 4.48-4.40 (qd, J=6.5, 0.7 Hz, 1H), 3.63 (s, 2H), 3.18 (s, 3H), 2.34 (s, 3H), 1.47 (d, J=6.5 Hz, 3H).

Example 369: 7-Fluoro-5-[2-isopropyl-6-(trifluoromethyl)pyrrolo[2,3-b]pyridin-1-yl]indolin-2-one

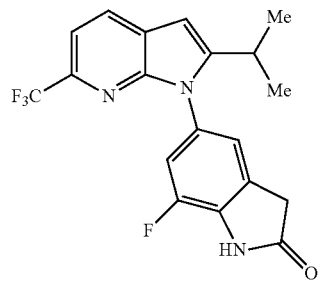 [SMILES: CC(C)c1cc2ccc(C(F)(F)F)nc2n1-c1cc(F)c2c(c1)CC(=O)N2]

The title compound was prepared in a manner analogous to Example 334. In Step A, using 2-chloro-3-(3-methylbut-1-yn-1-yl)-6-(trifluoromethyl)pyridine (Intermediate 32) and 5-amino-7-fluoroindolin-2-one (Intermediate 17). MS (ESI): mass calcd. for $C_{19}H_{15}F_4N_3O$, 377.1; m/z found, 378.1 [M+H]$^+$. $^{19}$F NMR (376 MHz, CD$_3$OD) δ −67.17 (s), −134.25 (d, J=10.6 Hz). $^1$H NMR (400 MHz, CD$_3$OD) δ 8.10-8.00 (d, J=8.1 Hz, 1H), 7.52-7.44 (d, J=8.1 Hz, 1H), 7.21-7.11 (d, J=8.3 Hz, 1H), 7.14 (s, 1H), 6.59-6.50 (d, J=0.7 Hz, 1H), 3.70 (s, 2H), 3.13-2.99 (hept, J=6.8 Hz, 1H), 1.31-1.22 (d, 6H).

Example 370: 2-Isopropyl-1-(7-methyl-1H-indazol-5-yl)-6-(trifluoromethyl)pyrrolo[2,3-b]pyridine

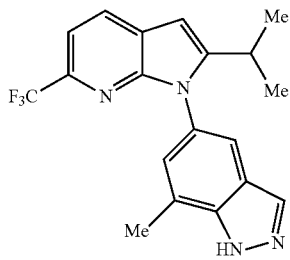 [SMILES: Cc1cc(-n2c(C(C)C)cc3ccc(C(F)(F)F)nc32)cc2cn[nH]c12]

The title compound was prepared in a manner analogous to Example 334. In Step A, using 2-chloro-3-(3-methylbut-1-yn-1-yl)-6-(trifluoromethyl)pyridine (Intermediate 32) and 7-methyl-1H-indazol-5-amine. MS (ESI): mass calcd. for $C_{19}H_{17}F_3N_4$, 358.1; m/z found, 359.3 [M+H]$^+$. $^{19}$F NMR (376 MHz, CD$_3$OD) δ −67.11 (s). $^1$H NMR (400 MHz, CD$_3$OD) δ 8.16 (s, 1H), 8.11-8.02 (d, J=8.2 Hz, 1H), 7.65 (s, 1H), 7.50-7.43 (d, J=8.0 Hz, 1H), 7.13 (s, 1H), 6.56 (s, 1H), 3.13-2.96 (hept, J=6.4 Hz, 1H), 2.65 (s, 3H), 1.27-1.19 (d, J=6.8 Hz, 6H).

Example 371: 2-(3-Fluoropropyl)-1-(7-methyl-1H-indazol-5-yl)-6-(trifluoromethyl)pyrrolo[2,3-b]pyridine

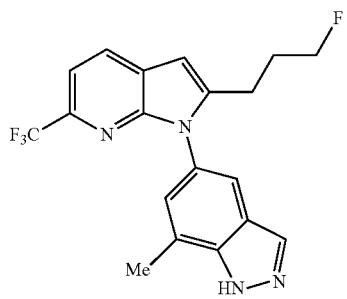 [SMILES: Cc1cc(-n2c(CCCF)cc3ccc(C(F)(F)F)nc32)cc2cn[nH]c12]

The title compound was prepared in a manner analogous to Example 334. In Step A, using 2-chloro-3-(5-fluoropent-1-yn-1-yl)-6-(trifluoromethyl)pyridine (Intermediate 24) and 7-methyl-1H-indazol-5-amine. MS (ESI): mass calcd. for $C_{19}H_{16}F_4N_4$, 376.1; m/z found, 377.1 [M+H]$^+$. $^1$H NMR (400 MHz, Acetonitrile-d$_3$) δ 8.14-8.07 (m, 2H), 7.63 (dd, J=1.9, 0.9 Hz, 1H), 7.52 (d, J=8.1 Hz, 1H), 7.13 (dq, J=1.9, 0.9 Hz, 1H), 6.59 (t, J=1.0 Hz, 1H), 4.40 (dt, J=47.1, 5.9 Hz, 2H), 2.81-2.72 (m, 2H), 2.62 (s, 3H), 2.06-1.88 (m, 2H).

Example 372: 1-(7-Chloro-1H-indazol-5-yl)-2-(3-fluoropropyl)-6-(trifluoromethyl)pyrrolo[2,3-b]pyridine

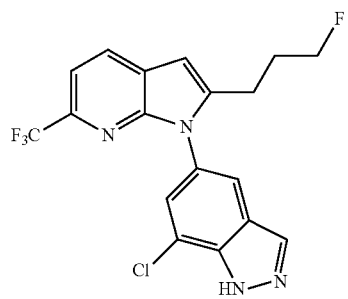 [SMILES: FCCCc1cc2ccc(C(F)(F)F)nc2n1-c1cc(Cl)c2[nH]ncc2c1]

The title compound was prepared in a manner analogous to Example 334. In Step A, using 2-chloro-3-(5-fluoropent-1-yn-1-yl)-6-(trifluoromethyl)pyridine (Intermediate 24) and 7-chloro-1H-indazol-5-amine. MS (ESI): mass calcd. for $C_{18}H_{13}ClF_4N_4$, 396.1; m/z found, 397.1 [M+H]$^+$. $^1$H NMR (400 MHz, Acetonitrile-d$_3$) δ 8.02 (d, J=3.3 Hz, 1H), 7.92 (dd, J=8.0, 1.0 Hz, 1H), 7.61 (d, J=1.6 Hz, 1H), 7.37-7.24 (m, 2H), 6.41 (m, 1H), 4.21 (td, J=47.1, 6.5 Hz, 2H), 2.61-2.57 (m, 2H), 1.87-1.69 (m, 2H).

Example 373: 2-Methyl-1-(7-methyl-1H-indazol-5-yl)-6-(trifluoromethyl)pyrrolo[2,3-b]pyridine

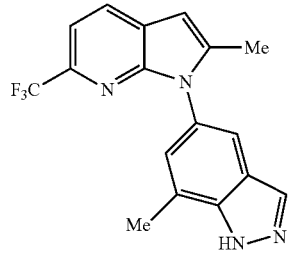 [SMILES: Cc1cc(-n2c(C)cc3ccc(C(F)(F)F)nc32)cc2cn[nH]c12]

The title compound was prepared in a manner analogous to Example 334. In Step A, using 2-chloro-3-(prop-1-yn-1-yl)-6-(trifluoromethyl)pyridine (Intermediate 26) and 7-methyl-1H-indazol-5-amine. MS (ESI): mass calcd. for $C_{17}H_{13}F_3N_4$, 330.1; m/z found, 331.0 [M+H]$^+$. $^1$H NMR (300 MHz, CDCl$_3$) δ 11.34 (s, 1H), 8.02 (d, J=8.0 Hz, 1H), 7.89 (s, 1H), 7.54 (d, J=8.0 Hz, 1H), 7.41 (s, 1H), 6.89 (s, 1H), 6.45 (s, 1H), 2.42 (s, 3H), 2.26 (s, 3H).

Example 374: 1-(7-Chloro-1H-indazol-5-yl)-2-methyl-6-(trifluoromethyl)pyrrolo[2,3-b]pyridine

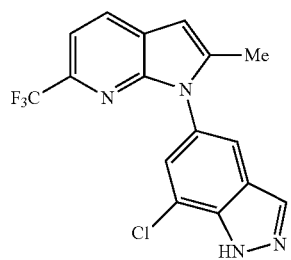 [SMILES: Cc1cc2ccc(C(F)(F)F)nc2n1-c1cc(Cl)c2[nH]ncc2c1]

The title compound was prepared in a manner analogous to Example 334. In Step A, using 2-chloro-3-(prop-1-yn-1-yl)-6-(trifluoromethyl)pyridine (Intermediate 26) and 7-chloro-1H-indazol-5-amine. MS (ESI): mass calcd. for C$_{16}$H$_{10}$ClF$_3$N$_4$, 350.1; m/z found, 351 [M+H]$^+$. $^1$H NMR (300 MHz, CDCl$_3$) δ 11.04 (s, 1H), 8.08 (s, 1H), 7.99 (d, J=8.0 Hz, 1H), 7.61 (d, J=1.5 Hz, 1H), 7.52 (d, J=8.1 Hz, 1H), 7.31 (d, J=1.5 Hz, 1H), 6.47 (d, J=0.7 Hz, 1H), 2.32 (s, 3H).

Example 375: 2-Methyl-1-(7-methyl-1H-indazol-5-yl)pyrrolo[2,3-b]pyridine

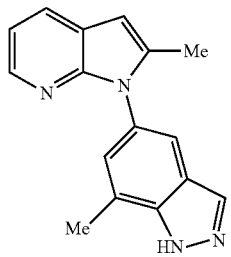 [SMILES: Cc1cc(-n2c(C)cc3cccnc32)cc2cn[nH]c12]

The title compound was prepared in a manner analogous to Example 334. In Step A, 2-Chloro-3-(prop-1-yn-1-yl)pyridine (Intermediate 27) and 7-methyl-1H-indazol-5-amine. MS (ESI): mass calcd. for C$_{16}$H$_{14}$N$_4$, 262.1; m/z found, 263.0 [M+H]$^+$. $^1$H NMR (300 MHz, CDCl$_3$) δ 8.32-8.27 (m, 1H), 7.95 (s, 1H), 7.91 (dd, J=7.7, 1.0 Hz, 1H), 7.46 (s, 1H), 7.11 (dd, J=7.7, 4.8 Hz, 1H), 6.96 (s, 1H), 6.37 (s, 1H), 2.41 (s, 3H), 2.28 (s, 3H).

Example 376: 5-[2-Isopropyl-6-(trifluoromethyl)pyrrolo[2,3-b]pyridin-1-yl]-1H-pyrazolo[3,4-b]pyridine

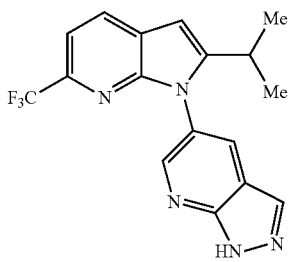 [SMILES: CC(C)c1cc2ccc(C(F)(F)F)nc2n1-c1cnc2[nH]ncc2c1]

The title compound was prepared in a manner analogous to Example 335, In Step A, using 2-chloro-3-(3-methylbut-1-yn-1-yl)-6-(trifluoromethyl)pyridine (Intermediate 32) and 1-((2-(trimethylsilyl)ethoxy)methyl)-1H-pyrazolo[3,4-b]pyridin-5-amine (Intermediate 20). MS (ESI): mass calcd. for C$_{17}$H$_{14}$F$_3$N$_5$, 345.1; m/z found, 346.0 [M+H]$^+$. $^1$H NMR (300 MHz, DMSO-d$_6$) δ 14.03 (s, 1H), 8.60 (d, J=2.1 Hz, 1H), 8.48 (d, J=1.7 Hz, 1H), 8.29 (s, 1H), 8.23 (d, J=8.1 Hz, 1H), 7.61 (d, J=8.1 Hz, 1H), 6.70 (s, 1H), 3.03-2.88 (m, 1H), 1.19 (d, J=6.8 Hz, 6H).

Example 377: 1-(7-Methyl-1H-indazol-5-yl)-6-(trifluoromethyl)pyrrolo[2,3-b]pyridine

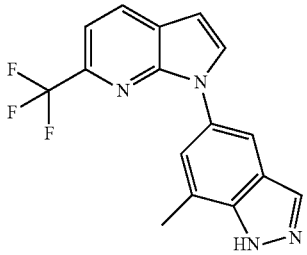 [SMILES: Cc1cc(-n2ccc3ccc(C(F)(F)F)nc32)cc2cn[nH]c12]

Phosphorus oxychloride (103 μL, 1.10 mmol) was added drop wise to DMF (2 mL) at 0° C. and stirred for 10 minutes. 7-Methyl-5-(6-(trifluoromethyl)-1H-pyrrolo[2,3-b]pyridin-1-yl)-2-((2-(trimethylsilyl)ethoxy)methyl)-2H-indazole (Intermediate 64, product from Step A, 350 mg, 0.784 mmol) in DMF (1 mL) was added slowly to the resulting solution. The mixture was stirred at ambient temperature for 1 hr, then at 50° C. for 15 min, then allowed to stand at 0° C. overnight. The mixture was then stirred again at 50° C. for 1 hr. The reaction mixture was added to water; the resulting mixture was treated with a saturated solution of NaHCO$_3$ (2 mL) until pH=9. The biphasic mixture was then extracted with EtOAc (5 mL×3), and the combined organic layers were dried (Na$_2$SO$_4$) and concentrated in vacuo. Purification (FCC, SiO$_2$, EtOAc:DCM, 0:100 to 25:75) afforded the title compound (85 mg, 39%). MS (ESI): mass calcd. for C$_{16}$H$_{11}$F$_3$N$_4$, 316.1; m/z found, 317.1 [M+H]$^+$. $^1$H NMR (400 MHz, CDCl$_3$) δ 10.38 (s, 1H), 8.16-8.08 (m, 2H), 7.83 (dd, J=1.8, 0.8 Hz, 1H), 7.67 (d, J=3.6 Hz, 1H), 7.55 (d, J=8.1 Hz, 1H), 7.50 (dd, J=1.9, 1.0 Hz, 1H), 6.72 (d, J=3.6 Hz, 1H), 2.61 (t, J=0.8 Hz, 3H).

Example 378: 7-Methyl-5-(6-methylpyrrolo[2,3-b]pyridin-1-yl)indolin-2-one

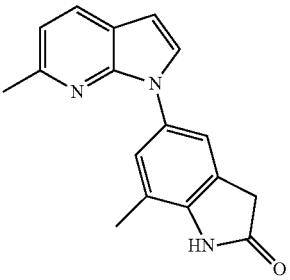

The title compound was prepared in a manner analogous to Example 341, Step A using 5-bromo-7-methylindolin-2-one and 6-methyl-1H-pyrrolo[2,3-b]pyridine. MS (ESI): mass calcd. for C$_{17}$H$_{15}$N$_3$O, 277.1; m/z found, 278.1 [M+H]$^+$. $^1$H NMR (500 MHz, CDCl$_3$) δ 8.10 (s, 1H), 7.84 (d, J=8.0 Hz, 1H), 7.51 (d, J=2.0 Hz, 1H), 7.38-7.34 (m, 1H), 7.33 (d, J=3.6 Hz, 1H), 7.00 (d, J=8.0 Hz, 1H), 6.54 (d, J=3.6 Hz, 1H), 3.65 (s, 2H), 2.63 (s, 3H), 2.34 (s, 3H).

Example 379: 7-Fluoro-5-(6-methylpyrrolo[2,3-b]pyridin-1-yl)indolin-2-one

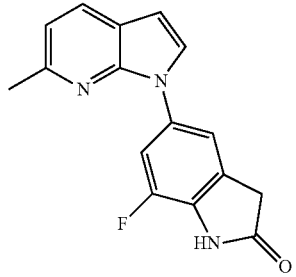 [SMILES: Cc1ccc2ccn(-c3cc(F)c4c(c3)CC(=O)N4)c2n1]

The title compound was prepared in a manner analogous to Example 341. Step A. using 5-bromo-7-fluoroindolin-2-one and 6-methyl-1H-pyrrolo[2,3-b]pyridine. MS (ESI): mass calcd. for $C_{16}H_{12}FN_3O$, 281.1; m/z found, 282.1 [M+H]$^+$. $^1$H NMR (500 MHz, CDCl$_3$) δ 7.84 (d, J=8.0 Hz, 1H), 7.67 (s, 1H), 7.58-7.48 (m, 2H), 7.34 (d, J=3.7 Hz, 1H), 7.02 (d, J=7.9 Hz, 1H), 6.57 (d, J=3.7 Hz, 1H), 3.68 (t, J=1.0 Hz, 2H), 2.63 (s, 3H).

Example 380: 5-(2-Cyclopropyl-6-methyl-pyrrolo[2,3-b]pyridin-1-yl)indolin-2-one

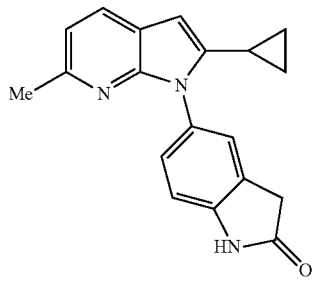

The title compound was prepared in a manner analogous to Example 342, starting with 2-bromo-3-(cyclopropylethynyl)-6-methylpyridine (Intermediate 39) and tert-butyl 5-amino-1H-indole-1-carboxylate (Intermediate 11). MS (ESI): mass calcd. for $C_{19}H_{17}N_3O$, 303.1; m/z found, 304.2 [M+H]$^+$. $^1$H NMR (500 MHz, DMSO-d$_6$) δ=10.56 (br s, 1H), 7.74 (br d, J=7.5 Hz, 1H), 7.41-7.16 (m, 2H), 7.11-6.84 (m, 2H), 6.15 (s, 1H), 3.59 (s, 2H), 2.40 (s, 3H), 1.65 (br s, 1H), 0.98-0.61 (m, 4H).

Example 381: 2-(4-Fluorophenyl)-1-(1H-indol-5-yl)-6-methyl-pyrrolo[2,3-b]pyridine

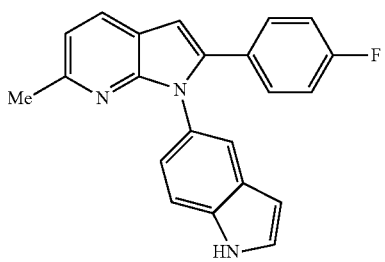 [SMILES: Cc1ccc2cc(-c3ccc(F)cc3)n(-c3ccc4[nH]ccc4c3)c2n1]

The title compound was prepared in a manner analogous to Example 342, omitting Step B, and starting with 2-bromo-3-((4-fluorophenyl)ethynyl)-6-methylpyridine (Intermediate 40) and tert-butyl 5-amino-1H-indole-1-carboxylate (Intermediate 11). MS (ESI): mass calcd. for $C_{22}H_{16}FN_3$, 341.1; m/z found, 342.1 [M+H]$^+$. $^1$H NMR (400 MHz, CDCl$_3$) δ 8.81 (br s, 1H), 7.86 (d, J=7.86 Hz, 1H), 7.50 (d, J=1.85 Hz, 1H), 7.22-7.27 (m, 2H), 7.19 (d, J=8.55 Hz, 1H), 7.12-7.14 (m, 1H), 6.97-7.03 (m, 2H), 6.83-6.91 (m, 2H), 6.64 (s, 1H), 6.44 (ddd, J=3.12, 2.08, 0.81 Hz, 1H), 2.59 (s, 3H).

Example 382: 5-[2-(4-Fluorophenyl)-6-methyl-pyrrolo[2,3-b]pyridin-1-yl]indolin-2-one

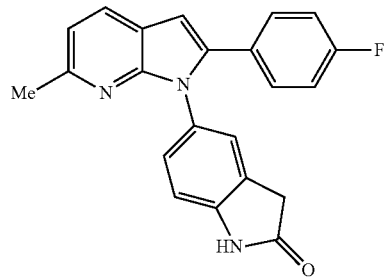

The title compound was prepared in a manner analogous to Example 342, starting with 2-bromo-3-((4-fluorophenyl)ethynyl)-6-methylpyridine (Intermediate 40) and 5-amino-indolin-2-one. MS (ESI): mass calcd. for $C_{22}H_{16}FN_3O$, 357.1; m/z found, 358.1 [M+H]$^+$. $^1$H NMR (500 MHz, CDCl$_3$) δ 8.37 (s, 1H), 7.84 (d, J=7.80 Hz, 1H), 7.20-7.26 (m, 3H), 7.06 (dd, J=8.38, 2.02 Hz, 1H), 7.01 (d, J=8.09 Hz, 1H), 6.94-7.00 (m, 2H), 6.79 (d, J=8.38 Hz, 1H), 6.62 (s, 1H), 3.52 (s, 2H), 2.60 (s, 3H).

Example 383: 5-[6-Chloro-2-(4-fluorophenyl)pyrrolo[2,3-b]pyridin-1-yl]indolin-2-one

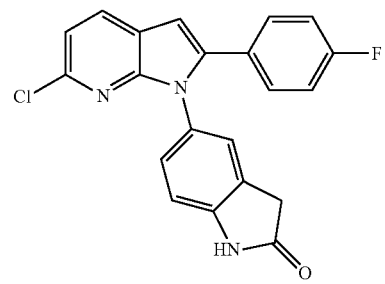 [SMILES: O=C1Cc2cc(-n3c(-c4ccc(F)cc4)cc4ccc(Cl)nc43)ccc2N1]

The title compound was prepared in a manner analogous to Example 342, Step B, employing 6-chloro-2-(4-fluorophenyl)-1-(1H-indol-5-yl)pyrrolo[2,3-b]pyridine (Example 385). MS (ESI): mass calcd. for $C_{21}H_{13}ClFN_3O$, 377.1; m/z found, 378.0 [M+H]$^+$. $^1$H NMR (300 MHz, DMSO-d$_6$) δ 10.56 (s, 1H), 8.12 (d, J=8.2 Hz, 1H), 7.44-7.29 (m, 2H), 7.30-7.13 (m, 4H), 7.05 (d, J=8.1 Hz, 1H), 6.94-6.80 (m, 2H), 3.53 (s, 2H).

Example 384: 5-[2-(4-Fluorophenyl)-6-methoxy-pyrrolo[2,3-b]pyridin-1-yl]indolin-2-one

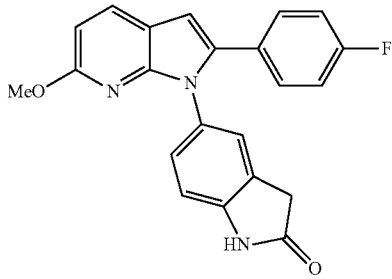 [SMILES: COc1ccc2cc(-c3ccc(F)cc3)n(-c3ccc4c(c3)CC(=O)N4)c2n1]

The title compound was prepared in a manner analogous to Example 342, Step B, employing 2-(4-fluorophenyl)-1-(1H-indol-5-yl)-6-methoxy-pyrrolo[2,3-b]pyridine (Example 343). MS (ESI): mass calcd. for $C_{22}H_{16}FN_3O_2$, 373.1; m/z found, 374 [M+H]$^+$. $^1$H NMR (300 MHz, DMSO-d$_6$) δ 10.55 (s, 1H), 7.43 (d, J=8.9 Hz, 1H), 7.36 (dd, J=8.6, 5.6 Hz, 2H), 7.23-7.12 (m, 3H), 7.02 (dd, J=8.3, 1.6 Hz, 1H), 6.87 (d, J=8.3 Hz, 1H), 6.84 (s, 1H), 6.60 (d, J=8.8 Hz, 1H), 3.89 (s, 3H), 3.52 (s, 2H).

Example 385: 6-Chloro-2-(4-fluorophenyl)-1-(1H-indol-5-yl)pyrrolo[2,3-b]pyridine

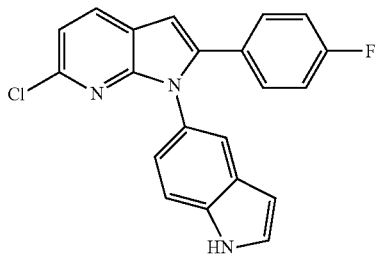 [SMILES: Fc1ccc(-c2cc3ccc(Cl)nc3n2-c2ccc3[nH]ccc3c2)cc1]

The title compound was prepared in a manner analogous to Example 343, starting with 2-bromo-6-chloro-3-((4-fluorophenyl)ethynyl)pyridine (Intermediate 43) and tert-butyl 5-amino-1H-indole-1-carboxylate (Intermediate 11). MS (ESI): mass calcd. for $C_{21}H_{13}ClFN_3$, 361.1; m/z found, 362 [M+H]$^+$. $^1$H NMR (300 MHz, DMSO-d$_6$) δ 11.34 (s, 1H), 8.12 (d, J=8.2 Hz, 1H), 7.52 (s, 1H), 7.49-7.41 (m, 2H), 7.35 (dd, J=8.7, 5.5 Hz, 2H), 7.23 (d, J=8.1 Hz, 1H), 7.12 (t, J=8.9 Hz, 2H), 6.96-6.87 (m, 2H), 6.48 (s, 1H).

Example 386: 6-tert-Butoxy-2-(4-fluorophenyl)-1-(1H-indol-5-yl)pyrrolo[2,3-b]pyridine

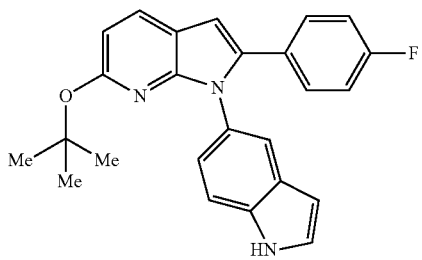 [SMILES: CC(C)(C)Oc1ccc2cc(-c3ccc(F)cc3)n(-c3ccc4[nH]ccc4c3)c2n1]

The title compound was a by-product from Example 385. MS (ESI): mass calcd. for $C_{25}H_{22}FN_3O$, 399.2; m/z found, 400 [M+H]$^+$. $^1$H NMR (300 MHz, DMSO-d$_6$) δ 11.24 (s, 1H), 7.88 (d, J=8.4 Hz, 1H), 7.44 (s, 1H), 7.43-7.36 (m, 2H), 7.28 (dd, J=8.6, 5.6 Hz, 2H), 7.08 (t, J=8.9 Hz, 2H), 6.96 (dd, J=8.5, 1.7 Hz, 1H), 6.72 (s, 1H), 6.49 (d, J=8.4 Hz, 1H), 6.42 (d, J=2.5 Hz, 1H), 1.38 (s, 9H).

Example 387: 2-(4-Fluorophenyl)-1-(1H-indol-5-yl)-6-(trifluoromethyl)pyrrolo[2,3-b]pyridine

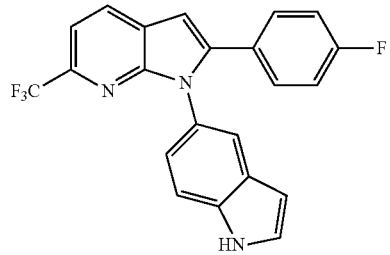 [SMILES: Fc1ccc(-c2cc3ccc(C(F)(F)F)nc3n2-c2ccc3[nH]ccc3c2)cc1]

The title compound was prepared in a manner analogous to Example 348, starting with 2-chloro-3-((4-fluorophenyl)ethynyl)-6-(trifluoromethyl)pyridine (Intermediate 34) and tert-butyl 5-amino-1H-indole-1-carboxylate (Intermediate 11). MS (ESI): mass calcd. for $C_{22}H_{13}F_4N_3$, 395.1; m/z found, 396.0 [M+H]$^+$. $^1$H NMR (300 MHz, DMSO-d$_6$) δ 11.36 (s, 1H), 8.32 (d, J=8.1 Hz, 1H), 7.64 (d, J=8.1 Hz, 1H), 7.53 (br s, 1H), 7.50-7.43 (m, 2H), 7.43-7.34 (m, 2H), 7.15 (t, J=8.8 Hz, 2H), 7.03 (s, 1H), 6.97 (dd, J=8.5, 1.5 Hz, 1H), 6.48 (s, 1H).

Example 388: 1-(1H-Indol-5-yl)-2-phenyl-6-(trifluoromethyl)pyrrolo[2,3-b]pyridine

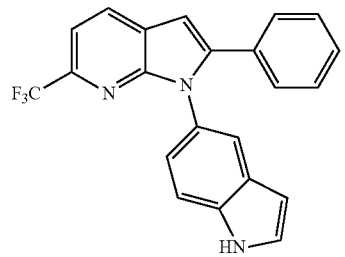

The title compound was prepared in a manner analogous to Example 348, starting with 2-chloro-3-(phenylethynyl)-6-(trifluoromethyl)pyridine (Intermediate 33) and tert-butyl 5-amino-1H-indole-1-carboxylate (Intermediate 11). MS (ESI): mass calcd. for $C_{22}H_{14}F_3N_3$, 377.1; m/z found, 378.0 [M+H]$^+$. $^1$H NMR (300 MHz, DMSO-d$_6$) δ 11.34 (s, 1H), 8.32 (d, J=8.1 Hz, 1H), 7.64 (d, J=8.1 Hz, 1H), 7.52 (br s, 1H), 7.49-7.42 (m, 2H), 7.40-7.32 (m, 2H), 7.32-7.24 (m, 3H), 7.04 (s, 1H), 6.98 (dd, J=8.5, 1.8 Hz, 1H), 6.47 (br s, 1H).

Example 389: 5-[3-Bromo-2-cyclopropyl-6-(trifluoromethyl)pyrrolo[2,3-b]pyridin-1-yl]indolin-2-one

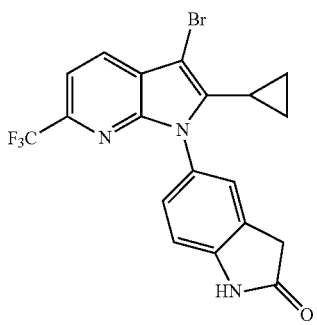 [SMILES: O=C1Cc2cc(-n3c(C4CC4)c(Br)c4ccc(C(F)(F)F)nc43)ccc2N1]

Step A: 2-Cyclopropyl-1-(1H-indol-5-yl)-6-(trifluoromethyl)-1H-pyrrolo[2,3-b]pyridine The title compound was prepared in a manner analogous to Example 348, using 2-chloro-3-(cyclopropylethynyl)-6-(trifluoromethyl)pyridine and tert-butyl 5-amino-1H-indole-1-carboxylate (Intermediate 11). MS (ESI): mass calcd. for $C_{24}H_{22}F_3N_3O_2$, 441.2; m/z found, 442.0 [M+H]$^+$.

Step B: 5-[3-Bromo-2-cyclopropyl-6-(trifluoromethyl)pyrrolo[2,3-b]pyridin-1-yl]indolin-2-one The title compound was prepared in a manner analogous to Example 349. MS (ESI): mass calcd. for $C_{19}H_{13}BrF_3N_3O$, 435.0; m/z found, 437.9 [M+H]$^+$. $^1$H NMR (300 MHz, DMSO-d$_6$) δ 10.62 (s, 1H), 8.08 (d, J=8.0 Hz, 1H), 7.67 (d, J=8.1 Hz, 1H), 7.37 (s, 1H), 7.31 (d, J=8.2 Hz, 1H), 6.99 (d, J=8.2 Hz, 1H), 3.59 (s, 2H), 1.94-1.79 (m, 1H), 0.87 (d, J=7.1 Hz, 4H).

Example 390: 6-Methyl-2-phenyl-1-(1H-pyrrolo[2,3-b]pyridin-5-yl)pyrrolo[2,3-b]pyridine

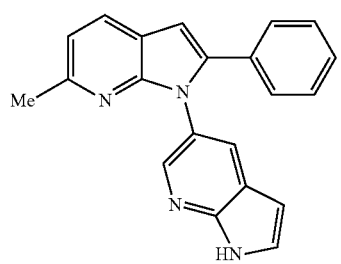

The title compound was prepared in a manner analogous to Example 348, starting with 2-bromo-6-methyl-3-(phenylethynyl)pyridine (Intermediate 41) and 1H-pyrrolo[2,3-b]pyridin-5-amine (Intermediate 15). MS (ESI): mass calcd. for $C_{21}H_{16}N_4$, 324.1; m/z found, 325.2 [M+H]$^+$.

Example 391: 2-Isopropyl-1-(1H-pyrrolo[2,3-b]pyridin-5-yl)-6-(trifluoromethyl)pyrrolo[2,3-b]pyridine

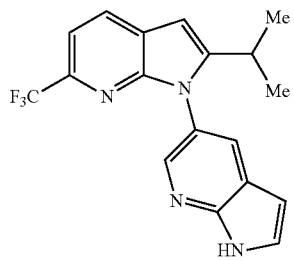

The title compound was prepared in a manner analogous to Example 348, starting with 2-chloro-3-(3-methylbut-1-yn-1-yl)-6-(trifluoromethyl)pyridine (Intermediate 32) and 1H-pyrrolo[2,3-b]pyridin-5-amine (Intermediate 15). MS (ESI): mass calcd. for $C_{18}H_{15}F_3N_4$, 344.1; m/z found, 344.9 [M+H]$^+$. $^1$H NMR (300 MHz, DMSO-d$_6$) δ 12.04 (s, 1H), 8.22 (dd, J=8.6, 5.2 Hz, 2H), 8.11 (d, J=1.8 Hz, 1H), 7.70-7.62 (m, 1H), 7.58 (d, J=8.1 Hz, 1H), 6.67 (s, 1H), 6.61-6.51 (m, 1H), 3.01-2.85 (m, 1H), 1.19 (d, J=6.8 Hz, 6H).

Example 392: 2-Methyl-1-(1H-pyrrolo[2,3-b]pyridin-5-yl)-6-(trifluoromethyl)pyrrolo[2,3-b]pyridine

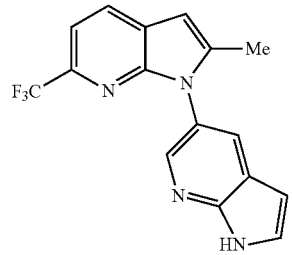 [SMILES: Cc1cc2ccc(C(F)(F)F)nc2n1-c1cnc2[nH]ccc2c1]

The title compound was prepared in a manner analogous to Example 348, starting with 2-chloro-3-(prop-1-yn-1-yl)-6-(trifluoromethyl)pyridine (Intermediate 26) and 1-((2-(trimethylsilyl)ethoxy)methyl)-1H-pyrrolo[2,3-b]pyridin-5-amine (Intermediate 21). MS (ESI): mass calcd. for $C_{16}H_{11}F_3N_4$, 316.1; m/z found, 317.0 [M+H]$^+$. $^1$H NMR (300 MHz, CDCl$_3$) δ 9.13 (s, 1H), 8.31 (d, J=1.5 Hz, 1H), 7.99-7.92 (m, 2H), 7.47 (d, J=8.1 Hz, 1H), 7.45-7.39 (m, 1H), 6.60 (dd, J=3.2, 1.9 Hz, 1H), 6.47 (s, 1H), 2.37 (s, 3H).

Example 393: 5-(3-Bromo-6-methyl-2-phenyl-pyrrolo[2,3-b]pyridin-1-yl)-1,3-dihydropyrrolo[2,3-b]pyridin-2-one

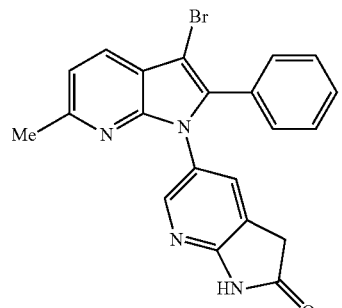

The title compound was prepared in a manner analogous to Example 349, starting with 6-methyl-2-phenyl-1-(1H-pyrrolo[2,3-b]pyridin-5-yl)pyrrolo[2,3-b]pyridine (Example 390). MS (ESI): mass calcd. for $C_{21}H_{15}BrN_4O$, 418.0; m/z found, 421.0 [M+H]⁺. ¹H NMR (300 MHz, DMSO-d₆) δ 11.12 (s, 1H), 7.93-7.84 (m, 2H), 7.59 (s, 1H), 7.39 (s, 5H), 7.21 (d, J=8.0 Hz, 1H), 3.57 (s, 2H), 2.49 (s, 3H).

Example 394: 5-[3-Bromo-2-isopropyl-6-(trifluoromethyl)pyrrolo[2,3-b]pyridin-1-yl]-1,3-dihydropyrrolo[2,3-b]pyridin-2-one

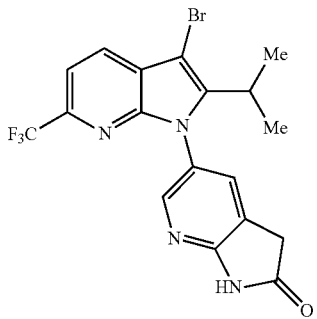 [SMILES: CC(C)c1c(Br)c2ccc(C(F)(F)F)nc2n1-c1cnc2c(c1)CC(=O)N2]

The title compound was prepared in a manner analogous to Example 349, starting with 2-isopropyl-1-(1H-pyrrolo[2,3-b]pyridin-5-yl)-6-(trifluoromethyl)pyrrolo[2,3-b]pyridine (Example 391). MS (ESI): mass calcd. for $C_{18}H_{14}BrF_3N_4O$, 438.0; m/z found, 440.8 [M+H]⁺. ¹H NMR (300 MHz, DMSO-d₆) δ 11.34 (s, 1H), 8.18 (s, 1H), 8.13 (d, J=8.1 Hz, 1H), 7.75 (s, 1H), 7.71 (d, J=8.1 Hz, 1H), 3.70 (d, J=3.5 Hz, 2H), 3.02 (hept, J=7.1 Hz, 1H), 1.36 (d, J=6.9 Hz, 6H).

Example 395: 5-[3-Bromo-2-methyl-6-(trifluoromethyl)pyrrolo[2,3-b]pyridin-1-yl]-1,3-dihydropyrrolo[2,3-b]pyridin-2-one

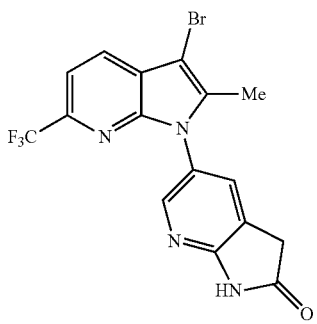 [SMILES: Cc1c(Br)c2ccc(C(F)(F)F)nc2n1-c1cnc2c(c1)CC(=O)N2]

The title compound was prepared in a manner analogous to Example 349, starting with 2-methyl-1-(1H-pyrrolo[2,3-b]pyridin-5-yl)-6-(trifluoromethyl)pyrrolo[2,3-b]pyridine (Example 392). MS (ESI): mass calcd. for $C_{16}H_{10}BrF_3N_4O$, 410.0; m/z found, 411.0 [M+H]⁺. ¹H NMR (300 MHz, CDCl₃) δ 8.16 (s, 1H), 8.05 (s, 1H), 7.96 (d, J=8.0 Hz, 1H), 7.59-7.53 (m, 2H), 3.73 (s, 2H), 2.41 (s, 3H).

Example 396: 5-[2-Isopropyl-6-(trifluoromethyl)pyrrolo[2,3-b]pyridin-1-yl]indolin-2-one

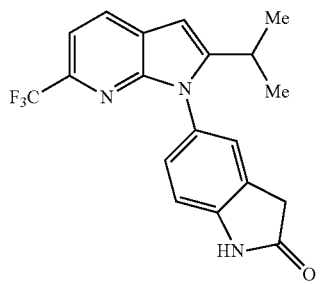

Step A: 1-(1H-Indol-5-yl)-2-isopropyl-6-(trifluoromethyl)-1H-pyrrolo[2,3-b]pyridine The title compound was prepared in a manner analogous to Example 348 starting with 2-chloro-3-(3-methylbut-1-yn-1-yl)-6-(trifluoromethyl)pyridine (Intermediate 32) and tert-butyl 5-amino-1H-indole-1-carboxylate (Intermediate 11). MS (ESI): mass calcd. for $C_{19}H_{16}F_3N_3$, 343.1; m/z found, 344.1 [M+H]⁺.

Step B: 5-(3-Bromo-2-isopropyl-6-(trifluoromethyl)-1H-pyrrolo[2,3-b]pyridin-1-yl)indolin-2-one The title compound was prepared in a manner analogous to Example 349. MS (ESI): mass calcd. for $C_{19}H_{15}BrF_3N_3O$, 437.0; m/z found, 438.7 [M+H]⁺.

Step C. 5-[2-Isopropyl-6-(trifluoromethyl)pyrrolo[2,3-b]pyridin-1-yl]indolin-2-one The title compound was prepared in a manner analogous to Example 347. MS (ESI): mass calcd. for $C_{19}H_{16}F_3N_3O$, 359.1; m/z found, 360.2 [M+H]⁺. ¹H NMR (300 MHz, DMSO-d₆) δ 10.62 (s, 1H), 8.17 (d, J=7.9 Hz, 1H), 7.55 (d, J=8.0 Hz, 1H), 7.28 (s, 1H), 7.23 (d, J=8.1 Hz, 1H), 7.00 (d, J=8.0 Hz, 1H), 6.61 (s, 1H), 3.60 (s, 2H), 3.09-2.78 (m, 1H), 1.18 (d, J=6.6 Hz, 6H).

Example 397: 5-[2-Phenyl-6-(trifluoromethyl)pyrrolo[2,3-b]pyridin-1-yl]indolin-2-one

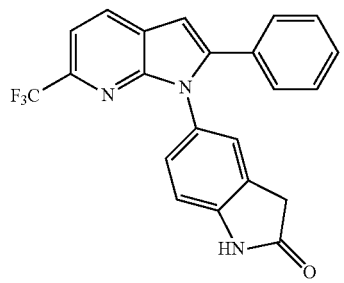 [SMILES: Cc1ccc2cc(-c3ccccc3)n(-c3cnc4c(c3)CC(=O)N4)c2n1]

The title compound was prepared in a manner analogous to Example 396, starting with 2-chloro-3-(phenylethynyl)-6-(trifluoromethyl)pyridine (Intermediate 33) and tert-butyl 5-amino-1H-indole-1-carboxylate (Intermediate 11). MS (ESI): mass calcd. for $C_{22}H_{14}F_3N_3O$, 393.1; m/z found, 394.0 [M+H]$^+$. $^1$H NMR (300 MHz, DMSO-d$_6$) δ 10.56 (s, 1H), 8.32 (d, J=8.0 Hz, 1H), 7.65 (d, J=8.1 Hz, 1H), 7.36 (s, 5H), 7.22 (s, 1H), 7.11 (d, J=8.0 Hz, 1H), 7.02 (s, 1H), 6.88 (d, J=8.1 Hz, 1H), 3.51 (s, 2H).

Example 398: 5-[2-(4-Fluorophenyl)-6-(trifluoromethyl)pyrrolo[2,3-b]pyridin-1-yl]indolin-2-one

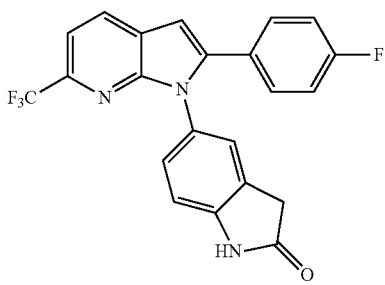

The title compound was prepared in a manner analogous to Example 396, starting with 2-chloro-3-((4-fluorophenyl)ethynyl)-6-(trifluoromethyl)pyridine (Intermediate 34) and tert-butyl 5-amino-1H-indole-1-carboxylate (Intermediate 11). MS (ESI): mass calcd. for $C_{22}H_{13}F_4N_3O$, 411.1; m/z found, 412.0 [M+H]$^+$. $^1$H NMR (300 MHz, DMSO-d$_6$) δ 10.56 (s, 1H), 8.32 (d, J=8.0 Hz, 1H), 7.65 (d, J=8.1 Hz, 1H), 7.46-7.35 (m, 2H), 7.28-7.16 (m, 3H), 7.11 (d, J=8.2 Hz, 1H), 7.02 (s, 1H), 6.89 (d, J=8.2 Hz, 1H), 3.51 (s, 2H).

Example 399: 5-[2-Cyclopropyl-6-(trifluoromethyl)pyrrolo[2,3-b]pyridin-1-yl]indolin-2-one

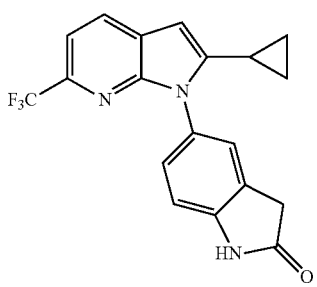

The title compound was prepared in a manner analogous to Example 347, starting with 5-[3-bromo-2-cyclopropyl-6-(trifluoromethyl)pyrrolo[2,3-b]pyridin-1-yl]indolin-2-one (Example 389). MS (ESI): mass calcd. for $C_{19}H_{14}F_3N_3O$, 357.1; m/z found, 358.0 [M+H]$^+$. $^1$H NMR (300 MHz, DMSO-d$_6$) δ 10.61 (s, 1H), 8.10 (d, J=8.0 Hz, 1H), 7.53 (d, J=8.1 Hz, 1H), 7.29 (d, J=8.1 Hz, 1H), 7.00 (d, J=8.1 Hz, 1H), 6.39 (s, 1H), 3.60 (s, 2H), 1.80-1.60 (m, 1H), 1.00-0.89 (m, 2H), 0.90-0.81 (m, 2H).

Example 400: 5-(6-Methyl-2-phenyl-pyrrolo[2,3-b]pyridin-1-yl)-1,3-dihydropyrrolo[2,3-b]pyridin-2-one

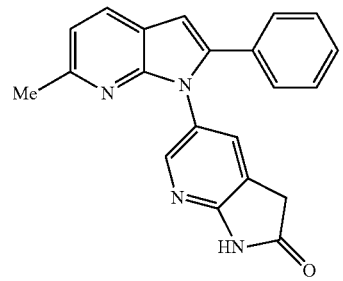

The title compound was prepared in a manner analogous to Example 347 starting with 5-(3-bromo-6-methyl-2-phenyl-pyrrolo[2,3-b]pyridin-1-yl)-1,3-dihydropyrrolo[2,3-b]pyridin-2-one (Example 393). MS (ESI): mass calcd. for $C_{21}H_{16}N_4O$, 340.1; m/z found, 340.9 [M+H]$^+$. $^1$H NMR (300 MHz, DMSO-d$_6$) δ 11.15 (s, 1H), 7.96 (d, J=7.9 Hz, 1H), 7.88 (s, 1H), 7.59 (s, 1H), 7.34 (s, 5H), 7.09 (d, J=7.9 Hz, 1H), 6.82 (s, 1H), 3.61 (s, 2H), 2.48 (s, 3H).

Example 401: 5-[2-Isopropyl-6-(trifluoromethyl)pyrrolo[2,3-b]pyridin-1-yl]-1,3-dihydropyrrolo[2,3-b]pyridin-2-one

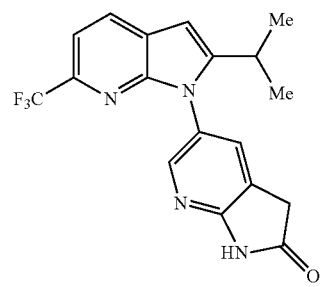 [SMILES: CC(C)c1cc2ccc(C(F)(F)F)nc2n1-c1cnc2c(c1)CC(=O)N2]

The title compound was prepared in a manner analogous to Example 347, starting with 5-[3-bromo-2-isopropyl-6-(trifluoromethyl)pyrrolo[2,3-b]pyridin-1-yl]-1,3-dihydropyrrolo[2,3-b]pyridin-2-one (Example 394). MS (ESI): mass calcd. for $C_{18}H_{15}F_3N_4O$, 360.1; m/z found, 361.1 [M+H]$^+$. $^1$H NMR (300 MHz, DMSO-d$_6$) δ 11.30 (s, 1H), 8.23-8.14 (m, 2H), 7.72 (s, 1H), 7.59 (d, J=8.0 Hz, 1H), 6.66 (s, 1H), 3.69 (s, 2H), 2.99-2.87 (m, 1H), 1.20 (d, J=6.8 Hz, 6H).

Example 402: 5-[2-Methyl-6-(trifluoromethyl)pyrrolo[2,3-b]pyridin-1-yl]-1,3-dihydropyrrolo[2,3-b]pyridin-2-one

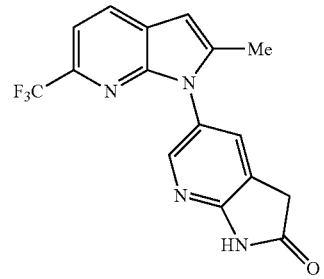 [SMILES: Cc1cc2ccc(C(F)(F)F)nc2n1-c1cnc2c(c1)CC(=O)N2]

The title compound was prepared in a manner analogous to Example 347, starting with 5-[3-bromo-2-methyl-6-(trifluoromethyl)pyrrolo[2,3-b]pyridin-1-yl]-1,3-dihydropyrrolo[2,3-b]pyridin-2-one (Example 395). MS (ESI): mass calcd. for $C_{16}H_{11}F_3N_4O$, 332.1; m/z found, 333.0 [M+H]$^+$. $^1$H NMR (300 MHz, CDCl$_3$) δ 8.45 (s, 1H), 8.17 (s, 1H), 7.95 (d, J=8.0 Hz, 1H), 7.58 (s, 1H), 7.48 (d, J=8.0 Hz, 1H), 6.47 (s, 1H), 3.72 (s, 2H), 2.40 (s, 3H).

Example 403: 5-(2-Ethylpyrrolo[2,3-b]pyridin-1-yl)-7-methyl-indolin-2-one

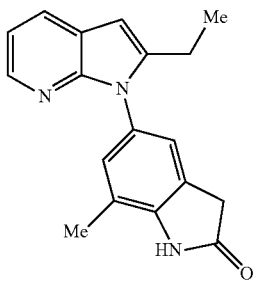 [SMILES: CCc1cc2cccnc2n1-c1cc(C)c2c(c1)CC(=O)N2]

The title compound was prepared in a manner analogous to Example 332, Step A, starting with 3-(but-1-yn-1-yl)-2-chloropyridine (Intermediate 38) and 5-amino-7-methylindolin-2-one (Intermediate 10). MS (ESI): mass calcd. for $C_{18}H_{17}N_3O$, 291.1; m/z found, 292.1 [M+H]$^+$. $^1$H NMR (400 MHz, CD$_3$OD) δ 8.03-7.99 (dd, J=4.8, 1.5 Hz, 1H), 7.95-7.91 (dd, J=7.8, 1.5 Hz, 1H), 7.12-7.05 (m, 2H), 7.03 (s, 1H), 6.41 (s, 1H), 3.62 (s, 2H), 2.64 (q, J=7.5 Hz, 2H), 2.33 (s, 3H), 1.23 (t, J=7.5 Hz, 3H).

Example 404: (*R)-2-(sec-Butyl)-3-(7-chloro-1H-indazol-5-yl)-5-(trifluoromethyl)-3H-imidazo[4,5-b]pyridine

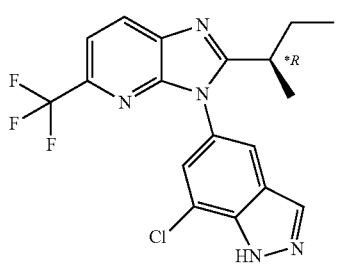 [SMILES: CC[C@@H](C)c1nc2ccc(C(F)(F)F)nc2n1-c1cc(Cl)c2[nH]ncc2c1]

The title compound was prepared in a manner analogous to Example 109 with a chiral separation. MS (ESI): mass calcd. for $C_{18}H_{15}ClF_3N_5$, 393.1; m/z found, 394.3 [M+H]$^+$. $^1$H NMR (500 MHz, CDCl$_3$) δ 8.27-8.23 (m, 1H), 8.00 (s, 1H), 7.75 (d, J=8.2 Hz, 1H), 7.57 (d, J=1.7 Hz, 1H), 7.23 (d, J=1.7 Hz, 1H), 2.85-2.76 (m, 1H), 2.01-1.89 (m, 1H), 1.74-1.63 (m, 1H), 1.34 (d, J=6.9 Hz, 3H), 0.87-0.80 (m, 3H).

Example 405: (*S)-2-(sec-Butyl)-3-(7-chloro-1H-indazol-5-yl)-5-(trifluoromethyl)-3H-imidazo[4,5-b]pyridine

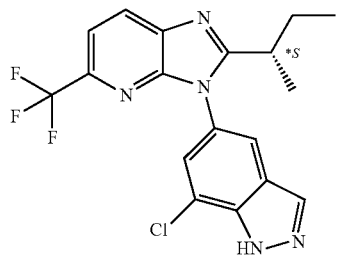 [SMILES: CC[C@H](C)c1nc2ccc(C(F)(F)F)nc2n1-c1cc(Cl)c2[nH]ncc2c1]

The title compound was prepared in a manner analogous to Example 109, Method B with a chiral separation. MS (ESI): mass calcd. for $C_{18}H_{15}ClF_3N_5$, 393.1; m/z found, 394.3 [M+H]$^+$. $^1$H NMR (500 MHz, CDCl$_3$) δ 8.27-8.23 (m, 1H), 8.01 (s, 1H), 7.75 (d, J=8.3 Hz, 1H), 7.57 (d, J=1.7 Hz, 1H), 7.23 (d, J=1.7 Hz, 1H), 2.85-2.76 (m, 1H), 2.01-1.90 (m, 1H), 1.74-1.63 (m, 1H), 1.34 (d, J=6.9 Hz, 3H), 0.84 (t, J=7.4 Hz, 3H).

Example 406: (*R)-2-(sec-Butyl)-3-(7-methyl-1H-indazol-5-yl)-5-(trifluoromethyl)-3H-imidazo[4,5-b]pyridine

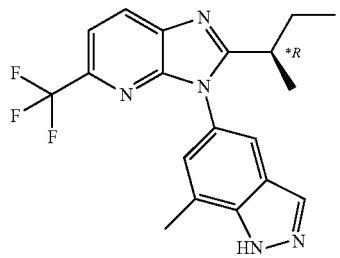 [SMILES: CC[C@@H](C)c1nc2ccc(C(F)(F)F)nc2n1-c1cc(C)c2[nH]ncc2c1]

The title compound was prepared in a manner analogous to Example 109, Method B with a chiral separation. MS (ESI): mass calcd. for $C_{19}H_{18}F_3N_5$, 373.1; m/z found, 374.1 [M+H]$^+$. $^1$H NMR (500 MHz, CDCl$_3$) δ 8.27-8.22 (m, 1H), 7.90 (s, 1H), 7.74 (d, J=8.3 Hz, 1H), 7.46-7.43 (m, 1H), 6.91-6.87 (m, 1H), 2.86-2.76 (m, 1H), 2.43 (s, 3H), 2.00-1.89 (m, 1H), 1.72-1.61 (m, 1H), 1.33 (d, J=6.9 Hz, 3H), 0.86-0.79 (m, 3H).

Example 407: (*S)-2-(sec-Butyl)-3-(7-methyl-1H-indazol-5-yl)-5-(trifluoromethyl)-3H-imidazo[4,5-b]pyridine

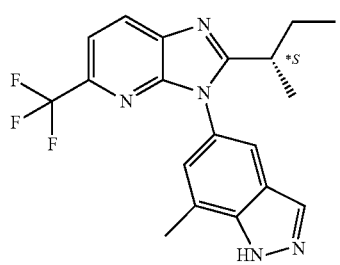 [SMILES: CC[C@H](C)c1nc2ccc(C(F)(F)F)nc2n1-c1cc(C)c2[nH]ncc2c1]

The title compound was prepared in a manner analogous to Example 109, Method B, with a chiral separation. MS (ESI): mass calcd. for $C_{19}H_{18}F_3N_5$, 373.1; m/z found, 374.1 [M+H]$^+$. $^1$H NMR (500 MHz, CDCl$_3$) δ 8.25 (d, J=8.3 Hz, 1H), 7.91 (s, 1H), 7.74 (d, J=8.3 Hz, 1H), 7.45 (d, J=1.7 Hz, 1H), 6.90 (dd, J=1.8, 1.0 Hz, 1H), 2.86-2.77 (m, 1H), 2.44 (s, 3H), 2.00-1.89 (m, 1H), 1.72-1.61 (m, 1H), 1.33 (d, J=6.9 Hz, 3H), 0.86-0.79 (m, 3H).

Example 408: (*R)-3-(7-Chloro-1H-indazol-5-yl)-2-(1-fluoroethyl)-5-(trifluoromethyl)-3H-imidazo[4,5-b]pyridine

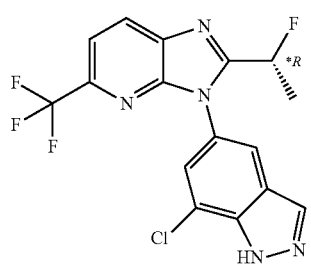 [SMILES: C[C@@H](F)c1nc2ccc(C(F)(F)F)nc2n1-c1cc(Cl)c2[nH]ncc2c1]

The title compound was prepared in a manner analogous to Example 117 with a chiral separation. MS (ESI): mass calcd. for $C_{16}H_{10}ClF_4N_5$, 383.1; m/z found, 384.1 [M+H]$^+$. $^1$H NMR (400 MHz, CDCl$_3$) δ11.34 (s, 1H), 8.30 (d, J=8.3 Hz, 1H), 8.01 (s, 1H), 7.73 (d, J=8.3 Hz, 1H), 7.65 (d, J=1.7 Hz, 1H), 7.33 (d, J=1.6 Hz, 1H), 5.73-5.51 (m, 1H), 1.87-1.73 (m, 3H).

Example 409: (*S)-3-(7-Chloro-1H-indazol-5-yl)-2-(1-fluoroethyl)-5-(trifluoromethyl)-3H-imidazo[4,5-b]pyridine

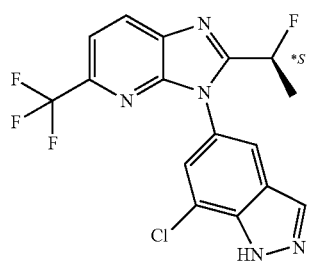 [SMILES: C[C@H](F)c1nc2ccc(C(F)(F)F)nc2n1-c1cc(Cl)c2[nH]ncc2c1]

The title compound was prepared in a manner analogous to Example 117 with a chiral separation. MS (ESI): mass calcd. for $C_{16}H_{10}ClF_4N_5$, 383.1; m/z found, 384.1 [M+H]$^+$. $^1$H NMR (400 MHz, CDCl$_3$) δ 11.45 (s, 1H), 8.30 (d, J=8.3 Hz, 1H), 8.00 (s, 1H), 7.73 (d, J=8.3 Hz, 1H), 7.65 (d, J=1.6 Hz, 1H), 7.32 (d, J=1.5 Hz, 1H), 5.72-5.51 (m, 1H), 1.87-1.73 (m, 3H).

Example 410: 3-(7-Chloro-1H-indazol-5-yl)-2-(1,1-difluoroethyl)-5-methyl-3H-imidazo[4,5-b]pyridine

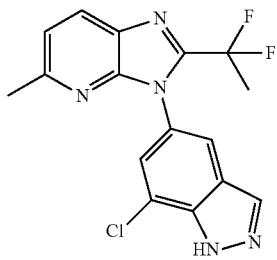

The title compound was prepared in a manner analogous to Example 134, Method B. MS (ESI): mass calcd. for $C_{16}H_{12}ClF_2N_5$, 347.1; m/z found, 348.1 [M+H]$^+$. $^1$H NMR (500 MHz, CDCl$_3$) δ 8.15 (d, J=8.3 Hz, 1H), 7.93 (s, 1H), 7.60 (d, J=1.6 Hz, 1H), 7.33 (d, J=1.4 Hz, 1H), 7.30 (d, J=8.3 Hz, 1H), 2.77 (s, 3H), 2.24-2.12 (m, 3H).

Example 411: 3-(7-Chloro-1H-indazol-5-yl)-2-(cyclopropylmethyl)-5-(trifluoromethyl)-3H-imidazo[4,5-b]pyridine

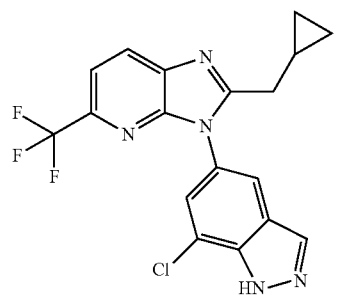 [SMILES: FC(F)(F)c1ccc2nc(CC3CC3)n(-c3cc(Cl)c4[nH]ncc4c3)c2n1]

The title compound was prepared in a manner analogous to Example 117. MS (ESI): mass calcd. for $C_{18}H_{13}ClF_3N_5$, 391.1; m/z found, 392.1 [M+H]$^+$. $^1$H NMR (400 MHz, CDCl$_3$) δ 11.64 (s, 1H), 8.26 (d, J=8.2 Hz, 1H), 8.04 (s, 1H), 7.74 (d, J=8.3 Hz, 1H), 7.61 (d, J=1.7 Hz, 1H), 7.28 (d, J=1.6 Hz, 1H), 2.72 (d, J=6.9 Hz, 2H), 1.16-1.05 (m, 1H), 0.60-0.52 (m, 2H), 0.18-0.11 (m, 2H).

Example 412: 3-(7-Chloro-1H-indazol-5-yl)-2-propyl-5-(trifluoromethyl)-3H-imidazo[4,5-b]pyridine

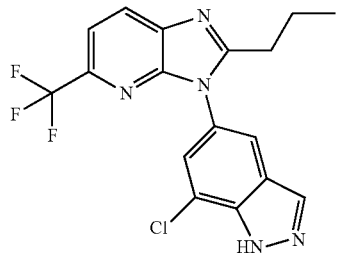 [SMILES: CCCc1nc2ccc(C(F)(F)F)nc2n1-c1cc(Cl)c2[nH]ncc2c1]

The title compound was prepared in a manner analogous to Example 117. MS (ESI): mass calcd. for $C_{17}H_{13}ClF_3N_5$, 379.1; m/z found, 380.1 [M+H]+. 1H NMR (400 MHz, MeOD) δ 8.32 (s, 1H), 8.24 (d, J=8.2 Hz, 1H), 7.96 (d, J=1.7 Hz, 1H), 7.78 (d, J=8.3 Hz, 1H), 7.61 (d, J=1.8 Hz, 1H), 2.94-2.85 (m, 2H), 1.90-1.77 (m, 2H), 1.01-0.93 (m, 3H).

Example 413: 3-(7-Chloro-1H-indazol-5-yl)-2-(methoxymethyl)-5-(trifluoromethyl)-3H-imidazo[4,5-b]pyridine

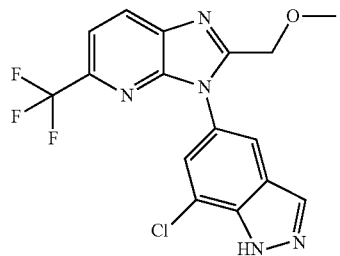 [SMILES: COCc1nc2ccc(C(F)(F)F)nc2n1-c1cc(Cl)c2[nH]ncc2c1]

The title compound was prepared in a manner analogous to Example 117. MS (ESI): mass calcd. for $C_{16}H_{11}ClF_3N_5O$, 381.1; m/z found, 382.1 [M+H]+. 1H NMR (400 MHz, MeOD) δ 8.35 (d, J=8.2 Hz, 1H), 8.32 (s, 1H), 8.01 (d, J=1.7 Hz, 1H), 7.83 (d, J=8.3 Hz, 1H), 7.67 (d, J=1.7 Hz, 1H), 4.68 (s, 2H), 3.38 (s, 3H).

Example 414: 3-(7-Chloro-1H-indazol-5-yl)-2-isobutyl-5-(trifluoromethyl)-3H-imidazo[4,5-b]pyridine

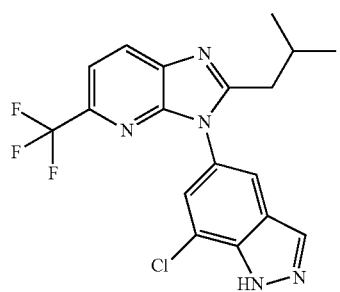 [SMILES: CC(C)Cc1nc2ccc(C(F)(F)F)nc2n1-c1cc(Cl)c2[nH]ncc2c1]

The title compound was prepared in a manner analogous to Example 197. MS (ESI): mass calcd. for $C_{18}H_{15}ClF_3N_5$, 393.1; m/z found, 394.1 [M+H]+. 1H NMR (500 MHz, CDCl3) δ 11.68 (s, 1H), 8.26 (d, J=8.3 Hz, 1H), 8.06 (s, 1H), 7.77 (d, J=8.4 Hz, 1H), 7.59 (d, J=1.7 Hz, 1H), 7.27 (d, J=1.7 Hz, 1H), 2.68 (d, J=7.3 Hz, 2H), 2.33-2.20 (m, 1H), 0.95 (d, J=6.6 Hz, 6H).

Example 415: 3-(7-Chloro-1H-indazol-5-yl)-5-methoxy-2-(trifluoromethyl)-3H-imidazo[4,5-b]pyridine

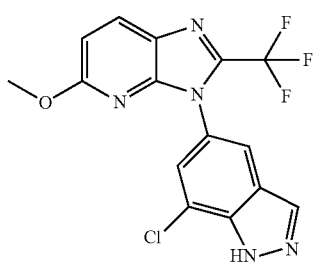 [SMILES: COc1ccc2nc(C(F)(F)F)n(-c3cc(Cl)c4[nH]ncc4c3)c2n1]

The title compound was prepared in a manner analogous to Example 134, Method B. MS (ESI): mass calcd. for $C_{15}H_9ClF_3N_5O$, 367.0; m/z found, 368.1 [M+H]+. 1H NMR (500 MHz, CDCl3) δ 8.27 (d, J=1.3 Hz, 1H), 8.10 (d, J=9.2 Hz, 1H), 7.80 (s, 1H), 7.49 (s, 1H), 6.91-6.84 (m, 1H), 3.82 (s, 3H).

Example 416: 3-(7-Chloro-1H-indazol-5-yl)-2-(2,2,2-trifluoroethyl)-5-(trifluoromethyl)-3H-imidazo[4,5-b]pyridine

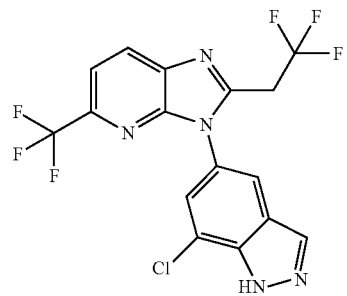 [SMILES: FC(F)(F)Cc1nc2ccc(C(F)(F)F)nc2n1-c1cc(Cl)c2[nH]ncc2c1]

The title compound was prepared in a manner analogous to Example 117. MS (ESI): mass calcd. for $C_{16}H_8ClF_6N_5$, 419.0; m/z found, 420.0 [M+H]+. 1H NMR (400 MHz, CDCl3) δ 11.32 (s, 1H), 8.36 (d, J=8.0 Hz, 1H), 8.12 (s, 1H), 7.81 (d, J=8.3 Hz, 1H), 7.66 (d, J=1.7 Hz, 1H), 7.32 (d, J=1.7 Hz, 1H), 3.77-3.65 (m, 2H).

Example 417: 2-(1,1-Difluoropropyl)-3-(7-methyl-1H-indazol-5-yl)-5-(trifluoromethyl)-3H-imidazo[4,5-b]pyridine

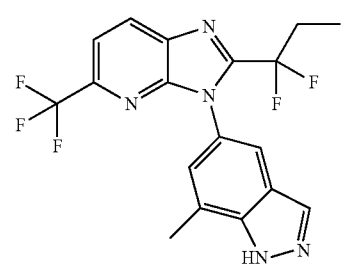 [SMILES: CCC(F)(F)c1nc2ccc(C(F)(F)F)nc2n1-c1cc(C)c2[nH]ncc2c1]

The title compound was prepared in a manner analogous to Example 134, Method B. MS (ESI): mass calcd. for $C_{18}H_{14}F_5N_5$, 395.1; m/z found, 396.1 [M+H]+. 1H NMR (400 MHz, CDCl3) δ 8.38 (d, J=8.4 Hz, 1H), 7.98 (s, 1H), 7.80 (d, J=8.4 Hz, 1H), 7.61 (d, J=1.7 Hz, 1H), 7.09-7.05 (m, 1H), 2.55-2.37 (m, 5H), 1.15-1.06 (m, 3H).

Example 418: 3-(7-Methyl-1H-indazol-5-yl)-5-(trifluoromethyl)-2-(3,3,3-trifluoropropyl)-3H-imidazo[4,5-b]pyridine

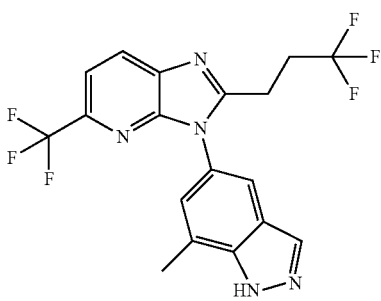 [SMILES: Cc1cc(-n2c(CCC(F)(F)F)nc3ccc(C(F)(F)F)nc32)cc2cn[nH]c12]

The title compound was prepared in a manner analogous to Example 117, from N²-(7-methyl-1H-indazol-5-yl)-6-(trifluoromethyl)pyridine-2,3-diamine (Intermediate 56). MS (ESI): mass calcd. for $C_{18}H_{13}F_6N_5$, 413.1; m/z found, 414.1 [M+H]⁺. ¹H NMR (400 MHz, MeOD) δ 8.24 (d, J=8.3 Hz, 1H), 8.21 (s, 1H), 7.79 (d, J=1.8 Hz, 1H), 7.75 (d, J=8.3 Hz, 1H), 7.26-7.23 (m, 1H), 3.17-3.09 (m, 2H), 2.87-2.73 (m, 2H), 2.68 (s, 3H).

Example 419: 3-(7-Chloro-1H-indazol-5-yl)-2,6-bis(trifluoromethyl)-3H-imidazo[4,5-b]pyridine

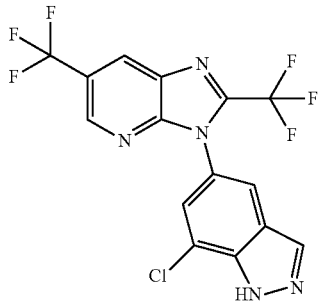 [SMILES: FC(F)(F)c1cnc2c(c1)nc(C(F)(F)F)n2-c1cc(Cl)c2[nH]ncc2c1]

The title compound was prepared in a manner analogous to Example 134, Method B. MS (ESI): mass calcd. for $C_{15}H_6ClF_6N_5$, 405.0; m/z found, 406.0 [M+H]⁺. ¹H NMR (400 MHz, MeOD) δ 8.82 (d, J=1.9 Hz, 1H), 8.69 (d, J=1.9 Hz, 1H), 8.31 (s, 1H), 8.02 (d, J=1.6 Hz, 1H), 7.66 (d, J=1.6 Hz, 1H).

Example 420: 5-(5-Fluoro-2-isopropyl-1H-pyrrolo[2,3-b]pyridin-1-yl)-7-methylindolin-2-one

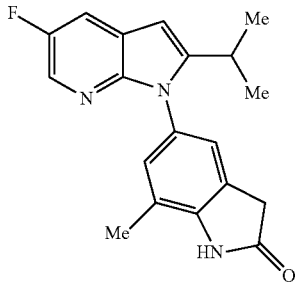 [SMILES: Cc1cc(-n2c(C(C)C)cc3cc(F)cnc32)cc2c1NC(=O)C2]

The title compound was prepared in a manner analogous to Example 334, using 2-chloro-5-fluoro-3-(3-methylbut-1-yn-1-yl)pyridine (Intermediate 66) and 5-amino-7-methylindolin-2-one (Intermediate 10). MS (ESI): mass calcd. for $C_{19}H_{18}FN_3O$, 323.1; m/z found, 324.1 [M+H]⁺. ¹H NMR (400 MHz, MeOD) δ 7.93-7.90 (dd, J=2.8, 1.9 Hz, 1H), 7.72-7.67 (dd, J=9.0, 2.7 Hz, 1H), 7.07 (s, 1H), 7.03 (s, 1H), 6.43 (d, J=0.8 Hz, 1H), 3.63 (s, 2H), 3.03-2.94 (m, 1H), 2.33 (s, 3H), 1.22 (d, J=6.9 Hz, 6H). ¹⁹F NMR (376 MHz, MeOD) δ -141.40 (d, J=8.9 Hz).

Example 421: 5-(6-(difluoromethyl)-2-methyl-1H-pyrrolo[2,3-b]pyridin-1-yl)-7-methylindolin-2-one

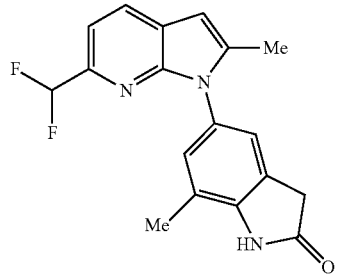 [SMILES: Cc1cc(-n2c(C)cc3ccc(C(F)F)nc32)cc2c1NC(=O)C2]

The title compound was prepared in a manner analogous to Example 334, using 2-chloro-6-(difluoromethyl)-3-(prop-1-yn-1-yl)pyridine (Intermediate 66) and 5-amino-7-methylindolin-2-one (Intermediate 10). MS (ESI): mass calcd. for $C_{18}H_{15}F_2N_3O$, 327.1; m/z found, 328.0 [M+H]⁺. ¹H NMR (400 MHz, MeOD) δ 8.00 (d, J=8.0 Hz, 1H), 7.39 (d, J=8.0 Hz, 1H), 7.09 (s, 1H), 7.05 (s, 1H), 6.59 (t, J=55.6 Hz, 1H), 6.45 (d, J=1.0 Hz, 1H), 3.63-3.59 (m, 2H), 2.32 (s, 3H), 2.34 (s, 3H). ¹⁹F NMR (376 MHz, MeOD) δ -112.93 (d, J=55.3 Hz).

Example 422: 1-(7-Methyl-2-oxoindolin-5-yl)-6-(trifluoromethyl)-1H-pyrrolo[2,3-b]pyridine-2-carbaldehyde

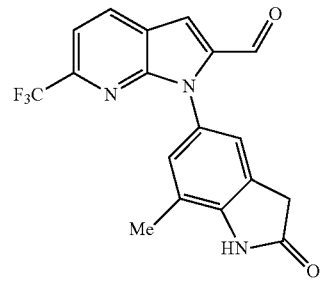 [SMILES: Cc1cc(-n2c(C=O)cc3ccc(C(F)(F)F)nc32)cc2c1NC(=O)C2]

The title compound is the product from Example 336, Step A. ¹H NMR (400 MHz, DMSO-d₆) δ 10.67 (s, 1H), 9.90 (s, 1H), 8.60 (d, J=8.3 Hz, 1H), 7.75 (d, J=8.2 Hz, 1H), 7.69 (s, 1H), 7.18 (s, 1H), 7.14 (s, 1H), 3.59 (s, 2H), 2.26 (s, 3H). ¹⁹F NMR (376 MHz, DMSO-d₆) δ -64.88 (s).

Example 423-Example 441 are prophetic examples.

Example 423: 3-(7-Ethyl-1H-indazol-5-yl)-2,5-bis(rifluoromethyl)-3H-imidazo[4,5-b]pyridine

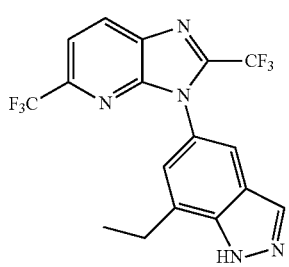 [SMILES: CCc1cc(-n2c(C(F)(F)F)nc3ccc(C(F)(F)F)nc32)cc2cn[nH]c12]

MS (ESI): mass calcd. for $C_{17}H_{11}F_6N_5$; 399.3.

Example 424: 3-(7-Isopropyl-1H-indazol-5-yl)-2,5-bis(trifluoromethyl)-3H-imidazo[4,5-b]pyridine

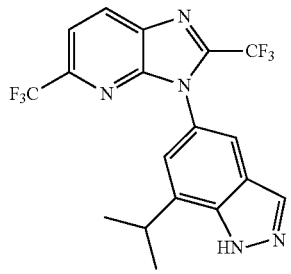 [SMILES: CC(C)c1cc(-n2c(C(F)(F)F)nc3ccc(C(F)(F)F)nc32)cc2cn[nH]c12]

MS (ESI): mass calcd. for $C_{18}H_{13}F_6N_5$; 413.3.

Example 425: 5-(2,5-Bis(trifluoromethyl)-3H-imidazo[4,5-b]pyridin-3-yl)-1H-indazole-7-carbonitrile

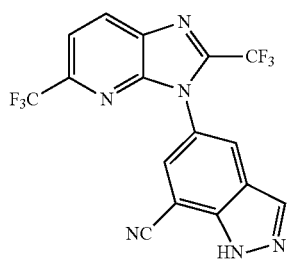 [SMILES: N#Cc1cc(-n2c(C(F)(F)F)nc3ccc(C(F)(F)F)nc32)cc2cn[nH]c12]

MS (ESI): mass calcd. for $C_{16}H_6F_6N_6$; 396.3.

Example 426: 3-(7-Chloro-1H-indazol-5-yl)-2-isopropyl-6-(trifluoromethyl)-3H-imidazo[4,5-b]pyridine

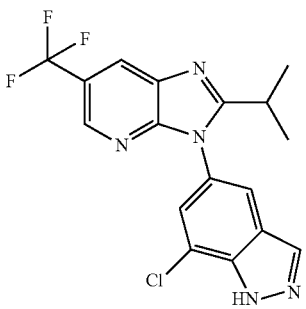 [SMILES: CC(C)c1nc2cc(C(F)(F)F)cnc2n1-c1cc(Cl)c2[nH]ncc2c1]

The title compound may be made analogously to Example 109, Method B. MS (ESI): mass calcd. for $C_{17}H_{13}ClF_3N_5$, 379.1.

Example 427: 3-(7-Chloro-1H-indazol-5-yl)-6-methyl-2-(trifluoromethyl)-3H-imidazo[4,5-b]pyridine

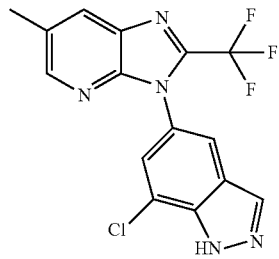 [SMILES: Cc1cnc2c(c1)nc(C(F)(F)F)n2-c1cc(Cl)c2[nH]ncc2c1]

The title compound may be made analogously to Example 134, Method B. MS (ESI): mass calcd. for $C_{15}H_9ClF_3N_5$, 351.1.

Example 428: 3-(7-Chloro-1H-indazol-5-yl)-7-methyl-2,5-bis(trifluoromethyl)-3H-imidazo[4,5-b]pyridine

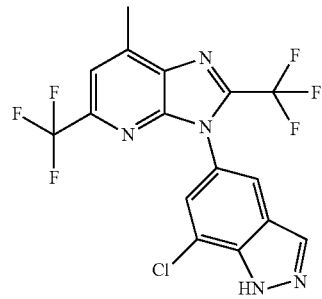 [SMILES: Cc1cc(C(F)(F)F)nc2c1nc(C(F)(F)F)n2-c1cc(Cl)c2[nH]ncc2c1]

The title compound may be made analogously to Example 134, Method B. MS (ESI): mass calcd. for $C_{16}H_5ClF_6N_5$, 419.0.

Example 429: 7-Methyl-3-(7-methyl-1H-indazol-5-yl)-2,5-bis(trifluoromethyl)-3H-imidazo[4,5-b]pyridine

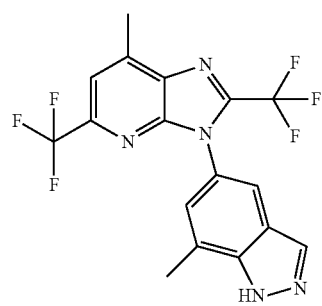 [SMILES: Cc1cc(C(F)(F)F)nc2c1nc(C(F)(F)F)n2-c1cc(C)c2[nH]ncc2c1]

The title compound may be made analogously to Example 134, Method B. MS (ESI): mass calcd. for $C_{17}H_{11}F_6N_5$, 399.1.

Example 430: 3-(7-Chloro-1H-indazol-5-yl)-2-isopropyl-7-methyl-5-(trifluoromethyl)-3H-imidazo[4,5-b]pyridine

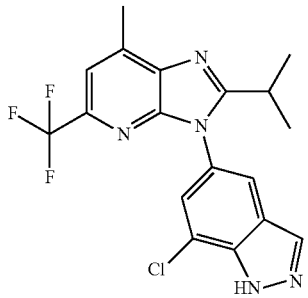 [SMILES: Cc1cc(C(F)(F)F)nc2c1nc(C(C)C)n2-c1cc(Cl)c2[nH]ncc2c1]

The title compound may be made analogously to Example 109, Method B. MS (ESI): mass calcd. for $C_{18}H_{15}ClF_3N_5$, 393.1.

Example 431: 3-(7-Chloro-1H-indazol-5-yl)-7-methoxy-2,5-bis(trifluoromethyl)-3H-imidazo[4,5-b]pyridine

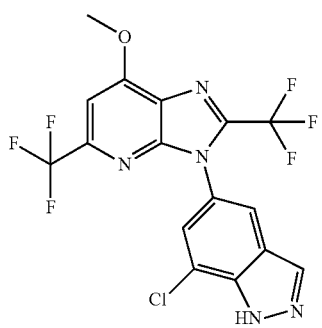 [SMILES: COc1cc(C(F)(F)F)nc2c1nc(C(F)(F)F)n2-c1cc(Cl)c2[nH]ncc2c1]

The title compound may be made analogously to Example 134, Method B. MS (ESI): mass calcd. for $C_{16}H_5ClF_6N_5O$, 435.0.

Example 432: 3-(7-Chloro-1H-indazol-5-yl)-2-(1-cyclopropylethyl)-5-(trifluoromethyl)-3H-imidazo[4,5-b]pyridine

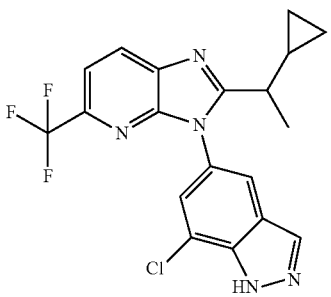 [SMILES: CC(c1nc2ccc(C(F)(F)F)nc2n1-c1cc(Cl)c2[nH]ncc2c1)C1CC1]

The title compound may be made analogously to Example 117. MS (ESI): mass calcd. for $C_{19}H_{15}ClF_3N_5$, 405.1.

Example 433: 3-(7-Chloro-1H-indazol-5-yl)-2-(1-methylcyclopropyl)-5-(trifluoromethyl)-3H-imidazo[4,5-b]pyridine

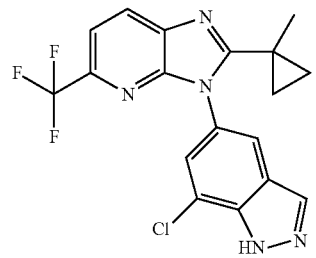

The title compound may be made analogously to Example 117. MS (ESI): mass calcd. for $C_{18}H_{13}ClF_3N_5$, 391.1.

Example 434: 3-(7-Methyl-1H-indazol-5-yl)-2-(1-methylcyclopropyl)-5-(trifluoromethyl)-3H-imidazo[4,5-b]pyridine

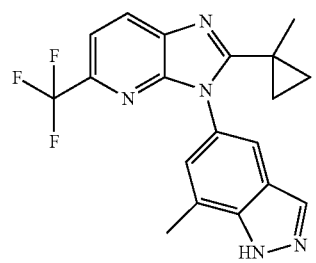 [SMILES: Cc1cc(-n2c(C3(C)CC3)nc3ccc(C(F)(F)F)nc32)cc2cn[nH]c12]

The title compound may be made analogously to Example 117 from $N^2$-(7-methyl-1H-indazol-5-yl)-6-(trifluoromethyl)pyridine-2,3-diamine (Intermediate 56). MS (ESI): mass calcd. for $C_{19}H_{16}F_3N_5$, 371.1.

Example 435: 3-(7-Chloro-1H-indazol-5-yl)-2-(1-methoxyethyl)-5-(trifluoromethyl)-3H-imidazo[4,5-b]pyridine

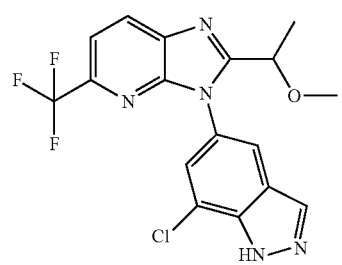 [SMILES: COC(C)c1nc2ccc(C(F)(F)F)nc2n1-c1cc(Cl)c2[nH]ncc2c1]

The title compound may be made analogously to Example 117. MS (ESI): mass calcd. for $C_{17}H_{13}ClF_3N_5O$, 395.1.

Example 436: 6-Chloro-3-(7-chloro-1H-indazol-5-yl)-2-(trifluoromethyl)-3H-imidazo[4,5-b]pyridine

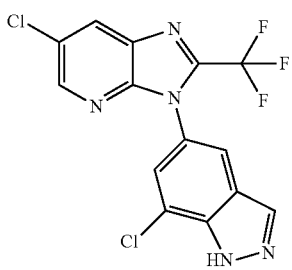 [SMILES: FC(F)(F)c1nc2cc(Cl)cnc2n1-c1cc(Cl)c2[nH]ncc2c1]

The title compound may be made analogously to Example 134, Method B. MS (ESI): mass calcd. for $C_{14}H_6Cl_2F_3N_5$, 371.0.

Example 437: 3-(7-Chloro-1H-indazol-5-yl)-5-(triflouromethyl)-2-(1,1,1-trifluoropropan-2-yl)-3H-imidazo[4,5-b]pyridine

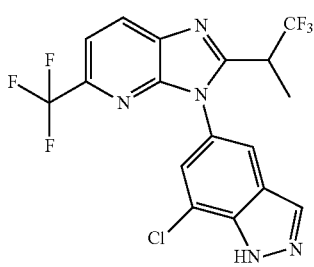 [SMILES: CC(c1nc2ccc(C(F)(F)F)nc2n1-c1cc(Cl)c2[nH]ncc2c1)C(F)(F)F]

The title compound may be made analogously to Example 109, Method B. MS (ESI): mass calcd. for $C_{17}H_{10}ClF_6N_5$, 433.0.

Example 438: 5-(4-(Dimethylamino)-2-methyl-1H-pyrrolo[2,3-b]pyridin-1-yl)-7-methylindolin-2-one

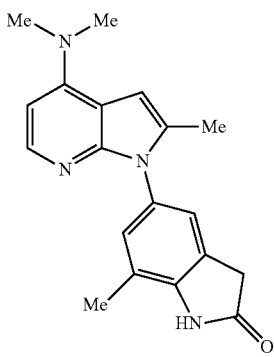 [SMILES: Cc1cc(-n2c(C)cc3c(N(C)C)ccnc32)cc2c1NC(=O)C2]

The title compound may be prepared in a manner analogous to Example 333. MS (ESI): mass calcd. for $C_{19}H_{20}N_4O$; 320.2.

Example 439: 5-(4-(Azetidin-1-yl)-2-methyl-1H-pyrrolo[2,3-b]pyridin-1-yl)-7-methylindolin-2-one

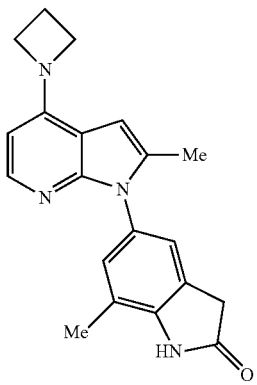 [SMILES: Cc1cc(-n2c(C)cc3c(N4CCC4)ccnc32)cc2c1NC(=O)C2]

The title compound may be prepared in a manner analogous to Example 333. MS (ESI): mass calcd. for $C_{20}H_{20}N_4O$; 332.2.

Example 440: 5-(4-Methoxy-2-methyl-1H-pyrrolo[2,3-b]pyridin-1-yl)-7-methylindolin-2-one

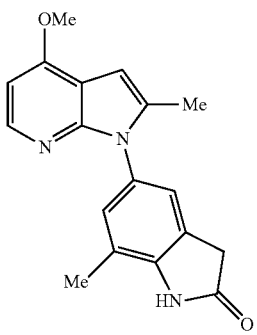 [SMILES: COc1ccnc2c1cc(C)n2-c1cc(C)c2c(c1)CC(=O)N2]

The title compound may be prepared in a manner analogous to Example 333. MS (ESI): mass calcd. for $C_{18}H_{17}N_3O_2$; 307.1.

Example 441: 5-(2,4-Dimethyl-1H-pyrrolo[2,3-b]pyridin-1-yl)-7-methylindolin-2-one

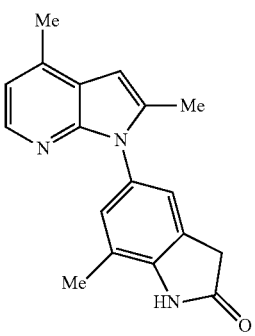 [SMILES: Cc1cc(-n2c(C)cc3c(C)ccnc32)cc2c1NC(=O)C2]

The title compound may be prepared in a manner analogous to Example 333. MS (ESI): mass calcd. for $C_{18}H_{17}N_3O$; 291.1.

Example 442: 2-(2-Chloro-4-pyridyl)-3-(7-methyl-1H-indazol-5-yl)-5-(trifluoromethyl)imidazo[4,5-b]pyridine

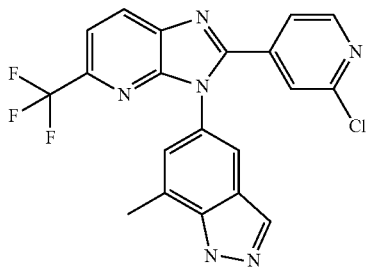 [SMILES: Cc1cc(-n2c(-c3ccnc(Cl)c3)nc3ccc(C(F)(F)F)nc32)cc2cn[nH]c12]

The title compound was prepared in a manner analogous to Example 217. MS-ESI: mass calcd. for $C_{20}H_{12}ClF_3N_6$, 428.1; m/z found, [M+H]+ 429.1. $^1$H NMR (500 MHz, Acetonitrile-$d_3$) δ 8.42 (dd, J=8.3, 0.8 Hz, 1H), 8.33 (dd, J=5.2, 0.7 Hz, 1H), 8.15 (s, 1H), 7.86 (d, J=8.3 Hz, 1H), 7.73 (dd, J=1.7, 0.8 Hz, 1H), 7.64 (dd, J=1.5, 0.7 Hz, 1H), 7.43 (dd, J=5.2, 1.5 Hz, 1H), 7.22 (dd, J=1.9, 1.0 Hz, 1H), 2.62 (s, 3H).

Example 443: 2-(2-Bromo-4-pyridyl)-3-(7-methyl-1H-indazol-5-yl)-5-(trifluoromethyl)imidazo[4,5-b]pyridine

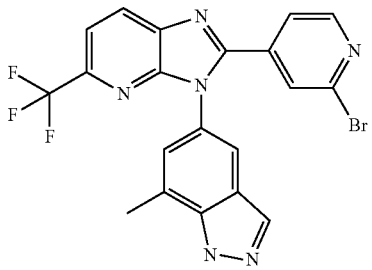 [SMILES: Cc1cc(-n2c(-c3ccnc(Br)c3)nc3ccc(C(F)(F)F)nc32)cc2cn[nH]c12]

The title compound was prepared in a manner analogous to Example 217. MS-ESI: mass calcd. for $C_{20}H_{12}BrF_3N_6$, 472.0; m/z found, [M+H]+ 473.1. $^1$H NMR (500 MHz, Acetonitrile-$d_3$) δ 8.42 (dd, J=8.4, 0.8 Hz, 1H), 8.31 (dd, J=5.2, 0.8 Hz, 1H), 8.15 (s, 1H), 7.86 (d, J=8.3 Hz, 1H), 7.79 (dd, J 5=1.5, 0.7 Hz, 1H), 7.73 (dd, J=1.7, 0.8 Hz, 1H), 7.46 (dd, J=5.2, 1.5 Hz, 1H), 7.22 (dt, J=2.0, 1.0 Hz, 1H), 2.63 (s, 3H).

Example 444: 2-(2-[$^{19}$F]fluoro-4-pyridyl)-3-(7-methyl-1H-indazol-5-yl)-5-(trifluoromethyl)imidazo[4,5-b]pyridine

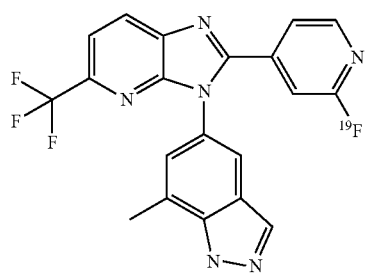 [SMILES: Cc1cc(-n2c(-c3ccnc([19F])c3)nc3ccc(C(F)(F)F)nc32)cc2cn[nH]c12]

To an oven-dried 4-mL vial charged with a mini stir bar, was added potassium fluoride (2 μL, 0.1M aq, 5 mol %) solution. Acetonitrile (1 mL×3) was added and co-evaporated to remove water under heating and vacuum. 2-(2-Bromo-4-pyridyl)-3-(7-methyl-1H-indazol-5-yl)-5-(trifluoromethyl)imidazo[4,5-b]pyridine (Example 443, 2 mg, 0.004 mmol), 4,7,13,16,21,24-hexaoxa-1,10-diazabicyclo[8.8.8]-hexacosane (Kryptofix-222) (5 mg, 0.013 mmol), $K_2CO_3$ (1.7 mg, 0.012 mmol) and dimethyl sulfone (0.2 mL, anhydrous, ample-packed) were added. The vial was sealed, and the mixture was placed in a pre-heated oil bath (160° C.) with vigorous stirring for 15 min. The mixture was analyzed on HPLC-MS right after removal from the oil bath. Based on ESI-MS analysis and UV absorption at 254 nm, the labeling reaction afforded 28% conversion to the analogous [F-19] compound of PET tracer. Analytical HPLC method: Phenomenex Kinetex-$^{18}$C 150×4.6 mm 5 um; mobile phase: MeCN/Water (0.05% TFA addition); 0.75 mL/min; gradient method 0-1 min 5% MeCN, 1-15 min 5-95% MeCN, 15-17 min 95% MeCN, 17-18 min 95-5% MeCN, 18-20 min 5% MeCN. Product identities were confirmed with attached MSD detector. Reference standard fluoride retention time is 11.695 min; the labeling precursor retention time is 12.231 min. Preparative HPLC method for immediate purification of PET tracer: Phenomenex Gemini-$^{18}$C 150×4.6 mm 5 um; mobile phase: MeCN/Water (45:55, 0.08% HCl in water); 1 mL/min; reference fluoride retention time was eluted at 9.27 min, and labeling precursor was eluted at 11.72 min.

Example 445: 2-(2-[$^{18}$F]fluoro-4-pyridyl)-3-(7-methyl-1H-indazol-5-yl)-5-(trifluoromethyl)imidazo[4,5-b]pyridine

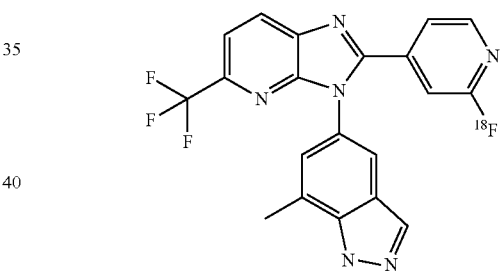

[$^{18}$F]fluoride in a shipping vial (obtained from the cyclotron facility) is transferred onto and trapped on an ion exchange cartridge then eluted into the reaction vessel (RV1) of the TRACERlab® module (platform for [$^{18}$F] tracer production) with a solution of $K_2CO_3$ (1.24 mg) and Kryptofix 222 (10 mg) in acetonitrile/water (1 mL, 8/2, v/v). The solution is first evaporated by heating at 95° C. for 4 min under vacuum and helium flow. Acetonitrile (1 mL) is added to RV1 and the evaporation is continued under the same conditions for 2 min. After a second addition of acetonitrile (1 mL), final evaporation is carried out at 95° C. for 2 min under vacuum and helium flow. The reactor is then cooled to 70° C. A solution of the 2-(2-bromo-4-pyridyl)-3-(7-methyl-1H-indazol-5-yl)-5-(trifluoromethyl)imidazo[4,5-b]pyridine (Example 443, 2 mg, 0.004 mmol) in anhydrous DMSO (0.8 mL) is added to reaction vessel. The reaction mixture is heated at 140° C. for 10 min. The reactor is cooled to 40° C. and diluted with semi-preparative HPLC mobile phase (2 mL) and the contents is transferred into the loop-loading vial reaction vessel 2 (RV2). The reactor is rinsed with 0.1 M hydrochloric acid and the rinse is transferred into RV2. The contents of RV2 are transferred into the HPLC injector loop for purification. Purification (HPLC using a semi-preparative Phenomenex Luna $^{18}$C (2) column (10 μm, 10×250 mm)

column eluted with a mixture of acetonitrile/water/hydrochloric acid (1M), 50/50/0.03, v/v/v, at 4 mL/min) afforded the title compound which is collected in Flask 1, containing 20 mL of diluted ascorbic acid in water for injection (WFI) (10 mg/mL). The diluted radiolabeled product is passed through a tC 18 solid-phase extraction cartridge and the cartridge is rinsed with 10 mL of diluted ascorbic acid in WFI. The radiolabeled product is eluted from the solid phase extraction (SPE) cartridge with 1.0 mL of 200-proof USP grade ethanol into the formulation flask, pre-loaded with 10 mL of formulation base. The cartridge is rinsed with 4 mL of formulation base and the rinse is mixed with the contents of the formulation flask. The resulting solution is passed through a sterilizing 0.2 μm membrane filter into a sterile, filter-vented vial (final product vial, FPV).

Biological Assays

Calcium Flux Assay

This assay was used to test compounds for their ability to inhibit TARP γ8 dependent AMPA receptor activity. The AMPA receptor is a non-selective cation channel activated by glutamate. Ionotropic glutamate receptors normally desensitize too rapidly to allow detectable calcium influx in a FLIPR assay (Strange et al. (2006). "Functional characterisation of homomeric ionotropic glutamate receptors GluR1-GluR6 in a fluorescence-based high throughput screening assay." *Comb Chem High Throughput Screen* 9(2): 147-158). But, this desensitization is incomplete, and a substantial steady-state current remains in the sustained presence of glutamate (Cho et al. (2007). "Two families of TARP isoforms that have distinct effects on the kinetic properties of AMPA receptors and synaptic currents." *Neuron* 55(6): 890-904).

An in vitro assay was used to determine the potency of test compounds as inhibitors of the glutamate response of the channel formed by GluA1o-γ8. To ensure a 1:1 stoichiometry of GluA1o and γ8 subunits in the expressed channel, a fusion of the cDNAs for GRIA1o and CACNG8 was used. Following Shi et al (2009) "The stoichiometry of AMPA receptors and TARPs varies by neuronal cell type." *Neuron* 62(5): 633-640), the C-terminus of the cDNA for GRIA1o was fused to the N-terminus of the cDNA for γ8. The linker sequence was QQQQQQQQQQEFAT. Channels expressed with this construct appear to have similar properties to channels formed by co-expression of GRIA1o with an excess of CACNG8 (Shi et al. 2009). A clonal cell line in HEK293 cells stably expressing this construct, with a geneticin selection marker, was generated for use in this assay.

Cell expressing the GRIA1o-CACNG8 fusion construct were grown in a monolayer in 96- or 384-well microtiter plates. They were washed with assay buffer (135 mM NaCl, 4 mM KCl, 3 mM $CaCl_2$, 1 mM $MgCl_2$, 5 mM glucose, 10 mM HEPES, pH 7.4, 300 mOs) using a Biotek EL405 plate washer. The cells were then loaded with a calcium-sensitive dye (Calcium-5 or Calcium-6, Molecular Devices) and the test compounds at a range of concentrations. Calcium flux following the addition of 15 μM glutamate was monitored using a Molecular Devices FLIPR Tetra. The fluorescence in each well was normalized to the fluorescence of negative and positive control wells. The negative control wells had no added compounds, and the positive control wells had been incubated with 10 μM CP465022 (a non-subtype-selective AMPA receptor antagonist) (Lazzaro et al. (2002). "Functional characterization of CP-465,022, a selective, noncompetitive AMPA receptor antagonist." *Neuropharmacology* 42(2): 143-153). The responses to glutamate as functions of the test compound concentrations were fitted to a four-parameter logistic function. The fitted parameter corresponding to the midpoint was taken to be the potency of inhibition of the compound. The data in Table 4 below illustrates the observed potentcy for the compounds described herein. $pIC_{50}$ refers to the negative log of the $IC_{50}$ in molar.

Using a similar protocol, compounds were also tested for their ability to inhibit TARP γ2 dependent AMPA receptor activity. The compounds that were tested for TARP γ2 AMPA receptor activity had $pIC_{50}$ values less than 6.

TABLE 4

| Ex. # | Compound Name | $pIC_{50}$ |
|---|---|---|
| 1 | 3-(1H-Indazol-5-yl)-2-phenyl-5-(trifluoromethyl)-3H-imidazo[4,5-b]pyridine; | 9.4 |
| 2 | 3-(1H-Indazol-5-yl)-2-phenyl-imidazo[4,5-b]pyridine; | 7.3 |
| 3 | 3-(1H-Indazol-5-yl)-5-methyl-2-phenyl-imidazo[4,5-b]pyridine; | 9.1 |
| 4 | 2-(4-Fluorophenyl)-3-(1H-indazol-5-yl)-5-methyl-imidazo[4,5-b]pyridine; | 9.0 |
| 5 | 2-(4-Fluorophenyl)-3-(1H-indol-5-yl)-5-methoxy-imidazo[4,5-b]pyridine; | 7.4 |
| 6 | 5-[2-(4-Fluorophenyl)-5-methoxy-imidazo[4,5-b]pyridin-3-yl]indolin-2-one; | 7.4 |
| 7 | 5-Chloro-2-(4-fluorophenyl)-3-(1H-indazol-5-yl)imidazo[4,5-b]pyridine; | 8.7 |
| 8 | 2-(2-Chlorophenyl)-3-(1H-indazol-5-yl)-5-methyl-imidazo[4,5-b]pyridine; | 7.2 |
| 9 | 3-(1H-Indazol-5-yl)-6-methyl-2-phenyl-imidazo[4,5-b]pyridine; | 7.6 |
| 10 | 5-Chloro-3-(1H-indazol-5-yl)-2-phenyl-imidazo[4,5-b]pyridine; | 9.0 |
| 11 | 5-Chloro-2-cyclopentyl-3-(1H-indazol-5-yl)imidazo[4,5-b]pyridine; | 8.0 |
| 12 | tert-Butyl 5-(5-methyl-2-phenyl-imidazo[4,5-b]pyridin-3-yl)indazole-1-carboxylate; | 7.7 |
| 13 | 3-(1H-Indol-5-yl)-2-phenyl-5-(trifluoromethyl)imidazo[4,5-b]pyridine; | 8.7 |
| 14 | 6-[2-Phenyl-5-(trifluoromethyl)imidazo[4,5-b]pyridin-3-yl]-3H-1,3-benzothiazol-2-one; | 9.8 |
| 15 | 6-(5-Fluoro-2-phenyl-imidazo[4,5-b]pyridin-3-yl)-3H-1,3-benzothiazol-2-one; | 8.5 |
| 16 | 6-[2-(4-Fluorophenyl)-5-(trifluoromethyl)imidazo[4,5-b]pyridin-3-yl]-3H-1,3-benzothiazol-2-one; | 9.2 |
| 17 | 6-(5-Methyl-2-phenyl-imidazo[4,5-b]pyridin-3-yl)-3H-1,3-benzothiazol-2-one; | 9.3 |
| 18 | 6-(5-Methoxy-2-phenyl-imidazo[4,5-b]pyridin-3-yl)-3H-1,3-benzothiazol-2-one; | 8.4 |
| 19 | 6-[2-tert-Butyl-5-(trifluoromethyl)imidazo[4,5-b]pyridin-3-yl]-3H-1,3-benzothiazol-2-one; | 8.9 |
| 20 | 6-[2-(4-Fluorophenyl)imidazo[4,5-b]pyridin-3-yl]-3H-1,3-benzothiazol-2-one; | 8.3 |
| 21 | 5-[2-(4-Fluorophenyl)imidazo[4,5-b]pyridin-3-yl]-1,3-dihydrobenzimidazol-2-one; | 8.0 |

TABLE 4-continued

| Ex. # | Compound Name | pIC$_{50}$ |
|---|---|---|
| 22 | 2-(4-Fluorophenyl)-3-(1H-indazol-5-yl)imidazo[4,5-b]pyridine; | 7.5 |
| 23 | 5-[2-(4-Fluorophenyl)imidazo[4,5-b]pyridin-3-yl]indolin-2-one; | 7.6 |
| 24 | 6-[2-(4-Fluorophenyl)imidazo[4,5-b]pyridin-3-yl]-3H-1,3-benzoxazol-2-one; | 6.5 |
| 25 | 6-(2-Phenylimidazo[4,5-b]pyridin-3-yl)-3H-1,3-benzothiazol-2-one; | 8.0 |
| 26 | 3-(1H-Indol-5-yl)-2-phenyl-imidazo[4,5-b]pyridine; | 6.3 |
| 27 | 6-[2-(4-Fluorophenyl)-5-methyl-imidazo[4,5-b]pyridin-3-yl]-3H-1,3-benzothiazol-2-one; | 9.1 |
| 28 | 6-[2-(6-Fluoro-3-pyridyl)imidazo[4,5-b]pyridin-3-yl]-3H-1,3-benzothiazol-2-one; | 6.6 |
| 29 | 6-[2-(2-Fluoro-4-pyridyl)-5-methyl-imidazo[4,5-b]pyridin-3-yl]-3H-1,3-benzothiazol-2-one; | 8.6 |
| 30 | 6-[5-Chloro-2-(4-fluorophenyl)imidazo[4,5-b]pyridin-3-yl]-3H-1,3-benzothiazol-2-one; | 9.7 |
| 31 | 6-[2-(2-Fluoro-4-pyridyl)-5-(trifluoromethyl)imidazo[4,5-b]pyridin-3-yl]-3H-1,3-benzothiazol-2-one; | 9.6 |
| 32 | 6-(5-Bromo-2-phenyl-imidazo[4,5-b]pyridin-3-yl)-3H-1,3-benzothiazol-2-one; | 9.3 |
| 33 | 5-[2-(4-Fluorophenyl)-5-(trifluoromethyl)imidazo[4,5-b]pyridin-3-yl]indolin-2-one; | 9.2 |
| 34 | 5-(2-Phenylimidazo[4,5-b]pyridin-3-yl)indolin-2-one; | 7.9 |
| 35 | 5-[2-(4-Fluorophenyl)-5-methyl-imidazo[4,5-b]pyridin-3-yl]indolin-2-one; | 8.5 |
| 36 | 5-[2-Phenyl-5-(trifluoromethyl)imidazo[4,5-b]pyridin-3-yl]indolin-2-one; | 9.4 |
| 37 | 5-[5-Fluoro-2-(4-fluorophenyl)imidazo[4,5-b]pyridin-3-yl]indolin-2-one; | 8.2 |
| 38 | 5-[2-Isopropyl-5-(trifluoromethyl)imidazo[4,5-b]pyridin-3-yl]indolin-2-one; | 9.0 |
| 39 | 6-[2-Cyclopentyl-5-(trifluoromethyl)imidazo[4,5-b]pyridin-3-yl]-3H-1,3-benzothiazol-2-one; | 9.7 |
| 40 | 6-[2-Cyclohexyl-5-(trifluoromethyl)imidazo[4,5-b]pyridin-3-yl]-3H-1,3-benzothiazol-2-one; | 9.8 |
| 41 | 6-[2-Cyclopropyl-5-(trifluoromethyl)imidazo[4,5-b]pyridin-3-yl]-3H-1,3-benzothiazol-2-one; | 9.4 |
| 42 | 6-[2-Tetrahydropyran-4-yl-5-(trifluoromethyl)imidazo[4,5-b]pyridin-3-yl]-3H-1,3-benzothiazol-2-one; | 7.4 |
| 43 | 2-Cyclopropyl-3-(1H-indazol-5-yl)-5-(trifluoromethyl)imidazo[4,5-b]pyridine; | 8.7 |
| 44 | 6-[2-Ethyl-5-(trifluoromethyl)imidazo[4,5-b]pyridin-3-yl]-3H-1,3-benzothiazol-2-one; | 9.4 |
| 45 | 6-[2-Isopropyl-5-(trifluoromethyl)imidazo[4,5-b]pyridin-3-yl]-3H-1,3-benzothiazol-2-one; | 9.4 |
| 46 | 6-[2-Methyl-5-(trifluoromethyl)imidazo[4,5-b]pyridin-3-yl]-3H-1,3-benzothiazol-2-one; | 8.2 |
| 47 | 5-[2-Methyl-5-(trifluoromethyl)imidazo[4,5-b]pyridin-3-yl]indolin-2-one; | 7.2 |
| 48 | 5-[2-Cyclohexyl-5-(trifluoromethyl)imidazo[4,5-b]pyridin-3-yl]indolin-2-one; | 9.2 |
| 49 | 5-[2-Cyclobutyl-5-(trifluoromethyl)imidazo[4,5-b]pyridin-3-yl]indolin-2-one; | 9.5 |
| 50 | 5-[2-Tetrahydropyran-4-yl-5-(trifluoromethyl)imidazo[4,5-b]pyridin-3-yl]indolin-2-one; | 7.2 |
| 51 | 5-[2-Isobutyl-5-(trifluoromethyl)imidazo[4,5-b]pyridin-3-yl]indolin-2-one; | 8.0 |
| 52 | (racemic)-5-[2-Tetrahydrofuran-3-yl-5-(trifluoromethyl)imidazo[4,5-b]pyridin-3-yl]indolin-2-one; | 7.7 |
| 53 | 5-[5-(Trifluoromethyl)-2-(3,3,3-trifluoropropyl)imidazo[4,5-b]pyridin-3-yl]indolin-2-one; | 7.1 |
| 54 | 5-[2-(Cyclopentylmethyl)-5-(trifluoromethyl)imidazo[4,5-b]pyridin-3-yl]indolin-2-one; | 8.2 |
| 55 | 5-[2-Cyclopropyl-5-(trifluoromethyl)imidazo[4,5-b]pyridin-3-yl]indolin-2-one; | 8.1 |
| 56 | 5-[2-Benzyl-5-(trifluoromethyl)imidazo[4,5-b]pyridin-3-yl]indolin-2-one; | |
| 57 | 5-[2-(Pyrazin-2-ylmethyl)-5-(trifluoromethyl)imidazo[4,5-b]pyridin-3-yl]indolin-2-one; | 4.8 |
| 58 | 2-Cyclopentyl-3-(1H-Indol-5-yl)-5-(trifluoromethyl)imidazo[4,5-b]pyridine; | 7.9 |
| 59 | 2-tert-Butyl-3-(1H-Indol-5-yl)-5-(trifluoromethyl)imidazo[4,5-b]pyridine; | 6.6 |
| 60 | 5-[2-Cyclopentyl-5-(trifluoromethyl)imidazo[4,5-b]pyridin-3-yl]indolin-2-one; | 8.7 |
| 61 | 5-[2-tert-Butyl-5-(trifluoromethyl)imidazo[4,5-b]pyridin-3-yl]indolin-2-one; | 7.9 |
| 62 | 4-[2-(4-Fluorophenyl)-3-(1H-indazol-5-yl)imidazo[4,5-b]pyridin-7-yl]morpholine; | 8.2 |
| 63 | 5-[2-(4-Fluorophenyl)-7-morpholino-imidazo[4,5-b]pyridin-3-yl]indolin-2-one; | 8.5 |
| 64 | 6-[2-Phenyl-5-(1-piperidyl)imidazo[4,5-b]pyridin-3-yl]-3H-1,3-benzothiazol-2-one; | 8.3 |
| 65 | 6-(5-Morpholino-2-phenyl-imidazo[4,5-b]pyridin-3-yl)-3H-1,3-benzothiazol-2-one; | 6.5 |
| 66 | 6-[5-(Dimethylamino)-2-phenyl-imidazo[4,5-b]pyridin-3-yl]-3H-1,3-benzothiazol-2-one; | 7.9 |

TABLE 4-continued

| Ex. # | Compound Name | pIC$_{50}$ |
|---|---|---|
| 67 | 6-(5-(Difluoromethyl)-2-phenyl-3H-imidazo[4,5-b]pyridin-3-yl)benzo[d]thiazol-2(3H)-one; | 10.0 |
| 68 | 6-[2-[4-(Difluoromethyl)phenyl]imidazo[4,5-b]pyridin-3-yl]-3H-1,3-benzothiazol-2-one; | 7.6 |
| 69 | 6-[7-(Difluoromethyl)-2-phenyl-imidazo[4,5-b]pyridin-3-yl]-3H-1,3-benzothiazol-2-one; | 8.9 |
| 70 | 6-(7-Isopropyl-2-phenyl-imidazo[4,5-b]pyridin-3-yl)-3H-1,3-benzothiazol-2-one; | 9.2 |
| 71 | 6-(2-(4-Fluorophenyl)-5-(hydroxymethyl)-3H-imidazo[4,5-b]pyridin-3-yl)benzo[d]thiazol-2(3H)-one; | 7.4 |
| 72 | 6-(2-(4-Fluorophenyl)-7-hydroxy-5-methyl-3H-imidazo[4,5-b]pyridin-3-yl)benzo[d]thiazol-2(3H)-one; | 7.6 |
| 73 | 5-(2-(3-Hydroxypropyl)-5-(trifluoromethyl)-3H-imidazo[4,5-b]pyridin-3-yl)indolin-2-one; | 5.9 |
| 74 | 5-(2-Cyclobutyl-5-methyl-imidazo[4,5-b]pyridin-3-yl)indolin-2-one; | 7.8 |
| 75 | 5-(2-Ethyl-5-methyl-imidazo[4,5-b]pyridin-3-yl)indolin-2-one; | 6.6 |
| 76 | 5-[2-(3-Methyloxetan-3-yl)-5-(trifluoromethyl)imidazo[4,5-b]pyridin-3-yl]indolin-2-one; | 6.3 |
| 77 | 5-[2-(2-Methoxyethyl)-5-(trifluoromethyl)imidazo[4,5-b]pyridin-3-yl]indolin-2-one; | 6.6 |
| 78 | 2-Cyclobutyl-5-cyclopropyl-3-(1H-indazol-5-yl)imidazo[4,5-b]pyridine; | 9.8 |
| 79 | 5-Cyclopropyl-3-(1H-indazol-5-yl)-2-isopropyl-imidazo[4,5-b]pyridine; | 8.7 |
| 80 | 6-[2-Cyclobutyl-5-(trifluoromethyl)imidazo[4,5-b]pyridin-3-yl]-3H-1,3-benzoxazol-2-one; | 8.7 |
| 81 | Azetidin-1-yl-[3-(1H-indazol-5-yl)-5-(trifluoromethyl)imidazo[4,5-b]pyridin-2-yl]methanone; | 6.3 |
| 82 | 6-[5-Amino-2-(4-fluorophenyl)imidazo[4,5-b]pyridin-3-yl]-3H-1,3-benzothiazol-2-one; | 7.2 |
| 83 | 5-[2-(1-Ethylpropyl)-5-(trifluoromethyl)imidazo[4,5-b]pyridin-3-yl]indolin-2-one; | 7.2 |
| 84 | 5-(2-Isopropyl-5-methyl-imidazo[4,5-b]pyridin-3-yl)indolin-2-one; | 7.2 |
| 85 | 3-(1H-Indazol-5-yl)-N-phenyl-5-(trifluoromethyl)imidazo[4,5-b]pyridine-2-carboxamide; | 7.1 |
| 86 | 5-Cyclopropyl-2-(4-fluorophenyl)-3-(1H-indazol-5-yl)imidazo[4,5-b]pyridine; | 9.1 |
| 87 | 5-(2-Cyclopropyl-5-methyl-imidazo[4,5-b]pyridin-3-yl)indolin-2-one; | 7.1 |
| 88 | 5-[2,5-Bis(trifluoromethyl)imidazo[4,5-b]pyridin-3-yl]indolin-2-one; | 8.8 |
| 89 | 3-(1H-Indazol-5-yl)-2,5-bis(trifluoromethyl)imidazo[4,5-b]pyridine; | 8.9 |
| 90 | 2-(Difluoromethyl)-3-(1H-indazol-5-yl)-5-(trifluoromethyl)imidazo[4,5-b]pyridine; | 8.5 |
| 91 | 3-(1H-Indazol-5-yl)-2-(2-thienyl)-5-(trifluoromethyl)imidazo[4,5-b]pyridine; | 8.4 |
| 92 | 2-(2-Furyl)-3-(1H-indazol-5-yl)-5-(trifluoromethyl)imidazo[4,5-b]pyridine; | 8.3 |
| 93 | 5-[2-(1,1-Difluoroethyl)-5-(trifluoromethyl)imidazo[4,5-b]pyridin-3-yl]indolin-2-one; | 8.1 |
| 94 | 5-[2-(Difluoromethyl)-5-(trifluoromethyl)imidazo[4,5-b]pyridin-3-yl]indolin-2-one; | 7.3 |
| 95 | 5-(5-Chloro-2-cyclopropyl-imidazo[4,5-b]pyridin-3-yl)indolin-2-one; | 7.4 |
| 96 | (racemic)-5-[2-sec-Butyl-5-(trifluoromethyl)imidazo[4,5-b]pyridin-3-yl]indolin-2-one; | 8.2 |
| 97 | 5-[2-(2,2-Dimethylpropyl)-5-(trifluoromethyl)imidazo[4,5-b]pyridin-3-yl]indolin-2-one; | 6.6 |
| 98 | 3-(1H-Indazol-5-yl)-2-methyl-5-(trifluoromethyl)imidazo[4,5-b]pyridine; | 7.2 |
| 99 | 5-[2-Ethyl-5-(trifluoromethyl)imidazo[4,5-b]pyridin-3-yl]indolin-2-one; | 7.9 |
| 100 | (racemic)-3-(1H-Iindazol-5-yl)-2-tetrahydrofuran-3-yl-5-(trifluoromethyl)imidazo[4,5-b]pyridine; | 6.6 |
| 101 | 3-(1H-Indazol-5-yl)-2-isobutyl-5-(trifluoromethyl)imidazo[4,5-b]pyridine; | 7.6 |
| 102 | (racemic)-3-(1H-Indazol-5-yl)-2-sec-butyl-5-(trifluoromethyl)imidazo[4,5-b]pyridine; | 8.0 |
| 103 | 2-Cyclobutyl-3-(1H-indazol-5-yl)-5-(trifluoromethyl)imidazo[4,5-b]pyridine; | 8.8 |
| 104 | 2-Cyclopentyl-3-(1H-indazol-5-yl)-5-(trifluoromethyl)imidazo[4,5-b]pyridine; | 8.3 |
| 105 | 2-Ethyl-3-(1H-indazol-5-yl)-5-(trifluoromethyl)imidazo[4,5-b]pyridine; | 8.1 |
| 106 | 5-[2-Cyclopropyl-5-(trifluoromethyl)imidazo[4,5-b]pyridin-3-yl]-1,3-dihydrobenzimidazol-2-one; | 8.6 |
| 107 | 6-[2-Cyclopropyl-5-(trifluoromethyl)imidazo[4,5-b]pyridin-3-yl]-3H-1,3-benzoxazol-2-one; | 7.8 |
| 108 | 2-tert-Butyl-3-(1H-indazol-5-yl)-5-(trifluoromethyl)imidazo[4,5-b]pyridine; | 7.7 |
| 109 | 3-(1H-Indazol-5-yl)-2-isopropyl-5-(trifluoromethyl)imidazo[4,5-b]pyridine; | 9.6 |
| 110 | 2-(4-Fluorophenyl)-3-(1H-indazol-5-yl)-5-(trifluoromethyl)imidazo[4,5-b]pyridine; | 9.5 |
| 111 | 6-(5-Hydroxy-2-phenyl-imidazo[4,5-b]pyridin-3-yl)-3H-1,3-benzothiazol-2-one; | 7.8 |
| 112 | 2-(4-Fluorophenyl)-3-(1H-pyrazolo[3,4-b]pyridin-5-yl)imidazo[4,5-b]pyridine; | 6.4 |

TABLE 4-continued

| Ex. # | Compound Name | pIC$_{50}$ |
|---|---|---|
| 113 | 3-(1H-Indazol-5-yl)-2-(2,2,2-trifluoroethyl)-5-(trifluoromethyl)imidazo[4,5-b]pyridine; | 6.6 |
| 114 | 2-Ethoxy-3-(1H-indazol-5-yl)-5-(trifluoromethyl)imidazo[4,5-b]pyridine; | 7.9 |
| 115 | 1-[3-(1H-Indazol-5-yl)-5-(trifluoromethyl)imidazo[4,5-b]pyridin-2-yl]cyclopropanol; | 6.7 |
| 116 | 2-(1,1-Difluoroethyl)-3-(1H-indazol-5-yl)-5-(trifluoromethyl)imidazo[4,5-b]pyridine; | 8.7 |
| 117 | (R/S)-2-(1-fluoroethyl)-3-(1H-indazol-5-yl)-5-(trifluoromethyl)imidazo[4,5-b]pyridine; | 8.3 |
| 118 | 5-tert-Butyl-2-(4-fluorophenyl)-3-(1H-indazol-5-yl)imidazo[4,5-b]pyridine; | 9.8 |
| 119 | 2-Cyclobutyl-3-(1H-indazol-5-yl)-5-isopropyl-imidazo[4,5-b]pyridine; | 10.5 |
| 120 | 2-(4-Fluorophenyl)-3-(1H-indazol-5-yl)-5-isopropyl-imidazo[4,5-b]pyridine; | 10.3 |
| 121 | 2-(4-Fluoro-3-methyl-phenyl)-3-(1H-indazol-5-yl)-5-(trifluoromethyl)imidazo[4,5-b]pyridine; | 9.3 |
| 122 | 3-(1H-Indazol-5-yl)-2-(m-tolyl)-5-(trifluoromethyl)imidazo[4,5-b]pyridine; | 9.5 |
| 123 | 3-(1H-Indazol-5-yl)-2-(p-tolyl)-5-(trifluoromethyl)imidazo[4,5-b]pyridine; | 8.4 |
| 124 | 3-(1H-Indazol-5-yl)-2-(4-pyridyl)-5-(trifluoromethyl)imidazo[4,5-b]pyridine; | 7.9 |
| 125 | 5-Cyclopropyl-3-(1H-indazol-5-yl)-2-(trifluoromethyl)imidazo[4,5-b]pyridine; | 9.1 |
| 126 | 3-(1H-Indazol-5-yl)-N,N-dimethyl-5-(trifluoromethyl)imidazo[4,5-b]pyridine-2-carboxamide; | 6.1 |
| 127 | 3-(1H-Indazol-5-yl)-N-methyl-5-(trifluoromethyl)imidazo[4,5-b]pyridine-2-carboxamide; | 6.1 |
| 128 | N-Cyclopropyl-3-(1H-indazol-5-yl)-5-(trifluoromethyl)imidazo[4,5-b]pyridine-2-carboxamide; | 6.3 |
| 129 | 3-(1H-Indazol-5-yl)-2-methoxy-5-(trifluoromethyl)imidazo[4,5-b]pyridine; | 7.8 |
| 130 | N-Ethyl-3-(1H-indazol-5-yl)-5-(trifluoromethyl)imidazo[4,5-b]pyridin-2-amine; | 7.0 |
| 131 | N-Cyclohexyl-3-(1H-indazol-5-yl)-5-(trifluoromethyl)imidazo[4,5-b]pyridin-2-amine; | 6.8 |
| 132 | 6-[2-Cyclobutyl-5-(trifluoromethyl)imidazo[4,5-b]pyridin-3-yl]-3H-1,3-benzothiazol-2-one; | 10.2 |
| 133 | 6-(2-Cyclobutyl-5-methyl-7-morpholino-imidazo[4,5-b]pyridin-3-yl)-3H-1,3-b enzothiazol-2-one; | 9.0 |
| 134 | 6-[2,5-Bis(trifluoromethyl)imidazo[4,5-b]pyridin-3-yl]-3H-1,3-benzothiazol-2-one; | 10.1 |
| 135 | 6-(2-Cyclopropyl-7-methyl-imidazo[4,5-b]pyridin-3-yl)-3H-1,3-benzothiazol-2-one; | 7.1 |
| 136 | 6-(2-Cyclopropyl-5-methyl-7-morpholino-imidazo[4,5-b]pyridin-3-yl)-3H-1,3-benzothiazol-2-one; | 8.3 |
| 137 | 5-Chloro-2-cyclobutyl-3-(1H-indazol-5-yl)-7-methyl-imidazo[4,5-b]pyridine; | 9.3 |
| 138 | 3-(7-Bromo-1H-indazol-5-yl)-2-cyclobutyl-5-(trifluoromethyl)imidazo[4,5-b]pyridine; | 10.7 |
| 139 | 5-[5-Methyl-2-(trifluoromethyl)imidazo[4,5-b]pyridin-3-yl]indolin-2-one; | 7.4 |
| 140 | 5-[2-Cyclopropyl-5-(difluoromethyl)imidazo[4,5-b]pyridin-3-yl]indolin-2-one; | 8.6 |
| 141 | 5-[5-(Difluoromethyl)-2-isopropyl-imidazo[4,5-b]pyridin-3-yl]indolin-2-one; | 8.9 |
| 142 | 6-[5-Methyl-2-(trifluoromethyl)imidazo[4,5-b]pyridin-3-yl]-3H-1,3-benzothiazol-2-one; | 8.8 |
| 143 | 6-(2-Cyclopropyl-5-methyl-imidazo[4,5-b]pyridin-3-yl)-3H-1,3-benzothiazol-2-one; | 9.0 |
| 144 | 6-(2-Isopropyl-5-methyl-imidazo[4,5-b]pyridin-3-yl)-3H-1,3-benzothiazol-2-one; | 8.8 |
| 145 | 6-(2-Cyclobutyl-5-methyl-imidazo[4,5-b]pyridin-3-yl)-3H-1,3-benzothiazol-2-one; | 9.6 |
| 146 | 5-[2-(1,1-Difluoroethyl)-5-methyl-imidazo[4,5-b]pyridin-3-yl]indolin-2-one; | 7.4 |
| 147 | 2-Cyclopropyl-3-(1H-indazol-5-yl)-5-methyl-imidazo[4,5-b]pyridine; | 8.0 |
| 148 | 3-(1H-Indazol-5-yl)-2-isopropyl-5-methyl-imidazo[4,5-b]pyridine; | 8.1 |
| 149 | 2-Cyclobutyl-3-(1H-indazol-5-yl)-5-methyl-imidazo[4,5-b]pyridine; | 9.1 |
| 150 | 6-[2-(1,1-Difluoroethyl)-5-methyl-imidazo[4,5-b]pyridin-3-yl]-3H-1,3-benzothiazol-2-one; | 8.8 |
| 151 | 3-(1H-Indazol-5-yl)-5-methyl-2-(trifluoromethyl)imidazo[4,5-b]pyridine; | 7.9 |
| 152 | 2-(1,1-Difluoroethyl)-3-(1H-indazol-5-yl)-5-methyl-imidazo[4,5-b]pyridine; | 7.4 |
| 153 | 5-[5-(Difluoromethyl)-2-(trifluoromethyl)imidazo[4,5-b]pyridin-3-yl]indolin-2-one; | 8.6 |
| 154 | 5-[2-(1,1-Difluoroethyl)-5-(difluoromethyl)imidazo[4,5-b]pyridin-3-yl]indolin-2-one; | 8.3 |
| 155 | 2-(4-Fluorophenyl)-3-(1H-indol-5-yl)-5-methylsulfanyl-imidazo[4,5-b]pyridine; | 7.4 |
| 156 | 3-(1H-Indazol-5-yl)-2-phenyl-imidazo[4,5-b]pyridin-5-ol; | 7.6 |
| 157 | 2-Cyclopropyl-3-(1H-indazol-5-yl)-5-methoxy-imidazo[4,5-b]pyridine; | 7.9 |

TABLE 4-continued

| Ex. # | Compound Name | pIC$_{50}$ |
|---|---|---|
| 158 | 6-[2-Ethyl-5-(trifluoromethyl)imidazo[4,5-b]pyridin-3-yl]-3H-1,3-benzoxazol-2-one; | 7.5 |
| 159 | 6-[2-Isopropyl-5-(trifluoromethyl)imidazo[4,5-b]pyridin-3-yl]-3H-1,3-benzoxazol-2-one; | 7.8 |
| 160 | 6-[2-Tetrahydropyran-4-yl-5-(trifluoromethyl)imidazo[4,5-b]pyridin-3-yl]-3H-1,3-benzoxazol-2-one; | 6.0 |
| 161 | (R/S)-6-[2-Tetrahydrofuran-3-yl-5-(trifluoromethyl)imidazo[4,5-b]pyridin-3-yl]-3H-1,3-benzoxazol-2-one; | 6.5 |
| 162 | 6-[2-(Ethoxymethyl)-5-(trifluoromethyl)imidazo[4,5-b]pyridin-3-yl]-3H-1,3-benzoxazol-2-one; | 6.2 |
| 163 | 6-[2-tert-Butyl-5-(trifluoromethyl)imidazo[4,5-b]pyridin-3-yl]-3H-1,3-benzoxazol-2-one; | 6.8 |
| 164 | 5-[2-(2-Fluoro-4-pyridyl)-5-(trifluoromethyl)imidazo[4,5-b]pyridin-3-yl]indolin-2-one; | 8.9 |
| 165 | 2-(2-Fluoro-4-pyridyl)-3-(1H-indazol-5-yl)-5-(trifluoromethyl)imidazo[4,5-b]pyridine; | 8.8 |
| 166 | 5-[2-(3-Fluorocyclobutyl)-5-(trifluoromethyl)imidazo[4,5-b]pyridin-3-yl]indolin-2-one; | 8.0 |
| 167 | (R)-3-(1H-Indazol-5-yl)-2-sec-butyl-5-(trifluoromethyl)imidazo[4,5-b]pyridine; | 8.7 |
| 168 | (S)-3-(1H-Indazol-5-yl)-2-sec-butyl-5-(trifluoromethyl)imidazo[4,5-b]pyridine; | 8.2 |
| 169 | 2-(5-Fluoro-2-pyridyl)-3-(1H-indazol-5-yl)-5-(trifluoromethyl)imidazo[4,5-b]pyridine; | 8.5 |
| 170 | 3-(1H-Indazol-5-yl)-5-isopropyl-2-(trifluoromethyl)imidazo[4,5-b]pyridine; | 9.2 |
| 171 | 5-tert-Butyl-3-(1H-indazol-5-yl)-2-(trifluoromethyl)imidazo[4,5-b]pyridine; | 8.5 |
| 172 | 3-(1H-Indazol-5-yl)-N-isopropyl-5-(trifluoromethyl)imidazo[4,5-b]pyridine-2-carboxamide; | 5.4 |
| 173 | [3-(1H-Indazol-5-yl)-5-(trifluoromethyl)imidazo[4,5-b]pyridin-2-yl]-pyrrolidin-1-yl-methanone; | 5.0 |
| 174 | 2-(4-Fluorophenyl)-3-(1H-indol-5-yl)imidazo[4,5-b]pyridine; | |
| 175 | 4-[2-(4-Fluorophenyl)-3-(1H-indol-5-yl)imidazo[4,5-b]pyridin-7-yl]morpholine; | |
| 176 | 3-(1H-Indazol-5-yl)-2-[4-(trifluoromethyl)phenyl]imidazo[4,5-b]pyridine; | 5.0 |
| 177 | 3-(1H-Indazol-5-yl)-2-[4-(trifluoromethoxy)phenyl]imidazo[4,5-b]pyridine; | 4.9 |
| 178 | 5-[2-[4-(Trifluoromethyl)phenyl]imidazo[4,5-b]pyridin-3-yl]indolin-2-one; | 5.5 |
| 179 | tert-Butyl 3-[3-(2-oxoindolin-5-yl)-5-(trifluoromethyl)imidazo[4,5-b]pyridin-2-yl]azetidine-1-carboxylate; | 5.5 |
| 180 | 5-[2-(Azetidin-3-yl)-5-(trifluoromethyl)imidazo[4,5-b]pyridin-3-yl]indolin-2-one; | 5.7 |
| 181 | 5-(2,5-Dimethylimidazo[4,5-b]pyridin-3-yl)indolin-2-one; | 5.6 |
| 182 | 2-Cyclopentyl-3-(1H-indol-5-yl)-5-piperazin-1-yl-imidazo[4,5-b]pyridine; | |
| 183 | Methyl 3-[3-(2-oxoindolin-5-yl)-5-(trifluoromethyl)imidazo[4,5-b]pyridin-2-yl]propanoate; | 5.7 |
| 184 | 3-(7-Bromo-1H-indazol-5-yl)-2-isopropyl-5-(trifluoromethyl)imidazo[4,5-b]pyridine; | 11.0 |
| 185 | 6-(2-Cyclobutyl-5-(trifluoromethyl)-3H-imidazo[4,5-b]pyridin-3-yl)-3-methylbenzo[d]thiazol-2(3H)-one; | 7.0 |
| 186 | 3-(7-$^3$H-1H-indazol-5-yl)-2-isopropyl-5-(trifluoromethyl)-3H-imidazo[4,5-b]pyridine; | |
| 187 | 3-(7-Bromo-1H-indazol-5-yl)-2,5-bis(trifluoromethyl)imidazo[4,5-b]pyridine; | 11.0 |
| 188 | 3-(7-Phenyl-1H-indazol-5-yl)-2,5-bis(trifluoromethyl)-3H-imidazo[4,5-b]pyridine; | 6.5 |
| 189 | 2,5-Bis(trifluoromethyl)-3-(7-vinyl-1H-indazol-5-yl)-3H-imidazo[4,5-b]pyridine; | 10.4 |
| 190 | 6-(5-(Trifluoromethyl)-3H-imidazo[4,5-b]pyridin-3-yl)benzo[d]thiazol-2(3H)-one; | 6.5 |
| 191 | 3-(3-Fluoro-1H-indazol-5-yl)-2-isopropyl-5-(trifluoromethyl)imidazo[4,5-b]pyridine; | 8.4 |
| 192 | 5-Chloro-3-(1H-indazol-5-yl)-2-(trifluoromethyl)imidazo[4,5-b]pyridine; | 8.6 |
| 193 | 5-Ethyl-3-(1H-indazol-5-yl)-2-(trifluoromethyl)imidazo[4,5-b]pyridine; | 8.8 |
| 194 | 3-(7-Methyl-1H-indazol-5-yl)-5-(trifluoromethyl)imidazo[4,5-b]pyridine; | 7.7 |
| 195 | 2-(4-Fluorophenyl)-3-(7-methyl-1H-indazol-5-yl)-5-(trifluoromethyl)imidazo[4,5-b]pyridine; | 10.9 |
| 196 | 2-Ethoxy-3-(3-fluoro-1H-indazol-5-yl)-5-(trifluoromethyl)imidazo[4,5-b]pyridine; | 7.6 |
| 197 | 2-Cyclopropyl-3-(3-fluoro-1H-indazol-5-yl)-5-(trifluoromethyl)imidazo[4,5-b]pyridine; | 8.2 |
| 198 | 2-Isopropyl-3-(7-methyl-1H-indazol-5-yl)-5-(trifluoromethyl)imidazo[4,5-b]pyridine; | 10.5 |
| 199 | 3-(7-Chloro-1H-indazol-5-yl)-2-(trifluoromethyl)imidazo[4,5-b]pyridine; | 8.7 |
| 200 | 3-(7-Chloro-1H-indazol-5-yl)-2-isopropyl-imidazo[4,5-b]pyridine; | 8.2 |
| 201 | 3-(1H-indazol-5-yl)-7-methyl-2-(trifluoromethyl)imidazo[4,5-b]pyridine; | 7.0 |

TABLE 4-continued

| Ex. # | Compound Name | pIC$_{50}$ |
|---|---|---|
| 202 | 3-(7-Chloro-1H-indazol-5-yl)-7-methyl-2-(trifluoromethyl)imidazo[4,5-b]pyridine; | 9.2 |
| 203 | 7-Methyl-3-(7-methyl-1H-indazol-5-yl)-2-(trifluoromethyl)imidazo[4,5-b]pyridine; | 8.3 |
| 204 | 3-(1H-pyrazolo[3,4-b]pyridin-5-yl)-2,5-bis(trifluoromethyl)imidazo[4,5-b]pyridine; | 7.9 |
| 205 | 3-(7-Oxido-1H-pyrazolo[3,4-b]pyridin-7-ium-5-yl)-2,5-bis(trifluoromethyl)imidazo[4,5-b]pyridine; | 6.4 |
| 206 | 6-[5-(difluoromethyl)-2-(trifluoromethyl)imidazo[4,5-b]pyridin-3-yl]-3H-1,3-benzothiazol-2-one; | 9.5 |
| 207 | 3-(7-Chloro-1H-indazol-5-yl)-2,5-bis(difluoromethyl)imidazo[4,5-b]pyridine; | 10.2 |
| 208 | 5-Cyclobutyl-3-(1H-indazol-5-yl)-2-(trifluoromethyl)imidazo[4,5-b]pyridine; | 9.8 |
| 209 | 5-(2-Ethyl-5-methyl-imidazo[4,5-b]pyridin-3-yl)indoline-2,3-dione; | |
| 210 | 5-(Difluoromethyl)-3-(1H-indazol-5-yl)-2-isopropyl-imidazo[4,5-b]pyridine; | 9.2 |
| 211 | 5-(1,1-Difluoroethyl)-3-(1H-indazol-5-yl)-2-isopropyl-imidazo[4,5-b]pyridine; | 8.3 |
| 212 | 2,5-Bis(difluoromethyl)-3-(7-methyl-1H-indazol-5-yl)imidazo[4,5-b]pyridine; | 10.1 |
| 213 | 2-(2-Fluoro-4-pyridyl)-5-methyl-3-(7-methyl-1H-indazol-5-yl)imidazo[4,5-b]pyridine; | 9.3 |
| 214 | N-(2-Fluoroethyl)-2-isopropyl-N-methyl-3-(7-methyl-1H-indazol-5-yl)-5-(trifluoromethyl)imidazo[4,5-b]pyridin-7-amine; | 9.8 |
| 215 | 5-[2-(2-Fluoro-4-pyridyl)-5-(trifluoromethyl)imidazo[4,5-b]pyridin-3-yl]indoline-2,3-dione; | 5.8 |
| 216 | Methyl 3-[3-(2,3-dioxoindolin-5-yl)-5-(trifluoromethyl)imidazo[4,5-b]pyridin-2-yl]propanoate; | NT |
| 217 | 2-(2-Fluoro-4-pyridyl)-3-(7-methyl-1H-indazol-5-yl)-5-(trifluoromethyl)imidazo[4,5-b]pyridine; | 10.3 |
| 218 | 3-(7-Chloro-1H-indazol-5-yl)-7-(2-fluoroethoxy)-2,5-bis(trifluoromethyl)imidazo[4,5-b]pyridine; | 10.3 |
| 219 | (E)-3-(5-(2,5-Bis(trifluoromethyl)-3H-imidazo[4,5-b]pyridin-3-yl)-1H-indazol-7-yl)prop-2-en-1-ol; | 7.8 |
| 220 | 3-(5-(2,5-Bis(trifluoromethyl)-3H-imidazo[4,5-b]pyridin-3-yl)-1H-indazol-7-yl)propan-1-ol; | 6.8 |
| 221 | 3-(7-Propyl-1H-indazol-5-yl)-2,5-bis(trifluoromethyl)-3H-imidazo[4,5-b]pyridine; | 9.9 |
| 222 | (E)-3-(3-(7-Methyl-1H-indazol-5-yl)-2-(trifluoromethyl)-3H-imidazo[4,5-b]pyridin-5-yl)prop-2-en-1-ol; | 7.5 |
| 223 | 3-(3-(7-Methyl-1H-indazol-5-yl)-2-(trifluoromethyl)-3H-imidazo[4,5-b]pyridin-5-yl)propan-1-ol; | 7.0 |
| 224 | 3-(7-Methyl-1H-indazol-5-yl)-5-propyl-2-(trifluoromethyl)-3H-imidazo[4,5-b]pyridine; | 9.8 |
| 225 | 4-[3-(1H-Indazol-5-yl)-5-(trifluoromethyl)imidazo[4,5-b]pyridin-2-yl]pyridin-2-ol; | 6.6 |
| 226 | 3-(1H-Indazol-5-yl)-5-(trifluoromethyl)imidazo[4,5-b]pyridine; | 6.4 |
| 227 | 3-(7-Chloro-1H-indazol-5-yl)-2-cyclopropyl-5-(difluoromethyl)imidazo[4,5-b]pyridine; | 10.3 |
| 228 | 5-(Difluoromethyl)-2-(4-fluorophenyl)-3-(7-methyl-1H-indazol-5-yl)imidazo[4,5-b]pyridine; | 10.8 |
| 229 | 3-(7-Chloro-1H-indazol-5-yl)-5-(difluoromethyl)-2-(4-fluorophenyl)imidazo[4,5-b]pyridine; | 11.2 |
| 230 | 6-[7-Morpholino-2,5-bis(trifluoromethyl)imidazo[4,5-b]pyridin-3-yl]-3H-1,3-benzothiazol-2-one; | 9.0 |
| 231 | 4-[3-(1H-Indazol-5-yl)-2,5-bis(trifluoromethyl)imidazo[4,5-b]pyridin-7-yl]morpholine; | 8.4 |
| 232 | 2-(1,1-Difluoropropyl)-3-(1H-indazol-5-yl)-5-(trifluoromethyl)imidazo[4,5-b]pyridine; | 7.8 |
| 233 | 6-[2-(1,1,2,2,2-Pentafluoroethyl)-5-(trifluoromethyl)imidazo[4,5-b]pyridin-3-yl]-3H-1,3-benzothiazol-2-one; | 9.5 |
| 234 | 6-[2-(Difluoromethyl)-5-(trifluoromethyl)imidazo[4,5-b]pyridin-3-yl]-3H-1,3-benzothiazol-2-one; | 10.1 |
| 235 | 6-[2-(Difluoromethyl)-5-(trifluoromethyl)imidazo[4,5-b]pyridin-3-yl]-3H-1,3-benzoxazol-2-one; | 7.2 |
| 236 | 6-[2,5-Bis(trifluoromethyl)imidazo[4,5-b]pyridin-3-yl]-3H-1,3-benzoxazol-2-one; | 8.2 |
| 237 | 3-(3-Fluoro-1H-indazol-5-yl)-2,5-bis(trifluoromethyl)imidazo[4,5-b]pyridine; | 8.6 |
| 238 | 5-(Difluoromethyl)-3-(1H-indazol-5-yl)-2-(trifluoromethyl)imidazo[4,5-b]pyridine; | 9.4 |
| 239 | 6-[2-Methoxy-5-(trifluoromethyl)imidazo[4,5-b]pyridin-3-yl]-3H-1,3-benzothiazol-2-one; | 8.7 |
| 240 | 6-[2-Ethoxy-5-(trifluoromethyl)imidazo[4,5-b]pyridin-3-yl]-3H-1,3-benzothiazol-2-one; | 9.0 |
| 241 | 2-Methoxy-3-(7-methyl-1H-indazol-5-yl)-5-(trifluoromethyl)imidazo[4,5-b]pyridine; | 9.4 |

TABLE 4-continued

| Ex. # | Compound Name | pIC$_{50}$ |
|---|---|---|
| 242 | 2-Ethoxy-3-(7-methyl-1H-indazol-5-yl)-5-(trifluoromethyl)imidazo[4,5-b]pyridine; | 9.4 |
| 243 | 5-[2-Ethoxy-5-(trifluoromethyl)imidazo[4,5-b]pyridin-3-yl]indolin-2-one; | 7.8 |
| 244 | 5-[2-Methoxy-5-(trifluoromethyl)imidazo[4,5-b]pyridin-3-yl]indolin-2-one; | 7.4 |
| 245 | 3-(1H-indazol-5-yl)-2-(methylsulfonylmethyl)-5-(trifluoromethyl)imidazo[4,5-b]pyridine; | 6.5 |
| 246 | 2-(3-Fluorocyclobutyl)-3-(7-methyl-1H-indazol-5-yl)-5-(trifluoromethyl)imidazo[4,5-b]pyridine; | 9.9 |
| 247 | 2-(3-Fluorocyclobutyl)-3-(7-methyl-1H-indazol-5-yl)-5-(trifluoromethyl)imidazo[4,5-b]pyridine; | 10.2 |
| 248 | 3-(7-Chloro-1H-indazol-5-yl)-2-(3-fluorocyclobutyl)-5-(trifluoromethyl)imidazo[4,5-b]pyridine; | 9.8 |
| 249 | 3-(7-Chloro-1H-indazol-5-yl)-2-(3-fluorocyclobutyl)-5-methyl-imidazo[4,5-b]pyridine; | 9.3 |
| 250 | 3-(7-Chloro-1H-indazol-5-yl)-2-(3-fluorocyclobutyl)-5-(trifluoromethyl)imidazo[4,5-b]pyridine; | 10.5 |
| 251 | 2-(1-Methoxy-1-methyl-ethyl)-3-(7-methyl-1H-indazol-5-yl)-5-(trifluoromethyl)imidazo[4,5-b]pyridine; | 8.6 |
| 252 | 2-(1,1-Difluoroethyl)-3-(7-methyl-1H-indazol-5-yl)-5-(trifluoromethyl)imidazo[4,5-b]pyridine; | 9.8 |
| 253 | 2-(1-Fluoro-1-methyl-ethyl)-3-(7-methyl-1H-indazol-5-yl)-5-(trifluoromethyl)imidazo[4,5-b]pyridine; | 9.7 |
| 254 | 3-(7-Chloro-1H-indazol-5-yl)-2-(1-fluoro-1-methyl-ethyl)-5-(trifluoromethyl)imidazo[4,5-b]pyridine; | 10.2 |
| 255 | 2-Cyclopropyl-3-(7-methyl-1H-indazol-5-yl)-5-(trifluoromethyl)imidazo[4,5-b]pyridine; | 10.5 |
| 256 | (*R)-2-(1-Fluoroethyl)-3-(7-methyl-1H-indazol-5-yl)-5-(trifluoromethyl)imidazo[4,5-b]pyridine; | 10.1 |
| 257 | (*S)-2-(1-Fluoroethyl)-3-(7-methyl-1H-indazol-5-yl)-5-(trifluoromethyl)imidazo[4,5-b]pyridine; | 10.3 |
| 258 | 3-(7-Chloro-1H-indazol-5-yl)-2-(1-fluorocyclopropyl)-5-(trifluoromethyl)imidazo[4,5-b]pyridine; | 10.2 |
| 259 | 2-(1-Fluorocyclopropyl)-3-(7-methyl-1H-indazol-5-yl)-5-(trifluoromethyl)imidazo[4,5-b]pyridine; | 10.1 |
| 260 | 3-(1H-Indazol-5-yl)-N-isopropyl-N-methyl-5-(trifluoromethyl)imidazo[4,5-b]pyridine-2-carboxamide; | NT |
| 261 | 2-(2-Chloro-4-pyridyl)-3-(7-methyl-1H-indazol-5-yl)-5-(trifluoromethyl)imidazo[4,5-b]pyridine; | NT |
| 262 | 2-(2-Bromo-4-pyridyl)-3-(7-methyl-1H-indazol-5-yl)-5-(trifluoromethyl)imidazo[4,5-b]pyridine; | NT |
| 263 | 5-(Difluoromethyl)-2-(2-fluoro-4-pyridyl)-3-(7-methyl-1H-indazol-5-yl)imidazo[4,5-b]pyridine; | 9.8 |
| 264 | 3-(7-Chloro-1H-indazol-5-yl)-5-(difluoromethyl)-2-(2-fluoro-4-pyridyl)imidazo[4,5-b]pyridine; | 10.0 |
| 265 | 3-(4-Chloro-1H-indazol-6-yl)-2,5-bis(trifluoromethyl)imidazo[4,5-b]pyridine; | 6.9 |
| 266 | 6-[2-(1,1-Difluoroethyl)-5-(trifluoromethyl)imidazo[4,5-b]pyridin-3-yl]-3H-1,3-benzothiazol-2-one; | 10.0 |
| 267 | 3-(7-Chloro-1H-indazol-5-yl)-2-(1,1-difluoroethyl)-5-(trifluoromethyl)imidazo[4,5-b]pyridine; | 10.8 |
| 268 | 3-(7-Chloro-1H-indazol-5-yl)-5-methyl-2-(trifluoromethyl)imidazo[4,5-b]pyridine; | 10.2 |
| 269 | 3-(7-Chloro-1H-indazol-5-yl)-5-(difluoromethyl)-2-isopropyl-imidazo[4,5-b]pyridine; | 10.5 |
| 270 | 3-(7-Chloro-1H-indazol-5-yl)-2,5-bis(trifluoromethyl)imidazo[4,5-b]pyridine; | 10.7 |
| 271 | 5-[2,5-Bis(trifluoromethyl)imidazo[4,5-b]pyridin-3-yl]-7-chloro-indolin-2-one; | 9.7 |
| 272 | 7-Chloro-5-[2-(difluoromethyl)-5-(trifluoromethyl)imidazo[4,5-b]pyridin-3-yl]indolin-2-one; | 9.7 |
| 273 | 5-(Difluoromethyl)-2-isopropyl-3-(7-methyl-1H-indazol-5-yl)imidazo[4,5-b]pyridine; | 10.2 |
| 274 | 3-(7-Chloro-1H-indazol-5-yl)-5-(difluoromethyl)-2-methyl-imidazo[4,5-b]pyridine; | 9.5 |
| 275 | 5-[2,5-Bis(trifluoromethyl)imidazo[4,5-b]pyridin-3-yl]-7-methyl-indolin-2-one; | 9.9 |
| 276 | 5-[2-(1,1-Difluoroethyl)-5-(trifluoromethyl)imidazo[4,5-b]pyridin-3-yl]-7-methyl-indolin-2-one; | 9.7 |
| 277 | 3-(7-Chloro-1H-indazol-5-yl)-2-(difluoromethyl)-5-(trifluoromethyl)imidazo[4,5-b]pyridine; | 10.2 |
| 278 | 3-(7-Chloro-1H-indazol-5-yl)-2-(difluoromethyl)-5-methyl-imidazo[4,5-b]pyridine; | 8.5 |
| 279 | 3-(7-Chloro-1H-indazol-5-yl)-6-fluoro-2-(trifluoromethyl)imidazo[4,5-b]pyridine; | 8.9 |
| 280 | 3-(7-Bromo-1H-indazol-5-yl)-2-(difluoromethyl)-5-(trifluoromethyl)imidazo[4,5-b]pyridine; | 10.8 |

TABLE 4-continued

| Ex. # | Compound Name | pIC$_{50}$ |
|---|---|---|
| 281 | 6-[2,5-Bis(trifluoromethyl)imidazo[4,5-b]pyridin-3-yl]-4-methyl-3H-1,3-benzothiazol-2-one; | 10.2 |
| 282 | 6-[2,5-Bis(trifluoromethyl)imidazo[4,5-b]pyridin-3-yl]-4-chloro-3H-1,3-benzothiazol-2-one; | 10.5 |
| 283 | 6-[2,5-Bis(trifluoromethyl)imidazo[4,5-b]pyridin-3-yl]-4-fluoro-3H-1,3-benzoxazol-2-one; | 8.6 |
| 284 | Methyl 5-[2,5-bis(trifluoromethyl)imidazo[4,5-b]pyridin-3-yl]-1H-indazole-7-carboxylate; | 6.9 |
| 285 | Methyl 5-[2-(difluoromethyl)-5-(trifluoromethyl)imidazo[4,5-b]pyridin-3-yl]-1H-indazole-7-carboxylate; | 6.6 |
| 286 | 2-(Difluoromethyl)-3-(7-methyl-1H-indazol-5-yl)-5-(trifluoromethyl)imidazo[4,5-b]pyridine; | 10.3 |
| 287 | 5-[2-(Difluoromethyl)-5-(trifluoromethyl)imidazo[4,5-b]pyridin-3-yl]-7-methyl-indolin-2-one; | 9.8 |
| 288 | 5-[2-(Difluoromethyl)-5-(trifluoromethyl)imidazo[4,5-b]pyridin-3-yl]-7-fluoro-indolin-2-one; | 8.2 |
| 289 | 3-(4-Methyl-1H-indazol-6-yl)-2,5-bis(trifluoromethyl)imidazo[4,5-b]pyridine; | 8.4 |
| 290 | 6-[2,5-Bis(trifluoromethyl)imidazo[4,5-b]pyridin-3-yl]-4-bromo-3H-1,3-benzoxazol-2-one; | 9.7 |
| 291 | 3-(1H-Indazol-6-yl)-2,5-bis(trifluoromethyl)imidazo[4,5-b]pyridine; | 7.2 |
| 292 | 5-[2,5-Bis(trifluoromethyl)imidazo[4,5-b]pyridin-3-yl]-1,3-dihydropyrrolo[2,3-b]pyridin-2-one; | 8.1 |
| 293 | 3-(1H-Pyrrolo[2,3-b]pyridin-5-yl)-2,5-bis(trifluoromethyl)imidazo[4,5-b]pyridine; | 7.4 |
| 294 | 3-(7-Methyl-1H-indazol-5-yl)-2,5-bis(trifluoromethyl)imidazo[4,5-b]pyridine; | 10.7 |
| 295 | 5-[2,5-Bis(trifluoromethyl)imidazo[4,5-b]pyridin-3-yl]-1H-indazole-3-carbonitrile; | 7.4 |
| 296 | 5-[2-(Difluoromethyl)-5-(trifluoromethyl)imidazo[4,5-b]pyridin-3-yl]-1H-indazol-3-ol; | 6.8 |
| 297 | 6-[2-Cyclopropyl-5-(trifluoromethyl)imidazo[4,5-b]pyridin-3-yl]indolin-2-one; | 6.0 |
| 298 | 3-(3-Bromo-1H-indazol-5-yl)-2-isopropyl-5-(trifluoromethyl)imidazo[4,5-b]pyridine; | 7.1 |
| 299 | 7-Chloro-5-[2-isopropyl-5-(trifluoromethyl)imidazo[4,5-b]pyridin-3-yl]indolin-2-one; | 9.7 |
| 300 | 3-(7-Chloro-1H-indazol-5-yl)-6-fluoro-2-isopropyl-imidazo[4,5-b]pyridine; | 8.6 |
| 301 | 5-[2-Isopropyl-5-(trifluoromethyl)imidazo[4,5-b]pyridin-3-yl]-1,3-dihydropyrrolo[2,3-b]pyridin-2-one; | 7.5 |
| 302 | 2-Isopropyl-3-(1H-pyrazolo[3,4-b]pyridin-5-yl)-5-(trifluoromethyl)imidazo[4,5-b]pyridine; | 7.4 |
| 303 | 2-Isopropyl-3-(1H-pyrrolo[2,3-b]pyridin-5-yl)-5-(trifluoromethyl)imidazo[4,5-b]pyridine; | 7.5 |
| 304 | 3-(7-Allyl-1H-indazol-5-yl)-2,5-bis(trifluoromethyl)-3H-imidazo[4,5-b]pyridine; | 7.2 |
| 305 | 3-(7-(Prop-1-en-2-yl)-1H-indazol-5-yl)-2,5-bis(trifluoromethyl)-3H-imidazo[4,5-b]pyridine; | 10.7 |
| 306 | 3-(7-Chloro-1H-indazol-5-yl)-5-(trifluoromethyl)imidazo[4,5-b]pyridine; | 8.6 |
| 307 | 3-(7-Chloro-1H-indazol-5-yl)-2-cyclopropyl-5-(trifluoromethyl)imidazo[4,5-b]pyridine; | 11.3 |
| 308 | 3-(7-Chloro-1H-indazol-5-yl)-2-cyclobutyl-5-(trifluoromethyl)imidazo[4,5-b]pyridine; | 11.3 |
| 309 | 7-Methyl-5-[2-methyl-5-(trifluoromethyl)imidazo[4,5-b]pyridin-3-yl]indolin-2-one; | 9.2 |
| 310 | 5-[2-Isopropyl-5-(trifluoromethyl)imidazo[4,5-b]pyridin-3-yl]-7-methyl-indolin-2-one; | 9.8 |
| 311 | 2-Isopropyl-3-(4-methyl-1H-indazol-6-yl)-5-(trifluoromethyl)imidazo[4,5-b]pyridine; | 7.8 |
| 312 | 3-(7-Chloro-1H-indazol-5-yl)-2-methyl-5-(trifluoromethyl)imidazo[4,5-b]pyridine; | 9.6 |
| 313 | 7-Chloro-5-[2-methyl-5-(trifluoromethyl)imidazo[4,5-b]pyridin-3-yl]indolin-2-one; | 9.0 |
| 314 | 3-(7-Chloro-1H-indazol-5-yl)-2-ethyl-5-(trifluoromethyl)imidazo[4,5-b]pyridine; | 10.5 |
| 315 | 2-Ethyl-3-(7-methyl-1H-indazol-5-yl)-5-(trifluoromethyl)imidazo[4,5-b]pyridine; | 10.0 |
| 316 | 3-(7-Chloro-1H-indazol-5-yl)-2-isopropyl-5-(trifluoromethyl)imidazo[4,5-b]pyridine; | 10.7 |
| 317 | 3-(7-Methyl-1H-indazol-5-yl)-2-(trifluoromethyl)imidazo[4,5-b]pyridine; | 8.0 |
| 318 | 7-Methyl-5-[2-(trifluoromethyl)imidazo[4,5-b]pyridin-3-yl]indolin-2-one; | 7.5 |
| 319 | 2-Methyl-3-(7-methyl-1H-indazol-5-yl)-5-(trifluoromethyl)imidazo[4,5-b]pyridine; | 9.2 |
| 320 | 3-(1H-Indazol-5-yl)-5-(2-pyridyl)-2-(trifluoromethyl)imidazo[4,5-b]pyridine; | 6.7 |
| 321 | 2-Cyclopropyl-5-(difluoromethyl)-3-(1H-indazol-5-yl)imidazo[4,5-b]pyridine; | 9.0 |

TABLE 4-continued

| Ex. # | Compound Name | pIC$_{50}$ |
|---|---|---|
| 322 | 5-(Difluoromethyl)-2-(4-fluorophenyl)-3-(1H-indazol-5-yl)imidazo[4,5-b]pyridine; | 10.2 |
| 323 | 5-(Difluoromethyl)-3-(1H-indazol-5-yl)-2-phenyl-imidazo[4,5-b]pyridine; | 10.3 |
| 324 | 3-(7-Chloro-1H-indazol-5-yl)-5-(difluoromethyl)-2-(trifluoromethyl)imidazo[4,5-b]pyridine; | 10.3 |
| 325 | 5-[5-(Difluoromethyl)-2-(trifluoromethyl)imidazo[4,5-b]pyridin-3-yl]-7-fluoro-indolin-2-one; | 9.5 |
| 326 | 5-(Difluoromethyl)-3-(7-methyl-1H-indazol-5-yl)-2-(trifluoromethyl)imidazo[4,5-b]pyridine; | 10.4 |
| 327 | 3-(7-Chloro-1H-indazol-5-yl)-2-(2-fluoro-4-pyridyl)-5-methyl-imidazo[4,5-b]pyridine; | 9.6 |
| 328 | 3-(7-Bromo-1H-indazol-5-yl)-2-(2-fluoro-4-pyridyl)-5-(trifluoromethyl)imidazo[4,5-b]pyridine; | NT |
| 329 | 5-(2-(Hydroxymethyl)-6-(trifluoromethyl)-1H-pyrrolo[2,3-b]pyridin-1-yl)-7-methylindolin-2-one; | 9.0 |
| 330 | (1-(1H-Indazol-5-yl)-6-(trifluoromethyl)-1H-pyrrolo[2,3-b]pyridin-2-yl)methanol; | 7.6 |
| 331 | 7-Methyl-5-(2-methyl-6-(trifluoromethyl)-1H-pyrrolo[2,3-b]pyridin-1-yl)indolin-2-one; | 11.0 |
| 332 | 5-(2-Isopropyl-1H-pyrrolo[2,3-b]pyridin-1-yl)-7-methyl-1H-indazole; | 10.4 |
| 333 | 1-(7-Chloro-1H-indazol-5-yl)-2-methyl-pyrrolo[2,3-b]pyridine; | 8.2 |
| 334 | 5-[6-(Difluoromethyl)-2-isopropyl-pyrrolo[2,3-b]pyridin-1-yl]-7-methyl-indolin-2-one; | 10.4 |
| 335 | 1-(1H-Indazol-5-yl)-2-isopropyl-6-(trifluoromethyl)pyrrolo[2,3-b]pyridine; | 10.8 |
| 336 | 5-[2-(Difluoromethyl)-6-(trifluoromethyl)pyrrolo[2,3-b]pyridin-1-yl]-7-methyl-indolin-2-one; | 11.0 |
| 337 | 6-[2-(Difluoromethyl)-6-(trifluoromethyl)pyrrolo[2,3-b]pyridin-1-yl]-3H-1,3-benzothiazol-2-one; | 9.9 |
| 338 | 7-Chloro-5-(2-methylpyrrolo[2,3-b]pyridin-1-yl)indolin-2-one; | 8.1 |
| 339 | 1-(7-Methyl-1H-indazol-5-yl)-6-(trifluoromethyl)pyrrolo[2,3-b]pyridin-3-ol; | 7.1 |
| 340 | 3-(Difluoromethyl)-1-(7-methyl-1H-indazol-5-yl)-6-(trifluoromethyl)pyrrolo[2,3-b]pyridine; | 7.9 |
| 341 | 6-Methyl-1-(7-methyl-1H-indazol-5-yl)pyrrolo[2,3-b]pyridine; | 7.8 |
| 342 | 5-(2-Isopropyl-6-methyl-pyrrolo[2,3-b]pyridin-1-yl)indolin-2-one; | 9.6 |
| 343 | 2-(4-Fluorophenyl)-1-(1H-indol-5-yl)-6-methoxy-pyrrolo[2,3-b]pyridine; | 6.2 |
| 344 | 2-(4-Fluorophenyl)-1-indolin-5-yl-pyrrolo[2,3-b]pyridine; | 6.3 |
| 345 | 2-(4-Fluorophenyl)-1-(1H-indol-5-yl)pyrrolo[2,3-b]pyridine; | 7.1 |
| 346 | 5-[3-Bromo-2-(4-fluorophenyl)pyrrolo[2,3-b]pyridin-1-yl]indolin-2-one; | 8.4 |
| 347 | 5-[2-(4-Fluorophenyl)pyrrolo[2,3-b]pyridin-1-yl]indolin-2-one; | 8.6 |
| 348 | 6-Fluoro-2-(4-fluorophenyl)-1-(1H-indol-5-yl)pyrrolo[2,3-b]pyridine; | 7.0 |
| 349 | 5-[3-Bromo-6-fluoro-2-(4-fluorophenyl)pyrrolo[2,3-b]pyridin-1-yl]indolin-2-one; | 8.4 |
| 350 | 5-[6-Fluoro-2-(4-fluorophenyl)pyrrolo[2,3-b]pyridin-1-yl]indolin-2-one; | 9.1 |
| 351 | 1-(1H-Indol-5-yl)-2-methyl-6-(trifluoromethyl)pyrrolo[2,3-b]pyridine; | 7.6 |
| 352 | 5-[2-Methyl-6-(trifluoromethyl)pyrrolo[2,3-b]pyridin-1-yl]indolin-2-one; | 9.3 |
| 353 | 7-Methyl-5-(2-methyl-1H-pyrrolo[2,3-b]pyridin-1-yl)indolin-2-one; | 7.9 |
| 354 | 5-(2-Methyl-6-(trifluoromethyl)-1H-pyrrolo[2,3-b]pyridin-1-yl)-1H-indazole; | 9.3 |
| 355 | 6-(2-Methyl-6-(trifluoromethyl)-1H-pyrrolo[2,3-b]pyridin-1-yl)benzo[d]thiazol-2(3H)-one; | 10.7 |
| 356 | 1-(7-Chloro-1H-indazol-5-yl)-2-isopropyl-pyrrolo[2,3-b]pyridine; | 10.7 |
| 357 | 7-Chloro-5-(2-isopropylpyrrolo[2,3-b]pyridin-1-yl)indolin-2-one; | 10.5 |
| 358 | 5-(2-Isopropylpyrrolo[2,3-b]pyridin-1-yl)-7-methyl-indolin-2-one; | 9.7 |
| 359 | 5-(2-Cyclopropylpyrrolo[2,3-b]pyridin-1-yl)-7-methyl-indolin-2-one; | 8.0 |
| 360 | 5-(2-Isopropyl-6-methyl-pyrrolo[2,3-b]pyridin-1-yl)-7-methyl-indolin-2-one; | 10.2 |
| 361 | 7-Fluoro-5-(2-isopropylpyrrolo[2,3-b]pyridin-1-yl)indolin-2-one; | 8.1 |
| 362 | 7-Fluoro-5-(2-isopropyl-6-methyl-pyrrolo[2,3-b]pyridin-1-yl)indolin-2-one; | 10.4 |
| 363 | 7-Fluoro-5-(2-methylpyrrolo[2,3-b]pyridin-1-yl)indolin-2-one; | 6.7 |
| 364 | 7-Fluoro-5-[2-methyl-6-(trifluoromethyl)pyrrolo[2,3-b]pyridin-1-yl]indolin-2-one; | 5.5 |
| 365 | (R/S)-7-Fluoro-5-[2-tetrahydrofuran-3-yl-6-(trifluoromethyl)pyrrolo[2,3-b]pyridin-1-yl]indolin-2-one; | 9.7 |
| 366 | 7-Fluoro-5-[2-(methoxymethyl)-6-(trifluoromethyl)pyrrolo[2,3-b]pyridin-1-yl]indolin-2-one; | 9.2 |
| 367 | 5-[2-Isopropyl-6-(trifluoromethyl)pyrrolo[2,3-b]pyridin-1-yl]-7-methyl-indolin-2-one; | 10.6 |
| 368 | (R/S)-5-[2-(1-Methoxyethyl)pyrrolo[2,3-b]pyridin-1-yl]-7-methyl-indolin-2-one; | 7.5 |
| 369 | 7-Fluoro-5-[2-isopropyl-6-(trifluoromethyl)pyrrolo[2,3-b]pyridin-1-yl]indolin-2-one; | 11.1 |
| 370 | 2-Isopropyl-1-(7-methyl-1H-indazol-5-yl)-6-(trifluoromethyl)pyrrolo[2,3-b]pyridine; | 11.1 |
| 371 | 2-(3-Fluoropropyl)-1-(7-methyl-1H-indazol-5-yl)-6-(trifluoromethyl)pyrrolo[2,3-b]pyridine; | 10.4 |

TABLE 4-continued

| Ex. # | Compound Name | pIC$_{50}$ |
|---|---|---|
| 372 | 1-(7-Chloro-1H-indazol-5-yl)-2-(3-fluoropropyl)-6-(trifluoromethyl)pyrrolo[2,3-b]pyridine; | 10.5 |
| 373 | 2-Methyl-1-(7-methyl-1H-indazol-5-yl)-6-(trifluoromethyl)pyrrolo[2,3-b]pyridine; | 10.3 |
| 374 | 1-(7-Chloro-1H-indazol-5-yl)-2-methyl-6-(trifluoromethyl)pyrrolo[2,3-b]pyridine; | 10.9 |
| 375 | 2-Methyl-1-(7-methyl-1H-indazol-5-yl)pyrrolo[2,3-b]pyridine; | 8.0 |
| 376 | 5-[2-Isopropyl-6-(trifluoromethyl)pyrrolo[2,3-b]pyridin-1-yl]-1H-pyrazolo[3,4-b]pyridine; | 10.3 |
| 377 | 1-(7-Methyl-1H-indazol-5-yl)-6-(trifluoromethyl)pyrrolo[2,3-b]pyridine; | 8.7 |
| 378 | 7-Methyl-5-(6-methylpyrrolo[2,3-b]pyridin-1-yl)indolin-2-one; | 7.0 |
| 379 | 7-Fluoro-5-(6-methylpyrrolo[2,3-b]pyridin-1-yl)indolin-2-one; | 7.0 |
| 380 | 5-(2-Cyclopropyl-6-methyl-pyrrolo[2,3-b]pyridin-1-yl)indolin-2-one; | 9.0 |
| 381 | 2-(4-Fluorophenyl)-1-(1H-indol-5-yl)-6-methyl-pyrrolo[2,3-b]pyridine; | 8.3 |
| 382 | 5-[2-(4-Fluorophenyl)-6-methyl-pyrrolo[2,3-b]pyridin-1-yl]indolin-2-one; | 9.4 |
| 383 | 5-[6-Chloro-2-(4-fluorophenyl)pyrrolo[2,3-b]pyridin-1-yl]indolin-2-one; | 10.0 |
| 384 | 5-[2-(4-Fluorophenyl)-6-methoxy-pyrrolo[2,3-b]pyridin-1-yl]indolin-2-one; | 8.3 |
| 385 | 6-Chloro-2-(4-fluorophenyl)-1-(1H-indol-5-yl)pyrrolo[2,3-b]pyridine; | 7.8 |
| 386 | 6-tert-Butoxy-2-(4-fluorophenyl)-1-(1H-indol-5-yl)pyrrolo[2,3-b]pyridine; | 5.8 |
| 387 | 2-(4-Fluorophenyl)-1-(1H-indol-5-yl)-6-(trifluoromethyl)pyrrolo[2,3-b]pyridine; | 8.2 |
| 388 | 1-(1H-Indol-5-yl)-2-phenyl-6-(trifluoromethyl)pyrrolo[2,3-b]pyridine; | 8.1 |
| 389 | 5-[3-Bromo-2-cyclopropyl-6-(trifluoromethyl)pyrrolo[2,3-b]pyridin-1-yl]indolin-2-one; | 10.2 |
| 390 | 6-Methyl-2-phenyl-1-(1H-pyrrolo[2,3-b]pyridin-5-yl)pyrrolo[2,3-b]pyridine; | 8.9 |
| 391 | 2-Isopropyl-1-(1H-pyrrolo[2,3-b]pyridin-5-yl)-6-(trifluoromethyl)pyrrolo[2,3-b]pyridine; | 9.2 |
| 392 | 2-Methyl-1-(1H-pyrrolo[2,3-b]pyridin-5-yl)-6-(trifluoromethyl)pyrrolo[2,3-b]pyridine; | NT |
| 393 | 5-(3-Bromo-6-methyl-2-phenyl-pyrrolo[2,3-b]pyridin-1-yl)-1,3-dihydropyrrolo[2,3-b]pyridin-2-one; | 8.5 |
| 394 | 5-[3-Bromo-2-isopropyl-6-(trifluoromethyl)pyrrolo[2,3-b]pyridin-1-yl]-1,3-dihydropyrrolo[2,3-b]pyridin-2-one; | 7.5 |
| 395 | 5-[3-Bromo-2-methyl-6-(trifluoromethyl)pyrrolo[2,3-b]pyridin-1-yl]-1,3-dihydropyrrolo[2,3-b]pyridin-2-one; | 7.6 |
| 396 | 5-[2-Isopropyl-6-(trifluoromethyl)pyrrolo[2,3-b]pyridin-1-yl]indolin-2-one; | 10.9 |
| 397 | 5-[2-Phenyl-6-(trifluoromethyl)pyrrolo[2,3-b]pyridin-1-yl]indolin-2-one; | 10.4 |
| 398 | 5-[2-(4-Fluorophenyl)-6-(trifluoromethyl)pyrrolo[2,3-b]pyridin-1-yl]indolin-2-one; | 10.2 |
| 399 | 5-[2-Cyclopropyl-6-(trifluoromethyl)pyrrolo[2,3-b]pyridin-1-yl]indolin-2-one; | 10.6 |
| 400 | 5-(6-Methyl-2-phenyl-pyrrolo[2,3-b]pyridin-1-yl)-1,3-dihydropyrrolo[2,3-b]pyridin-2-one; | 9.6 |
| 401 | 5-[2-Isopropyl-6-(trifluoromethyl)pyrrolo[2,3-b]pyridin-1-yl]-1,3-dihydropyrrolo[2,3-b]pyridin-2-one; | 10.5 |
| 402 | 5-[2-Methyl-6-(trifluoromethyl)pyrrolo[2,3-b]pyridin-1-yl]-1,3-dihydropyrrolo[2,3-b]pyridin-2-one; | 8.0 |
| 403 | 5-(2-Ethylpyrrolo[2,3-b]pyridin-1-yl)-7-methyl-indolin-2-one; | 8.9 |
| 404 | (*R)-2-(sec-Butyl)-3-(7-chloro-1H-indazol-5-yl)-5-(trifluoromethyl)-3H-imidazo[4,5-b]pyridine; | 10.0 |
| 405 | (*S)-2-(sec-Butyl)-3-(7-chloro-1H-indazol-5-yl)-5-(trifluoromethyl)-3H-imidazo[4,5-b]pyridine; | 10.2 |
| 406 | (*R)-2-(sec-Butyl)-3-(7-methyl-1H-indazol-5-yl)-5-(trifluoromethyl)-3H-imidazo[4,5-b]pyridine; | 9.9 |
| 407 | (*S)-2-(sec-Butyl)-3-(7-methyl-1H-indazol-5-yl)-5-(trifluoromethyl)-3H-imidazo[4,5-b]pyridine; | 10.0 |
| 408 | (*R)-3-(7-Chloro-1H-indazol-5-yl)-2-(1-fluoroethyl)-5-(trifluoromethyl)-3H-imidazo[4,5-b]pyridine; | 10.0 |
| 409 | (*S)-3-(7-Chloro-1H-indazol-5-yl)-2-(1-fluoroethyl)-5-(trifluoromethyl)-3H-imidazo[4,5-b]pyridine; | 10.1 |
| 410 | 3-(7-Chloro-1H-indazol-5-yl)-2-(1,1-difluoroethyl)-5-methyl-3H-imidazo[4,5-b]pyridine; | 8.9 |
| 411 | 3-(7-Chloro-1H-indazol-5-yl)-2-(cyclopropylmethyl)-5-(trifluoromethyl)-3H-imidazo[4,5-b]pyridine; | 9.8 |
| 412 | 3-(7-Chloro-1H-indazol-5-yl)-2-propyl-5-(trifluoromethyl)-3H-imidazo[4,5-b]pyridine; | 9.9 |
| 413 | 3-(7-Chloro-1H-indazol-5-yl)-2-(methoxymethyl)-5-(trifluoromethyl)-3H-imidazo[4,5-b]pyridine; | 9.4 |
| 414 | 3-(7-Chloro-1H-indazol-5-yl)-2-isobutyl-5-(trifluoromethyl)-3H-imidazo[4,5-b]pyridine; | 9.9 |
| 415 | 3-(7-Chloro-1H-indazol-5-yl)-5-methoxy-2-(trifluoromethyl)-3H-imidazo[4,5-b]pyridine; | 10.3 |
| 416 | 3-(7-Chloro-1H-indazol-5-yl)-2-(2,2,2-trifluoroethyl)-5-(trifluoromethyl)-3H-imidazo[4,5-b]pyridine; | 9.3 |

TABLE 4-continued

| Ex. # | Compound Name | pIC$_{50}$ |
|---|---|---|
| 417 | 2-(1,1-Difluoropropyl)-3-(7-methyl-1H-indazol-5-yl)-5-(trifluoromethyl)-3H-imidazo[4,5-b]pyridine; | 8.5 |
| 418 | 3-(7-Methyl-1H-indazol-5-yl)-5-(trifluoromethyl)-2-(3,3,3-trifluoropropyl)-3H-imidazo[4,5-b]pyridine; | 8.4 |
| 419 | 3-(7-Chloro-1H-indazol-5-yl)-2,6-bis(trifluoromethyl)-3H-imidazo[4,5-b]pyridine; | 9.2 |
| 420 | 5-(5-Fluoro-2-isopropyl-1H-pyrrolo[2,3-b]pyridin-1-yl)-7-methylindolin-2-one; | 9.9 |
| 421 | 5-(6-(Difluoromethyl)-2-methyl-1H-pyrrolo[2,3-b]pyridin-1-yl)-7-methylindolin-2-one; and | 10.1 |
| 422 | 1-(7-Methyl-2-oxoindolin-5-yl)-6-(trifluoromethyl)-1H-pyrrolo[2,3-b]pyridine-2-carbaldehyde. | 9.5 |

Electrophysiology Assay

The effects of selected compounds upon endogenous gamma8-containing AMPA receptor currents are evaluated using whole-cell electrophysiology on acutely-dissociated mouse hippocampal neurons. Hippocampus was chosen for this assay, since CACNG8 (the protein encoded by this gene is a type I transmembrane AMPA receptor regulatory protein i.e., TARP) is preferentially enriched in this brain region (Tomita et al. (2003). "Functional studies and distribution define a family of transmembrane AMPA receptor regulatory proteins." *J Cell Biol* 161(4): 805-816.2003). Hippocampi are dissected from C57black6 mice at 4-12 weeks postnatal, following the protocol described by Brewer (Brewer, G. J. (1997). "Isolation and culture of adult rat hippocampal neurons." *Journal of Neuroscience Methods* 71(2): 143-155). The following is a brief summary of the procedure. Mice are asphyxiated with CO$_2$ then decapitated. The brain is rapidly removed, then placed into ice-cold HABG medium. The recipe for HABG medium is: HibernateA supplemented with 2% B27 and 0.5 mM Glutamax (all reagents from Life Technologies). Hippocampi are microdissected from the brains, then washed with HABG without calcium (Hibernate A minus Calcium, BrainBits; 2% B27, Life Technologies; 0.5 mM glutamax, Life Technologies).

The hippocampi are then transferred to HABG without calcium, supplemented with 2 mg/mL papain (Worthington Biochemical). They are incubated at 30° C. on a roller for 40 min, then gently triturated with a fire-polished glass pipette. The supernatant containing dissociated neurons is collected, then centrifuged for 2 min at 200 g. The cell pellet is collected, and then resuspended in 8 mL of HABG. Live cells are counted, then plated onto 12 mm glass coverslips in 2 mL of HABG in 24-well plates at a density of 50-100 cells per coverslip. These cells are maintained at rt until use. Whole-cell electrophysiology is performed using 1.5 mm diameter glass capillary tubes (World Precision Instruments TW150-4), pulled to a fine tip with a Sutter P-97 micropipette puller. The intracellular buffer was 90 mM KF, 30 mM KCl, 10 mM HEPES, and 5 mM EGTA, pH 7.4, 290 mOs. The extracellular buffer was 135 mM NaCl, 4 mM KCl, 2 mM CaCl$_2$, 1 mM MgCl$_2$, 5 mM glucose, 10 mM HEPES, pH 7.4, 300 mOs. The open-tip resistances of the micropipettes using these solutions are 2-4 MΩ. Whole-cell recordings of neuron cell bodies are performed in voltage-clamp mode using an Axon Axopatch 200B amplifier. Whole-cell current is measured holding the interior of the cell at −60 mV, using a 5 kHz lowpass filter. The cells are continuously perfused through 7 mm square glass barrels using a solenoid-controlled solution switching device (Warner Instruments, PF-77B). The peak current in response to a 500 ms exposure to 10 mM glutamate every 5 seconds is measured, before and after exposure to test compound. For analysis, the mean peak current of 5 traces in the presence of test compound is divided by the mean peak current of 5 traces prior to the addition of test compound. Compounds are tested at concentrations at least ten times higher than their estimated potency in the calcium flux assay, in order to ensure near-saturating occupancy of the receptor.

All patents, patent applications, publications and presentations referred to herein are incorporated by reference in their entirety.

Any combination of the groups described above for the various variables is contemplated herein. Throughout the specification, groups and substituents thereof are chosen by one skilled in the field to provide stable moieties and compounds.

While the foregoing specification teaches the principles of the present invention, and specific embodiments of the invention have been described for the purposes of illustration, and examples have been provided for the purposes of illustration, it will be understood that various modifications may be made without deviating from the spirit and scope of the invention as come within the scope of the following claims and their equivalents.

What is claimed:

1. A compound of Formula (I):

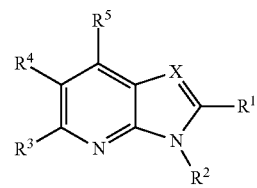

Wherein

X is N;

R$^1$ is a member selected from the group consisting of:
—C$_{1-5}$alkyl, —C$_{1-5}$haloalkyl, —C$_{1-5}$alkoxy, —C$_{3-8}$cycloalkyl or phenyl, wherein the —C$_{3-8}$cycloalkyl and phenyl are each independently optionally substituted with 1-3 substituents selected from the group consisting of: halo, —C$_{1-5}$alkyl, —C$_{1-5}$haloalkyl, —C$_{1-5}$ haloalkoxy, —OH, and —C(=O)OC$_{1-5}$alkyl;

$R^2$ is selected from the group consisting of:

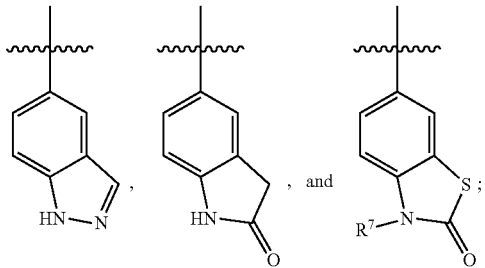

$R^3$ is selected from the group consisting of: H, —$C_{1-5}$ alkyl or —$C_{1-5}$haloalkyl;

$R^4$ is selected from the group consisting of: H, halo, —$CH_3$, and —$CF_3$;

$R^5$ is selected from the group consisting of: H, —OH, —$C_{1-5}$alkyl, —$C_{1-5}$alkoxy, —$C_{1-5}$haloalkyl, —$C_{1-5}$haloalkoxy, —$NR^{5a}R^{5b}$, azetidinyl, and morpholinyl; each $R^{5a}$ and $R^{5b}$ are independently selected from the group consisting of: —$C_{1-5}$alkyl, and —$C_{1-5}$haloalkyl; and $R^7$ is H;

or pharmaceutically acceptable salts, N-oxides, or solvates thereof.

2. A compound of claim 1, wherein the compound is: 5-[2,5-Bis(trifluoromethyl)imidazo[4,5-b]pyridin-3-yl]indolin-2-one, and pharmaceutically acceptable salts, N-oxides or solvates thereof.

3. A compound of claim 1, wherein the compound is: 2-(Difluoromethyl)-3-(1H-indazol-5-yl)-5-(trifluoromethyl) imidazo[4,5-b]pyridine, and pharmaceutically acceptable salts, N-oxides or solvates thereof.

4. A compound of claim 1, wherein the compound is: 3-(1H-Indazol-5-yl)-2-isopropyl-5-(trifluoromethyl)imidazo[4,5-b]pyridine, and pharmaceutically acceptable salts, N-oxides or solvates thereof.

5. A compound of claim 1, wherein the compound is: 6-[2,5-Bis(trifluoromethyl)imidazo[4,5-b]pyridin-3-yl]-3H-1,3-benzothiazol-2-one, and pharmaceutically acceptable salts, N-oxides or solvates thereof.

6. A compound of claim 1, wherein the compound is: 5-(Difluoromethyl)-3-(1H-indazol-5-yl)-2-(trifluoromethyl) imidazo[4,5-b]pyridine; and pharmaceutically acceptable salts, N-oxides or solvates thereof.

7. A pharmaceutical composition comprising an effective amount of at least one compound of claim 6 and at least one pharmaceutically acceptable excipient.

8. A pharmaceutical composition comprising:
(A) an effective amount of at least one compound of Formula (I):

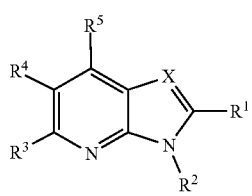

(I)

wherein

X is N;

$R^1$ is a member selected from the group consisting of:
—$C_{1-5}$alkyl, —$C_{1-5}$haloalkyl, —$C_{1-5}$alkoxy, —$C_{3-8}$cycloalkyl or phenyl, wherein the —$C_{3-8}$ cycloalkyl and phenyl are each independently optionally substituted with 1-3 substituents selected from the group consisting of: halo, —$C_{1-5}$alkyl, —$C_{1-5}$haloalkyl, —$C_{1-5}$haloalkoxy, —OH, and —C(=)O$C_{1-5}$alkyl;

$R^2$ is selected from the group consisting of:

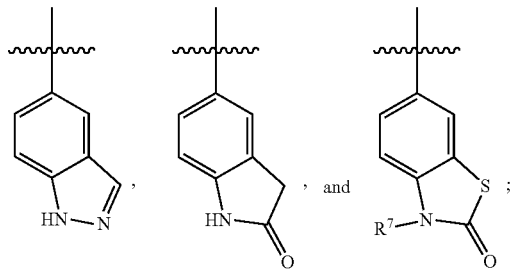

$R^3$ is selected from the group consisting of: H, —$C_{1-5}$ alkyl, or —$C_{1-5}$haloalkyl;

$R^4$ is selected from the group consisting of: H, halo, —$CH_3$, and —$CF_3$;

$R^5$ is selected from the group consisting of: H, —OH, —$C_{1-5}$alkyl, —$C_{1-5}$alkoxy, —$C_{1-5}$haloalkyl, —$C_{1-5}$haloalkoxy, —$NR^{5a}R^{5b}$, azetidinyl, and morpholinyl; each $R^{5a}$ and $R^{5b}$ are independently selected from the group consisting of: —$C_{1-5}$alkyl, and —$C_{1-5}$haloalkyl; and $R^7$ is H;

or pharmaceutically acceptable salts, N-oxides or solvates of compounds of Formula (I) and (B) at least one pharmaceutically acceptable excipient.

9. A method of inhibiting TARP γ2 dependent AMPA receptor activity in a subject suffering from or diagnosed with a disease, disorder, or medical condition comprising administering to a subject in need of such treatment an effective amount of at least one compound of Formula (I):

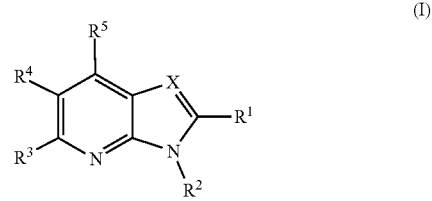

(I)

wherein

X is N;

$R^1$ is a member selected from the group consisting of:
—$C_{1-5}$alkyl, —$C_{1-5}$haloalkyl, —$C_{1-5}$alkoxy, —$C_{3-8}$cycloalkyl or phenyl, wherein the -$C_{3-8}$ cycloalkyl and phenyl are each independently optionally substituted with 1-3 substituents selected from the group consisting of: halo, —$C_{1-5}$alkyl, —$C_{1-5}$haloalkyl, —$C_{1-5}$haloalkoxy, —OH, and —C(=)O$C_{1-5}$alkyl;

$R^2$ is selected from the group consisting of:

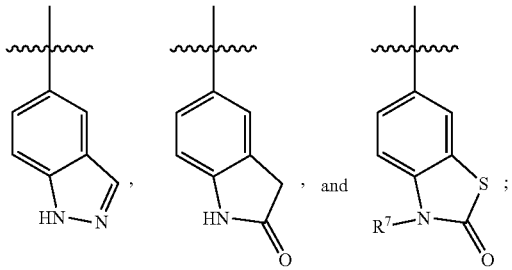

$R^3$ is selected from the group consisting of: H, —$C_{1-5}$alkyl, or —$C_{1-5}$haloalkyl;

$R^4$ is selected from the group consisting of: H, halo, —$CH_3$, and —$CF_3$;

$R^5$ is selected from the group consisting of: H, —OH, —$C_{1-5}$alkyl, —$C_{1-5}$alkoxy, —$C_{1-5}$haloalkyl, —$C_{1-5}$haloalkoxy, —$NR^{5a}R^{5b}$, azetidinyl, and morpholinyl; each $R^{5a}$ and $R^{5b}$ are independently selected from the group consisting of: —$C_{1-5}$alkyl, and —$C_{1-5}$haloalkyl; and $R^7$ is H; or pharmaceutically acceptable salts, N-oxides or solvates of compounds of Formula (I).

10. The method of claim 9, wherein the disease, disorder, or medical condition is selected from cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy, Guillain Barre syndrome, chronic inflammatory demyelinating polyneuropathy, multiple sclerosis, Marchifava-Bignami disease, central pontine myelinolysis, Devic syndrome, Balo disease, HV- or HTLV-myelopathy, progressive multifocal leucoencephalopathy, a secondary demyelinating disorder, CNS lupus erythematodes, polyarteritis nodosa, Sjogren syndrome, sarcoidosis, isolated cerebral vasculitis, schizophrenia, prodromal schizophrenia, cognitive disorder, depression, anxiety disorders, anxious depression, and bipolar disorder.

11. The method of claim 9, wherein the disease, disorder or condition is depression, post traumatic stress disorder, epilepsy, schizophrenia, prodromal schizophrenia, or a cognitive disorder.

* * * * *